(12) United States Patent
Simms et al.

(10) Patent No.: US 11,369,376 B2
(45) Date of Patent: Jun. 28, 2022

(54) SURGICAL STAPLING SYSTEMS

(71) Applicant: Ethicon LLC, Guaynabo, PR (US)

(72) Inventors: Robert J. Simms, Liberty Township, OH (US); Jason L. Harris, Lebanon, OH (US); Frederick E. Shelton, IV, Hillsboro, OH (US); Nichole Y. Kwee, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 483 days.

(21) Appl. No.: 16/287,314

(22) Filed: Feb. 27, 2019

(65) Prior Publication Data

US 2019/0192156 A1   Jun. 27, 2019

Related U.S. Application Data

(63) Continuation of application No. 15/385,916, filed on Dec. 21, 2016, now abandoned.

(51) Int. Cl.
*A61B 17/072* (2006.01)
*A61B 90/94* (2016.01)
(Continued)

(52) U.S. Cl.
CPC .... *A61B 17/07207* (2013.01); *A61B 17/0682* (2013.01); *A61B 17/072* (2013.01);
(Continued)

(58) Field of Classification Search
CPC ............... A61B 17/068; A61B 17/072; A61B 17/07207; A61B 17/115; A61B 90/92;
(Continued)

(56) References Cited

U.S. PATENT DOCUMENTS 66,052 A   6/1867  Smith
662,587 A   11/1900  Blake
(Continued)

FOREIGN PATENT DOCUMENTS

AU   2012200594 A1   2/2012
AU   2012203035 A1   6/2012
(Continued)

OTHER PUBLICATIONS

ASTM procedure D2240-00, "Standard Test Method for Rubber Property-Durometer Hardness," (Published Aug. 2000).
(Continued)

*Primary Examiner* — Scott A Smith

(57) ABSTRACT

A method is disclosed. The method can comprise obtaining a first staple cartridge and obtaining a second staple cartridge, wherein the first staple cartridge and the second staple cartridge comprise the same length and the same width. The method can further comprise inserting the first staple cartridge into a channel comprising a keyed profile, wherein complete insertion of the first staple cartridge into the channel is prevented by the keyed profile. Additionally, the method can comprise inserting the second staple cartridge into the channel, wherein complete insertion of the second staple cartridge into the channel is permitted by the keyed profile.

20 Claims, 67 Drawing Sheets

(51) Int. Cl.
  *A61B 17/28* (2006.01)
  *A61B 34/30* (2016.01)
  *A61B 17/068* (2006.01)
  A61B 17/00 (2006.01)
  A61B 90/00 (2016.01)
  A61B 90/92 (2016.01)
  A61B 17/29 (2006.01)
  A61B 18/14 (2006.01)

(52) U.S. Cl.
  CPC ...... *A61B 17/2816* (2013.01); *A61B 17/2833* (2013.01); *A61B 34/30* (2016.02); *A61B 90/94* (2016.02); A61B 17/00234 (2013.01); A61B 17/068 (2013.01); A61B 18/1445 (2013.01); A61B 90/92 (2016.02); A61B 2017/00017 (2013.01); A61B 2017/00039 (2013.01); A61B 2017/0046 (2013.01); A61B 2017/00398 (2013.01); A61B 2017/00469 (2013.01); A61B 2017/00477 (2013.01); A61B 2017/00734 (2013.01); A61B 2017/00818 (2013.01); A61B 2017/0725 (2013.01); A61B 2017/07214 (2013.01); A61B 2017/07221 (2013.01); A61B 2017/07228 (2013.01); A61B 2017/07235 (2013.01); A61B 2017/07242 (2013.01); A61B 2017/07257 (2013.01); A61B 2017/07264 (2013.01); A61B 2017/07271 (2013.01); A61B 2017/07278 (2013.01); A61B 2017/07285 (2013.01); A61B 2017/2912 (2013.01); A61B 2017/2927 (2013.01); A61B 2017/2929 (2013.01); A61B 2017/2933 (2013.01); A61B 2017/2934 (2013.01); A61B 2017/2936 (2013.01); A61B 2017/2937 (2013.01); A61B 2017/2939 (2013.01); A61B 2017/2943 (2013.01); A61B 2017/2946 (2013.01); A61B 2017/2947 (2013.01); A61B 2090/034 (2016.02); A61B 2090/037 (2016.02); A61B 2090/0808 (2016.02); A61B 2090/0811 (2016.02); A61B 2090/0814 (2016.02)

(58) Field of Classification Search
  CPC .......... A61B 90/94; A61B 2017/07214; A61B 2017/07271; A61B 2017/07278; A61B 2017/2933; A61B 2017/2927; A61B 2017/2929; A61B 2017/0046; A61B 2017/00477
  USPC .............. 606/1, 139, 153, 213, 219; 227/19, 227/175.1, 176.1, 175.2, 180.1
  See application file for complete search history.

(56) References Cited

U.S. PATENT DOCUMENTS

| | | |
|---|---|---|
| 670,748 A | 3/1901 | Weddeler |
| 719,487 A | 2/1903 | Minor |
| 804,229 A | 11/1905 | Hutchinson |
| 903,739 A | 11/1908 | Lesemann |
| 951,393 A | 3/1910 | Hahn |
| 1,075,556 A | 10/1913 | Fenoughty |
| 1,082,105 A | 12/1913 | Anderson |
| 1,188,721 A | 6/1916 | Bittner |
| 1,306,107 A | 6/1919 | Elliott |
| 1,314,601 A | 9/1919 | McCaskey |
| 1,466,128 A | 8/1923 | Hallenbeck |
| 1,677,337 A | 7/1928 | Grove |
| 1,794,907 A | 3/1931 | Kelly |
| 1,849,427 A | 3/1932 | Hook |
| 1,944,116 A | 1/1934 | Stratman |
| 1,954,048 A | 4/1934 | Jeffrey et al. |
| 2,028,635 A | 1/1936 | Wappler |
| 2,037,727 A | 4/1936 | La Chapelle |
| 2,120,951 A | 6/1938 | Hodgman |
| 2,132,295 A | 10/1938 | Hawkins |
| 2,161,632 A | 6/1939 | Nattenheimer |
| D120,434 S | 5/1940 | Gold |
| 2,211,117 A | 8/1940 | Hess |
| 2,214,870 A | 9/1940 | West |
| 2,224,108 A | 12/1940 | Ridgway |
| 2,224,882 A | 12/1940 | Peck |
| 2,318,379 A | 5/1943 | Davis et al. |
| 2,329,440 A | 9/1943 | La Place |
| 2,377,581 A | 6/1945 | Shaffrey |
| 2,406,389 A | 8/1946 | Lee |
| 2,420,552 A | 5/1947 | Morrill |
| 2,441,096 A | 5/1948 | Happe |
| 2,448,741 A | 9/1948 | Scott et al. |
| 2,450,527 A | 10/1948 | Smith |
| 2,491,872 A | 12/1949 | Neuman |
| 2,507,872 A | 5/1950 | Unsinger |
| 2,526,902 A | 10/1950 | Rublee |
| 2,527,256 A | 10/1950 | Jackson |
| 2,578,686 A | 12/1951 | Fish |
| 2,638,901 A | 5/1953 | Sugarbaker |
| 2,674,149 A | 4/1954 | Benson |
| 2,701,489 A | 2/1955 | Osborn |
| 2,711,461 A | 6/1955 | Happe |
| 2,724,289 A | 11/1955 | Wight |
| 2,742,955 A | 4/1956 | Dominguez |
| 2,804,848 A | 9/1957 | O'Farrell et al. |
| 2,808,482 A | 10/1957 | Zanichkowsky et al. |
| 2,825,178 A | 3/1958 | Hawkins |
| 2,853,074 A | 9/1958 | Olson |
| 2,856,192 A | 10/1958 | Schuster |
| 2,887,004 A | 5/1959 | Stewart |
| 2,957,353 A | 10/1960 | Lewis |
| 2,959,974 A | 11/1960 | Emrick |
| 3,026,744 A | 3/1962 | Rouse |
| 3,032,769 A | 5/1962 | Palmer |
| 3,035,256 A | 5/1962 | Egbert |
| 3,060,972 A | 10/1962 | Sheldon |
| 3,075,062 A | 1/1963 | Iaccarino |
| 3,078,465 A | 2/1963 | Bobrov |
| 3,079,606 A | 3/1963 | Bobrov et al. |
| 3,080,564 A | 3/1963 | Strekopitov et al. |
| 3,166,072 A | 1/1965 | Sullivan, Jr. |
| 3,180,236 A | 4/1965 | Beckett |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,269,631 A | 8/1966 | Takaro |
| 3,275,211 A | 9/1966 | Hirsch et al. |
| 3,315,863 A | 4/1967 | O'Dea |
| 3,317,103 A | 5/1967 | Cullen et al. |
| 3,317,105 A | 5/1967 | Astafjev et al. |
| 3,357,296 A | 12/1967 | Lefever |
| 3,359,978 A | 12/1967 | Smith, Jr. |
| 3,377,893 A | 4/1968 | Shorb |
| 3,480,193 A | 11/1969 | Ralston |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,509,629 A | 5/1970 | Kidokoro |
| 3,551,987 A | 1/1971 | Wilkinson |
| 3,568,675 A | 3/1971 | Harvey |
| 3,572,159 A | 3/1971 | Tschanz |
| 3,583,393 A | 6/1971 | Takahashi |
| 3,589,589 A | 6/1971 | Akopov |
| 3,598,943 A | 8/1971 | Barrett |
| 3,604,561 A | 9/1971 | Mallina et al. |
| 3,608,549 A | 9/1971 | Merrill |
| 3,618,842 A | 11/1971 | Bryan |
| 3,635,394 A | 1/1972 | Natelson |
| 3,638,652 A | 2/1972 | Kelley |
| 3,640,317 A | 2/1972 | Panfili |
| 3,643,851 A | 2/1972 | Green et al. |
| 3,650,453 A | 3/1972 | Smith, Jr. |
| 3,661,339 A | 5/1972 | Shimizu |

(56) References Cited

U.S. PATENT DOCUMENTS

| | | |
|---|---|---|
| 3,661,666 A | 5/1972 | Foster et al. |
| 3,662,939 A | 5/1972 | Bryan |
| 3,685,250 A | 8/1972 | Henry et al. |
| 3,688,966 A | 9/1972 | Perkins et al. |
| 3,695,646 A | 10/1972 | Mommsen |
| 3,709,221 A | 1/1973 | Riely |
| 3,717,294 A | 2/1973 | Green |
| 3,724,237 A | 4/1973 | Wood |
| 3,726,755 A | 4/1973 | Shannon |
| 3,727,904 A | 4/1973 | Gabbey |
| 3,734,207 A | 5/1973 | Fishbein |
| 3,740,994 A | 6/1973 | De Carlo, Jr. |
| 3,744,495 A | 7/1973 | Johnson |
| 3,746,002 A | 7/1973 | Haller |
| 3,747,603 A | 7/1973 | Adler |
| 3,747,692 A | 7/1973 | Davidson |
| 3,751,902 A | 8/1973 | Kingsbury et al. |
| 3,752,161 A | 8/1973 | Bent |
| 3,799,151 A | 3/1974 | Fukaumi et al. |
| 3,808,452 A | 4/1974 | Hutchinson |
| 3,815,476 A | 6/1974 | Green et al. |
| 3,819,100 A | 6/1974 | Noiles et al. |
| 3,821,919 A | 7/1974 | Knohl |
| 3,826,978 A | 7/1974 | Kelly |
| 3,836,171 A | 9/1974 | Hayashi et al. |
| 3,837,555 A | 9/1974 | Green |
| 3,841,474 A | 10/1974 | Maier |
| 3,851,196 A | 11/1974 | Hinds |
| 3,863,639 A | 2/1975 | Kleaveland |
| 3,863,940 A | 2/1975 | Cummings |
| 3,883,624 A | 5/1975 | McKenzie et al. |
| 3,885,491 A | 5/1975 | Curtis |
| 3,887,393 A | 6/1975 | La Rue, Jr. |
| 3,892,228 A | 7/1975 | Mitsui |
| 3,894,174 A | 7/1975 | Cartun |
| 3,902,247 A | 9/1975 | Fleer et al. |
| 3,940,844 A | 3/1976 | Colby et al. |
| 3,944,163 A | 3/1976 | Hayashi et al. |
| 3,950,686 A | 4/1976 | Randall |
| 3,952,747 A | 4/1976 | Kimmell, Jr. |
| 3,955,581 A | 5/1976 | Spasiano et al. |
| 3,959,879 A | 6/1976 | Sellers |
| RE28,932 E | 8/1976 | Noiles et al. |
| 3,972,734 A | 8/1976 | King |
| 3,973,179 A | 8/1976 | Weber et al. |
| 3,981,051 A | 9/1976 | Brumlik |
| 3,999,110 A | 12/1976 | Ramstrom et al. |
| 4,025,216 A | 5/1977 | Hives |
| 4,027,746 A | 6/1977 | Kine |
| 4,034,143 A | 7/1977 | Sweet |
| 4,038,987 A | 8/1977 | Komiya |
| 4,054,108 A | 10/1977 | Gill |
| 4,060,089 A | 11/1977 | Noiles |
| 4,066,133 A | 1/1978 | Voss |
| 4,085,337 A | 4/1978 | Moeller |
| 4,100,820 A | 7/1978 | Evett |
| 4,106,446 A | 8/1978 | Yamada et al. |
| 4,106,620 A | 8/1978 | Brimmer et al. |
| 4,108,211 A | 8/1978 | Tanaka |
| 4,111,206 A | 9/1978 | Vishnevsky et al. |
| 4,127,227 A | 11/1978 | Green |
| 4,129,059 A | 12/1978 | Van Eck |
| 4,132,146 A | 1/1979 | Uhlig |
| 4,135,517 A | 1/1979 | Reale |
| 4,149,461 A | 4/1979 | Simeth |
| 4,154,122 A | 5/1979 | Severin |
| 4,160,857 A | 7/1979 | Nardella et al. |
| 4,169,990 A | 10/1979 | Lerdman |
| 4,180,285 A | 12/1979 | Reneau |
| 4,185,701 A | 1/1980 | Boys |
| 4,190,042 A | 2/1980 | Sinnreich |
| 4,198,734 A | 4/1980 | Brumlik |
| 4,198,982 A | 4/1980 | Fortner et al. |
| 4,203,444 A | 5/1980 | Bonnell et al. |
| 4,207,898 A | 6/1980 | Becht |
| 4,213,562 A | 7/1980 | Garrett et al. |
| 4,226,242 A | 10/1980 | Jarvik |
| 4,239,431 A | 12/1980 | Davini |
| 4,241,861 A | 12/1980 | Fleischer |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,274,398 A | 6/1981 | Scott, Jr. |
| 4,275,813 A | 6/1981 | Noiles |
| 4,278,091 A | 7/1981 | Borzone |
| 4,282,573 A | 8/1981 | Imai et al. |
| 4,289,131 A | 9/1981 | Mueller |
| 4,289,133 A | 9/1981 | Rothfuss |
| 4,290,542 A | 9/1981 | Fedotov et al. |
| D261,356 S | 10/1981 | Robinson |
| 4,293,604 A | 10/1981 | Campbell |
| 4,296,654 A | 10/1981 | Mercer |
| 4,296,881 A | 10/1981 | Lee |
| 4,304,236 A | 12/1981 | Conta et al. |
| 4,305,539 A | 12/1981 | Korolkov et al. |
| 4,312,363 A | 1/1982 | Rothfuss et al. |
| 4,312,685 A | 1/1982 | Riedl |
| 4,317,451 A | 3/1982 | Cerwin et al. |
| 4,319,576 A | 3/1982 | Rothfuss |
| 4,321,002 A | 3/1982 | Froehlich |
| 4,321,746 A | 3/1982 | Grinage |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,348,603 A | 9/1982 | Huber |
| 4,349,028 A | 9/1982 | Green |
| 4,350,151 A | 9/1982 | Scott |
| 4,353,371 A | 10/1982 | Cosman |
| 4,357,940 A | 11/1982 | Muller |
| 4,361,057 A | 11/1982 | Kochera |
| 4,366,544 A | 12/1982 | Shima et al. |
| 4,369,013 A | 1/1983 | Abildgaard et al. |
| 4,373,147 A | 2/1983 | Carlson, Jr. |
| 4,376,380 A | 3/1983 | Burgess |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,389,963 A | 6/1983 | Pearson |
| 4,393,728 A | 7/1983 | Larson et al. |
| 4,394,613 A | 7/1983 | Cole |
| 4,396,139 A | 8/1983 | Hall et al. |
| 4,397,311 A | 8/1983 | Kanshin et al. |
| 4,402,445 A | 9/1983 | Green |
| 4,406,621 A | 9/1983 | Bailey |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,417,890 A | 11/1983 | Dennehey et al. |
| 4,421,264 A | 12/1983 | Arter et al. |
| 4,423,456 A | 12/1983 | Zaidenweber |
| 4,425,915 A | 1/1984 | Ivanov |
| 4,428,376 A | 1/1984 | Mericle |
| 4,429,695 A | 2/1984 | Green |
| 4,430,997 A | 2/1984 | DiGiovanni et al. |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,452,376 A | 6/1984 | Klieman et al. |
| 4,454,887 A | 6/1984 | Kruger |
| 4,459,519 A | 7/1984 | Erdman |
| 4,461,305 A | 7/1984 | Cibley |
| 4,467,805 A | 8/1984 | Fukuda |
| 4,468,597 A | 8/1984 | Baumard et al. |
| 4,469,481 A | 9/1984 | Kobayashi |
| 4,470,414 A | 9/1984 | Imagawa et al. |
| 4,471,780 A | 9/1984 | Menges et al. |

(56) References Cited

U.S. PATENT DOCUMENTS

| | | |
|---|---|---|
| 4,471,781 A | 9/1984 | Di Giovanni et al. |
| 4,473,077 A | 9/1984 | Noiles et al. |
| 4,475,679 A | 10/1984 | Fleury, Jr. |
| 4,476,864 A | 10/1984 | Tezel |
| 4,478,220 A | 10/1984 | Di Giovanni et al. |
| 4,480,641 A | 11/1984 | Failla et al. |
| 4,481,458 A | 11/1984 | Lane |
| 4,483,562 A | 11/1984 | Schoolman |
| 4,485,816 A | 12/1984 | Krumme |
| 4,485,817 A | 12/1984 | Swiggett |
| 4,486,928 A | 12/1984 | Tucker et al. |
| 4,488,523 A | 12/1984 | Shichman |
| 4,489,875 A | 12/1984 | Crawford et al. |
| 4,493,983 A | 1/1985 | Taggert |
| 4,494,057 A | 1/1985 | Hotta |
| 4,499,895 A | 2/1985 | Takayama |
| 4,500,024 A | 2/1985 | DiGiovanni et al. |
| D278,081 S | 3/1985 | Green |
| 4,503,842 A | 3/1985 | Takayama |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,512,038 A | 4/1985 | Alexander et al. |
| 4,514,477 A | 4/1985 | Kobayashi |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,357 A | 7/1985 | Pawloski et al. |
| 4,530,453 A | 7/1985 | Green |
| 4,531,522 A | 7/1985 | Bedi et al. |
| 4,532,927 A | 8/1985 | Miksza, Jr. |
| 4,540,202 A | 9/1985 | Amphoux et al. |
| 4,548,202 A | 10/1985 | Duncan |
| 4,556,058 A | 12/1985 | Green |
| 4,560,915 A | 12/1985 | Soultanian |
| 4,565,109 A | 1/1986 | Tsay |
| 4,565,189 A | 1/1986 | Mabuchi |
| 4,566,620 A | 1/1986 | Green et al. |
| 4,569,346 A | 2/1986 | Poirier |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,165 A | 3/1986 | Green et al. |
| 4,576,167 A | 3/1986 | Noiles |
| 4,580,712 A | 4/1986 | Green |
| 4,585,153 A | 4/1986 | Failla et al. |
| 4,586,501 A | 5/1986 | Claracq |
| 4,586,502 A | 5/1986 | Bedi et al. |
| 4,589,416 A | 5/1986 | Green |
| 4,589,582 A | 5/1986 | Bilotti |
| 4,589,870 A | 5/1986 | Citrin et al. |
| 4,591,085 A | 5/1986 | Di Giovanni |
| RE32,214 E | 7/1986 | Schramm |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,636 A | 8/1986 | Kula et al. |
| 4,607,638 A | 8/1986 | Crainich |
| 4,608,980 A | 9/1986 | Aihara |
| 4,608,981 A | 9/1986 | Rothfuss et al. |
| 4,610,250 A | 9/1986 | Green |
| 4,610,383 A | 9/1986 | Rothfuss et al. |
| 4,612,933 A | 9/1986 | Brinkerhoff et al. |
| D286,180 S | 10/1986 | Korthoff |
| D286,442 S | 10/1986 | Korthoff et al. |
| 4,617,893 A | 10/1986 | Donner et al. |
| 4,617,914 A | 10/1986 | Ueda |
| 4,619,262 A | 10/1986 | Taylor |
| 4,619,391 A | 10/1986 | Sharkany et al. |
| 4,624,401 A | 11/1986 | Gassner et al. |
| D287,278 S | 12/1986 | Spreckelmeier |
| 4,628,459 A | 12/1986 | Shinohara et al. |
| 4,628,636 A | 12/1986 | Folger |
| 4,629,107 A | 12/1986 | Fedotov et al. |
| 4,632,290 A | 12/1986 | Green et al. |
| 4,633,861 A | 1/1987 | Chow et al. |
| 4,633,874 A | 1/1987 | Chow et al. |
| 4,634,419 A | 1/1987 | Kreizman et al. |
| 4,635,638 A | 1/1987 | Weintraub et al. |
| 4,641,076 A | 2/1987 | Linden |
| 4,642,618 A | 2/1987 | Johnson et al. |
| 4,642,738 A | 2/1987 | Meller |
| 4,643,173 A | 2/1987 | Bell et al. |
| 4,643,731 A | 2/1987 | Eckenhoff |
| 4,646,722 A | 3/1987 | Silverstein et al. |
| 4,646,745 A | 3/1987 | Noiles |
| 4,651,734 A | 3/1987 | Doss et al. |
| 4,652,820 A | 3/1987 | Maresca |
| 4,654,028 A | 3/1987 | Suma |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,278 A | 6/1987 | Chin |
| 4,671,280 A | 6/1987 | Dorband et al. |
| 4,671,445 A | 6/1987 | Barker et al. |
| 4,672,964 A | 6/1987 | Dee et al. |
| 4,675,944 A | 6/1987 | Wells |
| 4,676,245 A | 6/1987 | Fukuda |
| 4,679,460 A | 7/1987 | Yoshigai |
| 4,679,719 A | 7/1987 | Kramer |
| 4,684,051 A | 8/1987 | Akopov et al. |
| 4,688,555 A | 8/1987 | Wardle |
| 4,691,703 A | 9/1987 | Auth et al. |
| 4,693,248 A | 9/1987 | Failla |
| 4,698,579 A | 10/1987 | Richter et al. |
| 4,700,703 A | 10/1987 | Resnick et al. |
| 4,705,038 A | 11/1987 | Sjostrom et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,721,099 A | 1/1988 | Chikama |
| 4,722,340 A | 2/1988 | Takayama et al. |
| 4,724,840 A | 2/1988 | McVay et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,744,363 A | 5/1988 | Hasson |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,755,070 A | 7/1988 | Cerutti |
| 4,761,326 A | 8/1988 | Barnes et al. |
| 4,763,669 A | 8/1988 | Jaeger |
| 4,767,044 A | 8/1988 | Green |
| D297,764 S | 9/1988 | Hunt et al. |
| 4,773,420 A | 9/1988 | Green |
| 4,777,780 A | 10/1988 | Holzwarth |
| 4,781,186 A | 11/1988 | Simpson et al. |
| 4,784,137 A | 11/1988 | Kulik et al. |
| 4,787,387 A | 11/1988 | Burbank, III et al. |
| 4,788,485 A | 11/1988 | Kawagishi et al. |
| D298,967 S | 12/1988 | Hunt |
| 4,790,225 A | 12/1988 | Moody et al. |
| 4,790,314 A | 12/1988 | Weaver |
| 4,805,617 A | 2/1989 | Bedi et al. |
| 4,805,823 A | 2/1989 | Rothfuss |
| 4,807,628 A | 2/1989 | Peters et al. |

(56) References Cited

U.S. PATENT DOCUMENTS

| | | |
|---|---|---|
| 4,809,695 A | 3/1989 | Gwathmey et al. |
| 4,815,460 A | 3/1989 | Porat et al. |
| 4,817,643 A | 4/1989 | Olson |
| 4,817,847 A | 4/1989 | Redtenbacher et al. |
| 4,819,853 A | 4/1989 | Green |
| 4,821,939 A | 4/1989 | Green |
| 4,827,552 A | 5/1989 | Bojar et al. |
| 4,827,911 A | 5/1989 | Broadwin et al. |
| 4,828,542 A | 5/1989 | Hermann |
| 4,828,944 A | 5/1989 | Yabe et al. |
| 4,830,855 A | 5/1989 | Stewart |
| 4,832,158 A | 5/1989 | Farrar et al. |
| 4,833,937 A | 5/1989 | Nagano |
| 4,834,096 A | 5/1989 | Oh et al. |
| 4,834,720 A | 5/1989 | Blinkhorn |
| 4,838,859 A | 6/1989 | Strassmann |
| 4,844,068 A | 7/1989 | Arata et al. |
| 4,848,637 A | 7/1989 | Pruitt |
| 4,856,078 A | 8/1989 | Konopka |
| 4,860,644 A | 8/1989 | Kohl et al. |
| 4,862,891 A | 9/1989 | Smith |
| 4,863,423 A | 9/1989 | Wallace |
| 4,865,030 A | 9/1989 | Polyak |
| 4,868,530 A | 9/1989 | Ahs |
| 4,868,958 A | 9/1989 | Suzuki et al. |
| 4,869,414 A | 9/1989 | Green et al. |
| 4,869,415 A | 9/1989 | Fox |
| 4,873,977 A | 10/1989 | Avant et al. |
| 4,875,486 A | 10/1989 | Rapoport et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,894,051 A | 1/1990 | Shiber |
| 4,896,584 A | 1/1990 | Stoll et al. |
| 4,896,678 A | 1/1990 | Ogawa |
| 4,900,303 A | 2/1990 | Lemelson |
| 4,903,697 A | 2/1990 | Resnick et al. |
| 4,909,789 A | 3/1990 | Taguchi et al. |
| 4,915,100 A | 4/1990 | Green |
| 4,919,679 A | 4/1990 | Averill et al. |
| 4,921,479 A | 5/1990 | Grayzel |
| 4,925,082 A | 5/1990 | Kim |
| 4,928,699 A | 5/1990 | Sasai |
| 4,930,503 A | 6/1990 | Pruitt |
| 4,930,674 A | 6/1990 | Barak |
| 4,931,047 A | 6/1990 | Broadwin et al. |
| 4,931,737 A | 6/1990 | Hishiki |
| 4,932,960 A | 6/1990 | Green et al. |
| 4,933,800 A | 6/1990 | Yang |
| 4,933,843 A | 6/1990 | Scheller et al. |
| D309,350 S | 7/1990 | Sutherland et al. |
| 4,938,408 A | 7/1990 | Bedi et al. |
| 4,941,623 A | 7/1990 | Pruitt |
| 4,943,182 A | 7/1990 | Hoblingre |
| 4,944,443 A | 7/1990 | Oddsen et al. |
| 4,946,067 A | 8/1990 | Kelsall |
| 4,948,327 A | 8/1990 | Crupi, Jr. |
| 4,949,707 A | 8/1990 | LeVahn et al. |
| 4,951,860 A | 8/1990 | Peters et al. |
| 4,951,861 A | 8/1990 | Schulze et al. |
| 4,954,960 A | 9/1990 | Lo et al. |
| 4,955,959 A | 9/1990 | Tompkins et al. |
| 4,957,212 A | 9/1990 | Duck et al. |
| 4,962,681 A | 10/1990 | Yang |
| 4,962,877 A | 10/1990 | Hervas |
| 4,964,559 A | 10/1990 | Deniega et al. |
| 4,964,863 A | 10/1990 | Kanshin et al. |
| 4,965,709 A | 10/1990 | Ngo |
| 4,970,656 A | 11/1990 | Lo et al. |
| 4,973,274 A | 11/1990 | Hirukawa |
| 4,973,302 A | 11/1990 | Armour et al. |
| 4,976,173 A | 12/1990 | Yang |
| 4,978,049 A | 12/1990 | Green |
| 4,978,333 A | 12/1990 | Broadwin et al. |
| 4,979,952 A | 12/1990 | Kubota et al. |
| 4,984,564 A | 1/1991 | Yuen |
| 4,986,808 A | 1/1991 | Broadwin et al. |
| 4,987,049 A | 1/1991 | Komamura et al. |
| 4,988,334 A | 1/1991 | Hornlein et al. |
| 4,995,877 A | 2/1991 | Ams et al. |
| 4,995,959 A | 2/1991 | Metzner |
| 4,996,975 A | 3/1991 | Nakamura |
| 5,001,649 A | 3/1991 | Lo et al. |
| 5,002,543 A | 3/1991 | Bradshaw et al. |
| 5,002,553 A | 3/1991 | Shiber |
| 5,005,754 A | 4/1991 | Van Overloop |
| 5,009,222 A | 4/1991 | Her |
| 5,009,661 A | 4/1991 | Michelson |
| 5,012,411 A | 4/1991 | Policastro et al. |
| 5,014,898 A | 5/1991 | Heidrich |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,024,652 A | 6/1991 | Dumenek et al. |
| 5,024,671 A | 6/1991 | Tu et al. |
| 5,025,559 A | 6/1991 | McCullough |
| 5,027,834 A | 7/1991 | Pruitt |
| 5,030,226 A | 7/1991 | Green et al. |
| 5,031,814 A | 7/1991 | Tompkins et al. |
| 5,033,552 A | 7/1991 | Hu |
| 5,035,040 A | 7/1991 | Kerrigan et al. |
| 5,037,018 A | 8/1991 | Matsuda et al. |
| 5,038,109 A | 8/1991 | Goble et al. |
| 5,038,247 A | 8/1991 | Kelley et al. |
| 5,040,715 A | 8/1991 | Green et al. |
| 5,042,707 A | 8/1991 | Taheri |
| 5,056,953 A | 10/1991 | Marot et al. |
| 5,060,658 A | 10/1991 | Dejter, Jr. et al. |
| 5,061,269 A | 10/1991 | Muller |
| 5,062,491 A | 11/1991 | Takeshima et al. |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,077,506 A | 12/1991 | Krause |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,089,606 A | 2/1992 | Cole et al. |
| 5,094,247 A | 3/1992 | Hernandez et al. |
| 5,098,004 A | 3/1992 | Kerrigan |
| 5,098,360 A | 3/1992 | Hirota |
| 5,100,042 A | 3/1992 | Gravener et al. |
| 5,100,420 A | 3/1992 | Green et al. |
| 5,100,422 A | 3/1992 | Berguer et al. |
| 5,104,025 A | 4/1992 | Main et al. |
| 5,104,397 A | 4/1992 | Vasconcelos et al. |
| 5,104,400 A | 4/1992 | Berguer et al. |
| 5,106,008 A | 4/1992 | Tompkins et al. |
| 5,108,368 A | 4/1992 | Hammerslag et al. |
| 5,109,722 A | 5/1992 | Hufnagle et al. |
| 5,111,987 A | 5/1992 | Moeinzadeh et al. |
| 5,116,349 A | 5/1992 | Aranyi |
| D327,323 S | 6/1992 | Hunt |
| 5,119,009 A | 6/1992 | McCaleb et al. |
| 5,122,156 A | 6/1992 | Granger et al. |
| 5,124,990 A | 6/1992 | Williamson |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,151,102 A | 9/1992 | Kamiyama et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,222 A | 10/1992 | Green et al. |

(56) References Cited

U.S. PATENT DOCUMENTS

| | | |
|---|---|---|
| 5,158,567 A | 10/1992 | Green |
| D330,699 S | 11/1992 | Gill |
| 5,163,598 A | 11/1992 | Peters et al. |
| 5,164,652 A | 11/1992 | Johnson et al. |
| 5,168,605 A | 12/1992 | Bartlett |
| 5,170,925 A | 12/1992 | Madden et al. |
| 5,171,247 A | 12/1992 | Hughett et al. |
| 5,171,249 A | 12/1992 | Stefanchik et al. |
| 5,171,253 A | 12/1992 | Klieman |
| 5,173,053 A | 12/1992 | Swanson et al. |
| 5,173,133 A | 12/1992 | Morin et al. |
| 5,176,677 A | 1/1993 | Wuchinich |
| 5,176,688 A | 1/1993 | Narayan et al. |
| 5,181,514 A | 1/1993 | Solomon et al. |
| 5,187,422 A | 2/1993 | Izenbaard et al. |
| 5,188,102 A | 2/1993 | Idemoto et al. |
| 5,188,111 A | 2/1993 | Yates et al. |
| 5,190,517 A | 3/1993 | Zieve et al. |
| 5,190,544 A | 3/1993 | Chapman et al. |
| 5,190,560 A | 3/1993 | Woods et al. |
| 5,190,657 A | 3/1993 | Heagle et al. |
| 5,192,288 A | 3/1993 | Thompson et al. |
| 5,193,731 A | 3/1993 | Aranyi |
| 5,195,505 A | 3/1993 | Josefsen |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,197,970 A | 3/1993 | Green et al. |
| 5,200,280 A | 4/1993 | Karasa |
| 5,201,750 A | 4/1993 | Hocherl et al. |
| 5,205,459 A | 4/1993 | Brinkerhoff et al. |
| 5,207,672 A | 5/1993 | Roth et al. |
| 5,207,697 A | 5/1993 | Carusillo et al. |
| 5,209,747 A | 5/1993 | Knoepfler |
| 5,209,756 A | 5/1993 | Seedhom et al. |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,220,269 A | 6/1993 | Chen et al. |
| 5,221,036 A | 6/1993 | Takase |
| 5,221,281 A | 6/1993 | Klicek |
| 5,222,945 A | 6/1993 | Basnight |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| D338,729 S | 8/1993 | Sprecklemeier et al. |
| 5,234,447 A | 8/1993 | Kaster et al. |
| 5,236,269 A | 8/1993 | Handy |
| 5,236,424 A | 8/1993 | Imran |
| 5,236,440 A | 8/1993 | Hlavacek |
| 5,239,981 A | 8/1993 | Anapliotis |
| 5,240,163 A | 8/1993 | Stein et al. |
| 5,242,456 A | 9/1993 | Nash et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,007 A | 11/1993 | Spetzler et al. |
| 5,258,008 A | 11/1993 | Wilk |
| 5,258,009 A | 11/1993 | Conners |
| 5,258,010 A | 11/1993 | Green et al. |
| 5,258,012 A | 11/1993 | Luscombe et al. |
| 5,259,366 A | 11/1993 | Reydel et al. |
| 5,259,835 A | 11/1993 | Clark et al. |
| 5,260,637 A | 11/1993 | Pizzi |
| 5,261,135 A | 11/1993 | Mitchell |
| 5,261,877 A | 11/1993 | Fine et al. |
| 5,261,922 A | 11/1993 | Hood |
| 5,263,629 A | 11/1993 | Trumbull et al. |
| 5,263,937 A | 11/1993 | Shipp |
| 5,263,973 A | 11/1993 | Cook |
| 5,264,218 A | 11/1993 | Rogozinski |
| 5,268,622 A | 12/1993 | Philipp |
| 5,269,794 A | 12/1993 | Rexroth |
| 5,271,543 A | 12/1993 | Grant et al. |
| 5,271,544 A | 12/1993 | Fox et al. |
| RE34,519 E | 1/1994 | Fox et al. |
| 5,275,322 A | 1/1994 | Brinkerhoff et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,281,400 A | 1/1994 | Berry, Jr. |
| 5,282,806 A | 2/1994 | Haber et al. |
| 5,282,826 A | 2/1994 | Quadri |
| 5,282,829 A | 2/1994 | Hermes |
| 5,284,128 A | 2/1994 | Hart |
| 5,285,381 A | 2/1994 | Iskarous et al. |
| 5,285,945 A | 2/1994 | Brinkerhoff et al. |
| 5,286,253 A | 2/1994 | Fucci |
| 5,289,963 A | 3/1994 | McGarry et al. |
| 5,290,271 A | 3/1994 | Jernberg |
| 5,290,310 A | 3/1994 | Makower et al. |
| 5,291,133 A | 3/1994 | Gokhale et al. |
| 5,292,053 A | 3/1994 | Bilotti et al. |
| 5,293,024 A | 3/1994 | Sugahara et al. |
| 5,297,714 A | 3/1994 | Kramer |
| 5,302,148 A | 4/1994 | Heinz |
| 5,303,606 A | 4/1994 | Kokinda |
| 5,304,204 A | 4/1994 | Bregen |
| D347,474 S | 5/1994 | Olson |
| 5,307,976 A | 5/1994 | Olson et al. |
| 5,308,353 A | 5/1994 | Beurrier |
| 5,308,358 A | 5/1994 | Bond et al. |
| 5,308,576 A | 5/1994 | Green et al. |
| 5,309,387 A | 5/1994 | Mori et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,313,935 A | 5/1994 | Kortenbach et al. |
| 5,313,967 A | 5/1994 | Lieber et al. |
| 5,314,424 A | 5/1994 | Nicholas |
| 5,314,445 A | 5/1994 | Heidmueller nee Degwitz et al. |
| 5,314,466 A | 5/1994 | Stern et al. |
| 5,318,221 A | 6/1994 | Green et al. |
| 5,320,627 A | 6/1994 | Sorensen et al. |
| D348,930 S | 7/1994 | Olson |
| 5,326,013 A | 7/1994 | Green et al. |
| 5,329,923 A | 7/1994 | Lundquist |
| 5,330,486 A | 7/1994 | Wilk |
| 5,330,487 A | 7/1994 | Thornton et al. |
| 5,330,502 A | 7/1994 | Hassler et al. |
| 5,331,971 A | 7/1994 | Bales et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,130 A | 8/1994 | Ray |
| 5,336,229 A | 8/1994 | Noda |
| 5,336,232 A | 8/1994 | Green et al. |
| 5,338,317 A | 8/1994 | Hasson et al. |
| 5,339,799 A | 8/1994 | Kami et al. |
| 5,341,724 A | 8/1994 | Vatel |
| 5,341,807 A | 8/1994 | Nardella |
| 5,341,810 A | 8/1994 | Dardel |
| 5,342,380 A | 8/1994 | Hood |
| 5,342,381 A | 8/1994 | Tidemand |
| 5,342,385 A | 8/1994 | Norelli et al. |
| 5,342,395 A | 8/1994 | Jarrett et al. |
| 5,342,396 A | 8/1994 | Cook |
| 5,343,382 A | 8/1994 | Hale et al. |
| 5,343,391 A | 8/1994 | Mushabac |
| 5,344,059 A | 9/1994 | Green et al. |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |

(56) References Cited

U.S. PATENT DOCUMENTS

| | | |
|---|---|---|
| 5,350,104 A | 9/1994 | Main et al. |
| 5,350,355 A | 9/1994 | Sklar |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,353,798 A | 10/1994 | Sieben |
| 5,354,250 A | 10/1994 | Christensen |
| 5,354,303 A | 10/1994 | Spaeth et al. |
| 5,356,006 A | 10/1994 | Alpern et al. |
| 5,356,064 A | 10/1994 | Green et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,359,993 A | 11/1994 | Slater et al. |
| 5,360,305 A | 11/1994 | Kerrigan |
| 5,360,428 A | 11/1994 | Hutchinson, Jr. |
| 5,361,902 A | 11/1994 | Abidin et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,369,565 A | 11/1994 | Chen et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,375,588 A | 12/1994 | Yoon |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,381,943 A | 1/1995 | Allen et al. |
| 5,382,247 A | 1/1995 | Cimino et al. |
| 5,383,460 A | 1/1995 | Jang et al. |
| 5,383,874 A | 1/1995 | Jackson et al. |
| 5,383,880 A | 1/1995 | Hooven |
| 5,383,881 A | 1/1995 | Green et al. |
| 5,383,882 A | 1/1995 | Buess et al. |
| 5,383,888 A | 1/1995 | Zvenyatsky et al. |
| 5,383,895 A | 1/1995 | Holmes et al. |
| 5,388,568 A | 2/1995 | van der Heide |
| 5,389,072 A | 2/1995 | Imran |
| 5,389,098 A | 2/1995 | Tsuruta et al. |
| 5,389,102 A | 2/1995 | Green et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit et al. |
| 5,397,046 A | 3/1995 | Savage et al. |
| 5,397,324 A | 3/1995 | Carroll et al. |
| 5,400,267 A | 3/1995 | Denen et al. |
| 5,403,276 A | 4/1995 | Schechter et al. |
| 5,403,312 A | 4/1995 | Yates et al. |
| 5,404,106 A | 4/1995 | Matsuda |
| 5,404,870 A | 4/1995 | Brinkerhoff et al. |
| 5,404,960 A | 4/1995 | Wada et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,408,409 A | 4/1995 | Glassman et al. |
| 5,409,498 A | 4/1995 | Braddock et al. |
| 5,409,703 A | 4/1995 | McAnalley et al. |
| D357,981 S | 5/1995 | Green et al. |
| 5,411,481 A | 5/1995 | Allen et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson et al. |
| 5,415,335 A | 5/1995 | Knodell, Jr. |
| 5,417,203 A | 5/1995 | Tovey et al. |
| 5,417,361 A | 5/1995 | Williamson, IV |
| 5,419,766 A | 5/1995 | Chang et al. |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,423,835 A | 6/1995 | Green et al. |
| 5,425,355 A | 6/1995 | Kulick |
| 5,425,745 A | 6/1995 | Green et al. |
| 5,427,298 A | 6/1995 | Tegtmeier |
| 5,431,322 A | 7/1995 | Green et al. |
| 5,431,323 A | 7/1995 | Smith et al. |
| 5,431,645 A | 7/1995 | Smith et al. |
| 5,431,654 A | 7/1995 | Nic |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,438,997 A | 8/1995 | Sieben et al. |
| 5,439,155 A | 8/1995 | Viola |
| 5,439,156 A | 8/1995 | Grant et al. |
| 5,439,479 A | 8/1995 | Shichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,441,499 A | 8/1995 | Fritzsch |
| 5,443,197 A | 8/1995 | Malis et al. |
| 5,443,198 A | 8/1995 | Viola et al. |
| 5,443,463 A | 8/1995 | Stern et al. |
| 5,444,113 A | 8/1995 | Sinclair et al. |
| 5,445,155 A | 8/1995 | Sieben |
| 5,445,304 A | 8/1995 | Plyley et al. |
| 5,445,604 A | 8/1995 | Lang |
| 5,445,644 A | 8/1995 | Pietrafitta et al. |
| 5,446,646 A | 8/1995 | Miyazaki |
| 5,447,265 A | 9/1995 | Vidal et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,822 A | 10/1995 | Schob et al. |
| 5,454,827 A | 10/1995 | Aust et al. |
| 5,456,401 A | 10/1995 | Green et al. |
| 5,456,917 A | 10/1995 | Wise et al. |
| 5,458,279 A | 10/1995 | Plyley |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,819 A | 11/1995 | Weilant et al. |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |

(56) References Cited

U.S. PATENT DOCUMENTS

| | | |
|---|---|---|
| 5,470,010 A | 11/1995 | Rothfuss et al. |
| 5,471,129 A | 11/1995 | Mann |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,474,570 A | 12/1995 | Kockerling et al. |
| 5,474,738 A | 12/1995 | Nichols et al. |
| 5,476,206 A | 12/1995 | Green et al. |
| 5,476,479 A | 12/1995 | Green et al. |
| 5,476,481 A | 12/1995 | Schondorf |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,483,952 A | 1/1996 | Aranyi |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,377 A | 1/1996 | Smith et al. |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,489,290 A | 2/1996 | Furnish |
| 5,490,819 A | 2/1996 | Nicholas et al. |
| 5,492,671 A | 2/1996 | Krafft |
| 5,496,312 A | 3/1996 | Klicek |
| 5,496,317 A | 3/1996 | Goble et al. |
| 5,497,933 A | 3/1996 | Defonzo et al. |
| 5,498,164 A | 3/1996 | Ward et al. |
| 5,498,838 A | 3/1996 | Furman |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,425 A | 4/1996 | Ziglioli |
| 5,507,426 A | 4/1996 | Young et al. |
| 5,507,773 A | 4/1996 | Huitema et al. |
| 5,509,596 A | 4/1996 | Green et al. |
| 5,509,916 A | 4/1996 | Taylor |
| 5,509,918 A | 4/1996 | Romano |
| 5,511,564 A | 4/1996 | Wilk |
| 5,514,129 A | 5/1996 | Smith |
| 5,514,149 A | 5/1996 | Green et al. |
| 5,514,157 A | 5/1996 | Nicholas et al. |
| 5,518,163 A | 5/1996 | Hooven |
| 5,518,164 A | 5/1996 | Hooven |
| 5,520,609 A | 5/1996 | Moll et al. |
| 5,520,634 A | 5/1996 | Fox et al. |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,264 A | 6/1996 | Moll et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,531,856 A | 7/1996 | Moll et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,540,705 A | 7/1996 | Meade et al. |
| 5,541,376 A | 7/1996 | Ladtkow et al. |
| 5,541,489 A | 7/1996 | Dunstan |
| 5,542,594 A | 8/1996 | McKean et al. |
| 5,542,945 A | 8/1996 | Fritzsch |
| 5,542,949 A | 8/1996 | Yoon |
| 5,543,119 A | 8/1996 | Sutter et al. |
| 5,543,695 A | 8/1996 | Culp et al. |
| 5,544,802 A | 8/1996 | Crainich |
| 5,547,117 A | 8/1996 | Hamblin et al. |
| 5,549,583 A | 8/1996 | Sanford et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,624 A | 9/1996 | Francese et al. |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,020 A | 9/1996 | Hou |
| 5,556,416 A | 9/1996 | Clark et al. |
| 5,558,533 A | 9/1996 | Hashizawa et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,561,881 A | 10/1996 | Klinger et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,563,481 A | 10/1996 | Krause |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,571,488 A | 11/1996 | Beerstecher et al. |
| 5,573,169 A | 11/1996 | Green et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,578,052 A | 11/1996 | Koros et al. |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,582,907 A | 12/1996 | Pall |
| 5,583,114 A | 12/1996 | Barrows et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,601,573 A | 2/1997 | Fogelberg et al. |
| 5,601,604 A | 2/1997 | Vincent |
| 5,602,449 A | 2/1997 | Krause et al. |
| 5,603,443 A | 2/1997 | Clark et al. |
| 5,605,272 A | 2/1997 | Witt et al. |

(56) References Cited

U.S. PATENT DOCUMENTS

| | | |
|---|---|---|
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,436 A | 3/1997 | Pratt et al. |
| 5,607,450 A | 3/1997 | Zvenyatsky et al. |
| 5,607,474 A | 3/1997 | Athanasiou et al. |
| 5,609,285 A | 3/1997 | Grant et al. |
| 5,609,601 A | 3/1997 | Kolesa et al. |
| 5,611,709 A | 3/1997 | McAnulty |
| 5,613,499 A | 3/1997 | Palmer et al. |
| 5,613,937 A | 3/1997 | Garrison et al. |
| 5,613,966 A | 3/1997 | Makower et al. |
| 5,614,887 A | 3/1997 | Buchbinder |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,326 A | 4/1997 | Younker |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,626,979 A | 5/1997 | Mitsui et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,631,973 A | 5/1997 | Green |
| 5,632,432 A | 5/1997 | Schulze et al. |
| 5,632,433 A | 5/1997 | Grant et al. |
| 5,633,374 A | 5/1997 | Humphrey et al. |
| 5,634,584 A | 6/1997 | Okorocha et al. |
| 5,636,779 A | 6/1997 | Palmer |
| 5,636,780 A | 6/1997 | Green et al. |
| 5,637,110 A | 6/1997 | Pennybacker et al. |
| 5,638,582 A | 6/1997 | Klatt et al. |
| 5,639,008 A | 6/1997 | Gallagher et al. |
| D381,077 S | 7/1997 | Hunt |
| 5,643,291 A | 7/1997 | Pier et al. |
| 5,643,293 A | 7/1997 | Kogasaka et al. |
| 5,643,294 A | 7/1997 | Tovey et al. |
| 5,643,319 A | 7/1997 | Green et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,651,762 A | 7/1997 | Bridges |
| 5,651,821 A | 7/1997 | Uchida |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,653,748 A | 8/1997 | Strecker |
| 5,655,698 A | 8/1997 | Yoon |
| 5,656,917 A | 8/1997 | Theobald |
| 5,657,417 A | 8/1997 | Di Troia |
| 5,657,429 A | 8/1997 | Wang et al. |
| 5,657,921 A | 8/1997 | Young et al. |
| 5,658,238 A | 8/1997 | Suzuki et al. |
| 5,658,281 A | 8/1997 | Heard |
| 5,658,298 A | 8/1997 | Vincent et al. |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,662,667 A | 9/1997 | Knodel |
| 5,664,404 A | 9/1997 | Ivanov et al. |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,667,864 A | 9/1997 | Landoll |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,672,945 A | 9/1997 | Krause |
| 5,673,840 A | 10/1997 | Schulze et al. |
| 5,673,841 A | 10/1997 | Schulze et al. |
| 5,673,842 A | 10/1997 | Bittner et al. |
| 5,674,184 A | 10/1997 | Hassler, Jr. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,681,341 A | 10/1997 | Lunsford et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,690,675 A | 11/1997 | Sawyer et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,700,276 A | 12/1997 | Benecke |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A * | 1/1998 | Sorrentino ........ A61B 17/07207 227/175.2 |
| 5,709,335 A | 1/1998 | Heck |
| 5,709,680 A | 1/1998 | Yates et al. |
| 5,709,706 A | 1/1998 | Kienzle et al. |
| 5,711,472 A | 1/1998 | Bryan |
| 5,711,960 A | 1/1998 | Shikinami |
| 5,712,460 A | 1/1998 | Carr et al. |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,604 A | 2/1998 | Lanzoni |
| 5,715,836 A | 2/1998 | Kliegis et al. |
| 5,715,987 A | 2/1998 | Kelley et al. |
| 5,715,988 A | 2/1998 | Palmer |
| 5,716,352 A | 2/1998 | Viola et al. |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,718,714 A | 2/1998 | Livneh |
| 5,720,744 A | 2/1998 | Eggleston et al. |
| D393,067 S | 3/1998 | Geary et al. |
| 5,724,025 A | 3/1998 | Tavori |
| 5,725,536 A | 3/1998 | Oberlin et al. |
| 5,725,554 A | 3/1998 | Simon et al. |
| 5,728,110 A | 3/1998 | Vidal et al. |

(56) References Cited

U.S. PATENT DOCUMENTS

| | | |
|---|---|---|
| 5,728,113 A | 3/1998 | Sherts |
| 5,728,121 A | 3/1998 | Bimbo et al. |
| 5,730,758 A | 3/1998 | Allgeyer |
| 5,732,712 A | 3/1998 | Adair |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,736,271 A | 4/1998 | Cisar et al. |
| 5,738,474 A | 4/1998 | Blewett |
| 5,738,629 A | 4/1998 | Moll et al. |
| 5,738,648 A | 4/1998 | Lands et al. |
| 5,741,271 A | 4/1998 | Nakao et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,749,896 A | 5/1998 | Cook |
| 5,749,968 A | 5/1998 | Melanson et al. |
| 5,752,644 A | 5/1998 | Bolanos et al. |
| 5,752,965 A | 5/1998 | Francis et al. |
| 5,752,970 A | 5/1998 | Yoon |
| 5,752,973 A | 5/1998 | Kieturakis |
| 5,755,717 A | 5/1998 | Yates et al. |
| 5,755,726 A | 5/1998 | Pratt et al. |
| 5,758,814 A | 6/1998 | Gallagher et al. |
| 5,762,255 A | 6/1998 | Chrisman et al. |
| 5,762,256 A | 6/1998 | Mastri et al. |
| 5,762,458 A | 6/1998 | Wang et al. |
| 5,765,565 A | 6/1998 | Adair |
| 5,766,186 A | 6/1998 | Faraz et al. |
| 5,766,188 A | 6/1998 | Igaki |
| 5,766,205 A | 6/1998 | Zvenyatsky et al. |
| 5,769,303 A | 6/1998 | Knodel et al. |
| 5,769,640 A | 6/1998 | Jacobus et al. |
| 5,769,748 A | 6/1998 | Eyerly et al. |
| 5,769,791 A | 6/1998 | Benaron et al. |
| 5,769,892 A | 6/1998 | Kingwell |
| 5,772,099 A | 6/1998 | Gravener |
| 5,772,379 A | 6/1998 | Evensen |
| 5,772,578 A | 6/1998 | Heimberger et al. |
| 5,772,659 A | 6/1998 | Becker et al. |
| 5,773,991 A | 6/1998 | Chen |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,748 A | 7/1998 | Palmer et al. |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,791,231 A | 8/1998 | Cohn et al. |
| 5,792,135 A | 8/1998 | Madhani et al. |
| 5,792,162 A | 8/1998 | Jolly et al. |
| 5,792,165 A | 8/1998 | Klieman et al. |
| 5,792,573 A | 8/1998 | Pitzen et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,637 A | 8/1998 | Ervin |
| 5,797,900 A | 8/1998 | Madhani et al. |
| 5,797,906 A | 8/1998 | Rhum et al. |
| 5,797,927 A | 8/1998 | Yoon |
| 5,797,941 A | 8/1998 | Schulze et al. |
| 5,797,959 A | 8/1998 | Castro et al. |
| 5,799,857 A | 9/1998 | Robertson et al. |
| 5,800,379 A | 9/1998 | Edwards |
| 5,800,423 A | 9/1998 | Jensen |
| 5,804,726 A | 9/1998 | Geib et al. |
| 5,804,936 A | 9/1998 | Brodsky et al. |
| 5,806,676 A | 9/1998 | Wasgien |
| 5,807,241 A | 9/1998 | Heimberger |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,812,188 A | 9/1998 | Adair |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,824,333 A | 10/1998 | Scopelianos et al. |
| 5,826,776 A | 10/1998 | Schulze et al. |
| 5,827,271 A | 10/1998 | Buysse et al. |
| 5,827,298 A | 10/1998 | Hart et al. |
| 5,827,323 A | 10/1998 | Klieman et al. |
| 5,829,662 A | 11/1998 | Allen et al. |
| 5,830,598 A | 11/1998 | Patterson |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,369 A | 11/1998 | Chatterjee et al. |
| 5,839,639 A | 11/1998 | Sauer et al. |
| 5,841,284 A | 11/1998 | Takahashi |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,847,566 A | 12/1998 | Marritt et al. |
| 5,849,011 A | 12/1998 | Jones et al. |
| 5,849,020 A | 12/1998 | Long et al. |
| 5,849,023 A | 12/1998 | Mericle |
| 5,851,179 A | 12/1998 | Ritson et al. |
| 5,851,212 A | 12/1998 | Zirps et al. |
| 5,853,366 A | 12/1998 | Dowlatshahi |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,865,638 A | 2/1999 | Trafton |
| 5,868,361 A | 2/1999 | Rinderer |
| 5,868,664 A | 2/1999 | Speier et al. |
| 5,868,760 A | 2/1999 | McGuckin, Jr. |
| 5,868,790 A | 2/1999 | Vincent et al. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,607 A | 3/1999 | Nunes et al. |
| 5,878,937 A | 3/1999 | Green et al. |
| 5,878,938 A | 3/1999 | Bittner et al. |
| 5,881,777 A | 3/1999 | Bassi et al. |
| 5,881,943 A | 3/1999 | Heck et al. |
| 5,891,094 A | 4/1999 | Masterson et al. |
| 5,891,160 A | 4/1999 | Williamson, IV et al. |
| 5,891,558 A | 4/1999 | Bell et al. |

(56) References Cited

U.S. PATENT DOCUMENTS

| | | |
|---|---|---|
| 5,893,506 A | 4/1999 | Powell |
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,824 A | 5/1999 | Kurtz et al. |
| 5,899,914 A | 5/1999 | Zirps et al. |
| 5,901,895 A | 5/1999 | Heaton et al. |
| 5,902,312 A | 5/1999 | Frater et al. |
| 5,903,117 A | 5/1999 | Gregory |
| 5,904,647 A | 5/1999 | Ouchi |
| 5,904,693 A | 5/1999 | Dicesare et al. |
| 5,904,702 A | 5/1999 | Ek et al. |
| 5,906,577 A | 5/1999 | Beane et al. |
| 5,906,625 A | 5/1999 | Bito et al. |
| 5,907,211 A | 5/1999 | Hall et al. |
| 5,907,664 A | 5/1999 | Wang et al. |
| 5,908,402 A | 6/1999 | Blythe |
| 5,908,427 A | 6/1999 | McKean et al. |
| 5,909,062 A | 6/1999 | Krietzman |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,924,864 A | 7/1999 | Loge et al. |
| 5,928,137 A | 7/1999 | Green |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,941,890 A | 8/1999 | Voegele et al. |
| 5,944,172 A | 8/1999 | Hannula |
| 5,944,715 A | 8/1999 | Goble et al. |
| 5,946,978 A | 9/1999 | Yamashita |
| 5,947,984 A | 9/1999 | Whipple |
| 5,947,996 A | 9/1999 | Logeman |
| 5,948,030 A | 9/1999 | Miller et al. |
| 5,948,429 A | 9/1999 | Bell et al. |
| 5,951,301 A | 9/1999 | Younker |
| 5,951,516 A | 9/1999 | Bunyan |
| 5,951,552 A | 9/1999 | Long et al. |
| 5,951,574 A | 9/1999 | Stefanchik et al. |
| 5,951,575 A | 9/1999 | Bolduc et al. |
| 5,951,581 A | 9/1999 | Saadat et al. |
| 5,954,259 A | 9/1999 | Viola et al. |
| 5,957,831 A | 9/1999 | Adair |
| 5,964,394 A | 10/1999 | Robertson |
| 5,964,774 A | 10/1999 | McKean et al. |
| 5,966,126 A | 10/1999 | Szabo |
| 5,971,916 A | 10/1999 | Koren |
| 5,973,221 A | 10/1999 | Collyer et al. |
| D416,089 S | 11/1999 | Barton et al. |
| 5,976,122 A | 11/1999 | Madhani et al. |
| 5,977,746 A | 11/1999 | Hershberger et al. |
| 5,980,248 A | 11/1999 | Kusakabe et al. |
| 5,984,949 A | 11/1999 | Levin |
| 5,988,479 A | 11/1999 | Palmer |
| 5,990,379 A | 11/1999 | Gregory |
| 5,993,466 A | 11/1999 | Yoon |
| 5,997,528 A | 12/1999 | Bisch et al. |
| 5,997,552 A | 12/1999 | Person et al. |
| 6,001,108 A | 12/1999 | Wang et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,007,521 A | 12/1999 | Bidwell et al. |
| 6,010,054 A | 1/2000 | Johnson et al. |
| 6,010,513 A | 1/2000 | Tormala et al. |
| 6,010,520 A | 1/2000 | Pattison |
| 6,012,494 A | 1/2000 | Balazs |
| 6,013,076 A | 1/2000 | Goble et al. |
| 6,013,991 A | 1/2000 | Philipp |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,018,227 A | 1/2000 | Kumar et al. |
| 6,019,745 A | 2/2000 | Gray |
| 6,019,780 A | 2/2000 | Lombardo et al. |
| 6,022,352 A | 2/2000 | Vandewalle |
| 6,023,641 A | 2/2000 | Thompson |
| 6,024,708 A | 2/2000 | Bales et al. |
| 6,024,741 A | 2/2000 | Williamson, IV et al. |
| 6,024,748 A | 2/2000 | Manzo et al. |
| 6,024,750 A | 2/2000 | Mastri et al. |
| 6,024,764 A | 2/2000 | Schroeppel |
| 6,027,501 A | 2/2000 | Goble et al. |
| 6,030,384 A | 2/2000 | Nezhat |
| 6,032,849 A | 3/2000 | Mastri et al. |
| 6,033,105 A | 3/2000 | Barker et al. |
| 6,033,378 A | 3/2000 | Lundquist et al. |
| 6,033,399 A | 3/2000 | Gines |
| 6,033,427 A | 3/2000 | Lee |
| 6,036,641 A | 3/2000 | Taylor et al. |
| 6,036,667 A | 3/2000 | Manna et al. |
| 6,037,724 A | 3/2000 | Buss et al. |
| 6,037,927 A | 3/2000 | Rosenberg |
| 6,039,126 A | 3/2000 | Hsieh |
| 6,039,733 A | 3/2000 | Buysse et al. |
| 6,039,734 A | 3/2000 | Goble |
| 6,042,601 A | 3/2000 | Smith |
| 6,042,607 A | 3/2000 | Williamson, IV et al. |
| 6,043,626 A | 3/2000 | Snyder et al. |
| 6,045,560 A | 4/2000 | McKean et al. |
| 6,047,861 A | 4/2000 | Vidal et al. |
| 6,049,145 A | 4/2000 | Austin et al. |
| 6,050,172 A | 4/2000 | Corves et al. |
| 6,050,472 A | 4/2000 | Shibata |
| 6,050,989 A | 4/2000 | Fox et al. |
| 6,050,990 A | 4/2000 | Tankovich et al. |
| 6,050,996 A | 4/2000 | Schmaltz et al. |
| 6,053,390 A | 4/2000 | Green et al. |
| 6,053,899 A | 4/2000 | Slanda et al. |
| 6,053,922 A | 4/2000 | Krause et al. |
| 6,054,142 A | 4/2000 | Li et al. |
| 6,055,062 A | 4/2000 | Dina et al. |
| RE36,720 E | 5/2000 | Green et al. |
| 6,056,735 A | 5/2000 | Okada et al. |
| 6,056,746 A | 5/2000 | Goble et al. |
| 6,059,806 A | 5/2000 | Hoegerle |
| 6,062,360 A | 5/2000 | Shields |
| 6,063,020 A | 5/2000 | Jones et al. |
| 6,063,025 A | 5/2000 | Bridges et al. |
| 6,063,050 A | 5/2000 | Manna et al. |
| 6,063,095 A | 5/2000 | Wang et al. |
| 6,063,097 A | 5/2000 | Oi et al. |
| 6,063,098 A | 5/2000 | Houser et al. |
| 6,065,679 A | 5/2000 | Levie et al. |
| 6,065,919 A | 5/2000 | Peck |
| 6,066,132 A | 5/2000 | Chen et al. |
| 6,066,151 A | 5/2000 | Miyawaki et al. |
| 6,068,627 A | 5/2000 | Orszulak et al. |
| 6,071,233 A | 6/2000 | Ishikawa et al. |
| 6,072,299 A | 6/2000 | Kurle et al. |
| 6,074,386 A | 6/2000 | Goble et al. |
| 6,074,401 A | 6/2000 | Gardiner et al. |
| 6,075,441 A | 6/2000 | Maloney |
| 6,077,280 A | 6/2000 | Fossum |
| 6,077,286 A | 6/2000 | Cuschieri et al. |
| 6,077,290 A | 6/2000 | Marini |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,223 A | 7/2000 | Baker |
| 6,083,234 A | 7/2000 | Nicholas et al. |
| 6,083,242 A | 7/2000 | Cook |
| 6,086,544 A | 7/2000 | Hibner et al. |

(56) References Cited

U.S. PATENT DOCUMENTS

| | | |
|---|---|---|
| 6,086,600 A | 7/2000 | Kortenbach |
| 6,090,106 A | 7/2000 | Goble et al. |
| 6,090,123 A | 7/2000 | Culp et al. |
| 6,093,186 A | 7/2000 | Goble |
| 6,094,021 A | 7/2000 | Noro et al. |
| D429,252 S | 8/2000 | Haitani et al. |
| 6,099,537 A * | 8/2000 | Sugai ............... A61B 17/0684 606/143 |
| 6,099,551 A | 8/2000 | Gabbay |
| 6,102,271 A | 8/2000 | Longo et al. |
| 6,102,926 A | 8/2000 | Tartaglia et al. |
| 6,104,162 A | 8/2000 | Sainsbury et al. |
| 6,104,304 A | 8/2000 | Clark et al. |
| 6,106,511 A | 8/2000 | Jensen |
| 6,109,500 A | 8/2000 | Alli et al. |
| 6,110,187 A | 8/2000 | Donlon |
| 6,113,618 A | 9/2000 | Nic |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,120,462 A | 9/2000 | Hibner et al. |
| 6,123,241 A | 9/2000 | Walter et al. |
| 6,123,701 A | 9/2000 | Nezhat |
| H1904 H | 10/2000 | Yates et al. |
| RE36,923 E | 10/2000 | Hiroi et al. |
| 6,126,058 A | 10/2000 | Adams et al. |
| 6,126,359 A | 10/2000 | Dittrich et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,134,962 A | 10/2000 | Sugitani |
| 6,139,546 A | 10/2000 | Koenig et al. |
| 6,142,149 A | 11/2000 | Steen |
| 6,142,933 A | 11/2000 | Longo et al. |
| 6,147,135 A | 11/2000 | Yuan et al. |
| 6,149,660 A | 11/2000 | Laufer et al. |
| 6,151,323 A | 11/2000 | O'Connell et al. |
| 6,152,935 A | 11/2000 | Kammerer et al. |
| 6,155,473 A | 12/2000 | Tompkins et al. |
| 6,156,056 A | 12/2000 | Kearns et al. |
| 6,157,169 A | 12/2000 | Lee |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,162,220 A | 12/2000 | Nezhat |
| 6,162,537 A | 12/2000 | Martin et al. |
| 6,165,175 A | 12/2000 | Wampler et al. |
| 6,165,184 A | 12/2000 | Verdura et al. |
| 6,165,188 A | 12/2000 | Saadat et al. |
| 6,167,185 A | 12/2000 | Smiley et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,173,074 B1 | 1/2001 | Russo |
| 6,174,308 B1 | 1/2001 | Goble et al. |
| 6,174,309 B1 | 1/2001 | Wrublewski et al. |
| 6,174,318 B1 | 1/2001 | Bates et al. |
| 6,175,290 B1 | 1/2001 | Forsythe et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,185,356 B1 | 2/2001 | Parker et al. |
| 6,186,142 B1 | 2/2001 | Schmidt et al. |
| 6,186,957 B1 | 2/2001 | Milam |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,311 B1 | 3/2001 | Danek et al. |
| 6,200,330 B1 | 3/2001 | Benderev et al. |
| 6,202,914 B1 | 3/2001 | Geiste et al. |
| 6,206,894 B1 | 3/2001 | Thompson et al. |
| 6,206,897 B1 | 3/2001 | Jamiolkowski et al. |
| 6,206,903 B1 | 3/2001 | Ramans |
| 6,206,904 B1 | 3/2001 | Ouchi |
| 6,209,414 B1 | 4/2001 | Uneme |
| 6,210,403 B1 | 4/2001 | Klicek |
| 6,211,626 B1 | 4/2001 | Lys et al. |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,221,007 B1 | 4/2001 | Green |
| 6,221,023 B1 | 4/2001 | Matsuba et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,080 B1 | 5/2001 | Gines |
| 6,228,081 B1 | 5/2001 | Goble |
| 6,228,083 B1 | 5/2001 | Lands et al. |
| 6,228,084 B1 | 5/2001 | Kirwan, Jr. |
| 6,228,089 B1 | 5/2001 | Wahrburg |
| 6,228,098 B1 | 5/2001 | Kayan et al. |
| 6,231,565 B1 | 5/2001 | Tovey et al. |
| 6,234,178 B1 | 5/2001 | Goble et al. |
| 6,237,604 B1 | 5/2001 | Burnside et al. |
| 6,238,384 B1 | 5/2001 | Peer |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,116 B1 | 6/2001 | Chevillon et al. |
| 6,248,117 B1 | 6/2001 | Blatter |
| 6,249,076 B1 | 6/2001 | Madden et al. |
| 6,249,105 B1 | 6/2001 | Andrews et al. |
| 6,250,532 B1 | 6/2001 | Green et al. |
| 6,251,485 B1 | 6/2001 | Harris et al. |
| D445,745 S | 7/2001 | Norman |
| 6,254,534 B1 | 7/2001 | Butler et al. |
| 6,254,619 B1 | 7/2001 | Garabet et al. |
| 6,254,642 B1 | 7/2001 | Taylor |
| 6,258,107 B1 | 7/2001 | Balazs et al. |
| 6,261,246 B1 | 7/2001 | Pantages et al. |
| 6,261,286 B1 | 7/2001 | Goble et al. |
| 6,261,679 B1 | 7/2001 | Chen et al. |
| 6,264,086 B1 | 7/2001 | McGuckin, Jr. |
| 6,264,087 B1 | 7/2001 | Whitman |
| 6,264,617 B1 | 7/2001 | Bales et al. |
| 6,269,997 B1 | 8/2001 | Balazs et al. |
| 6,270,508 B1 | 8/2001 | Klieman et al. |
| 6,270,916 B1 | 8/2001 | Sink et al. |
| 6,273,252 B1 | 8/2001 | Mitchell |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,280,407 B1 | 8/2001 | Manna et al. |
| 6,283,981 B1 | 9/2001 | Beaupre |
| 6,293,927 B1 | 9/2001 | McGuckin, Jr. |
| 6,293,942 B1 | 9/2001 | Goble et al. |
| 6,296,640 B1 | 10/2001 | Wampler et al. |
| 6,302,311 B1 | 10/2001 | Adams et al. |
| 6,302,743 B1 | 10/2001 | Chiu et al. |
| 6,305,891 B1 | 10/2001 | Burlingame |
| 6,306,134 B1 | 10/2001 | Goble et al. |
| 6,306,149 B1 | 10/2001 | Meade |
| 6,306,424 B1 | 10/2001 | Vyakarnam et al. |
| 6,309,397 B1 | 10/2001 | Julian et al. |
| 6,309,400 B2 | 10/2001 | Beaupre |
| 6,309,403 B1 | 10/2001 | Minor et al. |
| 6,312,435 B1 | 11/2001 | Wallace et al. |
| 6,315,184 B1 | 11/2001 | Whitman |
| 6,317,616 B1 | 11/2001 | Glossop |
| 6,319,510 B1 | 11/2001 | Yates |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,805 B1 | 12/2001 | Ogilvie et al. |
| 6,325,810 B1 | 12/2001 | Hamilton et al. |
| 6,328,498 B1 | 12/2001 | Mersch |

(56) References Cited

U.S. PATENT DOCUMENTS

| | | |
|---|---|---|
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,348,061 B1 | 2/2002 | Whitman |
| 6,349,868 B1 | 2/2002 | Mattingly et al. |
| D454,951 S | 3/2002 | Bon |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,358,263 B2 | 3/2002 | Mark et al. |
| 6,358,459 B1 | 3/2002 | Ziegler et al. |
| 6,361,542 B1 | 3/2002 | Dimitriu et al. |
| 6,364,828 B1 | 4/2002 | Yeung et al. |
| 6,364,877 B1 | 4/2002 | Goble et al. |
| 6,364,888 B1 | 4/2002 | Niemeyer et al. |
| 6,366,441 B1 | 4/2002 | Ozawa et al. |
| 6,370,981 B2 | 4/2002 | Watarai |
| 6,371,114 B1 | 4/2002 | Schmidt et al. |
| 6,373,152 B1 | 4/2002 | Wang et al. |
| 6,377,011 B1 | 4/2002 | Ben-Ur |
| 6,383,201 B1 | 5/2002 | Dong |
| 6,387,092 B1 | 5/2002 | Burnside et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,392,854 B1 | 5/2002 | O'Gorman |
| 6,394,998 B1 | 5/2002 | Wallace et al. |
| 6,398,779 B1 | 6/2002 | Buysse et al. |
| 6,398,781 B1 | 6/2002 | Goble et al. |
| 6,398,797 B2 | 6/2002 | Bombard et al. |
| 6,402,766 B2 | 6/2002 | Bowman et al. |
| 6,402,780 B2 | 6/2002 | Williamson, IV et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,412,639 B1 | 7/2002 | Hickey |
| 6,413,274 B1 | 7/2002 | Pedros |
| 6,415,542 B1 | 7/2002 | Bates et al. |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| 6,424,885 B1 | 7/2002 | Niemeyer et al. |
| RE37,814 E | 8/2002 | Allgeyer |
| 6,428,070 B1 | 8/2002 | Takanashi et al. |
| 6,428,487 B1 | 8/2002 | Burdorff et al. |
| 6,429,611 B1 | 8/2002 | Li |
| 6,430,298 B1 | 8/2002 | Kettl et al. |
| 6,432,065 B1 | 8/2002 | Burdorff et al. |
| 6,436,097 B1 | 8/2002 | Nardella |
| 6,436,107 B1 | 8/2002 | Wang et al. |
| 6,436,110 B2 | 8/2002 | Bowman et al. |
| 6,436,115 B1 | 8/2002 | Beaupre |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,441,577 B2 | 8/2002 | Blumenkranz et al. |
| D462,758 S | 9/2002 | Epstein et al. |
| 6,443,973 B1 | 9/2002 | Whitman |
| 6,445,530 B1 | 9/2002 | Baker |
| 6,447,518 B1 | 9/2002 | Krause et al. |
| 6,447,523 B1 | 9/2002 | Middleman et al. |
| 6,447,799 B1 | 9/2002 | Ullman |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,457,338 B1 | 10/2002 | Frenken |
| 6,457,625 B1 | 10/2002 | Tormala et al. |
| 6,458,077 B1 | 10/2002 | Boebel et al. |
| 6,458,142 B1 | 10/2002 | Faller et al. |
| 6,458,147 B1 | 10/2002 | Cruise et al. |
| 6,460,627 B1 | 10/2002 | Below et al. |
| 6,468,275 B1 | 10/2002 | Wampler et al. |
| 6,468,286 B2 | 10/2002 | Mastri et al. |
| 6,471,106 B1 | 10/2002 | Reining |
| 6,471,659 B2 | 10/2002 | Eggers et al. |
| 6,478,210 B2 | 11/2002 | Adams et al. |
| 6,482,063 B1 | 11/2002 | Frigard |
| 6,482,200 B2 | 11/2002 | Shippert |
| 6,482,217 B1 | 11/2002 | Pintor et al. |
| 6,485,490 B2 | 11/2002 | Wampler et al. |
| 6,485,503 B2 | 11/2002 | Jacobs et al. |
| 6,485,667 B1 | 11/2002 | Tan |
| 6,486,286 B1 | 11/2002 | McGall et al. |
| 6,488,196 B1 | 12/2002 | Fenton, Jr. |
| 6,488,197 B1 | 12/2002 | Whitman |
| 6,488,659 B1 | 12/2002 | Rosenman |
| 6,491,201 B1 | 12/2002 | Whitman |
| 6,491,690 B1 | 12/2002 | Goble et al. |
| 6,491,701 B2 | 12/2002 | Tierney et al. |
| 6,491,702 B2 | 12/2002 | Heilbrun et al. |
| 6,492,785 B1 | 12/2002 | Kasten et al. |
| 6,494,882 B1 | 12/2002 | Lebouitz et al. |
| 6,494,885 B1 | 12/2002 | Dhindsa |
| 6,494,888 B1 | 12/2002 | Laufer et al. |
| 6,494,896 B1 | 12/2002 | D'Alessio et al. |
| 6,498,480 B1 | 12/2002 | Manara |
| 6,500,176 B1 | 12/2002 | Truckai et al. |
| 6,500,189 B1 | 12/2002 | Lang et al. |
| 6,500,194 B2 | 12/2002 | Benderev et al. |
| D468,749 S | 1/2003 | Friedman |
| 6,503,139 B2 | 1/2003 | Coral |
| 6,503,257 B2 | 1/2003 | Grant et al. |
| 6,503,259 B2 | 1/2003 | Huxel et al. |
| 6,505,768 B2 | 1/2003 | Whitman |
| 6,506,197 B1 | 1/2003 | Rollero et al. |
| 6,506,399 B2 | 1/2003 | Donovan |
| 6,510,854 B2 | 1/2003 | Goble |
| 6,511,468 B1 | 1/2003 | Cragg et al. |
| 6,512,360 B1 | 1/2003 | Goto et al. |
| 6,514,252 B2 | 2/2003 | Nezhat et al. |
| 6,516,073 B1 | 2/2003 | Schulz et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,520,971 B1 | 2/2003 | Perry et al. |
| 6,520,972 B2 | 2/2003 | Peters |
| 6,522,101 B2 | 2/2003 | Malackowski |
| 6,524,180 B1 | 2/2003 | Simms et al. |
| 6,525,499 B2 | 2/2003 | Naganuma |
| D471,206 S | 3/2003 | Buzzard et al. |
| 6,527,782 B2 | 3/2003 | Hogg et al. |
| 6,527,785 B2 | 3/2003 | Sancoff et al. |
| 6,530,942 B2 | 3/2003 | Fogarty et al. |
| 6,532,958 B1 | 3/2003 | Buan et al. |
| 6,533,157 B1 | 3/2003 | Whitman |
| 6,533,723 B1 | 3/2003 | Lockery et al. |
| 6,533,784 B2 | 3/2003 | Truckai et al. |
| 6,535,764 B2 | 3/2003 | Imran et al. |
| 6,539,297 B2 | 3/2003 | Weiberle et al. |
| D473,239 S | 4/2003 | Cockerill |
| 6,539,816 B2 | 4/2003 | Kogiso et al. |
| 6,540,737 B2 | 4/2003 | Bacher et al. |
| 6,543,456 B2 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,844 B2 | 4/2003 | Lee et al. |
| 6,554,861 B2 | 4/2003 | Knox et al. |
| 6,555,770 B2 | 4/2003 | Kawase |

(56) References Cited

U.S. PATENT DOCUMENTS

| | | |
|---|---|---|
| 6,558,378 B2 | 5/2003 | Sherman et al. |
| 6,558,379 B1 | 5/2003 | Batchelor et al. |
| 6,558,429 B2 | 5/2003 | Taylor |
| 6,561,187 B2 | 5/2003 | Schmidt et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,572,629 B2 | 6/2003 | Kalloo et al. |
| 6,578,751 B2 | 6/2003 | Hartwick |
| 6,582,364 B2 | 6/2003 | Butler et al. |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,585,664 B2 | 7/2003 | Burdorff et al. |
| 6,586,898 B2 | 7/2003 | King et al. |
| 6,587,750 B2 | 7/2003 | Gerbi et al. |
| 6,588,277 B2 | 7/2003 | Giordano et al. |
| 6,588,643 B2 | 7/2003 | Bolduc et al. |
| 6,588,931 B2 | 7/2003 | Betzner et al. |
| 6,589,118 B1 | 7/2003 | Soma et al. |
| 6,589,164 B1 | 7/2003 | Flaherty |
| 6,592,538 B1 | 7/2003 | Hotchkiss et al. |
| 6,592,572 B1 | 7/2003 | Suzuta |
| 6,592,597 B2 | 7/2003 | Grant et al. |
| 6,594,552 B1 | 7/2003 | Nowlin et al. |
| 6,595,914 B2 | 7/2003 | Kato |
| 6,596,296 B1 | 7/2003 | Nelson et al. |
| 6,596,304 B1 | 7/2003 | Bayon et al. |
| 6,596,432 B2 | 7/2003 | Kawakami et al. |
| 6,599,295 B1 | 7/2003 | Tornier et al. |
| 6,599,323 B2 | 7/2003 | Melican et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,603,050 B2 | 8/2003 | Heaton |
| 6,605,078 B2 | 8/2003 | Adams |
| 6,605,669 B2 | 8/2003 | Awokola et al. |
| 6,605,911 B1 | 8/2003 | Klesing |
| 6,607,475 B2 | 8/2003 | Doyle et al. |
| 6,611,793 B1 | 8/2003 | Burnside et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,111 B2 | 9/2003 | Stephens et al. |
| 6,620,161 B2 | 9/2003 | Schulze et al. |
| 6,620,166 B1 | 9/2003 | Wenstrom, Jr. et al. |
| 6,625,517 B1 | 9/2003 | Bogdanov et al. |
| 6,626,834 B2 | 9/2003 | Dunne et al. |
| 6,626,938 B1 | 9/2003 | Butaric et al. |
| H2086 H | 10/2003 | Amsler |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,648,901 B2 | 11/2003 | Fleischman et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,659,940 B2 | 12/2003 | Adler |
| 6,660,008 B1 | 12/2003 | Foerster et al. |
| 6,663,623 B1 | 12/2003 | Oyama et al. |
| 6,663,641 B1 | 12/2003 | Kovac et al. |
| 6,666,854 B1 | 12/2003 | Lange |
| 6,666,860 B1 | 12/2003 | Takahashi |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,670,806 B2 | 12/2003 | Wendt et al. |
| 6,671,185 B2 | 12/2003 | Duval |
| D484,977 S | 1/2004 | Ryan et al. |
| 6,676,660 B2 | 1/2004 | Wampler et al. |
| 6,677,687 B2 | 1/2004 | Ho et al. |
| 6,679,269 B2 | 1/2004 | Swanson |
| 6,679,410 B2 | 1/2004 | Wursch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,682,544 B2 | 1/2004 | Mastri et al. |
| 6,685,698 B2 | 2/2004 | Morley et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,692,692 B2 | 2/2004 | Stetzel |
| 6,695,198 B2 | 2/2004 | Adams et al. |
| 6,695,199 B2 | 2/2004 | Whitman |
| 6,695,774 B2 | 2/2004 | Hale et al. |
| 6,695,849 B2 | 2/2004 | Michelson |
| 6,696,814 B2 | 2/2004 | Henderson et al. |
| 6,697,048 B2 | 2/2004 | Rosenberg et al. |
| 6,698,643 B2 | 3/2004 | Whitman |
| 6,699,177 B1 | 3/2004 | Wang et al. |
| 6,699,214 B2 | 3/2004 | Gellman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,215 B1 | 4/2004 | David et al. |
| 6,716,223 B2 | 4/2004 | Leopold et al. |
| 6,716,232 B1 | 4/2004 | Vidal et al. |
| 6,716,233 B1 | 4/2004 | Whitman |
| 6,720,734 B2 | 4/2004 | Norris |
| 6,722,550 B1 | 4/2004 | Ricordi et al. |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,723,106 B1 | 4/2004 | Charles et al. |
| 6,723,109 B2 | 4/2004 | Solingen |
| 6,726,651 B1 | 4/2004 | Robinson et al. |
| 6,726,697 B2 | 4/2004 | Nicholas et al. |
| 6,726,705 B2 | 4/2004 | Peterson et al. |
| 6,726,706 B2 | 4/2004 | Dominguez |
| 6,729,119 B2 | 5/2004 | Schnipke et al. |
| 6,731,976 B2 | 5/2004 | Penn et al. |
| 6,736,810 B2 | 5/2004 | Hoey et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,743,230 B2 | 6/2004 | Lutze et al. |
| 6,744,385 B2 | 6/2004 | Kazuya et al. |
| 6,747,121 B2 | 6/2004 | Gogolewski |
| 6,747,300 B2 | 6/2004 | Nadd et al. |
| 6,749,560 B1 | 6/2004 | Konstorum et al. |
| 6,749,600 B1 | 6/2004 | Levy |
| 6,752,768 B2 | 6/2004 | Burdorff et al. |
| 6,752,816 B2 | 6/2004 | Culp et al. |
| 6,754,959 B1 | 6/2004 | Guiette, III et al. |
| 6,755,195 B1 | 6/2004 | Lemke et al. |
| 6,755,338 B2 | 6/2004 | Hahnen et al. |
| 6,755,825 B2 | 6/2004 | Shoenman et al. |
| 6,755,843 B2 | 6/2004 | Chung et al. |
| 6,756,705 B2 | 6/2004 | Pulford, Jr. |
| 6,758,846 B2 | 7/2004 | Goble et al. |
| 6,761,685 B2 | 7/2004 | Adams et al. |
| 6,762,339 B1 | 7/2004 | Klun et al. |
| 6,763,307 B2 | 7/2004 | Berg et al. |

(56) References Cited

U.S. PATENT DOCUMENTS

| | | |
|---|---|---|
| 6,764,445 B2 | 7/2004 | Ramans et al. |
| 6,766,957 B2 | 7/2004 | Matsuura et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,070 B1 | 8/2004 | Balbierz |
| 6,770,072 B1 | 8/2004 | Truckai et al. |
| 6,770,078 B2 | 8/2004 | Bonutti |
| 6,773,409 B2 | 8/2004 | Truckai et al. |
| 6,773,437 B2 | 8/2004 | Ogilvie et al. |
| 6,773,438 B1 | 8/2004 | Knodel et al. |
| 6,775,575 B2 | 8/2004 | Bommannan et al. |
| 6,777,838 B2 | 8/2004 | Miekka et al. |
| 6,778,846 B1 | 8/2004 | Martinez et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,784,775 B2 | 8/2004 | Mandell et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,788,018 B1 | 9/2004 | Blumenkranz |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,793,669 B2 | 9/2004 | Nakamura et al. |
| 6,796,921 B1 | 9/2004 | Buck et al. |
| 6,799,669 B2 | 10/2004 | Fukumura et al. |
| 6,801,009 B2 | 10/2004 | Makaran et al. |
| 6,802,822 B1 | 10/2004 | Dodge |
| 6,802,843 B2 | 10/2004 | Truckai et al. |
| 6,802,844 B2 | 10/2004 | Ferree |
| 6,805,273 B2 | 10/2004 | Bilotti et al. |
| 6,806,808 B1 | 10/2004 | Watters et al. |
| 6,806,867 B1 | 10/2004 | Arruda et al. |
| 6,808,525 B2 | 10/2004 | Latterell et al. |
| 6,810,359 B2 | 10/2004 | Sakaguchi |
| 6,814,154 B2 | 11/2004 | Chou |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,836,611 B2 | 12/2004 | Popovic et al. |
| 6,837,846 B2 | 1/2005 | Jaffe et al. |
| 6,837,883 B2 | 1/2005 | Moll et al. |
| 6,838,493 B2 | 1/2005 | Williams et al. |
| 6,840,423 B2 | 1/2005 | Adams et al. |
| 6,840,938 B1 | 1/2005 | Morley et al. |
| 6,841,967 B2 | 1/2005 | Kim et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,847,190 B2 | 1/2005 | Schaefer et al. |
| 6,849,071 B2 | 2/2005 | Whitman et al. |
| 6,850,817 B1 | 2/2005 | Green |
| 6,852,122 B2 | 2/2005 | Rush |
| 6,852,330 B2 | 2/2005 | Bowman et al. |
| 6,853,879 B2 | 2/2005 | Sunaoshi |
| 6,858,005 B2 | 2/2005 | Ohline et al. |
| 6,859,882 B2 | 2/2005 | Fung |
| RE38,708 E | 3/2005 | Bolanos et al. |
| D502,994 S | 3/2005 | Blake, III |
| 6,861,142 B1 | 3/2005 | Wilkie et al. |
| 6,861,954 B2 | 3/2005 | Levin |
| 6,863,668 B2 | 3/2005 | Gillespie et al. |
| 6,863,694 B1 | 3/2005 | Boyce et al. |
| 6,863,924 B2 | 3/2005 | Ranganathan et al. |
| 6,866,178 B2 | 3/2005 | Adams et al. |
| 6,866,668 B2 | 3/2005 | Giannetti et al. |
| 6,866,671 B2 | 3/2005 | Tierney et al. |
| 6,867,248 B1 | 3/2005 | Martin et al. |
| 6,869,430 B2 | 3/2005 | Balbierz et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,876,850 B2 | 4/2005 | Maeshima et al. |
| 6,877,647 B2 | 4/2005 | Green et al. |
| 6,878,106 B1 | 4/2005 | Herrmann |
| 6,882,127 B2 | 4/2005 | Konigbauer |
| 6,883,199 B1 | 4/2005 | Lundell et al. |
| 6,884,392 B2 | 4/2005 | Malkin et al. |
| 6,884,428 B2 | 4/2005 | Binette et al. |
| 6,886,730 B2 | 5/2005 | Fujisawa et al. |
| 6,887,244 B1 | 5/2005 | Walker et al. |
| 6,887,710 B2 | 5/2005 | Call et al. |
| 6,889,116 B2 | 5/2005 | Jinno |
| 6,893,435 B2 | 5/2005 | Goble |
| 6,894,140 B2 | 5/2005 | Roby |
| 6,895,176 B2 | 5/2005 | Archer et al. |
| 6,899,538 B2 | 5/2005 | Matoba |
| 6,899,593 B1 | 5/2005 | Moeller et al. |
| 6,899,705 B2 | 5/2005 | Niemeyer |
| 6,899,915 B2 | 5/2005 | Yelick et al. |
| 6,905,057 B2 | 6/2005 | Swayze et al. |
| 6,905,497 B2 | 6/2005 | Truckai et al. |
| 6,905,498 B2 | 6/2005 | Hooven |
| 6,908,472 B2 | 6/2005 | Wiener et al. |
| 6,911,033 B2 | 6/2005 | de Guillebon et al. |
| 6,911,916 B1 | 6/2005 | Wang et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,923,819 B2 | 8/2005 | Meade et al. |
| 6,925,849 B2 | 8/2005 | Jairam |
| 6,926,716 B2 | 8/2005 | Baker et al. |
| 6,928,902 B1 | 8/2005 | Eyssallenne |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,936,948 B2 | 8/2005 | Bell et al. |
| D509,297 S | 9/2005 | Wells |
| D509,589 S | 9/2005 | Wells |
| 6,938,706 B2 | 9/2005 | Ng |
| 6,939,358 B2 | 9/2005 | Palacios et al. |
| 6,942,662 B2 | 9/2005 | Goble et al. |
| 6,942,674 B2 | 9/2005 | Belef et al. |
| 6,945,444 B2 | 9/2005 | Gresham et al. |
| 6,945,981 B2 | 9/2005 | Donofrio et al. |
| 6,949,196 B2 | 9/2005 | Schmitz et al. |
| 6,951,562 B2 | 10/2005 | Zwirnmann |
| 6,953,138 B1 | 10/2005 | Dworak et al. |
| 6,953,139 B2 | 10/2005 | Milliman et al. |
| 6,953,461 B2 | 10/2005 | McClurken et al. |
| 6,957,758 B2 | 10/2005 | Aranyi |
| 6,958,035 B2 | 10/2005 | Friedman et al. |

(56) References Cited

U.S. PATENT DOCUMENTS

| | | |
|---|---|---|
| D511,525 S | 11/2005 | Hernandez et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,962,587 B2 | 11/2005 | Johnson et al. |
| 6,963,792 B1 | 11/2005 | Green |
| 6,964,363 B2 | 11/2005 | Wales et al. |
| 6,966,907 B2 | 11/2005 | Goble |
| 6,966,909 B2 | 11/2005 | Marshall et al. |
| 6,968,908 B2 | 11/2005 | Tokunaga et al. |
| 6,969,385 B2 | 11/2005 | Moreyra |
| 6,969,395 B2 | 11/2005 | Eskuri |
| 6,971,988 B2 | 12/2005 | Orban, III |
| 6,972,199 B2 | 12/2005 | Lebouitz et al. |
| 6,974,435 B2 | 12/2005 | Daw et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,989,034 B2 | 1/2006 | Hammer et al. |
| 6,990,731 B2 | 1/2006 | Haytayan |
| 6,990,796 B2 | 1/2006 | Schnipke et al. |
| 6,991,146 B2 | 1/2006 | Sinisi et al. |
| 6,993,200 B2 | 1/2006 | Tastl et al. |
| 6,993,413 B2 | 1/2006 | Sunaoshi |
| 6,994,708 B2 | 2/2006 | Manzo |
| 6,995,729 B2 | 2/2006 | Govari et al. |
| 6,996,433 B2 | 2/2006 | Burbank et al. |
| 6,997,931 B2 | 2/2006 | Sauer et al. |
| 6,997,935 B2 | 2/2006 | Anderson et al. |
| 6,998,736 B2 | 2/2006 | Lee et al. |
| 6,998,816 B2 | 2/2006 | Wieck et al. |
| 6,999,821 B2 | 2/2006 | Jenney et al. |
| 7,000,818 B2 | 2/2006 | Shelton, IV et al. |
| 7,000,819 B2 | 2/2006 | Swayze et al. |
| 7,000,911 B2 | 2/2006 | McCormick et al. |
| 7,001,380 B2 | 2/2006 | Goble |
| 7,001,408 B2 | 2/2006 | Knodel et al. |
| 7,004,174 B2 | 2/2006 | Eggers et al. |
| 7,007,176 B2 | 2/2006 | Goodfellow et al. |
| 7,008,433 B2 | 3/2006 | Voellmicke et al. |
| 7,008,435 B2 | 3/2006 | Cummins |
| 7,009,039 B2 | 3/2006 | Yayon et al. |
| 7,011,213 B2 | 3/2006 | Clark et al. |
| 7,011,657 B2 | 3/2006 | Truckai et al. |
| 7,014,640 B2 | 3/2006 | Kemppainen et al. |
| 7,018,357 B2 | 3/2006 | Emmons |
| 7,018,390 B2 | 3/2006 | Turovskiy et al. |
| 7,021,399 B2 | 4/2006 | Driessen |
| 7,021,669 B1 | 4/2006 | Lindermeir et al. |
| 7,022,131 B1 | 4/2006 | Derowe et al. |
| 7,023,159 B2 | 4/2006 | Gorti et al. |
| 7,025,064 B2 | 4/2006 | Wang et al. |
| 7,025,732 B2 | 4/2006 | Thompson et al. |
| 7,025,743 B2 | 4/2006 | Mann et al. |
| 7,025,774 B2 | 4/2006 | Freeman et al. |
| 7,025,775 B2 | 4/2006 | Gadberry et al. |
| 7,028,570 B2 | 4/2006 | Ohta et al. |
| 7,029,435 B2 | 4/2006 | Nakao |
| 7,029,439 B2 | 4/2006 | Roberts et al. |
| 7,030,904 B2 | 4/2006 | Adair et al. |
| 7,032,798 B2 | 4/2006 | Whitman et al. |
| 7,032,799 B2 | 4/2006 | Viola et al. |
| 7,033,356 B2 | 4/2006 | Latterell et al. |
| 7,033,378 B2 | 4/2006 | Smith et al. |
| 7,035,716 B2 | 4/2006 | Harris et al. |
| 7,035,762 B2 | 4/2006 | Menard et al. |
| 7,036,680 B1 | 5/2006 | Flannery |
| 7,037,314 B2 | 5/2006 | Armstrong |
| 7,037,344 B2 | 5/2006 | Kagan et al. |
| 7,038,421 B2 | 5/2006 | Trifilo |
| 7,041,088 B2 | 5/2006 | Nawrocki et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,350 B2 | 5/2006 | Kameyama et al. |
| 7,044,352 B2 | 5/2006 | Shelton, IV et al. |
| 7,044,353 B2 | 5/2006 | Mastri et al. |
| 7,046,082 B2 | 5/2006 | Komiya et al. |
| 7,048,165 B2 | 5/2006 | Haramiishi |
| 7,048,687 B1 | 5/2006 | Reuss et al. |
| 7,048,716 B1 | 5/2006 | Kucharczyk et al. |
| 7,048,745 B2 | 5/2006 | Tierney et al. |
| 7,052,454 B2 | 5/2006 | Taylor |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,123 B2 | 6/2006 | Gregorio et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,064,509 B1 | 6/2006 | Fu et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,081,318 B2 | 7/2006 | Lee et al. |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,083,626 B2 | 8/2006 | Hart et al. |
| 7,086,267 B2 | 8/2006 | Dworak et al. |
| 7,087,049 B2 | 8/2006 | Nowlin et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,091,191 B2 | 8/2006 | Laredo et al. |
| 7,091,412 B2 | 8/2006 | Wang et al. |
| 7,093,492 B2 | 8/2006 | Treiber et al. |
| 7,094,202 B2 | 8/2006 | Nobis et al. |
| 7,094,247 B2 | 8/2006 | Monassevitch et al. |
| 7,094,916 B2 | 8/2006 | DeLuca et al. |
| 7,096,972 B2 | 8/2006 | Orozco, Jr. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,101,187 B1 | 9/2006 | Deconinck et al. |
| 7,101,371 B2 | 9/2006 | Dycus et al. |
| 7,101,394 B2 | 9/2006 | Hamm et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,768 B2 | 9/2006 | Cummins et al. |
| 7,111,769 B2 | 9/2006 | Wales et al. |
| 7,112,214 B2 | 9/2006 | Peterson et al. |

(56) References Cited

U.S. PATENT DOCUMENTS

| | | |
|---|---|---|
| RE39,358 E | 10/2006 | Goble |
| D530,339 S | 10/2006 | Hernandez et al. |
| 7,114,642 B2 | 10/2006 | Whitman |
| 7,116,100 B1 | 10/2006 | Mock et al. |
| 7,118,020 B2 | 10/2006 | Lee et al. |
| 7,118,528 B1 | 10/2006 | Piskun |
| 7,118,563 B2 | 10/2006 | Weckwerth et al. |
| 7,118,582 B1 | 10/2006 | Wang et al. |
| 7,119,534 B2 | 10/2006 | Butzmann |
| 7,121,446 B2 | 10/2006 | Arad et al. |
| 7,121,773 B2 | 10/2006 | Mikiya et al. |
| 7,122,028 B2 | 10/2006 | Looper et al. |
| 7,125,403 B2 | 10/2006 | Julian et al. |
| 7,125,409 B2 | 10/2006 | Truckai et al. |
| 7,126,303 B2 | 10/2006 | Farritor et al. |
| 7,126,879 B2 | 10/2006 | Snyder |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,364 B2 | 11/2006 | Kageler et al. |
| 7,134,587 B2 | 11/2006 | Schwemberger et al. |
| 7,135,027 B2 | 11/2006 | Delmotte |
| 7,137,980 B2 | 11/2006 | Buysse et al. |
| 7,137,981 B2 | 11/2006 | Long |
| 7,139,016 B2 | 11/2006 | Squilla et al. |
| 7,140,527 B2 | 11/2006 | Ehrenfels et al. |
| 7,140,528 B2 | 11/2006 | Shelton, IV |
| 7,141,055 B2 | 11/2006 | Abrams et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,146,191 B2 | 12/2006 | Kerner et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,648 B2 | 12/2006 | Lin |
| 7,147,650 B2 | 12/2006 | Lee |
| 7,150,748 B2 | 12/2006 | Ebbutt et al. |
| 7,153,300 B2 | 12/2006 | Goble |
| 7,153,314 B2 | 12/2006 | Laufer et al. |
| 7,155,316 B2 | 12/2006 | Sutherland et al. |
| 7,156,863 B2 | 1/2007 | Sonnenschein et al. |
| 7,159,750 B2 | 1/2007 | Racenet et al. |
| 7,160,296 B2 | 1/2007 | Pearson et al. |
| 7,160,299 B2 | 1/2007 | Baily |
| 7,161,036 B2 | 1/2007 | Oikawa et al. |
| 7,161,580 B2 | 1/2007 | Bailey et al. |
| 7,162,758 B2 | 1/2007 | Skinner |
| 7,163,563 B2 | 1/2007 | Schwartz et al. |
| 7,166,117 B2 | 1/2007 | Hellenkamp |
| 7,166,133 B2 | 1/2007 | Evans et al. |
| 7,168,604 B2 | 1/2007 | Milliman et al. |
| 7,170,910 B2 | 1/2007 | Chen et al. |
| 7,171,279 B2 | 1/2007 | Buckingham et al. |
| 7,172,104 B2 | 2/2007 | Scirica et al. |
| 7,172,593 B2 | 2/2007 | Trieu et al. |
| 7,172,615 B2 | 2/2007 | Morriss et al. |
| 7,174,202 B2 | 2/2007 | Bladen et al. |
| 7,174,636 B2 | 2/2007 | Lowe |
| 7,177,533 B2 | 2/2007 | McFarlin et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,187,960 B2 | 3/2007 | Abreu |
| 7,188,758 B2 | 3/2007 | Viola et al. |
| 7,189,207 B2 | 3/2007 | Viola |
| 7,190,147 B2 | 3/2007 | Gileff et al. |
| 7,193,199 B2 | 3/2007 | Jang |
| 7,195,627 B2 | 3/2007 | Amoah et al. |
| 7,196,911 B2 | 3/2007 | Takano et al. |
| D541,418 S | 4/2007 | Schechter et al. |
| 7,197,965 B1 | 4/2007 | Anderson |
| 7,199,537 B2 | 4/2007 | Okamura et al. |
| 7,199,545 B2 | 4/2007 | Oleynikov et al. |
| 7,202,576 B1 | 4/2007 | Dechene et al. |
| 7,202,653 B2 | 4/2007 | Pai |
| 7,204,404 B2 | 4/2007 | Nguyen et al. |
| 7,204,835 B2 | 4/2007 | Latterell et al. |
| 7,205,959 B2 | 4/2007 | Henriksson |
| 7,206,626 B2 | 4/2007 | Quaid |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,211,979 B2 | 5/2007 | Khatib et al. |
| 7,213,736 B2 | 5/2007 | Wales et al. |
| 7,214,224 B2 | 5/2007 | Goble |
| 7,215,517 B2 | 5/2007 | Takamatsu |
| 7,217,285 B2 | 5/2007 | Vargas et al. |
| 7,220,260 B2 | 5/2007 | Fleming et al. |
| 7,220,272 B2 | 5/2007 | Weadock |
| 7,225,959 B2 | 6/2007 | Patton et al. |
| 7,225,963 B2 | 6/2007 | Scirica |
| 7,225,964 B2 | 6/2007 | Mastri et al. |
| 7,226,450 B2 | 6/2007 | Athanasiou et al. |
| 7,226,467 B2 | 6/2007 | Lucatero et al. |
| 7,228,505 B2 | 6/2007 | Shimazu et al. |
| 7,229,408 B2 | 6/2007 | Douglas et al. |
| 7,234,624 B2 | 6/2007 | Gresham et al. |
| 7,235,072 B2 | 6/2007 | Sartor et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,238,901 B2 | 7/2007 | Kim et al. |
| 7,239,657 B1 | 7/2007 | Gunnarsson |
| 7,241,288 B2 | 7/2007 | Braun |
| 7,241,289 B2 | 7/2007 | Braun |
| 7,246,734 B2 | 7/2007 | Shelton, IV |
| 7,247,161 B2 | 7/2007 | Johnston et al. |
| 7,249,267 B2 | 7/2007 | Chapuis |
| 7,252,641 B2 | 8/2007 | Thompson et al. |
| 7,252,660 B2 | 8/2007 | Kunz |
| 7,255,012 B2 | 8/2007 | Hedtke |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,677 B2 | 9/2007 | Johnson et al. |
| 7,267,679 B2 | 9/2007 | McGuckin, Jr. et al. |
| 7,272,002 B2 | 9/2007 | Drapeau |
| 7,273,483 B2 | 9/2007 | Wiener et al. |
| D552,623 S | 10/2007 | Vong et al. |
| 7,275,674 B2 | 10/2007 | Racenet et al. |
| 7,276,044 B2 | 10/2007 | Ferry et al. |
| 7,276,068 B2 | 10/2007 | Johnson et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,283,096 B2 | 10/2007 | Geisheimer et al. |
| 7,286,850 B2 | 10/2007 | Frielink et al. |
| 7,287,682 B1 | 10/2007 | Ezzat et al. |
| 7,289,139 B2 | 10/2007 | Amling et al. |
| 7,293,685 B2 | 11/2007 | Ehrenfels et al. |
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |

(56) References Cited

U.S. PATENT DOCUMENTS

| | | |
|---|---|---|
| 7,300,373 B2 | 11/2007 | Jinno et al. |
| 7,300,431 B2 | 11/2007 | Dubrovsky |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,311,238 B2 | 12/2007 | Liu |
| 7,313,430 B2 | 12/2007 | Urquhart et al. |
| 7,314,473 B2 | 1/2008 | Jinno et al. |
| 7,320,704 B2 | 1/2008 | Lashinski et al. |
| 7,322,859 B2 | 1/2008 | Evans |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,331,343 B2 | 2/2008 | Schmidt et al. |
| 7,331,403 B2 | 2/2008 | Berry et al. |
| 7,331,406 B2 | 2/2008 | Wottreng, Jr. et al. |
| 7,331,969 B1 | 2/2008 | Inganas et al. |
| 7,334,717 B2 | 2/2008 | Rethy et al. |
| 7,334,718 B2 | 2/2008 | McAlister et al. |
| 7,335,199 B2 | 2/2008 | Goble et al. |
| 7,335,401 B2 | 2/2008 | Finke et al. |
| 7,336,045 B2 | 2/2008 | Clermonts |
| 7,336,048 B2 | 2/2008 | Lohr |
| 7,336,183 B2 | 2/2008 | Reddy et al. |
| 7,336,184 B2 | 2/2008 | Smith et al. |
| 7,337,774 B2 | 3/2008 | Webb |
| 7,338,505 B2 | 3/2008 | Belson |
| 7,338,513 B2 | 3/2008 | Lee et al. |
| 7,341,554 B2 | 3/2008 | Sekine et al. |
| 7,341,555 B2 | 3/2008 | Ootawara et al. |
| 7,341,591 B2 | 3/2008 | Grinberg |
| 7,343,920 B2 | 3/2008 | Toby et al. |
| 7,344,532 B2 | 3/2008 | Goble et al. |
| 7,344,533 B2 | 3/2008 | Pearson et al. |
| 7,346,344 B2 | 3/2008 | Fontaine |
| 7,346,406 B2 | 3/2008 | Brotto et al. |
| 7,348,763 B1 | 3/2008 | Reinhart et al. |
| 7,348,875 B2 | 3/2008 | Hughes et al. |
| RE40,237 E | 4/2008 | Bilotti et al. |
| 7,351,258 B2 | 4/2008 | Ricotta et al. |
| 7,354,398 B2 | 4/2008 | Kanazawa |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,168 B2 | 4/2008 | Makower et al. |
| 7,361,195 B2 | 4/2008 | Schwartz et al. |
| 7,362,062 B2 | 4/2008 | Schneider et al. |
| 7,364,060 B2 | 4/2008 | Milliman |
| 7,364,061 B2 | 4/2008 | Swayze et al. |
| 7,367,485 B2 | 5/2008 | Shelton, IV et al. |
| 7,367,973 B2 | 5/2008 | Manzo et al. |
| 7,368,124 B2 | 5/2008 | Chun et al. |
| 7,371,210 B2 | 5/2008 | Brock et al. |
| 7,371,403 B2 | 5/2008 | McCarthy et al. |
| 7,375,493 B2 | 5/2008 | Calhoon et al. |
| 7,377,918 B2 | 5/2008 | Amoah |
| 7,377,928 B2 | 5/2008 | Zubik et al. |
| 7,378,817 B2 | 5/2008 | Calhoon et al. |
| RE40,388 E | 6/2008 | Gines |
| D570,868 S | 6/2008 | Hosokawa et al. |
| 7,380,695 B2 | 6/2008 | Doll et al. |
| 7,380,696 B2 | 6/2008 | Shelton, IV et al. |
| 7,384,403 B2 | 6/2008 | Sherman |
| 7,384,417 B2 | 6/2008 | Cucin |
| 7,386,365 B2 | 6/2008 | Nixon |
| 7,386,730 B2 | 6/2008 | Uchikubo |
| 7,388,217 B2 | 6/2008 | Buschbeck et al. |
| 7,388,484 B2 | 6/2008 | Hsu |
| 7,391,173 B2 | 6/2008 | Schena |
| 7,394,190 B2 | 7/2008 | Huang |
| 7,396,356 B2 | 7/2008 | Mollenauer |
| 7,397,364 B2 | 7/2008 | Govari |
| 7,398,707 B2 | 7/2008 | Morley et al. |
| 7,398,907 B2 | 7/2008 | Racenet et al. |
| 7,398,908 B2 | 7/2008 | Holsten et al. |
| 7,400,107 B2 | 7/2008 | Schneider et al. |
| 7,400,752 B2 | 7/2008 | Zacharias |
| 7,401,000 B2 | 7/2008 | Nakamura |
| 7,401,721 B2 | 7/2008 | Holsten et al. |
| 7,404,449 B2 | 7/2008 | Bermingham et al. |
| 7,404,508 B2 | 7/2008 | Smith et al. |
| 7,404,509 B2 | 7/2008 | Ortiz et al. |
| 7,404,822 B2 | 7/2008 | Viart et al. |
| D575,793 S | 8/2008 | Ording |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,408,310 B2 | 8/2008 | Hong et al. |
| 7,410,085 B2 | 8/2008 | Wolf et al. |
| 7,410,086 B2 | 8/2008 | Ortiz et al. |
| 7,410,483 B2 | 8/2008 | Danitz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,321 B2 | 9/2008 | Tereschouk |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| D578,644 S | 10/2008 | Shumer et al. |
| 7,430,772 B2 | 10/2008 | Van Es |
| 7,431,188 B1 | 10/2008 | Marczyk |
| 7,431,189 B2 | 10/2008 | Shelton, IV et al. |
| 7,431,230 B2 | 10/2008 | McPherson et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,435,249 B2 | 10/2008 | Buysse et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,443,547 B2 | 10/2008 | Moreno et al. |
| 7,446,131 B1 | 11/2008 | Liu et al. |
| 7,448,525 B2 | 11/2008 | Shelton, IV et al. |
| 7,450,010 B1 | 11/2008 | Gravelle et al. |
| 7,450,991 B2 | 11/2008 | Smith et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,455,687 B2 | 11/2008 | Saunders et al. |
| D582,934 S | 12/2008 | Byeon |
| 7,461,767 B2 | 12/2008 | Viola et al. |
| 7,462,187 B2 | 12/2008 | Johnston et al. |
| 7,464,845 B2 | 12/2008 | Chou |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |

(56) References Cited

U.S. PATENT DOCUMENTS

| | | |
|---|---|---|
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,221 B2 | 1/2009 | Ewers et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,147 B2 | 1/2009 | Honeycutt et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,124 B2 | 2/2009 | Kuhns et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,489,055 B2 | 2/2009 | Jeong et al. |
| 7,490,749 B2 | 2/2009 | Schall et al. |
| 7,491,232 B2 | 2/2009 | Bolduc et al. |
| 7,492,261 B2 | 2/2009 | Cambre et al. |
| 7,494,039 B2 | 2/2009 | Racenet et al. |
| 7,494,460 B2 | 2/2009 | Haarstad et al. |
| 7,494,499 B2 | 2/2009 | Nagase et al. |
| 7,494,501 B2 | 2/2009 | Ahlberg et al. |
| 7,497,137 B2 | 3/2009 | Tellenbach et al. |
| 7,500,979 B2 | 3/2009 | Hueil et al. |
| 7,501,198 B2 | 3/2009 | Barley et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,534 B2 | 3/2009 | Burdorff et al. |
| 7,510,566 B2 | 3/2009 | Jacobs et al. |
| 7,513,407 B1 | 4/2009 | Chang |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,527,632 B2 | 5/2009 | Houghton et al. |
| 7,530,984 B2 | 5/2009 | Sonnenschein et al. |
| 7,530,985 B2 | 5/2009 | Takemoto et al. |
| 7,533,906 B2 | 5/2009 | Luettgen et al. |
| 7,534,259 B2 | 5/2009 | Lashinski et al. |
| 7,540,867 B2 | 6/2009 | Jinno et al. |
| 7,540,872 B2 | 6/2009 | Schechter et al. |
| 7,542,807 B2 | 6/2009 | Bertolero et al. |
| 7,543,730 B1 | 6/2009 | Marczyk |
| 7,544,197 B2 | 6/2009 | Kelsch et al. |
| 7,546,939 B2 | 6/2009 | Adams et al. |
| 7,546,940 B2 | 6/2009 | Milliman et al. |
| 7,547,287 B2 | 6/2009 | Boecker et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,553,173 B2 | 6/2009 | Kowalick |
| 7,553,275 B2 | 6/2009 | Padget et al. |
| 7,554,343 B2 | 6/2009 | Bromfield |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,561,637 B2 | 7/2009 | Jonsson et al. |
| 7,562,910 B2 | 7/2009 | Kertesz et al. |
| 7,563,269 B2 | 7/2009 | Hashiguchi |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,572,285 B2 | 8/2009 | Frey et al. |
| 7,575,144 B2 | 8/2009 | Ortiz et al. |
| 7,578,825 B2 | 8/2009 | Huebner |
| D600,712 S | 9/2009 | LaManna et al. |
| 7,583,063 B2 | 9/2009 | Dooley |
| 7,584,880 B2 | 9/2009 | Racenet et al. |
| 7,586,289 B2 | 9/2009 | Andruk et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,591,818 B2 | 9/2009 | Bertolero et al. |
| 7,593,766 B2 | 9/2009 | Faber et al. |
| 7,595,642 B2 | 9/2009 | Doyle |
| 7,597,229 B2 | 10/2009 | Boudreaux et al. |
| 7,597,230 B2 | 10/2009 | Racenet et al. |
| 7,597,693 B2 | 10/2009 | Garrison |
| 7,597,699 B2 | 10/2009 | Rogers |
| 7,598,972 B2 | 10/2009 | Tomita |
| 7,600,663 B2 | 10/2009 | Green |
| 7,604,118 B2 | 10/2009 | Iio et al. |
| 7,604,150 B2 | 10/2009 | Boudreaux |
| 7,604,151 B2 | 10/2009 | Hess et al. |
| 7,604,668 B2 | 10/2009 | Farnsworth et al. |
| 7,605,826 B2 | 10/2009 | Sauer |
| 7,607,557 B2 | 10/2009 | Shelton, IV et al. |
| 7,608,091 B2 | 10/2009 | Goldfarb et al. |
| D604,325 S | 11/2009 | Ebeling et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,006 B2 | 11/2009 | Abe |
| 7,615,067 B2 | 11/2009 | Lee et al. |
| 7,617,961 B2 | 11/2009 | Viola |
| 7,618,427 B2 | 11/2009 | Ortiz et al. |
| D605,201 S | 12/2009 | Lorenz et al. |
| D606,992 S | 12/2009 | Liu et al. |
| D607,010 S | 12/2009 | Kocmick |
| 7,624,902 B2 | 12/2009 | Marczyk et al. |
| 7,624,903 B2 | 12/2009 | Green et al. |
| 7,625,370 B2 | 12/2009 | Hart et al. |
| 7,625,388 B2 | 12/2009 | Boukhny et al. |
| 7,625,662 B2 | 12/2009 | Vaisnys et al. |
| 7,630,841 B2 | 12/2009 | Comisky et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,635,922 B2 | 12/2009 | Becker |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,641,671 B2 | 1/2010 | Crainich |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,055 B2 | 1/2010 | Marczyk |
| 7,648,457 B2 | 1/2010 | Stefanchik et al. |
| 7,648,519 B2 | 1/2010 | Lee et al. |
| 7,650,185 B2 | 1/2010 | Maile et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,003 B2 | 2/2010 | Lorang et al. |
| 7,655,004 B2 | 2/2010 | Long |
| 7,655,288 B2 | 2/2010 | Bauman et al. |
| 7,655,584 B2 | 2/2010 | Biran et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,658,705 B2 | 2/2010 | Melvin et al. |
| 7,659,219 B2 | 2/2010 | Biran et al. |
| 7,661,448 B2 | 2/2010 | Kim et al. |

(56) References Cited

U.S. PATENT DOCUMENTS

| | | |
|---|---|---|
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,666,195 B2 | 2/2010 | Kelleher et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,678,121 B1 | 3/2010 | Knodel |
| 7,682,307 B2 | 3/2010 | Danitz et al. |
| 7,682,367 B2 | 3/2010 | Shah et al. |
| 7,682,686 B2 | 3/2010 | Curro et al. |
| 7,686,201 B2 | 3/2010 | Csiky |
| 7,686,804 B2 | 3/2010 | Johnson et al. |
| 7,686,826 B2 | 3/2010 | Lee et al. |
| 7,688,028 B2 | 3/2010 | Phillips et al. |
| 7,690,547 B2 | 4/2010 | Racenet et al. |
| 7,691,098 B2 | 4/2010 | Wallace et al. |
| 7,691,103 B2 | 4/2010 | Fernandez et al. |
| 7,691,106 B2 | 4/2010 | Schenberger et al. |
| 7,694,864 B2 | 4/2010 | Okada et al. |
| 7,694,865 B2 | 4/2010 | Scirica |
| 7,695,485 B2 | 4/2010 | Whitman et al. |
| 7,695,493 B2 | 4/2010 | Saadat et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,699,868 B2 | 4/2010 | Frank et al. |
| 7,703,653 B2 | 4/2010 | Shah et al. |
| 7,705,559 B2 | 4/2010 | Powell et al. |
| 7,706,853 B2 | 4/2010 | Hacker et al. |
| 7,708,180 B2 | 5/2010 | Murray et al. |
| 7,708,181 B2 | 5/2010 | Cole et al. |
| 7,708,182 B2 | 5/2010 | Viola |
| 7,708,758 B2 | 5/2010 | Lee et al. |
| 7,708,768 B2 | 5/2010 | Danek et al. |
| 7,709,136 B2 | 5/2010 | Touchton et al. |
| 7,712,182 B2 | 5/2010 | Zeiler et al. |
| 7,713,190 B2 | 5/2010 | Brock et al. |
| 7,713,542 B2 | 5/2010 | Xu et al. |
| 7,714,239 B2 | 5/2010 | Smith |
| 7,714,334 B2 | 5/2010 | Lin |
| 7,717,312 B2 | 5/2010 | Beetel |
| 7,717,313 B2 | 5/2010 | Criscuolo et al. |
| 7,717,846 B2 | 5/2010 | Zirps et al. |
| 7,717,873 B2 | 5/2010 | Swick |
| 7,717,915 B2 | 5/2010 | Miyazawa |
| 7,717,926 B2 | 5/2010 | Whitfield et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,932 B2 | 5/2010 | Cole et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,725,214 B2 | 5/2010 | Diolaiti |
| 7,726,171 B2 | 6/2010 | Langlotz et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,728,553 B2 | 6/2010 | Carrier et al. |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,735,704 B2 | 6/2010 | Bilotti |
| 7,736,254 B2 | 6/2010 | Schena |
| 7,736,306 B2 | 6/2010 | Brustad et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,742,036 B2 | 6/2010 | Grant et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,747,146 B2 | 6/2010 | Milano et al. |
| 7,748,587 B2 | 7/2010 | Haramiishi et al. |
| 7,748,632 B2 | 7/2010 | Coleman et al. |
| 7,749,204 B2 | 7/2010 | Dhanaraj et al. |
| 7,749,240 B2 | 7/2010 | Takahashi et al. |
| 7,751,870 B2 | 7/2010 | Whitman |
| 7,753,245 B2 | 7/2010 | Boudreaux et al. |
| 7,753,246 B2 | 7/2010 | Scirica |
| 7,753,904 B2 | 7/2010 | Shelton, IV et al. |
| 7,757,924 B2 | 7/2010 | Gerbi et al. |
| 7,758,594 B2 | 7/2010 | Lamson et al. |
| 7,758,612 B2 | 7/2010 | Shipp |
| 7,758,613 B2 | 7/2010 | Whitman |
| 7,762,462 B2 | 7/2010 | Gelbman |
| 7,762,998 B2 | 7/2010 | Birk et al. |
| D622,286 S | 8/2010 | Umezawa |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,658 B2 | 8/2010 | Ito et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,772,725 B2 | 8/2010 | Siman-Tov |
| 7,775,972 B2 | 8/2010 | Brock et al. |
| 7,776,037 B2 | 8/2010 | Odom |
| 7,776,060 B2 | 8/2010 | Mooradian et al. |
| 7,776,065 B2 | 8/2010 | Griffiths et al. |
| 7,778,004 B2 | 8/2010 | Nerheim et al. |
| 7,779,614 B1 | 8/2010 | McGonagle et al. |
| 7,779,737 B2 | 8/2010 | Newman, Jr. et al. |
| 7,780,054 B2 | 8/2010 | Wales |
| 7,780,055 B2 | 8/2010 | Scirica et al. |
| 7,780,309 B2 | 8/2010 | McMillan et al. |
| 7,780,651 B2 | 8/2010 | Madhani et al. |
| 7,780,663 B2 | 8/2010 | Yates et al. |
| 7,780,685 B2 | 8/2010 | Hunt et al. |
| 7,782,382 B2 | 8/2010 | Fujimura |
| 7,784,662 B2 | 8/2010 | Wales et al. |
| 7,784,663 B2 | 8/2010 | Shelton, IV |
| 7,787,256 B2 | 8/2010 | Chan et al. |
| 7,789,283 B2 | 9/2010 | Shah |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,871 B2 | 10/2010 | Li et al. |
| 7,806,891 B2 | 10/2010 | Nowlin et al. |
| 7,810,690 B2 | 10/2010 | Bilotti et al. |
| 7,810,691 B2 | 10/2010 | Boyden et al. |

(56) References Cited

U.S. PATENT DOCUMENTS

| | | |
|---|---|---|
| 7,810,692 B2 | 10/2010 | Hall et al. |
| 7,810,693 B2 | 10/2010 | Broehl et al. |
| 7,811,275 B2 | 10/2010 | Birk et al. |
| 7,814,816 B2 | 10/2010 | Alberti et al. |
| 7,815,092 B2 | 10/2010 | Whitman et al. |
| 7,815,565 B2 | 10/2010 | Stefanchik et al. |
| 7,815,662 B2 | 10/2010 | Spivey et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,799 B2 | 10/2010 | Merril et al. |
| 7,819,884 B2 | 10/2010 | Lee et al. |
| 7,819,885 B2 | 10/2010 | Cooper |
| 7,819,886 B2 | 10/2010 | Whitfield et al. |
| 7,819,894 B2 | 10/2010 | Mitsuishi et al. |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,422 B2 | 11/2010 | Benchetrit |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,829,416 B2 | 11/2010 | Kudou et al. |
| 7,831,292 B2 | 11/2010 | Quaid et al. |
| 7,832,408 B2 | 11/2010 | Shelton, IV et al. |
| 7,832,611 B2 | 11/2010 | Boyden et al. |
| 7,832,612 B2 | 11/2010 | Baxter et al. |
| 7,833,234 B2 | 11/2010 | Bailly et al. |
| 7,835,823 B2 | 11/2010 | Sillman et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,425 B2 | 11/2010 | Saeki et al. |
| 7,837,685 B2 | 11/2010 | Weinberg et al. |
| 7,837,687 B2 | 11/2010 | Harp |
| 7,837,694 B2 | 11/2010 | Tethrake et al. |
| 7,838,789 B2 | 11/2010 | Stoffers et al. |
| 7,839,109 B2 | 11/2010 | Carmen, Jr. et al. |
| 7,840,253 B2 | 11/2010 | Tremblay et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,843,158 B2 | 11/2010 | Prisco |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,845,538 B2 | 12/2010 | Whitman |
| 7,845,912 B2 | 12/2010 | Sung et al. |
| 7,846,085 B2 | 12/2010 | Silverman et al. |
| 7,846,149 B2 | 12/2010 | Jankowski |
| 7,846,161 B2 | 12/2010 | Dumbauld et al. |
| 7,848,066 B2 | 12/2010 | Yanagishima |
| 7,850,623 B2 | 12/2010 | Griffin et al. |
| 7,850,642 B2 | 12/2010 | Moll et al. |
| 7,850,982 B2 | 12/2010 | Stopek et al. |
| 7,853,813 B2 | 12/2010 | Lee |
| 7,854,735 B2 | 12/2010 | Houser et al. |
| 7,854,736 B2 | 12/2010 | Ryan |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,502 B2 | 1/2011 | Pool et al. |
| 7,862,546 B2 | 1/2011 | Conlon et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,871,440 B2 | 1/2011 | Schwartz et al. |
| 7,875,055 B2 | 1/2011 | Cichocki, Jr. |
| 7,879,063 B2 | 2/2011 | Khosravi |
| 7,879,070 B2 | 2/2011 | Ortiz et al. |
| 7,883,461 B2 | 2/2011 | Albrecht et al. |
| 7,883,465 B2 | 2/2011 | Donofrio et al. |
| 7,883,540 B2 | 2/2011 | Niwa et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,887,536 B2 | 2/2011 | Johnson et al. |
| 7,887,563 B2 | 2/2011 | Cummins |
| 7,887,755 B2 | 2/2011 | Mingerink et al. |
| 7,891,531 B1 | 2/2011 | Ward |
| 7,891,532 B2 | 2/2011 | Mastri et al. |
| 7,892,200 B2 | 2/2011 | Birk et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,671 B2 | 3/2011 | Kim et al. |
| 7,896,869 B2 | 3/2011 | Disilvestro et al. |
| 7,896,877 B2 | 3/2011 | Hall et al. |
| 7,896,895 B2 | 3/2011 | Boudreaux et al. |
| 7,896,897 B2 | 3/2011 | Gresham et al. |
| 7,896,900 B2 | 3/2011 | Frank et al. |
| 7,898,198 B2 | 3/2011 | Murphree |
| 7,900,805 B2 | 3/2011 | Shelton, IV et al. |
| 7,900,806 B2 | 3/2011 | Chen et al. |
| 7,901,381 B2 | 3/2011 | Birk et al. |
| 7,905,380 B2 | 3/2011 | Shelton, IV et al. |
| 7,905,381 B2 | 3/2011 | Baxter, III et al. |
| 7,905,881 B2 | 3/2011 | Masuda et al. |
| 7,905,889 B2 | 3/2011 | Catanese, III et al. |
| 7,905,890 B2 | 3/2011 | Whitfield et al. |
| 7,905,902 B2 | 3/2011 | Huitema et al. |
| 7,909,039 B2 | 3/2011 | Hur |
| 7,909,191 B2 | 3/2011 | Baker et al. |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,521 B2 | 3/2011 | Wang et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,918,848 B2 | 4/2011 | Lau et al. |
| 7,918,861 B2 | 4/2011 | Brock et al. |
| 7,918,867 B2 | 4/2011 | Dana et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,923,144 B2 | 4/2011 | Kohn et al. |
| 7,926,691 B2 | 4/2011 | Viola et al. |
| 7,926,692 B2 | 4/2011 | Racenet et al. |
| 7,927,328 B2 | 4/2011 | Orszulak et al. |
| 7,928,281 B2 | 4/2011 | Augustine |
| 7,930,040 B1 | 4/2011 | Kelsch et al. |
| 7,930,065 B2 | 4/2011 | Larkin et al. |
| 7,931,660 B2 | 4/2011 | Aranyi et al. |
| 7,931,695 B2 | 4/2011 | Ringeisen |
| 7,931,877 B2 | 4/2011 | Steffens et al. |
| 7,934,630 B2 | 5/2011 | Shelton, IV et al. |
| 7,934,631 B2 | 5/2011 | Balbierz et al. |
| 7,934,896 B2 | 5/2011 | Schnier |
| 7,935,130 B2 | 5/2011 | Williams |
| 7,935,773 B2 | 5/2011 | Hadba et al. |
| 7,936,142 B2 | 5/2011 | Otsuka et al. |
| 7,938,307 B2 | 5/2011 | Bettuchi |
| 7,939,152 B2 | 5/2011 | Haskin et al. |
| 7,941,865 B2 | 5/2011 | Seman, Jr. et al. |

(56) References Cited

U.S. PATENT DOCUMENTS

| | | | |
|---|---|---|---|
| 7,942,300 B2 * | 5/2011 | Rethy | A61B 17/07207 |
| | | | 227/175.1 |
| 7,942,303 B2 | 5/2011 | Shah | |
| 7,942,890 B2 | 5/2011 | D'Agostino et al. | |
| 7,944,175 B2 | 5/2011 | Mori et al. | |
| 7,945,792 B2 | 5/2011 | Cherpantier | |
| 7,945,798 B2 | 5/2011 | Carlson et al. | |
| 7,946,453 B2 | 5/2011 | Voegele et al. | |
| 7,947,011 B2 | 5/2011 | Birk et al. | |
| 7,948,381 B2 | 5/2011 | Lindsay et al. | |
| 7,950,560 B2 | 5/2011 | Zemlok et al. | |
| 7,950,561 B2 | 5/2011 | Aranyi | |
| 7,950,562 B2 | 5/2011 | Beardsley et al. | |
| 7,951,071 B2 | 5/2011 | Whitman et al. | |
| 7,951,166 B2 | 5/2011 | Orban, III et al. | |
| 7,954,682 B2 | 6/2011 | Giordano et al. | |
| 7,954,684 B2 | 6/2011 | Boudreaux | |
| 7,954,685 B2 | 6/2011 | Viola | |
| 7,954,686 B2 | 6/2011 | Baxter, III et al. | |
| 7,954,687 B2 | 6/2011 | Zemlok et al. | |
| 7,954,688 B2 | 6/2011 | Argentine et al. | |
| 7,955,253 B2 | 6/2011 | Ewers et al. | |
| 7,955,257 B2 | 6/2011 | Frasier et al. | |
| 7,955,322 B2 | 6/2011 | Devengenzo et al. | |
| 7,955,327 B2 | 6/2011 | Sartor et al. | |
| 7,955,380 B2 | 6/2011 | Chu et al. | |
| 7,959,050 B2 | 6/2011 | Smith et al. | |
| 7,959,051 B2 | 6/2011 | Smith et al. | |
| 7,959,052 B2 | 6/2011 | Sonnenschein et al. | |
| 7,963,432 B2 | 6/2011 | Knodel et al. | |
| 7,963,433 B2 | 6/2011 | Whitman et al. | |
| 7,963,913 B2 | 6/2011 | Devengenzo et al. | |
| 7,963,963 B2 | 6/2011 | Francischelli et al. | |
| 7,963,964 B2 | 6/2011 | Santilli et al. | |
| 7,964,206 B2 | 6/2011 | Suokas et al. | |
| 7,966,236 B2 | 6/2011 | Noriega et al. | |
| 7,966,269 B2 | 6/2011 | Bauer et al. | |
| 7,966,799 B2 | 6/2011 | Morgan et al. | |
| 7,967,178 B2 | 6/2011 | Scirica et al. | |
| 7,967,179 B2 | 6/2011 | Olson et al. | |
| 7,967,180 B2 | 6/2011 | Scirica | |
| 7,967,181 B2 | 6/2011 | Viola et al. | |
| 7,967,791 B2 | 6/2011 | Franer et al. | |
| 7,967,839 B2 | 6/2011 | Flock et al. | |
| 7,972,298 B2 | 7/2011 | Wallace et al. | |
| 7,972,315 B2 | 7/2011 | Birk et al. | |
| 7,976,213 B2 | 7/2011 | Bertolotti et al. | |
| 7,976,508 B2 | 7/2011 | Hoag | |
| 7,976,563 B2 | 7/2011 | Summerer | |
| 7,979,137 B2 | 7/2011 | Tracey et al. | |
| 7,980,443 B2 | 7/2011 | Scheib et al. | |
| 7,981,025 B2 | 7/2011 | Pool et al. | |
| 7,981,102 B2 | 7/2011 | Patel et al. | |
| 7,981,132 B2 | 7/2011 | Dubrul et al. | |
| 7,987,405 B2 | 7/2011 | Turner et al. | |
| 7,988,015 B2 | 8/2011 | Mason, II et al. | |
| 7,988,026 B2 | 8/2011 | Knodel et al. | |
| 7,988,027 B2 | 8/2011 | Olson et al. | |
| 7,988,028 B2 | 8/2011 | Farascioni et al. | |
| 7,988,779 B2 | 8/2011 | Disalvo et al. | |
| 7,992,757 B2 | 8/2011 | Wheeler et al. | |
| 7,993,360 B2 | 8/2011 | Hacker et al. | |
| 7,994,670 B2 | 8/2011 | Ji | |
| 7,997,054 B2 | 8/2011 | Bertsch et al. | |
| 7,997,468 B2 | 8/2011 | Farascioni | |
| 7,997,469 B2 | 8/2011 | Olson et al. | |
| 8,002,696 B2 | 8/2011 | Suzuki | |
| 8,002,784 B2 | 8/2011 | Jinno et al. | |
| 8,002,785 B2 | 8/2011 | Weiss et al. | |
| 8,002,795 B2 | 8/2011 | Beetel | |
| 8,006,365 B2 | 8/2011 | Levin et al. | |
| 8,006,885 B2 | 8/2011 | Marczyk | |
| 8,006,889 B2 | 8/2011 | Adams et al. | |
| 8,007,370 B2 | 8/2011 | Hirsch et al. | |
| 8,007,465 B2 | 8/2011 | Birk et al. | |
| 8,007,479 B2 | 8/2011 | Birk et al. | |
| 8,007,511 B2 | 8/2011 | Brock et al. | |
| 8,007,513 B2 | 8/2011 | Nalagatla et al. | |
| 8,008,598 B2 | 8/2011 | Whitman et al. | |
| 8,010,180 B2 | 8/2011 | Quaid et al. | |
| 8,011,550 B2 | 9/2011 | Aranyi et al. | |
| 8,011,551 B2 | 9/2011 | Marczyk et al. | |
| 8,011,553 B2 | 9/2011 | Mastri et al. | |
| 8,011,555 B2 | 9/2011 | Tarinelli et al. | |
| 8,012,170 B2 | 9/2011 | Whitman et al. | |
| 8,016,176 B2 | 9/2011 | Kasvikis et al. | |
| 8,016,177 B2 | 9/2011 | Bettuchi et al. | |
| 8,016,178 B2 | 9/2011 | Olson et al. | |
| 8,016,849 B2 | 9/2011 | Wenchell | |
| 8,016,855 B2 | 9/2011 | Whitman et al. | |
| 8,016,858 B2 | 9/2011 | Whitman | |
| 8,016,881 B2 | 9/2011 | Furst | |
| 8,020,742 B2 | 9/2011 | Marczyk | |
| 8,020,743 B2 | 9/2011 | Shelton, IV | |
| 8,021,375 B2 | 9/2011 | Aldrich et al. | |
| 8,025,199 B2 | 9/2011 | Whitman et al. | |
| 8,025,896 B2 | 9/2011 | Malaviya et al. | |
| 8,028,835 B2 | 10/2011 | Yasuda et al. | |
| 8,028,882 B2 | 10/2011 | Viola | |
| 8,028,883 B2 | 10/2011 | Stopek | |
| 8,028,884 B2 | 10/2011 | Sniffin et al. | |
| 8,028,885 B2 | 10/2011 | Smith et al. | |
| 8,029,510 B2 | 10/2011 | Hoegerle | |
| 8,031,069 B2 | 10/2011 | Cohn et al. | |
| 8,033,438 B2 | 10/2011 | Scirica | |
| 8,033,439 B2 | 10/2011 | Racenet et al. | |
| 8,033,440 B2 | 10/2011 | Wenchell et al. | |
| 8,033,442 B2 | 10/2011 | Racenet et al. | |
| 8,034,077 B2 | 10/2011 | Smith et al. | |
| 8,034,337 B2 | 10/2011 | Simard | |
| 8,034,363 B2 | 10/2011 | Li et al. | |
| 8,035,487 B2 | 10/2011 | Malackowski | |
| 8,037,591 B2 | 10/2011 | Spivey et al. | |
| 8,038,044 B2 | 10/2011 | Viola | |
| 8,038,045 B2 | 10/2011 | Bettuchi et al. | |
| 8,038,046 B2 | 10/2011 | Smith et al. | |
| 8,038,686 B2 | 10/2011 | Huitema et al. | |
| 8,043,207 B2 | 10/2011 | Adams | |
| 8,043,328 B2 | 10/2011 | Hahnen et al. | |
| 8,044,536 B2 | 10/2011 | Nguyen et al. | |
| 8,044,604 B2 | 10/2011 | Hagino et al. | |
| 8,047,236 B2 | 11/2011 | Perry | |
| 8,048,503 B2 | 11/2011 | Farnsworth et al. | |
| 8,052,636 B2 | 11/2011 | Moll et al. | |
| 8,056,787 B2 | 11/2011 | Boudreaux et al. | |
| 8,056,788 B2 | 11/2011 | Mastri et al. | |
| 8,056,789 B1 | 11/2011 | White et al. | |
| 8,057,508 B2 | 11/2011 | Shelton, IV | |
| 8,058,771 B2 | 11/2011 | Giordano et al. | |
| 8,060,250 B2 | 11/2011 | Reiland et al. | |
| 8,061,014 B2 | 11/2011 | Smith et al. | |
| 8,061,576 B2 | 11/2011 | Cappola | |
| 8,062,236 B2 | 11/2011 | Soltz | |
| 8,062,306 B2 | 11/2011 | Nobis et al. | |
| 8,062,330 B2 | 11/2011 | Prommersberger et al. | |
| 8,063,619 B2 | 11/2011 | Zhu et al. | |
| 8,066,158 B2 | 11/2011 | Vogel et al. | |
| 8,066,166 B2 | 11/2011 | Demmy et al. | |
| 8,066,167 B2 | 11/2011 | Measamer et al. | |
| 8,066,168 B2 | 11/2011 | Vidal et al. | |
| 8,066,720 B2 | 11/2011 | Knodel et al. | |
| D650,074 S | 12/2011 | Hunt et al. | |
| D650,789 S | 12/2011 | Arnold | |
| 8,070,033 B2 | 12/2011 | Milliman et al. | |
| 8,070,034 B1 | 12/2011 | Knodel | |
| 8,070,035 B2 | 12/2011 | Holsten et al. | |
| 8,070,743 B2 | 12/2011 | Kagan et al. | |
| 8,074,858 B2 | 12/2011 | Marczyk | |
| 8,074,859 B2 | 12/2011 | Kostrzewski | |
| 8,074,861 B2 | 12/2011 | Ehrenfels et al. | |
| 8,075,476 B2 | 12/2011 | Vargas | |
| 8,075,571 B2 | 12/2011 | Vitali et al. | |
| 8,079,950 B2 | 12/2011 | Stern et al. | |
| 8,079,989 B2 | 12/2011 | Birk et al. | |

(56) References Cited

U.S. PATENT DOCUMENTS

| | | |
|---|---|---|
| 8,080,004 B2 | 12/2011 | Downey et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,084,969 B2 | 12/2011 | David et al. |
| 8,085,013 B2 | 12/2011 | Wei et al. |
| 8,087,562 B1 | 1/2012 | Manoux et al. |
| 8,087,563 B1 | 1/2012 | Milliman et al. |
| 8,089,509 B2 | 1/2012 | Chatenever et al. |
| 8,091,753 B2 | 1/2012 | Viola |
| 8,091,756 B2 | 1/2012 | Viola |
| 8,092,443 B2 | 1/2012 | Bischoff |
| 8,092,932 B2 | 1/2012 | Phillips et al. |
| 8,093,572 B2 | 1/2012 | Kuduvalli |
| 8,096,458 B2 | 1/2012 | Hessler |
| 8,096,459 B2 | 1/2012 | Ortiz et al. |
| 8,097,017 B2 | 1/2012 | Viola |
| 8,100,310 B2 | 1/2012 | Zemlok |
| 8,100,824 B2 | 1/2012 | Hegeman et al. |
| 8,100,872 B2 | 1/2012 | Patel |
| 8,102,138 B2 | 1/2012 | Sekine et al. |
| 8,102,278 B2 | 1/2012 | Deck et al. |
| 8,105,320 B2 | 1/2012 | Manzo |
| 8,105,350 B2 | 1/2012 | Lee et al. |
| 8,107,925 B2 | 1/2012 | Natsuno et al. |
| 8,108,033 B2 | 1/2012 | Drew et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,114,017 B2 | 2/2012 | Bacher |
| 8,114,100 B2 | 2/2012 | Smith et al. |
| 8,114,345 B2 | 2/2012 | Dlugos, Jr. et al. |
| 8,118,206 B2 | 2/2012 | Zand et al. |
| 8,118,207 B2 | 2/2012 | Racenet et al. |
| 8,120,301 B2 | 2/2012 | Goldberg et al. |
| 8,122,128 B2 | 2/2012 | Burke, II et al. |
| 8,123,103 B2 | 2/2012 | Milliman |
| 8,123,523 B2 | 2/2012 | Carron et al. |
| 8,123,766 B2 | 2/2012 | Bauman et al. |
| 8,123,767 B2 | 2/2012 | Bauman et al. |
| 8,125,168 B2 | 2/2012 | Johnson et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,128,662 B2 | 3/2012 | Altarac et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,133,500 B2 | 3/2012 | Ringeisen et al. |
| 8,134,306 B2 | 3/2012 | Drader et al. |
| 8,136,711 B2 | 3/2012 | Beardsley et al. |
| 8,136,712 B2 | 3/2012 | Zingman |
| 8,136,713 B2 | 3/2012 | Hathaway et al. |
| 8,137,339 B2 | 3/2012 | Jinno et al. |
| 8,140,417 B2 | 3/2012 | Shibata |
| 8,141,762 B2 | 3/2012 | Bedi et al. |
| 8,141,763 B2 | 3/2012 | Milliman |
| 8,142,200 B2 | 3/2012 | Crunkilton et al. |
| 8,142,425 B2 | 3/2012 | Eggers |
| 8,142,461 B2 | 3/2012 | Houser et al. |
| 8,142,515 B2 | 3/2012 | Therin et al. |
| 8,143,520 B2 | 3/2012 | Cutler |
| 8,146,790 B2 | 4/2012 | Milliman |
| 8,147,421 B2 | 4/2012 | Farquhar et al. |
| 8,147,456 B2 | 4/2012 | Fisher et al. |
| 8,147,485 B2 | 4/2012 | Wham et al. |
| 8,152,041 B2 | 4/2012 | Kostrzewski |
| 8,152,756 B2 | 4/2012 | Webster et al. |
| 8,154,239 B2 | 4/2012 | Katsuki et al. |
| 8,157,145 B2 | 4/2012 | Shelton, IV et al. |
| 8,157,148 B2 * | 4/2012 | Scirica ............ A61B 17/07207 227/175.1 |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,157,834 B2 | 4/2012 | Conlon |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,162,668 B2 | 4/2012 | Toly |
| 8,162,933 B2 | 4/2012 | Francischelli et al. |
| 8,162,965 B2 | 4/2012 | Reschke et al. |
| 8,167,185 B2 | 5/2012 | Shelton, IV et al. |
| 8,167,622 B2 | 5/2012 | Zhou |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,004 B2 | 5/2012 | Ho |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,776 B2 | 5/2012 | Humayun et al. |
| 8,177,797 B2 | 5/2012 | Shimoji et al. |
| 8,179,705 B2 | 5/2012 | Chapuis |
| 8,180,458 B2 | 5/2012 | Kane et al. |
| 8,181,839 B2 | 5/2012 | Beetel |
| 8,181,840 B2 | 5/2012 | Milliman |
| 8,182,422 B2 | 5/2012 | Bayer et al. |
| 8,182,444 B2 | 5/2012 | Uber, III et al. |
| 8,183,807 B2 | 5/2012 | Tsai et al. |
| 8,186,555 B2 | 5/2012 | Shelton, IV et al. |
| 8,186,556 B2 | 5/2012 | Viola |
| 8,186,558 B2 | 5/2012 | Sapienza |
| 8,186,560 B2 | 5/2012 | Hess et al. |
| 8,190,238 B2 | 5/2012 | Moll et al. |
| 8,191,752 B2 | 6/2012 | Scirica |
| 8,192,350 B2 | 6/2012 | Ortiz et al. |
| 8,192,460 B2 | 6/2012 | Orban, III et al. |
| 8,192,651 B2 | 6/2012 | Young et al. |
| 8,193,129 B2 | 6/2012 | Tagawa et al. |
| 8,196,795 B2 | 6/2012 | Moore et al. |
| 8,196,796 B2 | 6/2012 | Shelton, IV et al. |
| 8,197,501 B2 | 6/2012 | Shadeck et al. |
| 8,197,502 B2 | 6/2012 | Smith et al. |
| 8,197,837 B2 | 6/2012 | Jamiolkowski et al. |
| 8,201,720 B2 | 6/2012 | Hessler |
| 8,201,721 B2 | 6/2012 | Zemlok et al. |
| 8,202,549 B2 | 6/2012 | Stucky et al. |
| 8,205,779 B2 | 6/2012 | Ma et al. |
| 8,205,780 B2 | 6/2012 | Sorrentino et al. |
| 8,205,781 B2 | 6/2012 | Baxter, III et al. |
| 8,207,863 B2 | 6/2012 | Neubauer et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,210,721 B2 | 7/2012 | Chen et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,532 B2 | 7/2012 | Marczyk |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,402 B2 | 7/2012 | Francischelli et al. |
| 8,221,424 B2 | 7/2012 | Cha |
| 8,221,433 B2 | 7/2012 | Lozier et al. |
| 8,225,799 B2 | 7/2012 | Bettuchi |
| 8,225,979 B2 * | 7/2012 | Farascioni ........ A61B 17/07207 227/175.2 |
| 8,226,553 B2 | 7/2012 | Shelton, IV et al. |
| 8,226,635 B2 | 7/2012 | Petrie et al. |
| 8,226,675 B2 | 7/2012 | Houser et al. |
| 8,226,715 B2 | 7/2012 | Hwang et al. |
| 8,227,946 B2 | 7/2012 | Kim |

(56) References Cited

U.S. PATENT DOCUMENTS

| | | |
|---|---|---|
| 8,228,020 B2 | 7/2012 | Shin et al. |
| 8,228,048 B2 | 7/2012 | Spencer |
| 8,229,549 B2 | 7/2012 | Whitman et al. |
| 8,231,040 B2 | 7/2012 | Zemlok et al. |
| 8,231,042 B2 | 7/2012 | Hessler et al. |
| 8,231,043 B2 | 7/2012 | Tarinelli et al. |
| 8,235,272 B2 | 8/2012 | Nicholas et al. |
| 8,235,274 B2 * | 8/2012 | Cappola ............ A61B 17/072 227/175.1 |
| 8,236,010 B2 | 8/2012 | Ortiz et al. |
| 8,236,011 B2 | 8/2012 | Harris et al. |
| 8,236,020 B2 | 8/2012 | Smith et al. |
| 8,237,388 B2 | 8/2012 | Jinno et al. |
| 8,240,537 B2 | 8/2012 | Marczyk |
| 8,241,271 B2 | 8/2012 | Millman et al. |
| 8,241,284 B2 | 8/2012 | Dycus et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stope |
| 8,246,608 B2 | 8/2012 | Omori et al. |
| 8,246,637 B2 | 8/2012 | Viola et al. |
| 8,252,009 B2 | 8/2012 | Weller et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,386 B2 | 9/2012 | Lee et al. |
| 8,257,391 B2 | 9/2012 | Orban, III et al. |
| 8,257,634 B2 | 9/2012 | Scirica |
| 8,258,745 B2 | 9/2012 | Smith et al. |
| 8,261,958 B1 | 9/2012 | Knodel |
| 8,262,560 B2 | 9/2012 | Whitman |
| 8,262,655 B2 | 9/2012 | Ghabrial et al. |
| 8,266,232 B2 | 9/2012 | Piper et al. |
| 8,267,300 B2 | 9/2012 | Boudreaux |
| 8,267,849 B2 | 9/2012 | Wazer et al. |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,268,344 B2 | 9/2012 | Ma et al. |
| 8,269,121 B2 | 9/2012 | Smith |
| 8,272,553 B2 | 9/2012 | Mastri et al. |
| 8,272,554 B2 | 9/2012 | Whitman et al. |
| 8,272,918 B2 | 9/2012 | Lam |
| 8,273,404 B2 | 9/2012 | Dave et al. |
| 8,276,594 B2 | 10/2012 | Shah |
| 8,276,801 B2 | 10/2012 | Zemlok et al. |
| 8,276,802 B2 | 10/2012 | Kostrzewski |
| 8,277,473 B2 | 10/2012 | Sunaoshi et al. |
| 8,281,446 B2 | 10/2012 | Moskovich |
| 8,281,973 B2 | 10/2012 | Wenchell et al. |
| 8,281,974 B2 | 10/2012 | Hessler et al. |
| 8,282,654 B2 | 10/2012 | Ferrari et al. |
| 8,285,367 B2 | 10/2012 | Hyde et al. |
| 8,286,723 B2 | 10/2012 | Puzio et al. |
| 8,286,845 B2 | 10/2012 | Perry et al. |
| 8,286,846 B2 | 10/2012 | Smith et al. |
| 8,286,847 B2 | 10/2012 | Taylor |
| 8,287,487 B2 | 10/2012 | Estes |
| 8,287,522 B2 | 10/2012 | Moses et al. |
| 8,287,561 B2 | 10/2012 | Nunez et al. |
| 8,288,984 B2 | 10/2012 | Yang |
| 8,289,403 B2 | 10/2012 | Dobashi et al. |
| 8,290,883 B2 | 10/2012 | Takeuchi et al. |
| 8,292,147 B2 | 10/2012 | Viola |
| 8,292,148 B2 | 10/2012 | Viola |
| 8,292,150 B2 | 10/2012 | Bryant |
| 8,292,151 B2 | 10/2012 | Viola |
| 8,292,152 B2 | 10/2012 | Milliman et al. |
| 8,292,155 B2 | 10/2012 | Shelton, IV et al. |
| 8,292,157 B2 | 10/2012 | Smith et al. |
| 8,292,158 B2 | 10/2012 | Sapienza |
| 8,292,801 B2 | 10/2012 | Dejima et al. |
| 8,292,888 B2 | 10/2012 | Whitman |
| 8,292,906 B2 | 10/2012 | Taylor et al. |
| 8,294,399 B2 | 10/2012 | Suzuki et al. |
| 8,298,161 B2 | 10/2012 | Vargas |
| 8,298,189 B2 | 10/2012 | Fisher et al. |
| 8,298,233 B2 | 10/2012 | Mueller |
| 8,298,677 B2 | 10/2012 | Wiesner et al. |
| 8,302,323 B2 | 11/2012 | Fortier et al. |
| 8,303,621 B2 | 11/2012 | Miyamoto et al. |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 * | 11/2012 | Bindra ............ A61B 17/07207 227/176.1 |
| 8,308,046 B2 | 11/2012 | Prommersberger |
| 8,308,659 B2 | 11/2012 | Scheibe et al. |
| 8,308,725 B2 | 11/2012 | Bell et al. |
| 8,310,188 B2 | 11/2012 | Nakai |
| 8,313,496 B2 | 11/2012 | Sauer et al. |
| 8,313,499 B2 | 11/2012 | Magnusson et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,437 B2 | 11/2012 | Merkley et al. |
| 8,317,744 B2 | 11/2012 | Kirschenman |
| 8,317,790 B2 | 11/2012 | Bell et al. |
| 8,319,002 B2 | 11/2012 | Daniels et al. |
| D672,784 S | 12/2012 | Clanton et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,322,901 B2 | 12/2012 | Michelotti |
| 8,323,271 B2 | 12/2012 | Humayun et al. |
| 8,323,789 B2 | 12/2012 | Rozhin et al. |
| 8,324,585 B2 | 12/2012 | McBroom et al. |
| 8,327,514 B2 | 12/2012 | Kim |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,065 B2 | 12/2012 | Shah |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,691 B2 | 12/2012 | Schaaf |
| 8,333,764 B2 | 12/2012 | Francischelli et al. |
| 8,333,779 B2 | 12/2012 | Smith et al. |
| 8,334,468 B2 | 12/2012 | Palmer et al. |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,343,150 B2 | 1/2013 | Artale |
| 8,347,978 B2 | 1/2013 | Forster et al. |
| 8,348,118 B2 | 1/2013 | Segura |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,837 B2 | 1/2013 | Wenchell |
| 8,348,959 B2 | 1/2013 | Wolford et al. |
| 8,348,972 B2 | 1/2013 | Soltz et al. |
| 8,349,987 B2 | 1/2013 | Kapiamba et al. |
| 8,352,004 B2 | 1/2013 | Mannheimer et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |

(56) References Cited

U.S. PATENT DOCUMENTS

| | | | |
|---|---|---|---|
| 8,357,158 B2 | 1/2013 | McKenna et al. | |
| 8,357,161 B2 | 1/2013 | Mueller | |
| 8,359,174 B2 | 1/2013 | Nakashima et al. | |
| 8,360,296 B2 | 1/2013 | Zingman | |
| 8,360,297 B2* | 1/2013 | Shelton, IV | A61B 17/105 |
| | | | 227/176.1 |
| 8,360,298 B2 | 1/2013 | Farascioni et al. | |
| 8,360,299 B2 | 1/2013 | Zemlok et al. | |
| 8,361,501 B2 | 1/2013 | DiTizio et al. | |
| D676,866 S | 2/2013 | Chaudhri | |
| 8,365,972 B2 | 2/2013 | Aranyi et al. | |
| 8,365,973 B1 | 2/2013 | White et al. | |
| 8,365,975 B1 | 2/2013 | Manoux et al. | |
| 8,365,976 B2 | 2/2013 | Hess et al. | |
| 8,366,559 B2 | 2/2013 | Papenfuss et al. | |
| 8,366,719 B2 | 2/2013 | Markey et al. | |
| 8,366,787 B2 | 2/2013 | Brown et al. | |
| 8,368,327 B2 | 2/2013 | Benning et al. | |
| 8,369,056 B2 | 2/2013 | Senriuchi et al. | |
| 8,371,393 B2 | 2/2013 | Higuchi et al. | |
| 8,371,491 B2 | 2/2013 | Huitema et al. | |
| 8,371,492 B2 | 2/2013 | Aranyi et al. | |
| 8,371,493 B2 | 2/2013 | Aranyi et al. | |
| 8,371,494 B2 | 2/2013 | Racenet et al. | |
| 8,372,094 B2 | 2/2013 | Bettuchi et al. | |
| 8,374,723 B2 | 2/2013 | Zhao et al. | |
| 8,376,865 B2 | 2/2013 | Forster et al. | |
| 8,377,029 B2 | 2/2013 | Nagao et al. | |
| 8,377,044 B2 | 2/2013 | Coe et al. | |
| 8,377,059 B2 | 2/2013 | Deville et al. | |
| 8,381,828 B2 | 2/2013 | Whitman et al. | |
| 8,382,773 B2 | 2/2013 | Whitfield et al. | |
| 8,382,790 B2 | 2/2013 | Uenohara et al. | |
| D677,273 S | 3/2013 | Randall et al. | |
| 8,387,848 B2 | 3/2013 | Johnson et al. | |
| 8,388,633 B2 | 3/2013 | Rousseau et al. | |
| 8,389,588 B2 | 3/2013 | Ringeisen et al. | |
| 8,393,513 B2 | 3/2013 | Jankowski | |
| 8,393,514 B2 | 3/2013 | Shelton, IV et al. | |
| 8,393,516 B2 | 3/2013 | Kostrzewski | |
| 8,397,832 B2 | 3/2013 | Blickle et al. | |
| 8,397,971 B2 | 3/2013 | Yates et al. | |
| 8,397,972 B2* | 3/2013 | Kostrzewski | A61B 17/068 |
| | | | 227/175.2 |
| 8,397,973 B1 | 3/2013 | Hausen | |
| 8,398,633 B2 | 3/2013 | Mueller | |
| 8,398,669 B2 | 3/2013 | Kim | |
| 8,398,673 B2 | 3/2013 | Hinchliffe et al. | |
| 8,398,674 B2 | 3/2013 | Prestel | |
| 8,400,108 B2 | 3/2013 | Powell et al. | |
| 8,400,851 B2 | 3/2013 | Byun | |
| 8,403,138 B2 | 3/2013 | Weisshaupt et al. | |
| 8,403,195 B2 | 3/2013 | Beardsley et al. | |
| 8,403,196 B2 | 3/2013 | Beardsley et al. | |
| 8,403,198 B2 | 3/2013 | Sorrentino et al. | |
| 8,403,832 B2 | 3/2013 | Cunningham et al. | |
| 8,403,926 B2 | 3/2013 | Nobis et al. | |
| 8,403,945 B2 | 3/2013 | Whitfield et al. | |
| 8,403,946 B2 | 3/2013 | Whitfield et al. | |
| 8,403,950 B2 | 3/2013 | Palmer et al. | |
| D680,646 S | 4/2013 | Hunt et al. | |
| 8,408,439 B2 | 4/2013 | Huang et al. | |
| 8,408,442 B2 | 4/2013 | Racenet et al. | |
| 8,409,079 B2 | 4/2013 | Okamoto et al. | |
| 8,409,174 B2 | 4/2013 | Omori | |
| 8,409,175 B2 | 4/2013 | Lee et al. | |
| 8,409,211 B2 | 4/2013 | Baroud | |
| 8,409,222 B2 | 4/2013 | Whitfield et al. | |
| 8,409,223 B2 | 4/2013 | Sorrentino et al. | |
| 8,411,500 B2 | 4/2013 | Gapihan et al. | |
| 8,413,661 B2 | 4/2013 | Rousseau et al. | |
| 8,413,870 B2 | 4/2013 | Pastorelli et al. | |
| 8,413,871 B2 | 4/2013 | Racenet et al. | |
| 8,413,872 B2 | 4/2013 | Patel | |
| 8,414,469 B2 | 4/2013 | Diolaiti | |
| 8,414,577 B2 | 4/2013 | Boudreaux et al. | |
| 8,414,598 B2 | 4/2013 | Brock et al. | |
| 8,418,073 B2 | 4/2013 | Mohr et al. | |
| 8,418,906 B2 | 4/2013 | Farascioni et al. | |
| 8,418,907 B2 | 4/2013 | Johnson et al. | |
| 8,418,908 B1 | 4/2013 | Beardsley | |
| 8,418,909 B2 | 4/2013 | Kostrzewski | |
| 8,419,635 B2 | 4/2013 | Shelton, IV et al. | |
| 8,419,717 B2 | 4/2013 | Diolaiti et al. | |
| 8,419,747 B2 | 4/2013 | Hinman et al. | |
| 8,419,754 B2 | 4/2013 | Laby et al. | |
| 8,419,755 B2 | 4/2013 | Deem et al. | |
| 8,423,182 B2 | 4/2013 | Robinson et al. | |
| 8,424,737 B2 | 4/2013 | Scirica | |
| 8,424,739 B2 | 4/2013 | Racenet et al. | |
| 8,424,740 B2 | 4/2013 | Shelton, IV et al. | |
| 8,424,741 B2 | 4/2013 | McGuckin, Jr. et al. | |
| 8,425,600 B2 | 4/2013 | Maxwell | |
| 8,427,430 B2 | 4/2013 | Lee et al. | |
| 8,430,292 B2 | 4/2013 | Patel et al. | |
| 8,430,892 B2 | 4/2013 | Bindra et al. | |
| 8,430,898 B2 | 4/2013 | Wiener et al. | |
| 8,435,257 B2 | 5/2013 | Smith et al. | |
| 8,439,246 B1 | 5/2013 | Knodel | |
| 8,439,830 B2 | 5/2013 | McKinley et al. | |
| 8,444,036 B2 | 5/2013 | Shelton, IV | |
| 8,444,037 B2 | 5/2013 | Nicholas et al. | |
| 8,444,549 B2 | 5/2013 | Viola et al. | |
| 8,449,536 B2 | 5/2013 | Selig | |
| 8,449,560 B2 | 5/2013 | Roth et al. | |
| 8,453,904 B2 | 6/2013 | Eskaros et al. | |
| 8,453,906 B2 | 6/2013 | Huang et al. | |
| 8,453,907 B2 | 6/2013 | Laurent et al. | |
| 8,453,908 B2 | 6/2013 | Bedi et al. | |
| 8,453,912 B2 | 6/2013 | Mastri et al. | |
| 8,453,914 B2 | 6/2013 | Laurent et al. | |
| 8,454,495 B2 | 6/2013 | Kawano et al. | |
| 8,454,551 B2 | 6/2013 | Allen et al. | |
| 8,454,628 B2 | 6/2013 | Smith et al. | |
| 8,454,640 B2 | 6/2013 | Johnston et al. | |
| 8,457,757 B2 | 6/2013 | Cauller et al. | |
| 8,459,520 B2 | 6/2013 | Giordano et al. | |
| 8,459,521 B2 | 6/2013 | Zemlok et al. | |
| 8,459,524 B2 | 6/2013 | Pribanic et al. | |
| 8,459,525 B2 | 6/2013 | Yates et al. | |
| 8,464,922 B2 | 6/2013 | Marczyk | |
| 8,464,923 B2 | 6/2013 | Shelton, IV | |
| 8,464,924 B2 | 6/2013 | Gresham et al. | |
| 8,464,925 B2 | 6/2013 | Hull et al. | |
| 8,465,475 B2 | 6/2013 | Isbell, Jr. | |
| 8,465,502 B2 | 6/2013 | Zergiebel | |
| 8,465,515 B2 | 6/2013 | Drew et al. | |
| 8,469,254 B2 | 6/2013 | Czernik et al. | |
| 8,469,946 B2 | 6/2013 | Sugita | |
| 8,469,973 B2 | 6/2013 | Meade et al. | |
| 8,470,355 B2 | 6/2013 | Skalla et al. | |
| D686,240 S | 7/2013 | Lin | |
| D686,244 S | 7/2013 | Moriya et al. | |
| 8,474,677 B2 | 7/2013 | Woodard, Jr. et al. | |
| 8,475,453 B2 | 7/2013 | Marczyk et al. | |
| 8,475,454 B1 | 7/2013 | Alshemari | |
| 8,475,474 B2 | 7/2013 | Bombard et al. | |
| 8,479,968 B2 | 7/2013 | Hodgkinson et al. | |
| 8,479,969 B2 | 7/2013 | Shelton, IV | |
| 8,480,703 B2 | 7/2013 | Nicholas et al. | |
| 8,483,509 B2 | 7/2013 | Matsuzaka | |
| 8,485,412 B2 | 7/2013 | Shelton, IV et al. | |
| 8,485,413 B2 | 7/2013 | Scheib et al. | |
| 8,485,970 B2 | 7/2013 | Widenhouse et al. | |
| 8,486,047 B2 | 7/2013 | Stope | |
| 8,487,199 B2 | 7/2013 | Palmer et al. | |
| 8,487,487 B2 | 7/2013 | Dietz et al. | |
| 8,490,851 B2 | 7/2013 | Blier et al. | |
| 8,490,852 B2 | 7/2013 | Viola | |
| 8,490,853 B2 | 7/2013 | Criscuolo et al. | |
| 8,491,581 B2 | 7/2013 | Deville et al. | |
| 8,491,603 B2 | 7/2013 | Yeung et al. | |
| 8,496,153 B2 | 7/2013 | Demmy et al. | |
| 8,496,154 B2 | 7/2013 | Marczyk et al. | |

(56) References Cited

U.S. PATENT DOCUMENTS

| | | |
|---|---|---|
| 8,496,156 B2 | 7/2013 | Sniffin et al. |
| 8,496,683 B2 | 7/2013 | Prommersberger et al. |
| 8,498,691 B2 | 7/2013 | Moll et al. |
| 8,499,673 B2 | 8/2013 | Keller |
| 8,499,966 B2 | 8/2013 | Palmer et al. |
| 8,499,992 B2 | 8/2013 | Whitman et al. |
| 8,499,993 B2 | 8/2013 | Shelton, IV et al. |
| 8,499,994 B2 | 8/2013 | D'Arcangelo |
| 8,500,721 B2 | 8/2013 | Jinno |
| 8,500,762 B2 | 8/2013 | Sholev et al. |
| 8,502,091 B2 | 8/2013 | Palmer et al. |
| 8,505,799 B2 | 8/2013 | Viola et al. |
| 8,505,801 B2 | 8/2013 | Ehrenfels et al. |
| 8,506,555 B2 | 8/2013 | Ruiz Morales |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,511,308 B2 | 8/2013 | Hecox et al. |
| 8,512,359 B2 | 8/2013 | Whitman et al. |
| 8,512,402 B2 | 8/2013 | Marczyk et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,517,938 B2 | 8/2013 | Eisenhardt et al. |
| 8,518,024 B2 | 8/2013 | Williams et al. |
| 8,521,273 B2 | 8/2013 | Kliman |
| 8,523,042 B2 | 9/2013 | Masiakos et al. |
| 8,523,043 B2 | 9/2013 | Ullrich et al. |
| 8,523,787 B2 | 9/2013 | Ludwin et al. |
| 8,523,881 B2 | 9/2013 | Cabiri et al. |
| 8,523,882 B2 | 9/2013 | Huitema et al. |
| 8,523,900 B2 | 9/2013 | Jinno et al. |
| 8,529,588 B2 | 9/2013 | Ahlberg et al. |
| 8,529,599 B2 | 9/2013 | Holsten |
| 8,529,600 B2 | 9/2013 | Woodard, Jr. et al. |
| 8,529,819 B2 | 9/2013 | Ostapoff et al. |
| 8,532,747 B2 | 9/2013 | Nock et al. |
| 8,534,527 B2 | 9/2013 | Brendel et al. |
| 8,534,528 B2 | 9/2013 | Shelton, IV |
| 8,535,304 B2 | 9/2013 | Sklar et al. |
| 8,535,340 B2 | 9/2013 | Allen |
| 8,539,866 B2 | 9/2013 | Nayak et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,646 B2 | 9/2013 | Mendez-Coll |
| 8,540,733 B2 | 9/2013 | Whitman et al. |
| 8,540,735 B2 | 9/2013 | Mitelberg et al. |
| 8,550,984 B2 | 10/2013 | Takemoto |
| 8,551,076 B2 | 10/2013 | Duval et al. |
| 8,555,660 B2 | 10/2013 | Takenaka et al. |
| 8,556,151 B2 | 10/2013 | Viola |
| 8,556,918 B2 | 10/2013 | Bauman et al. |
| 8,556,935 B1 | 10/2013 | Knodel et al. |
| 8,560,147 B2 | 10/2013 | Taylor et al. |
| 8,561,617 B2 | 10/2013 | Lindh et al. |
| 8,561,870 B2 | 10/2013 | Baxter, III et al. |
| 8,561,871 B2 | 10/2013 | Rajappa et al. |
| 8,561,873 B2 | 10/2013 | Ingmanson et al. |
| 8,562,592 B2 | 10/2013 | Conlon et al. |
| 8,562,598 B2 | 10/2013 | Falkenstein et al. |
| 8,567,656 B2 | 10/2013 | Shelton, IV et al. |
| 8,568,416 B2 | 10/2013 | Schmitz et al. |
| 8,568,425 B2 | 10/2013 | Ross et al. |
| D692,916 S | 11/2013 | Granchi et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,465 B2 | 11/2013 | Shelton, IV |
| 8,574,199 B2 | 11/2013 | von Bulow et al. |
| 8,574,263 B2 | 11/2013 | Mueller |
| 8,575,880 B2 | 11/2013 | Grantz |
| 8,575,895 B2 | 11/2013 | Garrastacho et al. |
| 8,579,176 B2 | 11/2013 | Smith et al. |
| 8,579,178 B2 | 11/2013 | Holsten et al. |
| 8,579,897 B2 | 11/2013 | Vakharia et al. |
| 8,579,937 B2 | 11/2013 | Gresham |
| 8,584,919 B2 | 11/2013 | Hueil et al. |
| 8,584,920 B2 | 11/2013 | Hodgkinson |
| 8,584,921 B2 | 11/2013 | Scirica |
| 8,585,583 B2 | 11/2013 | Sakaguchi et al. |
| 8,585,598 B2 | 11/2013 | Razzaque et al. |
| 8,585,721 B2 | 11/2013 | Kirsch |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,591,400 B2 | 11/2013 | Sugiyama |
| 8,596,515 B2 | 12/2013 | Okoniewski |
| 8,597,745 B2 | 12/2013 | Farnsworth et al. |
| 8,599,450 B2 | 12/2013 | Kubo et al. |
| 8,602,125 B2 | 12/2013 | King |
| 8,602,287 B2 | 12/2013 | Yates et al. |
| 8,602,288 B2 | 12/2013 | Shelton, IV et al. |
| 8,603,077 B2 | 12/2013 | Cooper et al. |
| 8,603,089 B2 | 12/2013 | Viola |
| 8,603,110 B2 | 12/2013 | Maruyama et al. |
| 8,603,135 B2 | 12/2013 | Mueller |
| 8,608,043 B2 | 12/2013 | Scirica |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,431 B2 | 12/2013 | Timm et al. |
| 8,617,155 B2 | 12/2013 | Johnson et al. |
| 8,620,473 B2 | 12/2013 | Diolaiti et al. |
| 8,622,274 B2 | 1/2014 | Yates et al. |
| 8,622,275 B2 | 1/2014 | Baxter, III et al. |
| 8,627,993 B2 | 1/2014 | Smith et al. |
| 8,627,994 B2 | 1/2014 | Zemlok et al. |
| 8,627,995 B2 | 1/2014 | Smith et al. |
| 8,628,467 B2 | 1/2014 | Whitman et al. |
| 8,628,518 B2 | 1/2014 | Blumenkranz et al. |
| 8,628,544 B2 | 1/2014 | Farascioni |
| 8,628,545 B2 | 1/2014 | Cabrera et al. |
| 8,631,987 B2 | 1/2014 | Shelton, IV et al. |
| 8,631,992 B1 | 1/2014 | Hausen et al. |
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,539 B2 | 1/2014 | Twomey et al. |
| 8,632,563 B2 | 1/2014 | Nagase et al. |
| 8,636,187 B2 | 1/2014 | Hueil et al. |
| 8,636,190 B2 | 1/2014 | Zemlok et al. |
| 8,636,191 B2 | 1/2014 | Meagher |
| 8,636,193 B2 | 1/2014 | Whitman et al. |
| 8,636,736 B2 | 1/2014 | Yates et al. |
| 8,636,766 B2 | 1/2014 | Milliman et al. |
| 8,639,936 B2 | 1/2014 | Hu et al. |
| 8,640,788 B2 | 2/2014 | Dachs, II et al. |
| 8,646,674 B2 | 2/2014 | Schulte et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,652,155 B2 | 2/2014 | Houser et al. |
| 8,656,929 B2 | 2/2014 | Miller et al. |
| 8,657,174 B2 | 2/2014 | Yates et al. |
| 8,657,175 B2 | 2/2014 | Sonnenschein et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,657,482 B2 | 2/2014 | Malackowski et al. |
| 8,657,808 B2 | 2/2014 | McPherson et al. |
| 8,657,814 B2 | 2/2014 | Werneth et al. |
| 8,657,821 B2 | 2/2014 | Palermo |
| D701,238 S | 3/2014 | Lai et al. |
| 8,662,370 B2 | 3/2014 | Takei |
| 8,663,106 B2 | 3/2014 | Stivoric et al. |

(56) References Cited

U.S. PATENT DOCUMENTS

| | | | |
|---|---|---|---|
| 8,663,192 B2 | 3/2014 | Hester et al. |
| 8,663,245 B2 | 3/2014 | Francischelli et al. |
| 8,663,262 B2 | 3/2014 | Smith et al. |
| 8,663,270 B2 | 3/2014 | Donnigan et al. |
| 8,664,792 B2 | 3/2014 | Rebsdorf |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,672,209 B2 | 3/2014 | Crainich |
| 8,672,922 B2 | 3/2014 | Loh et al. |
| 8,672,935 B2 | 3/2014 | Okada et al. |
| 8,672,951 B2 | 3/2014 | Smith et al. |
| 8,673,210 B2 | 3/2014 | Deshays |
| 8,675,820 B2 | 3/2014 | Bale et al. |
| 8,678,263 B2 | 3/2014 | Viola |
| 8,678,994 B2 | 3/2014 | Sonnenschein et al. |
| 8,679,093 B2 | 3/2014 | Farra |
| 8,679,098 B2 | 3/2014 | Hart |
| 8,679,137 B2 | 3/2014 | Bauman et al. |
| 8,679,154 B2 | 3/2014 | Smith et al. |
| 8,679,156 B2 | 3/2014 | Smith et al. |
| 8,679,454 B2 | 3/2014 | Guire et al. |
| 8,684,248 B2 | 4/2014 | Milliman |
| 8,684,249 B2 | 4/2014 | Racenet et al. |
| 8,684,250 B2 | 4/2014 | Bettuchi et al. |
| 8,684,253 B2 | 4/2014 | Giordano et al. |
| 8,684,962 B2 | 4/2014 | Kirschenman et al. |
| 8,685,004 B2 | 4/2014 | Zemlock et al. |
| 8,685,020 B2 | 4/2014 | Weizman et al. |
| 8,690,893 B2 | 4/2014 | Deitch et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,706,316 B1 | 4/2014 | Hoevenaar |
| 8,708,210 B2 | 4/2014 | Zemlok et al. |
| 8,708,211 B2 | 4/2014 | Zemlok et al. |
| 8,708,212 B2 | 4/2014 | Williams |
| 8,708,213 B2 | 4/2014 | Shelton, IV et al. |
| 8,709,012 B2 | 4/2014 | Muller |
| 8,714,352 B2 | 5/2014 | Farascioni et al. |
| 8,714,429 B2 | 5/2014 | Demmy |
| 8,714,430 B2 | 5/2014 | Natarajan et al. |
| 8,715,256 B2 | 5/2014 | Greener |
| 8,715,302 B2 | 5/2014 | Ibrahim et al. |
| 8,720,766 B2 | 5/2014 | Hess et al. |
| 8,721,630 B2 | 5/2014 | Ortiz et al. |
| 8,721,666 B2 | 5/2014 | Schroeder et al. |
| 8,727,197 B2 | 5/2014 | Hess et al. |
| 8,727,199 B2 | 5/2014 | Wenchell |
| 8,727,200 B2 | 5/2014 | Roy |
| 8,727,961 B2 | 5/2014 | Ziv |
| 8,728,099 B2 | 5/2014 | Cohn et al. |
| 8,728,119 B2 | 5/2014 | Cummins |
| 8,733,470 B2 | 5/2014 | Matthias et al. |
| 8,733,611 B2 | 5/2014 | Milliman |
| 8,733,612 B2 | 5/2014 | Ma |
| 8,733,613 B2 | 5/2014 | Huitema et al. |
| 8,733,614 B2 | 5/2014 | Ross et al. |
| 8,734,336 B2 | 5/2014 | Bonadio et al. |
| 8,734,359 B2 | 5/2014 | Ibanez et al. |
| 8,734,478 B2 | 5/2014 | Widenhouse et al. |
| 8,734,831 B2 | 5/2014 | Kim et al. |
| 8,739,033 B2 | 5/2014 | Rosenberg |
| 8,739,417 B2 | 6/2014 | Tokunaga et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,740,987 B2 | 6/2014 | Geremakis et al. |
| 8,746,529 B2 | 6/2014 | Shelton, IV et al. |
| 8,746,530 B2 | 6/2014 | Giordano et al. |
| 8,746,533 B2 | 6/2014 | Whitman et al. |
| 8,746,535 B2 | 6/2014 | Shelton, IV et al. |
| 8,747,238 B2 | 6/2014 | Shelton, IV et al. |
| 8,747,441 B2 | 6/2014 | Konieczynski et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,748 B2 | 6/2014 | Whitman et al. |
| 8,752,749 B2 | 6/2014 | Moore et al. |
| 8,753,664 B2 | 6/2014 | Dao et al. |
| 8,757,287 B2 | 6/2014 | Mak |
| 8,757,465 B2 | 6/2014 | Woodard, Jr. et al. |
| 8,758,235 B2 | 6/2014 | Jaworek |
| 8,758,366 B2 | 6/2014 | McLean et al. |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,876 B2 | 7/2014 | Kostrzewski |
| 8,763,877 B2 | 7/2014 | Schall et al. |
| 8,763,879 B2 | 7/2014 | Shelton, IV et al. |
| 8,764,732 B2 | 7/2014 | Hartwell |
| 8,765,942 B2 | 7/2014 | Feraud et al. |
| 8,770,458 B2 | 7/2014 | Scirica |
| 8,770,459 B2 | 7/2014 | Racenet et al. |
| 8,770,460 B2 | 7/2014 | Belzer |
| 8,771,169 B2 | 7/2014 | Whitman et al. |
| 8,771,260 B2 | 7/2014 | Conlon et al. |
| 8,777,004 B2 | 7/2014 | Shelton, IV et al. |
| 8,777,082 B2 | 7/2014 | Scirica |
| 8,777,083 B2 | 7/2014 | Racenet et al. |
| 8,777,898 B2 | 7/2014 | Suon et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,304 B2 | 7/2014 | Mikkaichi et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,658 B2 | 7/2014 | Cigarini et al. |
| 8,790,684 B2 | 7/2014 | Dave et al. |
| D711,905 S | 8/2014 | Morrison et al. |
| 8,794,496 B2 | 8/2014 | Scirica |
| 8,794,497 B2 | 8/2014 | Zingman |
| 8,795,159 B2 | 8/2014 | Moriyama |
| 8,795,276 B2 | 8/2014 | Dietz et al. |
| 8,795,308 B2 | 8/2014 | Valin |
| 8,795,324 B2 | 8/2014 | Kawai et al. |
| 8,795,995 B2 | 8/2014 | Cunanan et al. |
| 8,800,681 B2 | 8/2014 | Rousson et al. |
| 8,800,837 B2 | 8/2014 | Zemlok |
| 8,800,838 B2 | 8/2014 | Shelton, IV |
| 8,800,839 B2 | 8/2014 | Beetel |
| 8,800,840 B2 | 8/2014 | Jankowski |
| 8,800,841 B2 | 8/2014 | Ellerhorst et al. |
| 8,801,710 B2 | 8/2014 | Ullrich et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,801,801 B2 | 8/2014 | Datta et al. |
| 8,806,973 B2 | 8/2014 | Ross et al. |
| 8,807,414 B2 | 8/2014 | Ross et al. |
| 8,808,161 B2 | 8/2014 | Gregg et al. |
| 8,808,164 B2 | 8/2014 | Hoffman et al. |
| 8,808,274 B2 | 8/2014 | Hartwell |
| 8,808,294 B2 | 8/2014 | Fox et al. |
| 8,808,308 B2 | 8/2014 | Boukhny et al. |
| 8,808,311 B2 | 8/2014 | Heinrich et al. |
| 8,808,325 B2 | 8/2014 | Hess et al. |
| 8,810,197 B2 | 8/2014 | Juergens |
| 8,811,017 B2 | 8/2014 | Fujii et al. |
| 8,813,866 B2 | 8/2014 | Suzuki |
| 8,814,024 B2 | 8/2014 | Woodard, Jr. et al. |
| 8,814,025 B2 | 8/2014 | Miller et al. |
| 8,814,836 B2 | 8/2014 | Ignon et al. |
| 8,815,594 B2 | 8/2014 | Harris et al. |
| 8,818,523 B2 | 8/2014 | Olson et al. |
| 8,820,603 B2 | 9/2014 | Shelton, IV et al. |
| 8,820,605 B2 | 9/2014 | Shelton, IV |

(56) References Cited

U.S. PATENT DOCUMENTS

| | | |
|---|---|---|
| 8,820,606 B2 | 9/2014 | Hodgkinson |
| 8,820,607 B2 | 9/2014 | Marczyk |
| 8,820,608 B2 | 9/2014 | Miyamoto |
| 8,821,514 B2 | 9/2014 | Aranyi |
| 8,822,934 B2 | 9/2014 | Sayeh et al. |
| 8,825,164 B2 | 9/2014 | Tweden et al. |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,828,046 B2 | 9/2014 | Stefanchik et al. |
| 8,831,779 B2 | 9/2014 | Ortmaier et al. |
| 8,833,219 B2 | 9/2014 | Pierce |
| 8,833,630 B2 | 9/2014 | Milliman |
| 8,833,632 B2 | 9/2014 | Swensgard |
| 8,834,353 B2 | 9/2014 | Dejima et al. |
| 8,834,465 B2 | 9/2014 | Ramstein et al. |
| 8,834,498 B2 | 9/2014 | Byrum et al. |
| 8,834,518 B2 | 9/2014 | Faller et al. |
| 8,840,003 B2 | 9/2014 | Morgan et al. |
| 8,840,603 B2 | 9/2014 | Shelton, IV et al. |
| 8,840,609 B2 | 9/2014 | Stuebe |
| 8,840,876 B2 | 9/2014 | Eemeta et al. |
| 8,844,789 B2 | 9/2014 | Shelton, IV et al. |
| 8,844,790 B2 | 9/2014 | Demmy et al. |
| 8,851,215 B2 | 10/2014 | Goto |
| 8,851,354 B2 | 10/2014 | Swensgard et al. |
| 8,851,355 B2 | 10/2014 | Aranyi et al. |
| 8,852,174 B2 | 10/2014 | Burbank |
| 8,852,185 B2 | 10/2014 | Twomey |
| 8,852,199 B2 | 10/2014 | Deslauriers et al. |
| 8,852,218 B2 | 10/2014 | Hughett, Sr. et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,547 B2 | 10/2014 | Brogna |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,864,010 B2 | 10/2014 | Williams |
| 8,864,750 B2 | 10/2014 | Ross et al. |
| 8,869,912 B2 | 10/2014 | Roβkamp et al. |
| 8,869,913 B2 | 10/2014 | Matthias et al. |
| 8,870,050 B2 | 10/2014 | Hodgkinson |
| 8,870,867 B2 | 10/2014 | Walberg et al. |
| 8,870,912 B2 | 10/2014 | Brisson et al. |
| 8,875,971 B2 | 11/2014 | Hall et al. |
| 8,875,972 B2 | 11/2014 | Weisenburgh, II et al. |
| 8,876,698 B2 | 11/2014 | Sakamoto et al. |
| 8,876,857 B2 | 11/2014 | Burbank |
| 8,876,858 B2 | 11/2014 | Braun |
| 8,882,660 B2 | 11/2014 | Phee et al. |
| 8,882,792 B2 | 11/2014 | Dietz et al. |
| 8,884,560 B2 | 11/2014 | Ito |
| 8,887,979 B2 | 11/2014 | Mastri et al. |
| 8,888,688 B2 | 11/2014 | Julian et al. |
| 8,888,695 B2 | 11/2014 | Piskun et al. |
| 8,888,792 B2 | 11/2014 | Harris et al. |
| 8,888,809 B2 | 11/2014 | Davison et al. |
| 8,893,946 B2 | 11/2014 | Boudreaux et al. |
| 8,893,949 B2 | 11/2014 | Shelton, IV et al. |
| 8,894,647 B2 | 11/2014 | Beardsley et al. |
| 8,894,654 B2 | 11/2014 | Anderson |
| 8,899,460 B2 | 12/2014 | Wojcicki |
| 8,899,461 B2 | 12/2014 | Farascioni |
| 8,899,462 B2 | 12/2014 | Kostrzewski et al. |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,900,267 B2 | 12/2014 | Woolfson et al. |
| 8,905,287 B2 | 12/2014 | Racenet et al. |
| 8,905,977 B2 | 12/2014 | Shelton et al. |
| 8,910,846 B2 | 12/2014 | Viola |
| 8,910,847 B2 | 12/2014 | Nalagatla et al. |
| 8,911,426 B2 | 12/2014 | Coppeta et al. |
| 8,911,448 B2 | 12/2014 | Stein |
| 8,911,460 B2 | 12/2014 | Neurohr et al. |
| 8,911,471 B2 | 12/2014 | Spivey et al. |
| 8,912,746 B2 | 12/2014 | Reid et al. |
| 8,915,842 B2 | 12/2014 | Weisenburgh, II et al. |
| 8,920,368 B2 | 12/2014 | Sandhu et al. |
| 8,920,433 B2 | 12/2014 | Barrier et al. |
| 8,920,435 B2 | 12/2014 | Smith et al. |
| 8,920,438 B2 | 12/2014 | Aranyi et al. |
| 8,920,443 B2 | 12/2014 | Hiles et al. |
| 8,920,444 B2 | 12/2014 | Hiles et al. |
| 8,922,163 B2 | 12/2014 | Macdonald |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,506 B2 | 1/2015 | Widenhouse et al. |
| 8,926,598 B2 | 1/2015 | Mollere et al. |
| 8,931,576 B2 | 1/2015 | Iwata |
| 8,931,679 B2 | 1/2015 | Kostrzewski |
| 8,931,680 B2 | 1/2015 | Milliman |
| 8,931,682 B2 | 1/2015 | Timm et al. |
| 8,931,692 B2 | 1/2015 | Sancak |
| 8,936,614 B2 | 1/2015 | Allen, IV |
| 8,939,343 B2 | 1/2015 | Milliman et al. |
| 8,939,344 B2 | 1/2015 | Olson et al. |
| 8,939,898 B2 | 1/2015 | Omoto |
| 8,944,069 B2 | 2/2015 | Miller et al. |
| 8,945,095 B2 | 2/2015 | Blumenkranz et al. |
| 8,945,098 B2 | 2/2015 | Seibold et al. |
| 8,945,163 B2 | 2/2015 | Voegele et al. |
| 8,955,732 B2 | 2/2015 | Zemlok et al. |
| 8,956,342 B1 | 2/2015 | Russo et al. |
| 8,956,390 B2 | 2/2015 | Shah et al. |
| 8,958,860 B2 | 2/2015 | Banerjee et al. |
| 8,960,519 B2 | 2/2015 | Whitman et al. |
| 8,960,520 B2 | 2/2015 | McCuen |
| 8,960,521 B2 | 2/2015 | Kostrzewski |
| 8,961,191 B2 | 2/2015 | Hanshew |
| 8,961,504 B2 | 2/2015 | Hoarau et al. |
| 8,961,542 B2 | 2/2015 | Whitfield et al. |
| 8,963,714 B2 | 2/2015 | Medhal et al. |
| D725,674 S | 3/2015 | Jung et al. |
| 8,967,443 B2 | 3/2015 | McCuen |
| 8,967,444 B2 | 3/2015 | Beetel |
| 8,967,446 B2 | 3/2015 | Beardsley et al. |
| 8,967,448 B2 | 3/2015 | Carter et al. |
| 8,968,276 B2 | 3/2015 | Zemlok et al. |
| 8,968,308 B2 | 3/2015 | Horner et al. |
| 8,968,312 B2 | 3/2015 | Marczyk et al. |
| 8,968,337 B2 | 3/2015 | Whitfield et al. |
| 8,968,340 B2 | 3/2015 | Chowaniec et al. |
| 8,968,355 B2 | 3/2015 | Malkowski et al. |
| 8,968,358 B2 | 3/2015 | Reschke |
| 8,970,507 B2 | 3/2015 | Holbein et al. |
| 8,973,803 B2 | 3/2015 | Hall et al. |
| 8,973,804 B2 | 3/2015 | Hess et al. |
| 8,973,805 B2 | 3/2015 | Scirica et al. |
| 8,974,440 B2 | 3/2015 | Farritor et al. |
| 8,974,542 B2 | 3/2015 | Fujimoto et al. |
| 8,974,932 B2 | 3/2015 | McGahan et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,843 B2 | 3/2015 | Timm et al. |
| 8,979,890 B2 | 3/2015 | Boudreaux |
| 8,982,195 B2 | 3/2015 | Claus et al. |
| 8,984,711 B2 | 3/2015 | Ota et al. |
| 8,985,240 B2 | 3/2015 | Winnard |
| 8,985,429 B2 | 3/2015 | Balek et al. |
| 8,986,302 B2 | 3/2015 | Aldridge et al. |
| 8,989,903 B2 | 3/2015 | Weir et al. |
| 8,991,676 B2 | 3/2015 | Hess et al. |
| 8,991,677 B2 | 3/2015 | Moore et al. |
| 8,991,678 B2 | 3/2015 | Wellman et al. |
| 8,992,042 B2 | 3/2015 | Eichenholz |
| 8,992,422 B2 | 3/2015 | Spivey et al. |
| 8,992,565 B2 | 3/2015 | Brisson et al. |
| 8,996,165 B2 | 3/2015 | Wang et al. |

(56) References Cited

U.S. PATENT DOCUMENTS

| | | |
|---|---|---|
| 8,998,058 B2 | 4/2015 | Moore et al. |
| 8,998,059 B2 | 4/2015 | Smith et al. |
| 8,998,060 B2 | 4/2015 | Bruewer et al. |
| 8,998,061 B2 | 4/2015 | Williams et al. |
| 8,998,939 B2 | 4/2015 | Price et al. |
| 9,000,720 B2 | 4/2015 | Stulen et al. |
| 9,002,518 B2 | 4/2015 | Manzo et al. |
| 9,004,339 B1 | 4/2015 | Park |
| 9,004,799 B1 | 4/2015 | Tibbits |
| 9,005,230 B2 | 4/2015 | Yates et al. |
| 9,005,238 B2 | 4/2015 | DeSantis et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,611 B2 | 4/2015 | Ross et al. |
| 9,011,437 B2 | 4/2015 | Woodruff et al. |
| 9,011,439 B2 | 4/2015 | Shalaby et al. |
| 9,011,471 B2 | 4/2015 | Timm et al. |
| 9,014,856 B2 | 4/2015 | Manzo et al. |
| 9,016,539 B2 | 4/2015 | Kostrzewski et al. |
| 9,016,540 B2 | 4/2015 | Whitman et al. |
| 9,016,541 B2 | 4/2015 | Viola et al. |
| 9,016,542 B2 | 4/2015 | Shelton, IV et al. |
| 9,016,545 B2 | 4/2015 | Aranyi et al. |
| 9,017,331 B2 | 4/2015 | Fox |
| 9,017,355 B2 | 4/2015 | Smith et al. |
| 9,017,369 B2 | 4/2015 | Renger et al. |
| 9,017,371 B2 | 4/2015 | Whitman et al. |
| 9,017,849 B2 | 4/2015 | Stulen et al. |
| 9,017,851 B2 | 4/2015 | Felder et al. |
| D729,274 S | 5/2015 | Clement et al. |
| 9,021,684 B2 | 5/2015 | Lenker et al. |
| 9,023,014 B2 | 5/2015 | Chowaniec et al. |
| 9,023,069 B2 | 5/2015 | Kasvikis et al. |
| 9,023,071 B2 | 5/2015 | Miller et al. |
| 9,026,347 B2 | 5/2015 | Gadh et al. |
| 9,027,817 B2 | 5/2015 | Milliman et al. |
| 9,028,468 B2 | 5/2015 | Scarfogliero et al. |
| 9,028,494 B2 | 5/2015 | Shelton, IV et al. |
| 9,028,495 B2 | 5/2015 | Mueller et al. |
| 9,028,510 B2 | 5/2015 | Miyamoto et al. |
| 9,028,511 B2 | 5/2015 | Weller et al. |
| 9,028,519 B2 | 5/2015 | Yates et al. |
| 9,030,166 B2 | 5/2015 | Kano |
| 9,030,169 B2 | 5/2015 | Christensen et al. |
| 9,033,203 B2 | 5/2015 | Woodard, Jr. et al. |
| 9,033,204 B2 | 5/2015 | Shelton, IV et al. |
| 9,034,505 B2 | 5/2015 | Detry et al. |
| 9,038,881 B1 | 5/2015 | Schaller et al. |
| 9,039,690 B2 | 5/2015 | Kersten et al. |
| 9,039,694 B2 | 5/2015 | Ross et al. |
| 9,039,720 B2 | 5/2015 | Madan |
| 9,040,062 B2 | 5/2015 | Maeda et al. |
| 9,043,027 B2 | 5/2015 | Durant et al. |
| 9,044,227 B2 | 6/2015 | Shelton, IV et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,044,238 B2 | 6/2015 | Orszulak |
| 9,044,241 B2 | 6/2015 | Barner et al. |
| 9,044,261 B2 | 6/2015 | Houser |
| 9,044,281 B2 | 6/2015 | Pool et al. |
| 9,050,083 B2 | 6/2015 | Yates et al. |
| 9,050,084 B2 | 6/2015 | Schmid et al. |
| 9,050,089 B2 | 6/2015 | Orszulak |
| 9,050,100 B2 | 6/2015 | Yates et al. |
| 9,050,120 B2 | 6/2015 | Swarup et al. |
| 9,050,123 B2 | 6/2015 | Krause et al. |
| 9,050,176 B2 | 6/2015 | Datta et al. |
| 9,050,192 B2 | 6/2015 | Mansmann |
| 9,055,941 B2 | 6/2015 | Schmid et al. |
| 9,055,942 B2 | 6/2015 | Balbierz et al. |
| 9,055,943 B2 | 6/2015 | Zemlok et al. |
| 9,055,944 B2 | 6/2015 | Hodgkinson et al. |
| 9,055,961 B2 | 6/2015 | Manzo et al. |
| 9,060,770 B2 | 6/2015 | Shelton, IV et al. |
| 9,060,776 B2 | 6/2015 | Yates et al. |
| 9,060,794 B2 | 6/2015 | Kang et al. |
| 9,060,894 B2 | 6/2015 | Wubbeling |
| 9,061,392 B2 | 6/2015 | Forgues et al. |
| 9,070,068 B2 | 6/2015 | Coveley et al. |
| 9,072,515 B2 | 7/2015 | Hall et al. |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,654 B2 | 7/2015 | Whitman et al. |
| 9,084,586 B2 | 7/2015 | Hafner et al. |
| 9,084,601 B2 | 7/2015 | Moore et al. |
| 9,084,602 B2 | 7/2015 | Gleiman |
| 9,086,875 B2 | 7/2015 | Harrat et al. |
| 9,089,326 B2 | 7/2015 | Krumanaker et al. |
| 9,089,330 B2 | 7/2015 | Widenhouse et al. |
| 9,089,338 B2 | 7/2015 | Smith et al. |
| 9,089,352 B2 | 7/2015 | Jeong |
| 9,089,360 B2 | 7/2015 | Messerly et al. |
| 9,091,588 B2 | 7/2015 | Lefler |
| D736,792 S | 8/2015 | Brinda et al. |
| 9,095,339 B2 | 8/2015 | Moore et al. |
| 9,095,346 B2 | 8/2015 | Houser et al. |
| 9,095,362 B2 | 8/2015 | Dachs, II et al. |
| 9,095,367 B2 | 8/2015 | Olson et al. |
| 9,096,033 B2 | 8/2015 | Holop et al. |
| 9,098,153 B2 | 8/2015 | Shen et al. |
| 9,099,863 B2 | 8/2015 | Smith et al. |
| 9,099,877 B2 | 8/2015 | Banos et al. |
| 9,099,922 B2 | 8/2015 | Toosky et al. |
| 9,101,358 B2 | 8/2015 | Kerr et al. |
| 9,101,359 B2 | 8/2015 | Smith et al. |
| 9,101,385 B2 | 8/2015 | Shelton, IV et al. |
| 9,101,475 B2 | 8/2015 | Wei et al. |
| 9,101,621 B2 | 8/2015 | Zeldis |
| 9,107,663 B2 | 8/2015 | Swensgard |
| 9,107,667 B2 | 8/2015 | Hodgkinson |
| 9,107,690 B2 | 8/2015 | Bales, Jr. et al. |
| 9,110,587 B2 | 8/2015 | Kim et al. |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,868 B2 | 8/2015 | Felder et al. |
| 9,113,873 B2 | 8/2015 | Marczyk et al. |
| 9,113,874 B2 | 8/2015 | Shelton, IV et al. |
| 9,113,876 B2 | 8/2015 | Zemlok et al. |
| 9,113,879 B2 | 8/2015 | Felder et al. |
| 9,113,880 B2 | 8/2015 | Zemlok et al. |
| 9,113,881 B2 | 8/2015 | Scirica |
| 9,113,883 B2 | 8/2015 | Aronhalt et al. |
| 9,113,884 B2 | 8/2015 | Shelton, IV et al. |
| 9,113,887 B2 | 8/2015 | Behnke, II et al. |
| 9,119,615 B2 | 9/2015 | Felder et al. |
| 9,119,657 B2 | 9/2015 | Shelton, IV et al. |
| 9,119,898 B2 | 9/2015 | Bayon et al. |
| 9,119,957 B2 | 9/2015 | Gantz et al. |
| 9,123,286 B2 | 9/2015 | Park |
| 9,124,097 B2 | 9/2015 | Cruz |
| 9,125,651 B2 | 9/2015 | Mandakolathur Vasudevan et al. |
| 9,125,654 B2 | 9/2015 | Aronhalt et al. |
| 9,125,662 B2 | 9/2015 | Shelton, IV |
| 9,126,317 B2 | 9/2015 | Lawton et al. |
| 9,131,835 B2 | 9/2015 | Widenhouse et al. |
| 9,131,940 B2 | 9/2015 | Huitema et al. |
| 9,131,950 B2 | 9/2015 | Matthew |
| 9,131,957 B2 | 9/2015 | Skarbnik et al. |
| 9,138,225 B2 | 9/2015 | Huang et al. |
| 9,138,226 B2 | 9/2015 | Racenet et al. |
| 9,144,455 B2 | 9/2015 | Kennedy et al. |
| D740,414 S | 10/2015 | Katsura |
| D741,882 S | 10/2015 | Shmilov et al. |
| 9,149,274 B2 | 10/2015 | Spivey et al. |
| 9,149,324 B2 | 10/2015 | Huang et al. |
| 9,149,325 B2 | 10/2015 | Worrell et al. |
| 9,153,994 B2 | 10/2015 | Wood et al. |
| 9,161,753 B2 | 10/2015 | Prior |
| 9,161,769 B2 | 10/2015 | Stoddard et al. |

(56) References Cited

U.S. PATENT DOCUMENTS

| | | |
|---|---|---|
| 9,161,803 B2 | 10/2015 | Yates et al. |
| 9,161,807 B2 | 10/2015 | Garrison |
| 9,161,855 B2 | 10/2015 | Rousseau et al. |
| 9,164,271 B2 | 10/2015 | Ebata et al. |
| 9,167,960 B2 | 10/2015 | Yamaguchi et al. |
| 9,168,038 B2 | 10/2015 | Shelton, IV et al. |
| 9,168,039 B1 | 10/2015 | Knodel |
| 9,168,042 B2 | 10/2015 | Milliman |
| 9,168,054 B2 | 10/2015 | Turner et al. |
| 9,168,144 B2 | 10/2015 | Rivin et al. |
| 9,171,244 B2 | 10/2015 | Endou et al. |
| 9,179,832 B2 | 11/2015 | Diolaiti |
| 9,179,911 B2 | 11/2015 | Morgan et al. |
| 9,179,912 B2 | 11/2015 | Yates et al. |
| 9,180,223 B2 | 11/2015 | Yu et al. |
| 9,182,244 B2 | 11/2015 | Luke et al. |
| 9,186,046 B2 | 11/2015 | Ramamurthy et al. |
| 9,186,137 B2 | 11/2015 | Farascioni et al. |
| 9,186,140 B2 | 11/2015 | Hiles et al. |
| 9,186,142 B2 | 11/2015 | Fanelli et al. |
| 9,186,143 B2 | 11/2015 | Timm et al. |
| 9,186,148 B2 | 11/2015 | Felder et al. |
| 9,186,221 B2 | 11/2015 | Burbank |
| 9,192,376 B2 | 11/2015 | Almodovar |
| 9,192,380 B2 | 11/2015 | (Tarinelli) Racenet et al. |
| 9,192,384 B2 | 11/2015 | Bettuchi |
| 9,192,430 B2 | 11/2015 | Rachlin et al. |
| 9,192,434 B2 | 11/2015 | Twomey et al. |
| 9,193,045 B2 | 11/2015 | Saur et al. |
| 9,197,079 B2 | 11/2015 | Yip et al. |
| D744,528 S | 12/2015 | Agrawal |
| D746,459 S | 12/2015 | Kaercher et al. |
| 9,198,642 B2 | 12/2015 | Storz |
| 9,198,644 B2 | 12/2015 | Balek et al. |
| 9,198,661 B2 | 12/2015 | Swensgard |
| 9,198,662 B2 | 12/2015 | Barton et al. |
| 9,198,683 B2 | 12/2015 | Friedman et al. |
| 9,204,830 B2 | 12/2015 | Zand et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,204,881 B2 | 12/2015 | Penna |
| 9,204,923 B2 | 12/2015 | Manzo et al. |
| 9,204,924 B2 | 12/2015 | Marczyk et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,013 B2 | 12/2015 | Scirica et al. |
| 9,216,019 B2 | 12/2015 | Schmid et al. |
| 9,216,020 B2 | 12/2015 | Zhang et al. |
| 9,216,030 B2 | 12/2015 | Fan et al. |
| 9,216,062 B2 | 12/2015 | Duque et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,220,504 B2 | 12/2015 | Viola et al. |
| 9,220,508 B2 | 12/2015 | Dannaher |
| 9,220,559 B2 | 12/2015 | Worrell et al. |
| 9,220,570 B2 | 12/2015 | Kim et al. |
| D746,854 S | 1/2016 | Shardlow et al. |
| 9,226,750 B2 | 1/2016 | Weir et al. |
| 9,226,751 B2 | 1/2016 | Shelton, IV et al. |
| 9,226,754 B2 | 1/2016 | D'Agostino et al. |
| 9,226,760 B2 | 1/2016 | Shelton, IV |
| 9,226,761 B2 | 1/2016 | Burbank |
| 9,226,767 B2 | 1/2016 | Stulen et al. |
| 9,226,799 B2 | 1/2016 | Lightcap et al. |
| 9,232,941 B2 | 1/2016 | Mandakolathur Vasudevan et al. |
| 9,232,945 B2 | 1/2016 | Zingman |
| 9,232,979 B2 | 1/2016 | Parihar et al. |
| 9,233,610 B2 | 1/2016 | Kim et al. |
| 9,237,891 B2 | 1/2016 | Shelton, IV |
| 9,237,892 B2 | 1/2016 | Hodgkinson |
| 9,237,895 B2 | 1/2016 | McCarthy et al. |
| 9,237,900 B2 | 1/2016 | Boudreaux et al. |
| 9,237,921 B2 | 1/2016 | Messerly et al. |
| 9,239,064 B2 | 1/2016 | Helbig et al. |
| 9,240,740 B2 | 1/2016 | Zeng et al. |
| 9,241,711 B2 | 1/2016 | Ivanko |
| 9,241,712 B2 | 1/2016 | Zemlok et al. |
| 9,241,714 B2 | 1/2016 | Timm et al. |
| 9,241,716 B2 | 1/2016 | Whitman |
| 9,241,731 B2 | 1/2016 | Boudreaux et al. |
| 9,241,758 B2 | 1/2016 | Franer et al. |
| 9,244,524 B2 | 1/2016 | Inoue et al. |
| D748,668 S | 2/2016 | Kim et al. |
| D749,128 S | 2/2016 | Perez et al. |
| D749,623 S | 2/2016 | Gray et al. |
| D750,122 S | 2/2016 | Shardlow et al. |
| D750,129 S | 2/2016 | Kwon |
| 9,254,131 B2 | 2/2016 | Soltz et al. |
| 9,254,170 B2 | 2/2016 | Parihar et al. |
| 9,259,265 B2 | 2/2016 | Harris et al. |
| 9,259,274 B2 | 2/2016 | Prisco |
| 9,259,275 B2 | 2/2016 | Burbank |
| 9,261,172 B2 | 2/2016 | Solomon et al. |
| 9,265,500 B2 | 2/2016 | Sorrentino et al. |
| 9,265,510 B2 | 2/2016 | Dietzel et al. |
| 9,265,516 B2 | 2/2016 | Casey et al. |
| 9,265,585 B2 | 2/2016 | Wingardner et al. |
| 9,271,718 B2 | 3/2016 | Milad et al. |
| 9,271,727 B2 | 3/2016 | McGuckin, Jr. et al. |
| 9,271,753 B2 | 3/2016 | Butler et al. |
| 9,271,799 B2 | 3/2016 | Shelton, IV et al. |
| 9,272,406 B2 | 3/2016 | Aronhalt et al. |
| 9,274,095 B2 | 3/2016 | Humayun et al. |
| 9,277,919 B2 | 3/2016 | Timmer et al. |
| 9,277,922 B2 | 3/2016 | Carter et al. |
| 9,277,969 B2 | 3/2016 | Brannan et al. |
| 9,282,962 B2 | 3/2016 | Schmid et al. |
| 9,282,963 B2 | 3/2016 | Bryant |
| 9,282,966 B2 | 3/2016 | Shelton, IV et al. |
| 9,282,974 B2 | 3/2016 | Shelton, IV |
| 9,283,028 B2 | 3/2016 | Johnson |
| 9,283,045 B2 | 3/2016 | Rhee et al. |
| 9,283,054 B2 | 3/2016 | Morgan et al. |
| 9,289,206 B2 | 3/2016 | Hess et al. |
| 9,289,207 B2 | 3/2016 | Shelton, IV |
| 9,289,210 B2 | 3/2016 | Baxter, III et al. |
| 9,289,211 B2 | 3/2016 | Williams et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,293,757 B2 | 3/2016 | Toussaint et al. |
| 9,295,464 B2 | 3/2016 | Shelton, IV et al. |
| 9,295,465 B2 | 3/2016 | Farascioni |
| 9,295,466 B2 | 3/2016 | Hodgkinson et al. |
| 9,295,467 B2 | 3/2016 | Scirica |
| 9,295,468 B2 | 3/2016 | Heinrich et al. |
| 9,295,514 B2 | 3/2016 | Shelton, IV et al. |
| 9,295,522 B2 | 3/2016 | Kostrzewski |
| 9,295,565 B2 | 3/2016 | McLean |
| 9,295,784 B2 | 3/2016 | Eggert et al. |
| D753,167 S | 4/2016 | Yu et al. |
| 9,301,691 B2 | 4/2016 | Hufnagel et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,301,811 B2 | 4/2016 | Goldberg et al. |
| 9,307,965 B2 | 4/2016 | Ming et al. |
| 9,307,986 B2 | 4/2016 | Hall et al. |
| 9,307,987 B2 | 4/2016 | Swensgard et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,308,009 B2 | 4/2016 | Madan et al. |
| 9,308,011 B2 | 4/2016 | Chao et al. |
| 9,308,646 B2 | 4/2016 | Lim et al. |
| 9,313,915 B2 | 4/2016 | Niu et al. |
| 9,314,246 B2 | 4/2016 | Shelton, IV et al. |
| 9,314,247 B2 | 4/2016 | Shelton, IV et al. |
| 9,314,261 B2 | 4/2016 | Bales, Jr. et al. |

(56) References Cited

U.S. PATENT DOCUMENTS

| | | |
|---|---|---|
| 9,314,291 B2 | 4/2016 | Schall et al. |
| 9,314,339 B2 | 4/2016 | Mansmann |
| 9,314,908 B2 | 4/2016 | Tanimoto et al. |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,325,516 B2 | 4/2016 | Pera et al. |
| D755,196 S | 5/2016 | Meyers et al. |
| D756,373 S | 5/2016 | Raskin et al. |
| D756,377 S | 5/2016 | Connolly et al. |
| D757,028 S | 5/2016 | Goldenberg et al. |
| 9,326,767 B2 | 5/2016 | Koch et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,326,788 B2 | 5/2016 | Batross et al. |
| 9,326,812 B2 | 5/2016 | Waaler et al. |
| 9,326,824 B2 | 5/2016 | Inoue et al. |
| 9,327,061 B2 | 5/2016 | Govil et al. |
| 9,331,721 B2 | 5/2016 | Martinez Nuevo et al. |
| 9,332,890 B2 | 5/2016 | Ozawa |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,333,040 B2 | 5/2016 | Shellenberger et al. |
| 9,333,082 B2 | 5/2016 | Wei et al. |
| 9,337,668 B2 | 5/2016 | Yip |
| 9,339,226 B2 | 5/2016 | van der Walt et al. |
| 9,339,342 B2 | 5/2016 | Prisco et al. |
| 9,345,477 B2 | 5/2016 | Anim et al. |
| 9,345,479 B2 | 5/2016 | (Tarinelli) Racenet et al. |
| 9,345,480 B2 | 5/2016 | Hessler et al. |
| 9,345,481 B2 | 5/2016 | Hall et al. |
| 9,345,503 B2 | 5/2016 | Ishida et al. |
| 9,351,726 B2 | 5/2016 | Leimbach et al. |
| 9,351,727 B2 | 5/2016 | Leimbach et al. |
| 9,351,728 B2 | 5/2016 | Sniffin et al. |
| 9,351,730 B2 | 5/2016 | Schmid et al. |
| 9,351,731 B2 | 5/2016 | Carter et al. |
| 9,351,732 B2 | 5/2016 | Hodgkinson |
| 9,352,071 B2 | 5/2016 | Landgrebe et al. |
| D758,433 S | 6/2016 | Lee et al. |
| D759,063 S | 6/2016 | Chen |
| 9,358,003 B2 | 6/2016 | Hall et al. |
| 9,358,004 B2 | 6/2016 | Sniffin et al. |
| 9,358,005 B2 | 6/2016 | Shelton, IV et al. |
| 9,358,015 B2 | 6/2016 | Sorrentino et al. |
| 9,358,031 B2 | 6/2016 | Manzo |
| 9,358,065 B2 | 6/2016 | Ladtkow et al. |
| 9,364,217 B2 | 6/2016 | Kostrzewski et al. |
| 9,364,219 B2 | 6/2016 | Olson et al. |
| 9,364,220 B2 | 6/2016 | Williams |
| 9,364,223 B2 | 6/2016 | Scirica |
| 9,364,226 B2 | 6/2016 | Zemlok et al. |
| 9,364,229 B2 | 6/2016 | D'Agostino et al. |
| 9,364,230 B2 | 6/2016 | Shelton, IV et al. |
| 9,364,231 B2 | 6/2016 | Wenchell |
| 9,364,233 B2 | 6/2016 | Alexander, III et al. |
| 9,364,279 B2 | 6/2016 | Houser et al. |
| 9,368,991 B2 | 6/2016 | Qahouq |
| 9,370,341 B2 | 6/2016 | Ceniccola et al. |
| 9,370,358 B2 | 6/2016 | Shelton, IV et al. |
| 9,370,361 B2 | 6/2016 | Viola et al. |
| 9,370,362 B2 | 6/2016 | Petty et al. |
| 9,370,364 B2 | 6/2016 | Smith et al. |
| 9,370,400 B2 | 6/2016 | Parihar |
| 9,375,206 B2 | 6/2016 | Vidal et al. |
| 9,375,218 B2 | 6/2016 | Wheeler et al. |
| 9,375,230 B2 | 6/2016 | Ross et al. |
| 9,375,232 B2 | 6/2016 | Hunt et al. |
| 9,375,255 B2 | 6/2016 | Houser et al. |
| D761,309 S | 7/2016 | Lee et al. |
| 9,381,058 B2 | 7/2016 | Houser et al. |
| 9,383,881 B2 | 7/2016 | Day et al. |
| 9,385,640 B2 | 7/2016 | Sun et al. |
| 9,386,983 B2 | 7/2016 | Swensgard et al. |
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,387,003 B2 | 7/2016 | Kaercher et al. |
| 9,392,885 B2 | 7/2016 | Vogler et al. |
| 9,393,015 B2 | 7/2016 | Laurent et al. |
| 9,393,017 B2 | 7/2016 | Flanagan et al. |
| 9,393,018 B2 | 7/2016 | Wang et al. |
| 9,393,354 B2 | 7/2016 | Freedman et al. |
| 9,396,369 B1 | 7/2016 | Whitehurst et al. |
| 9,396,669 B2 | 7/2016 | Karkanias et al. |
| 9,398,905 B2 | 7/2016 | Martin |
| 9,398,911 B2 | 7/2016 | Auld |
| D763,277 S | 8/2016 | Ahmed et al. |
| D764,498 S | 8/2016 | Capela et al. |
| 9,402,604 B2 | 8/2016 | Williams et al. |
| 9,402,625 B2 | 8/2016 | Coleman et al. |
| 9,402,626 B2 | 8/2016 | Ortiz et al. |
| 9,402,627 B2 | 8/2016 | Stevenson et al. |
| 9,402,629 B2 | 8/2016 | Ehrenfels et al. |
| 9,402,679 B2 | 8/2016 | Ginnebaugh et al. |
| 9,402,688 B2 | 8/2016 | Min et al. |
| 9,408,604 B2 | 8/2016 | Shelton, IV et al. |
| 9,408,605 B1 | 8/2016 | Knodel et al. |
| 9,408,606 B2 | 8/2016 | Shelton, IV |
| 9,408,622 B2 | 8/2016 | Stulen et al. |
| 9,411,370 B2 | 8/2016 | Benni et al. |
| 9,413,128 B2 | 8/2016 | Tien et al. |
| 9,414,838 B2 | 8/2016 | Shelton, IV et al. |
| 9,414,849 B2 | 8/2016 | Nagashimada |
| 9,414,880 B2 | 8/2016 | Monson et al. |
| 9,420,967 B2 | 8/2016 | Zand et al. |
| 9,421,003 B2 | 8/2016 | Williams et al. |
| 9,421,014 B2 | 8/2016 | Ingmanson et al. |
| 9,421,030 B2 | 8/2016 | Cole et al. |
| 9,421,060 B2 | 8/2016 | Monson et al. |
| 9,421,062 B2 | 8/2016 | Houser et al. |
| 9,421,682 B2 | 8/2016 | McClaskey et al. |
| 9,427,223 B2 | 8/2016 | Park et al. |
| 9,427,231 B2 | 8/2016 | Racenet et al. |
| 9,429,204 B2 | 8/2016 | Stefan et al. |
| D767,624 S | 9/2016 | Lee et al. |
| 9,433,411 B2 | 9/2016 | Racenet et al. |
| 9,433,414 B2 | 9/2016 | Chen et al. |
| 9,433,419 B2 | 9/2016 | Gonzalez et al. |
| 9,433,420 B2 | 9/2016 | Hodgkinson |
| 9,439,649 B2 | 9/2016 | Shelton, IV et al. |
| 9,439,650 B2 | 9/2016 | McGuckin, Jr. et al. |
| 9,439,651 B2 | 9/2016 | Smith et al. |
| 9,439,668 B2 | 9/2016 | Timm et al. |
| 9,445,808 B2 | 9/2016 | Woodard, Jr. et al. |
| 9,445,813 B2 | 9/2016 | Shelton, IV et al. |
| 9,445,816 B2 | 9/2016 | Swayze et al. |
| 9,445,817 B2 | 9/2016 | Bettuchi |
| 9,446,226 B2 | 9/2016 | Zilberman |
| 9,451,938 B2 | 9/2016 | Res et al. |
| 9,451,958 B2 | 9/2016 | Shelton, IV et al. |
| D768,152 S | 10/2016 | Gutierrez et al. |
| D768,156 S | 10/2016 | Frincke |
| D768,167 S | 10/2016 | Jones et al. |
| D769,315 S | 10/2016 | Scotti |
| D769,930 S | 10/2016 | Agrawal |
| 9,461,340 B2 | 10/2016 | Li et al. |
| 9,463,012 B2 | 10/2016 | Bonutti et al. |
| 9,463,040 B2 | 10/2016 | Jeong et al. |
| 9,463,260 B2 | 10/2016 | Stope |
| 9,468,438 B2 | 10/2016 | Baber et al. |
| 9,468,447 B2 | 10/2016 | Aman et al. |
| 9,470,297 B2 | 10/2016 | Aranyi et al. |
| 9,471,969 B2 | 10/2016 | Zeng et al. |
| 9,474,506 B2 | 10/2016 | Magnin et al. |
| 9,474,513 B2 | 10/2016 | Ishida et al. |
| 9,474,523 B2 | 10/2016 | Meade et al. |
| 9,474,540 B2 | 10/2016 | Stokes et al. |
| 9,475,180 B2 | 10/2016 | Eshleman et al. |
| D770,476 S | 11/2016 | Jitkoff et al. |

(56) References Cited

U.S. PATENT DOCUMENTS

| | | |
|---|---|---|
| D770,515 S | 11/2016 | Cho et al. |
| D771,116 S | 11/2016 | Dellinger et al. |
| D772,905 S | 11/2016 | Ingenlath |
| 9,480,476 B2 | 11/2016 | Aldridge et al. |
| 9,480,492 B2 | 11/2016 | Aranyi et al. |
| 9,483,095 B2 | 11/2016 | Tran et al. |
| 9,486,186 B2 | 11/2016 | Fiebig et al. |
| 9,486,213 B2 | 11/2016 | Altman et al. |
| 9,486,214 B2 | 11/2016 | Shelton, IV |
| 9,486,215 B2 | 11/2016 | Olson et al. |
| 9,486,302 B2 | 11/2016 | Boey et al. |
| 9,488,197 B2 | 11/2016 | Wi |
| 9,492,146 B2 | 11/2016 | Kostrzewski et al. |
| 9,492,167 B2 | 11/2016 | Shelton, IV et al. |
| 9,492,170 B2 | 11/2016 | Bear et al. |
| 9,492,172 B2 | 11/2016 | Weisshaupt et al. |
| 9,492,189 B2 | 11/2016 | Williams et al. |
| 9,492,192 B2 | 11/2016 | To et al. |
| 9,492,237 B2 | 11/2016 | Kang et al. |
| 9,498,213 B2 | 11/2016 | Marczyk et al. |
| 9,498,219 B2 | 11/2016 | Moore et al. |
| 9,498,231 B2 | 11/2016 | Haider et al. |
| 9,504,455 B2 | 11/2016 | Whitman et al. |
| 9,504,483 B2 | 11/2016 | Houser et al. |
| 9,504,520 B2 | 11/2016 | Worrell et al. |
| 9,504,521 B2 | 11/2016 | Deutmeyer et al. |
| 9,504,528 B2 | 11/2016 | Ivinson et al. |
| 9,507,399 B2 | 11/2016 | Chien |
| D774,547 S | 12/2016 | Capela et al. |
| D775,336 S | 12/2016 | Shelton, IV et al. |
| 9,510,827 B2 | 12/2016 | Kostrzewski |
| 9,510,828 B2 | 12/2016 | Yates et al. |
| 9,510,830 B2 | 12/2016 | Shelton, IV et al. |
| 9,510,846 B2 | 12/2016 | Sholev et al. |
| 9,510,895 B2 | 12/2016 | Houser et al. |
| 9,510,925 B2 | 12/2016 | Hotter et al. |
| 9,517,063 B2 | 12/2016 | Swayze et al. |
| 9,517,065 B2 | 12/2016 | Simms et al. |
| 9,517,068 B2 | 12/2016 | Shelton, IV et al. |
| 9,517,326 B2 | 12/2016 | Hinman et al. |
| 9,521,996 B2 | 12/2016 | Armstrong |
| 9,522,003 B2 | 12/2016 | Weir et al. |
| 9,522,014 B2 | 12/2016 | Nishizawa et al. |
| 9,522,029 B2 | 12/2016 | Yates et al. |
| 9,526,481 B2 | 12/2016 | Storz et al. |
| 9,526,499 B2 | 12/2016 | Kostrzewski et al. |
| 9,526,563 B2 | 12/2016 | Twomey |
| 9,526,564 B2 | 12/2016 | Rusin |
| 9,526,921 B2 | 12/2016 | Kimball et al. |
| D776,683 S | 1/2017 | Gobinski et al. |
| D777,773 S | 1/2017 | Shi |
| 9,532,783 B2 | 1/2017 | Swayze et al. |
| 9,539,060 B2 | 1/2017 | Lightcap et al. |
| 9,539,726 B2 | 1/2017 | Simaan et al. |
| 9,545,253 B2 | 1/2017 | Worrell et al. |
| 9,545,258 B2 | 1/2017 | Smith et al. |
| 9,549,732 B2 | 1/2017 | Yates et al. |
| 9,549,733 B2 | 1/2017 | Knodel |
| 9,549,735 B2 | 1/2017 | Shelton, IV et al. |
| 9,549,750 B2 | 1/2017 | Shelton, IV et al. |
| 9,554,794 B2 | 1/2017 | Baber et al. |
| 9,554,796 B2 | 1/2017 | Kostrzewski |
| 9,554,803 B2 | 1/2017 | Smith et al. |
| 9,554,812 B2 | 1/2017 | Inkpen et al. |
| 9,559,624 B2 | 1/2017 | Philipp |
| 9,561,013 B2 | 2/2017 | Tsuchiya |
| 9,561,029 B2 | 2/2017 | Scheib et al. |
| 9,561,030 B2 | 2/2017 | Zhang et al. |
| 9,561,031 B2 | 2/2017 | Heinrich et al. |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,561,072 B2 | 2/2017 | Ko |
| 9,566,061 B2 | 2/2017 | Aronhalt et al. |
| 9,566,062 B2 | 2/2017 | Boudreaux |
| 9,566,065 B2 | 2/2017 | Knodel |
| 9,566,067 B2 | 2/2017 | Milliman et al. |
| 9,572,574 B2 | 2/2017 | Shelton, IV et al. |
| 9,572,576 B2 | 2/2017 | Hodgkinson et al. |
| 9,572,577 B2 | 2/2017 | Lloyd et al. |
| 9,572,592 B2 | 2/2017 | Price et al. |
| 9,574,644 B2 | 2/2017 | Parihar |
| 9,579,088 B2 | 2/2017 | Farritor et al. |
| 9,579,143 B2 | 2/2017 | Ullrich et al. |
| 9,579,158 B2 | 2/2017 | Brianza et al. |
| D780,803 S | 3/2017 | Gill et al. |
| D781,879 S | 3/2017 | Butcher et al. |
| D782,530 S | 3/2017 | Paek et al. |
| 9,585,550 B2 | 3/2017 | Abel et al. |
| 9,585,657 B2 | 3/2017 | Shelton, IV et al. |
| 9,585,658 B2 | 3/2017 | Shelton, IV |
| 9,585,659 B2 | 3/2017 | Viola et al. |
| 9,585,660 B2 | 3/2017 | Laurent et al. |
| 9,585,662 B2 | 3/2017 | Shelton, IV et al. |
| 9,585,663 B2 | 3/2017 | Shelton, IV et al. |
| 9,585,672 B2 | 3/2017 | Bastia |
| 9,590,433 B2 | 3/2017 | Li |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,592,054 B2 | 3/2017 | Schmid et al. |
| 9,597,073 B2 | 3/2017 | Sorrentino et al. |
| 9,597,075 B2 | 3/2017 | Shelton, IV et al. |
| 9,597,078 B2 | 3/2017 | Scirica et al. |
| 9,597,080 B2 | 3/2017 | Milliman et al. |
| 9,597,104 B2 | 3/2017 | Nicholas et al. |
| 9,597,143 B2 | 3/2017 | Madan et al. |
| 9,603,595 B2 | 3/2017 | Shelton, IV et al. |
| 9,603,598 B2 | 3/2017 | Shelton, IV et al. |
| 9,603,599 B2 | 3/2017 | Miller et al. |
| 9,603,991 B2 | 3/2017 | Shelton, IV et al. |
| D783,658 S | 4/2017 | Hurst et al. |
| 9,610,068 B2 | 4/2017 | Kappel et al. |
| 9,610,079 B2 | 4/2017 | Kamei et al. |
| 9,610,080 B2 | 4/2017 | Whitfield et al. |
| 9,610,412 B2 | 4/2017 | Zemlok et al. |
| 9,614,258 B2 | 4/2017 | Takahashi et al. |
| 9,615,826 B2 | 4/2017 | Shelton, IV et al. |
| 9,622,745 B2 | 4/2017 | Ingmanson et al. |
| 9,622,746 B2 | 4/2017 | Simms et al. |
| 9,629,623 B2 | 4/2017 | Lytle, IV et al. |
| 9,629,626 B2 | 4/2017 | Soltz et al. |
| 9,629,627 B2 | 4/2017 | Kostrzewski et al. |
| 9,629,628 B2 | 4/2017 | Aranyi |
| 9,629,629 B2 | 4/2017 | Leimbach et al. |
| 9,629,631 B2 | 4/2017 | Nicholas et al. |
| 9,629,632 B2 | 4/2017 | Linder et al. |
| 9,629,652 B2 | 4/2017 | Mumaw et al. |
| 9,629,814 B2 | 4/2017 | Widenhouse et al. |
| D785,794 S | 5/2017 | Magno, Jr. |
| D786,280 S | 5/2017 | Ma |
| D786,896 S | 5/2017 | Kim et al. |
| D787,547 S | 5/2017 | Basargin et al. |
| D788,123 S | 5/2017 | Shan et al. |
| D788,140 S | 5/2017 | Hemsley et al. |
| 9,636,091 B2 | 5/2017 | Beardsley et al. |
| 9,636,111 B2 | 5/2017 | Wenchell |
| 9,636,112 B2 | 5/2017 | Penna et al. |
| 9,636,113 B2 | 5/2017 | Wenchell |
| 9,636,850 B2 | 5/2017 | Stopek (nee Prommersberger) et al. |
| 9,641,122 B2 | 5/2017 | Romanowich et al. |
| 9,642,620 B2 | 5/2017 | Baxter, III et al. |
| 9,642,642 B2 | 5/2017 | Lim |
| 9,649,096 B2 | 5/2017 | Sholev |
| 9,649,110 B2 | 5/2017 | Parihar et al. |
| 9,649,111 B2 | 5/2017 | Shelton, IV et al. |
| 9,649,190 B2 | 5/2017 | Mathies |
| 9,655,613 B2 | 5/2017 | Schaller |
| 9,655,614 B2 | 5/2017 | Swensgard et al. |
| 9,655,615 B2 | 5/2017 | Knodel et al. |
| 9,655,616 B2 | 5/2017 | Aranyi |
| 9,655,624 B2 | 5/2017 | Shelton, IV et al. |
| 9,661,991 B2 | 5/2017 | Glossop |

(56) References Cited

U.S. PATENT DOCUMENTS

| | | |
|---|---|---|
| 9,662,108 B2 | 5/2017 | Williams |
| 9,662,110 B2 | 5/2017 | Huang et al. |
| 9,662,116 B2 | 5/2017 | Smith et al. |
| 9,662,131 B2 | 5/2017 | Omori et al. |
| D788,792 S | 6/2017 | Alessandri et al. |
| D789,384 S | 6/2017 | Lin et al. |
| D790,570 S | 6/2017 | Butcher et al. |
| 9,668,728 B2 | 6/2017 | Williams et al. |
| 9,668,729 B2 | 6/2017 | Williams et al. |
| 9,668,732 B2 | 6/2017 | Patel et al. |
| 9,668,733 B2 | 6/2017 | Williams |
| 9,668,734 B2 | 6/2017 | Kostrzewski et al. |
| 9,668,735 B2 | 6/2017 | Beetel |
| 9,675,344 B2 | 6/2017 | Combrowski et al. |
| 9,675,348 B2 | 6/2017 | Smith et al. |
| 9,675,351 B2 | 6/2017 | Hodgkinson et al. |
| 9,675,354 B2 | 6/2017 | Weir et al. |
| 9,675,355 B2 | 6/2017 | Shelton, IV et al. |
| 9,675,368 B2 | 6/2017 | Guo et al. |
| 9,675,372 B2 | 6/2017 | Laurent et al. |
| 9,675,375 B2 | 6/2017 | Houser et al. |
| 9,675,405 B2 | 6/2017 | Trees et al. |
| 9,675,819 B2 | 6/2017 | Dunbar et al. |
| 9,681,870 B2 | 6/2017 | Baxter, III et al. |
| 9,681,873 B2 | 6/2017 | Smith et al. |
| 9,681,884 B2 | 6/2017 | Clem et al. |
| 9,687,230 B2 | 6/2017 | Leimbach et al. |
| 9,687,231 B2 | 6/2017 | Baxter, III et al. |
| 9,687,232 B2 | 6/2017 | Shelton, IV et al. |
| 9,687,233 B2 | 6/2017 | Fernandez et al. |
| 9,687,236 B2 | 6/2017 | Leimbach et al. |
| 9,687,237 B2 | 6/2017 | Schmid et al. |
| 9,687,253 B2 | 6/2017 | Detry et al. |
| 9,689,466 B2 | 6/2017 | Kanai et al. |
| 9,690,362 B2 | 6/2017 | Leimbach et al. |
| 9,693,772 B2 | 7/2017 | Ingmanson et al. |
| 9,693,774 B2 | 7/2017 | Gettinger et al. |
| 9,693,775 B2 | 7/2017 | Agarwal et al. |
| 9,693,777 B2 | 7/2017 | Schellin et al. |
| 9,700,309 B2 | 7/2017 | Jaworek et al. |
| 9,700,310 B2 | 7/2017 | Morgan et al. |
| 9,700,312 B2 | 7/2017 | Kostrzewski et al. |
| 9,700,314 B2 | 7/2017 | Marczyk |
| 9,700,315 B2 | 7/2017 | Chen et al. |
| 9,700,317 B2 | 7/2017 | Aronhalt et al. |
| 9,700,318 B2 | 7/2017 | Scirica et al. |
| 9,700,319 B2 | 7/2017 | Motooka et al. |
| 9,700,320 B2 | 7/2017 | Dinardo et al. |
| 9,700,321 B2 | 7/2017 | Shelton, IV et al. |
| 9,700,334 B2 | 7/2017 | Hinman et al. |
| 9,702,823 B2 | 7/2017 | Maher et al. |
| 9,706,674 B2 | 7/2017 | Collins et al. |
| 9,706,981 B2 | 7/2017 | Nicholas et al. |
| 9,706,991 B2 | 7/2017 | Hess et al. |
| 9,706,993 B2 | 7/2017 | Hessler et al. |
| 9,707,003 B2 | 7/2017 | Hoell, Jr. et al. |
| 9,707,005 B2 | 7/2017 | Strobl et al. |
| 9,707,026 B2 | 7/2017 | Malackowski et al. |
| 9,707,033 B2 | 7/2017 | Parihar et al. |
| 9,707,043 B2 | 7/2017 | Bozung |
| 9,707,684 B2 | 7/2017 | Ruiz Morales et al. |
| 9,713,468 B2 | 7/2017 | Harris et al. |
| 9,713,470 B2 | 7/2017 | Scirica et al. |
| 9,713,474 B2 | 7/2017 | Lorenz |
| D795,919 S | 8/2017 | Bischoff et al. |
| 9,717,497 B2 | 8/2017 | Zerkle et al. |
| 9,717,498 B2 | 8/2017 | Aranyi et al. |
| 9,718,190 B2 | 8/2017 | Larkin et al. |
| 9,722,236 B2 | 8/2017 | Sathrum |
| 9,724,091 B2 | 8/2017 | Shelton, IV et al. |
| 9,724,092 B2 | 8/2017 | Baxter, III et al. |
| 9,724,094 B2 | 8/2017 | Baber et al. |
| 9,724,095 B2 | 8/2017 | Gupta et al. |
| 9,724,096 B2 | 8/2017 | Thompson et al. |
| 9,724,098 B2 | 8/2017 | Baxter, III et al. |
| 9,724,118 B2 | 8/2017 | Schulte et al. |
| 9,724,163 B2 | 8/2017 | Orban |
| 9,730,692 B2 | 8/2017 | Shelton, IV et al. |
| 9,730,695 B2 | 8/2017 | Leimbach et al. |
| 9,730,697 B2 | 8/2017 | Morgan et al. |
| 9,730,717 B2 | 8/2017 | Katsuki et al. |
| 9,730,757 B2 | 8/2017 | Brudniok |
| 9,731,410 B2 | 8/2017 | Hirabayashi et al. |
| 9,733,663 B2 | 8/2017 | Leimbach et al. |
| 9,737,297 B2 | 8/2017 | Racenet et al. |
| 9,737,298 B2 | 8/2017 | Isbell, Jr. |
| 9,737,299 B2 | 8/2017 | Yan |
| 9,737,301 B2 | 8/2017 | Baber et al. |
| 9,737,302 B2 | 8/2017 | Shelton, IV et al. |
| 9,737,303 B2 | 8/2017 | Shelton, IV et al. |
| 9,737,365 B2 | 8/2017 | Hegeman et al. |
| 9,743,927 B2 | 8/2017 | Whitman |
| 9,743,928 B2 | 8/2017 | Shelton, IV et al. |
| 9,743,929 B2 | 8/2017 | Leimbach et al. |
| D798,319 S | 9/2017 | Bergstrand et al. |
| 9,750,498 B2 | 9/2017 | Timm et al. |
| 9,750,499 B2 | 9/2017 | Leimbach et al. |
| 9,750,501 B2 | 9/2017 | Shelton, IV et al. |
| 9,750,502 B2 | 9/2017 | Scirica et al. |
| 9,750,503 B2 | 9/2017 | Milliman |
| 9,750,639 B2 | 9/2017 | Barnes et al. |
| 9,757,123 B2 | 9/2017 | Giordano et al. |
| 9,757,124 B2 | 9/2017 | Schellin et al. |
| 9,757,126 B2 | 9/2017 | Cappola |
| 9,757,128 B2 | 9/2017 | Baber et al. |
| 9,757,129 B2 | 9/2017 | Williams |
| 9,757,130 B2 | 9/2017 | Shelton, IV |
| 9,763,662 B2 | 9/2017 | Shelton, IV et al. |
| 9,763,668 B2 | 9/2017 | Whitfield et al. |
| 9,770,245 B2 | 9/2017 | Swayze et al. |
| 9,770,274 B2 | 9/2017 | Pool et al. |
| D798,886 S | 10/2017 | Prophete et al. |
| D800,742 S | 10/2017 | Rhodes |
| D800,744 S | 10/2017 | Jitkoff et al. |
| D800,766 S | 10/2017 | Park et al. |
| D800,904 S | 10/2017 | Leimbach et al. |
| 9,775,608 B2 | 10/2017 | Aronhalt et al. |
| 9,775,609 B2 | 10/2017 | Shelton, IV et al. |
| 9,775,610 B2 | 10/2017 | Nicholas et al. |
| 9,775,611 B2 | 10/2017 | Kostrzewski |
| 9,775,613 B2 | 10/2017 | Shelton, IV et al. |
| 9,775,614 B2 | 10/2017 | Shelton, IV et al. |
| 9,775,618 B2 | 10/2017 | Bettuchi et al. |
| 9,775,635 B2 | 10/2017 | Takei |
| 9,775,678 B2 | 10/2017 | Lohmeier |
| 9,782,169 B2 | 10/2017 | Kimsey et al. |
| 9,782,170 B2 | 10/2017 | Zemlok et al. |
| 9,782,180 B2 | 10/2017 | Smith et al. |
| 9,782,187 B2 | 10/2017 | Zergiebel et al. |
| 9,782,193 B2 | 10/2017 | Thistle |
| 9,782,214 B2 | 10/2017 | Houser et al. |
| 9,788,834 B2 | 10/2017 | Schmid et al. |
| 9,788,835 B2 | 10/2017 | Morgan et al. |
| 9,788,836 B2 | 10/2017 | Overmyer et al. |
| 9,788,847 B2 | 10/2017 | Jinno |
| 9,788,851 B2 | 10/2017 | Dannaher et al. |
| 9,788,902 B2 | 10/2017 | Inoue et al. |
| 9,795,379 B2 | 10/2017 | Leimbach et al. |
| 9,795,380 B2 | 10/2017 | Shelton, IV et al. |
| 9,795,381 B2 | 10/2017 | Shelton, IV |
| 9,795,382 B2 | 10/2017 | Shelton, IV |
| 9,795,383 B2 | 10/2017 | Aldridge et al. |
| 9,795,384 B2 | 10/2017 | Weaner et al. |
| 9,797,486 B2 | 10/2017 | Zergiebel et al. |
| 9,801,626 B2 | 10/2017 | Parihar et al. |
| 9,801,627 B2 | 10/2017 | Harris et al. |
| 9,801,628 B2 | 10/2017 | Harris et al. |
| 9,801,634 B2 | 10/2017 | Shelton, IV et al. |
| 9,802,033 B2 | 10/2017 | Hibner et al. |
| 9,804,618 B2 | 10/2017 | Leimbach et al. |
| D803,234 S | 11/2017 | Day et al. |
| D803,235 S | 11/2017 | Markson et al. |
| D803,850 S | 11/2017 | Chang et al. |
| 9,808,244 B2 | 11/2017 | Leimbach et al. |

(56) References Cited

U.S. PATENT DOCUMENTS

| | | |
|---|---|---|
| 9,808,246 B2 | 11/2017 | Shelton, IV et al. |
| 9,808,247 B2 | 11/2017 | Shelton, IV et al. |
| 9,808,248 B2 | 11/2017 | Hoffman |
| 9,808,249 B2 | 11/2017 | Shelton, IV |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,814,530 B2 | 11/2017 | Weir et al. |
| 9,814,561 B2 | 11/2017 | Forsell |
| 9,815,118 B1 | 11/2017 | Schmitt et al. |
| 9,820,445 B2 | 11/2017 | Simpson et al. |
| 9,820,737 B2 | 11/2017 | Beardsley et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,825,455 B2 | 11/2017 | Sandhu et al. |
| 9,826,976 B2 | 11/2017 | Parihar et al. |
| 9,826,977 B2 | 11/2017 | Leimbach et al. |
| 9,826,978 B2 | 11/2017 | Shelton, IV et al. |
| 9,829,698 B2 | 11/2017 | Haraguchi et al. |
| D806,108 S | 12/2017 | Day |
| 9,833,235 B2 | 12/2017 | Penna et al. |
| 9,833,236 B2 | 12/2017 | Shelton, IV et al. |
| 9,833,238 B2 | 12/2017 | Baxter, III et al. |
| 9,833,239 B2 | 12/2017 | Yates et al. |
| 9,833,241 B2 | 12/2017 | Huitema et al. |
| 9,833,242 B2 | 12/2017 | Baxter, III et al. |
| 9,839,420 B2 | 12/2017 | Shelton, IV et al. |
| 9,839,421 B2 | 12/2017 | Zerkle et al. |
| 9,839,422 B2 | 12/2017 | Schellin et al. |
| 9,839,423 B2 | 12/2017 | Vendely et al. |
| 9,839,427 B2 | 12/2017 | Swayze et al. |
| 9,839,428 B2 | 12/2017 | Baxter, III et al. |
| 9,839,429 B2 | 12/2017 | Weisenburgh, II et al. |
| 9,839,480 B2 | 12/2017 | Pribanic et al. |
| 9,839,481 B2 | 12/2017 | Blumenkranz et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,871 B2 | 12/2017 | Harris et al. |
| 9,848,873 B2 | 12/2017 | Shelton, IV |
| 9,848,875 B2 | 12/2017 | Aronhalt et al. |
| 9,848,877 B2 | 12/2017 | Shelton, IV et al. |
| 9,850,994 B2 | 12/2017 | Schena |
| D808,989 S | 1/2018 | Ayvazian et al. |
| 9,855,039 B2 | 1/2018 | Racenet et al. |
| 9,855,040 B2 | 1/2018 | Kostrzewski |
| 9,855,662 B2 | 1/2018 | Ruiz Morales et al. |
| 9,861,261 B2 | 1/2018 | Shahinian |
| 9,861,359 B2 | 1/2018 | Shelton, IV et al. |
| 9,861,361 B2 | 1/2018 | Aronhalt et al. |
| 9,861,362 B2 | 1/2018 | Whitman et al. |
| 9,861,366 B2 | 1/2018 | Aranyi |
| 9,861,382 B2 | 1/2018 | Smith et al. |
| 9,861,446 B2 | 1/2018 | Lang |
| 9,867,612 B2 | 1/2018 | Parihar et al. |
| 9,867,613 B2 | 1/2018 | Marczyk et al. |
| 9,867,615 B2 | 1/2018 | Fanelli et al. |
| 9,867,617 B2 | 1/2018 | Ma |
| 9,867,618 B2 | 1/2018 | Hall et al. |
| 9,867,620 B2 | 1/2018 | Fischvogt et al. |
| 9,868,198 B2 | 1/2018 | Nicholas et al. |
| 9,872,682 B2 | 1/2018 | Hess et al. |
| 9,872,683 B2 | 1/2018 | Hopkins et al. |
| 9,872,684 B2 | 1/2018 | Hall et al. |
| 9,872,722 B2 | 1/2018 | Lech |
| 9,877,721 B2 | 1/2018 | Schellin et al. |
| 9,877,722 B2 | 1/2018 | Schellin et al. |
| 9,877,723 B2 | 1/2018 | Hall et al. |
| 9,877,776 B2 | 1/2018 | Boudreaux |
| D810,099 S | 2/2018 | Riedel |
| 9,883,843 B2 | 2/2018 | Garlow |
| 9,883,860 B2 | 2/2018 | Leimbach |
| 9,883,861 B2 | 2/2018 | Shelton, IV et al. |
| 9,884,456 B2 | 2/2018 | Schellin et al. |
| 9,888,914 B2 | 2/2018 | Martin et al. |
| 9,888,919 B2 | 2/2018 | Leimbach et al. |
| 9,888,921 B2 | 2/2018 | Williams et al. |
| 9,888,924 B2 | 2/2018 | Ebersole et al. |
| 9,889,230 B2 | 2/2018 | Bennett et al. |
| 9,895,147 B2 | 2/2018 | Shelton, IV |
| 9,895,148 B2 | 2/2018 | Shelton, IV et al. |
| 9,895,813 B2 | 2/2018 | Blumenkranz et al. |
| 9,901,339 B2 | 2/2018 | Farascioni |
| 9,901,341 B2 | 2/2018 | Kostrzewski |
| 9,901,342 B2 | 2/2018 | Shelton, IV et al. |
| 9,901,344 B2 | 2/2018 | Moore et al. |
| 9,901,345 B2 | 2/2018 | Moore et al. |
| 9,901,346 B2 | 2/2018 | Moore et al. |
| 9,901,406 B2 | 2/2018 | State et al. |
| 9,901,412 B2 | 2/2018 | Lathrop et al. |
| D813,899 S | 3/2018 | Erant et al. |
| 9,907,456 B2 | 3/2018 | Miyoshi |
| 9,907,552 B2 | 3/2018 | Measamer et al. |
| 9,907,553 B2 | 3/2018 | Cole et al. |
| 9,907,600 B2 | 3/2018 | Stulen et al. |
| 9,907,620 B2 | 3/2018 | Shelton, IV et al. |
| 9,913,641 B2 | 3/2018 | Takemoto et al. |
| 9,913,642 B2 | 3/2018 | Leimbach et al. |
| 9,913,644 B2 | 3/2018 | McCuen |
| 9,913,646 B2 | 3/2018 | Shelton, IV |
| 9,913,647 B2 | 3/2018 | Weisenburgh, II et al. |
| 9,913,648 B2 | 3/2018 | Shelton, IV et al. |
| 9,913,694 B2 | 3/2018 | Brisson |
| 9,913,733 B2 | 3/2018 | Piron et al. |
| 9,918,704 B2 | 3/2018 | Shelton, IV et al. |
| 9,918,714 B2 | 3/2018 | Gibbons, Jr. |
| 9,918,715 B2 | 3/2018 | Menn |
| 9,918,716 B2 | 3/2018 | Baxter, III et al. |
| 9,918,717 B2 | 3/2018 | Czernik |
| 9,918,730 B2 | 3/2018 | Trees et al. |
| 9,924,941 B2 | 3/2018 | Burbank |
| 9,924,942 B2 | 3/2018 | Swayze et al. |
| 9,924,943 B2 | 3/2018 | Mohan Pinjala et al. |
| 9,924,944 B2 | 3/2018 | Shelton, IV et al. |
| 9,924,945 B2 | 3/2018 | Zheng et al. |
| 9,924,946 B2 | 3/2018 | Vendely et al. |
| 9,924,947 B2 | 3/2018 | Shelton, IV et al. |
| 9,924,961 B2 | 3/2018 | Shelton, IV et al. |
| 9,931,106 B2 | 4/2018 | Au et al. |
| 9,931,116 B2 | 4/2018 | Racenet et al. |
| 9,931,118 B2 | 4/2018 | Shelton, IV et al. |
| 9,931,120 B2 | 4/2018 | Chen et al. |
| 9,936,949 B2 | 4/2018 | Measamer et al. |
| 9,936,950 B2 | 4/2018 | Shelton, IV et al. |
| 9,936,951 B2 | 4/2018 | Hufnagel et al. |
| 9,936,952 B2 | 4/2018 | Demmy |
| 9,936,954 B2 | 4/2018 | Shelton, IV et al. |
| 9,937,626 B2 | 4/2018 | Rockrohr |
| 9,943,309 B2 | 4/2018 | Shelton, IV et al. |
| 9,943,310 B2 | 4/2018 | Harris et al. |
| 9,943,312 B2 | 4/2018 | Posada et al. |
| 9,949,754 B2 | 4/2018 | Newhauser et al. |
| 9,953,193 B2 | 4/2018 | Butler et al. |
| D819,072 S | 5/2018 | Clediere |
| 9,955,954 B2 | 5/2018 | Destoumieux et al. |
| 9,955,965 B2 | 5/2018 | Chen et al. |
| 9,955,966 B2 | 5/2018 | Zergiebel |
| 9,956,677 B2 | 5/2018 | Baskar et al. |
| 9,962,129 B2 | 5/2018 | Jerebko et al. |
| 9,962,157 B2 | 5/2018 | Sapre |
| 9,962,158 B2 | 5/2018 | Hall et al. |
| 9,962,159 B2 | 5/2018 | Heinrich et al. |
| 9,962,161 B2 | 5/2018 | Scheib et al. |
| 9,968,354 B2 | 5/2018 | Shelton, IV et al. |
| 9,968,355 B2 | 5/2018 | Shelton, IV et al. |
| 9,968,356 B2 | 5/2018 | Shelton, IV et al. |
| 9,968,397 B2 | 5/2018 | Taylor et al. |
| 9,974,529 B2 | 5/2018 | Shelton, IV et al. |

(56) References Cited

U.S. PATENT DOCUMENTS

| | | |
|---|---|---|
| 9,974,538 B2 | 5/2018 | Baxter, III et al. |
| 9,974,539 B2 | 5/2018 | Yates et al. |
| 9,974,541 B2 | 5/2018 | Calderoni |
| 9,974,542 B2 | 5/2018 | Hodgkinson |
| 9,980,713 B2 | 5/2018 | Aronhalt et al. |
| 9,980,724 B2 | 5/2018 | Farascioni et al. |
| 9,980,729 B2 | 5/2018 | Moore et al. |
| 9,980,769 B2 | 5/2018 | Trees et al. |
| D819,680 S | 6/2018 | Nguyen |
| D819,682 S | 6/2018 | Howard et al. |
| D819,684 S | 6/2018 | Dart |
| D820,307 S | 6/2018 | Jian et al. |
| D820,867 S | 6/2018 | Dickens et al. |
| 9,987,000 B2 | 6/2018 | Shelton, IV et al. |
| 9,987,003 B2 | 6/2018 | Timm et al. |
| 9,987,006 B2 | 6/2018 | Morgan et al. |
| 9,987,008 B2 | 6/2018 | Scirica et al. |
| 9,987,095 B2 | 6/2018 | Chowaniec et al. |
| 9,987,097 B2 | 6/2018 | van der Weide et al. |
| 9,993,248 B2 | 6/2018 | Shelton, IV et al. |
| 9,993,258 B2 | 6/2018 | Shelton, IV et al. |
| 9,993,284 B2 | 6/2018 | Boudreaux |
| 9,999,408 B2 | 6/2018 | Boudreaux et al. |
| 9,999,423 B2 | 6/2018 | Schuckmann et al. |
| 9,999,426 B2 | 6/2018 | Moore et al. |
| 9,999,431 B2 | 6/2018 | Shelton, IV et al. |
| 9,999,472 B2 | 6/2018 | Weir et al. |
| 10,004,497 B2 | 6/2018 | Overmyer et al. |
| 10,004,498 B2 | 6/2018 | Morgan et al. |
| 10,004,500 B2 | 6/2018 | Shelton, IV et al. |
| 10,004,501 B2 | 6/2018 | Shelton, IV et al. |
| 10,004,505 B2 | 6/2018 | Moore et al. |
| 10,004,506 B2 | 6/2018 | Shelton, IV et al. |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,010,395 B2 | 7/2018 | Puckett et al. |
| 10,013,049 B2 | 7/2018 | Leimbach et al. |
| 10,016,199 B2 | 7/2018 | Baber et al. |
| 10,016,656 B2 | 7/2018 | Devor et al. |
| 10,022,120 B2 | 7/2018 | Martin et al. |
| 10,022,123 B2 | 7/2018 | Williams et al. |
| 10,022,125 B2 | 7/2018 | (Prommersberger) Stopek et al. |
| 10,024,407 B2 | 7/2018 | Aranyi et al. |
| 10,028,742 B2 | 7/2018 | Shelton, IV et al. |
| 10,028,743 B2 | 7/2018 | Shelton, IV et al. |
| 10,028,744 B2 | 7/2018 | Shelton, IV et al. |
| 10,028,761 B2 | 7/2018 | Leimbach et al. |
| 10,029,108 B2 | 7/2018 | Powers et al. |
| 10,029,125 B2 | 7/2018 | Shapiro et al. |
| 10,034,344 B2 | 7/2018 | Yoshida |
| 10,034,668 B2 | 7/2018 | Ebner |
| D826,405 S | 8/2018 | Shelton, IV et al. |
| 10,039,440 B2 | 8/2018 | Fenech et al. |
| 10,039,529 B2 | 8/2018 | Kerr et al. |
| 10,039,532 B2 | 8/2018 | Srinivas et al. |
| 10,039,545 B2 | 8/2018 | Sadowski et al. |
| 10,041,822 B2 | 8/2018 | Zemlok |
| 10,045,769 B2 | 8/2018 | Aronhalt et al. |
| 10,045,776 B2 | 8/2018 | Shelton, IV et al. |
| 10,045,778 B2 | 8/2018 | Yates et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,045,869 B2 | 8/2018 | Forsell |
| 10,052,044 B2 | 8/2018 | Shelton, IV et al. |
| 10,052,099 B2 | 8/2018 | Morgan et al. |
| 10,052,100 B2 | 8/2018 | Morgan et al. |
| 10,052,102 B2 | 8/2018 | Baxter, III et al. |
| 10,052,104 B2 | 8/2018 | Shelton, IV et al. |
| 10,052,164 B2 | 8/2018 | Overmyer |
| 10,058,317 B2 | 8/2018 | Fan et al. |
| 10,058,327 B2 | 8/2018 | Weisenburgh, II et al. |
| 10,058,373 B2 | 8/2018 | Takashino et al. |
| 10,058,395 B2 | 8/2018 | Devengenzo et al. |
| 10,058,963 B2 | 8/2018 | Shelton, IV et al. |
| 10,064,620 B2 | 9/2018 | Gettinger et al. |
| 10,064,621 B2 | 9/2018 | Kerr et al. |
| 10,064,622 B2 | 9/2018 | Murthy Aravalli |
| 10,064,624 B2 | 9/2018 | Shelton, IV et al. |
| 10,064,639 B2 | 9/2018 | Ishida et al. |
| 10,064,649 B2 | 9/2018 | Golebieski et al. |
| 10,064,688 B2 | 9/2018 | Shelton, IV et al. |
| 10,070,861 B2 | 9/2018 | Spivey et al. |
| 10,070,863 B2 | 9/2018 | Swayze et al. |
| 10,071,452 B2 | 9/2018 | Shelton, IV et al. |
| 10,076,325 B2 | 9/2018 | Huang et al. |
| 10,076,326 B2 | 9/2018 | Yates et al. |
| 10,076,340 B2 | 9/2018 | Belagali et al. |
| 10,080,552 B2 | 9/2018 | Nicholas et al. |
| D830,550 S | 10/2018 | Miller et al. |
| D831,209 S | 10/2018 | Huitema et al. |
| D831,676 S | 10/2018 | Park et al. |
| D832,301 S | 10/2018 | Smith |
| 10,085,624 B2 | 10/2018 | Isoda et al. |
| 10,085,643 B2 | 10/2018 | Bandic et al. |
| 10,085,728 B2 | 10/2018 | Jogasaki et al. |
| 10,085,746 B2 | 10/2018 | Fischvogt |
| 10,085,748 B2 | 10/2018 | Morgan et al. |
| 10,085,749 B2 | 10/2018 | Cappola et al. |
| 10,085,750 B2 | 10/2018 | Zergiebel et al. |
| 10,085,751 B2 | 10/2018 | Overmyer et al. |
| 10,085,754 B2 | 10/2018 | Sniffin et al. |
| 10,085,806 B2 | 10/2018 | Hagn et al. |
| 10,092,290 B2 | 10/2018 | Yigit et al. |
| 10,092,292 B2 | 10/2018 | Boudreaux et al. |
| 10,098,635 B2 | 10/2018 | Burbank |
| 10,098,636 B2 | 10/2018 | Shelton, IV et al. |
| 10,098,640 B2 | 10/2018 | Bertolero et al. |
| 10,098,642 B2 | 10/2018 | Baxter, III et al. |
| 10,099,303 B2 | 10/2018 | Yoshida et al. |
| 10,101,861 B2 | 10/2018 | Kiyoto |
| 10,105,126 B2 | 10/2018 | Sauer |
| 10,105,128 B2 | 10/2018 | Cooper et al. |
| 10,105,136 B2 | 10/2018 | Yates et al. |
| 10,105,139 B2 | 10/2018 | Yates et al. |
| 10,105,140 B2 | 10/2018 | Malinouskas et al. |
| 10,105,142 B2 | 10/2018 | Baxter, III et al. |
| 10,105,149 B2 | 10/2018 | Haider et al. |
| 10,106,932 B2 | 10/2018 | Anderson et al. |
| 10,111,657 B2 | 10/2018 | McCuen |
| 10,111,658 B2 | 10/2018 | Chowaniec et al. |
| 10,111,660 B2 | 10/2018 | Hemmann |
| 10,111,665 B2 | 10/2018 | Aranyi et al. |
| 10,111,679 B2 | 10/2018 | Baber et al. |
| 10,111,698 B2 | 10/2018 | Scheib et al. |
| 10,111,702 B2 | 10/2018 | Kostrzewski |
| D833,608 S | 11/2018 | Miller et al. |
| 10,117,649 B2 | 11/2018 | Baxter et al. |
| 10,117,650 B2 | 11/2018 | Nicholas et al. |
| 10,117,652 B2 | 11/2018 | Schmid et al. |
| 10,117,653 B2 | 11/2018 | Leimbach et al. |
| 10,117,654 B2 | 11/2018 | Ingmanson et al. |
| 10,123,798 B2 | 11/2018 | Baxter, III et al. |
| 10,123,845 B2 | 11/2018 | Yeung |
| 10,124,493 B2 | 11/2018 | Rothfuss et al. |
| 10,130,352 B2 | 11/2018 | Widenhouse et al. |
| 10,130,359 B2 | 11/2018 | Hess et al. |
| 10,130,361 B2 | 11/2018 | Yates et al. |
| 10,130,363 B2 | 11/2018 | Huitema et al. |
| 10,130,366 B2 | 11/2018 | Shelton, IV et al. |
| 10,130,382 B2 | 11/2018 | Gladstone |
| 10,130,738 B2 | 11/2018 | Shelton, IV et al. |
| 10,130,830 B2 | 11/2018 | Miret Carceller et al. |
| 10,133,248 B2 | 11/2018 | Fitzsimmons et al. |
| 10,135,242 B2 | 11/2018 | Baber et al. |
| 10,136,879 B2 | 11/2018 | Ross et al. |
| 10,136,887 B2 | 11/2018 | Shelton, IV et al. |
| 10,136,889 B2 | 11/2018 | Shelton, IV et al. |
| 10,136,890 B2 | 11/2018 | Shelton, IV et al. |
| 10,136,891 B2 | 11/2018 | Shelton, IV et al. |
| D835,659 S | 12/2018 | Anzures et al. |
| D836,124 S | 12/2018 | Fan |
| 10,143,474 B2 | 12/2018 | Bucciaglia et al. |

(56) References Cited

U.S. PATENT DOCUMENTS

| | | |
|---|---|---|
| 10,149,679 B2 | 12/2018 | Shelton, IV et al. |
| 10,149,680 B2 | 12/2018 | Parihar et al. |
| 10,149,682 B2 | 12/2018 | Shelton, IV et al. |
| 10,149,683 B2 | 12/2018 | Smith et al. |
| 10,149,712 B2 | 12/2018 | Manwaring et al. |
| 10,152,789 B2 | 12/2018 | Carnes et al. |
| 10,154,841 B2 | 12/2018 | Weaner et al. |
| 10,159,481 B2 | 12/2018 | Whitman et al. |
| 10,159,482 B2 | 12/2018 | Swayze et al. |
| 10,159,483 B2 | 12/2018 | Beckman et al. |
| 10,159,506 B2 | 12/2018 | Boudreaux et al. |
| 10,161,816 B2 | 12/2018 | Jackson et al. |
| 10,163,065 B1 | 12/2018 | Koski et al. |
| 10,163,589 B2 | 12/2018 | Zergiebel et al. |
| 10,164,466 B2 | 12/2018 | Calderoni |
| D837,244 S | 1/2019 | Kuo et al. |
| D837,245 S | 1/2019 | Kuo et al. |
| 10,166,023 B2 | 1/2019 | Vendely et al. |
| 10,166,025 B2 | 1/2019 | Leimbach et al. |
| 10,166,026 B2 | 1/2019 | Shelton, IV et al. |
| 10,172,611 B2 | 1/2019 | Shelton, IV et al. |
| 10,172,615 B2 | 1/2019 | Marczyk et al. |
| 10,172,616 B2 | 1/2019 | Murray et al. |
| 10,172,617 B2 | 1/2019 | Shelton, IV et al. |
| 10,172,618 B2 | 1/2019 | Shelton, IV et al. |
| 10,172,619 B2 | 1/2019 | Harris et al. |
| 10,172,620 B2 | 1/2019 | Harris et al. |
| 10,172,636 B2 | 1/2019 | Stulen et al. |
| 10,172,669 B2 | 1/2019 | Felder et al. |
| 10,175,127 B2 | 1/2019 | Collins et al. |
| 10,178,992 B2 | 1/2019 | Wise et al. |
| 10,180,463 B2 | 1/2019 | Beckman et al. |
| 10,182,813 B2 | 1/2019 | Leimbach et al. |
| 10,182,815 B2 | 1/2019 | Williams et al. |
| 10,182,816 B2 | 1/2019 | Shelton, IV et al. |
| 10,182,818 B2 | 1/2019 | Hensel et al. |
| 10,182,819 B2 | 1/2019 | Shelton, IV |
| 10,182,868 B2 | 1/2019 | Meier et al. |
| 10,188,385 B2 | 1/2019 | Kerr et al. |
| 10,188,389 B2 | 1/2019 | Vendely et al. |
| 10,188,393 B2 | 1/2019 | Smith et al. |
| 10,188,394 B2 | 1/2019 | Shelton, IV et al. |
| 10,190,888 B2 | 1/2019 | Hryb et al. |
| D839,900 S | 2/2019 | Gan |
| D841,667 S | 2/2019 | Coren |
| 10,194,801 B2 | 2/2019 | Elhawary et al. |
| 10,194,904 B2 | 2/2019 | Viola et al. |
| 10,194,907 B2 | 2/2019 | Marczyk et al. |
| 10,194,908 B2 | 2/2019 | Duque et al. |
| 10,194,910 B2 | 2/2019 | Shelton, IV et al. |
| 10,194,913 B2 | 2/2019 | Nalagatla et al. |
| 10,194,976 B2 | 2/2019 | Boudreaux |
| 10,194,992 B2 | 2/2019 | Robinson |
| 10,201,348 B2 | 2/2019 | Scheib et al. |
| 10,201,349 B2 | 2/2019 | Leimbach et al. |
| 10,201,363 B2 | 2/2019 | Shelton, IV |
| 10,201,364 B2 | 2/2019 | Leimbach et al. |
| 10,201,365 B2 | 2/2019 | Boudreaux et al. |
| 10,201,381 B2 | 2/2019 | Zergiebel et al. |
| 10,206,605 B2 | 2/2019 | Shelton, IV et al. |
| 10,206,676 B2 | 2/2019 | Shelton, IV |
| 10,206,677 B2 | 2/2019 | Harris et al. |
| 10,206,678 B2 | 2/2019 | Shelton, IV et al. |
| 10,206,748 B2 | 2/2019 | Burbank |
| 10,210,244 B1 | 2/2019 | Branavan et al. |
| 10,211,586 B2 | 2/2019 | Adams et al. |
| 10,213,198 B2 | 2/2019 | Aronhalt et al. |
| 10,213,201 B2 | 2/2019 | Shelton, IV et al. |
| 10,213,202 B2 | 2/2019 | Flanagan et al. |
| 10,213,203 B2 | 2/2019 | Swayze et al. |
| 10,213,204 B2 | 2/2019 | Aranyi et al. |
| 10,213,262 B2 | 2/2019 | Shelton, IV et al. |
| D842,328 S | 3/2019 | Jian et al. |
| 10,219,811 B2 | 3/2019 | Haider et al. |
| 10,219,832 B2 | 3/2019 | Bagwell et al. |
| 10,220,522 B2 | 3/2019 | Rockrohr |
| 10,226,239 B2 | 3/2019 | Nicholas et al. |
| 10,226,249 B2 | 3/2019 | Jaworek et al. |
| 10,226,250 B2 | 3/2019 | Beckman et al. |
| 10,226,251 B2 | 3/2019 | Scheib et al. |
| 10,226,274 B2 | 3/2019 | Worrell et al. |
| 10,231,634 B2 | 3/2019 | Zand et al. |
| 10,231,653 B2 | 3/2019 | Bohm et al. |
| 10,231,734 B2 | 3/2019 | Thompson et al. |
| 10,231,794 B2 | 3/2019 | Shelton, IV et al. |
| 10,238,385 B2 | 3/2019 | Yates et al. |
| 10,238,386 B2 | 3/2019 | Overmyer et al. |
| 10,238,387 B2 | 3/2019 | Yates et al. |
| 10,238,389 B2 | 3/2019 | Yates et al. |
| 10,238,390 B2 | 3/2019 | Harris et al. |
| 10,238,391 B2 | 3/2019 | Leimbach et al. |
| D844,666 S | 4/2019 | Espeleta et al. |
| D844,667 S | 4/2019 | Espeleta et al. |
| D845,342 S | 4/2019 | Espeleta et al. |
| D847,199 S | 4/2019 | Whitmore |
| 10,244,991 B2 | 4/2019 | Shademan et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,032 B2 | 4/2019 | Shelton, IV |
| 10,245,033 B2 | 4/2019 | Overmyer et al. |
| 10,245,034 B2 | 4/2019 | Shelton, IV et al. |
| 10,245,035 B2 | 4/2019 | Swayze et al. |
| 10,245,038 B2 | 4/2019 | Hopkins et al. |
| 10,245,058 B2 | 4/2019 | Omori et al. |
| 10,251,648 B2 | 4/2019 | Harris et al. |
| 10,251,649 B2 | 4/2019 | Schellin et al. |
| 10,251,725 B2 | 4/2019 | Valentine et al. |
| 10,258,322 B2 | 4/2019 | Fanton et al. |
| 10,258,330 B2 | 4/2019 | Shelton, IV et al. |
| 10,258,331 B2 | 4/2019 | Shelton, IV et al. |
| 10,258,332 B2 | 4/2019 | Schmid et al. |
| 10,258,333 B2 | 4/2019 | Shelton, IV et al. |
| 10,258,336 B2 | 4/2019 | Baxter, III et al. |
| 10,258,418 B2 | 4/2019 | Shelton, IV et al. |
| 10,264,797 B2 | 4/2019 | Zhang et al. |
| 10,265,065 B2 | 4/2019 | Shelton, IV et al. |
| 10,265,067 B2 | 4/2019 | Yates et al. |
| 10,265,068 B2 | 4/2019 | Harris et al. |
| 10,265,072 B2 | 4/2019 | Shelton, IV et al. |
| 10,265,073 B2 | 4/2019 | Scheib et al. |
| 10,265,074 B2 | 4/2019 | Shelton, IV et al. |
| 10,265,090 B2 | 4/2019 | Ingmanson et al. |
| 10,271,840 B2 | 4/2019 | Sapre |
| 10,271,844 B2 | 4/2019 | Valentine et al. |
| 10,271,845 B2 | 4/2019 | Shelton, IV |
| 10,271,846 B2 | 4/2019 | Shelton, IV et al. |
| 10,271,847 B2 | 4/2019 | Racenet et al. |
| 10,271,849 B2 | 4/2019 | Vendely et al. |
| 10,271,851 B2 | 4/2019 | Shelton, IV et al. |
| D847,989 S | 5/2019 | Shelton, IV et al. |
| D848,473 S | 5/2019 | Zhu et al. |
| D849,046 S | 5/2019 | Kuo et al. |
| 10,278,696 B2 | 5/2019 | Gurumurthy et al. |
| 10,278,697 B2 | 5/2019 | Shelton, IV et al. |
| 10,278,702 B2 | 5/2019 | Shelton, IV et al. |
| 10,278,703 B2 | 5/2019 | Nativ et al. |
| 10,278,707 B2 | 5/2019 | Thompson et al. |
| 10,278,722 B2 | 5/2019 | Shelton, IV et al. |
| 10,278,780 B2 | 5/2019 | Shelton, IV |
| 10,285,694 B2 | 5/2019 | Viola et al. |
| 10,285,695 B2 | 5/2019 | Jaworek et al. |
| 10,285,699 B2 | 5/2019 | Vendely et al. |
| 10,285,700 B2 | 5/2019 | Scheib |
| 10,285,705 B2 | 5/2019 | Shelton, IV et al. |
| 10,292,701 B2 | 5/2019 | Scheib et al. |
| 10,292,704 B2 | 5/2019 | Harris et al. |
| 10,292,707 B2 | 5/2019 | Shelton, IV et al. |
| 10,293,100 B2 | 5/2019 | Shelton, IV et al. |
| 10,293,553 B2 | 5/2019 | Racenet et al. |
| 10,299,787 B2 | 5/2019 | Shelton, IV |
| 10,299,788 B2 | 5/2019 | Heinrich et al. |
| 10,299,789 B2 | 5/2019 | Marczyk et al. |

(56) References Cited

U.S. PATENT DOCUMENTS

| | | |
|---|---|---|
| 10,299,790 B2 | 5/2019 | Beardsley |
| 10,299,792 B2 | 5/2019 | Huitema et al. |
| 10,299,817 B2 | 5/2019 | Shelton, IV et al. |
| 10,299,818 B2 | 5/2019 | Riva |
| 10,299,878 B2 | 5/2019 | Shelton, IV et al. |
| 10,303,851 B2 | 5/2019 | Nguyen et al. |
| D850,617 S | 6/2019 | Shelton, IV et al. |
| D851,676 S | 6/2019 | Foss et al. |
| D851,762 S | 6/2019 | Shelton, IV et al. |
| 10,307,159 B2 | 6/2019 | Harris et al. |
| 10,307,160 B2 | 6/2019 | Vendely et al. |
| 10,307,161 B2 | 6/2019 | Jankowski |
| 10,307,163 B2 | 6/2019 | Moore et al. |
| 10,307,170 B2 | 6/2019 | Parfett et al. |
| 10,307,202 B2 | 6/2019 | Smith et al. |
| 10,314,559 B2 | 6/2019 | Razzaque et al. |
| 10,314,577 B2 | 6/2019 | Laurent et al. |
| 10,314,578 B2 | 6/2019 | Leimbach et al. |
| 10,314,580 B2 | 6/2019 | Scheib et al. |
| 10,314,582 B2 | 6/2019 | Shelton, IV et al. |
| 10,314,584 B2 | 6/2019 | Scirica et al. |
| 10,314,587 B2 | 6/2019 | Harris et al. |
| 10,314,588 B2 | 6/2019 | Turner et al. |
| 10,314,589 B2 | 6/2019 | Shelton, IV et al. |
| 10,314,590 B2 | 6/2019 | Shelton, IV et al. |
| 10,315,566 B2 | 6/2019 | Choi et al. |
| 10,321,907 B2 | 6/2019 | Shelton, IV et al. |
| 10,321,909 B2 | 6/2019 | Shelton, IV et al. |
| 10,321,927 B2 | 6/2019 | Hinman |
| 10,327,743 B2 | 6/2019 | St. Goar et al. |
| 10,327,764 B2 | 6/2019 | Harris et al. |
| 10,327,765 B2 | 6/2019 | Timm et al. |
| 10,327,767 B2 | 6/2019 | Shelton, IV et al. |
| 10,327,769 B2 | 6/2019 | Overmyer et al. |
| 10,327,776 B2 | 6/2019 | Harris et al. |
| 10,327,777 B2 | 6/2019 | Harris et al. |
| D854,032 S | 7/2019 | Jones et al. |
| D854,151 S | 7/2019 | Shelton, IV et al. |
| 10,335,144 B2 | 7/2019 | Shelton, IV et al. |
| 10,335,145 B2 | 7/2019 | Harris et al. |
| 10,335,147 B2 | 7/2019 | Rector et al. |
| 10,335,148 B2 | 7/2019 | Shelton, IV et al. |
| 10,335,149 B2 | 7/2019 | Baxter, III et al. |
| 10,335,150 B2 | 7/2019 | Shelton, IV |
| 10,335,151 B2 | 7/2019 | Shelton, IV et al. |
| 10,337,148 B2 | 7/2019 | Rouse et al. |
| 10,342,533 B2 | 7/2019 | Shelton, IV et al. |
| 10,342,535 B2 | 7/2019 | Scheib et al. |
| 10,342,541 B2 | 7/2019 | Shelton, IV et al. |
| 10,342,543 B2 | 7/2019 | Shelton, IV et al. |
| 10,342,623 B2 | 7/2019 | Huelman et al. |
| 10,349,937 B2 | 7/2019 | Williams |
| 10,349,939 B2 | 7/2019 | Shelton, IV et al. |
| 10,349,941 B2 | 7/2019 | Marczyk et al. |
| 10,349,963 B2 | 7/2019 | Fiksen et al. |
| 10,350,016 B2 | 7/2019 | Burbank et al. |
| 10,357,246 B2 | 7/2019 | Shelton, IV et al. |
| 10,357,247 B2 | 7/2019 | Shelton, IV et al. |
| 10,357,248 B2 | 7/2019 | Dalessandro et al. |
| 10,357,252 B2 | 7/2019 | Harris et al. |
| 10,363,031 B2 | 7/2019 | Alexander, III et al. |
| 10,363,033 B2 | 7/2019 | Timm et al. |
| 10,363,036 B2 | 7/2019 | Yates et al. |
| 10,363,037 B2 | 7/2019 | Aronhalt et al. |
| D855,634 S | 8/2019 | Kim |
| D856,359 S | 8/2019 | Huang et al. |
| 10,368,838 B2 | 8/2019 | Williams et al. |
| 10,368,861 B2 | 8/2019 | Baxter, III et al. |
| 10,368,863 B2 | 8/2019 | Timm et al. |
| 10,368,864 B2 | 8/2019 | Harris et al. |
| 10,368,865 B2 | 8/2019 | Harris et al. |
| 10,368,867 B2 | 8/2019 | Harris et al. |
| 10,368,892 B2 | 8/2019 | Stulen et al. |
| 10,376,263 B2 | 8/2019 | Morgan et al. |
| 10,383,626 B2 | 8/2019 | Soltz |
| 10,383,628 B2 | 8/2019 | Kang et al. |
| 10,383,629 B2 | 8/2019 | Ross et al. |
| 10,383,630 B2 | 8/2019 | Shelton, IV et al. |
| 10,383,633 B2 | 8/2019 | Shelton, IV et al. |
| 10,383,634 B2 | 8/2019 | Shelton, IV et al. |
| 10,390,823 B2 | 8/2019 | Shelton, IV et al. |
| 10,390,825 B2 | 8/2019 | Shelton, IV et al. |
| 10,390,828 B2 | 8/2019 | Vendely et al. |
| 10,390,829 B2 | 8/2019 | Eckert et al. |
| 10,390,830 B2 | 8/2019 | Schulz |
| 10,390,841 B2 | 8/2019 | Shelton, IV et al. |
| 10,390,897 B2 | 8/2019 | Kostrzewski |
| D860,219 S | 9/2019 | Rasmussen et al. |
| D861,035 S | 9/2019 | Park et al. |
| 10,398,433 B2 | 9/2019 | Boudreaux et al. |
| 10,398,434 B2 | 9/2019 | Shelton, IV et al. |
| 10,398,436 B2 | 9/2019 | Shelton, IV et al. |
| 10,398,460 B2 | 9/2019 | Overmyer |
| 10,404,136 B2 | 9/2019 | Oktavec et al. |
| 10,405,854 B2 | 9/2019 | Schmid et al. |
| 10,405,857 B2 | 9/2019 | Shelton, IV et al. |
| 10,405,859 B2 | 9/2019 | Harris et al. |
| 10,405,863 B2 | 9/2019 | Wise et al. |
| 10,405,914 B2 | 9/2019 | Manwaring et al. |
| 10,405,932 B2 | 9/2019 | Overmyer |
| 10,405,937 B2 | 9/2019 | Black et al. |
| 10,413,155 B2 | 9/2019 | Inoue |
| 10,413,291 B2 | 9/2019 | Worthington et al. |
| 10,413,293 B2 | 9/2019 | Shelton, IV et al. |
| 10,413,294 B2 | 9/2019 | Shelton, IV et al. |
| 10,413,297 B2 | 9/2019 | Harris et al. |
| 10,413,370 B2 | 9/2019 | Yates et al. |
| 10,413,373 B2 | 9/2019 | Yates et al. |
| 10,420,548 B2 | 9/2019 | Whitman et al. |
| 10,420,549 B2 | 9/2019 | Yates et al. |
| 10,420,550 B2 | 9/2019 | Shelton, IV |
| 10,420,551 B2 | 9/2019 | Calderoni |
| 10,420,552 B2 | 9/2019 | Shelton, IV et al. |
| 10,420,553 B2 | 9/2019 | Shelton, IV et al. |
| 10,420,554 B2 | 9/2019 | Collings et al. |
| 10,420,555 B2 | 9/2019 | Shelton, IV et al. |
| 10,420,558 B2 | 9/2019 | Nalagatla et al. |
| 10,420,559 B2 | 9/2019 | Marczyk et al. |
| 10,420,560 B2 | 9/2019 | Shelton, IV et al. |
| 10,420,561 B2 | 9/2019 | Shelton, IV et al. |
| 10,420,577 B2 | 9/2019 | Chowaniec et al. |
| D861,707 S | 10/2019 | Yang |
| D862,518 S | 10/2019 | Niven et al. |
| D863,343 S | 10/2019 | Mazlish et al. |
| D864,388 S | 10/2019 | Barber |
| D865,174 S | 10/2019 | Auld et al. |
| D865,175 S | 10/2019 | Widenhouse et al. |
| 10,426,463 B2 | 10/2019 | Shelton, IV et al. |
| 10,426,466 B2 | 10/2019 | Contini et al. |
| 10,426,467 B2 | 10/2019 | Miller et al. |
| 10,426,468 B2 | 10/2019 | Contini et al. |
| 10,426,469 B2 | 10/2019 | Shelton, IV et al. |
| 10,426,471 B2 | 10/2019 | Shelton, IV et al. |
| 10,426,476 B2 | 10/2019 | Harris et al. |
| 10,426,477 B2 | 10/2019 | Harris et al. |
| 10,426,478 B2 | 10/2019 | Shelton, IV et al. |
| 10,426,481 B2 | 10/2019 | Aronhalt et al. |
| 10,426,555 B2 | 10/2019 | Crowley et al. |
| 10,433,837 B2 | 10/2019 | Worthington et al. |
| 10,433,839 B2 | 10/2019 | Scheib et al. |
| 10,433,840 B2 | 10/2019 | Shelton, IV et al. |
| 10,433,844 B2 | 10/2019 | Shelton, IV et al. |
| 10,433,845 B2 | 10/2019 | Baxter, III et al. |
| 10,433,846 B2 | 10/2019 | Vendely et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,280 B2 | 10/2019 | Timm et al. |
| 10,441,281 B2 | 10/2019 | Shelton, IV et al. |
| 10,441,285 B2 | 10/2019 | Shelton, IV et al. |
| 10,441,286 B2 | 10/2019 | Shelton, IV et al. |
| 10,441,345 B2 | 10/2019 | Aldridge et al. |
| 10,441,369 B2 | 10/2019 | Shelton, IV et al. |
| 10,448,948 B2 | 10/2019 | Shelton, IV et al. |

(56) References Cited

U.S. PATENT DOCUMENTS

| | | |
|---|---|---|
| 10,448,950 B2 | 10/2019 | Shelton, IV et al. |
| 10,448,952 B2 | 10/2019 | Shelton, IV et al. |
| 10,456,122 B2 | 10/2019 | Koltz et al. |
| 10,456,132 B2 | 10/2019 | Gettinger et al. |
| 10,456,133 B2 | 10/2019 | Yates et al. |
| 10,456,137 B2 | 10/2019 | Vendely et al. |
| 10,456,140 B2 | 10/2019 | Shelton, IV et al. |
| D865,796 S | 11/2019 | Xu et al. |
| 10,463,367 B2 | 11/2019 | Kostrzewski et al. |
| 10,463,369 B2 | 11/2019 | Shelton, IV et al. |
| 10,463,370 B2 | 11/2019 | Yates et al. |
| 10,463,371 B2 | 11/2019 | Kostrzewski |
| 10,463,372 B2 | 11/2019 | Shelton, IV et al. |
| 10,463,373 B2 | 11/2019 | Mozdzierz et al. |
| 10,463,382 B2 | 11/2019 | Ingmanson et al. |
| 10,463,383 B2 | 11/2019 | Shelton, IV et al. |
| 10,463,384 B2 | 11/2019 | Shelton, IV et al. |
| 10,470,762 B2 | 11/2019 | Leimbach et al. |
| 10,470,763 B2 | 11/2019 | Yates et al. |
| 10,470,764 B2 | 11/2019 | Baxter, III et al. |
| 10,470,767 B2 | 11/2019 | Gleiman et al. |
| 10,470,768 B2 | 11/2019 | Harris et al. |
| 10,470,769 B2 | 11/2019 | Shelton, IV et al. |
| 10,471,282 B2 | 11/2019 | Kirk et al. |
| 10,471,576 B2 | 11/2019 | Totsu |
| 10,471,607 B2 | 11/2019 | Butt |
| 10,478,181 B2 | 11/2019 | Shelton, IV et al. |
| 10,478,182 B2 | 11/2019 | Taylor |
| 10,478,185 B2 | 11/2019 | Nicholas |
| 10,478,187 B2 | 11/2019 | Shelton, IV et al. |
| 10,478,188 B2 | 11/2019 | Harris et al. |
| 10,478,189 B2 | 11/2019 | Bear et al. |
| 10,478,190 B2 | 11/2019 | Miller et al. |
| 10,478,207 B2 | 11/2019 | Lathrop |
| 10,482,292 B2 | 11/2019 | Clouser et al. |
| 10,485,536 B2 | 11/2019 | Ming et al. |
| 10,485,537 B2 | 11/2019 | Yates et al. |
| 10,485,539 B2 | 11/2019 | Shelton, IV et al. |
| 10,485,541 B2 | 11/2019 | Shelton, IV et al. |
| 10,485,542 B2 | 11/2019 | Shelton, IV et al. |
| 10,485,543 B2 | 11/2019 | Shelton, IV et al. |
| 10,485,546 B2 | 11/2019 | Shelton, IV et al. |
| 10,485,547 B2 | 11/2019 | Shelton, IV et al. |
| D869,655 S | 12/2019 | Shelton, IV et al. |
| D870,742 S | 12/2019 | Cornell |
| 10,492,783 B2 | 12/2019 | Shelton, IV et al. |
| 10,492,785 B2 | 12/2019 | Overmyer et al. |
| 10,492,787 B2 | 12/2019 | Smith et al. |
| 10,492,814 B2 | 12/2019 | Snow et al. |
| 10,492,847 B2 | 12/2019 | Godara et al. |
| 10,492,851 B2 | 12/2019 | Hughett, Sr. et al. |
| 10,498,269 B2 | 12/2019 | Zemlok et al. |
| 10,499,890 B2 | 12/2019 | Shelton, IV et al. |
| 10,499,914 B2 | 12/2019 | Huang et al. |
| 10,499,917 B2 | 12/2019 | Scheib et al. |
| 10,499,918 B2 | 12/2019 | Schellin et al. |
| 10,500,000 B2 | 12/2019 | Swayze et al. |
| 10,500,309 B2 | 12/2019 | Shah et al. |
| 10,508,720 B2 | 12/2019 | Nicholas |
| 10,512,461 B2 | 12/2019 | Gupta et al. |
| 10,517,590 B2 | 12/2019 | Giordano et al. |
| 10,517,592 B2 | 12/2019 | Shelton, IV et al. |
| 10,517,594 B2 | 12/2019 | Shelton, IV et al. |
| 10,517,595 B2 | 12/2019 | Hunter et al. |
| 10,517,596 B2 | 12/2019 | Hunter et al. |
| 10,517,599 B2 | 12/2019 | Baxter, III et al. |
| 10,517,682 B2 | 12/2019 | Giordano et al. |
| 10,524,784 B2 | 1/2020 | Kostrzewski |
| 10,524,787 B2 | 1/2020 | Shelton, IV et al. |
| 10,524,788 B2 | 1/2020 | Vendely et al. |
| 10,524,789 B2 | 1/2020 | Swayze et al. |
| 10,524,790 B2 | 1/2020 | Shelton, IV et al. |
| 10,524,795 B2 | 1/2020 | Nalagatla et al. |
| 10,531,874 B2 | 1/2020 | Morgan et al. |
| 10,531,887 B2 | 1/2020 | Shelton, IV et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,908 B2 | 1/2020 | Mei et al. |
| 10,542,974 B2 | 1/2020 | Yates et al. |
| 10,542,976 B2 | 1/2020 | Calderon et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,985 B2 | 1/2020 | Zhan et al. |
| 10,542,988 B2 | 1/2020 | Schellin et al. |
| 10,542,991 B2 | 1/2020 | Shelton, IV et al. |
| 10,548,504 B2 | 2/2020 | Shelton, IV et al. |
| 10,548,593 B2 | 2/2020 | Shelton, IV et al. |
| 10,548,600 B2 | 2/2020 | Shelton, IV et al. |
| 10,548,673 B2 | 2/2020 | Harris et al. |
| 10,561,418 B2 | 2/2020 | Richard et al. |
| 10,561,419 B2 | 2/2020 | Beardsley |
| 10,561,420 B2 | 2/2020 | Harris et al. |
| 10,561,422 B2 | 2/2020 | Schellin et al. |
| 10,561,432 B2 | 2/2020 | Estrella et al. |
| 10,561,474 B2 | 2/2020 | Adams et al. |
| 10,562,160 B2 | 2/2020 | Iwata et al. |
| 10,568,493 B2 | 2/2020 | Blase et al. |
| 10,568,621 B2 | 2/2020 | Shelton, IV et al. |
| 10,568,624 B2 | 2/2020 | Shelton, IV et al. |
| 10,568,625 B2 | 2/2020 | Harris et al. |
| 10,568,626 B2 | 2/2020 | Shelton, IV et al. |
| 10,568,629 B2 | 2/2020 | Shelton, IV et al. |
| 10,568,632 B2 | 2/2020 | Miller et al. |
| 10,568,652 B2 | 2/2020 | Hess et al. |
| 10,569,071 B2 | 2/2020 | Harris et al. |
| D879,808 S | 3/2020 | Harris et al. |
| D879,809 S | 3/2020 | Harris et al. |
| 10,575,868 B2 | 3/2020 | Hall et al. |
| 10,580,320 B2 | 3/2020 | Kamiguchi et al. |
| 10,582,928 B2 | 3/2020 | Hunter et al. |
| 10,588,231 B2 | 3/2020 | Sgroi, Jr. et al. |
| 10,588,623 B2 | 3/2020 | Schmid et al. |
| 10,588,625 B2 | 3/2020 | Weaner et al. |
| 10,588,626 B2 | 3/2020 | Overmyer et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,633 B2 | 3/2020 | Shelton, IV et al. |
| 10,595,835 B2 | 3/2020 | Kerr et al. |
| 10,595,862 B2 | 3/2020 | Shelton, IV et al. |
| 10,595,882 B2 | 3/2020 | Parfett et al. |
| 10,595,887 B2 | 3/2020 | Shelton, IV et al. |
| 10,595,929 B2 | 3/2020 | Boudreaux et al. |
| 10,603,036 B2 | 3/2020 | Hunter et al. |
| 10,603,039 B2 | 3/2020 | Vendely et al. |
| 10,603,041 B2 | 3/2020 | Miller et al. |
| 10,603,117 B2 | 3/2020 | Schings et al. |
| 10,603,128 B2 | 3/2020 | Zergiebel et al. |
| 10,610,224 B2 | 4/2020 | Shelton, IV et al. |
| 10,610,236 B2 | 4/2020 | Baril |
| 10,610,313 B2 | 4/2020 | Bailey et al. |
| 10,610,346 B2 | 4/2020 | Schwartz |
| 10,617,411 B2 | 4/2020 | Williams |
| 10,617,412 B2 | 4/2020 | Shelton, IV et al. |
| 10,617,413 B2 | 4/2020 | Shelton, IV et al. |
| 10,617,414 B2 | 4/2020 | Shelton, IV et al. |
| 10,617,416 B2 | 4/2020 | Leimbach et al. |
| 10,617,417 B2 | 4/2020 | Baxter, III et al. |
| 10,617,418 B2 | 4/2020 | Barton et al. |
| 10,617,420 B2 | 4/2020 | Shelton, IV et al. |
| 10,624,616 B2 | 4/2020 | Mukherjee et al. |
| 10,624,630 B2 | 4/2020 | Deville et al. |
| 10,624,633 B2 | 4/2020 | Shelton, IV et al. |
| 10,624,634 B2 | 4/2020 | Shelton, IV et al. |
| 10,624,635 B2 | 4/2020 | Harris et al. |
| 10,624,709 B2 | 4/2020 | Remm |
| 10,624,861 B2 | 4/2020 | Widenhouse et al. |
| 10,625,062 B2 | 4/2020 | Matlock et al. |
| 10,631,857 B2 | 4/2020 | Kostrzewski |
| 10,631,858 B2 | 4/2020 | Burbank |
| 10,631,859 B2 | 4/2020 | Shelton, IV et al. |

(56) References Cited

U.S. PATENT DOCUMENTS

| | | |
|---|---|---|
| 10,631,860 B2 | 4/2020 | Bakos et al. |
| 10,636,104 B2 | 4/2020 | Mazar et al. |
| 10,639,018 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,089 B2 | 5/2020 | Manwaring et al. |
| 10,639,115 B2 | 5/2020 | Shelton, IV et al. |
| 10,645,905 B2 | 5/2020 | Gandola et al. |
| 10,646,220 B2 | 5/2020 | Shelton, IV et al. |
| 10,646,292 B2 | 5/2020 | Solomon et al. |
| 10,653,413 B2 | 5/2020 | Worthington et al. |
| 10,653,417 B2 | 5/2020 | Shelton, IV et al. |
| 10,653,435 B2 | 5/2020 | Shelton, IV et al. |
| 10,660,640 B2 | 5/2020 | Yates et al. |
| 10,667,408 B2 | 5/2020 | Sgroi, Jr. et al. |
| D888,953 S | 6/2020 | Baxter, III et al. |
| 10,667,808 B2 | 6/2020 | Baxter, III et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,818 B2 | 6/2020 | McLain et al. |
| 10,674,895 B2 | 6/2020 | Yeung et al. |
| 10,675,021 B2 | 6/2020 | Harris et al. |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,028 B2 | 6/2020 | Shelton, IV et al. |
| 10,675,035 B2 | 6/2020 | Zingman |
| 10,675,102 B2 | 6/2020 | Forgione et al. |
| 10,677,035 B2 | 6/2020 | Balan et al. |
| 10,682,134 B2 | 6/2020 | Shelton, IV et al. |
| 10,682,136 B2 | 6/2020 | Harris et al. |
| 10,682,137 B2 | 6/2020 | Stokes et al. |
| 10,682,138 B2 | 6/2020 | Shelton, IV et al. |
| 10,682,141 B2 | 6/2020 | Moore et al. |
| 10,682,142 B2 | 6/2020 | Shelton, IV et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,812 B2 | 6/2020 | Shelton, IV et al. |
| 10,687,813 B2 | 6/2020 | Shelton, IV et al. |
| 10,687,817 B2 | 6/2020 | Shelton, IV et al. |
| 10,687,819 B2 | 6/2020 | Stokes et al. |
| 10,687,904 B2 | 6/2020 | Harris et al. |
| 10,695,053 B2 | 6/2020 | Hess et al. |
| 10,695,055 B2 | 6/2020 | Shelton, IV et al. |
| 10,695,057 B2 | 6/2020 | Shelton, IV et al. |
| 10,695,058 B2 | 6/2020 | Lytle, IV et al. |
| 10,695,062 B2 | 6/2020 | Leimbach et al. |
| 10,695,063 B2 | 6/2020 | Morgan et al. |
| 10,695,074 B2 | 6/2020 | Carusillo |
| 10,695,081 B2 | 6/2020 | Shelton, IV et al. |
| 10,695,123 B2 | 6/2020 | Allen, IV |
| 10,695,187 B2 | 6/2020 | Moskowitz et al. |
| D890,784 S | 7/2020 | Shelton, IV et al. |
| 10,702,266 B2 | 7/2020 | Parihar et al. |
| 10,702,267 B2 | 7/2020 | Hess et al. |
| 10,702,270 B2 | 7/2020 | Shelton, IV et al. |
| 10,702,271 B2 | 7/2020 | Aranyi et al. |
| 10,705,660 B2 | 7/2020 | Xiao |
| 10,709,446 B2 | 7/2020 | Harris et al. |
| 10,709,468 B2 | 7/2020 | Shelton, IV et al. |
| 10,709,469 B2 | 7/2020 | Shelton, IV et al. |
| 10,709,496 B2 | 7/2020 | Moua et al. |
| 10,716,563 B2 | 7/2020 | Shelton, IV et al. |
| 10,716,565 B2 | 7/2020 | Shelton, IV et al. |
| 10,716,568 B2 | 7/2020 | Hall et al. |
| 10,716,614 B2 | 7/2020 | Yates et al. |
| 10,717,179 B2 | 7/2020 | Koenig et al. |
| 10,722,232 B2 | 7/2020 | Yates et al. |
| 10,722,233 B2 | 7/2020 | Wellman |
| 10,722,292 B2 | 7/2020 | Arya et al. |
| 10,722,293 B2 | 7/2020 | Arya et al. |
| 10,722,317 B2 | 7/2020 | Ward et al. |
| D893,717 S | 8/2020 | Messerly et al. |
| 10,729,432 B2 | 8/2020 | Shelton, IV et al. |
| 10,729,436 B2 | 8/2020 | Shelton, IV et al. |
| 10,729,443 B2 | 8/2020 | Cabrera et al. |
| 10,729,458 B2 | 8/2020 | Stoddard et al. |
| 10,729,501 B2 | 8/2020 | Leimbach et al. |
| 10,729,509 B2 | 8/2020 | Shelton, IV et al. |
| 10,736,616 B2 | 8/2020 | Scheib et al. |
| 10,736,628 B2 | 8/2020 | Yates et al. |
| 10,736,629 B2 | 8/2020 | Shelton, IV et al. |
| 10,736,630 B2 | 8/2020 | Huang et al. |
| 10,736,633 B2 | 8/2020 | Vendely et al. |
| 10,736,634 B2 | 8/2020 | Shelton, IV et al. |
| 10,736,636 B2 | 8/2020 | Baxter, III et al. |
| 10,736,644 B2 | 8/2020 | Windolf et al. |
| 10,743,849 B2 | 8/2020 | Shelton, IV et al. |
| 10,743,851 B2 | 8/2020 | Swayze et al. |
| 10,743,868 B2 | 8/2020 | Shelton, IV et al. |
| 10,743,870 B2 | 8/2020 | Hall et al. |
| 10,743,872 B2 | 8/2020 | Leimbach et al. |
| 10,743,873 B2 | 8/2020 | Overmyer et al. |
| 10,743,874 B2 | 8/2020 | Shelton, IV et al. |
| 10,743,875 B2 | 8/2020 | Shelton, IV et al. |
| 10,743,877 B2 | 8/2020 | Shelton, IV et al. |
| 10,743,930 B2 | 8/2020 | Nagtegaal |
| 10,751,048 B2 | 8/2020 | Whitman et al. |
| 10,751,053 B2 | 8/2020 | Harris et al. |
| 10,751,076 B2 | 8/2020 | Laurent et al. |
| 10,751,138 B2 | 8/2020 | Giordano et al. |
| 10,758,229 B2 | 9/2020 | Shelton, IV et al. |
| 10,758,230 B2 | 9/2020 | Shelton, IV et al. |
| 10,758,232 B2 | 9/2020 | Shelton, IV et al. |
| 10,758,233 B2 | 9/2020 | Scheib et al. |
| 10,758,259 B2 | 9/2020 | Demmy et al. |
| 10,765,425 B2 | 9/2020 | Yates et al. |
| 10,765,427 B2 | 9/2020 | Shelton, IV et al. |
| 10,765,429 B2 | 9/2020 | Leimbach et al. |
| 10,765,430 B2 | 9/2020 | Wixey |
| 10,765,432 B2 | 9/2020 | Moore et al. |
| 10,765,442 B2 | 9/2020 | Strobl |
| 10,772,625 B2 | 9/2020 | Shelton, IV et al. |
| 10,772,628 B2 | 9/2020 | Chen et al. |
| 10,772,629 B2 | 9/2020 | Shelton, IV et al. |
| 10,772,630 B2 | 9/2020 | Wixey |
| 10,772,631 B2 | 9/2020 | Zergiebel et al. |
| 10,772,632 B2 | 9/2020 | Kostrzewski |
| 10,772,651 B2 | 9/2020 | Shelton, IV et al. |
| 10,779,818 B2 | 9/2020 | Zemlok et al. |
| 10,779,820 B2 | 9/2020 | Harris et al. |
| 10,779,821 B2 | 9/2020 | Harris et al. |
| 10,779,822 B2 | 9/2020 | Yates et al. |
| 10,779,823 B2 | 9/2020 | Shelton, IV et al. |
| 10,779,824 B2 | 9/2020 | Shelton, IV et al. |
| 10,779,825 B2 | 9/2020 | Shelton, IV et al. |
| 10,779,826 B2 | 9/2020 | Shelton, IV et al. |
| 10,779,903 B2 | 9/2020 | Wise et al. |
| 10,780,539 B2 | 9/2020 | Shelton, IV et al. |
| 10,786,248 B2 | 9/2020 | Rousseau et al. |
| 10,786,253 B2 | 9/2020 | Shelton, IV et al. |
| 10,786,255 B2 | 9/2020 | Hodgkinson et al. |
| 10,792,038 B2 | 10/2020 | Becerra et al. |
| 10,796,471 B2 | 10/2020 | Leimbach et al. |
| 10,799,240 B2 | 10/2020 | Shelton, IV et al. |
| 10,799,306 B2 | 10/2020 | Robinson et al. |
| 10,806,448 B2 | 10/2020 | Shelton, IV et al. |
| 10,806,449 B2 | 10/2020 | Shelton, IV et al. |
| 10,806,450 B2 | 10/2020 | Yates et al. |
| 10,806,451 B2 | 10/2020 | Harris et al. |
| 10,806,453 B2 | 10/2020 | Chen et al. |
| 10,806,479 B2 | 10/2020 | Shelton, IV et al. |
| 10,813,638 B2 | 10/2020 | Shelton, IV et al. |
| 10,813,639 B2 | 10/2020 | Shelton, IV et al. |
| 10,813,640 B2 | 10/2020 | Adams et al. |
| 10,813,641 B2 | 10/2020 | Setser et al. |
| 10,813,683 B2 | 10/2020 | Baxter, III et al. |
| 10,813,705 B2 | 10/2020 | Hares et al. |
| 10,813,710 B2 | 10/2020 | Grubbs |
| 10,820,939 B2 | 11/2020 | Sartor |

(56) References Cited

U.S. PATENT DOCUMENTS

| | | |
|---|---|---|
| 10,828,028 B2 | 11/2020 | Harris et al. |
| 10,828,030 B2 | 11/2020 | Weir et al. |
| 10,828,032 B2 | 11/2020 | Leimbach et al. |
| 10,828,033 B2 | 11/2020 | Shelton, IV et al. |
| 10,828,089 B2 | 11/2020 | Clark et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,835,249 B2 | 11/2020 | Schellin et al. |
| 10,835,251 B2 | 11/2020 | Shelton, IV et al. |
| 10,835,330 B2 | 11/2020 | Shelton, IV et al. |
| 10,842,357 B2 | 11/2020 | Moskowitz et al. |
| 10,842,473 B2 | 11/2020 | Scheib et al. |
| 10,842,488 B2 | 11/2020 | Swayze et al. |
| 10,842,489 B2 | 11/2020 | Shelton, IV |
| 10,842,490 B2 | 11/2020 | DiNardo et al. |
| 10,842,491 B2 | 11/2020 | Shelton, IV et al. |
| 10,842,492 B2 | 11/2020 | Shelton, IV et al. |
| D904,612 S | 12/2020 | Wynn et al. |
| D906,355 S | 12/2020 | Messerly et al. |
| 10,849,621 B2 | 12/2020 | Whitfield et al. |
| 10,849,623 B2 | 12/2020 | Dunki-Jacobs et al. |
| 10,849,697 B2 | 12/2020 | Yates et al. |
| 10,856,866 B2 | 12/2020 | Shelton, IV et al. |
| 10,856,867 B2 | 12/2020 | Shelton, IV et al. |
| 10,856,868 B2 | 12/2020 | Shelton, IV et al. |
| 10,856,869 B2 | 12/2020 | Shelton, IV et al. |
| 10,856,870 B2 | 12/2020 | Harris et al. |
| 10,863,981 B2 | 12/2020 | Overmyer et al. |
| 10,863,984 B2 | 12/2020 | Shelton, IV et al. |
| 10,863,986 B2 | 12/2020 | Yates et al. |
| 10,869,664 B2 | 12/2020 | Shelton, IV |
| 10,869,665 B2 | 12/2020 | Shelton, IV et al. |
| 10,869,666 B2 | 12/2020 | Shelton, IV et al. |
| 10,869,669 B2 | 12/2020 | Shelton, IV et al. |
| 10,874,290 B2 | 12/2020 | Walen et al. |
| 10,874,391 B2 | 12/2020 | Shelton, IV et al. |
| 10,874,392 B2 | 12/2020 | Scirica et al. |
| 10,874,393 B2 | 12/2020 | Satti, III et al. |
| 10,874,396 B2 | 12/2020 | Moore et al. |
| 10,874,399 B2 | 12/2020 | Zhang |
| 10,879,275 B2 | 12/2020 | Li et al. |
| D907,647 S | 1/2021 | Siebel et al. |
| D907,648 S | 1/2021 | Siebel et al. |
| D908,216 S | 1/2021 | Messerly et al. |
| 10,881,395 B2 | 1/2021 | Merchant et al. |
| 10,881,396 B2 | 1/2021 | Shelton, IV et al. |
| 10,881,399 B2 | 1/2021 | Shelton, IV et al. |
| 10,881,401 B2 | 1/2021 | Baber et al. |
| 10,881,446 B2 | 1/2021 | Strobl |
| 10,888,318 B2 | 1/2021 | Parihar et al. |
| 10,888,321 B2 | 1/2021 | Shelton, IV et al. |
| 10,888,322 B2 | 1/2021 | Morgan et al. |
| 10,888,323 B2 | 1/2021 | Chen et al. |
| 10,888,325 B2 | 1/2021 | Harris et al. |
| 10,888,328 B2 | 1/2021 | Shelton, IV et al. |
| 10,888,329 B2 | 1/2021 | Moore et al. |
| 10,888,330 B2 | 1/2021 | Moore et al. |
| 10,888,369 B2 | 1/2021 | Messerly et al. |
| 10,892,899 B2 | 1/2021 | Shelton, IV et al. |
| 10,893,853 B2 | 1/2021 | Shelton, IV et al. |
| 10,893,863 B2 | 1/2021 | Shelton, IV et al. |
| 10,893,864 B2 | 1/2021 | Harris et al. |
| 10,893,867 B2 | 1/2021 | Leimbach et al. |
| 10,898,183 B2 | 1/2021 | Shelton, IV et al. |
| 10,898,184 B2 | 1/2021 | Yates et al. |
| 10,898,185 B2 | 1/2021 | Overmyer et al. |
| 10,898,186 B2 | 1/2021 | Bakos et al. |
| 10,898,190 B2 | 1/2021 | Yates et al. |
| 10,898,193 B2 | 1/2021 | Shelton, IV et al. |
| 10,898,194 B2 | 1/2021 | Moore et al. |
| 10,898,195 B2 | 1/2021 | Moore et al. |
| 10,903,685 B2 | 1/2021 | Yates et al. |
| D910,847 S | 2/2021 | Shelton, IV et al. |
| 10,905,415 B2 | 2/2021 | DiNardo et al. |
| 10,905,418 B2 | 2/2021 | Shelton, IV et al. |
| 10,905,420 B2 | 2/2021 | Jasemian et al. |
| 10,905,422 B2 | 2/2021 | Bakos et al. |
| 10,905,423 B2 | 2/2021 | Baber et al. |
| 10,905,426 B2 | 2/2021 | Moore et al. |
| 10,905,427 B2 | 2/2021 | Moore et al. |
| 10,911,515 B2 | 2/2021 | Blasi et al. |
| 10,912,559 B2 | 2/2021 | Harris et al. |
| 10,912,562 B2 | 2/2021 | Dunki-Jacobs et al. |
| 10,912,575 B2 | 2/2021 | Shelton, IV et al. |
| 10,918,364 B2 | 2/2021 | Applegate et al. |
| 10,918,380 B2 | 2/2021 | Morgan et al. |
| 10,918,385 B2 | 2/2021 | Overmyer et al. |
| 10,918,386 B2 | 2/2021 | Shelton, IV et al. |
| 10,919,156 B2 | 2/2021 | Roberts et al. |
| 10,925,600 B2 | 2/2021 | McCuen |
| 10,925,605 B2 | 2/2021 | Moore et al. |
| D914,878 S | 3/2021 | Shelton, IV et al. |
| 10,932,772 B2 | 3/2021 | Shelton, IV et al. |
| 10,932,774 B2 | 3/2021 | Shelton, IV |
| 10,932,775 B2 | 3/2021 | Shelton, IV et al. |
| 10,932,778 B2 | 3/2021 | Smith et al. |
| 10,932,779 B2 | 3/2021 | Vendely et al. |
| 10,932,804 B2 | 3/2021 | Scheib et al. |
| 10,932,806 B2 | 3/2021 | Shelton, IV et al. |
| 10,932,872 B2 | 3/2021 | Shelton, IV et al. |
| 10,944,728 B2 | 3/2021 | Wiener et al. |
| 10,945,727 B2 | 3/2021 | Shelton, IV et al. |
| 10,945,728 B2 | 3/2021 | Morgan et al. |
| 10,945,729 B2 | 3/2021 | Shelton, IV et al. |
| 10,945,731 B2 | 3/2021 | Baxter, III et al. |
| 10,952,708 B2 | 3/2021 | Scheib et al. |
| 10,952,727 B2 | 3/2021 | Giordano et al. |
| 10,952,728 B2 | 3/2021 | Shelton, IV et al. |
| 10,952,759 B2 | 3/2021 | Messerly et al. |
| 10,952,767 B2 | 3/2021 | Kostrzewski et al. |
| 10,959,722 B2 | 3/2021 | Morgan et al. |
| 10,959,725 B2 | 3/2021 | Kerr et al. |
| 10,959,727 B2 | 3/2021 | Hunter et al. |
| 10,959,731 B2 | 3/2021 | Casasanta, Jr. et al. |
| 10,959,744 B2 | 3/2021 | Shelton, IV et al. |
| D917,500 S | 4/2021 | Siebel et al. |
| 10,966,627 B2 | 4/2021 | Shelton, IV et al. |
| 10,966,717 B2 | 4/2021 | Shah et al. |
| 10,966,718 B2 | 4/2021 | Shelton, IV et al. |
| 10,966,791 B2 | 4/2021 | Harris et al. |
| 10,973,515 B2 | 4/2021 | Harris et al. |
| 10,973,516 B2 | 4/2021 | Shelton, IV et al. |
| 10,973,517 B2 | 4/2021 | Wixey |
| 10,973,519 B2 | 4/2021 | Weir et al. |
| 10,973,520 B2 | 4/2021 | Shelton, IV et al. |
| 10,980,534 B2 | 4/2021 | Yates et al. |
| 10,980,535 B2 | 4/2021 | Yates et al. |
| 10,980,536 B2 | 4/2021 | Weaner et al. |
| 10,980,537 B2 | 4/2021 | Shelton, IV et al. |
| 10,980,538 B2 | 4/2021 | Nalagatla et al. |
| 10,980,539 B2 | 4/2021 | Harris et al. |
| 10,980,560 B2 | 4/2021 | Shelton, IV et al. |
| 10,983,646 B2 | 4/2021 | Yoon et al. |
| 10,987,102 B2 | 4/2021 | Gonzalez et al. |
| 10,987,178 B2 | 4/2021 | Shelton, IV et al. |
| 10,993,713 B2 | 5/2021 | Shelton, IV et al. |
| 10,993,715 B2 | 5/2021 | Shelton, IV et al. |
| 10,993,716 B2 | 5/2021 | Shelton, IV et al. |
| 10,993,717 B2 | 5/2021 | Shelton, IV et al. |
| 11,000,274 B2 | 5/2021 | Shelton, IV et al. |
| 11,000,275 B2 | 5/2021 | Shelton, IV et al. |
| 11,000,277 B2 | 5/2021 | Giordano et al. |
| 11,000,278 B2 | 5/2021 | Shelton, IV et al. |
| 11,000,279 B2 | 5/2021 | Shelton, IV et al. |
| 11,006,951 B2 | 5/2021 | Giordano et al. |
| 11,006,955 B2 | 5/2021 | Shelton, IV et al. |
| 11,007,004 B2 | 5/2021 | Shelton, IV et al. |
| 11,007,022 B2 | 5/2021 | Shelton, IV et al. |
| 11,013,511 B2 | 5/2021 | Huang et al. |
| 11,013,552 B2 | 5/2021 | Widenhouse et al. |
| 11,013,563 B2 | 5/2021 | Shelton, IV et al. |
| 11,020,016 B2 | 6/2021 | Wallace et al. |
| 11,020,112 B2 | 6/2021 | Shelton, IV et al. |

(56) References Cited

U.S. PATENT DOCUMENTS

| | | |
|---|---|---|
| 11,020,113 B2 | 6/2021 | Shelton, IV et al. |
| 11,020,114 B2 | 6/2021 | Shelton, IV et al. |
| 11,020,115 B2 | 6/2021 | Scheib et al. |
| 11,026,678 B2 | 6/2021 | Overmyer et al. |
| 11,026,680 B2 | 6/2021 | Shelton, IV et al. |
| 11,026,684 B2 | 6/2021 | Shelton, IV et al. |
| 11,026,687 B2 | 6/2021 | Shelton, IV et al. |
| 11,026,712 B2 | 6/2021 | Shelton, IV et al. |
| 11,026,713 B2 | 6/2021 | Stokes et al. |
| 11,026,751 B2 | 6/2021 | Shelton, IV et al. |
| 11,033,267 B2 | 6/2021 | Shelton, IV et al. |
| 11,039,834 B2 | 6/2021 | Harris et al. |
| 11,039,836 B2 | 6/2021 | Shelton, IV et al. |
| 11,039,837 B2 | 6/2021 | Shelton, IV et al. |
| 11,045,189 B2 | 6/2021 | Yates et al. |
| 11,045,191 B2 | 6/2021 | Shelton, IV et al. |
| 11,045,192 B2 | 6/2021 | Harris et al. |
| 11,045,197 B2 | 6/2021 | Shelton, IV et al. |
| 11,045,270 B2 | 6/2021 | Shelton, IV et al. |
| 11,051,807 B2 | 7/2021 | Shelton, IV et al. |
| 11,051,810 B2 | 7/2021 | Harris et al. |
| 11,051,811 B2 | 7/2021 | Shelton, IV et al. |
| 11,051,813 B2 | 7/2021 | Shelton, IV et al. |
| 11,051,836 B2 | 7/2021 | Shelton, IV et al. |
| 11,051,840 B2 | 7/2021 | Shelton, IV et al. |
| 11,051,873 B2 | 7/2021 | Wiener et al. |
| 11,058,418 B2 | 7/2021 | Shelton, IV et al. |
| 11,058,420 B2 | 7/2021 | Shelton, IV et al. |
| 11,058,422 B2 | 7/2021 | Harris et al. |
| 11,058,423 B2 | 7/2021 | Shelton, IV et al. |
| 11,058,424 B2 | 7/2021 | Shelton, IV et al. |
| 11,058,425 B2 | 7/2021 | Widenhouse et al. |
| 11,058,426 B2 | 7/2021 | Nalagatla et al. |
| 11,058,498 B2 | 7/2021 | Shelton, IV et al. |
| 11,064,997 B2 | 7/2021 | Shelton, IV et al. |
| 11,064,998 B2 | 7/2021 | Shelton, IV |
| 11,065,048 B2 | 7/2021 | Messerly et al. |
| 11,069,012 B2 | 7/2021 | Shelton, IV et al. |
| 11,071,543 B2 | 7/2021 | Shelton, IV et al. |
| 11,071,545 B2 | 7/2021 | Baber et al. |
| 11,071,554 B2 | 7/2021 | Parfett et al. |
| 11,071,560 B2 | 7/2021 | Deck et al. |
| 11,076,853 B2 | 8/2021 | Parfett et al. |
| 11,076,854 B2 | 8/2021 | Baber et al. |
| 11,076,921 B2 | 8/2021 | Shelton, IV et al. |
| 11,076,929 B2 | 8/2021 | Shelton, IV et al. |
| 11,083,452 B2 | 8/2021 | Schmid et al. |
| 11,083,453 B2 | 8/2021 | Shelton, IV et al. |
| 11,083,454 B2 | 8/2021 | Harris et al. |
| 11,083,455 B2 | 8/2021 | Shelton, IV et al. |
| 11,083,456 B2 | 8/2021 | Shelton, IV et al. |
| 11,083,457 B2 | 8/2021 | Shelton, IV et al. |
| 11,083,458 B2 | 8/2021 | Harris et al. |
| 11,090,045 B2 | 8/2021 | Shelton, IV |
| 11,090,046 B2 | 8/2021 | Shelton, IV et al. |
| 11,090,047 B2 | 8/2021 | Shelton, IV et al. |
| 11,090,048 B2 | 8/2021 | Fanelli et al. |
| 11,090,049 B2 | 8/2021 | Bakos et al. |
| 11,090,075 B2 | 8/2021 | Hunter et al. |
| 11,096,688 B2 | 8/2021 | Shelton, IV et al. |
| 11,096,689 B2 | 8/2021 | Overmyer et al. |
| 11,100,631 B2 | 8/2021 | Yates et al. |
| 11,123,069 B2 | 9/2021 | Baxter, III et al. |
| 11,202,633 B2 | 12/2021 | Harris et al. |
| 2001/0000531 A1 | 4/2001 | Casscells et al. |
| 2001/0025183 A1 | 9/2001 | Shahidi |
| 2001/0025184 A1 | 9/2001 | Messerly |
| 2001/0034530 A1 | 10/2001 | Malackowski et al. |
| 2002/0014510 A1 | 2/2002 | Richter et al. |
| 2002/0022810 A1 | 2/2002 | Urich |
| 2002/0022836 A1 | 2/2002 | Goble et al. |
| 2002/0022861 A1 | 2/2002 | Jacobs et al. |
| 2002/0023126 A1 | 2/2002 | Flavin |
| 2002/0029032 A1 | 3/2002 | Arkin |
| 2002/0029036 A1 | 3/2002 | Goble et al. |
| 2002/0042620 A1 | 4/2002 | Julian et al. |
| 2002/0087048 A1 | 7/2002 | Brock et al. |
| 2002/0091374 A1 | 7/2002 | Cooper |
| 2002/0095175 A1 | 7/2002 | Brock et al. |
| 2002/0103494 A1 | 8/2002 | Pacey |
| 2002/0111624 A1 | 8/2002 | Witt et al. |
| 2002/0116063 A1 | 8/2002 | Giannetti et al. |
| 2002/0117534 A1 | 8/2002 | Green et al. |
| 2002/0127265 A1 | 9/2002 | Bowman et al. |
| 2002/0128633 A1 | 9/2002 | Brock et al. |
| 2002/0134811 A1 | 9/2002 | Napier et al. |
| 2002/0135474 A1 | 9/2002 | Sylliassen |
| 2002/0138086 A1 | 9/2002 | Sixto et al. |
| 2002/0143340 A1 | 10/2002 | Kaneko |
| 2002/0151770 A1 | 10/2002 | Noll et al. |
| 2002/0158593 A1 | 10/2002 | Henderson et al. |
| 2002/0177848 A1 | 11/2002 | Truckai et al. |
| 2002/0185514 A1 | 12/2002 | Adams et al. |
| 2002/0188170 A1 | 12/2002 | Santamore et al. |
| 2002/0188287 A1 | 12/2002 | Zvuloni et al. |
| 2003/0009193 A1 | 1/2003 | Corsaro |
| 2003/0011245 A1 | 1/2003 | Fiebig |
| 2003/0012805 A1 | 1/2003 | Chen et al. |
| 2003/0040670 A1 | 2/2003 | Govari |
| 2003/0045835 A1 | 3/2003 | Anderson et al. |
| 2003/0047230 A1 | 3/2003 | Kim |
| 2003/0050654 A1 | 3/2003 | Whitman et al. |
| 2003/0066858 A1 | 4/2003 | Holgersson |
| 2003/0078647 A1 | 4/2003 | Vallana et al. |
| 2003/0083648 A1 | 5/2003 | Wang et al. |
| 2003/0084983 A1 | 5/2003 | Rangachari et al. |
| 2003/0093103 A1 | 5/2003 | Malackowski et al. |
| 2003/0094356 A1 | 5/2003 | Waldron |
| 2003/0096158 A1 | 5/2003 | Takano et al. |
| 2003/0114851 A1 | 6/2003 | Truckai et al. |
| 2003/0121586 A1 | 7/2003 | Mitra et al. |
| 2003/0139741 A1 | 7/2003 | Goble et al. |
| 2003/0149406 A1 | 8/2003 | Martineau et al. |
| 2003/0153908 A1 | 8/2003 | Goble et al. |
| 2003/0153968 A1 | 8/2003 | Geis et al. |
| 2003/0163029 A1 | 8/2003 | Sonnenschein et al. |
| 2003/0163085 A1 | 8/2003 | Tanner et al. |
| 2003/0164172 A1 | 9/2003 | Chumas et al. |
| 2003/0181900 A1 | 9/2003 | Long |
| 2003/0190584 A1 | 10/2003 | Heasley |
| 2003/0195387 A1 | 10/2003 | Kortenbach et al. |
| 2003/0205029 A1 | 11/2003 | Chapolini et al. |
| 2003/0212005 A1 | 11/2003 | Petito et al. |
| 2003/0216732 A1 | 11/2003 | Truckai et al. |
| 2003/0236505 A1 | 12/2003 | Bonadio et al. |
| 2004/0006335 A1 | 1/2004 | Garrison |
| 2004/0006340 A1 | 1/2004 | Latterell et al. |
| 2004/0007608 A1 | 1/2004 | Ehrenfels et al. |
| 2004/0024457 A1 | 2/2004 | Boyce et al. |
| 2004/0028502 A1 | 2/2004 | Cummins |
| 2004/0030333 A1 | 2/2004 | Goble |
| 2004/0034287 A1 | 2/2004 | Hickle |
| 2004/0034357 A1 | 2/2004 | Beane et al. |
| 2004/0044295 A1 | 3/2004 | Reinert et al. |
| 2004/0044364 A1 | 3/2004 | DeVries et al. |
| 2004/0049121 A1 | 3/2004 | Yaron |
| 2004/0049172 A1 | 3/2004 | Root et al. |
| 2004/0059362 A1 | 3/2004 | Knodel et al. |
| 2004/0068161 A1 | 4/2004 | Couvillon |
| 2004/0068224 A1 | 4/2004 | Couvillon et al. |
| 2004/0068307 A1 | 4/2004 | Goble |
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0082952 A1 | 4/2004 | Dycus et al. |
| 2004/0085180 A1 | 5/2004 | Juang |
| 2004/0092992 A1 | 5/2004 | Adams et al. |
| 2004/0093020 A1 | 5/2004 | Sinton |
| 2004/0093024 A1 | 5/2004 | Lousararian et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin et al. |
| 2004/0108357 A1 | 6/2004 | Milliman et al. |
| 2004/0110439 A1 | 6/2004 | Chaikof et al. |

(56) References Cited

U.S. PATENT DOCUMENTS

| | | |
|---|---|---|
| 2004/0115022 A1 | 6/2004 | Albertson et al. |
| 2004/0116952 A1 | 6/2004 | Sakurai et al. |
| 2004/0119185 A1 | 6/2004 | Chen |
| 2004/0122419 A1 | 6/2004 | Neuberger |
| 2004/0122423 A1 | 6/2004 | Dycus et al. |
| 2004/0133095 A1 | 7/2004 | Dunki-Jacobs et al. |
| 2004/0133189 A1 | 7/2004 | Sakurai |
| 2004/0143297 A1 | 7/2004 | Ramsey |
| 2004/0147909 A1 | 7/2004 | Johnston et al. |
| 2004/0153100 A1 | 8/2004 | Ahlberg et al. |
| 2004/0158261 A1 | 8/2004 | Vu |
| 2004/0164123 A1 | 8/2004 | Racenet et al. |
| 2004/0166169 A1 | 8/2004 | Malaviya et al. |
| 2004/0167572 A1 | 8/2004 | Roth et al. |
| 2004/0181219 A1 | 9/2004 | Goble et al. |
| 2004/0193189 A1 | 9/2004 | Kortenbach et al. |
| 2004/0197367 A1 | 10/2004 | Rezania et al. |
| 2004/0199181 A1 | 10/2004 | Knodel et al. |
| 2004/0204735 A1 | 10/2004 | Shiroff et al. |
| 2004/0218451 A1 | 11/2004 | Said et al. |
| 2004/0222268 A1 | 11/2004 | Bilotti et al. |
| 2004/0225186 A1 | 11/2004 | Horne et al. |
| 2004/0232201 A1 | 11/2004 | Wenchell et al. |
| 2004/0236352 A1 | 11/2004 | Wang et al. |
| 2004/0239582 A1 | 12/2004 | Seymour |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0247415 A1 | 12/2004 | Mangone |
| 2004/0249366 A1 | 12/2004 | Kunz |
| 2004/0254455 A1 | 12/2004 | Iddan |
| 2004/0254566 A1 | 12/2004 | Plicchi et al. |
| 2004/0254590 A1 | 12/2004 | Hoffman et al. |
| 2004/0260315 A1 | 12/2004 | Deli et al. |
| 2004/0267310 A1 | 12/2004 | Racenet et al. |
| 2005/0010158 A1 | 1/2005 | Brugger et al. |
| 2005/0010213 A1 | 1/2005 | Stad et al. |
| 2005/0021078 A1 | 1/2005 | Vleugels et al. |
| 2005/0032511 A1 | 2/2005 | Malone et al. |
| 2005/0033352 A1 | 2/2005 | Zepf et al. |
| 2005/0051163 A1 | 3/2005 | Deem et al. |
| 2005/0054946 A1 | 3/2005 | Krzyzanowski |
| 2005/0057225 A1 | 3/2005 | Marquet |
| 2005/0058890 A1 | 3/2005 | Brazell et al. |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080342 A1 | 4/2005 | Gilreath et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0116673 A1 | 6/2005 | Carl et al. |
| 2005/0120836 A1 | 6/2005 | Anderson |
| 2005/0124855 A1 | 6/2005 | Jaffe et al. |
| 2005/0125897 A1 | 6/2005 | Wyslucha et al. |
| 2005/0129735 A1 | 6/2005 | Cook et al. |
| 2005/0130682 A1 | 6/2005 | Takara et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0139636 A1 | 6/2005 | Schwemberger et al. |
| 2005/0143759 A1 | 6/2005 | Kelly |
| 2005/0143769 A1 | 6/2005 | White et al. |
| 2005/0145671 A1 | 7/2005 | Viola |
| 2005/0150928 A1 | 7/2005 | Kameyama et al. |
| 2005/0154258 A1 | 7/2005 | Tartaglia et al. |
| 2005/0154406 A1 | 7/2005 | Bombard et al. |
| 2005/0159778 A1 | 7/2005 | Heinrich et al. |
| 2005/0165419 A1 | 7/2005 | Sauer et al. |
| 2005/0169974 A1 | 8/2005 | Tenerz et al. |
| 2005/0171522 A1 | 8/2005 | Christopherson |
| 2005/0177176 A1 | 8/2005 | Gerbi et al. |
| 2005/0177181 A1 | 8/2005 | Kagan et al. |
| 2005/0177249 A1 | 8/2005 | Kladakis et al. |
| 2005/0182298 A1 | 8/2005 | Ikeda et al. |
| 2005/0182443 A1 | 8/2005 | Jonn et al. |
| 2005/0184121 A1 | 8/2005 | Heinrich |
| 2005/0186240 A1 | 8/2005 | Ringeisen et al. |
| 2005/0187545 A1 | 8/2005 | Hooven et al. |
| 2005/0191936 A1 | 9/2005 | Marine et al. |
| 2005/0203550 A1 | 9/2005 | Laufer et al. |
| 2005/0209614 A1 | 9/2005 | Fenter et al. |
| 2005/0216055 A1 | 9/2005 | Scirica et al. |
| 2005/0222587 A1 | 10/2005 | Jinno et al. |
| 2005/0222611 A1 | 10/2005 | Weitkamp |
| 2005/0222616 A1 | 10/2005 | Rethy et al. |
| 2005/0222665 A1 | 10/2005 | Aranyi |
| 2005/0228224 A1 | 10/2005 | Okada et al. |
| 2005/0228446 A1 | 10/2005 | Mooradian et al. |
| 2005/0230453 A1 | 10/2005 | Viola |
| 2005/0240178 A1 | 10/2005 | Morley et al. |
| 2005/0242950 A1 | 11/2005 | Lindsay et al. |
| 2005/0245965 A1 | 11/2005 | Orban, III et al. |
| 2005/0246881 A1 | 11/2005 | Kelly et al. |
| 2005/0251063 A1 | 11/2005 | Basude |
| 2005/0256452 A1 | 11/2005 | DeMarchi et al. |
| 2005/0256546 A1 | 11/2005 | Vaisnys et al. |
| 2005/0258963 A1 | 11/2005 | Rodriguez et al. |
| 2005/0261676 A1 | 11/2005 | Hall et al. |
| 2005/0263563 A1 | 12/2005 | Racenet et al. |
| 2005/0267455 A1 | 12/2005 | Eggers et al. |
| 2005/0274034 A1 | 12/2005 | Hayashida et al. |
| 2005/0283188 A1 | 12/2005 | Loshakove et al. |
| 2005/0283226 A1 | 12/2005 | Haverkost |
| 2006/0008787 A1 | 1/2006 | Hayman et al. |
| 2006/0015009 A1 | 1/2006 | Jaffe et al. |
| 2006/0020167 A1 | 1/2006 | Sitzmann |
| 2006/0020258 A1 | 1/2006 | Strauss et al. |
| 2006/0020336 A1 | 1/2006 | Liddicoat |
| 2006/0025812 A1 | 2/2006 | Shelton |
| 2006/0041188 A1 | 2/2006 | Dirusso et al. |
| 2006/0047275 A1 | 3/2006 | Goble |
| 2006/0049229 A1 | 3/2006 | Milliman et al. |
| 2006/0052824 A1 | 3/2006 | Ransick et al. |
| 2006/0052825 A1 | 3/2006 | Ransick et al. |
| 2006/0064086 A1 | 3/2006 | Odom |
| 2006/0079735 A1 | 4/2006 | Martone et al. |
| 2006/0079874 A1 | 4/2006 | Faller et al. |
| 2006/0079879 A1 | 4/2006 | Faller et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0097699 A1 | 5/2006 | Kamenoff |
| 2006/0100643 A1 | 5/2006 | Laufer et al. |
| 2006/0100649 A1 | 5/2006 | Hart |
| 2006/0106369 A1 | 5/2006 | Desai et al. |
| 2006/0111711 A1 | 5/2006 | Goble |
| 2006/0111723 A1 | 5/2006 | Chapolini et al. |
| 2006/0116634 A1 | 6/2006 | Shachar |
| 2006/0142772 A1 | 6/2006 | Ralph et al. |
| 2006/0144898 A1 | 7/2006 | Bilotti et al. |
| 2006/0154546 A1 | 7/2006 | Murphy et al. |
| 2006/0161050 A1 | 7/2006 | Butler et al. |
| 2006/0161185 A1 | 7/2006 | Saadat et al. |
| 2006/0167471 A1 | 7/2006 | Phillips |
| 2006/0173290 A1 | 8/2006 | Lavallee et al. |
| 2006/0173470 A1 | 8/2006 | Oray et al. |
| 2006/0176031 A1 | 8/2006 | Forman et al. |
| 2006/0176242 A1 | 8/2006 | Jaramaz et al. |
| 2006/0178556 A1 | 8/2006 | Hasser et al. |
| 2006/0180633 A1 | 8/2006 | Emmons |
| 2006/0180634 A1 | 8/2006 | Shelton et al. |
| 2006/0185682 A1 | 8/2006 | Marczyk |
| 2006/0199999 A1 | 9/2006 | Ikeda et al. |
| 2006/0201989 A1 | 9/2006 | Ojeda |
| 2006/0206100 A1 | 9/2006 | Eskridge et al. |
| 2006/0217729 A1 | 9/2006 | Eskridge et al. |
| 2006/0226957 A1 | 10/2006 | Miller et al. |
| 2006/0235368 A1 | 10/2006 | Oz |
| 2006/0241666 A1 | 10/2006 | Briggs et al. |

(56) References Cited

U.S. PATENT DOCUMENTS

| | | |
|---|---|---|
| 2006/0244460 A1 | 11/2006 | Weaver |
| 2006/0247584 A1 | 11/2006 | Sheetz et al. |
| 2006/0252981 A1 | 11/2006 | Matsuda et al. |
| 2006/0252990 A1 | 11/2006 | Kubach |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0261763 A1 | 11/2006 | Iott et al. |
| 2006/0263444 A1 | 11/2006 | Ming et al. |
| 2006/0264831 A1 | 11/2006 | Skwarek et al. |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0282064 A1 | 12/2006 | Shimizu et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0005045 A1 | 1/2007 | Mintz et al. |
| 2007/0009570 A1 | 1/2007 | Kim et al. |
| 2007/0010702 A1 | 1/2007 | Wang et al. |
| 2007/0010838 A1 | 1/2007 | Shelton et al. |
| 2007/0016235 A1 | 1/2007 | Tanaka et al. |
| 2007/0018958 A1 | 1/2007 | Tavakoli et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027551 A1 | 2/2007 | Farnsworth et al. |
| 2007/0043387 A1 | 2/2007 | Vargas et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0055228 A1 | 3/2007 | Berg et al. |
| 2007/0073341 A1 | 3/2007 | Smith et al. |
| 2007/0073389 A1 | 3/2007 | Bolduc et al. |
| 2007/0078328 A1 | 4/2007 | Ozaki et al. |
| 2007/0078484 A1 | 4/2007 | Talarico et al. |
| 2007/0084897 A1 | 4/2007 | Shelton et al. |
| 2007/0088376 A1 | 4/2007 | Zacharias |
| 2007/0090788 A1 | 4/2007 | Hansford et al. |
| 2007/0093869 A1 | 4/2007 | Bloom et al. |
| 2007/0102472 A1 | 5/2007 | Shelton |
| 2007/0103437 A1 | 5/2007 | Rosenberg |
| 2007/0106113 A1 | 5/2007 | Ravo |
| 2007/0106317 A1 | 5/2007 | Shelton et al. |
| 2007/0118115 A1 | 5/2007 | Artale et al. |
| 2007/0134251 A1 | 6/2007 | Ashkenazi et al. |
| 2007/0135686 A1 | 6/2007 | Pruitt et al. |
| 2007/0135803 A1 | 6/2007 | Belson |
| 2007/0152612 A1 | 7/2007 | Chen et al. |
| 2007/0152829 A1 | 7/2007 | Lindsay et al. |
| 2007/0155010 A1 | 7/2007 | Farnsworth et al. |
| 2007/0170225 A1 | 7/2007 | Shelton et al. |
| 2007/0173687 A1 | 7/2007 | Shima et al. |
| 2007/0173813 A1 | 7/2007 | Odom |
| 2007/0173872 A1 | 7/2007 | Neuenfeldt |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179477 A1 | 8/2007 | Danger |
| 2007/0185545 A1 | 8/2007 | Duke |
| 2007/0187857 A1 | 8/2007 | Riley et al. |
| 2007/0190110 A1 | 8/2007 | Pameijer et al. |
| 2007/0191868 A1 | 8/2007 | Theroux et al. |
| 2007/0191915 A1 | 8/2007 | Strother et al. |
| 2007/0194079 A1 | 8/2007 | Hueil et al. |
| 2007/0194082 A1 | 8/2007 | Morgan et al. |
| 2007/0197954 A1 | 8/2007 | Keenan |
| 2007/0198039 A1 | 8/2007 | Jones et al. |
| 2007/0203510 A1 | 8/2007 | Bettuchi |
| 2007/0207010 A1 | 9/2007 | Caspi |
| 2007/0208359 A1 | 9/2007 | Hoffman |
| 2007/0208375 A1 | 9/2007 | Nishizawa et al. |
| 2007/0213750 A1 | 9/2007 | Weadock |
| 2007/0225562 A1 | 9/2007 | Spivey et al. |
| 2007/0233163 A1 | 10/2007 | Bombard et al. |
| 2007/0243227 A1 | 10/2007 | Gertner |
| 2007/0244471 A1 | 10/2007 | Malackowski |
| 2007/0244496 A1 | 10/2007 | Hellenkamp |
| 2007/0246505 A1 | 10/2007 | Pace-Floridia et al. |
| 2007/0260132 A1 | 11/2007 | Sterling |
| 2007/0262592 A1 | 11/2007 | Hwang et al. |
| 2007/0270660 A1 | 11/2007 | Caylor et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0290027 A1 | 12/2007 | Maatta et al. |
| 2007/0296286 A1 | 12/2007 | Avenell |
| 2008/0003196 A1 | 1/2008 | Jonn et al. |
| 2008/0015598 A1 | 1/2008 | Prommersberger |
| 2008/0021486 A1 | 1/2008 | Oyola et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0039746 A1 | 2/2008 | Hissong et al. |
| 2008/0042861 A1 | 2/2008 | Dacquay et al. |
| 2008/0051833 A1 | 2/2008 | Gramuglia et al. |
| 2008/0064920 A1 | 3/2008 | Bakos et al. |
| 2008/0064921 A1 | 3/2008 | Larkin et al. |
| 2008/0065153 A1 | 3/2008 | Allard et al. |
| 2008/0069736 A1 | 3/2008 | Mingerink et al. |
| 2008/0071328 A1 | 3/2008 | Haubrich et al. |
| 2008/0077158 A1 | 3/2008 | Haider et al. |
| 2008/0078802 A1 | 4/2008 | Hess et al. |
| 2008/0081948 A1 | 4/2008 | Weisenburgh et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083807 A1 | 4/2008 | Beardsley et al. |
| 2008/0083811 A1 | 4/2008 | Marczyk |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0108443 A1 | 5/2008 | Jinno et al. |
| 2008/0114250 A1 | 5/2008 | Urbano et al. |
| 2008/0125634 A1 | 5/2008 | Ryan et al. |
| 2008/0125749 A1 | 5/2008 | Olson |
| 2008/0128469 A1 | 6/2008 | Dalessandro et al. |
| 2008/0129253 A1 | 6/2008 | Shiue et al. |
| 2008/0135600 A1 | 6/2008 | Hiranuma et al. |
| 2008/0140115 A1 | 6/2008 | Stopek |
| 2008/0140159 A1 | 6/2008 | Bornhoft et al. |
| 2008/0149682 A1 | 6/2008 | Uhm |
| 2008/0154299 A1 | 6/2008 | Livneh |
| 2008/0154335 A1 | 6/2008 | Thrope et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0177392 A1 | 7/2008 | Williams et al. |
| 2008/0190989 A1 | 8/2008 | Crews et al. |
| 2008/0196253 A1 | 8/2008 | Ezra et al. |
| 2008/0196419 A1 | 8/2008 | Dube |
| 2008/0197167 A1 | 8/2008 | Viola et al. |
| 2008/0200755 A1 | 8/2008 | Bakos |
| 2008/0200762 A1 | 8/2008 | Stokes et al. |
| 2008/0200835 A1 | 8/2008 | Monson et al. |
| 2008/0200911 A1 | 8/2008 | Long |
| 2008/0200933 A1 | 8/2008 | Bakos et al. |
| 2008/0200934 A1 | 8/2008 | Fox |
| 2008/0206186 A1 | 8/2008 | Butler et al. |
| 2008/0208058 A1 | 8/2008 | Sabata et al. |
| 2008/0234709 A1 | 9/2008 | Houser |
| 2008/0234866 A1 | 9/2008 | Kishi et al. |
| 2008/0242939 A1 | 10/2008 | Johnston |
| 2008/0243088 A1 | 10/2008 | Evans |
| 2008/0249536 A1 | 10/2008 | Stahler et al. |
| 2008/0249608 A1 | 10/2008 | Dave |
| 2008/0255413 A1 | 10/2008 | Zemlok et al. |
| 2008/0255420 A1 | 10/2008 | Lee et al. |
| 2008/0255663 A1 | 10/2008 | Akpek et al. |

(56) References Cited

U.S. PATENT DOCUMENTS

| | | |
|---|---|---|
| 2008/0262654 A1 | 10/2008 | Omori et al. |
| 2008/0269596 A1 | 10/2008 | Revie et al. |
| 2008/0281171 A1 | 11/2008 | Fennell et al. |
| 2008/0281332 A1 | 11/2008 | Taylor |
| 2008/0287944 A1 | 11/2008 | Pearson et al. |
| 2008/0293910 A1 | 11/2008 | Kapiamba et al. |
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0298784 A1 | 12/2008 | Kastner |
| 2008/0308602 A1 | 12/2008 | Timm et al. |
| 2008/0308603 A1 | 12/2008 | Shelton et al. |
| 2008/0312686 A1 | 12/2008 | Ellingwood |
| 2008/0312687 A1 | 12/2008 | Blier |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0012534 A1 | 1/2009 | Madhani et al. |
| 2009/0015195 A1 | 1/2009 | Loth-Krausser |
| 2009/0020958 A1 | 1/2009 | Soul |
| 2009/0048583 A1 | 2/2009 | Williams et al. |
| 2009/0048589 A1 | 2/2009 | Takashino et al. |
| 2009/0076506 A1 | 3/2009 | Baker |
| 2009/0078736 A1 | 3/2009 | Van Lue |
| 2009/0081313 A1 | 3/2009 | Aghion et al. |
| 2009/0088659 A1 | 4/2009 | Graham et al. |
| 2009/0090763 A1 | 4/2009 | Zemlok et al. |
| 2009/0099579 A1 | 4/2009 | Nentwick et al. |
| 2009/0099876 A1 | 4/2009 | Whitman |
| 2009/0110533 A1 | 4/2009 | Jinno |
| 2009/0112234 A1 | 4/2009 | Crainich et al. |
| 2009/0118762 A1 | 5/2009 | Crainch et al. |
| 2009/0119011 A1 | 5/2009 | Kondo et al. |
| 2009/0131819 A1 | 5/2009 | Ritchie et al. |
| 2009/0132400 A1 | 5/2009 | Conway |
| 2009/0135280 A1 | 5/2009 | Johnston et al. |
| 2009/0143855 A1 | 6/2009 | Weber et al. |
| 2009/0149871 A9 | 6/2009 | Kagan et al. |
| 2009/0171147 A1 | 7/2009 | Lee et al. |
| 2009/0177218 A1 | 7/2009 | Young et al. |
| 2009/0177226 A1 | 7/2009 | Reinprecht et al. |
| 2009/0181290 A1 | 7/2009 | Baldwin et al. |
| 2009/0188964 A1 | 7/2009 | Orlov |
| 2009/0192534 A1 | 7/2009 | Ortiz et al. |
| 2009/0198272 A1 | 8/2009 | Kerver et al. |
| 2009/0204108 A1 | 8/2009 | Steffen |
| 2009/0204109 A1 | 8/2009 | Grove et al. |
| 2009/0206125 A1 | 8/2009 | Huitema et al. |
| 2009/0206126 A1 | 8/2009 | Huitema et al. |
| 2009/0206131 A1* | 8/2009 | Weisenburgh, II ............ A61B 17/3205 227/175.2 |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0221993 A1 | 9/2009 | Sohi et al. |
| 2009/0227834 A1 | 9/2009 | Nakamoto et al. |
| 2009/0234273 A1 | 9/2009 | Intoccia et al. |
| 2009/0242610 A1 | 10/2009 | Shelton, IV et al. |
| 2009/0246873 A1 | 10/2009 | Yamamoto et al. |
| 2009/0247368 A1 | 10/2009 | Chiang |
| 2009/0247901 A1 | 10/2009 | Zimmer |
| 2009/0248100 A1 | 10/2009 | Vaisnys et al. |
| 2009/0253959 A1 | 10/2009 | Yoshie et al. |
| 2009/0255974 A1 | 10/2009 | Viola |
| 2009/0261141 A1 | 10/2009 | Stratton et al. |
| 2009/0262078 A1 | 10/2009 | Pizzi |
| 2009/0270895 A1 | 10/2009 | Churchill et al. |
| 2009/0273353 A1 | 11/2009 | Kroh et al. |
| 2009/0277288 A1 | 11/2009 | Doepker et al. |
| 2009/0278406 A1 | 11/2009 | Hoffman |
| 2009/0290016 A1 | 11/2009 | Suda |
| 2009/0292283 A1 | 11/2009 | Odom |
| 2009/0306639 A1 | 12/2009 | Nevo et al. |
| 2009/0308907 A1 | 12/2009 | Nalagatla et al. |
| 2009/0318557 A1 | 12/2009 | Stockel |
| 2009/0325859 A1 | 12/2009 | Ameer et al. |
| 2010/0005035 A1 | 1/2010 | Carpenter et al. |
| 2010/0012703 A1 | 1/2010 | Calabrese et al. |
| 2010/0015104 A1 | 1/2010 | Fraser et al. |
| 2010/0016853 A1 | 1/2010 | Burbank |
| 2010/0016888 A1 | 1/2010 | Calabrese et al. |
| 2010/0017715 A1 | 1/2010 | Balassanian |
| 2010/0023024 A1 | 1/2010 | Zeiner et al. |
| 2010/0030233 A1 | 2/2010 | Whitman et al. |
| 2010/0030239 A1 | 2/2010 | Viola et al. |
| 2010/0032179 A1 | 2/2010 | Hanspers et al. |
| 2010/0036370 A1 | 2/2010 | Mirel et al. |
| 2010/0051668 A1 | 3/2010 | Milliman et al. |
| 2010/0057118 A1 | 3/2010 | Dietz et al. |
| 2010/0065604 A1 | 3/2010 | Weng |
| 2010/0069833 A1 | 3/2010 | Wenderow et al. |
| 2010/0069942 A1 | 3/2010 | Shelton, IV |
| 2010/0076483 A1 | 3/2010 | Imuta |
| 2010/0076489 A1 | 3/2010 | Stopek et al. |
| 2010/0081883 A1 | 4/2010 | Murray et al. |
| 2010/0094340 A1 | 4/2010 | Stopek et al. |
| 2010/0094400 A1 | 4/2010 | Bolduc et al. |
| 2010/0100123 A1 | 4/2010 | Bennett |
| 2010/0100124 A1 | 4/2010 | Calabrese et al. |
| 2010/0116519 A1 | 5/2010 | Gareis |
| 2010/0122339 A1 | 5/2010 | Boccacci |
| 2010/0133317 A1 | 6/2010 | Shelton, IV et al. |
| 2010/0137990 A1 | 6/2010 | Apatsidis et al. |
| 2010/0138659 A1 | 6/2010 | Carmichael et al. |
| 2010/0145146 A1 | 6/2010 | Melder |
| 2010/0147921 A1 | 6/2010 | Olson |
| 2010/0147922 A1 | 6/2010 | Olson |
| 2010/0159435 A1 | 6/2010 | Mueller et al. |
| 2010/0179022 A1 | 7/2010 | Shirokoshi |
| 2010/0180711 A1 | 7/2010 | Kilibarda et al. |
| 2010/0191262 A1 | 7/2010 | Harris et al. |
| 2010/0191292 A1 | 7/2010 | Demeo et al. |
| 2010/0193566 A1 | 8/2010 | Scheib et al. |
| 2010/0204717 A1 | 8/2010 | Knodel |
| 2010/0204721 A1 | 8/2010 | Young et al. |
| 2010/0217281 A1 | 8/2010 | Matsuoka et al. |
| 2010/0222901 A1 | 9/2010 | Swayze et al. |
| 2010/0228250 A1 | 9/2010 | Brogna |
| 2010/0234687 A1 | 9/2010 | Azarbarzin et al. |
| 2010/0241137 A1 | 9/2010 | Doyle et al. |
| 2010/0245102 A1 | 9/2010 | Yokoi |
| 2010/0249497 A1 | 9/2010 | Peine et al. |
| 2010/0249947 A1 | 9/2010 | Lesh et al. |
| 2010/0256675 A1 | 10/2010 | Romans |
| 2010/0258327 A1 | 10/2010 | Esenwein et al. |
| 2010/0267662 A1 | 10/2010 | Fielder et al. |
| 2010/0274160 A1 | 10/2010 | Yachi et al. |
| 2010/0291184 A1 | 11/2010 | Clark et al. |
| 2010/0292540 A1 | 11/2010 | Hess et al. |
| 2010/0298636 A1 | 11/2010 | Castro et al. |
| 2010/0301097 A1 | 12/2010 | Scirica et al. |
| 2010/0310623 A1 | 12/2010 | Laurencin et al. |
| 2010/0312261 A1 | 12/2010 | Suzuki et al. |
| 2010/0318085 A1 | 12/2010 | Austin et al. |
| 2010/0331856 A1 | 12/2010 | Carlson et al. |
| 2011/0006101 A1 | 1/2011 | Hall et al. |
| 2011/0009694 A1 | 1/2011 | Schultz et al. |
| 2011/0011916 A1 | 1/2011 | Levine |
| 2011/0016960 A1 | 1/2011 | Debrailly |
| 2011/0021871 A1 | 1/2011 | Berkelaar |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0025311 A1 | 2/2011 | Chauvin et al. |
| 2011/0028991 A1 | 2/2011 | Ikeda et al. |
| 2011/0029270 A1 | 2/2011 | Mueglitz |
| 2011/0036891 A1 | 2/2011 | Zemlok et al. |
| 2011/0046667 A1 | 2/2011 | Culligan et al. |
| 2011/0052660 A1 | 3/2011 | Yang et al. |

(56) References Cited

U.S. PATENT DOCUMENTS

| | | |
|---|---|---|
| 2011/0056717 A1 | 3/2011 | Herisse |
| 2011/0060363 A1 | 3/2011 | Hess et al. |
| 2011/0066156 A1 | 3/2011 | McGahan et al. |
| 2011/0082538 A1 | 4/2011 | Dahlgren et al. |
| 2011/0087276 A1 | 4/2011 | Bedi et al. |
| 2011/0088921 A1 | 4/2011 | Forgues et al. |
| 2011/0091515 A1 | 4/2011 | Zilberman et al. |
| 2011/0095064 A1 | 4/2011 | Taylor et al. |
| 2011/0095067 A1 | 4/2011 | Ohdaira |
| 2011/0101069 A1 | 5/2011 | Bombard et al. |
| 2011/0101794 A1 | 5/2011 | Schroeder et al. |
| 2011/0112517 A1 | 5/2011 | Peine et al. |
| 2011/0112530 A1 | 5/2011 | Keller |
| 2011/0114697 A1 | 5/2011 | Baxter, III et al. |
| 2011/0118708 A1 | 5/2011 | Burbank et al. |
| 2011/0125149 A1 | 5/2011 | El-Galley et al. |
| 2011/0125176 A1 | 5/2011 | Yates et al. |
| 2011/0127945 A1 | 6/2011 | Yoneda |
| 2011/0129706 A1 | 6/2011 | Takahashi et al. |
| 2011/0144764 A1 | 6/2011 | Bagga et al. |
| 2011/0147433 A1 | 6/2011 | Shelton, IV et al. |
| 2011/0160725 A1 | 6/2011 | Kabaya et al. |
| 2011/0163146 A1 | 7/2011 | Ortiz et al. |
| 2011/0172495 A1 | 7/2011 | Armstrong |
| 2011/0174861 A1 | 7/2011 | Shelton, IV et al. |
| 2011/0192882 A1 | 8/2011 | Hess et al. |
| 2011/0199225 A1 | 8/2011 | Touchberry et al. |
| 2011/0218400 A1 | 9/2011 | Ma et al. |
| 2011/0218550 A1 | 9/2011 | Ma |
| 2011/0220381 A1 | 9/2011 | Friese et al. |
| 2011/0225105 A1 | 9/2011 | Scholer et al. |
| 2011/0230713 A1 | 9/2011 | Kleemann et al. |
| 2011/0235168 A1 | 9/2011 | Sander |
| 2011/0238044 A1 | 9/2011 | Main et al. |
| 2011/0241597 A1 | 10/2011 | Zhu et al. |
| 2011/0251606 A1 | 10/2011 | Kerr |
| 2011/0256266 A1 | 10/2011 | Orme et al. |
| 2011/0271186 A1 | 11/2011 | Owens |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0279268 A1 | 11/2011 | Konishi et al. |
| 2011/0285507 A1 | 11/2011 | Nelson |
| 2011/0290856 A1 | 12/2011 | Shelton, IV et al. |
| 2011/0290858 A1 | 12/2011 | Whitman et al. |
| 2011/0292258 A1 | 12/2011 | Adler et al. |
| 2011/0293690 A1 | 12/2011 | Griffin et al. |
| 2011/0295295 A1 | 12/2011 | Shelton, IV et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0007442 A1 | 1/2012 | Rhodes et al. |
| 2012/0008880 A1 | 1/2012 | Toth |
| 2012/0016239 A1 | 1/2012 | Barthe et al. |
| 2012/0016413 A1 | 1/2012 | Timm et al. |
| 2012/0016467 A1 | 1/2012 | Chen et al. |
| 2012/0029272 A1 | 2/2012 | Shelton, IV et al. |
| 2012/0033360 A1 | 2/2012 | Hsu |
| 2012/0059286 A1 | 3/2012 | Hastings et al. |
| 2012/0064483 A1 | 3/2012 | Lint et al. |
| 2012/0074200 A1 | 3/2012 | Schmid et al. |
| 2012/0078243 A1 | 3/2012 | Worrell et al. |
| 2012/0078244 A1 | 3/2012 | Worrell et al. |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |
| 2012/0080498 A1 | 4/2012 | Shelton, IV et al. |
| 2012/0086276 A1 | 4/2012 | Sawyers |
| 2012/0095458 A1 | 4/2012 | Cybulski et al. |
| 2012/0109186 A1 | 5/2012 | Parrott et al. |
| 2012/0116261 A1 | 5/2012 | Mumaw et al. |
| 2012/0116262 A1 | 5/2012 | Houser et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0118595 A1 | 5/2012 | Pellenc |
| 2012/0123463 A1 | 5/2012 | Jacobs |
| 2012/0125792 A1 | 5/2012 | Cassivi |
| 2012/0130217 A1 | 5/2012 | Kauphusman et al. |
| 2012/0132286 A1 | 5/2012 | Lim et al. |
| 2012/0171539 A1 | 7/2012 | Rejman et al. |
| 2012/0175398 A1 | 7/2012 | Sandborn et al. |
| 2012/0190964 A1 | 7/2012 | Hyde et al. |
| 2012/0197272 A1 | 8/2012 | Oray et al. |
| 2012/0211542 A1 | 8/2012 | Racenet |
| 2012/0220990 A1 | 8/2012 | Mckenzie et al. |
| 2012/0234895 A1 | 9/2012 | O'Connor et al. |
| 2012/0234897 A1 | 9/2012 | Shelton, IV et al. |
| 2012/0239068 A1 | 9/2012 | Morris et al. |
| 2012/0248169 A1 | 10/2012 | Widenhouse et al. |
| 2012/0251861 A1 | 10/2012 | Liang et al. |
| 2012/0253328 A1 | 10/2012 | Cunningham et al. |
| 2012/0271327 A1 | 10/2012 | West et al. |
| 2012/0283707 A1 | 11/2012 | Giordano et al. |
| 2012/0289811 A1 | 11/2012 | Viola et al. |
| 2012/0289979 A1 | 11/2012 | Eskaros et al. |
| 2012/0292367 A1 | 11/2012 | Morgan et al. |
| 2012/0296342 A1 | 11/2012 | Haglund Wendelschafer |
| 2012/0298722 A1 | 11/2012 | Hess et al. |
| 2012/0301498 A1 | 11/2012 | Altreuter et al. |
| 2012/0316424 A1 | 12/2012 | Stopek |
| 2012/0330329 A1 | 12/2012 | Harris et al. |
| 2013/0006227 A1 | 1/2013 | Takashino |
| 2013/0008937 A1 | 1/2013 | Viola |
| 2013/0012983 A1 | 1/2013 | Kleyman |
| 2013/0018400 A1 | 1/2013 | Milton et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0023910 A1 | 1/2013 | Solomon et al. |
| 2013/0026208 A1 | 1/2013 | Shelton, IV et al. |
| 2013/0026210 A1 | 1/2013 | Shelton, IV et al. |
| 2013/0030462 A1 | 1/2013 | Keating et al. |
| 2013/0041292 A1 | 2/2013 | Cunningham |
| 2013/0057162 A1 | 3/2013 | Pollischansky |
| 2013/0068816 A1 | 3/2013 | Mandakolathur Vasudevan et al. |
| 2013/0075447 A1 | 3/2013 | Weisenburgh, II et al. |
| 2013/0087597 A1 | 4/2013 | Shelton, IV et al. |
| 2013/0090534 A1 | 4/2013 | Burns et al. |
| 2013/0096568 A1 | 4/2013 | Justis |
| 2013/0098970 A1 | 4/2013 | Racenet et al. |
| 2013/0106352 A1 | 5/2013 | Nagamine |
| 2013/0112729 A1 | 5/2013 | Beardsley et al. |
| 2013/0116669 A1 | 5/2013 | Shelton, IV et al. |
| 2013/0123816 A1 | 5/2013 | Hodgkinson et al. |
| 2013/0126202 A1 | 5/2013 | Oomori et al. |
| 2013/0131476 A1 | 5/2013 | Siu et al. |
| 2013/0131651 A1 | 5/2013 | Strobl et al. |
| 2013/0136969 A1 | 5/2013 | Yasui et al. |
| 2013/0153641 A1 | 6/2013 | Shelton, IV et al. |
| 2013/0158390 A1 | 6/2013 | Tan et al. |
| 2013/0162198 A1 | 6/2013 | Yokota et al. |
| 2013/0169217 A1 | 7/2013 | Watanabe et al. |
| 2013/0172713 A1 | 7/2013 | Kirschenman |
| 2013/0172878 A1 | 7/2013 | Smith |
| 2013/0175317 A1 | 7/2013 | Yates et al. |
| 2013/0183769 A1 | 7/2013 | Tajima |
| 2013/0211244 A1 | 8/2013 | Nathaniel |
| 2013/0214025 A1 | 8/2013 | Zemlok et al. |
| 2013/0215449 A1 | 8/2013 | Yamasaki |
| 2013/0231681 A1 | 9/2013 | Robinson et al. |
| 2013/0233906 A1 | 9/2013 | Hess et al. |
| 2013/0238021 A1 | 9/2013 | Gross et al. |
| 2013/0248578 A1 | 9/2013 | Arteaga Gonzalez |
| 2013/0253480 A1 | 9/2013 | Kimball et al. |
| 2013/0256373 A1 | 10/2013 | Schmid et al. |
| 2013/0256380 A1 | 10/2013 | Schmid et al. |
| 2013/0267978 A1 | 10/2013 | Trissel |
| 2013/0270322 A1 | 10/2013 | Scheib et al. |
| 2013/0277410 A1 | 10/2013 | Fernandez et al. |
| 2013/0284792 A1 | 10/2013 | Ma |
| 2013/0293353 A1 | 11/2013 | McPherson et al. |
| 2013/0303845 A1 | 11/2013 | Skula et al. |
| 2013/0306704 A1 | 11/2013 | Balbierz et al. |

(56) References Cited

U.S. PATENT DOCUMENTS

| | | |
|---|---|---|
| 2013/0327552 A1 | 12/2013 | Lovelass et al. |
| 2013/0333910 A1 | 12/2013 | Tanimoto et al. |
| 2013/0334280 A1 | 12/2013 | Krehel et al. |
| 2013/0334283 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1* | 1/2014 | Shelton, IV ........... A61B 17/29 227/175.3 |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005718 A1 | 1/2014 | Shelton, IV et al. |
| 2014/0008289 A1 | 1/2014 | Williams et al. |
| 2014/0014704 A1 | 1/2014 | Onukuri et al. |
| 2014/0014705 A1 | 1/2014 | Baxter, III |
| 2014/0014707 A1 | 1/2014 | Onukuri et al. |
| 2014/0018832 A1 | 1/2014 | Shelton, IV |
| 2014/0022283 A1 | 1/2014 | Chan et al. |
| 2014/0039549 A1 | 2/2014 | Belsky et al. |
| 2014/0041191 A1 | 2/2014 | Knodel |
| 2014/0048580 A1 | 2/2014 | Merchant et al. |
| 2014/0081176 A1 | 3/2014 | Hassan |
| 2014/0094681 A1 | 4/2014 | Valentine et al. |
| 2014/0100558 A1 | 4/2014 | Schmitz et al. |
| 2014/0107697 A1 | 4/2014 | Patani et al. |
| 2014/0115229 A1 | 4/2014 | Kothamasu et al. |
| 2014/0131418 A1 | 5/2014 | Kostrzewski |
| 2014/0135832 A1 | 5/2014 | Park et al. |
| 2014/0151433 A1 | 6/2014 | Shelton, IV et al. |
| 2014/0155916 A1 | 6/2014 | Hodgkinson et al. |
| 2014/0158747 A1 | 6/2014 | Measamer et al. |
| 2014/0166723 A1 | 6/2014 | Beardsley et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175147 A1 | 6/2014 | Manoux et al. |
| 2014/0175150 A1 | 6/2014 | Shelton, IV et al. |
| 2014/0175152 A1 | 6/2014 | Hess et al. |
| 2014/0181710 A1 | 6/2014 | Baalu et al. |
| 2014/0183244 A1 | 7/2014 | Duque et al. |
| 2014/0188091 A1 | 7/2014 | Vidal et al. |
| 2014/0188159 A1 | 7/2014 | Steege |
| 2014/0207124 A1 | 7/2014 | Aldridge et al. |
| 2014/0209658 A1 | 7/2014 | Skalla et al. |
| 2014/0224857 A1 | 8/2014 | Schmid |
| 2014/0228632 A1 | 8/2014 | Sholev et al. |
| 2014/0228867 A1 | 8/2014 | Thomas et al. |
| 2014/0239047 A1 | 8/2014 | Hodgkinson et al. |
| 2014/0243865 A1 | 8/2014 | Swayze et al. |
| 2014/0246475 A1 | 9/2014 | Hall et al. |
| 2014/0248167 A1 | 9/2014 | Sugimoto et al. |
| 2014/0249557 A1 | 9/2014 | Koch et al. |
| 2014/0249573 A1 | 9/2014 | Arav |
| 2014/0262408 A1 | 9/2014 | Woodard |
| 2014/0263541 A1 | 9/2014 | Leimbach et al. |
| 2014/0263552 A1 | 9/2014 | Hall et al. |
| 2014/0263558 A1 | 9/2014 | Hausen et al. |
| 2014/0276730 A1 | 9/2014 | Boudreaux et al. |
| 2014/0284371 A1 | 9/2014 | Morgan et al. |
| 2014/0288460 A1 | 9/2014 | Ouyang et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0303660 A1 | 10/2014 | Boyden et al. |
| 2014/0330161 A1 | 11/2014 | Swayze et al. |
| 2014/0330298 A1 | 11/2014 | Arshonsky et al. |
| 2014/0330579 A1 | 11/2014 | Cashman et al. |
| 2014/0358163 A1 | 12/2014 | Farin et al. |
| 2014/0367445 A1 | 12/2014 | Ingmanson et al. |
| 2014/0374130 A1 | 12/2014 | Nakamura et al. |
| 2014/0378950 A1 | 12/2014 | Chiu |
| 2015/0001272 A1 | 1/2015 | Sniffin |
| 2015/0002089 A1 | 1/2015 | Rejman et al. |
| 2015/0025549 A1 | 1/2015 | Kilroy et al. |
| 2015/0025571 A1 | 1/2015 | Suzuki et al. |
| 2015/0039010 A1 | 2/2015 | Beardsley et al. |
| 2015/0053737 A1 | 2/2015 | Leimbach et al. |
| 2015/0053743 A1 | 2/2015 | Yates et al. |
| 2015/0053746 A1 | 2/2015 | Shelton, IV et al. |
| 2015/0053748 A1 | 2/2015 | Yates et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0066000 A1 | 3/2015 | An et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076211 A1 | 3/2015 | Irka et al. |
| 2015/0082624 A1 | 3/2015 | Craig et al. |
| 2015/0083781 A1 | 3/2015 | Giordano et al. |
| 2015/0083782 A1 | 3/2015 | Scheib et al. |
| 2015/0087952 A1 | 3/2015 | Albert et al. |
| 2015/0088127 A1 | 3/2015 | Craig et al. |
| 2015/0088547 A1 | 3/2015 | Balram et al. |
| 2015/0090760 A1 | 4/2015 | Giordano et al. |
| 2015/0090762 A1 | 4/2015 | Giordano et al. |
| 2015/0127021 A1 | 5/2015 | Harris et al. |
| 2015/0134077 A1 | 5/2015 | Shelton, IV et al. |
| 2015/0150620 A1 | 6/2015 | Miyamoto et al. |
| 2015/0173749 A1 | 6/2015 | Shelton, IV et al. |
| 2015/0173756 A1 | 6/2015 | Baxter et al. |
| 2015/0173789 A1 | 6/2015 | Baxter et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0201918 A1 | 7/2015 | Kumar et al. |
| 2015/0201932 A1 | 7/2015 | Swayze et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209045 A1 | 7/2015 | Hodgkinson et al. |
| 2015/0222212 A1 | 8/2015 | Iwata |
| 2015/0223868 A1 | 8/2015 | Brandt et al. |
| 2015/0230697 A1 | 8/2015 | Phee et al. |
| 2015/0230794 A1 | 8/2015 | Wellman et al. |
| 2015/0231409 A1 | 8/2015 | Racenet et al. |
| 2015/0238118 A1 | 8/2015 | Legassey et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0297200 A1 | 10/2015 | Fitzsimmons et al. |
| 2015/0297222 A1 | 10/2015 | Huitema et al. |
| 2015/0297223 A1 | 10/2015 | Huitema et al. |
| 2015/0297225 A1 | 10/2015 | Huitema et al. |
| 2015/0297228 A1 | 10/2015 | Huitema et al. |
| 2015/0297233 A1 | 10/2015 | Huitema et al. |
| 2015/0297824 A1 | 10/2015 | Cabiri et al. |
| 2015/0303417 A1 | 10/2015 | Koeder et al. |
| 2015/0313594 A1 | 11/2015 | Shelton, IV et al. |
| 2015/0324317 A1 | 11/2015 | Collins et al. |
| 2015/0352699 A1 | 12/2015 | Sakai et al. |
| 2015/0366560 A1* | 12/2015 | Chen ................. A61B 17/1155 227/176.1 |
| 2015/0366585 A1 | 12/2015 | Lemay et al. |
| 2015/0367497 A1 | 12/2015 | Ito et al. |
| 2015/0372265 A1 | 12/2015 | Morisaku et al. |
| 2015/0374372 A1 | 12/2015 | Zergiebel et al. |
| 2015/0374378 A1 | 12/2015 | Giordano et al. |
| 2016/0000437 A1 | 1/2016 | Giordano et al. |
| 2016/0000452 A1 | 1/2016 | Yates et al. |
| 2016/0000453 A1 | 1/2016 | Yates et al. |
| 2016/0029998 A1 | 2/2016 | Brister et al. |
| 2016/0030042 A1 | 2/2016 | Heinrich et al. |
| 2016/0030043 A1 | 2/2016 | Fanelli et al. |
| 2016/0051316 A1 | 2/2016 | Boudreaux |
| 2016/0066913 A1 | 3/2016 | Swayze et al. |
| 2016/0069449 A1 | 3/2016 | Kanai et al. |
| 2016/0074035 A1 | 3/2016 | Whitman et al. |

(56) References Cited

U.S. PATENT DOCUMENTS

| | | |
|---|---|---|
| 2016/0074040 A1 | 3/2016 | Widenhouse et al. |
| 2016/0082161 A1 | 3/2016 | Zilberman et al. |
| 2016/0120545 A1 | 5/2016 | Shelton, IV et al. |
| 2016/0135835 A1 | 5/2016 | Onuma |
| 2016/0135895 A1 | 5/2016 | Faasse et al. |
| 2016/0139666 A1 | 5/2016 | Rubin et al. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0192960 A1 | 7/2016 | Bueno et al. |
| 2016/0199063 A1 | 7/2016 | Mandakolathur Vasudevan et al. |
| 2016/0199956 A1 | 7/2016 | Shelton, IV et al. |
| 2016/0235494 A1 | 8/2016 | Shelton, IV et al. |
| 2016/0242783 A1 | 8/2016 | Shelton, IV et al. |
| 2016/0242855 A1 | 8/2016 | Fichtinger et al. |
| 2016/0249910 A1 | 9/2016 | Shelton, IV et al. |
| 2016/0249922 A1 | 9/2016 | Morgan et al. |
| 2016/0249928 A1* | 9/2016 | Cappola ............... A61B 90/90 227/176.1 |
| 2016/0256159 A1 | 9/2016 | Pinjala et al. |
| 2016/0256221 A1 | 9/2016 | Smith |
| 2016/0256229 A1 | 9/2016 | Morgan et al. |
| 2016/0262745 A1 | 9/2016 | Morgan et al. |
| 2016/0262921 A1 | 9/2016 | Balbierz et al. |
| 2016/0270781 A1 | 9/2016 | Scirica |
| 2016/0287265 A1 | 10/2016 | Macdonald et al. |
| 2016/0287279 A1 | 10/2016 | Bovay et al. |
| 2016/0302820 A1 | 10/2016 | Hibner et al. |
| 2016/0310143 A1 | 10/2016 | Bettuchi |
| 2016/0314716 A1 | 10/2016 | Grubbs |
| 2016/0314717 A1 | 10/2016 | Grubbs |
| 2016/0345972 A1 | 12/2016 | Beardsley et al. |
| 2016/0367122 A1 | 12/2016 | Ichimura et al. |
| 2016/0374716 A1 | 12/2016 | Kessler |
| 2017/0007234 A1 | 1/2017 | Chin et al. |
| 2017/0007244 A1 | 1/2017 | Shelton, IV et al. |
| 2017/0007245 A1 | 1/2017 | Shelton, IV et al. |
| 2017/0007347 A1 | 1/2017 | Jaworek et al. |
| 2017/0027572 A1 | 2/2017 | Nalagatla et al. |
| 2017/0055819 A1 | 3/2017 | Hansen et al. |
| 2017/0056005 A1 | 3/2017 | Shelton, IV et al. |
| 2017/0066054 A1 | 3/2017 | Birky |
| 2017/0079642 A1 | 3/2017 | Overmyer et al. |
| 2017/0086829 A1 | 3/2017 | Vendely et al. |
| 2017/0086830 A1 | 3/2017 | Yates et al. |
| 2017/0086831 A1 | 3/2017 | Shelton, IV et al. |
| 2017/0086842 A1 | 3/2017 | Shelton, IV et al. |
| 2017/0086930 A1 | 3/2017 | Thompson et al. |
| 2017/0095922 A1 | 4/2017 | Licht et al. |
| 2017/0105733 A1 | 4/2017 | Scheib et al. |
| 2017/0106302 A1 | 4/2017 | Cummings et al. |
| 2017/0135711 A1 | 5/2017 | Overmyer et al. |
| 2017/0135717 A1 | 5/2017 | Boudreaux et al. |
| 2017/0135747 A1 | 5/2017 | Broderick et al. |
| 2017/0172382 A1 | 6/2017 | Nir et al. |
| 2017/0172549 A1 | 6/2017 | Smaby et al. |
| 2017/0172662 A1 | 6/2017 | Panescu et al. |
| 2017/0182195 A1 | 6/2017 | Wagner |
| 2017/0182211 A1 | 6/2017 | Raxworthy et al. |
| 2017/0196558 A1 | 7/2017 | Morgan et al. |
| 2017/0196649 A1 | 7/2017 | Yates et al. |
| 2017/0202770 A1 | 7/2017 | Friedrich et al. |
| 2017/0209145 A1 | 7/2017 | Swayze et al. |
| 2017/0224332 A1 | 8/2017 | Hunter et al. |
| 2017/0224334 A1 | 8/2017 | Worthington et al. |
| 2017/0231627 A1 | 8/2017 | Shelton, IV et al. |
| 2017/0231628 A1 | 8/2017 | Shelton, IV et al. |
| 2017/0231629 A1 | 8/2017 | Stopek et al. |
| 2017/0238962 A1 | 8/2017 | Hansen et al. |
| 2017/0242455 A1 | 8/2017 | Dickens |
| 2017/0245949 A1 | 8/2017 | Randle |
| 2017/0249431 A1 | 8/2017 | Shelton, IV et al. |
| 2017/0255799 A1 | 9/2017 | Zhao et al. |
| 2017/0262110 A1 | 9/2017 | Polishchuk et al. |
| 2017/0265774 A1 | 9/2017 | Johnson et al. |
| 2017/0281186 A1 | 10/2017 | Shelton, IV et al. |
| 2017/0281189 A1 | 10/2017 | Nalagatla et al. |
| 2017/0296169 A1 | 10/2017 | Yates et al. |
| 2017/0296173 A1 | 10/2017 | Shelton, IV et al. |
| 2017/0296185 A1 | 10/2017 | Swensgard et al. |
| 2017/0296213 A1 | 10/2017 | Swensgard et al. |
| 2017/0312042 A1 | 11/2017 | Giordano et al. |
| 2017/0319047 A1 | 11/2017 | Poulsen et al. |
| 2017/0319201 A1 | 11/2017 | Morgan et al. |
| 2017/0333034 A1 | 11/2017 | Morgan et al. |
| 2017/0333035 A1 | 11/2017 | Morgan et al. |
| 2017/0348010 A1 | 12/2017 | Chiang |
| 2017/0348043 A1 | 12/2017 | Wang et al. |
| 2017/0354413 A1 | 12/2017 | Chen et al. |
| 2017/0358052 A1 | 12/2017 | Yuan |
| 2017/0360441 A1 | 12/2017 | Sgroi |
| 2018/0000545 A1 | 1/2018 | Giordano et al. |
| 2018/0008356 A1 | 1/2018 | Giordano et al. |
| 2018/0042611 A1 | 2/2018 | Swayze et al. |
| 2018/0049794 A1 | 2/2018 | Swayze et al. |
| 2018/0051780 A1 | 2/2018 | Shelton, IV et al. |
| 2018/0055501 A1 | 3/2018 | Zemlok et al. |
| 2018/0055513 A1 | 3/2018 | Shelton, IV et al. |
| 2018/0064442 A1 | 3/2018 | Shelton, IV et al. |
| 2018/0085116 A1 | 3/2018 | Yates et al. |
| 2018/0085117 A1 | 3/2018 | Shelton, IV et al. |
| 2018/0085120 A1 | 3/2018 | Viola |
| 2018/0092710 A1 | 4/2018 | Bosisio et al. |
| 2018/0110522 A1 | 4/2018 | Shelton, IV et al. |
| 2018/0110523 A1 | 4/2018 | Shelton, IV |
| 2018/0114591 A1 | 4/2018 | Pribanic et al. |
| 2018/0116658 A1 | 5/2018 | Aronhalt, IV et al. |
| 2018/0116662 A1 | 5/2018 | Shelton, IV et al. |
| 2018/0125481 A1 | 5/2018 | Yates et al. |
| 2018/0125487 A1 | 5/2018 | Beardsley |
| 2018/0125488 A1 | 5/2018 | Morgan et al. |
| 2018/0125590 A1 | 5/2018 | Giordano et al. |
| 2018/0125594 A1 | 5/2018 | Beardsley |
| 2018/0126504 A1 | 5/2018 | Shelton, IV et al. |
| 2018/0132845 A1 | 5/2018 | Schmid et al. |
| 2018/0132849 A1 | 5/2018 | Miller et al. |
| 2018/0132850 A1 | 5/2018 | Leimbach et al. |
| 2018/0132926 A1 | 5/2018 | Asher et al. |
| 2018/0132952 A1 | 5/2018 | Spivey et al. |
| 2018/0133521 A1 | 5/2018 | Frushour et al. |
| 2018/0140299 A1 | 5/2018 | Weaner et al. |
| 2018/0146960 A1 | 5/2018 | Shelton, IV et al. |
| 2018/0153542 A1 | 6/2018 | Shelton, IV et al. |
| 2018/0153634 A1 | 6/2018 | Zemlok et al. |
| 2018/0168572 A1 | 6/2018 | Burbank |
| 2018/0168574 A1 | 6/2018 | Robinson et al. |
| 2018/0168575 A1 | 6/2018 | Simms et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168584 A1 | 6/2018 | Harris et al. |
| 2018/0168590 A1 | 6/2018 | Overmyer et al. |
| 2018/0168592 A1 | 6/2018 | Overmyer et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0168754 A1 | 6/2018 | Overmyer |
| 2018/0228490 A1 | 8/2018 | Richard et al. |
| 2018/0235609 A1 | 8/2018 | Harris et al. |
| 2018/0236181 A1 | 8/2018 | Marlin et al. |
| 2018/0242970 A1 | 8/2018 | Mozdzierz |
| 2018/0250001 A1 | 9/2018 | Aronhalt et al. |

(56) References Cited

U.S. PATENT DOCUMENTS

| | | |
|---|---|---|
| 2018/0271520 A1 | 9/2018 | Shelton, IV et al. |
| 2018/0271604 A1 | 9/2018 | Grout et al. |
| 2018/0273597 A1 | 9/2018 | Stimson |
| 2018/0289369 A1 | 10/2018 | Shelton, IV et al. |
| 2018/0289371 A1 | 10/2018 | Wang et al. |
| 2018/0296211 A1 | 10/2018 | Timm et al. |
| 2018/0296216 A1 | 10/2018 | Shelton, IV et al. |
| 2018/0296290 A1 | 10/2018 | Namiki et al. |
| 2018/0317905 A1 | 11/2018 | Olson et al. |
| 2018/0333155 A1 | 11/2018 | Hall et al. |
| 2018/0333169 A1 | 11/2018 | Leimbach et al. |
| 2018/0353176 A1 | 12/2018 | Shelton, IV et al. |
| 2018/0353177 A1 | 12/2018 | Shelton, IV et al. |
| 2018/0353178 A1 | 12/2018 | Shelton, IV et al. |
| 2018/0353179 A1 | 12/2018 | Shelton, IV et al. |
| 2018/0360446 A1 | 12/2018 | Shelton, IV et al. |
| 2018/0360456 A1 | 12/2018 | Shelton, IV et al. |
| 2018/0360472 A1 | 12/2018 | Harris et al. |
| 2018/0360473 A1 | 12/2018 | Shelton, IV et al. |
| 2018/0368066 A1 | 12/2018 | Howell et al. |
| 2018/0368833 A1 | 12/2018 | Shelton, IV et al. |
| 2018/0368839 A1 | 12/2018 | Shelton, IV et al. |
| 2018/0368843 A1 | 12/2018 | Shelton, IV et al. |
| 2018/0368844 A1 | 12/2018 | Bakos et al. |
| 2018/0368846 A1 | 12/2018 | Shelton, IV et al. |
| 2018/0372806 A1 | 12/2018 | Laughery et al. |
| 2019/0000459 A1 | 1/2019 | Shelton, IV et al. |
| 2019/0000461 A1 | 1/2019 | Shelton, IV et al. |
| 2019/0000462 A1 | 1/2019 | Shelton, IV et al. |
| 2019/0000470 A1 | 1/2019 | Yates et al. |
| 2019/0000471 A1 | 1/2019 | Shelton, IV et al. |
| 2019/0000472 A1 | 1/2019 | Shelton, IV et al. |
| 2019/0000474 A1 | 1/2019 | Shelton, IV et al. |
| 2019/0000475 A1 | 1/2019 | Shelton, IV et al. |
| 2019/0000476 A1 | 1/2019 | Shelton, IV et al. |
| 2019/0000477 A1 | 1/2019 | Shelton, IV et al. |
| 2019/0000478 A1 | 1/2019 | Messerly et al. |
| 2019/0000481 A1 | 1/2019 | Harris et al. |
| 2019/0000525 A1 | 1/2019 | Messerly et al. |
| 2019/0008515 A1 | 1/2019 | Beardsley et al. |
| 2019/0015102 A1 | 1/2019 | Baber et al. |
| 2019/0015165 A1 | 1/2019 | Giordano et al. |
| 2019/0021733 A1 | 1/2019 | Burbank |
| 2019/0029682 A1 | 1/2019 | Huitema et al. |
| 2019/0029701 A1 | 1/2019 | Shelton, IV et al. |
| 2019/0033955 A1 | 1/2019 | Leimbach et al. |
| 2019/0038279 A1 | 2/2019 | Shelton, IV et al. |
| 2019/0038281 A1 | 2/2019 | Shelton, IV et al. |
| 2019/0038282 A1 | 2/2019 | Shelton, IV et al. |
| 2019/0038283 A1 | 2/2019 | Shelton, IV et al. |
| 2019/0038285 A1 | 2/2019 | Mozdzierz |
| 2019/0076143 A1 | 3/2019 | Smith |
| 2019/0090871 A1 | 3/2019 | Shelton, IV et al. |
| 2019/0091183 A1 | 3/2019 | Tomat et al. |
| 2019/0099179 A1 | 4/2019 | Leimbach et al. |
| 2019/0099181 A1 | 4/2019 | Shelton, IV et al. |
| 2019/0099229 A1 | 4/2019 | Spivey et al. |
| 2019/0104919 A1 | 4/2019 | Shelton, IV et al. |
| 2019/0105035 A1 | 4/2019 | Shelton, IV et al. |
| 2019/0105036 A1 | 4/2019 | Morgan et al. |
| 2019/0105037 A1 | 4/2019 | Morgan et al. |
| 2019/0105039 A1 | 4/2019 | Morgan et al. |
| 2019/0105043 A1 | 4/2019 | Jaworek et al. |
| 2019/0105044 A1 | 4/2019 | Shelton, IV et al. |
| 2019/0110779 A1 | 4/2019 | Gardner et al. |
| 2019/0110791 A1 | 4/2019 | Shelton, IV et al. |
| 2019/0110792 A1 | 4/2019 | Shelton, IV et al. |
| 2019/0117224 A1 | 4/2019 | Setser et al. |
| 2019/0125320 A1 | 5/2019 | Shelton, IV et al. |
| 2019/0125321 A1 | 5/2019 | Shelton, IV et al. |
| 2019/0125324 A1 | 5/2019 | Scheib et al. |
| 2019/0125335 A1 | 5/2019 | Shelton, IV et al. |
| 2019/0125336 A1 | 5/2019 | Deck et al. |
| 2019/0125338 A1 | 5/2019 | Shelton, IV et al. |
| 2019/0125342 A1 | 5/2019 | Beardsley et al. |
| 2019/0125343 A1 | 5/2019 | Wise et al. |
| 2019/0125348 A1 | 5/2019 | Shelton, IV et al. |
| 2019/0125353 A1 | 5/2019 | Shelton, IV et al. |
| 2019/0125356 A1 | 5/2019 | Shelton, IV et al. |
| 2019/0125357 A1 | 5/2019 | Shelton, IV et al. |
| 2019/0125358 A1 | 5/2019 | Shelton, IV et al. |
| 2019/0125359 A1 | 5/2019 | Shelton, IV et al. |
| 2019/0125360 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125379 A1 | 5/2019 | Shelton, IV et al. |
| 2019/0125384 A1 | 5/2019 | Scheib et al. |
| 2019/0125387 A1 | 5/2019 | Parihar et al. |
| 2019/0125388 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133422 A1 | 5/2019 | Nakamura |
| 2019/0138770 A1 | 5/2019 | Compaijen et al. |
| 2019/0142421 A1 | 5/2019 | Shelton, IV |
| 2019/0150925 A1 | 5/2019 | Marczyk et al. |
| 2019/0151029 A1 | 5/2019 | Robinson |
| 2019/0159778 A1 | 5/2019 | Shelton, IV et al. |
| 2019/0175847 A1 | 6/2019 | Pocreva, III et al. |
| 2019/0183499 A1 | 6/2019 | Shelton, IV et al. |
| 2019/0183502 A1 | 6/2019 | Shelton, IV et al. |
| 2019/0192138 A1 | 6/2019 | Shelton, IV et al. |
| 2019/0192141 A1 | 6/2019 | Shelton, IV et al. |
| 2019/0192146 A1 | 6/2019 | Widenhouse et al. |
| 2019/0192147 A1 | 6/2019 | Shelton, IV et al. |
| 2019/0192148 A1 | 6/2019 | Shelton, IV et al. |
| 2019/0192149 A1 | 6/2019 | Shelton, IV et al. |
| 2019/0192150 A1 | 6/2019 | Widenhouse et al. |
| 2019/0192151 A1 | 6/2019 | Shelton, IV et al. |
| 2019/0192152 A1 | 6/2019 | Morgan et al. |
| 2019/0192153 A1 | 6/2019 | Shelton, IV et al. |
| 2019/0192154 A1 | 6/2019 | Shelton, IV et al. |
| 2019/0192155 A1 | 6/2019 | Shelton, IV et al. |
| 2019/0192157 A1 | 6/2019 | Scott et al. |
| 2019/0192158 A1 | 6/2019 | Scott et al. |
| 2019/0192159 A1 | 6/2019 | Simms et al. |
| 2019/0192227 A1 | 6/2019 | Shelton, IV et al. |
| 2019/0192235 A1 | 6/2019 | Harris et al. |
| 2019/0192236 A1 | 6/2019 | Shelton, IV et al. |
| 2019/0200844 A1 | 7/2019 | Shelton, IV et al. |
| 2019/0200863 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200981 A1 | 7/2019 | Harris et al. |
| 2019/0200998 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201028 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201104 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201115 A1 | 7/2019 | Shelton, IV et al. |
| 2019/0201116 A1 | 7/2019 | Shelton, IV et al. |
| 2019/0201118 A1 | 7/2019 | Shelton, IV et al. |
| 2019/0201120 A1 | 7/2019 | Shelton, IV et al. |

(56) References Cited

U.S. PATENT DOCUMENTS

| | | |
|---|---|---|
| 2019/0201135 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201138 A1 | 7/2019 | Yates et al. |
| 2019/0201139 A1 | 7/2019 | Shelton, IV et al. |
| 2019/0201140 A1 | 7/2019 | Yates et al. |
| 2019/0201141 A1 | 7/2019 | Shelton, IV et al. |
| 2019/0201142 A1 | 7/2019 | Shelton, IV et al. |
| 2019/0201594 A1 | 7/2019 | Shelton, IV et al. |
| 2019/0205001 A1 | 7/2019 | Messerly et al. |
| 2019/0205566 A1 | 7/2019 | Shelton, IV et al. |
| 2019/0205567 A1 | 7/2019 | Shelton, IV et al. |
| 2019/0206003 A1 | 7/2019 | Harris et al. |
| 2019/0206551 A1 | 7/2019 | Yates et al. |
| 2019/0206555 A1 | 7/2019 | Morgan et al. |
| 2019/0206561 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0208641 A1 | 7/2019 | Yates et al. |
| 2019/0209164 A1 | 7/2019 | Timm et al. |
| 2019/0209165 A1 | 7/2019 | Timm et al. |
| 2019/0209171 A1 | 7/2019 | Shelton, IV et al. |
| 2019/0209172 A1 | 7/2019 | Shelton, IV et al. |
| 2019/0209247 A1 | 7/2019 | Giordano et al. |
| 2019/0209248 A1 | 7/2019 | Giordano et al. |
| 2019/0209249 A1 | 7/2019 | Giordano et al. |
| 2019/0209250 A1 | 7/2019 | Giordano et al. |
| 2019/0216558 A1 | 7/2019 | Giordano et al. |
| 2019/0261983 A1 | 8/2019 | Granger et al. |
| 2019/0261984 A1 | 8/2019 | Nelson et al. |
| 2019/0261987 A1 | 8/2019 | Viola et al. |
| 2019/0261991 A1 | 8/2019 | Beckman et al. |
| 2019/0269400 A1 | 9/2019 | Mandakolathur Vasudevan et al. |
| 2019/0269402 A1 | 9/2019 | Murray et al. |
| 2019/0269407 A1 | 9/2019 | Swensgard et al. |
| 2019/0269428 A1 | 9/2019 | Allen et al. |
| 2019/0274677 A1 | 9/2019 | Shelton, IV |
| 2019/0274678 A1 | 9/2019 | Shelton, IV |
| 2019/0274679 A1 | 9/2019 | Shelton, IV |
| 2019/0274685 A1 | 9/2019 | Olson et al. |
| 2019/0282233 A1 | 9/2019 | Burbank et al. |
| 2019/0290263 A1 | 9/2019 | Morgan et al. |
| 2019/0290264 A1 | 9/2019 | Morgan et al. |
| 2019/0290265 A1 | 9/2019 | Shelton, IV et al. |
| 2019/0290266 A1 | 9/2019 | Scheib et al. |
| 2019/0290267 A1 | 9/2019 | Baxter, III et al. |
| 2019/0290274 A1 | 9/2019 | Shelton, IV |
| 2019/0290281 A1 | 9/2019 | Aronhalt et al. |
| 2019/0290297 A1 | 9/2019 | Haider et al. |
| 2019/0298340 A1 | 10/2019 | Shelton, IV et al. |
| 2019/0298341 A1 | 10/2019 | Shelton, IV et al. |
| 2019/0298342 A1 | 10/2019 | Shelton, IV et al. |
| 2019/0298343 A1 | 10/2019 | Shelton, IV et al. |
| 2019/0298346 A1 | 10/2019 | Shelton, IV et al. |
| 2019/0298347 A1 | 10/2019 | Shelton, IV et al. |
| 2019/0298350 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298354 A1 | 10/2019 | Shelton, IV et al. |
| 2019/0298356 A1 | 10/2019 | Shelton, IV et al. |
| 2019/0298357 A1 | 10/2019 | Shelton, IV et al. |
| 2019/0298360 A1 | 10/2019 | Shelton, IV et al. |
| 2019/0298361 A1 | 10/2019 | Shelton, IV et al. |
| 2019/0298362 A1 | 10/2019 | Shelton, IV et al. |
| 2019/0307452 A1 | 10/2019 | Shelton, IV et al. |
| 2019/0307453 A1 | 10/2019 | Shelton, IV et al. |
| 2019/0307454 A1 | 10/2019 | Shelton, IV et al. |
| 2019/0307455 A1 | 10/2019 | Shelton, IV et al. |
| 2019/0307456 A1 | 10/2019 | Shelton, IV et al. |
| 2019/0307476 A1 | 10/2019 | Shelton, IV et al. |
| 2019/0307477 A1 | 10/2019 | Shelton, IV et al. |
| 2019/0307478 A1 | 10/2019 | Shelton, IV et al. |
| 2019/0307479 A1 | 10/2019 | Shelton, IV et al. |
| 2019/0314016 A1 | 10/2019 | Huitema et al. |
| 2019/0314017 A1 | 10/2019 | Huitema et al. |
| 2019/0314018 A1 | 10/2019 | Huitema et al. |
| 2019/0321040 A1 | 10/2019 | Shelton, IV |
| 2019/0321041 A1 | 10/2019 | Shelton, IV |
| 2019/0328386 A1 | 10/2019 | Harris et al. |
| 2019/0328387 A1 | 10/2019 | Overmyer et al. |
| 2019/0328390 A1 | 10/2019 | Harris et al. |
| 2019/0343515 A1 | 11/2019 | Morgan et al. |
| 2019/0343518 A1 | 11/2019 | Shelton, IV |
| 2019/0343525 A1 | 11/2019 | Shelton, IV et al. |
| 2019/0350581 A1 | 11/2019 | Baxter, III et al. |
| 2019/0350582 A1 | 11/2019 | Shelton, IV et al. |
| 2019/0357909 A1 | 11/2019 | Huitema et al. |
| 2019/0365384 A1 | 12/2019 | Baxter, III et al. |
| 2019/0374224 A1 | 12/2019 | Huitema et al. |
| 2020/0000461 A1 | 1/2020 | Yates et al. |
| 2020/0000469 A1 | 1/2020 | Shelton, IV et al. |
| 2020/0000471 A1 | 1/2020 | Shelton, IV et al. |
| 2020/0000531 A1 | 1/2020 | Giordano et al. |
| 2020/0008800 A1 | 1/2020 | Shelton, IV et al. |
| 2020/0008802 A1 | 1/2020 | Aronhalt et al. |
| 2020/0008809 A1 | 1/2020 | Shelton, IV et al. |
| 2020/0015819 A1 | 1/2020 | Shelton, IV et al. |
| 2020/0015915 A1 | 1/2020 | Swayze et al. |
| 2020/0022702 A1 | 1/2020 | Shelton, IV et al. |
| 2020/0029964 A1 | 1/2020 | Overmyer et al. |
| 2020/0038016 A1 | 2/2020 | Shelton, IV et al. |
| 2020/0038018 A1 | 2/2020 | Shelton, IV et al. |
| 2020/0038020 A1 | 2/2020 | Yates et al. |
| 2020/0046348 A1 | 2/2020 | Shelton, IV et al. |
| 2020/0046893 A1 | 2/2020 | Shelton, IV et al. |
| 2020/0054320 A1 | 2/2020 | Harris et al. |
| 2020/0054321 A1 | 2/2020 | Harris et al. |
| 2020/0054323 A1 | 2/2020 | Harris et al. |
| 2020/0054324 A1 | 2/2020 | Shelton, IV et al. |
| 2020/0054330 A1 | 2/2020 | Harris et al. |
| 2020/0054332 A1 | 2/2020 | Shelton, IV et al. |
| 2020/0054333 A1 | 2/2020 | Shelton, IV et al. |
| 2020/0054334 A1 | 2/2020 | Shelton, IV et al. |
| 2020/0054355 A1 | 2/2020 | Laurent et al. |
| 2020/0060523 A1 | 2/2020 | Matsuda et al. |
| 2020/0060680 A1 | 2/2020 | Shelton, IV et al. |
| 2020/0060681 A1 | 2/2020 | Shelton, IV et al. |
| 2020/0060713 A1 | 2/2020 | Leimbach et al. |
| 2020/0077994 A1 | 3/2020 | Shelton, IV et al. |
| 2020/0078015 A1 | 3/2020 | Miller et al. |
| 2020/0078016 A1 | 3/2020 | Swayze et al. |
| 2020/0085427 A1 | 3/2020 | Giordano et al. |
| 2020/0085431 A1 | 3/2020 | Swayze et al. |
| 2020/0085435 A1 | 3/2020 | Shelton, IV et al. |
| 2020/0085436 A1 | 3/2020 | Beckman et al. |
| 2020/0085518 A1 | 3/2020 | Giordano et al. |
| 2020/0093484 A1 | 3/2020 | Shelton, IV et al. |
| 2020/0093485 A1 | 3/2020 | Shelton, IV et al. |
| 2020/0093506 A1 | 3/2020 | Leimbach et al. |
| 2020/0093550 A1 | 3/2020 | Spivey et al. |
| 2020/0100699 A1 | 4/2020 | Shelton, IV et al. |
| 2020/0100783 A1 | 4/2020 | Yates et al. |
| 2020/0100787 A1 | 4/2020 | Shelton, IV et al. |
| 2020/0107829 A1 | 4/2020 | Shelton, IV et al. |
| 2020/0138434 A1 | 5/2020 | Miller et al. |
| 2020/0138435 A1 | 5/2020 | Shelton, IV et al. |
| 2020/0138436 A1 | 5/2020 | Yates et al. |
| 2020/0138437 A1 | 5/2020 | Vendely et al. |
| 2020/0138534 A1 | 5/2020 | Garcia Kilroy et al. |
| 2020/0146676 A1 | 5/2020 | Yates et al. |
| 2020/0146678 A1 | 5/2020 | Leimbach et al. |
| 2020/0146741 A1 | 5/2020 | Long et al. |
| 2020/0155151 A1 | 5/2020 | Overmyer et al. |
| 2020/0155155 A1 | 5/2020 | Shelton, IV et al. |
| 2020/0178958 A1 | 6/2020 | Overmyer et al. |
| 2020/0187943 A1 | 6/2020 | Shelton, IV et al. |
| 2020/0197027 A1 | 6/2020 | Hershberger et al. |
| 2020/0214706 A1 | 7/2020 | Vendely et al. |
| 2020/0214731 A1 | 7/2020 | Shelton, IV et al. |
| 2020/0222047 A1 | 7/2020 | Shelton, IV et al. |
| 2020/0229812 A1 | 7/2020 | Parihar et al. |

(56) References Cited

U.S. PATENT DOCUMENTS

| | | |
|---|---|---|
| 2020/0229814 A1 | 7/2020 | Amariglio et al. |
| 2020/0229816 A1 | 7/2020 | Bakos et al. |
| 2020/0237371 A1 | 7/2020 | Huitema et al. |
| 2020/0246001 A1 | 8/2020 | Ming et al. |
| 2020/0253605 A1 | 8/2020 | Swayze et al. |
| 2020/0261075 A1 | 8/2020 | Boudreaux et al. |
| 2020/0261076 A1 | 8/2020 | Boudreaux et al. |
| 2020/0261077 A1 | 8/2020 | Shelton, IV et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |
| 2020/0261082 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0261089 A1 | 8/2020 | Shelton, IV et al. |
| 2020/0261106 A1 | 8/2020 | Hess et al. |
| 2020/0268377 A1 | 8/2020 | Schmid et al. |
| 2020/0268394 A1 | 8/2020 | Parfett et al. |
| 2020/0275926 A1 | 9/2020 | Shelton, IV et al. |
| 2020/0275927 A1 | 9/2020 | Shelton, IV et al. |
| 2020/0275928 A1 | 9/2020 | Shelton, IV et al. |
| 2020/0275930 A1 | 9/2020 | Harris et al. |
| 2020/0280219 A1 | 9/2020 | Laughery et al. |
| 2020/0281585 A1 | 9/2020 | Timm et al. |
| 2020/0281587 A1 | 9/2020 | Schmid et al. |
| 2020/0281590 A1 | 9/2020 | Shelton, IV et al. |
| 2020/0289112 A1 | 9/2020 | Whitfield et al. |
| 2020/0297340 A1 | 9/2020 | Hess et al. |
| 2020/0297341 A1 | 9/2020 | Yates et al. |
| 2020/0297346 A1 | 9/2020 | Shelton, IV et al. |
| 2020/0297438 A1 | 9/2020 | Shelton, IV et al. |
| 2020/0305862 A1 | 10/2020 | Yates et al. |
| 2020/0305863 A1 | 10/2020 | Yates et al. |
| 2020/0305864 A1 | 10/2020 | Yates et al. |
| 2020/0305865 A1 | 10/2020 | Shelton, IV |
| 2020/0305868 A1 | 10/2020 | Shelton, IV |
| 2020/0305869 A1 | 10/2020 | Shelton, IV |
| 2020/0305870 A1 | 10/2020 | Shelton, IV |
| 2020/0305871 A1 | 10/2020 | Shelton, IV et al. |
| 2020/0305872 A1 | 10/2020 | Weidner et al. |
| 2020/0305874 A1 | 10/2020 | Huitema et al. |
| 2020/0315612 A1 | 10/2020 | Shelton, IV et al. |
| 2020/0315625 A1 | 10/2020 | Hall et al. |
| 2020/0315983 A1 | 10/2020 | Widenhouse et al. |
| 2020/0323526 A1 | 10/2020 | Huang et al. |
| 2020/0330092 A1 | 10/2020 | Shelton, IV et al. |
| 2020/0330093 A1 | 10/2020 | Shelton, IV et al. |
| 2020/0330094 A1 | 10/2020 | Baxter, III et al. |
| 2020/0330096 A1 | 10/2020 | Shelton, IV et al. |
| 2020/0330181 A1 | 10/2020 | Junger et al. |
| 2020/0337693 A1 | 10/2020 | Shelton, IV et al. |
| 2020/0337702 A1 | 10/2020 | Shelton, IV et al. |
| 2020/0337703 A1 | 10/2020 | Shelton, IV et al. |
| 2020/0337791 A1 | 10/2020 | Shelton, IV et al. |
| 2020/0345346 A1 | 11/2020 | Shelton, IV et al. |
| 2020/0345349 A1 | 11/2020 | Kimball et al. |
| 2020/0345352 A1 | 11/2020 | Shelton, IV et al. |
| 2020/0345353 A1 | 11/2020 | Leimbach et al. |
| 2020/0345354 A1 | 11/2020 | Leimbach et al. |
| 2020/0345355 A1 | 11/2020 | Baxter, III et al. |
| 2020/0345356 A1 | 11/2020 | Leimbach et al. |
| 2020/0345357 A1 | 11/2020 | Leimbach et al. |
| 2020/0345358 A1 | 11/2020 | Jenkins |
| 2020/0345359 A1 | 11/2020 | Baxter, III et al. |
| 2020/0345360 A1 | 11/2020 | Leimbach et al. |
| 2020/0345446 A1 | 11/2020 | Kimball et al. |
| 2020/0352562 A1 | 11/2020 | Timm et al. |
| 2020/0367885 A1 | 11/2020 | Yates et al. |
| 2020/0367886 A1 | 11/2020 | Shelton, IV et al. |
| 2020/0375585 A1 | 12/2020 | Swayze et al. |
| 2020/0375592 A1 | 12/2020 | Hall et al. |
| 2020/0375593 A1 | 12/2020 | Hunter et al. |
| 2020/0375597 A1 | 12/2020 | Shelton, IV et al. |
| 2020/0390444 A1 | 12/2020 | Harris et al. |
| 2020/0397433 A1 | 12/2020 | Lytle, IV et al. |
| 2020/0397434 A1 | 12/2020 | Overmyer et al. |
| 2020/0405290 A1 | 12/2020 | Shelton, IV et al. |
| 2020/0405292 A1 | 12/2020 | Shelton, IV et al. |
| 2020/0405293 A1 | 12/2020 | Shelton, IV et al. |
| 2020/0405294 A1 | 12/2020 | Shelton, IV |
| 2020/0405295 A1 | 12/2020 | Shelton, IV et al. |
| 2020/0405296 A1 | 12/2020 | Shelton, IV et al. |
| 2020/0405297 A1 | 12/2020 | Shelton, IV et al. |
| 2020/0405301 A1 | 12/2020 | Shelton, IV et al. |
| 2020/0405302 A1 | 12/2020 | Shelton, IV et al. |
| 2020/0405303 A1 | 12/2020 | Shelton, IV |
| 2020/0405305 A1 | 12/2020 | Shelton, IV et al. |
| 2020/0405306 A1 | 12/2020 | Shelton, IV et al. |
| 2020/0405307 A1 | 12/2020 | Shelton, IV et al. |
| 2020/0405308 A1 | 12/2020 | Shelton, IV |
| 2020/0405309 A1 | 12/2020 | Shelton, IV et al. |
| 2020/0405311 A1 | 12/2020 | Shelton, IV et al. |
| 2020/0405312 A1 | 12/2020 | Shelton, IV et al. |
| 2020/0405313 A1 | 12/2020 | Shelton, IV |
| 2020/0405314 A1 | 12/2020 | Shelton, IV et al. |
| 2020/0405316 A1 | 12/2020 | Shelton, IV et al. |
| 2020/0405341 A1 | 12/2020 | Hess et al. |
| 2020/0405409 A1 | 12/2020 | Shelton, IV et al. |
| 2020/0405410 A1 | 12/2020 | Shelton, IV |
| 2020/0405416 A1 | 12/2020 | Shelton, IV et al. |
| 2020/0405422 A1 | 12/2020 | Shelton, IV et al. |
| 2020/0405436 A1 | 12/2020 | Shelton, IV et al. |
| 2020/0405437 A1 | 12/2020 | Shelton, IV et al. |
| 2020/0405438 A1 | 12/2020 | Shelton, IV et al. |
| 2020/0405439 A1 | 12/2020 | Shelton, IV et al. |
| 2020/0405440 A1 | 12/2020 | Shelton, IV et al. |
| 2020/0405441 A1 | 12/2020 | Shelton, IV et al. |
| 2020/0410177 A1 | 12/2020 | Shelton, IV |
| 2020/0410180 A1 | 12/2020 | Shelton, IV et al. |
| 2021/0000466 A1 | 1/2021 | Leimbach et al. |
| 2021/0000467 A1 | 1/2021 | Shelton, IV et al. |
| 2021/0000470 A1 | 1/2021 | Leimbach et al. |
| 2021/0015480 A1 | 1/2021 | Shelton, IV et al. |
| 2021/0022741 A1 | 1/2021 | Baxter, III et al. |
| 2021/0030416 A1 | 2/2021 | Shelton, IV et al. |
| 2021/0045742 A1 | 2/2021 | Shelton, IV et al. |
| 2021/0052271 A1 | 2/2021 | Harris et al. |
| 2021/0059661 A1 | 3/2021 | Schmid et al. |
| 2021/0059662 A1 | 3/2021 | Shelton, IV |
| 2021/0059664 A1 | 3/2021 | Hensel et al. |
| 2021/0059666 A1 | 3/2021 | Schmid et al. |
| 2021/0059669 A1 | 3/2021 | Yates et al. |
| 2021/0059670 A1 | 3/2021 | Overmyer et al. |
| 2021/0059671 A1 | 3/2021 | Shelton, IV et al. |
| 2021/0059672 A1 | 3/2021 | Giordano et al. |
| 2021/0059673 A1 | 3/2021 | Shelton, IV et al. |
| 2021/0068817 A1 | 3/2021 | Shelton, IV et al. |
| 2021/0068818 A1 | 3/2021 | Overmyer et al. |
| 2021/0068820 A1 | 3/2021 | Parihar et al. |
| 2021/0068829 A1 | 3/2021 | Miller et al. |
| 2021/0068830 A1 | 3/2021 | Baber et al. |
| 2021/0068831 A1 | 3/2021 | Baber et al. |
| 2021/0068832 A1 | 3/2021 | Yates et al. |
| 2021/0068835 A1 | 3/2021 | Shelton, IV et al. |
| 2021/0077092 A1 | 3/2021 | Parihar et al. |
| 2021/0077099 A1 | 3/2021 | Shelton, IV et al. |
| 2021/0077100 A1 | 3/2021 | Shelton, IV et al. |
| 2021/0077109 A1 | 3/2021 | Harris et al. |
| 2021/0085313 A1 | 3/2021 | Morgan et al. |
| 2021/0085314 A1 | 3/2021 | Schmid et al. |
| 2021/0085315 A1 | 3/2021 | Aronhalt et al. |
| 2021/0085316 A1 | 3/2021 | Harris et al. |
| 2021/0085317 A1 | 3/2021 | Miller et al. |
| 2021/0085318 A1 | 3/2021 | Swayze et al. |
| 2021/0085319 A1 | 3/2021 | Swayze et al. |
| 2021/0085320 A1 | 3/2021 | Leimbach et al. |
| 2021/0085321 A1 | 3/2021 | Shelton, IV et al. |
| 2021/0085325 A1 | 3/2021 | Shelton, IV et al. |
| 2021/0085326 A1 | 3/2021 | Vendely et al. |
| 2021/0093321 A1 | 4/2021 | Auld et al. |

(56) References Cited

U.S. PATENT DOCUMENTS

| | | |
|---|---|---|
| 2021/0093323 A1 | 4/2021 | Scirica et al. |
| 2021/0100541 A1 | 4/2021 | Shelton, IV et al. |
| 2021/0100550 A1 | 4/2021 | Shelton, IV et al. |
| 2021/0100982 A1 | 4/2021 | Laby et al. |
| 2021/0106333 A1 | 4/2021 | Shelton, IV et al. |
| 2021/0107031 A1 | 4/2021 | Bales, Jr. et al. |
| 2021/0121175 A1 | 4/2021 | Yates et al. |
| 2021/0128146 A1 | 5/2021 | Shelton, IV et al. |
| 2021/0137522 A1 | 5/2021 | Shelton, IV et al. |
| 2021/0186490 A1 | 6/2021 | Shelton, IV et al. |
| 2021/0186492 A1 | 6/2021 | Shelton, IV et al. |
| 2021/0186493 A1 | 6/2021 | Shelton, IV et al. |
| 2021/0186494 A1 | 6/2021 | Shelton, IV et al. |
| 2021/0186495 A1 | 6/2021 | Shelton, IV et al. |
| 2021/0186497 A1 | 6/2021 | Shelton, IV et al. |
| 2021/0186498 A1 | 6/2021 | Boudreaux et al. |
| 2021/0186499 A1 | 6/2021 | Shelton, IV et al. |
| 2021/0186500 A1 | 6/2021 | Shelton, IV et al. |
| 2021/0186501 A1 | 6/2021 | Shelton, IV et al. |
| 2021/0186502 A1 | 6/2021 | Shelton, IV et al. |
| 2021/0186503 A1 | 6/2021 | Shelton, IV et al. |
| 2021/0186504 A1 | 6/2021 | Shelton, IV et al. |
| 2021/0186505 A1 | 6/2021 | Shelton, IV et al. |
| 2021/0186506 A1 | 6/2021 | Shelton, IV et al. |
| 2021/0186507 A1 | 6/2021 | Shelton, IV et al. |
| 2021/0212691 A1 | 7/2021 | Smith et al. |
| 2021/0212776 A1 | 7/2021 | Schmitt et al. |
| 2021/0219976 A1 | 7/2021 | DiNardo et al. |
| 2021/0228209 A1 | 7/2021 | Shelton, IV et al. |
| 2021/0236117 A1 | 8/2021 | Morgan et al. |
| 2021/0236124 A1 | 8/2021 | Shelton, IV et al. |
| 2021/0244406 A1 | 8/2021 | Kerr et al. |
| 2021/0244407 A1 | 8/2021 | Shelton, IV et al. |
| 2021/0244410 A1 | 8/2021 | Swayze et al. |
| 2021/0244412 A1 | 8/2021 | Vendely et al. |
| 2021/0259681 A1 | 8/2021 | Shelton, IV et al. |
| 2021/0259687 A1 | 8/2021 | Gonzalez et al. |
| 2021/0259986 A1 | 8/2021 | Widenhouse et al. |
| 2021/0259987 A1 | 8/2021 | Widenhouse et al. |
| 2021/0267589 A1 | 9/2021 | Swayze et al. |
| 2021/0267592 A1 | 9/2021 | Baxter, III et al. |
| 2021/0267594 A1 | 9/2021 | Morgan et al. |
| 2021/0267595 A1 | 9/2021 | Posada et al. |
| 2021/0267596 A1 | 9/2021 | Fanelli et al. |
| 2021/0275053 A1 | 9/2021 | Shelton, IV et al. |
| 2021/0275172 A1 | 9/2021 | Harris et al. |
| 2021/0275173 A1 | 9/2021 | Shelton, IV et al. |
| 2021/0275176 A1 | 9/2021 | Beckman et al. |
| 2021/0282767 A1 | 9/2021 | Shelton, IV et al. |
| 2021/0282769 A1 | 9/2021 | Baxter, III et al. |
| 2021/0282774 A1 | 9/2021 | Shelton, IV et al. |
| 2021/0282776 A1 | 9/2021 | Overmyer et al. |
| 2021/0290226 A1 | 9/2021 | Mandakolathur Vasudevan et al. |
| 2021/0290231 A1 | 9/2021 | Baxter, III et al. |
| 2021/0290232 A1 | 9/2021 | Harris et al. |
| 2021/0290233 A1 | 9/2021 | Shelton, IV et al. |
| 2021/0290236 A1 | 9/2021 | Moore et al. |
| 2021/0298745 A1 | 9/2021 | Leimbach et al. |
| 2021/0298746 A1 | 9/2021 | Leimbach et al. |
| 2021/0307748 A1 | 10/2021 | Harris et al. |
| 2021/0307754 A1 | 10/2021 | Shelton, IV et al. |
| 2021/0315566 A1 | 10/2021 | Yates et al. |
| 2021/0315570 A1 | 10/2021 | Shelton, IV |
| 2021/0315571 A1 | 10/2021 | Swayze et al. |
| 2021/0315573 A1 | 10/2021 | Shelton, IV et al. |
| 2021/0315574 A1 | 10/2021 | Shelton, IV et al. |
| 2021/0315576 A1 | 10/2021 | Shelton, IV et al. |
| 2021/0315577 A1 | 10/2021 | Shelton, IV et al. |
| 2021/0322009 A1 | 10/2021 | Huang et al. |
| 2021/0330321 A1 | 10/2021 | Leimbach et al. |
| 2021/0338233 A1 | 11/2021 | Shelton, IV et al. |
| 2021/0338234 A1 | 11/2021 | Shelton, IV et al. |
| 2021/0369273 A1 | 12/2021 | Yates et al. |
| 2021/0378669 A1 | 12/2021 | Shelton, IV et al. |
| 2021/0393260 A1 | 12/2021 | Shelton, IV et al. |
| 2021/0393261 A1 | 12/2021 | Harris et al. |
| 2021/0393262 A1 | 12/2021 | Shelton, IV et al. |
| 2021/0393268 A1 | 12/2021 | Shelton, IV et al. |
| 2021/0393366 A1 | 12/2021 | Shelton, IV et al. |
| 2022/0000478 A1 | 1/2022 | Shelton, IV et al. |

FOREIGN PATENT DOCUMENTS

| | | |
|---|---|---|
| AU | 2012268848 A1 | 1/2013 |
| AU | 2011218702 B2 | 6/2013 |
| AU | 2012200178 B2 | 7/2013 |
| BR | 112013027777 A2 | 1/2017 |
| CA | 1015829 A | 8/1977 |
| CA | 1125615 A | 6/1982 |
| CA | 2520413 A1 | 3/2007 |
| CA | 2725181 A1 | 11/2007 |
| CA | 2851239 A1 | 11/2007 |
| CA | 2664874 A1 | 11/2009 |
| CA | 2813230 A1 | 4/2012 |
| CA | 2940510 A1 | 8/2015 |
| CA | 2698728 C | 8/2016 |
| CN | 1163558 A | 10/1997 |
| CN | 2488482 Y | 5/2002 |
| CN | 1634601 A | 7/2005 |
| CN | 2716900 Y | 8/2005 |
| CN | 2738962 Y | 11/2005 |
| CN | 1777406 A | 5/2006 |
| CN | 2785249 Y | 5/2006 |
| CN | 2796654 Y | 7/2006 |
| CN | 2868212 Y | 2/2007 |
| CN | 200942099 Y | 9/2007 |
| CN | 200984209 Y | 12/2007 |
| CN | 200991269 Y | 12/2007 |
| CN | 201001747 Y | 1/2008 |
| CN | 101143105 A | 3/2008 |
| CN | 201029899 Y | 3/2008 |
| CN | 101188900 A | 5/2008 |
| CN | 101203085 A | 6/2008 |
| CN | 101273908 A | 10/2008 |
| CN | 101378791 A | 3/2009 |
| CN | 101507635 A | 8/2009 |
| CN | 101522120 A | 9/2009 |
| CN | 101669833 A | 3/2010 |
| CN | 101716090 A | 6/2010 |
| CN | 101721236 A | 6/2010 |
| CN | 101756727 A | 6/2010 |
| CN | 101828940 A | 9/2010 |
| CN | 101856250 A | 10/2010 |
| CN | 101873834 A | 10/2010 |
| CN | 201719298 U | 1/2011 |
| CN | 102038532 A | 5/2011 |
| CN | 201879759 U | 6/2011 |
| CN | 201949071 U | 8/2011 |
| CN | 102217961 A | 10/2011 |
| CN | 102217963 A | 10/2011 |
| CN | 102243850 A | 11/2011 |
| CN | 102247182 A | 11/2011 |
| CN | 102247183 A | 11/2011 |
| CN | 101779977 B | 12/2011 |
| CN | 102309352 A | 1/2012 |
| CN | 101912284 B | 7/2012 |
| CN | 102125450 B | 7/2012 |
| CN | 202313537 U | 7/2012 |
| CN | 202397539 U | 8/2012 |
| CN | 202426586 U | 9/2012 |
| CN | 102743201 A | 10/2012 |
| CN | 202489990 U | 10/2012 |
| CN | 102228387 B | 11/2012 |
| CN | 102835977 A | 12/2012 |
| CN | 202568350 U | 12/2012 |
| CN | 103037781 A | 4/2013 |
| CN | 103083053 A | 5/2013 |
| CN | 103391037 A | 11/2013 |
| CN | 203328751 U | 12/2013 |
| CN | 103505264 A | 1/2014 |
| CN | 103584893 A | 2/2014 |
| CN | 103635150 A | 3/2014 |
| CN | 103690212 A | 4/2014 |
| CN | 203564285 U | 4/2014 |

(56) References Cited

FOREIGN PATENT DOCUMENTS

| | | |
|---|---|---|
| CN | 203564287 U | 4/2014 |
| CN | 203597997 U | 5/2014 |
| CN | 103829981 A | 6/2014 |
| CN | 103829983 A | 6/2014 |
| CN | 103860221 A | 6/2014 |
| CN | 103908313 A | 7/2014 |
| CN | 203693685 U | 7/2014 |
| CN | 203736251 U | 7/2014 |
| CN | 103981635 A | 8/2014 |
| CN | 104027145 A | 9/2014 |
| CN | 203815517 U | 9/2014 |
| CN | 102783741 B | 10/2014 |
| CN | 102973300 B | 10/2014 |
| CN | 204092074 U | 1/2015 |
| CN | 104337556 A | 2/2015 |
| CN | 204158440 U | 2/2015 |
| CN | 204158441 U | 2/2015 |
| CN | 102469995 B | 3/2015 |
| CN | 104422849 A | 3/2015 |
| CN | 104586463 A | 5/2015 |
| CN | 204520822 U | 8/2015 |
| CN | 204636451 U | 9/2015 |
| CN | 103860225 B | 3/2016 |
| CN | 103750872 B | 5/2016 |
| CN | 105919642 A | 9/2016 |
| CN | 103648410 B | 10/2016 |
| CN | 105997173 A | 10/2016 |
| CN | 106344091 A | 1/2017 |
| CN | 104349800 B | 11/2017 |
| CN | 107635483 A | 1/2018 |
| CN | 208625784 U | 3/2019 |
| DE | 273689 C | 5/1914 |
| DE | 1775926 A | 1/1972 |
| DE | 3036217 A1 | 4/1982 |
| DE | 3210466 A1 | 9/1983 |
| DE | 3709067 A1 | 9/1988 |
| DE | 19534043 A1 | 3/1997 |
| DE | 19851291 A1 | 1/2000 |
| DE | 19924311 A1 | 11/2000 |
| DE | 20016423 U1 | 2/2001 |
| DE | 20112837 U1 | 10/2001 |
| DE | 20121753 U1 | 4/2003 |
| DE | 202004012389 U1 | 9/2004 |
| DE | 10314072 A1 | 10/2004 |
| DE | 102004014011 A1 | 10/2005 |
| DE | 102004041871 A1 | 3/2006 |
| DE | 102004063606 A1 | 7/2006 |
| DE | 202007003114 U1 | 6/2007 |
| DE | 102010013150 A1 | 9/2011 |
| DE | 102012213322 A1 | 1/2014 |
| DE | 102013101158 A1 | 8/2014 |
| EM | 002220467-0008 | 4/2013 |
| EP | 0000756 A1 | 2/1979 |
| EP | 0122046 A1 | 10/1984 |
| EP | 0129442 B1 | 11/1987 |
| EP | 0255631 A1 | 2/1988 |
| EP | 0169044 B1 | 6/1991 |
| EP | 0541950 A1 | 5/1993 |
| EP | 0548998 A1 | 6/1993 |
| EP | 0594148 A1 | 4/1994 |
| EP | 0646357 A1 | 4/1995 |
| EP | 0505036 B1 | 5/1995 |
| EP | 0669104 A1 | 8/1995 |
| EP | 0705571 A1 | 4/1996 |
| EP | 0528478 B1 | 5/1996 |
| EP | 0770355 A1 | 5/1997 |
| EP | 0625335 B1 | 11/1997 |
| EP | 0879742 A1 | 11/1998 |
| EP | 0650701 B1 | 3/1999 |
| EP | 0923907 A1 | 6/1999 |
| EP | 0484677 B2 | 7/2000 |
| EP | 1034747 A1 | 9/2000 |
| EP | 1034748 A1 | 9/2000 |
| EP | 0726632 B1 | 10/2000 |
| EP | 1053719 A1 | 11/2000 |
| EP | 1055399 A1 | 11/2000 |
| EP | 1055400 A1 | 11/2000 |
| EP | 1064882 A1 | 1/2001 |
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 1234587 A1 | 8/2002 |
| EP | 1284120 A1 | 2/2003 |
| EP | 0717967 B1 | 5/2003 |
| EP | 0869742 B1 | 5/2003 |
| EP | 1374788 A1 | 1/2004 |
| EP | 1407719 A2 | 4/2004 |
| EP | 0996378 B1 | 6/2004 |
| EP | 1558161 A1 | 8/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 1632191 A2 | 3/2006 |
| EP | 1082944 B1 | 5/2006 |
| EP | 1253866 B1 | 7/2006 |
| EP | 1723914 A1 | 11/2006 |
| EP | 1285633 B1 | 12/2006 |
| EP | 1011494 B1 | 1/2007 |
| EP | 1767163 A1 | 3/2007 |
| EP | 1837041 A1 | 9/2007 |
| EP | 0922435 B1 | 10/2007 |
| EP | 1599146 B1 | 10/2007 |
| EP | 1330201 B1 | 6/2008 |
| EP | 2039302 A2 | 3/2009 |
| EP | 1719461 B1 | 6/2009 |
| EP | 2116196 A2 | 11/2009 |
| EP | 1769754 B1 | 6/2010 |
| EP | 1627605 B1 | 12/2010 |
| EP | 2316345 A1 | 5/2011 |
| EP | 1962711 B1 | 2/2012 |
| EP | 2486862 A2 | 8/2012 |
| EP | 2486868 A2 | 8/2012 |
| EP | 2517638 A1 | 10/2012 |
| EP | 2606812 A1 | 6/2013 |
| EP | 2649948 A1 | 10/2013 |
| EP | 2649949 A1 | 10/2013 |
| EP | 2668910 A2 | 12/2013 |
| EP | 2687164 A2 | 1/2014 |
| EP | 2713902 A1 | 4/2014 |
| EP | 2743042 A2 | 6/2014 |
| EP | 2764827 A2 | 8/2014 |
| EP | 2777524 A2 | 9/2014 |
| EP | 2789299 A1 | 10/2014 |
| EP | 2842500 A1 | 3/2015 |
| EP | 2853220 A1 | 4/2015 |
| EP | 2878274 A1 | 6/2015 |
| EP | 2298220 B1 | 6/2016 |
| EP | 2510891 B1 | 6/2016 |
| EP | 3031404 A1 | 6/2016 |
| EP | 3047806 A1 | 7/2016 |
| EP | 3078334 A1 | 10/2016 |
| EP | 2364651 B1 | 11/2016 |
| EP | 2747235 B1 | 11/2016 |
| EP | 3095399 A2 | 11/2016 |
| EP | 3120781 A2 | 1/2017 |
| EP | 3135225 A2 | 3/2017 |
| EP | 2789299 B1 | 5/2017 |
| EP | 3225190 A2 | 10/2017 |
| EP | 3326548 A1 | 5/2018 |
| EP | 3363378 A1 | 8/2018 |
| EP | 3476334 A1 | 5/2019 |
| EP | 3275378 B1 | 7/2019 |
| ES | 1070456 U | 9/2009 |
| FR | 459743 A | 11/1913 |
| FR | 999646 A | 2/1952 |
| FR | 1112936 A | 3/1956 |
| FR | 2598905 A1 | 11/1987 |
| FR | 2689749 B1 | 7/1994 |
| FR | 2765794 A1 | 1/1999 |
| FR | 2815842 A1 | 5/2002 |
| GB | 939929 A | 10/1963 |

(56) References Cited

FOREIGN PATENT DOCUMENTS

| | | |
|---|---|---|
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2090534 B | 6/1984 |
| GB | 2272159 A | 5/1994 |
| GB | 2336214 A | 10/1999 |
| GB | 2509523 A | 7/2014 |
| GR | 930100110 A | 11/1993 |
| JP | S4711908 Y1 | 5/1972 |
| JP | S5033988 U | 4/1975 |
| JP | S5367286 A | 6/1978 |
| JP | S56112235 A | 9/1981 |
| JP | S60113007 A | 6/1985 |
| JP | S62170011 U | 10/1987 |
| JP | S63270040 A | 11/1988 |
| JP | S63318824 A | 12/1988 |
| JP | H0129503 B2 | 6/1989 |
| JP | H02106189 A | 4/1990 |
| JP | H0378514 U | 8/1991 |
| JP | H0385009 U | 8/1991 |
| JP | H04215747 A | 8/1992 |
| JP | H04131860 U | 12/1992 |
| JP | H0584252 A | 4/1993 |
| JP | H05123325 A | 5/1993 |
| JP | H05226945 A | 9/1993 |
| JP | H0630945 A | 2/1994 |
| JP | H06237937 A | 8/1994 |
| JP | H06304176 A | 11/1994 |
| JP | J06327684 A | 11/1994 |
| JP | H079622 U | 2/1995 |
| JP | H07124166 A | 5/1995 |
| JP | H07163573 A | 6/1995 |
| JP | H07255735 A | 10/1995 |
| JP | H07285089 A | 10/1995 |
| JP | H0833642 A | 2/1996 |
| JP | H08164141 A | 6/1996 |
| JP | H08182684 A | 7/1996 |
| JP | H08507708 A | 8/1996 |
| JP | H08229050 A | 9/1996 |
| JP | H08289895 A | 11/1996 |
| JP | H09-323068 A | 12/1997 |
| JP | H10118090 A | 5/1998 |
| JP | H10-200699 A | 7/1998 |
| JP | H10296660 A | 11/1998 |
| JP | 2000014632 A | 1/2000 |
| JP | 2000033071 A | 2/2000 |
| JP | 2000112002 A | 4/2000 |
| JP | 2000166932 A | 6/2000 |
| JP | 2000171730 A | 6/2000 |
| JP | 2000210299 A | 8/2000 |
| JP | 2000271141 A | 10/2000 |
| JP | 2000287987 A | 10/2000 |
| JP | 2000325303 A | 11/2000 |
| JP | 2001-69758 A | 3/2001 |
| JP | 2001087272 A | 4/2001 |
| JP | 2001208655 A | 8/2001 |
| JP | 2001514541 A | 9/2001 |
| JP | 2001276091 A | 10/2001 |
| JP | 2002051974 A | 2/2002 |
| JP | 2002054903 A | 2/2002 |
| JP | 2002085415 A | 3/2002 |
| JP | 2002143078 A | 5/2002 |
| JP | 2002153481 A | 5/2002 |
| JP | 2002528161 A | 9/2002 |
| JP | 2002314298 A | 10/2002 |
| JP | 2003135473 A | 5/2003 |
| JP | 2003521301 A | 7/2003 |
| JP | 3442423 B2 | 9/2003 |
| JP | 2003300416 A | 10/2003 |
| JP | 2004147701 A | 5/2004 |
| JP | 2004162035 A | 6/2004 |
| JP | 2004229976 A | 8/2004 |
| JP | 2005013573 A | 1/2005 |
| JP | 2005080702 A | 3/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005187954 A | 7/2005 |
| JP | 2005211455 A | 8/2005 |
| JP | 2005328882 A | 12/2005 |
| JP | 2005335432 A | 12/2005 |
| JP | 2005342267 A | 12/2005 |
| JP | 3791856 B2 | 6/2006 |
| JP | 2006187649 A | 7/2006 |
| JP | 2006218228 A | 8/2006 |
| JP | 2006281405 A | 10/2006 |
| JP | 2006291180 A | 10/2006 |
| JP | 2006346445 A | 12/2006 |
| JP | 2007-97252 A | 4/2007 |
| JP | 2007289715 A | 11/2007 |
| JP | 2007304057 A | 11/2007 |
| JP | 2007306710 A | 11/2007 |
| JP | D1322057 | 2/2008 |
| JP | 2008154804 A | 7/2008 |
| JP | 2008220032 A | 9/2008 |
| JP | 2009507526 A | 2/2009 |
| JP | 2009189838 A | 8/2009 |
| JP | 2009189846 A | 8/2009 |
| JP | 2009207260 A | 9/2009 |
| JP | 2009226028 A | 10/2009 |
| JP | 2009538684 A | 11/2009 |
| JP | 2009539420 A | 11/2009 |
| JP | D1383743 | 2/2010 |
| JP | 2010065594 A | 3/2010 |
| JP | 2010069307 A | 4/2010 |
| JP | 2010069310 A | 4/2010 |
| JP | 2010098844 A | 4/2010 |
| JP | 2010214128 A | 9/2010 |
| JP | 2011072574 A | 4/2011 |
| JP | 4722849 B2 | 7/2011 |
| JP | 4728996 B2 | 7/2011 |
| JP | 2011524199 A | 9/2011 |
| JP | 2011200665 A | 10/2011 |
| JP | D1432094 | 12/2011 |
| JP | 2012115542 A | 6/2012 |
| JP | 2012143283 A | 8/2012 |
| JP | 5154710 B1 | 2/2013 |
| JP | 2013099551 A | 5/2013 |
| JP | 2013126430 A | 6/2013 |
| JP | D1481426 | 9/2013 |
| JP | 2013541982 A | 11/2013 |
| JP | 2013541983 A | 11/2013 |
| JP | 2013541997 A | 11/2013 |
| JP | D1492363 | 2/2014 |
| JP | 2014121599 A | 7/2014 |
| JP | 2014171879 A | 9/2014 |
| JP | 1517663 S | 2/2015 |
| JP | 2015512725 A | 4/2015 |
| JP | 2015513956 A | 5/2015 |
| JP | 2015513958 A | 5/2015 |
| JP | 2015514471 A | 5/2015 |
| JP | 2015516838 A | 6/2015 |
| JP | 2015521524 A | 7/2015 |
| JP | 2015521525 A | 7/2015 |
| JP | 2016007800 A | 1/2016 |
| JP | 2016508792 A | 3/2016 |
| JP | 2016512057 A | 4/2016 |
| JP | 2016530949 A | 10/2016 |
| JP | 2017513563 A | 6/2017 |
| JP | 1601498 S | 4/2018 |
| JP | 2019513530 A | 5/2019 |
| KR | 20100110134 A | 10/2010 |
| KR | 20110003229 A | 1/2011 |
| KR | 300631507 | 3/2012 |
| KR | 300747646 | 6/2014 |
| RU | 1814161 C | 5/1993 |
| RU | 2008830 C1 | 3/1994 |
| RU | 2052979 C1 | 1/1996 |
| RU | 2066128 C1 | 9/1996 |

(56) References Cited

FOREIGN PATENT DOCUMENTS

| | | |
|---|---|---|
| RU | 2069981 C1 | 12/1996 |
| RU | 2098025 C1 | 12/1997 |
| RU | 2104671 C1 | 2/1998 |
| RU | 2110965 C1 | 5/1998 |
| RU | 2141279 C1 | 11/1999 |
| RU | 2144791 C1 | 1/2000 |
| RU | 2161450 C1 | 1/2001 |
| RU | 2181566 C2 | 4/2002 |
| RU | 2187249 C2 | 8/2002 |
| RU | 32984 U1 | 10/2003 |
| RU | 2225170 C2 | 3/2004 |
| RU | 42750 U1 | 12/2004 |
| RU | 61114 U1 | 2/2007 |
| RU | 61122 U1 | 2/2007 |
| RU | 2430692 C2 | 10/2011 |
| SU | 189517 A | 1/1967 |
| SU | 297156 A | 5/1971 |
| SU | 328636 A | 9/1972 |
| SU | 511939 A1 | 4/1976 |
| SU | 674747 A1 | 7/1979 |
| SU | 728848 A1 | 4/1980 |
| SU | 1009439 A | 4/1983 |
| SU | 1042742 A1 | 9/1983 |
| SU | 1271497 A1 | 11/1986 |
| SU | 1333319 A2 | 8/1987 |
| SU | 1377052 A1 | 2/1988 |
| SU | 1377053 A1 | 2/1988 |
| SU | 1443874 A1 | 12/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO-9308754 A1 | 5/1993 |
| WO | WO-9315648 A1 | 8/1993 |
| WO | WO-9420030 A1 | 9/1994 |
| WO | WO-9517855 A1 | 7/1995 |
| WO | WO-9520360 A1 | 8/1995 |
| WO | WO-9623448 A1 | 8/1996 |
| WO | WO-9635464 A1 | 11/1996 |
| WO | WO-9639086 A1 | 12/1996 |
| WO | WO-9639088 A1 | 12/1996 |
| WO | WO-9724073 A1 | 7/1997 |
| WO | WO-9734533 A1 | 9/1997 |
| WO | WO-9827870 A1 | 7/1998 |
| WO | WO-9903407 A1 | 1/1999 |
| WO | WO-9903409 A1 | 1/1999 |
| WO | WO-9948430 A1 | 9/1999 |
| WO | WO-0024322 A1 | 5/2000 |
| WO | WO-0024330 A1 | 5/2000 |
| WO | WO-0053112 A2 | 9/2000 |
| WO | WO-0024448 A2 | 10/2000 |
| WO | WO-0057796 A1 | 10/2000 |
| WO | WO-0105702 A1 | 1/2001 |
| WO | WO-0154594 A1 | 8/2001 |
| WO | WO-0158371 A1 | 8/2001 |
| WO | WO-0162164 A2 | 8/2001 |
| WO | WO-0162169 A2 | 8/2001 |
| WO | WO-0191646 A1 | 12/2001 |
| WO | WO-0219932 A1 | 3/2002 |
| WO | WO-0226143 A1 | 4/2002 |
| WO | WO-0236028 A1 | 5/2002 |
| WO | WO-02065933 A2 | 8/2002 |
| WO | WO-03055402 A1 | 7/2003 |
| WO | WO-03094747 A1 | 11/2003 |
| WO | WO-03079909 A3 | 3/2004 |
| WO | WO-2004019803 A1 | 3/2004 |
| WO | WO-2004032783 A1 | 4/2004 |
| WO | WO-2004047626 A1 | 6/2004 |
| WO | WO-2004047653 A2 | 6/2004 |
| WO | WO-2004056277 A1 | 7/2004 |
| WO | WO-2004078050 A2 | 9/2004 |
| WO | WO-2004078051 A2 | 9/2004 |
| WO | WO-2004096015 A2 | 11/2004 |
| WO | WO-2006044581 A2 | 4/2006 |
| WO | WO-2006051252 A1 | 5/2006 |
| WO | WO-2006059067 A1 | 6/2006 |
| WO | WO-2006073581 A2 | 7/2006 |
| WO | WO-2006085389 A1 | 8/2006 |
| WO | WO-2007015971 A2 | 2/2007 |
| WO | WO-2007074430 A1 | 7/2007 |
| WO | WO-2007129121 A1 | 11/2007 |
| WO | WO-2007137304 A2 | 11/2007 |
| WO | WO-2007142625 A2 | 12/2007 |
| WO | WO-2008021969 A2 | 2/2008 |
| WO | WO-2008061566 A1 | 5/2008 |
| WO | WO-2008089404 A2 | 7/2008 |
| WO | WO-2009005969 A2 | 1/2009 |
| WO | WO-2009067649 A2 | 5/2009 |
| WO | WO-2009091497 A2 | 7/2009 |
| WO | WO-2010126129 A1 | 11/2010 |
| WO | WO-2010134913 A1 | 11/2010 |
| WO | WO-2011008672 A2 | 1/2011 |
| WO | WO-2011044343 A2 | 4/2011 |
| WO | WO-2012006306 A2 | 1/2012 |
| WO | WO-2012013577 A1 | 2/2012 |
| WO | WO-2012044606 A2 | 4/2012 |
| WO | WO-2012061725 A1 | 5/2012 |
| WO | WO-2012072133 A1 | 6/2012 |
| WO | WO-2012166503 A1 | 12/2012 |
| WO | WO-2013087092 A1 | 6/2013 |
| WO | WO-2013151888 A1 | 10/2013 |
| WO | WO-2014004209 A2 | 1/2014 |
| WO | WO-2014113438 A1 | 7/2014 |
| WO | WO-2014175894 A1 | 10/2014 |
| WO | WO-2015032797 A1 | 3/2015 |
| WO | WO-2015076780 A1 | 5/2015 |
| WO | WO-2015137040 A1 | 9/2015 |
| WO | WO-2015138760 A1 | 9/2015 |
| WO | WO-2015187107 A1 | 12/2015 |
| WO | WO-2016100682 A1 | 6/2016 |
| WO | WO-2016107448 A1 | 7/2016 |
| WO | WO-2019036490 A1 | 2/2019 |

OTHER PUBLICATIONS

ASTM procedure D2240-05, "Standard Test Method for Rubber Property-Durometer Hardness," (Published Apr. 2010).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

Disclosed Anonymously, "Motor-Driven Surgical Stapler Improvements," Research Disclosure Database No. 526041, Published: Feb. 2008.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).

Miyata et al., "Biomolecule-Sensitive Hydrogels," Advanced Drug Delivery Reviews, 54 (2002) pp. 79-98.

Jeong et al., "Thermosensitive Sol-Gel Reversible Hydrogels," Advanced Drug Delivery Reviews, 54 (2002) pp. 37-51.

Covidien Brochure, "Endo GIA™ Ultra Universal Stapler," (2010), 2 pages.

Qiu et al., "Environment-Sensitive Hydrogels for Drug Delivery," Advanced Drug Delivery Reviews, 53 (2001) pp. 321-339.

(56) References Cited

OTHER PUBLICATIONS

Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Peppas, Editor "Hydrogels in Medicine and Pharmacy," vol. I, Fundamentals, CRC Press, 1986.
Young, "Microcellular foams via phase separation," Journal of Vacuum Science & Technology A 4(3), (May/Jun. 1986).
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Solorio et al., "Gelatin Microspheres Crosslinked with Genipin for Local Delivery of Growth Factors," J. Tissue Eng. Regen. Med. (2010), 4(7): pp. 514-523.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Pitt et al., "Attachment of Hyaluronan to Metallic Surfaces," J. Biomed. Mater. Res. 68A: pp. 95-106, 2004.
Indian Standard: Automotive Vehicles—Brakes and Braking Systems (IS 11852-1:2001), Mar. 1, 2001.
Patrick J. Sweeney: "RFID for Dummies", Mar. 11, 2010, pp. 365-365, XP055150775, ISBN: 978-1-11 -805447-5, Retrieved from the Internet: URL: books.google.de/books?isbn=1118054474 [retrieved on Nov. 4, 2014]—book not attached.
Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.
Data Sheet of LM4F230H5QR, 2007.
Seils et al., Covidien Summary: Clinical Study "UCONN Biodynamics: Final Report on Results," (2 pages).
Byrne et al., "Molecular Imprinting Within Hydrogels," Advanced Drug Delivery Reviews, 54 (2002) pp. 149-161.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Chen et al., "Elastomeric Biomaterials for Tissue Engineering," Progress in Polymer Science 38 (2013), pp. 584-671.
Matsuda, "Thermodynamics of Formation of Porous Polymeric Membrane from Solutions," Polymer Journal, vol. 23, No. 5, pp. 435-444 (1991).
Covidien Brochure, "Endo GIA™ Black Reload with Tri-Staple™ Technology," (2012), 2 pages.
Biomedical Coatings, Fort Wayne Metals, Research Products Corporation, obtained online at www.fwmetals.com on Jun. 21, 2010 (1 page).

The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileld=db3a304332d040720132d939503e5f17 [retrieved on Oct. 18, 2016].
Mouser Electronics, "LM317M 3-Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3-Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Yan et al., Comparison of the effects of Mg—6Zn and Ti—3Al-2.5V alloys on TGF-β/TNF-α/VEGF/b-FGF in the healing of the intestinal track in vivo, Biomed. Mater. 9 (2014), 11 pages.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Anonymous, Analog Devices Wiki, Chapter 11: The Current Mirror, Aug. 20, 2017, 22 pages. https://wiki.analog.com/university/courses/electronics/text/chapter-11 ?rev=1503222341.
Yan et al., "Comparison of the effects of Mg—6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Mech. Behavior of Biomed. Mater. 7(2012) pp. 87-95.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B-Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press LTD, 2012, pp. 1-29.
Youtube.com; video by Fibran (retrieved from URL https://www.youtube.com/watch?v=vN2Qjt51gFQ); (Year: 2018).
Foot and Ankle: Core Knowledge in Orthopaedics; by DiGiovanni MD, Elsevier; (p. 27, left column, heading "Materials for Soft Orthoses", 7th bullet point); (Year: 2007).
Lee, Youbok, "Antenna Circuit Design for RFID Applications," 2003, pp. 1-5 DS00710C, Microchip Technology Inc., Available: http://ww1.microchip.com/downloads/en/AppNotes/Q0710c.pdf.
Kawamura, Atsuo, et al. "Wireless Transmission of Power and Information through One High-Frequency Resonant AC Link Inverter for Robot Manipulator Applications," Journal, May/Jun. 1996, pp. 503-508, vol. 32, No. 3, IEEE Transactions on Industry.

(56) References Cited

OTHER PUBLICATIONS

Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd]. {Year: 2016).

Slow Safety Sign, shutterstock.com [online], published on or before May 9, 2017, [May 31, 2019], retrieved from the https://www.shutterstock.com/image-victor/slow-safety-sign-twodimensional-turtle-symbolizing-. . . see PDF in file for full URL] (Year: 2017).

Warning Sign Beveled Buttons, by Peter, flarestock.com [online], published on or Jan. 1, 2017, [retrieved on Jun. 4, 2019], retrieved from the Internet [URL: https://www.flarestock.com/stock-images/warning-sign-beveled-buttons/70257] (Year: 2017).

Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).

Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).

Tutorial overview of inductively coupled RFID Systems, UPM, May 2003, pp. 1-7, UPM Rafsec,<http://cdn.mobiusconsultinq.com/papers/rfidsystems.pdf>.

Schroeter, John, "Demystifying UHF Gen 2 RFID, HF RFID," Online Article, Jun. 2, 2008, pp. 1-3, <https://www.edn.com/design/industrial-control/4019123/Demystifying-UHF-Gen-2-RFID-HF-RDID-22 .

Adeeb, et al., "An Inductive Link-Based Wireless Pcwer Transfer System fcr Biomedical Applicatipns," Research Article, Nov. 14, 2011, pp. 1-12, vol. 2012, Article ID 879294, Hindawi Publishing Corporation.

Pushing Pixels (GIF), published on dribble. com, 2013.

Sodium stearate C18H35NaO2, Chemspider Search and Share Chemistry, Royal Society of Chemistry, pp. 1-3, 2015, http://www.chemspider.ccm/Chemical-Structure.12639.html, accessed May 23, 2016.

NF Monographs: Sodium Stearate, U.S. Pharmacopeia, http://www.pharmacopeia.cn/v29240/usp29nf24s0_m77360.html, accessed May 23, 2016.

Fischer, Martin H, "Colloid-Chemical Studies on Soaps", The Chemical Engineer, pp. 184-193, Aug. 1919.

V.K. Ahluwalia and Madhuri Goyal, A Textbook of Organic Chemistry, Section 19.11.3, p. 356, 2000.

A.V. Kasture and S.G. Wadodkar, Pharmaceutical Chemistry-II: Second Year Diploma in Pharmacy, Nirali Prakashan, p. 339, 2007.

Forum discussion regarding "Speed is Faster", published on Oct. 1, 2014 and retrieved on Nov. 8, 2019 from URL https://english.stackexchange.com/questions/199018/how-is-that-correct-speed-is-faster-or-prices-are-cheaper (Year: 2014).

"Understanding the Requirements of ISO/IEC 14443 for Type B Proximity Contactless Identification Cards," retrieved from https://www.digchip.com/application-notes/22/15746.php on Mar. 2, 2020, pp. 1-28 (Nov. 2005).

Jauchem, J.R., "Effects of low-level radio-frequency (3 kHz to 300 GHz) enery on human cardiovascular, reproductive, immune, and other systems: A review of the recent literatured," Int. J. Hyg. Environ. Health 211 (2008) 1-29.

Sandvik, "Welding Handbook," https://www.meting.rs/wp-content/uploads/2018/05/welding-handbook.pdf, retrieved on Jun. 22, 2020. pp. 5-6.

Ludois, Daniel C., "Capacitive Power Transfer for Rotor Field Current in Synchronous Machines," IEEE Transactions on Power Electronics, Institute of Electrical and Electronics Engineers, USA, vol. 27, No. 11, Nov. 1, 2012, pp. 4638-4645.

Rotary Systems: Sealed Slip Ring Categories, Rotary Systems, May 22, 2017, retrieved from the internet: http://web.archive.org/we/20170522174710/http:/rotarysystems.com: 80/slip-rings/sealed/, retrieved on Aug. 12, 2020, pp. 1-2.

IEEE Std 802.3-2012 (Revision of IEEE Std 802.3-2008, published Dec. 28, 2012.

"ATM-MPLS Network Interworking Version 2.0, af-aic-0178.001" ATM Standard, The ATM Forum Technical Committee, published Aug. 2003.

Yang et al.; "4D printing reconfigurable, deployable and mechanically tunable metamaterials," Material Horizions, vol. 6, pp. 1244-1250 (2019).

"Council Directive 93/42/EEC of Jun. 14, 1993 Concerning Medical Devices," Official Journal of the European Communities, L&C. Ligislation and Competition, S, No. L 169, Jun. 14, 1993, pp. 1-43.

\* cited by examiner

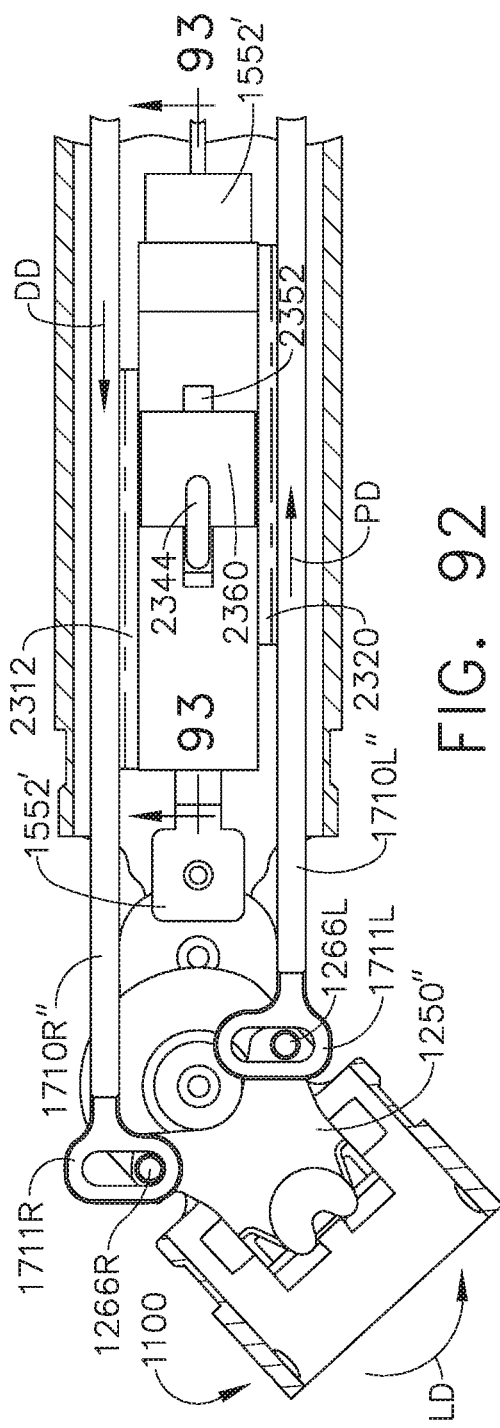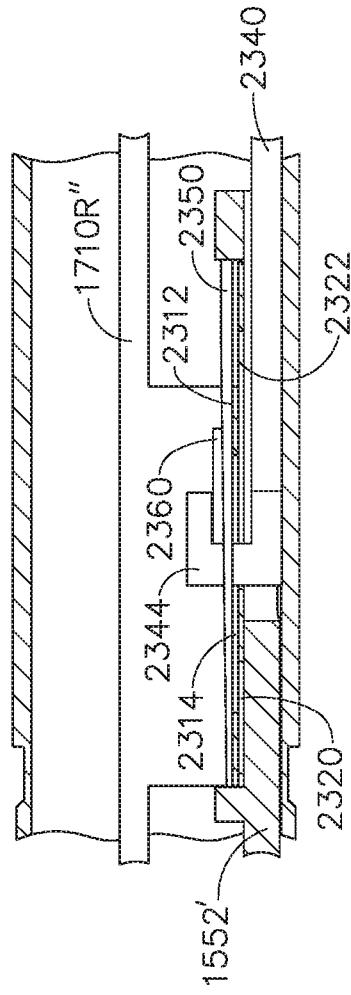

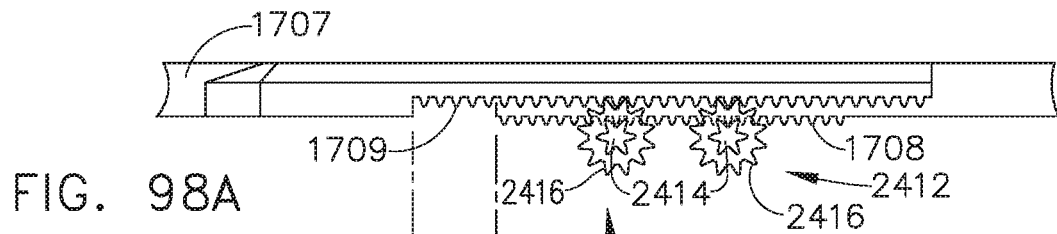
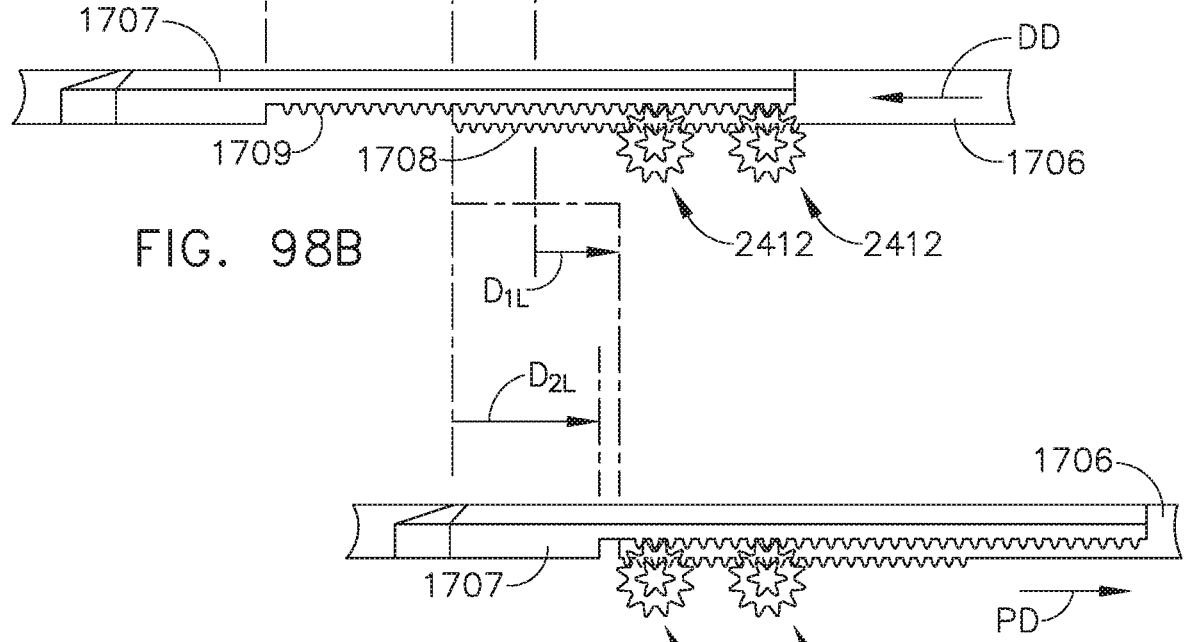

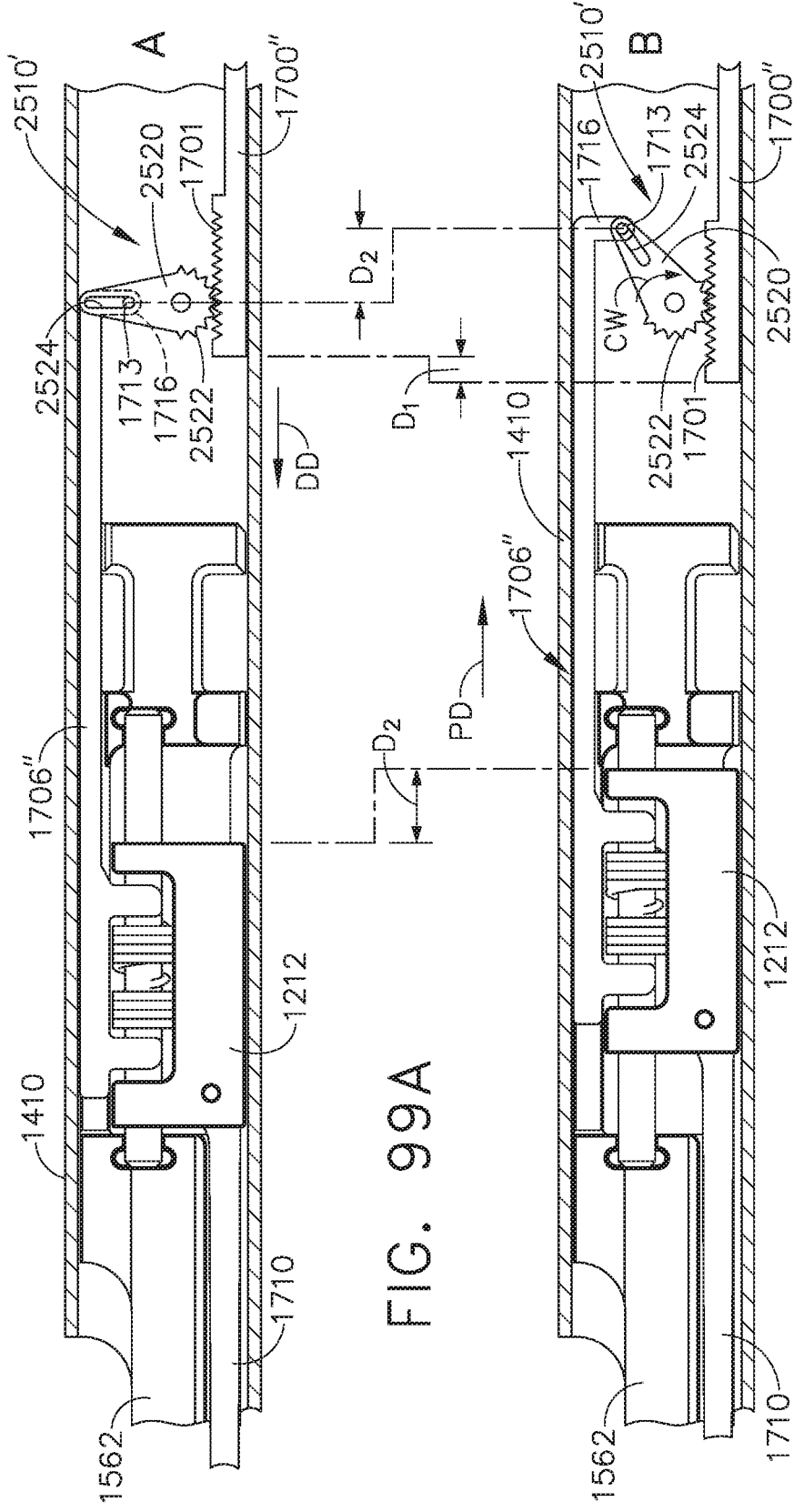

| END EFFECTOR | SHORT LABEL | LONG LABEL | |
|---|---|---|---|
| #1 | E 45 | E 60 | ← 4104 |
| #2 | W 45 | W 60 | ← 4108 |
| #3 | A 40 | A 55 | ← 4112 |

FIG. 114

| END EFFECTOR | SHORT LABEL | LONG LABEL | |
|---|---|---|---|
| #1 | [45] | [60] | ← 4134 |
| #2 | △45 | △60 | ← 4138 |
| #3 | (40) | (55) | ← 4142 |

FIG. 115

SURGICAL STAPLING SYSTEMS

CROSS-REFERENCE TO RELATED APPLICATION

This application is a continuation application claiming priority under 35 U.S.C. § 120 to U.S. patent application Ser. No. 15/385,916, entitled SURGICAL STAPLING SYSTEMS, filed Dec. 21, 2016, now U.S. Patent Application Publication No. 2018/0168575, the entire disclosure of which is hereby incorporated by reference herein.

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 92 is another top cross-sectional view of the interchangeable surgical tool assembly of FIG. 91 with the surgical end effector thereof in an articulated configuration and the articulation lock in an unlocked configuration;

FIG. 93 is a partial cross-sectional view of the articulation lock of FIG. 92 taken along line 93-93 in FIG. 92;

FIG. 98A is a top view of portions of the articulation stroke multiplier embodiment of FIG. 96 in an unactuated configuration;

FIG. 98B is another top view of the portions of the articulation stroke multiplier of FIG. 98A after application of an axial articulation motion thereto in a first axial direction;

FIG. 98C is another top view of the portions of the articulation stroke multiplier of FIG. 98A after application of another axial articulation motion thereto in a second axial direction;

FIG. 99A is a top cross-sectional view of portions of a shaft assembly of an interchangeable surgical tool assembly embodiment with another articulation stroke multiplier embodiment in an unactuated configuration;

FIG. 99B is another top cross-sectional view of the shaft assembly and articulation stroke multiplier of FIG. 99A after an axial articulation motion has been applied thereto in a first axial direction;

FIG. 111 is a perspective view of a portion of a staple cartridge;

FIG. 112 is a perspective view of a portion of a staple cartridge;

FIG. 113 is a perspective view of an end effector; and

FIGS. 114 and 115 depict tables of identifications for different types of end effectors.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
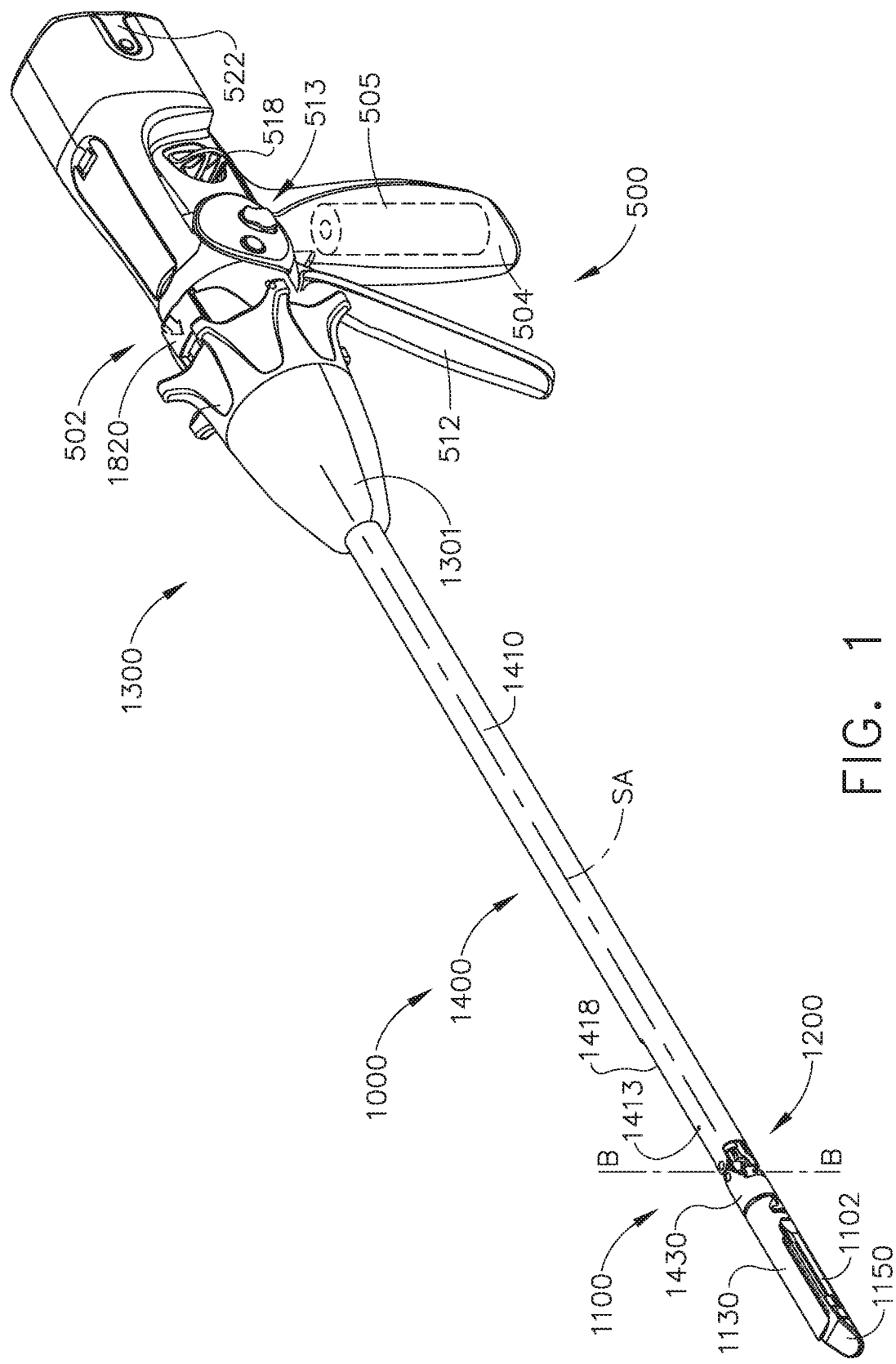
FIG. 1 is a perspective view of an interchangeable surgical tool assembly embodiment that is operably coupled to a handle assembly embodiment.

Applicant of the present application owns the following U.S. patent applications that were filed on Dec. 21, 2016 and which are each herein incorporated by reference in their respective entireties:

U.S. patent application Ser. No. 15/386,185, entitled SURGICAL STAPLING INSTRUMENTS AND REPLACEABLE TOOL ASSEMBLIES THEREOF;

U.S. patent application Ser. No. 15/386,221, entitled LOCKOUT ARRANGEMENTS FOR SURGICAL END EFFECTORS;

U.S. patent application Ser. No. 15/386,209, entitled SURGICAL END EFFECTORS AND FIRING MEMBERS THEREOF;

U.S. patent application Ser. No. 15/386,198, entitled LOCKOUT ARRANGEMENTS FOR SURGICAL END EFFECTORS AND REPLACEABLE TOOL ASSEMBLIES; and U.S. patent application Ser. No. 15/386,240, entitled SURGICAL END EFFECTORS AND ADAPTABLE FIRING MEMBERS THEREFOR.

Applicant of the present application owns the following U.S. patent applications that were filed on Dec. 21, 2016 and which are each herein incorporated by reference in their respective entireties:

U.S. patent application Ser. No. 15/385,939, entitled STAPLE CARTRIDGES AND ARRANGEMENTS OF STAPLES AND STAPLE CAVITIES THEREIN;

U.S. patent application Ser. No. 15/385,941, entitled SURGICAL TOOL ASSEMBLIES WITH CLUTCHING ARRANGEMENTS FOR SHIFTING BETWEEN CLOSURE SYSTEMS WITH CLOSURE STROKE REDUCTION FEATURES AND ARTICULATION AND FIRING SYSTEMS;

U.S. patent application Ser. No. 15/385,943, entitled SURGICAL STAPLING INSTRUMENTS AND STAPLE-FORMING ANVILS;

U.S. patent application Ser. No. 15/385,950, entitled SURGICAL TOOL ASSEMBLIES WITH CLOSURE STROKE REDUCTION FEATURES;

U.S. patent application Ser. No. 15/385,945, entitled STAPLE CARTRIDGES AND ARRANGEMENTS OF STAPLES AND STAPLE CAVITIES THEREIN;

U.S. patent application Ser. No. 15/385,946, entitled SURGICAL STAPLING INSTRUMENTS AND STAPLE-FORMING ANVILS;

U.S. patent application Ser. No. 15/385,951, entitled SURGICAL INSTRUMENTS WITH JAW OPENING FEATURES FOR INCREASING A JAW OPENING DISTANCE;

U.S. patent application Ser. No. 15/385,953, entitled METHODS OF STAPLING TISSUE;

U.S. patent application Ser. No. 15/385,954, entitled FIRING MEMBERS WITH NON-PARALLEL JAW ENGAGEMENT FEATURES FOR SURGICAL END EFFECTORS;

U.S. patent application Ser. No. 15/385,955, entitled SURGICAL END EFFECTORS WITH EXPANDABLE TISSUE STOP ARRANGEMENTS;

U.S. patent application Ser. No. 15/385,948, entitled SURGICAL STAPLING INSTRUMENTS AND STAPLE-FORMING ANVILS;

U.S. patent application Ser. No. 15/385,956, entitled SURGICAL INSTRUMENTS WITH POSITIVE JAW OPENING FEATURES;

U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT; and U.S. patent application Ser. No. 15/385,947, entitled STAPLE CARTRIDGES AND ARRANGEMENTS OF STAPLES AND STAPLE CAVITIES THEREIN.

Applicant of the present application owns the following U.S. patent applications that were filed on Dec. 21, 2016 and which are each herein incorporated by reference in their respective entireties:

U.S. patent application Ser. No. 15/385,896, entitled METHOD FOR RESETTING A FUSE OF A SURGICAL INSTRUMENT SHAFT;

U.S. patent application Ser. No. 15/385,898, entitled STAPLE FORMING POCKET ARRANGEMENT TO ACCOMMODATE DIFFERENT TYPES OF STAPLES;

U.S. patent application Ser. No. 15/385,899, entitled SURGICAL INSTRUMENT COMPRISING IMPROVED JAW CONTROL;

U.S. patent application Ser. No. 15/385,901, entitled STAPLE CARTRIDGE AND STAPLE CARTRIDGE CHANNEL COMPRISING WINDOWS DEFINED THEREIN;

U.S. patent application Ser. No. 15/385,902, entitled SURGICAL INSTRUMENT COMPRISING A CUTTING MEMBER;

U.S. patent application Ser. No. 15/385,904, entitled STAPLE FIRING MEMBER COMPRISING A MISSING CARTRIDGE AND/OR SPENT CARTRIDGE LOCKOUT;

U.S. patent application Ser. No. 15/385,905, entitled FIRING ASSEMBLY COMPRISING A LOCKOUT;

U.S. patent application Ser. No. 15/385,907, entitled SURGICAL INSTRUMENT SYSTEM COMPRISING AN END EFFECTOR LOCKOUT AND A FIRING ASSEMBLY LOCKOUT;

U.S. patent application Ser. No. 15/385,908, entitled FIRING ASSEMBLY COMPRISING A FUSE; and U.S. patent application Ser. No. 15/385,909, entitled FIRING ASSEMBLY COMPRISING A MULTIPLE FAILED-STATE FUSE.

Applicant of the present application owns the following U.S. patent applications that were filed on Dec. 21, 2016 and which are each herein incorporated by reference in their respective entireties:

U.S. patent application Ser. No. 15/385,920, entitled STAPLE FORMING POCKET ARRANGEMENTS;

U.S. patent application Ser. No. 15/385,913, entitled ANVIL ARRANGEMENTS FOR SURGICAL STAPLERS;

U.S. patent application Ser. No. 15/385,914, entitled METHOD OF DEFORMING STAPLES FROM TWO DIFFERENT TYPES OF STAPLE CARTRIDGES WITH THE SAME SURGICAL STAPLING INSTRUMENT;

U.S. patent application Ser. No. 15/385,893, entitled BILATERALLY ASYMMETRIC STAPLE FORMING POCKET PAIRS;

U.S. patent application Ser. No. 15/385,929, entitled CLOSURE MEMBERS WITH CAM SURFACE ARRANGEMENTS FOR SURGICAL INSTRUMENTS WITH SEPARATE AND DISTINCT CLOSURE AND FIRING SYSTEMS;

U.S. patent application Ser. No. 15/385,911, entitled SURGICAL STAPLERS WITH INDEPENDENTLY ACTUATABLE CLOSING AND FIRING SYSTEMS;

U.S. patent application Ser. No. 15/385,927, entitled SURGICAL STAPLING INSTRUMENTS WITH SMART STAPLE CARTRIDGES;

U.S. patent application Ser. No. 15/385,917, entitled STAPLE CARTRIDGE COMPRISING STAPLES WITH DIFFERENT CLAMPING BREADTHS;

U.S. patent application Ser. No. 15/385,900, entitled STAPLE FORMING POCKET ARRANGEMENTS COMPRISING PRIMARY SIDEWALLS AND POCKET SIDEWALLS;

U.S. patent application Ser. No. 15/385,931, entitled NO-CARTRIDGE AND SPENT CARTRIDGE LOCKOUT ARRANGEMENTS FOR SURGICAL STAPLERS;

U.S. patent application Ser. No. 15/385,915, entitled FIRING MEMBER PIN ANGLE;

U.S. patent application Ser. No. 15/385,897, entitled STAPLE FORMING POCKET ARRANGEMENTS COMPRISING ZONED FORMING SURFACE GROOVES;

U.S. patent application Ser. No. 15/385,922, entitled SURGICAL INSTRUMENT WITH MULTIPLE FAILURE RESPONSE MODES;

U.S. patent application Ser. No. 15/385,924, entitled SURGICAL INSTRUMENT WITH PRIMARY AND SAFETY PROCESSORS;

U.S. patent application Ser. No. 15/385,912, entitled SURGICAL INSTRUMENTS WITH JAWS THAT ARE PIVOTABLE ABOUT A FIXED AXIS AND INCLUDE SEPARATE AND DISTINCT CLOSURE AND FIRING SYSTEMS;

U.S. patent application Ser. No. 15/385,910, entitled ANVIL HAVING A KNIFE SLOT WIDTH;

U.S. patent application Ser. No. 15/385,903, entitled CLOSURE MEMBER ARRANGEMENTS FOR SURGICAL INSTRUMENTS; and U.S. patent application Ser. No. 15/385,906, entitled FIRING MEMBER PIN CONFIGURATIONS.

Applicant of the present application owns the following U.S. patent applications that were filed on Dec. 21, 2016 and which are each herein incorporated by reference in their respective entireties:

U.S. patent application Ser. No. 15/386,188, entitled STEPPED STAPLE CARTRIDGE WITH ASYMMETRICAL STAPLES;

U.S. patent application Ser. No. 15/386,192, entitled STEPPED STAPLE CARTRIDGE WITH TISSUE RETENTION AND GAP SETTING FEATURES;

U.S. patent application Ser. No. 15,386,206, entitled STAPLE CARTRIDGE WITH DEFORMABLE DRIVER RETENTION FEATURES;

U.S. patent application Ser. No. 15/386,226, entitled DURABILITY FEATURES FOR END EFFECTORS AND FIRING ASSEMBLIES OF SURGICAL STAPLING INSTRUMENTS;

U.S. patent application Ser. No. 15/386,222, entitled SURGICAL STAPLING INSTRUMENTS HAVING END EFFECTORS WITH POSITIVE OPENING FEATURES; and U.S. patent application Ser. No. 15/386,236, entitled CONNECTION PORTIONS FOR DISPOSABLE LOADING UNITS FOR SURGICAL STAPLING INSTRUMENTS.

Applicant of the present application owns the following U.S. patent applications that were filed on Dec. 21, 2016 and which are each herein incorporated by reference in their respective entireties:

U.S. patent application Ser. No. 15/385,887, entitled METHOD FOR ATTACHING A SHAFT ASSEMBLY TO A SURGICAL INSTRUMENT AND, ALTERNATIVELY, TO A SURGICAL ROBOT;

U.S. patent application Ser. No. 15/385,889, entitled SHAFT ASSEMBLY COMPRISING A MANUALLY-OPERABLE RETRACTION SYSTEM FOR USE WITH A MOTORIZED SURGICAL INSTRUMENT SYSTEM;

U.S. patent application Ser. No. 15/385,890, entitled SHAFT ASSEMBLY COMPRISING SEPARATELY ACTUATABLE AND RETRACTABLE SYSTEMS;

U.S. patent application Ser. No. 15/385,891, entitled SHAFT ASSEMBLY COMPRISING A CLUTCH CONFIGURED TO ADAPT THE OUTPUT OF A ROTARY FIRING MEMBER TO TWO DIFFERENT SYSTEMS;

U.S. patent application Ser. No. 15/385,892, entitled SURGICAL SYSTEM COMPRISING A FIRING MEMBER ROTATABLE INTO AN ARTICULATION STATE TO ARTICULATE AN END EFFECTOR OF THE SURGICAL SYSTEM;

U.S. patent application Ser. No. 15/385,894, entitled SHAFT ASSEMBLY COMPRISING A LOCKOUT; and U.S. patent application Ser. No. 15/385,895, entitled SHAFT ASSEMBLY COMPRISING FIRST AND SECOND ARTICULATION LOCKOUTS.

Applicant of the present application owns the following U.S. patent applications that were filed on Dec. 21, 2016 and which are each herein incorporated by reference in their respective entireties:

U.S. patent application Ser. No. 15/385,918, entitled SURGICAL STAPLING SYSTEMS;

U.S. patent application Ser. No. 15/385,919, entitled SURGICAL STAPLING SYSTEMS;

U.S. patent application Ser. No. 15/385,921, entitled SURGICAL STAPLE CARTRIDGE WITH MOVABLE CAMMING MEMBER CONFIGURED TO DISENGAGE FIRING MEMBER LOCKOUT FEATURES;

U.S. patent application Ser. No. 15/385,923, entitled SURGICAL STAPLING SYSTEMS;

U.S. patent application Ser. No. 15/385,925, entitled JAW ACTUATED LOCK ARRANGEMENTS FOR PREVENTING ADVANCEMENT OF A FIRING MEMBER IN A SURGICAL END EFFECTOR UNLESS AN UNFIRED CARTRIDGE IS INSTALLED IN THE END EFFECTOR;

U.S. patent application Ser. No. 15/385,926, entitled AXIALLY MOVABLE CLOSURE SYSTEM ARRANGEMENTS FOR APPLYING CLOSURE MOTIONS TO JAWS OF SURGICAL INSTRUMENTS;

U.S. patent application Ser. No. 15/385,928, entitled PROTECTIVE COVER ARRANGEMENTS FOR A JOINT INTERFACE BETWEEN A MOVABLE JAW AND ACTUATOR SHAFT OF A SURGICAL INSTRUMENT;

U.S. patent application Ser. No. 15/385,930, entitled SURGICAL END EFFECTOR WITH TWO SEPARATE COOPERATING OPENING FEATURES FOR OPENING AND CLOSING END EFFECTOR JAWS;

U.S. patent application Ser. No. 15/385,932, entitled ARTICULATABLE SURGICAL END EFFECTOR WITH ASYMMETRIC SHAFT ARRANGEMENT;

U.S. patent application Ser. No. 15/385,933, entitled ARTICULATABLE SURGICAL INSTRUMENT WITH INDEPENDENT PIVOTABLE LINKAGE DISTAL OF AN ARTICULATION LOCK;

U.S. patent application Ser. No. 15/385,934, entitled ARTICULATION LOCK ARRANGEMENTS FOR LOCKING AN END EFFECTOR IN AN ARTICULATED POSITION IN RESPONSE TO ACTUATION OF A JAW CLOSURE SYSTEM;

U.S. patent application Ser. No. 15/385,935, entitled LATERALLY ACTUATABLE ARTICULATION LOCK ARRANGEMENTS FOR LOCKING AN END EFFECTOR OF A SURGICAL INSTRUMENT IN AN ARTICULATED CONFIGURATION; and U.S. patent application Ser. No. 15/385,936, entitled ARTICULATABLE SURGICAL INSTRUMENTS WITH ARTICULATION STROKE AMPLIFICATION FEATURES.

Applicant of the present application owns the following U.S. patent applications that were filed on Jun. 24, 2016 and which are each herein incorporated by reference in their respective entireties:

U.S. patent application Ser. No. 15/191,775, entitled STAPLE CARTRIDGE COMPRISING WIRE STAPLES AND STAMPED STAPLES;

U.S. patent application Ser. No. 15/191,807, entitled STAPLING SYSTEM FOR USE WITH WIRE STAPLES AND STAMPED STAPLES;

U.S. patent application Ser. No. 15/191,834, entitled STAMPED STAPLES AND STAPLE CARTRIDGES USING THE SAME;

U.S. patent application Ser. No. 15/191,788, entitled STAPLE CARTRIDGE COMPRISING OVERDRIVEN STAPLES; and U.S. patent application Ser. No. 15/191,818, entitled STAPLE CARTRIDGE COMPRISING OFFSET LONGITUDINAL STAPLE ROWS.

Applicant of the present application owns the following U.S. patent applications that were filed on Jun. 24, 2016 and which are each herein incorporated by reference in their respective entireties:

U.S. Design patent application Ser. No. 29/569,218, entitled SURGICAL FASTENER;

U.S. Design patent application Ser. No. 29/569,227, entitled SURGICAL FASTENER;

U.S. Design patent application Ser. No. 29/569,259, entitled SURGICAL FASTENER CARTRIDGE; and U.S. Design patent application Ser. No. 29/569,264, entitled SURGICAL FASTENER CARTRIDGE.

Applicant of the present application owns the following patent applications that were filed on Apr. 1, 2016 and which are each herein incorporated by reference in their respective entireties:

U.S. patent application Ser. No. 15/089,325, entitled METHOD FOR OPERATING A SURGICAL STAPLING SYSTEM;

U.S. patent application Ser. No. 15/089,321, entitled MODULAR SURGICAL STAPLING SYSTEM COMPRISING A DISPLAY;

U.S. patent application Ser. No. 15/089,326, entitled SURGICAL STAPLING SYSTEM COMPRISING A DISPLAY INCLUDING A RE-ORIENTABLE DISPLAY FIELD;

U.S. patent application Ser. No. 15/089,263, entitled SURGICAL INSTRUMENT HANDLE ASSEMBLY WITH RECONFIGURABLE GRIP PORTION;

U.S. patent application Ser. No. 15/089,262, entitled ROTARY POWERED SURGICAL INSTRUMENT WITH MANUALLY ACTUATABLE BAILOUT SYSTEM;

U.S. patent application Ser. No. 15/089,277, entitled SURGICAL CUTTING AND STAPLING END EFFECTOR WITH ANVIL CONCENTRIC DRIVE MEMBER;

U.S. patent application Ser. No. 15/089,296, entitled INTERCHANGEABLE SURGICAL TOOL ASSEMBLY WITH A SURGICAL END EFFECTOR THAT IS SELECTIVELY ROTATABLE ABOUT A SHAFT AXIS;

U.S. patent application Ser. No. 15/089,258, entitled SURGICAL STAPLING SYSTEM COMPRISING A SHIFTABLE TRANSMISSION;

U.S. patent application Ser. No. 15/089,278, entitled SURGICAL STAPLING SYSTEM CONFIGURED TO PROVIDE SELECTIVE CUTTING OF TISSUE;

U.S. patent application Ser. No. 15/089,284, entitled SURGICAL STAPLING SYSTEM COMPRISING A CONTOURABLE SHAFT;

U.S. patent application Ser. No. 15/089,295, entitled SURGICAL STAPLING SYSTEM COMPRISING A TISSUE COMPRESSION LOCKOUT;

U.S. patent application Ser. No. 15/089,300, entitled SURGICAL STAPLING SYSTEM COMPRISING AN UNCLAMPING LOCKOUT;

U.S. patent application Ser. No. 15/089,196, entitled SURGICAL STAPLING SYSTEM COMPRISING A JAW CLOSURE LOCKOUT;

U.S. patent application Ser. No. 15/089,203, entitled SURGICAL STAPLING SYSTEM COMPRISING A JAW ATTACHMENT LOCKOUT;

U.S. patent application Ser. No. 15/089,210, entitled SURGICAL STAPLING SYSTEM COMPRISING A SPENT CARTRIDGE LOCKOUT;

U.S. patent application Ser. No. 15/089,324, entitled SURGICAL INSTRUMENT COMPRISING A SHIFTING MECHANISM;

U.S. patent application Ser. No. 15/089,335, entitled SURGICAL STAPLING INSTRUMENT COMPRISING MULTIPLE LOCKOUTS;

U.S. patent application Ser. No. 15/089,339, entitled SURGICAL STAPLING INSTRUMENT;

U.S. patent application Ser. No. 15/089,253, entitled SURGICAL STAPLING SYSTEM CONFIGURED TO APPLY ANNULAR ROWS OF STAPLES HAVING DIFFERENT HEIGHTS;

U.S. patent application Ser. No. 15/089,304, entitled SURGICAL STAPLING SYSTEM COMPRISING A GROOVED FORMING POCKET;

U.S. patent application Ser. No. 15/089,331, entitled ANVIL MODIFICATION MEMBERS FOR SURGICAL STAPLERS;

U.S. patent application Ser. No. 15/089,336, entitled STAPLE CARTRIDGES WITH ATRAUMATIC FEATURES;

U.S. patent application Ser. No. 15/089,312, entitled CIRCULAR STAPLING SYSTEM COMPRISING AN INCISABLE TISSUE SUPPORT;

U.S. patent application Ser. No. 15/089,309, entitled CIRCULAR STAPLING SYSTEM COMPRISING ROTARY FIRING SYSTEM; and U.S. patent application Ser. No. 15/089,349, entitled CIRCULAR STAPLING SYSTEM COMPRISING LOAD CONTROL.

Applicant of the present application also owns the U.S. patent applications identified below which were filed on Dec. 31, 2015 which are each herein incorporated by reference in their respective entireties:

U.S. patent application Ser. No. 14/984,488, entitled MECHANISMS FOR COMPENSATING FOR BATTERY PACK FAILURE IN POWERED SURGICAL INSTRUMENTS;

U.S. patent application Ser. No. 14/984,525, entitled MECHANISMS FOR COMPENSATING FOR DRIVETRAIN FAILURE IN POWERED SURGICAL INSTRUMENTS; and U.S. patent application Ser. No. 14/984,552, entitled SURGICAL INSTRUMENTS WITH SEPARABLE MOTORS AND MOTOR CONTROL CIRCUITS.

Applicant of the present application also owns the U.S. patent applications identified below which were filed on Feb. 9, 2016 which are each herein incorporated by reference in their respective entireties:

U.S. patent application Ser. No. 15/019,220, entitled SURGICAL INSTRUMENT WITH ARTICULATING AND AXIALLY TRANSLATABLE END EFFECTOR;

U.S. patent application Ser. No. 15/019,228, entitled SURGICAL INSTRUMENTS WITH MULTIPLE LINK ARTICULATION ARRANGEMENTS;

U.S. patent application Ser. No. 15/019,196, entitled SURGICAL INSTRUMENT ARTICULATION MECHANISM WITH SLOTTED SECONDARY CONSTRAINT;

U.S. patent application Ser. No. 15/019,206, entitled SURGICAL INSTRUMENTS WITH AN END EFFECTOR THAT IS HIGHLY ARTICULATABLE RELATIVE TO AN ELONGATE SHAFT ASSEMBLY;

U.S. patent application Ser. No. 15/019,215, entitled SURGICAL INSTRUMENTS WITH NON-SYMMETRICAL ARTICULATION ARRANGEMENTS;

U.S. patent application Ser. No. 15/019,227, entitled ARTICULATABLE SURGICAL INSTRUMENTS WITH SINGLE ARTICULATION LINK ARRANGEMENTS;

U.S. patent application Ser. No. 15/019,235, entitled SURGICAL INSTRUMENTS WITH TENSIONING ARRANGEMENTS FOR CABLE DRIVEN ARTICULATION SYSTEMS;

U.S. patent application Ser. No. 15/019,230, entitled ARTICULATABLE SURGICAL INSTRUMENTS WITH OFF-AXIS FIRING BEAM ARRANGEMENTS; and U.S. patent application Ser. No. 15/019,245, entitled SURGICAL INSTRUMENTS WITH CLOSURE STROKE REDUCTION ARRANGEMENTS.

Applicant of the present application also owns the U.S. patent applications identified below which were filed on Feb. 12, 2016 which are each herein incorporated by reference in their respective entireties:

U.S. patent application Ser. No. 15/043,254, entitled MECHANISMS FOR COMPENSATING FOR DRIVETRAIN FAILURE IN POWERED SURGICAL INSTRUMENTS;

U.S. patent application Ser. No. 15/043,259, entitled MECHANISMS FOR COMPENSATING FOR DRIVETRAIN FAILURE IN POWERED SURGICAL INSTRUMENTS;

U.S. patent application Ser. No. 15/043,275, entitled MECHANISMS FOR COMPENSATING FOR DRIVETRAIN FAILURE IN POWERED SURGICAL INSTRUMENTS; and U.S. patent application Ser. No. 15/043,289, entitled MECHANISMS FOR COMPENSATING FOR DRIVETRAIN FAILURE IN POWERED SURGICAL INSTRUMENTS.

Applicant of the present application owns the following patent applications that were filed on Jun. 18, 2015 and which are each herein incorporated by reference in their respective entireties:

U.S. patent application Ser. No. 14/742,925, entitled SURGICAL END EFFECTORS WITH POSITIVE JAW OPENING ARRANGEMENTS;

U.S. patent application Ser. No. 14/742,941, entitled SURGICAL END EFFECTORS WITH DUAL CAM ACTUATED JAW CLOSING FEATURES;

U.S. patent application Ser. No. 14/742,914, entitled MOVABLE FIRING BEAM SUPPORT ARRANGEMENTS FOR ARTICULATABLE SURGICAL INSTRUMENTS;

U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT;

U.S. patent application Ser. No. 14/742,885, entitled DUAL ARTICULATION DRIVE SYSTEM ARRANGEMENTS FOR ARTICULATABLE SURGICAL INSTRUMENTS; and U.S. patent application Ser. No. 14/742,876, entitled PUSH/PULL ARTICULATION DRIVE SYSTEMS FOR ARTICULATABLE SURGICAL INSTRUMENTS.

Applicant of the present application owns the following patent applications that were filed on Mar. 6, 2015 and which are each herein incorporated by reference in their respective entireties:

U.S. patent application Ser. No. 14/640,746, entitled POWERED SURGICAL INSTRUMENT, now U.S. Patent Application Publication No. 2016/0256184;

U.S. patent application Ser. No. 14/640,795, entitled MULTIPLE LEVEL THRESHOLDS TO MODIFY OPERATION OF POWERED SURGICAL INSTRUMENTS, now U.S. Patent Application Publication No. 2016/02561185;

U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Patent Application Publication No. 2016/0256154;

U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Patent Application Publication No. 2016/0256071;

U.S. patent application Ser. No. 14/640,831, entitled MONITORING SPEED CONTROL AND PRECISION INCREMENTING OF MOTOR FOR POWERED SURGICAL INSTRUMENTS, now U.S. Patent Application Publication No. 2016/0256153;

U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Patent Application Publication No. 2016/0256187;

U.S. patent application Ser. No. 14/640,817, entitled INTERACTIVE FEEDBACK SYSTEM FOR POWERED SURGICAL INSTRUMENTS, now U.S. Patent Application Publication No. 2016/0256186;

U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Patent Application Publication No. 2016/0256155;

U.S. patent application Ser. No. 14/640,837, entitled SMART SENSORS WITH LOCAL SIGNAL PROCESSING, now U.S. Patent Application Publication No. 2016/0256163;

U.S. patent application Ser. No. 14/640,765, entitled SYSTEM FOR DETECTING THE MIS-INSERTION OF A STAPLE CARTRIDGE INTO A SURGICAL STAPLER, now U.S. Patent Application Publication No. 2016/0256160;

U.S. patent application Ser. No. 14/640,799, entitled SIGNAL AND POWER COMMUNICATION SYSTEM POSITIONED ON A ROTATABLE SHAFT, now U.S. Patent Application Publication No. 2016/0256162; and U.S. patent application Ser. No. 14/640,780, entitled SURGICAL INSTRUMENT COMPRISING A LOCKABLE BATTERY HOUSING, now U.S. Patent Application Publication No. 2016/0256161.

Applicant of the present application owns the following patent applications that were filed on Feb. 27, 2015, and which are each herein incorporated by reference in their respective entireties:

U.S. patent application Ser. No. 14/633,576, entitled SURGICAL INSTRUMENT SYSTEM COMPRISING AN INSPECTION STATION, now U.S. Patent Application Publication No. 2016/0249919;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Patent Application Publication No. 2016/0249915;

U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910;

U.S. patent application Ser. No. 14/633,566, entitled CHARGING SYSTEM THAT ENABLES EMERGENCY RESOLUTIONS FOR CHARGING A BATTERY, now U.S. Patent Application Publication No. 2016/0249918;

U.S. patent application Ser. No. 14/633,555, entitled SYSTEM FOR MONITORING WHETHER A SURGICAL INSTRUMENT NEEDS TO BE SERVICED, now U.S. Patent Application Publication No. 2016/0249916;

U.S. patent application Ser. No. 14/633,542, entitled REINFORCED BATTERY FOR A SURGICAL INSTRUMENT, now U.S. Patent Application Publication No. 2016/0249908;

U.S. patent application Ser. No. 14/633,548, entitled POWER ADAPTER FOR A SURGICAL INSTRUMENT, now U.S. Patent Application Publication No. 2016/0249909;

U.S. patent application Ser. No. 14/633,526, entitled ADAPTABLE SURGICAL INSTRUMENT HANDLE, now U.S. Patent Application Publication No. 2016/0249945;

U.S. patent application Ser. No. 14/633,541, entitled MODULAR STAPLING ASSEMBLY, now U.S. Patent Application Publication No. 2016/0249927; and U.S. patent application Ser. No. 14/633,562, entitled SURGICAL APPARATUS CONFIGURED TO TRACK AN END-OF-LIFE PARAMETER, now U.S. Patent Application Publication No. 2016/0249917.

Applicant of the present application owns the following patent applications that were filed on Dec. 18, 2014 and which are each herein incorporated by reference in their respective entireties:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER, now U.S. Patent Application Publication No. 2016/0174977;

U.S. patent application Ser. No. 14/574,483, entitled SURGICAL INSTRUMENT ASSEMBLY COMPRISING LOCKABLE SYSTEMS, now U.S. Patent Application Publication No. 2016/0174969;

U.S. patent application Ser. No. 14/575,139, entitled DRIVE ARRANGEMENTS FOR ARTICULATABLE SURGICAL INSTRUMENTS, now U.S. Patent Application Publication No. 2016/0174978;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Patent Application Publication No. 2016/0174976;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Patent Application Publication No. 2016/0174972;

U.S. patent application Ser. No. 14/575,143, entitled SURGICAL INSTRUMENTS WITH IMPROVED CLOSURE ARRANGEMENTS, now U.S. Patent Application Publication No. 2016/0174983;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Patent Application Publication No. 2016/0174975;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Patent Application Publication No. 2016/0174973;

U.S. patent application Ser. No. 14/574,493, entitled SURGICAL INSTRUMENT ASSEMBLY COMPRISING A FLEXIBLE ARTICULATION SYSTEM, now U.S. Patent Application Publication No. 2016/0174970; and U.S. patent application Ser. No. 14/574,500, entitled SURGICAL INSTRUMENT ASSEMBLY COMPRISING A LOCKABLE ARTICULATION SYSTEM, now U.S. Patent Application Publication No. 2016/0174971.

Applicant of the present application owns the following patent applications that were filed on Mar. 1, 2013 and which are each herein incorporated by reference in their respective entireties:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Patent Application Publication No. 2014/0246471;

U.S. patent application Ser. No. 13/782,323, entitled ROTARY POWERED ARTICULATION JOINTS FOR SURGICAL INSTRUMENTS, now U.S. Patent Application Publication No. 2014/0246472;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Patent Application Publication No. 2014/0246478;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entireties:

U.S. patent application Ser. No. 13/803,097, entitled ARTICULATABLE SURGICAL INSTRUMENT COMPRISING A FIRING DRIVE, now U.S. Patent Application Publication No. 2014/0263542;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Patent Application Publication No. 2014/0263564;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Patent Application Publication No. 2014/0263538;

U.S. patent application Ser. No. 13/803,148, entitled MULTI-FUNCTION MOTOR FOR A SURGICAL INSTRUMENT, now U.S. Patent Application Publication No. 2014/0263554;

U.S. patent application Ser. No. 13/803,066, entitled DRIVE SYSTEM LOCKOUT ARRANGEMENTS FOR MODULAR SURGICAL INSTRUMENTS, now U.S. Patent Application Publication No. 2014/0263565;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Patent Application Publication No. 2014/0277017.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Patent Application Publication No. 2014/0263539.

Applicant of the present application also owns the following patent applications that were filed on Mar. 26, 2014 and are each herein incorporated by reference in their respective entireties:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Patent Application Publication No. 2015/0272581;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Patent Application Publication No. 2015/0272574;

U.S. patent application Ser. No. 14/226,075, entitled MODULAR POWERED SURGICAL INSTRUMENT WITH DETACHABLE SHAFT ASSEMBLIES, now U.S. Patent Application Publication No. 2015/0272579;

U.S. patent application Ser. No. 14/226,093, entitled FEEDBACK ALGORITHMS FOR MANUAL BAILOUT SYSTEMS FOR SURGICAL INSTRUMENTS, now U.S. Patent Application Publication No. 2015/0272569;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Patent Application Publication No. 2015/0272578;

U.S. patent application Ser. No. 14/226,097, entitled SURGICAL INSTRUMENT COMPRISING INTERACTIVE SYSTEMS, now U.S. Patent Application Publication No. 2015/0272570;

U.S. patent application Ser. No. 14/226,126, entitled INTERFACE SYSTEMS FOR USE WITH SURGICAL INSTRUMENTS, now U.S. Patent Application Publication No. 2015/0272572;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Patent Application Publication No. 2015/0277471;

U.S. patent application Ser. No. 14/226,076, entitled POWER MANAGEMENT THROUGH SEGMENTED CIRCUIT AND VARIABLE VOLTAGE PROTECTION, now U.S. Patent Application Publication No. 2015/0280424;

U.S. patent application Ser. No. 14/226,111, entitled SURGICAL STAPLING INSTRUMENT SYSTEM, now U.S. Patent Application Publication No. 2015/0272583; and U.S. patent application Ser. No. 14/226,125, entitled SURGICAL INSTRUMENT COMPRISING A ROTATABLE SHAFT, now U.S. Patent Application Publication No. 2015/0280384.

Applicant of the present application also owns the following patent applications that were filed on Sep. 5, 2014 and which are each herein incorporated by reference in their respective entireties:

U.S. patent application Ser. No. 14/479,103, entitled CIRCUITRY AND SENSORS FOR POWERED MEDICAL DEVICE, now U.S. Patent Application Publication No. 2016/0066912;

U.S. patent application Ser. No. 14/479,119, entitled ADJUNCT WITH INTEGRATED SENSORS TO QUANTIFY TISSUE COMPRESSION, now U.S. Patent Application Publication No. 2016/0066914;

U.S. patent application Ser. No. 14/478,908, entitled MONITORING DEVICE DEGRADATION BASED ON COMPONENT EVALUATION, now U.S. Patent Application Publication No. 2016/0066910;

U.S. patent application Ser. No. 14/478,895, entitled MULTIPLE SENSORS WITH ONE SENSOR AFFECTING A SECOND SENSOR'S OUTPUT OR INTERPRETATION, now U.S. Patent Application Publication No. 2016/0066909;

U.S. patent application Ser. No. 14/479,110, entitled POLARITY OF HALL MAGNET TO DETECT MISLOADED CARTRIDGE, now U.S. Patent Application Publication No. 2016/0066915;

U.S. patent application Ser. No. 14/479,098, entitled SMART CARTRIDGE WAKE UP OPERATION AND DATA RETENTION, now U.S. Patent Application Publication No. 2016/0066911;

U.S. patent application Ser. No. 14/479,115, entitled MULTIPLE MOTOR CONTROL FOR POWERED MEDICAL DEVICE, now U.S. Patent Application Publication No. 2016/0066916; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entireties:

U.S. patent application Ser. No. 14/248,590, entitled MOTOR DRIVEN SURGICAL INSTRUMENTS WITH LOCKABLE DUAL DRIVE SHAFTS, now U.S. Patent Application Publication No. 2014/0305987;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Patent Application Publication No. 2014/0305989;

U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Patent Application Publication No. 2014/0305988;

U.S. patent application Ser. No. 14/248,588, entitled POWERED LINEAR SURGICAL STAPLER, now U.S. Patent Application Publication No. 2014/0309666;

U.S. patent application Ser. No. 14/248,591, entitled TRANSMISSION ARRANGEMENT FOR A SURGICAL INSTRUMENT, now U.S. Patent Application Publication No. 2014/0305991;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Patent Application Publication No. 2014/0305994;

U.S. patent application Ser. No. 14/248,587, entitled POWERED SURGICAL STAPLER, now U.S. Patent Application Publication No. 2014/0309665;

U.S. patent application Ser. No. 14/248,586, entitled DRIVE SYSTEM DECOUPLING ARRANGEMENT FOR A SURGICAL INSTRUMENT, now U.S. Patent Application Publication No. 2014/0305990; and U.S. patent application Ser. No. 14/248,607, entitled MODULAR MOTOR DRIVEN SURGICAL INSTRUMENTS WITH STATUS INDICATION ARRANGEMENTS, now U.S. Patent Application Publication No. 2014/0305992.

Applicant of the present application also owns the following patent applications that were filed on Apr. 16, 2013 and which are each herein incorporated by reference in their respective entireties:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

FIG. 1 depicts one form of an interchangeable surgical tool assembly 1000 that is operably coupled to a motor driven handle assembly 500. The interchangeable surgical tool assembly 1000 may also be effectively employed with a tool drive assembly of a robotically controlled or automated surgical system. For example, the surgical tool assemblies disclosed herein may be employed with various robotic systems, instruments, components and methods such as, but not limited to, those disclosed in U.S. Pat. No. 9,072,535, entitled SURGICAL STAPLING INSTRUMENTS WITH ROTATABLE STAPLE DEPLOYMENT ARRANGEMENTS, which is hereby incorporated by reference herein in its entirety. The handle assembly 500, as well as the tool drive assembly of a robotic system may also be referred to herein as "control systems" or "control units".

Figure 2:
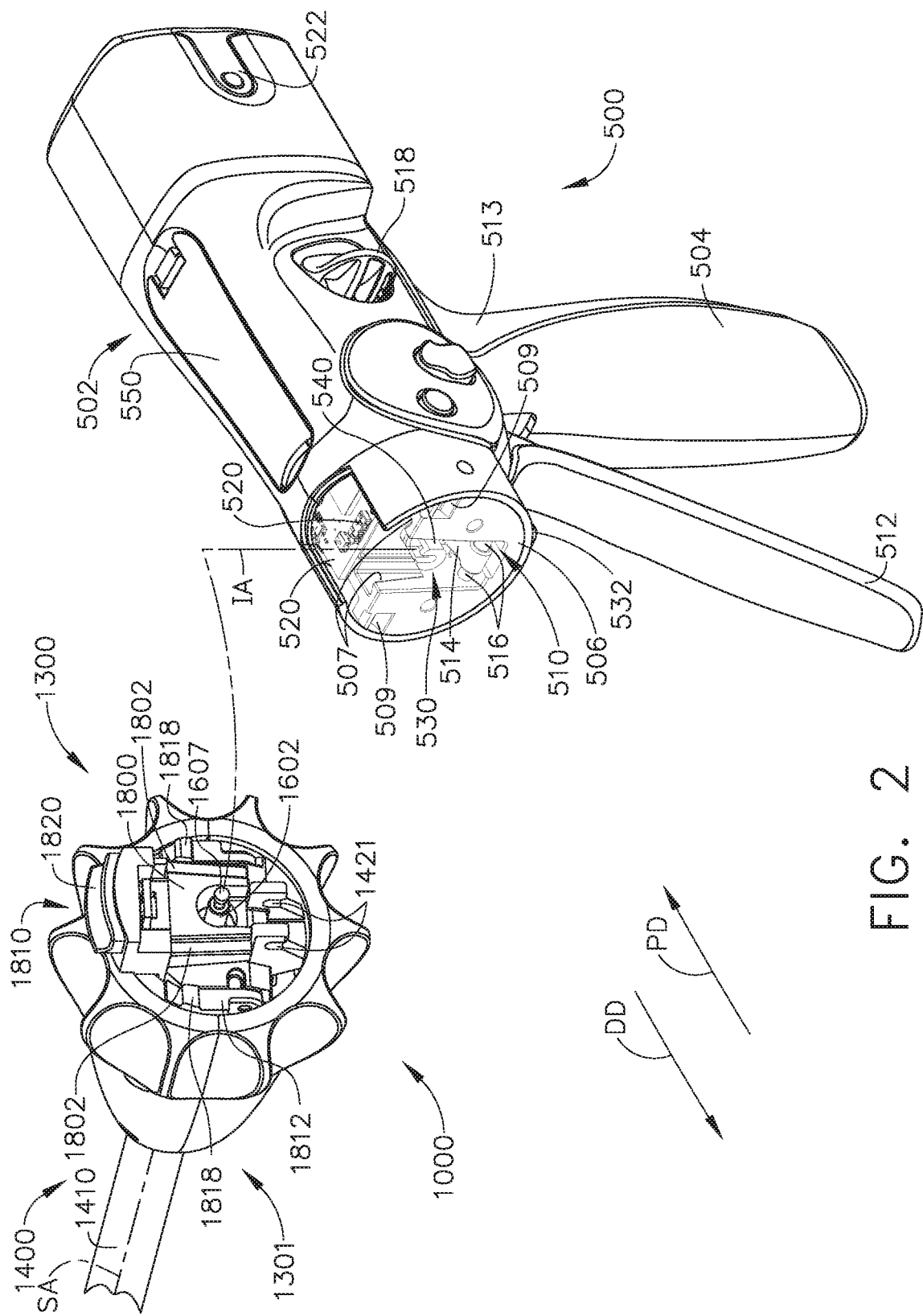
FIG. 2 is an exploded assembly view of portions of the handle assembly and interchangeable surgical tool assembly of FIG. 1.

FIG. 2 illustrates attachment of the interchangeable surgical tool assembly 1000 to the handle assembly 500. The handle assembly 500 may comprise a handle housing 502 that includes a pistol grip portion 504 that can be gripped and manipulated by the clinician. The handle assembly 500 may further include a frame 506 that operably supports the plurality of drive systems. For example, the frame 506 can operably support a "first" or closure drive system, generally designated as 510, which may be employed to apply closing and opening motions to the interchangeable surgical tool assembly 1000 that is operably attached or coupled to the handle assembly 500. In at least one form, the closure drive system 510 may include an actuator in the form of a closure trigger 512 that is pivotally supported by the frame 506. Such arrangement enables the closure trigger 512 to be manipulated by a clinician such that when the clinician grips the pistol grip portion 504 of the handle assembly 500, the closure trigger 512 may be easily pivoted from a starting or "unactuated" position to an "actuated" position and more particularly to a fully compressed or fully actuated position. In various forms, the closure drive system 510 further includes a closure linkage assembly 514 that is pivotally coupled to the closure trigger 512 or otherwise operably interfaces therewith. As will be discussed in further detail below, in the illustrated example, the closure linkage assembly 514 includes a transverse attachment pin 516 that facilitates attachment to a corresponding drive system on the surgical tool assembly. In use, to actuate the closure drive system 510, the clinician depresses the closure trigger 512 towards the pistol grip portion 504. As described in further detail in U.S. patent application Ser. No. 14/226,142, entitled SURGICAL INSTRUMENT COMPRISING A SENSOR SYSTEM, now U.S. Patent Application Publication No. 2015/0272575, which is hereby incorporated by reference in its entirety herein, when the clinician fully depresses the closure trigger 512 to attain a "full" closure stroke, the closure drive system 510 is configured to lock the closure trigger 512 into the fully depressed or fully actuated position. When the clinician desires to unlock the closure trigger 512 to permit it to be biased to the unactuated position, the clinician simply activates a closure release button assembly 518 which enables the closure trigger 512 to return to the unactuated position. The closure release button assembly 518 may also be configured to interact with various sensors that communicate with a microcontroller 520 in the handle assembly 500 for tracking the position of the closure trigger 512. Further details concerning the configuration and operation of the closure release button assembly 518 may be found in U.S. Patent Application Publication No. 2015/0272575.

In at least one form, the handle assembly 500 and the frame 506 may operably support another drive system referred to herein as a firing drive system 530 that is configured to apply axial or firing motions to corresponding portions of the interchangeable surgical tool assembly that is attached thereto. As was described in detail in U.S. Patent Application Publication No. 2015/0272575, the firing drive system 530 may employ an electric motor 505 that is located in the pistol grip portion 504 of the handle assembly 500. In various forms, the motor 505 may be a DC brushed driving motor having a maximum rotation of, approximately, 25,000 RPM, for example. In other arrangements, the motor 505 may include a brushless motor, a cordless motor, a synchronous motor, a stepper motor, or any other suitable electric motor. The motor 505 may be powered by a power source 522 that in one form may comprise a removable power pack. The power pack may support a plurality of Lithium Ion ("LI") or other suitable batteries therein. A number of batteries may be connected in series may be used as the power source 522 for the handle assembly 500. In addition, the power source 522 may be replaceable and/or rechargeable.

The electric motor 505 is configured to axially drive a longitudinally movable drive member 540 in distal and proximal directions depending upon the polarity of the motor. For example, when the motor 505 is driven in one rotary direction, the longitudinally movable drive member 540 will be axially driven in the distal direction "DD". When the motor 505 is driven in the opposite rotary direction, the longitudinally movable drive member 540 will be axially driven in a proximal direction "PD". The handle assembly 500 can include a switch 513 which can be configured to reverse the polarity applied to the electric motor 505 by the power source 522 or otherwise control the motor 505. The handle assembly 500 can also include a sensor or sensors (not shown) that is configured to detect the position of the drive member 540 and/or the direction in which the drive member 540 is being moved. Actuation of the motor 505 can be controlled by a firing trigger 532 that is pivotally supported on the handle assembly 500. The firing trigger 532 may be pivoted between an unactuated position and an actuated position. The firing trigger 532 may be biased into the unactuated position by a spring (not shown) or other biasing arrangement such that when the clinician releases the firing trigger 532, it may be pivoted or otherwise returned to the unactuated position by the spring or biasing arrangement. In at least one form, the firing trigger 532 can be positioned "outboard" of the closure trigger 512 as was discussed above. As discussed in U.S. Patent Application Publication No. 2015/0272575, the handle assembly 500 may be equipped with a firing trigger safety button (not shown) to prevent inadvertent actuation of the firing trigger 532. When the closure trigger 512 is in the unactuated position, the safety button is contained in the handle assembly 500 where the clinician cannot readily access it and move it between a safety position preventing actuation of the firing trigger 532 and a firing position wherein the firing trigger 532 may be fired. As the clinician depresses the closure trigger 512, the safety button and the firing trigger 532 may pivot down wherein they can then be manipulated by the clinician.

In at least one form, the longitudinally movable drive member 540 may have a rack of teeth (not shown) formed thereon for meshing engagement with a corresponding drive gear arrangement (not shown) that interfaces with the motor 505. Further details regarding those features may be found in U.S. Patent Application Publication No. 2015/0272575. At least one form also includes a manually-actuatable "bailout" assembly that is configured to enable the clinician to manually retract the longitudinally movable drive member 540 should the motor 505 become disabled. The bailout assembly may include a lever or bailout handle assembly that is stored within the handle assembly 500 under a releasable door 550. The lever is configured to be manually pivoted into ratcheting engagement with the teeth in the drive member 540. Thus, the clinician can manually retract the drive member 540 by using the bailout handle assembly to ratchet the drive member 540 in the proximal direction "PD". U.S. patent application Ser. No. 12/249,117, entitled POWERED SURGICAL CUTTING AND STAPLING APPARATUS WITH MANUALLY RETRACTABLE FIRING SYSTEM, now U.S. Patent Application Publication No. 2010/0089970, the entire disclosure of which is hereby incorporated by reference herein discloses bailout arrangements and other components, arrangements and systems that may also be employed with the tool assembly 1000.

Figure 3:
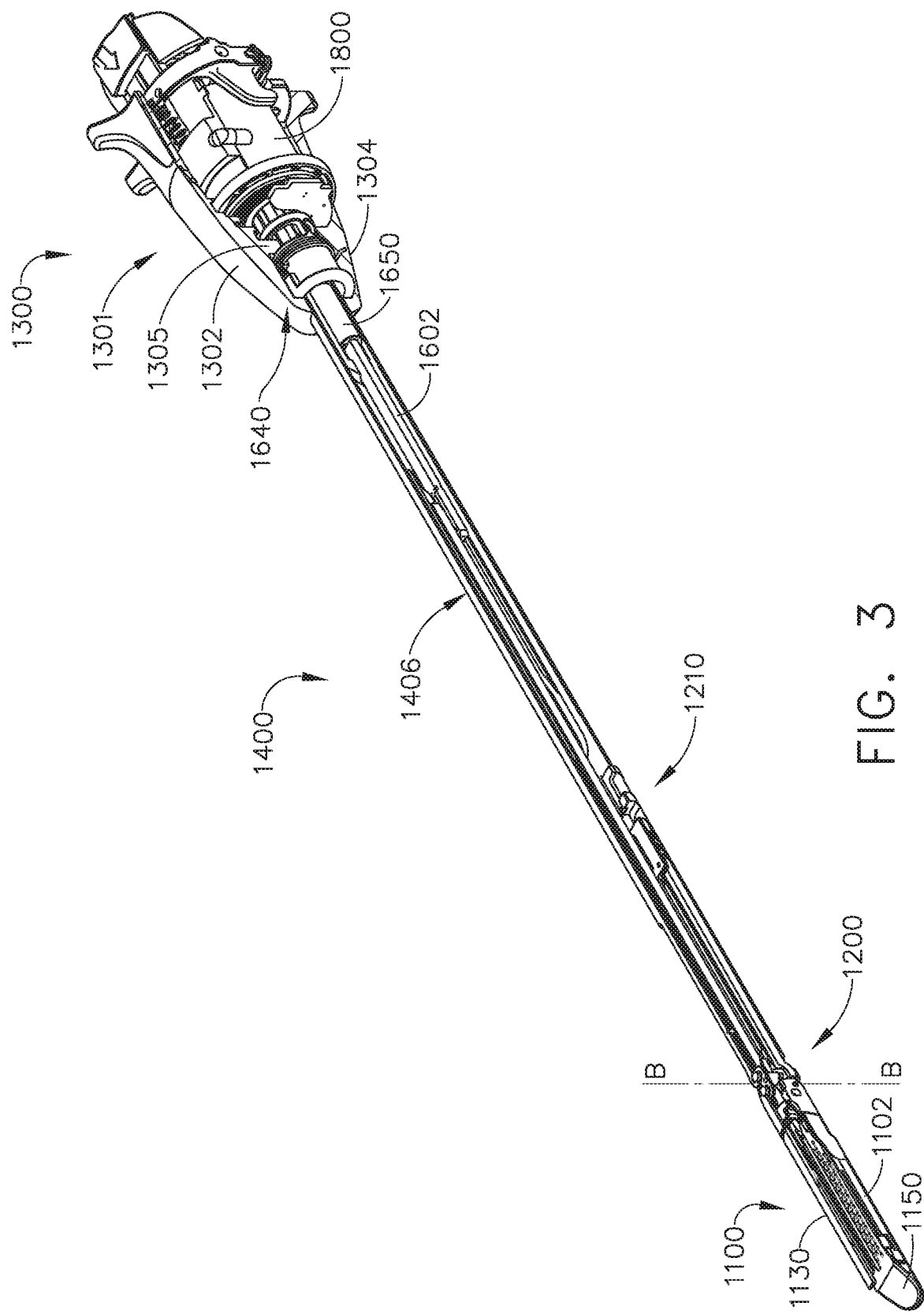
FIG. 3 is a perspective view of the interchangeable surgical tool assembly embodiment depicted in FIGS. 1 and 2 with portions thereof omitted for clarity.
Figure 5:
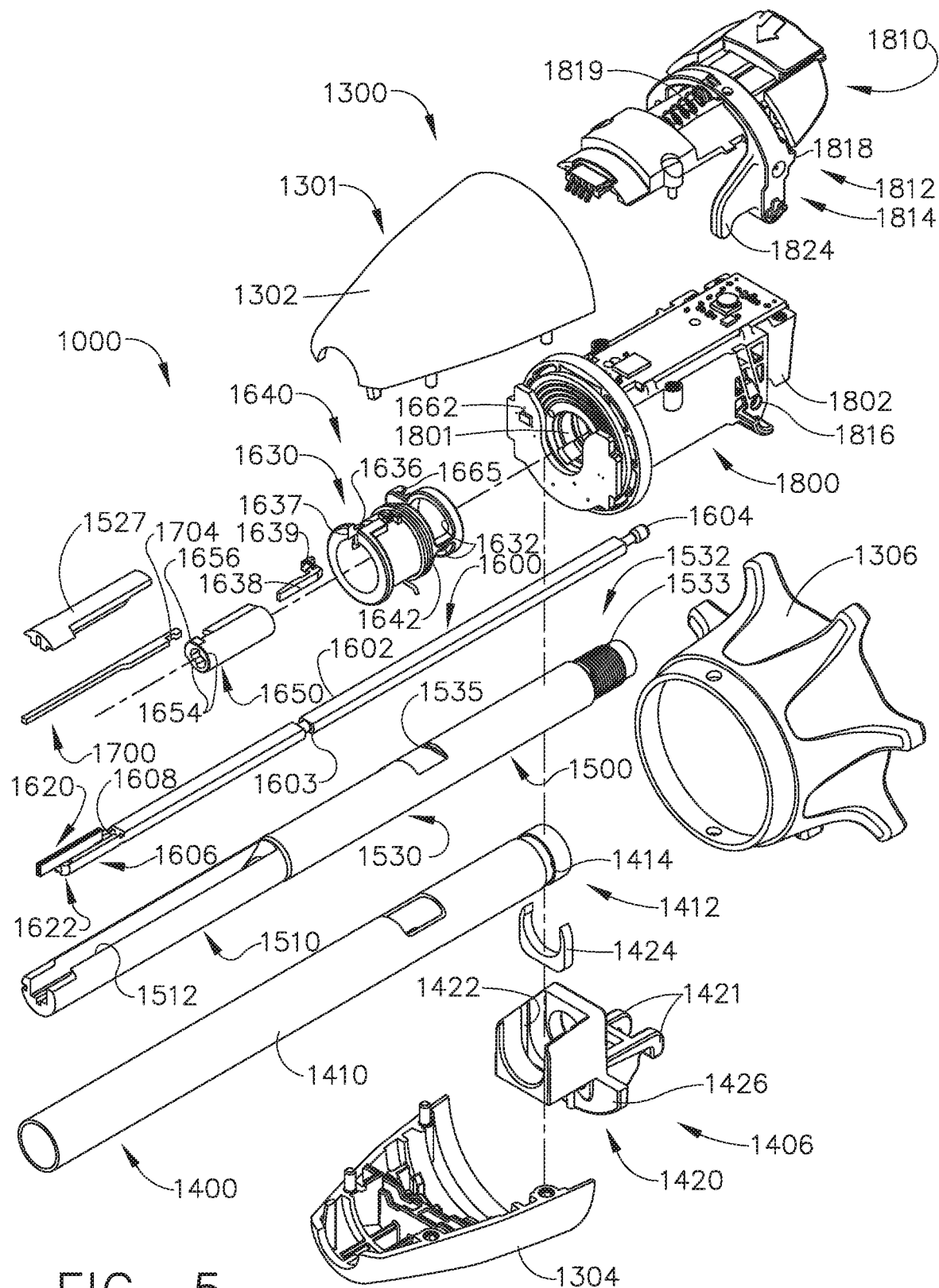
FIG. 5 is an exploded assembly view of proximal portions of the interchangeable surgical tool assembly of FIGS. 1-4.
Figure 6:
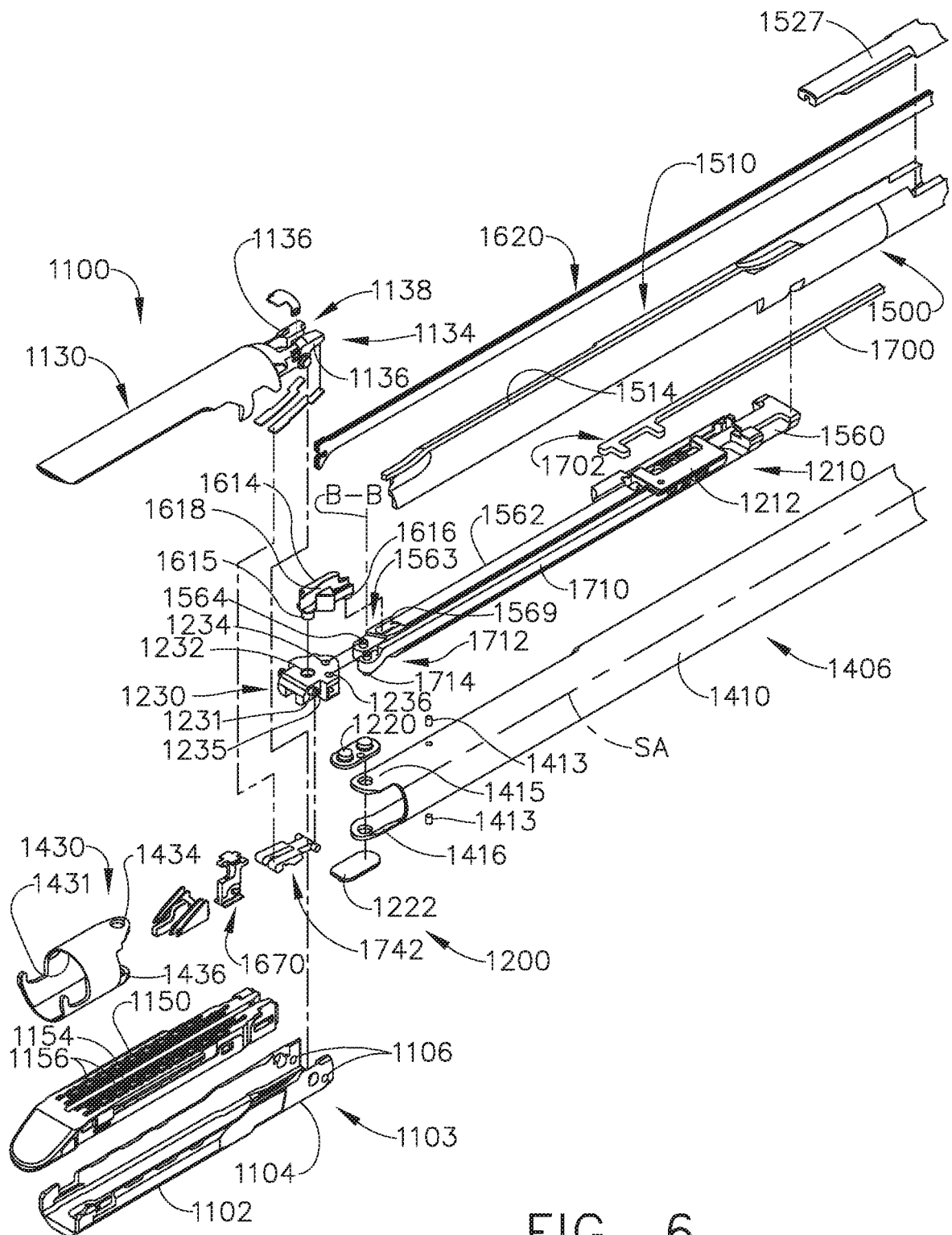
FIG. 6 is an exploded assembly view of distal portions of the interchangeable surgical tool assembly of FIGS. 1-5.

Turning now to FIGS. 5 and 6, the interchangeable surgical tool assembly 1000 includes a shaft mounting portion 1300 that is operably attached to an elongate shaft assembly 1400. A surgical end effector 1100 that comprises an elongate channel 1102 that is configured to operably support a surgical staple cartridge 1150 therein is operably attached to the elongate shaft assembly 1400. See FIGS. 3 and 6. The surgical end effector 1100 may further include an anvil 1130 that is pivotally supported relative to the elongate channel 1102. The elongate channel 1102 with a staple cartridge 1150 installed therein and the anvil 1130 may also be referred to as the end effector "jaws". The interchangeable surgical tool assembly 1000 may further include an articulation joint 1200 and an articulation lock 1210 (FIGS. 3 and 6) which can be configured to releasably hold the surgical end effector 1100 in a desired articulated position about an articulation axis B-B which is transverse to a shaft axis SA. Many details regarding the construction and operation of the articulation lock 1210 may be found in in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, the entire disclosure of which is hereby incorporated by reference herein. Additional details concerning the articulation lock 1210 may also be found in U.S. patent application Ser. No. 15/019,196, filed Feb. 9, 2016, entitled SURGICAL INSTRUMENT ARTICULATION MECHANISM WITH SLOTTED SECONDARY CONSTRAINT, the entire disclosure of which is hereby incorporated by reference herein.

As can be seen in FIGS. 5 and 6, the shaft mounting portion 1300 includes a proximal housing or nozzle 1301 comprised of nozzle portions 1302, 1304 as well as an actuator wheel portion 1306 that is configured to be coupled to the assembled nozzle portions 1302, 1304 by snaps, lugs, screws, etc. In the illustrated embodiment, the interchangeable surgical tool assembly 1000 further includes a closure assembly 1406 which can be utilized to close and/or open the anvil 1130 relative to the elongate channel 1102 of the surgical end effector 1100 as will be discussed in further detail below. In addition, the illustrated interchangeable surgical tool assembly 1000 includes a spine assembly 1500 which operably supports the articulation lock 1210. The spine assembly 1500 is configured to, one, slidably support a firing member assembly 1600 therein and, two, slidably support the closure assembly 1406 which extends around the spine assembly 1500 or is otherwise movably supported thereby.

In the illustrated arrangement, the surgical end effector 1100 is operably coupled to the elongate shaft assembly 1400 by an articulation joint 1200 that facilitates selective articulation of the surgical end effector 1100 about an articulation axis B-B that is transverse to the shaft axis SA. See FIG. 1. As can be seen in FIGS. 5 and 6, the spine assembly 1500 slidably supports a proximal articulation driver 1700 that operably interfaces with an articulation lock 1210. The articulation lock 1210 is supported on a distal frame segment 1560 that also comprises a portion of the spine assembly 1500. As can be seen in FIG. 6, the distal frame segment 1560 comprises a distal spine extension 1562 that is pivotally coupled to the elongate channel 1102 by an end effector mounting assembly 1230. In one arrangement, for example, a distal end 1563 of the distal frame segment 1560 has a spine attachment pin 1564 formed thereon. The spine attachment pin 1564 is adapted to be pivotally received within a spine attachment hole 1234 that is formed in the end effector mounting assembly 1230. See FIG. 6.

Referring again to FIG. 6, in the illustrated embodiment, the proximal articulation driver 1700 has a distal end 1702 that is configured to operably engage the articulation lock 1210. The articulation lock 1210 includes an articulation frame 1212 that is pivotally coupled or pinned to a distal articulation link 1710 that is also configured to be pivotally attached to the end effector mounting assembly 1230. In particular, as can be seen in FIG. 6, a distal end 1712 of the distal articulation link 1710 includes an articulation pin 1714 that is configured to be pivotally received within corresponding articulation holes 1236 in the end effector mounting assembly 1230. The distal articulation link 1710 is slidably supported by the distal spine extension 1562. The end effector mounting assembly 1230 is attached to a proximal end 1103 of the elongate channel 1102 by a spring pin connector 1235 that extends through a transverse mounting hole 1231 in the end effector mounting assembly 1230 to be received within channel or jaw mounting holes 1106 that are provided in the proximal end 1103 of the elongate channel 1102. The spine attachment pin 1564 defines an articulation axis B-B that is transverse to the shaft axis SA. Such arrangement facilitates pivotal travel (i.e., articulation) of the surgical end effector 1100 about the articulation axis B-B relative to the spine assembly 1500. As indicated above, further details regarding the operation of the articulation lock 1210 and the articulation frame 1212 may be found in U.S. patent application Ser. No. 13/803,086, now U.S. Patent Application Publication No. 2014/0263541.

In various circumstances, the spine assembly 1500 further comprises an intermediate spine segment 1510 that is attached to the distal frame segment 1560 of the articulation lock 1210. The spine assembly 1500 further comprises a proximal spine mounting segment 1530 that includes a proximal end portion 1532 that has opposing notches 1535 (only one can be seen in FIG. 5) for receiving a corresponding mounting lug 1308 (shown in FIG. 4) that protrude inwardly from each of the nozzle portions 1302, 1304. Such arrangement facilitates rotation of the proximal spine assembly 1500 about the shaft axis SA by rotating the nozzle 1301 about the shaft axis SA. The interchangeable surgical tool assembly 1000 includes a chassis 1800 that rotatably supports the shaft assembly 1400. The proximal end portion 1532 of the proximal spine mounting segment is rotatably supported in a central shaft hole 1801 that is formed in the chassis 1800. See FIG. 5. In one arrangement, for example, the proximal end portion 1532 has threads 1533 thereon for attachment to a spine bearing (not shown) or other wise supported in a spine bearing that is mounted within the chassis 1800. Such an arrangement facilitates rotatable attachment of the spine assembly 1500 to the chassis 1800 such that the spine assembly 1500 may be selectively rotated about a shaft axis SA relative to the chassis 1800.

The closure assembly 1406 comprises an elongate proximal closure member 1410 and a distal closure member 1430. In the illustrated arrangement, the proximal closure member 1410 comprises a hollow tubular member that is slidably supported on the spine assembly 1500. Hence, the proximal closure member 1410 may also be referred to herein as the "proximal closure tube". Similarly, the distal closure member 1430 may also be referred to as the "distal closure tube".

Referring primarily to FIG. 5, the interchangeable surgical tool assembly 1000 includes a closure shuttle 1420 that is slidably supported within the chassis 1800 such that it may be axially moved relative thereto. In one form, the closure shuttle 1420 includes a pair of proximally-protruding hooks 1421 that are configured for attachment to the transverse attachment pin 516 (FIG. 2) that is attached to the closure linkage assembly 514 of the handle assembly 500. Thus, when the hooks 1421 are hooked over the transverse attachment pin 516, actuation of the closure trigger 512 will result in the axial movement of the closure shuttle 1420 and ultimately, the closure assembly 1406 on the spine assembly 1500. A closure spring (not shown) may also be journaled on the closure assembly 1406 and serves to bias the closure assembly 1406 in the proximal direction "PD" which can serve to pivot the closure trigger 512 into the unactuated position when the surgical tool assembly 1000 is operably coupled to the handle assembly 500. In use, the closure assembly 1406 is translated distally (direction DD) to close the jaws 1130, 1102 for example, in response to the actuation of the closure trigger 512.

The closure linkage assembly 514 may also be referred to herein as a "closure actuator" and the closure linkage assembly 514 and the closure shuttle 1420 may be collectively referred to herein as a "closure actuator assembly". A proximal end 1412 of the proximal closure member 1410 is coupled to the closure shuttle 1420 for relative rotation thereto. For example, a U-shaped connector 1424 is inserted into an annular slot 1414 in the proximal end 1412 of the proximal closure member 1410 and is retained within vertical slots 1422 in the closure shuttle 1420. See FIG. 5. Such arrangement serves to attach the proximal closure member 1410 to the closure shuttle 1420 for axial travel therewith while enabling the closure assembly 1406 to rotate relative to the closure shuttle 1420 about the shaft axis SA.

As indicated above, the illustrated interchangeable surgical tool assembly 1000 includes an articulation joint 1200. As can be seen in FIG. 6, upper and lower tangs 1415, 1416 protrude distally from a distal end of the proximal closure member 1410 to be movably coupled to the distal closure member 1430. As can also be seen in FIG. 6, the distal closure member 1430 includes upper and lower tangs 1434, 1436 that protrude proximally from a proximal end thereof. The proximal closure member 1410 and the distal closure member 1430 are coupled together by an upper double pivot link 1220. The upper double pivot link 1220 includes proximal and distal pins that engage corresponding holes in the upper tangs 1415, 1434 of the proximal closure member 1410 and distal closure member 1430, respectively. The proximal closure member 1410 and the distal closure member 1430 are also coupled together by a lower double pivot link 1222. The lower double pivot link 1222 includes proximal and distal pins that engage corresponding holes in the lower tangs 1416 and 1436 of the proximal closure member 1410 and distal closure member 1430, respectively. As will be discussed in further detail below, distal and proximal axial translation of the closure assembly 1406 will result in the closing and opening of the anvil 1130.

The interchangeable surgical tool assembly 1000 depicted in FIGS. 1-6 includes a surgical end effector 1100 that is capable of articulating about the articulation axis B-B in one direction. As noted above, the articulation axis B-B is defined by the spine attachment pin 1564 that is rotatably received within the spine attachment hole 1234 that is formed in the end effector mounting assembly 1230. In the illustrated arrangement, the spine attachment hole 1234 may be transversely axially aligned with the shaft axis SA. In other arrangements, the spine attachment hole 1234 may be slightly laterally offset from the shaft axis. In the illustrated example, the articulation axis B-B is transverse to and intersects the shaft axis SA. The illustrated example only employs a proximal articulation driver 1700 that interfaces with a single distal articulation link 1710 (through the articulation lock 1210) that operably interfaces with the end effector mounting assembly 1230 to apply articulation motions thereto. For example, distally advancing the distal articulation link 1710 will cause the surgical end effector 1100 to articulate in a single "first" articulation direction. In one arrangement, for example, the surgical end effector 1100 may be selectively articulatable from a first unarticulated position wherein the surgical end effector 1100 is axially aligned with the shaft assembly 1400 (for insertion through a trocar or other access opening) through an articulation angle of approximately 110° (after the surgical end effector 1100 has exited the trocar into the patient). Other articulation angle arrangements may be achieved.

Figure 7:
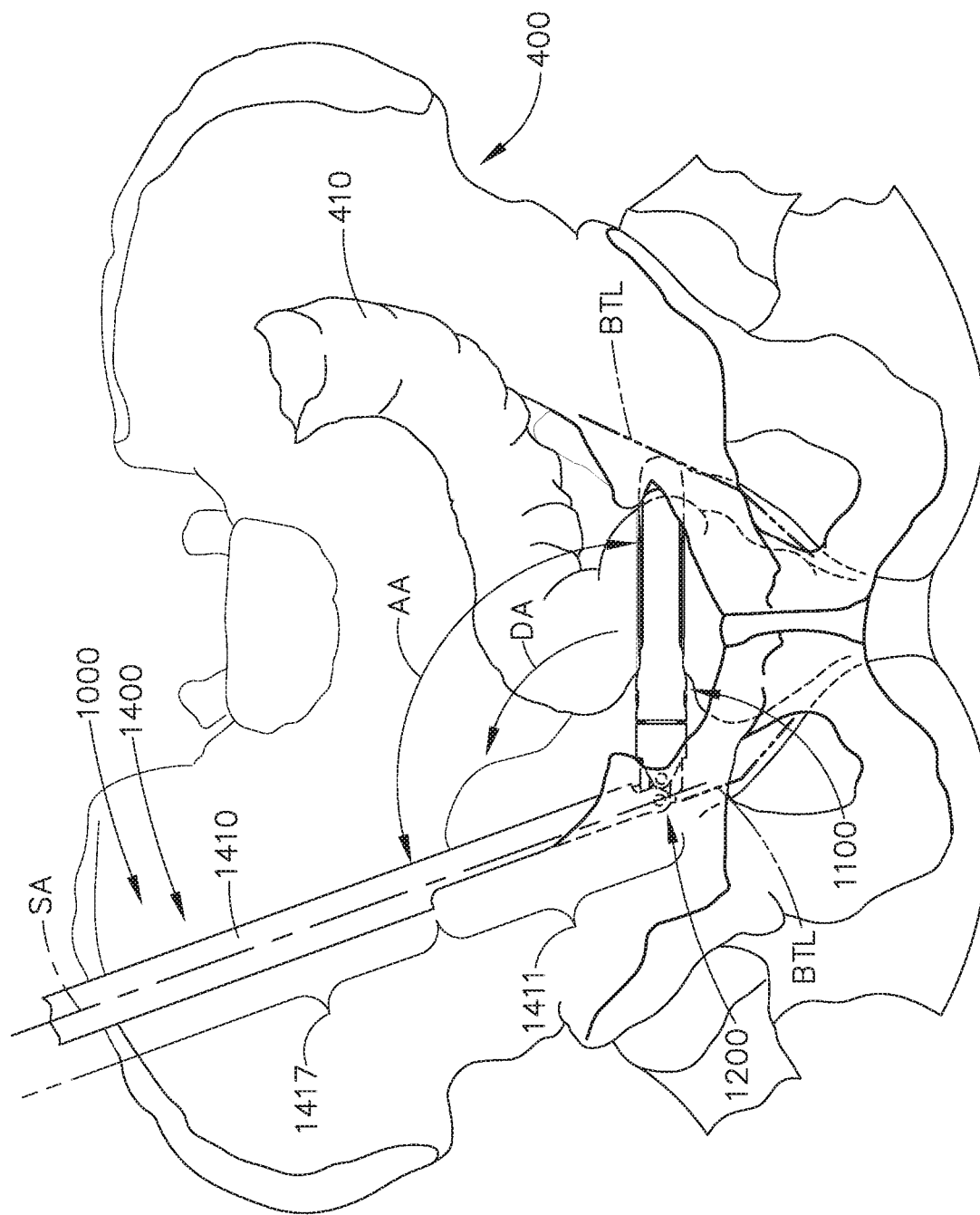
FIG. 7 illustrates use of an interchangeable surgical tool assembly embodiment to perform a medical procedure known as a lower anterior resection within a human pelvis area.

As can be seen in FIG. 7, for example, the interchangeable surgical tool assembly 1000 may be well-suited for use in connection with a medical procedure known as a lower anterior resection "LAR". Such procedure commonly involves removal of a diseased portion of the colon. For example, this procedure may comprise removal of the blood vessels and lymph nodes associated with this portion of the bowel. The surgeon then re-joins the remaining colon and the remaining part of the rectum (which may be referred to as an anastomosis). One challenge commonly facing the surgeon during this procedure is associated with getting the end effector into the pelvic area far enough to complete the procedure. FIG. 7 illustrates a desired position of the surgical end effector 1100 within the pelvis 400 of a patient during the resection of the patient's colon 410. Lines BTL in FIG. 7 may illustrate travel limits commonly created by the patient's pelvic bone structure and associated tissue. In the illustrated arrangement, the surgical tool assembly 1000 employs an "asymmetric" proximal closure member 1410 that is configured to provide additional clearance and maneuverability for the surgical tool assembly 1000 within that region.

Figure 8:
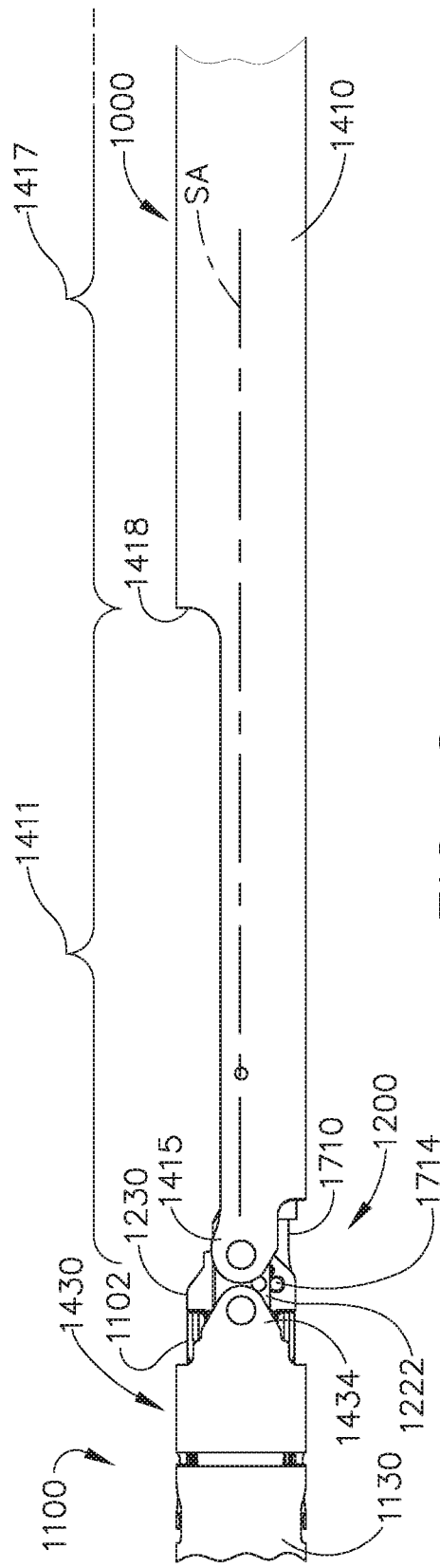
FIG. 8 is a top view of a portion of the interchangeable surgical tool assembly depicted in FIG. 7.
Figure 9:
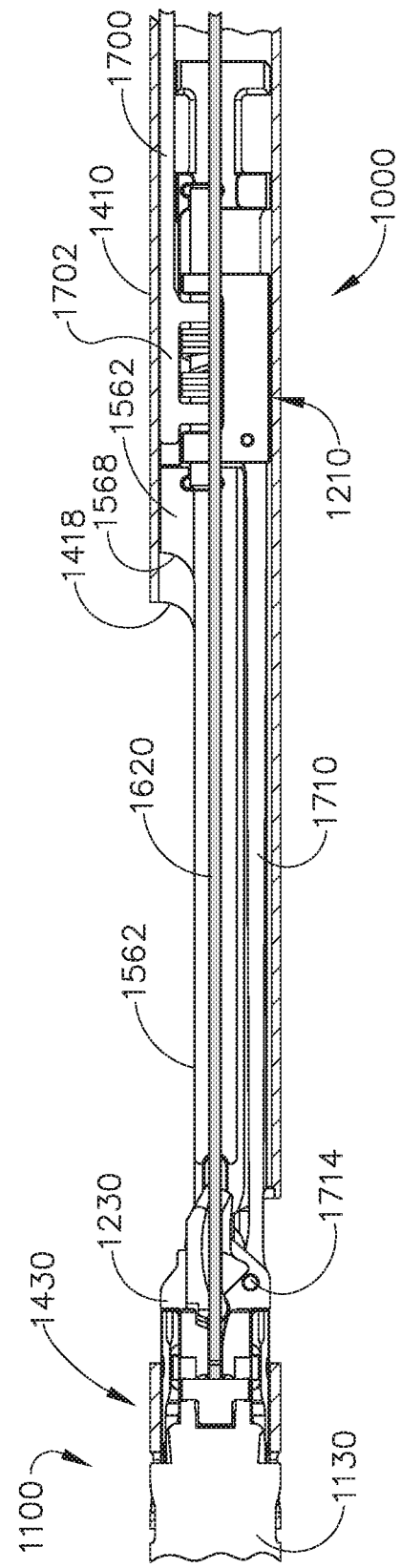
FIG. 9 is another top view of the interchangeable surgical tool assembly depicted in FIG. 8 with portions thereof shown in cross-section.

As can be seen in FIG. 7, in one example, the proximal closure member 1410 of the shaft assembly 1400 includes an elongate proximal end portion 1417 and an elongate distal end portion 1411 that extends from the proximal end portion 1417. As can be seen in FIGS. 7-9, to facilitate more clearance between the shaft assembly 1400 and the pelvic structure for example, an asymmetric cut out or notched area 1418 is provided in the distal end portion 1411 of the proximal closure member 1410. In at least one example, the notched area 1418 extends for the entire distal end portion 1411. In such arrangement, an axial length of the distal end portion is less than an axial length of the proximal end portion 1417.

Figure 10:
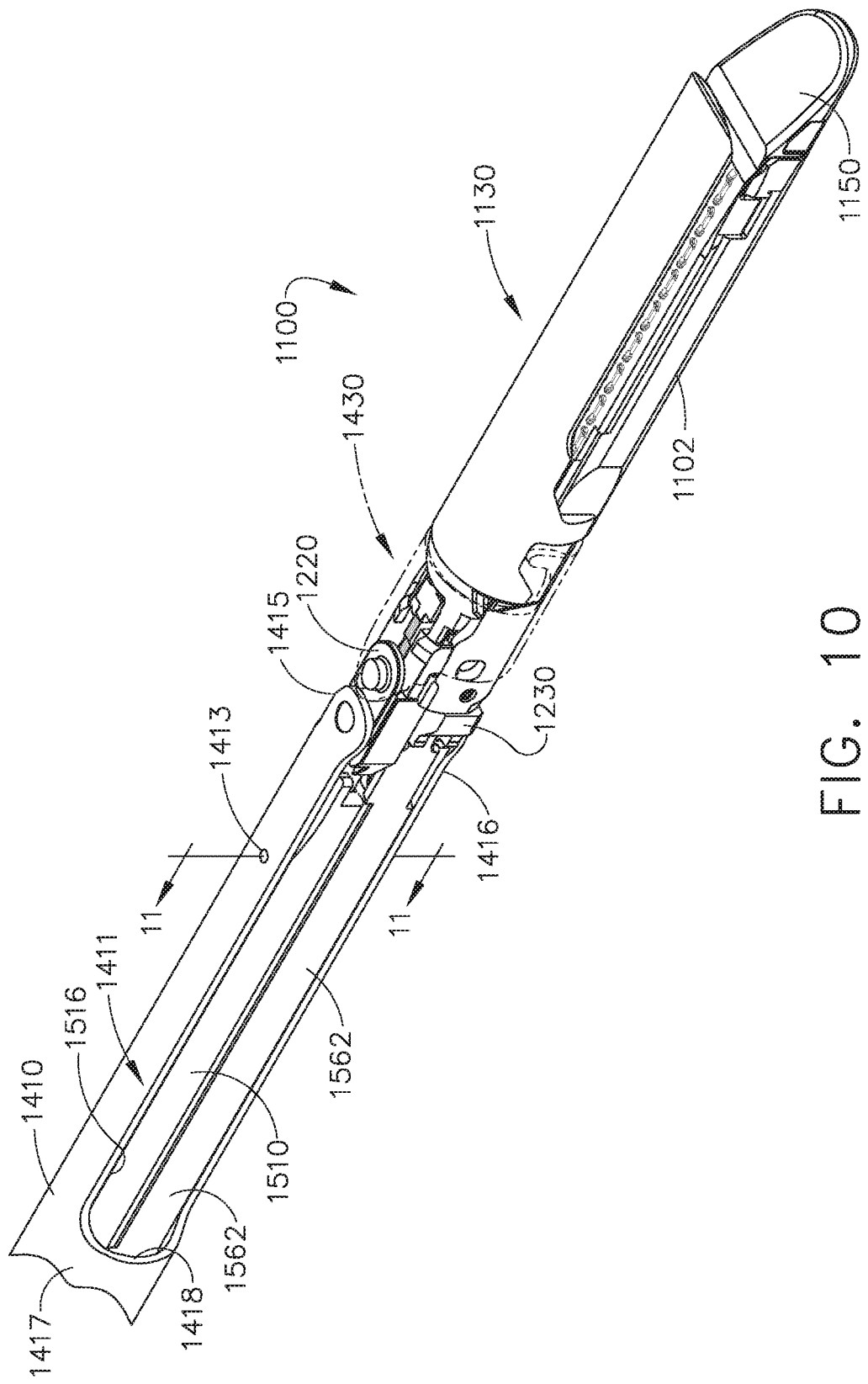
FIG. 10 is a partial perspective view of a distal portion of the interchangeable surgical tool assembly of FIG. 9.
Figure 11:
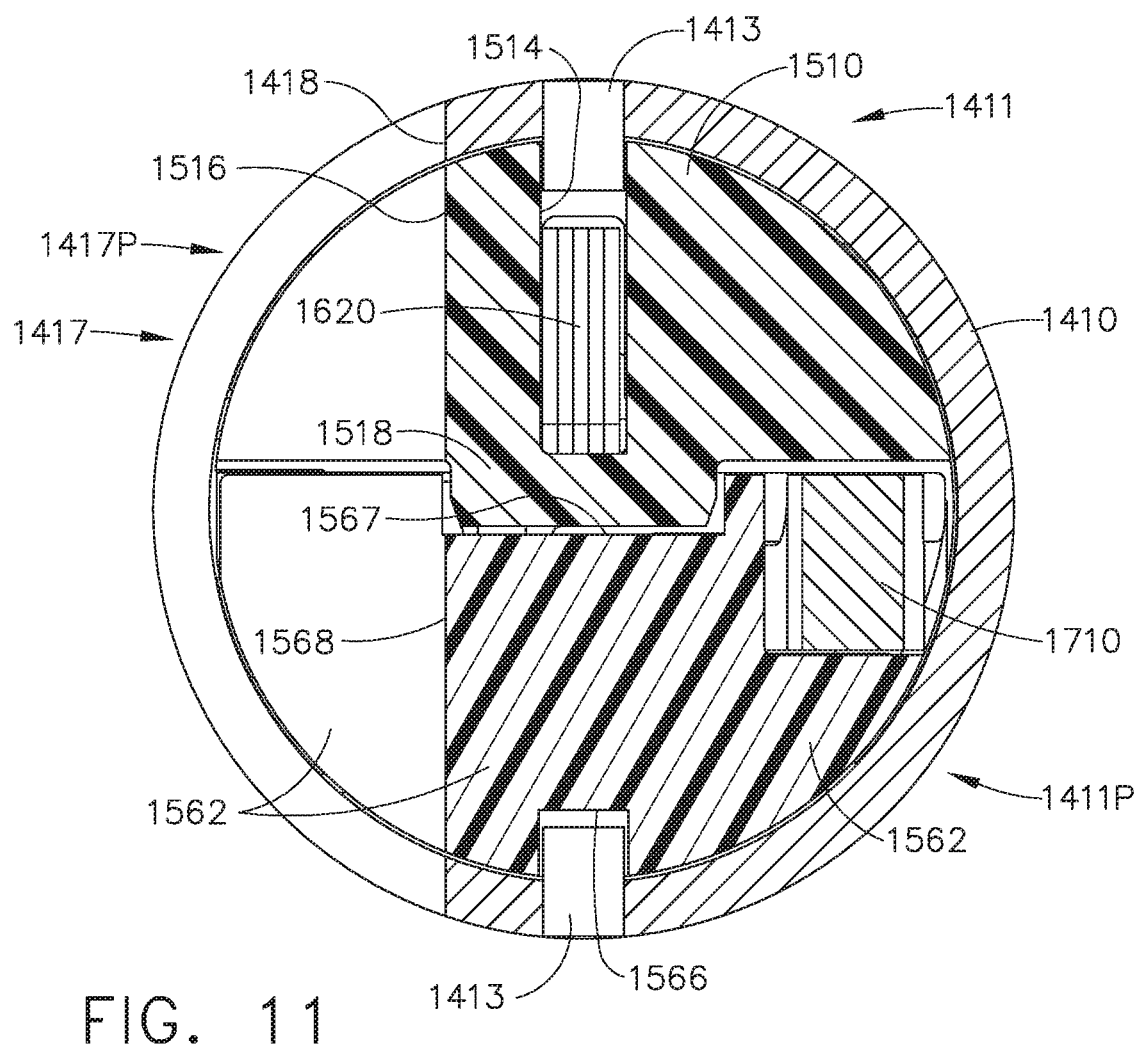
FIG. 11 is a cross-sectional view of the interchangeable surgical tool assembly of FIG. 10 taken along line 11-11 in FIG. 10.

Referring now to FIG. 11, in the illustrated example, the proximal end portion 1417 has an uninterrupted or "continuous" "proximal" outer perimeter or perimetrical shape 1417P. At least a portion of the distal end portion 1411 has a discontinuous or interrupted "distal" outer perimeter or outer perimetrical shape 1411P. As can also be seen in FIG. 9, for example, the distal spine extension 1562 has a similar notched area 1568 therein. Also, the intermediate spine segment 1510 may also have an asymmetric notch 1516 therein that matches the notched areas 1418 and 1568. See FIGS. 10 and 11. Such arrangement may permit the clinician to position the shaft assembly 1400 and the surgical end effector 1100 into the position shown in FIG. 7 within the pelvic region. In the illustrated arrangement, for example, the articulation angle AA may be approximately 110°. Thus, such arrangement may afford the clinician the ability to position the surgical end effector 1100 deeper within the pelvic region as compared with other tool and end effector arrangements. In the illustrated arrangement, the notched areas 1418, 1516, 1568 are located on the opposite side of the shaft axis SA from which the end effector 1100 articulates (e.g., direction of articulation DA). In other arrangements, however, it is conceivable that the notched areas 1418, 1516, 1568 are provided on the same side of the shaft axis SA from which the surgical end effector articulates.

Figure 12:
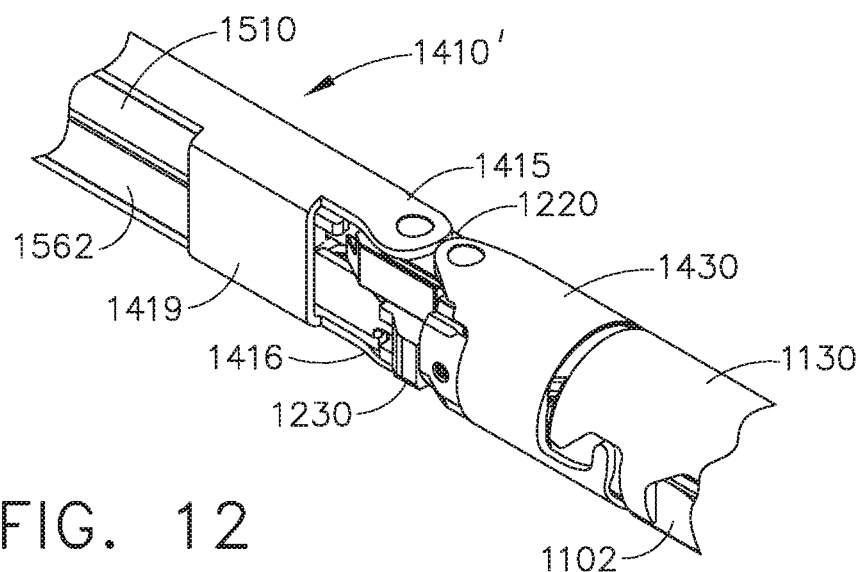
FIG. 12 is a partial perspective view of a portion of another interchangeable surgical tool assembly.

In one example, to maintain the proximal closure member 1410 in axial alignment on the spine assembly 1500 as it moves axially thereon and to retard or prevent buckling of the shaft components during articulation and closing of the end effector jaws 1130, 1102, opposed closure alignment members 1413 are employed. In one arrangement, for example, a pair of diametrically-opposed alignment pins 1413 are attached to and extend inwardly from the proximal closure member 1410 to be slidably received within corresponding alignment slots 1514, 1566 in the intermediate spine segment 1510 and the distal spine extension 1562, respectively. See FIGS. 10 and 11. As can also be seen in FIG. 11, the distal spine extension 1562 may have a recessed area 1567 for receiving a downwardly protruding lug portion 1518 that is formed on the underside of the intermediate spine segment 1510. Such arrangement may serve to somewhat laterally interlock the intermediate spine segment 1510 and the distal spine extension 1562 together to thereby resist any lateral deflection from occurring between those components. FIG. 12 illustrates an alternative proximal closure member 1410' that is identical to the proximal closure member 1410 described above, except that the proximal closure member 1410' includes a connector bridge 1419 that extends between the upper and lower tangs 1415 and 1416 which may serve to limit any tendency of the upper and lower tangs 1415, 1416 from spreading apart during use.

Figure 13:
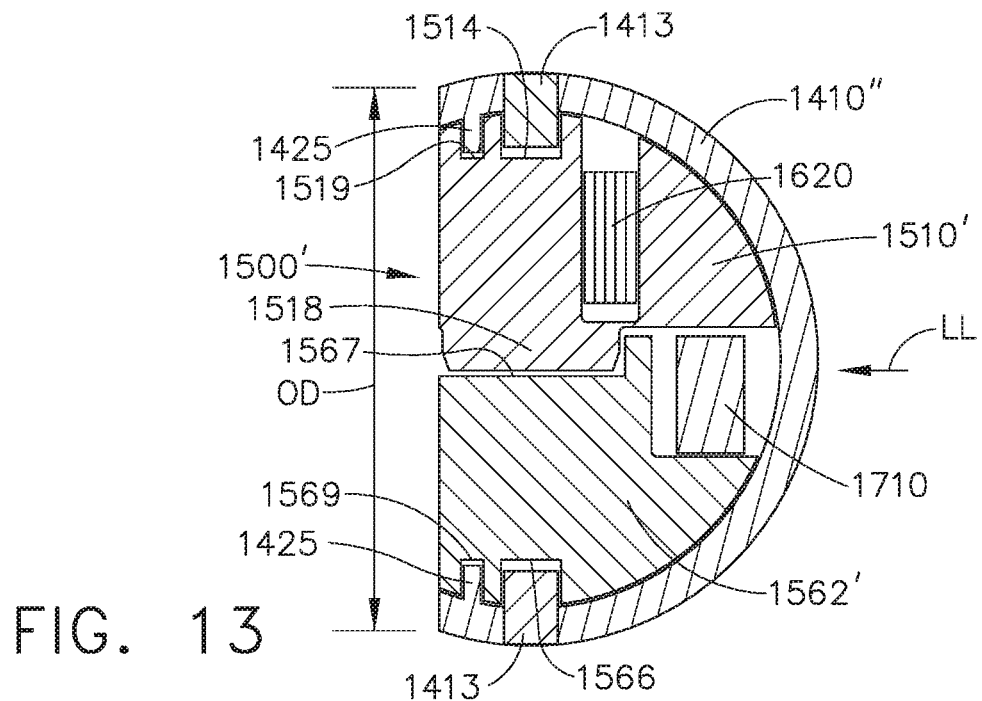
FIG. 13 is a cross-sectional end view of a shaft assembly portion of another interchangeable surgical tool embodiment.
Figure 14:
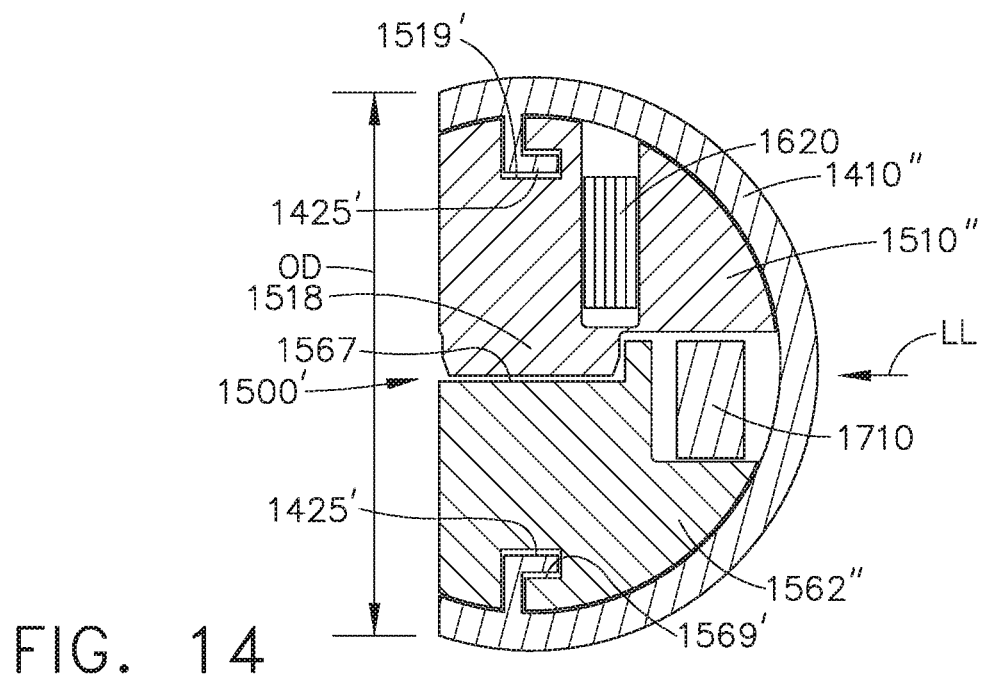
FIG. 14 is a cross-sectional end view of a shaft assembly portion of another interchangeable surgical tool embodiment.

FIG. 13 illustrates another arrangement that is configured to prevent or limit the opening of a proximal closure member 1410" in the directions OD when a lateral load LL is applied laterally to the shaft assembly 1400 in the notched areas. The proximal closure member 1410" may be identical to proximal closure member 1410 except for the differences noted herein. As can be seen in FIG. 13, the proximal closure member 1410" additionally includes a pair of inwardly protruding, somewhat diametrically opposed flexure tabs 1425. One flexure tab 1425 is slidably received within a corresponding axially extending slot 1519 and the other flexure tab 1425 is slidably received within a corresponding axial slot 1569 in the distal spine extension 1562. Such arrangement serves to slidably interlock the proximal closure member 1410" on the spine assembly 1500' to thereby cause the proximal closure member 1410" to resist opening (in the OD directions) when a lateral load LL is applied thereto. FIG. 14 illustrates an alternative arrangement that employs flexure tabs 1425' are somewhat L-shaped and are slidably received within corresponding L-shaped slots 1514' and 1569'.

As mentioned above, the interchangeable surgical tool assembly 1000 further includes a firing member assembly 1600 that is supported for axial travel within the spine assembly 1500. In the illustrated embodiment, the firing member assembly 1600 includes a proximal firing shaft segment 1602 and a distal cutting portion or distal firing bar 1620. The firing member assembly 1600 may also be referred to herein as a "second shaft" and/or a "second shaft assembly". As can be seen in FIG. 5, the proximal firing shaft segment 1602 includes a proximal attachment lug 1604 that protrudes proximally from a proximal end thereof that is configured to be operably received within the firing shaft attachment cradle 542 in the longitudinally movable drive member 540 that is supported in the handle assembly 500. See FIG. 2.

Referring again to FIG. 5, a distal end 1606 of the proximal firing shaft segment 1602 includes a longitudinal slot 1608 which is configured to receive a tab (not shown) on the proximal end of the distal firing bar 1620. The longitudinal slot 1608 and the proximal end of the distal firing bar 1620 can be sized and configured to permit relative movement therebetween and can comprise a slip joint 1622. The slip joint 1622 can permit the proximal firing shaft segment 1602 to move during the articulation actuation without moving, or at least substantially moving, the distal firing bar 1620. Once the end effector 1100 has been suitably oriented, the proximal firing shaft segment 1602 can be advanced distally until a proximal end wall of the slot 1608 comes into contact with the tab on the distal firing bar 1620 to advance the distal firing bar 1620 and fire the surgical staple cartridge 1150 that is positioned within the elongate channel 1102. As can be further seen in FIG. 5, the intermediate spine segment 1510 includes a channel 1512 for slidably supporting the proximal firing shaft segment 1602 therein. To facilitate assembly of the proximal firing shaft segment 1602 and the spine assembly 1500, a top spine cover 1527 may be engaged with the intermediate spine segment 1510 to enclose those portions of the firing member assembly 1600 therein.

Figure 15:
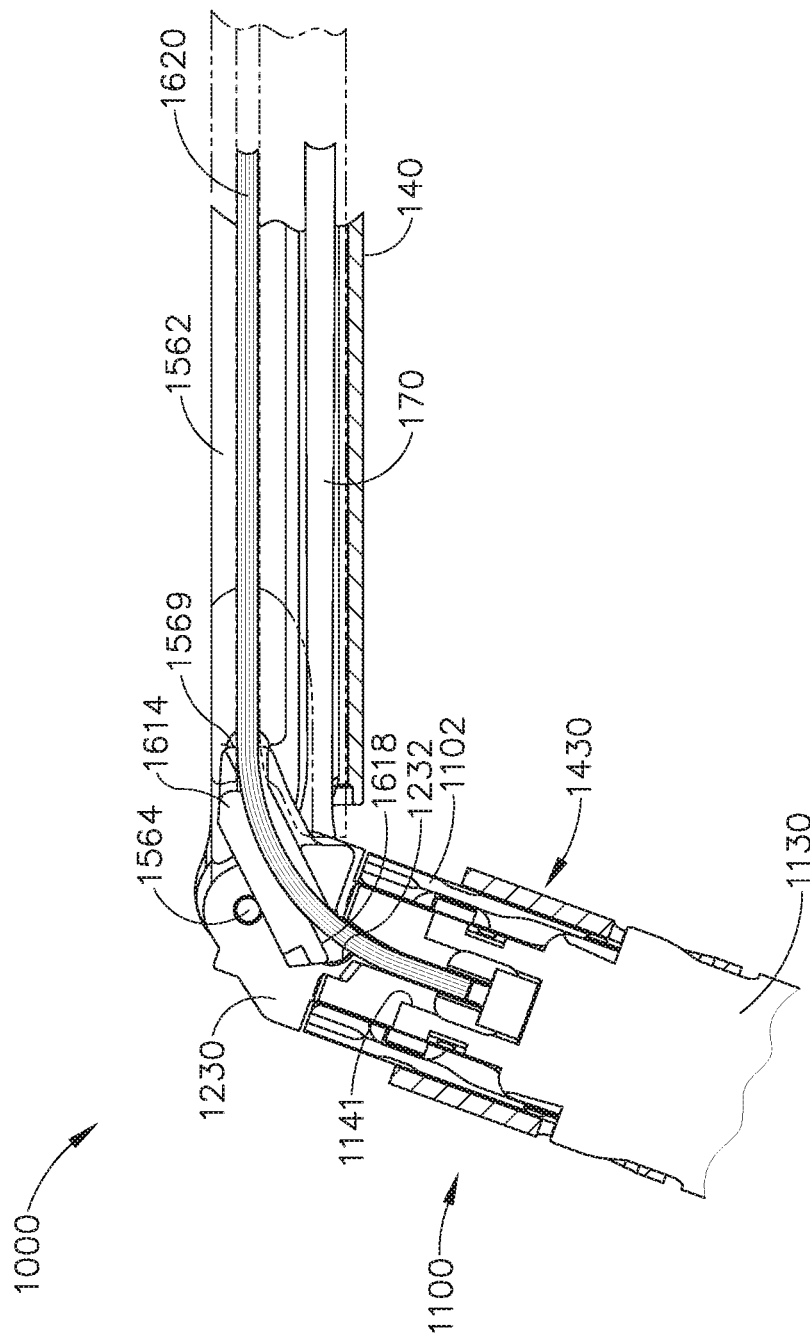
FIG. 15 is a top cross-sectional view of a portion of an interchangeable surgical tool embodiment in an articulated configuration.

FIG. 15 illustrates the surgical end effector 1100 in an articulated position. As can be seen in FIG. 15, as well as in FIG. 6, a middle support member 1614 is employed to provide lateral support to the distal firing bar 1620 as it flexes to accommodate articulation of the surgical end effector 1100. In one example, a distal pivot pin 1615 protrudes from a distal end of the middle support member 1614 and is received within a spine attachment hole 1234 in the end effector mounting assembly 1230. A proximal pivot pin 1616 is received within an elongate slot 1569 in the distal spine extension 1562. In addition, the middle support member 1614 includes a passageway 1618 therein that provides lateral support to the distal firing bar 1620 as the surgical end effector 1100 is articulated. Further details concerning the middle support member and alternative knife bar support arrangements are disclosed in U.S. patent application Ser. No. 15/019,245 which has been herein incorporated by reference in its entirety.

Figure 15A:
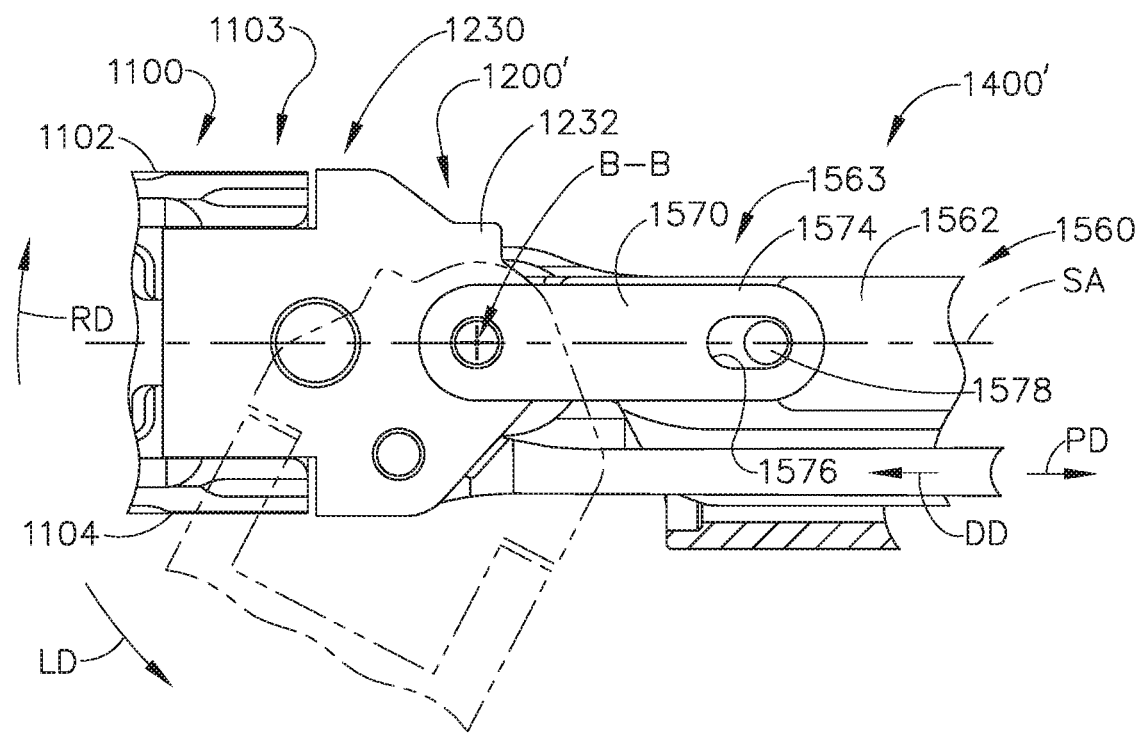
FIG. 15A is a top view of portions of another surgical end effector and elongate shaft assembly arrangement with the surgical end effector in an unarticulated position (solid lines) and an articulated position (phantom lines)

FIG. 15A illustrates an alternative articulation joint 1200' that facilitates articulation of the surgical end effector 1100 about an articulation axis B-B that is transverse to a shaft axis SA that is defined by the elongate shaft assembly 1400' to which it is operably attached. In the illustrated example, the surgical end effector 1100 is selectively articulatable to one side of the shaft axis SA. Such articulation direction is represented by arrow LD. Similar to the embodiment described above, an end effector mounting assembly 1230 is pivotally attached to a proximal end 1103 of an elongate channel 1102 of the surgical end effector 1100. The end effector mounting assembly 1230 is pivotally attached to a distal spine extension 1562 of a distal frame segment 1560 of the elongate shaft assembly 1400'. Similar to the above described embodiment, the distal frame segment 1560 may operably support an articulation lock 1210 (FIG. 6) that is actuated by a proximal articulation driver 1700 (FIG. 6) that operably interfaces with a source of articulation and retraction motions as described in detail herein. In the example illustrated in FIG. 15A, the end effector mounting assembly 1230 is pivotally attached to the distal spine extension 1562 by a distal support link 1570. In one arrangement for example, the end effector mounting assembly 1230 is pinned to a distal end 1572 of the distal support link 1570 by an articulation pin 1580 that defines the articulation axis B-B. A proximal end 1574 of the distal support link 1570 is attached to a distal end 1563 of the distal spine extension 1562 for axial and pivotal travel relative thereto.

As can be further seen in FIG. 15A, the proximal end 1574 of the distal support link 1570 includes an axial slot 1576 that is sized to slidably and pivotally receive therein a proximal attachment pin 1578 that is attached to the distal spine extension 1562. Such arrangement serves to couple the surgical end effector 1100 to the distal frame segment 1560 for selective pivotal travel (articulation) about the articulation axis B-B as well as some limited axial travel relative thereto. In the illustrated arrangement, articulation motions are applied to the surgical end effector 1100 by a distal articulation link 1710 that is pivotally coupled to or otherwise operably interfaces with the articulation lock 1210. Axial movement of the distal articulation link 1710 in the proximal direction PD (which is constrained to move axially along one side of the shaft axis SA), will cause the surgical end effector 1100 to articulate in the left direction LD from an unarticulated position wherein the surgical end effector 1100 is axially aligned on the shaft axis SA to articulated positions on the left side of the shaft axis SA (represented in phantom lines in FIG. 15A). Axial movement of the distal articulation link 1710 in the distal direction DD will move the surgical end effector 1100 from an articulated position towards the unactuated position (arrow RD). In one arrangement, a stop member or stop formation 1232 is formed or otherwise attached to the end effector mounting assembly 1230 to contact the distal end 1563 of the distal spine extension when the surgical end effector 1100 has attained the unactuated position to prevent any further travel thereof in the right direction RD. Such articulation joint arrangement may provide improved articulation travel and closure stability.

Further to the above, the interchangeable surgical tool assembly 1000 includes a clutch assembly 1640 which can be configured to selectively and releasably couple the proximal articulation driver 1700 to the firing member assembly 1600. In one form, the clutch assembly 1640 includes a rotary lock assembly that, in at least one embodiment, comprises a lock collar, or lock sleeve 1650 that is positioned around the firing member assembly 1600. The lock sleeve 1650 is configured to be rotated between an engaged position in which the lock sleeve 1650 couples the proximal articulation driver 1700 to the firing member assembly 1600 and a disengaged position in which the proximal articulation driver 1700 is not operably coupled to the firing member assembly 1600. When lock sleeve 1650 is in its engaged position, distal movement of the firing member assembly 1600 can move the proximal articulation driver 1700 distally and, correspondingly, proximal movement of the firing member assembly 1600 can move the proximal articulation driver 1700 proximally. When lock sleeve 1650 is in its disengaged position, movement of the firing member assembly 1600 is not transmitted to the proximal articulation driver 1700 and, as a result, the firing member assembly 1600 can move independently of the proximal articulation driver 1700. In various circumstances, the proximal articulation driver 1700 can be held in position by the articulation lock 1210 when the proximal articulation driver 1700 is not being moved in the proximal or distal directions by the firing member assembly 1600.

Figure 4:
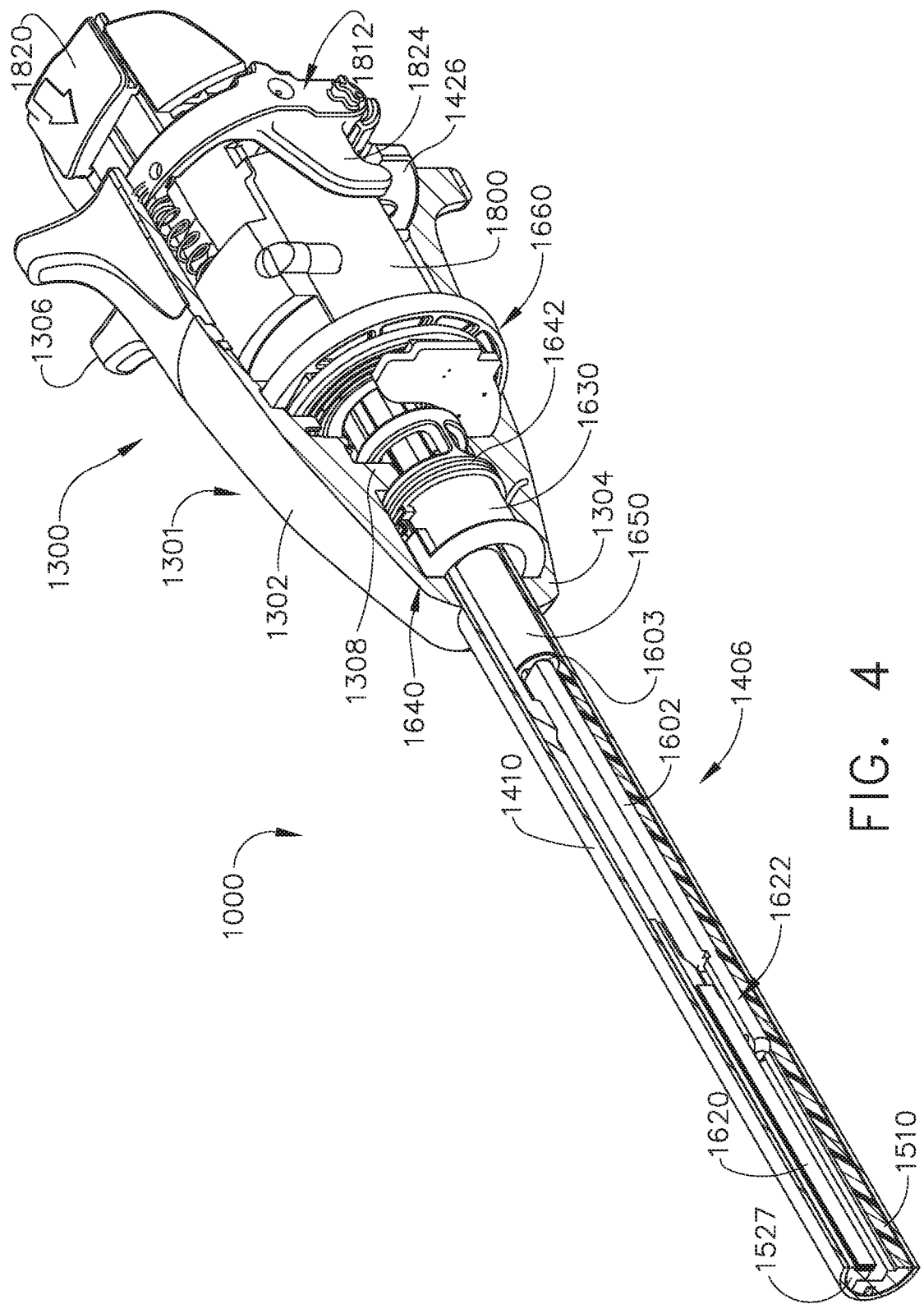
FIG. 4 is a perspective view of a proximal portion of the interchangeable surgical tool assembly embodiment depicted in FIGS. 1-3 with portions thereof omitted for clarity.

Referring primarily to FIGS. 4 and 5, the lock sleeve 1650 comprises a cylindrical, or an at least substantially cylindrical, body that includes a longitudinal aperture 1652 that is configured to receive the proximal firing shaft segment 1602 of the firing member assembly 1600. The lock sleeve 1650 also has two diametrically-opposed, inwardly-facing lock protrusions 1654 and an outwardly protruding second lock member 1656 formed thereon. The lock protrusions 1654 can be configured to be selectively engaged with the proximal firing shaft segment 1602 of the firing member assembly 1600. More particularly, when the lock sleeve 1650 is in its engaged position, the lock protrusions 1654 are positioned within a drive notch 1603 that is provided in the proximal firing shaft segment 1602 such that a distal pushing force and/or a proximal pulling force can be transmitted from the firing member assembly 1600 to the lock sleeve 1650. When the lock sleeve 1650 is in its engaged position, the second lock member 1656 is received within a drive notch 1704 that is defined in the proximal articulation driver 1700 such that the distal pushing force and/or the proximal pulling force applied to the lock sleeve 1650 can be transmitted to the articulation driver 1700. In effect, the firing member assembly 1600, the lock sleeve 1650, and the proximal articulation driver 1700 will move together when the lock sleeve 1650 is in its engaged position. On the other hand, when the lock sleeve 1650 is in its disengaged position, the lock protrusions 1654 may not be positioned within the drive notch 1603 of the proximal firing shaft segment 1602 of the firing member assembly 1600 and, as a result, a distal pushing force and/or a proximal pulling force may not be transmitted from the firing member assembly 1600 to the lock sleeve 1650. Correspondingly, the distal pushing force and/or the proximal pulling force may not be transmitted to the proximal articulation driver 1700. In such circumstances, the firing member assembly 1600 can be slid proximally and/or distally relative to the lock sleeve 1650 and the proximal articulation driver 1700.

The clutch assembly 1640 further includes a switch drum 1630 that interfaces with the lock sleeve 1650. Further details concerning the operation of the switch drum 1630 and lock sleeve 1650 may be found in U.S. patent application Ser. No. 13/803,086 and U.S. patent application Ser. No. 15/019,196, which have each been herein incorporated by reference in their respective entireties. The switch drum 1630 can further comprise at least partially circumferentially extending openings 1632 defined therein which can receive circumferential mounts 1305 that extend from the nozzle portions 1302, 1304 and permit relative rotation, but not translation, between the switch drum 1630 and the proximal nozzle 1301. See FIG. 6. Rotation of the nozzle 1301 to a point where the mounts reach the end of their respective openings 1632 in the switch drum 1630 will result in rotation of the switch drum 1630 about the shaft axis SA. Rotation of the switch drum 1630 will ultimately result in the movement of the lock sleeve 1650 between its engaged and disengaged positions. In alternative embodiments, the nozzle 1301 may be employed to operably engage and disengage the articulation drive system with the firing drive system. As indicated above, clutch assembly 1640 may operate in the various manners described in further detail in U.S. patent application Ser. No. 13/803,086 and U.S. patent application Ser. No. 15/019,196.

In the illustrated arrangement, the switch drum 1630 includes an L-shaped slot 1636 that extends into a distal opening 1637 in the switch drum 1630. The distal opening 1637 receives a transverse switch pin 1639 of a shifter plate 1638. In one example, the shifter plate 1638 is received within a longitudinal slot (not shown) that is provided in the lock sleeve 1650 to facilitate axial movement of the lock sleeve 1650 when engaged with the proximal articulation driver 1700. Further details regarding the operation of the shifter plate and shift drum arrangements may be found in U.S. patent application Ser. No. 14/868,718, filed Sep. 28, 2015, entitled SURGICAL STAPLING INSTRUMENT WITH SHAFT RELEASE, POWERED FIRING AND POWERED ARTICULATION, the entire disclosure of which is hereby incorporated by reference herein.

Also in the illustrated embodiment, the switch drum 1630 includes a magnet support arm 1665 that supports a magnet or other sensor arrangement that is configured to operably interface with a Hall effect sensor 1662 that interfaces with a slip ring assembly 1660 that is operably mounted to the chassis 1800. The slip ring assembly 1660 is configured to conduct electrical power to and/or from the interchangeable surgical tool assembly 1000 and/or communicate signals to and/or from the interchangeable surgical tool assembly 1000 components back to the microcontroller 520 in the handle assembly 500 (FIG. 2) or robotic system controller, for example. Further details concerning the slip ring assembly 1660 and associated connectors may be found in U.S. patent application Ser. No. 13/803,806 and U.S. patent application Ser. No. 15/019,196 which have each been herein incorporated by reference in their respective entireties as well as in U.S. patent application Ser. No. 13/800,067, entitled STAPLE CARTRIDGE TISSUE THICKNESS SENSOR SYSTEM, now U.S. Patent Application Publication No. 2014/0263552, which is hereby incorporated by reference herein in its entirety. The magnet or magnets supported on the magnet support arm 1665 cooperate with the Hall effect sensor 1662 or other sensor arrangement to detect the rotary position of the switch drum 1630 and convey that information to the microcontroller 520 which may serve to provide an indication or indications to the user in the various manners discussed in the aforementioned incorporated references. Other sensor arrangements may also be employed.

Referring again to FIGS. 2 and 5, the chassis 1800 includes at least one, and preferably two, tapered attachment portions 1802 that are formed thereon and are adapted to be received within corresponding dovetail slots 507 that are formed within the distal end portion of the frame 506 of the handle assembly 500. As can be further seen in FIG. 2, a shaft attachment lug 1607 is formed on the proximal end of the proximal firing shaft segment 1602. As will be discussed in further detail below, when the interchangeable surgical tool assembly 1000 is coupled to the handle assembly 500, the shaft attachment lug 1607 is received in a firing shaft attachment cradle 542 that is formed in the distal end of the longitudinally movable drive member 540. See FIG. 2.

The interchangeable surgical tool assembly 1000 employs a latch system 1810 for removably coupling the interchangeable surgical tool assembly 1000 to the frame 506 of the handle assembly 500. As can be seen in FIG. 5, for example, in at least one form, the latch system 1810 includes a lock member or lock yoke 1812 that is movably coupled to the chassis 1800. In the illustrated embodiment, for example, the lock yoke 1812 has a U-shape and includes two downwardly extending legs 1814. The legs 1814 each have a pivot lug (not shown) formed thereon that is adapted to be received in corresponding holes 1816 that are formed in the chassis 1800. Such arrangement facilitates pivotal attachment of the lock yoke 1812 to the chassis 1800. The lock yoke 1812 may include two proximally protruding lock lugs 1818 that are configured for releasable engagement with corresponding lock detents or grooves 509 in the distal end of the frame 506 of the handle assembly 500. See FIG. 2. In various forms, the lock yoke 1812 is biased in the proximal direction by a spring or biasing member 1819. Actuation of the lock yoke 1812 may be accomplished by a latch button 1820 that is slidably mounted on a latch actuator assembly 1822 that is mounted to the chassis 1800. The latch button 1820 may be biased in a proximal direction relative to the lock yoke 1812. The lock yoke 1812 may be moved to an unlocked position by biasing the latch button 1820 in the distal direction which also causes the lock yoke 1812 to pivot out of retaining engagement with the distal end of the frame 506. When the lock yoke 1812 is in "retaining engagement" with the distal end of the frame 506, the lock lugs 1818 are retainingly seated within the corresponding lock detents or grooves 509 in the distal end of the frame 506.

In the illustrated arrangement, the lock yoke 1812 includes at least one and preferably two lock hooks 1824 that are adapted to contact corresponding lock lug portions 1426 that are formed on the closure shuttle 1420. When the closure shuttle 1420 is in an unactuated position, the lock yoke 1812 may be pivoted in a distal direction to unlock the interchangeable surgical tool assembly 1000 from the handle assembly 500. When in that position, the lock hooks 1824 do not contact the lock lug portions 1426 on the closure shuttle 1420. However, when the closure shuttle 1420 is moved to an actuated position, the lock yoke 1812 is prevented from being pivoted to an unlocked position. Stated another way, if the clinician were to attempt to pivot the lock yoke 1812 to an unlocked position or, for example, the lock yoke 1812 was inadvertently bumped or contacted in a manner that might otherwise cause it to pivot distally, the lock hooks 1824 on the lock yoke 1812 will contact the lock lugs 1426 on the closure shuttle 1420 and prevent movement of the lock yoke 1812 to an unlocked position. See FIG. 5. Further details concerning the latching system may be found in U.S. Patent Application Publication No. 2014/0263541.

Attachment of the interchangeable surgical tool assembly 1000 to the handle assembly 500 will now be described with reference to FIG. 2. To commence the coupling process, the clinician may position the chassis 1800 of the interchangeable surgical tool assembly 1000 above or adjacent to the distal end of the frame 506 such that the tapered attachment portions 1802 formed on the chassis 1800 are aligned with the dovetail slots 507 in the frame 506. The clinician may then move the surgical tool assembly 1000 along an installation axis IA that is perpendicular to the shaft axis SA to seat the tapered attachment portions 1802 in "operable engagement" with the corresponding dovetail receiving slots 507 in the distal end of the frame 506. In doing so, the shaft attachment lug 1606 on the proximal firing shaft segment 1602 will also be seated in the cradle 542 in the longitudinally movable drive member 540 and the portions of the transverse attachment pin 516 on the closure linkage assembly 514 will be seated in the corresponding hooks 1421 in the closure shuttle 1420. As used herein, the term "operable engagement" in the context of two components means that the two components are sufficiently engaged with each other so that upon application of an actuation motion thereto, the components may carry out their intended action, function and/or procedure.

Referring again to FIGS. 11 and 15, the distal firing bar 1620 may comprise a laminated beam structure that includes at least two beam layers. Such beam layers may comprise, for example, stainless steel bands that are interconnected by, for example, welding or pinning together at their proximal ends and/or at other locations along their length. In alternative embodiments, the distal ends of the bands are not connected together to allow the laminates or bands to splay relative to each other when the end effector is articulated. Such arrangement permits the distal firing bar 1620 to be sufficiently flexible to accommodate articulation of the end effector. Various other suitable laminated knife bar arrangements are disclosed in U.S. patent application Ser. No. 15/019,245. As can also be seen in FIG. 4, a middle support member 1614 is employed to provide lateral support to the distal firing bar 1620 as it flexes to accommodate articulation of the surgical end effector 1100. Further details concerning the middle support member and alternative knife bar support arrangements are disclosed in U.S. patent application Ser. No. 15/019,245.

After the interchangeable surgical tool assembly 1000 has been operably coupled to the handle assembly 500 (FIG. 1), the clinician may operate the surgical tool assembly 1000 as follows. As discussed above, when the closure drive system 510 is in its unactuated position (i.e., the closure trigger 512 has not been actuated), a torsion spring 1642 has biased the clutch assembly 1640 and, more particularly, the switch pin 1639 and the lock sleeve 1650 into the articulation position. When in that mode, the magnet or magnets in the magnet support arm 1665 may cooperate with the Hall effect sensor 1662 or other sensor arrangements as to indicate to the microcontroller 520 that the surgical tool assembly 1000 is in the articulation mode. When the clinician actuates the firing trigger 532, the motor drives the proximal firing shaft segment 1602 distally. As mentioned above, however, the slip joint 1622 facilitates movement of the proximal firing shaft segment 1602 without moving, or at least substantially moving, the distal firing bar 1620. Because the lock sleeve 1650 is in operable engagement with the proximal firing shaft segment 1602 and the proximal articulation driver 1700 is in engagement with the lock sleeve 1650, actuation of the proximal firing shaft segment 1602 results in the distal movement of the proximal articulation driver 1700. Distal movement of the proximal articulation driver 1700 causes the surgical end effector 1100 to articulate around the articulation axis B-B. During this time, the clinician can also partially close the jaws of the surgical end effector 1100 by partially depressing the closure trigger. Such arrangement facilitates axial movement of the proximal closure member 1410 without automatically shifting the clutch assembly 1640 to the firing mode. This feature may enable the clinician to use the jaws to grasp and manipulate tissue prior to clamping onto the target tissue.

Once the clinician has articulated the surgical end effector 1100 into a desired position and the jaws have been positioned in a desired orientation relative to the target tissue, the clinician releases the firing trigger 532 which will discontinue the motorized movement of the proximal firing shaft segment 1602 as well as the proximal articulation driver 1700. The articulation lock 1210 will lock the proximal articulation driver 1700 in that position to prevent further articulation of the surgical end effector 1100. The clinician may clamp the target tissue between the jaws by depressing the closure trigger 512 to the fully depressed position. Such action moves the proximal closure member 1410 distally. Such distal movement of the proximal closure member 1410 causes the shifter plate 1638 to rotate the lock sleeve 1650 to rotate to a disengaged position with the proximal firing shaft segment 1602. When in that position, the lock protrusions 1654 have disengaged from the drive notch 1603 in the proximal firing shaft segment 1602. Thus, the proximal firing shaft segment 1602 can move axially without moving the lock sleeve 1650 and the proximal articulation driver 1700. As the proximal closure member 1410 is moved distally to the fully actuated position (by depressing the closure trigger 512), the proximal and distal closure members 1410 and 1430 move distally to close the jaws 1130, 1102. When in this position, the closure drive system 510 in the handle assembly 500 may be locked and the clinician can release the closure trigger 512. When the clutch assembly 1640 has been moved to this firing mode, the magnet or other sensors in the magnet support arm 1665 or other portion is in communication with the Hall effect sensor 1662 to indicate the position of the clutch assembly 1640 to the microcontroller 520.

The microcontroller 520 may provide the clinician with an indication of the position of the distal firing bar 1620 as it is advanced distally through the target tissue that is clamped between the end effector jaws. Once the distal firing bar 1620 and, more specifically, the firing member or knife member attached thereto has been advanced to a fully fired position, the microcontroller 520, by means of sensor arrangements, detects the position of a portion of the firing member assembly 1600 and may then reverse the motor to retract the distal firing bar 1620 to its starting position. This action may be automatic or the clinician may have to depress the firing trigger 532 during the retraction process. Once the distal firing bar 1620 has been fully retracted to its starting position, the microcontroller 520 may provide the clinician with an indication that the distal firing bar 1620 has been fully retracted and the closure trigger 512 may be unlocked to enable the closure assembly 1406 to be returned to the unactuated position which thereby moves the jaws to the open position.

Figure 16:
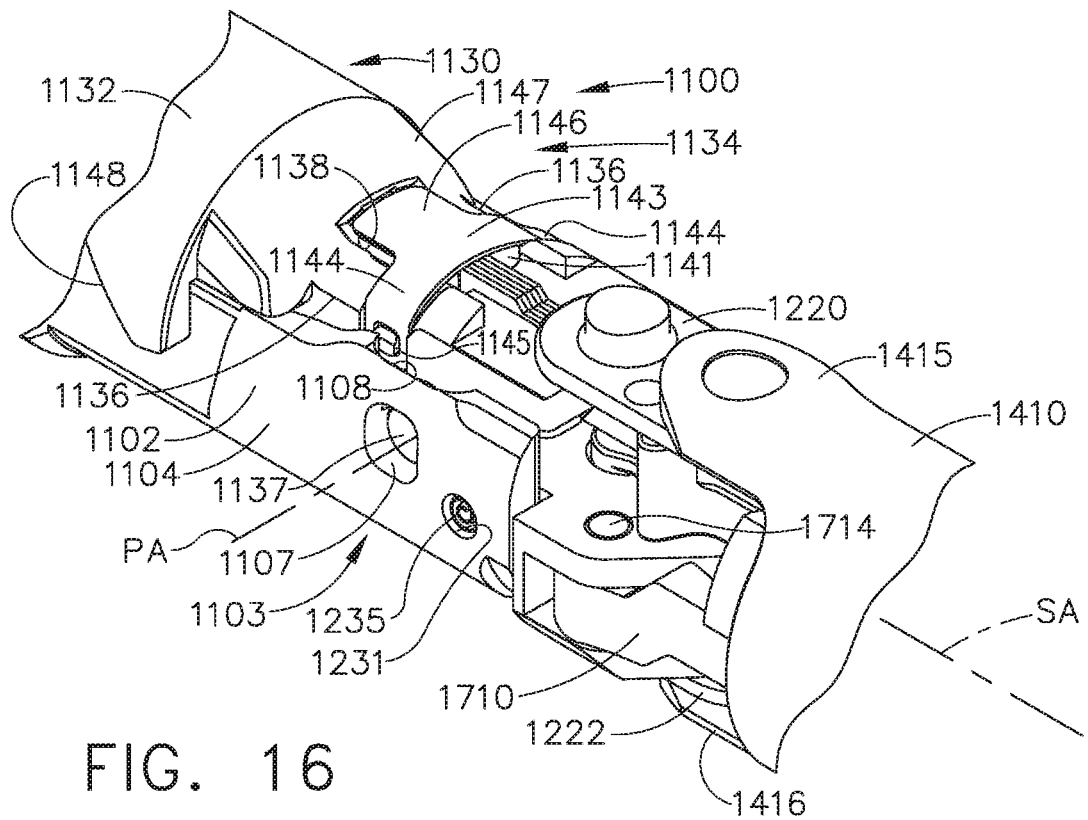
FIG. 16 is a perspective view of a portion of an interchangeable surgical tool end effector employing an anvil cap to cover a portion of a firing member parking area within an end effector thereof.
Figure 17:
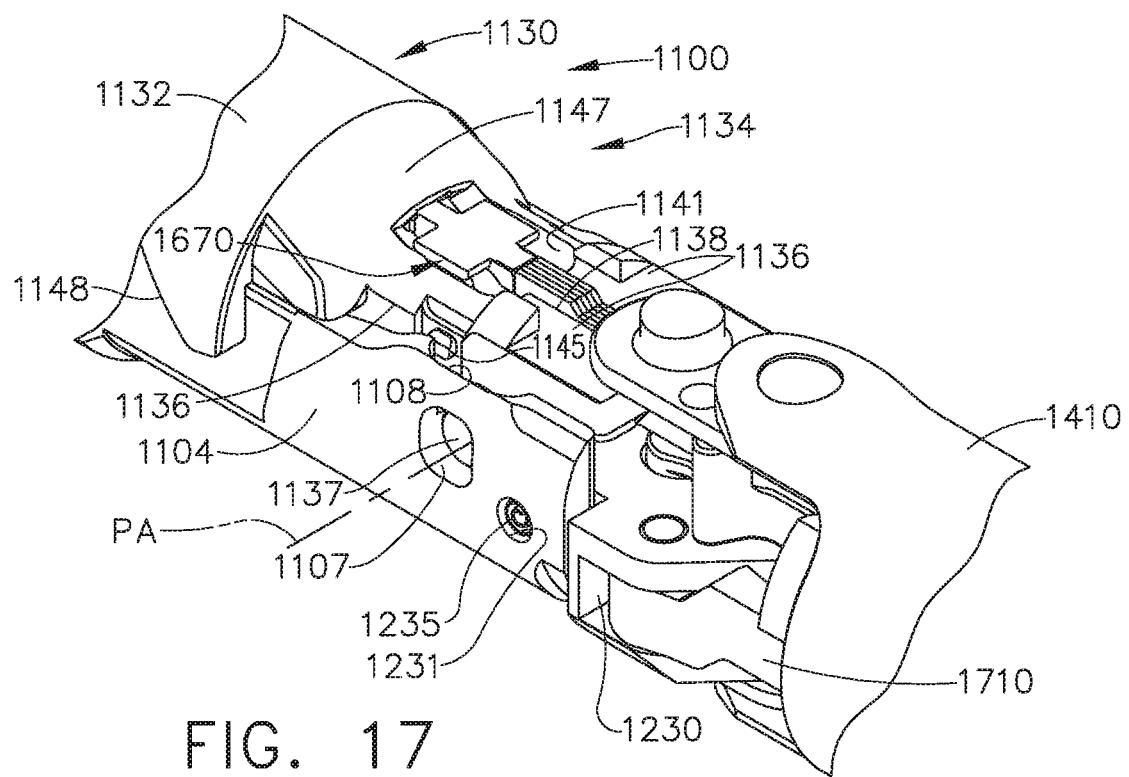
FIG. 17 is another perspective view of a portion of the surgical end effector of FIG. 16 with the anvil cap omitted for clarity.

In one example, the elongate channel 1102 is roughly C-shaped with two upstanding sidewall portions 1104. The anvil 1130 includes an anvil body portion 1132 and an anvil mounting portion 1134. The anvil mounting portion 1134 comprises a pair of anvil mounting walls 1136 that are separated by a slot 1138 (FIG. 6). As discussed above, the end effector mounting assembly 1230 is pivotally attached to the proximal end 1103 of the elongate channel 1102 by a spring pin connector 1235 that extends through a transverse mounting hole 1231 in the end effector mounting assembly 1230 to be received within channel mounting holes 1106 provided in the sidewalls 1104 of the elongate channel 1102. Each of the anvil mounting walls 1136 has an anvil trunnion 1137 protruding therefrom that are each adapted to be rotatably received within a corresponding anvil mounting hole 1107 in the proximal end 1103 of the elongate channel 1102. As can be seen in FIGS. 16 and 17, each of the channel sidewalls 1104 may have a vertical slot or relieved area 1108 that corresponds to each anvil mounting hole 1107 that enables the anvil trunnions 1137 to be vertically dropped into each slot 1108 for ease of assembly. The anvil trunnions define a pivot axis PA about which the anvil 1130 is selectively pivotable relative to the elongate channel 1102. In various examples, the pivot axis PA is transverse to the shaft axis SA. See FIG. 16.

The elongate channel 1102 is configured to removably support a surgical staple cartridge 1150 therein. The surgical staple cartridge 1150 includes a cartridge body 1151 that defines a deck surface 1152 that faces a staple-forming undersurface 1133 of the anvil body portion 1132. The cartridge body 1151 has an elongate slot 1154 extending therethrough for permitting the passage of a firing member 1670 that is attached to a distal end of the distal firing bar 1620. The cartridge body 1151 has a plurality of anvil pockets 1156 that are serially arranged in lines on both sides of the elongate slot 1154. See FIG. 6. Housed within these pockets 1156 are staple drivers that operably support one or more surgical staples or fasteners thereon. When the target tissue is clamped between the staple forming undersurface 1133 of the anvil body portion 1132 and the staple cartridge deck surface 1152, the target tissue must be positioned so that the tissue that is severed is stapled on each side of the cut line. To avoid the target tissue from being positioned proximal of the proximal most staples or fasteners, the anvil 1130 may include two downwardly extending tissue stops 1140. See FIG. 18. The tissue stops 1140 when extending downward past the cartridge deck surface 1152 serve to block the target tissue from getting too far proximal between the anvil 1130 and the surgical staple cartridge 1150.

Figure 18:
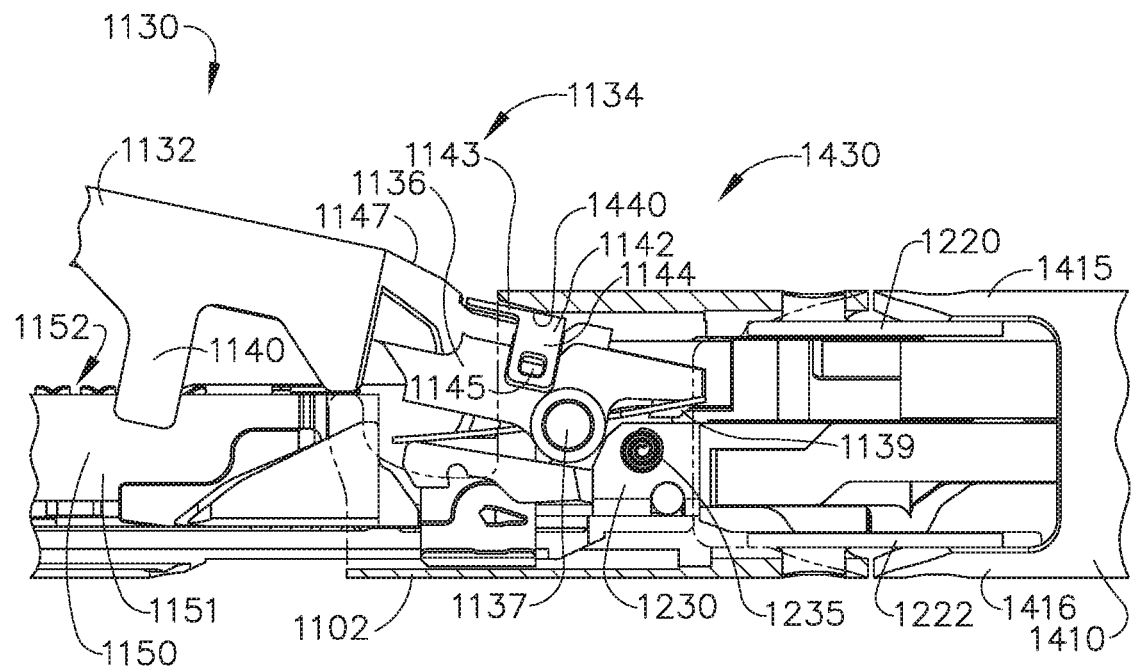
FIG. 18 is a side elevational view of the surgical end effector of FIG. 16 with the anvil thereof in an open configuration.
Figure 19:
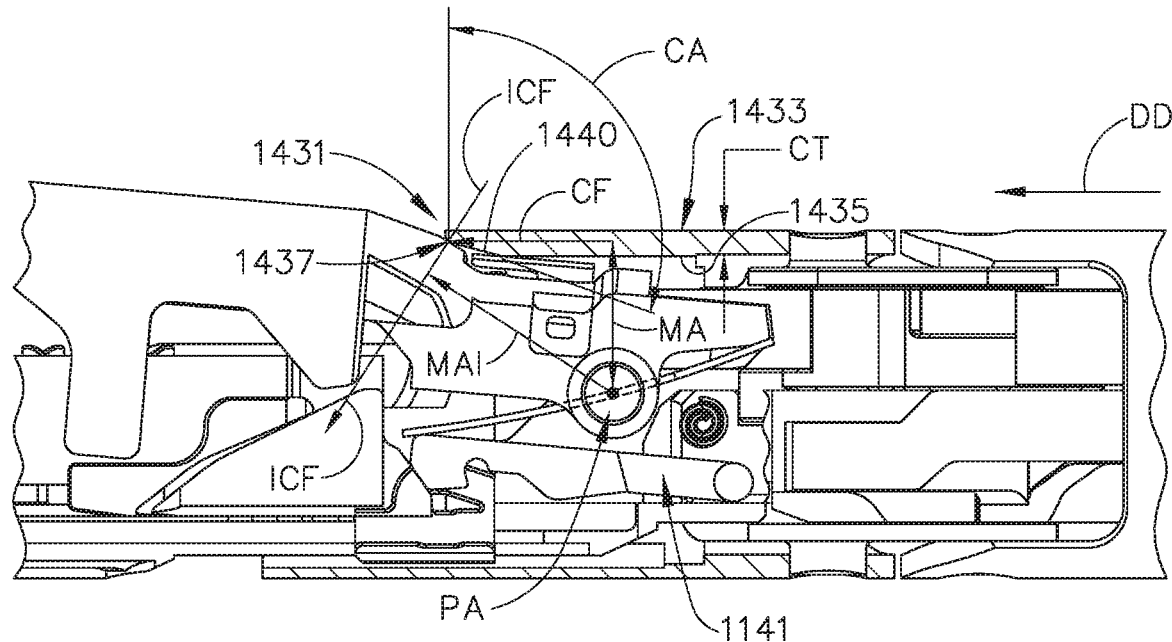
FIG. 19 is a cross-sectional side view of the surgical end effector of FIG. 18 during initiation of an anvil closure process.

Still referring to FIGS. 18 and 19, in the illustrated example the anvil mounting walls 1136 are somewhat elongated and extend proximally. In one example, one or both of the anvil mounting walls 1136 include an opening limiter 1139 (FIG. 18) formed thereon that is configured to contact the end effector mounting assembly 1230 to prevent the anvil 1130 from opening too far. See FIG. 18. Such anvil opening limiter 1139 may prevent the anvil 1130 from being too loose and sloppy on the elongate channel 1102. In addition, the opening limiter 1139 prevents the anvil 1130 from opening to a position wherein the tissue stops 1140 extend above the cartridge deck surface 1152. If that were to occur, tissue could be permitted to extend too far proximally between the anvil 1130 and the surgical staple cartridge 1150 and potentially be severed but not stapled. Such arrangement may also serve to prevent the anvil from being perceived as being too loose and sloppy relative to the elongate channel.

Figure 20:
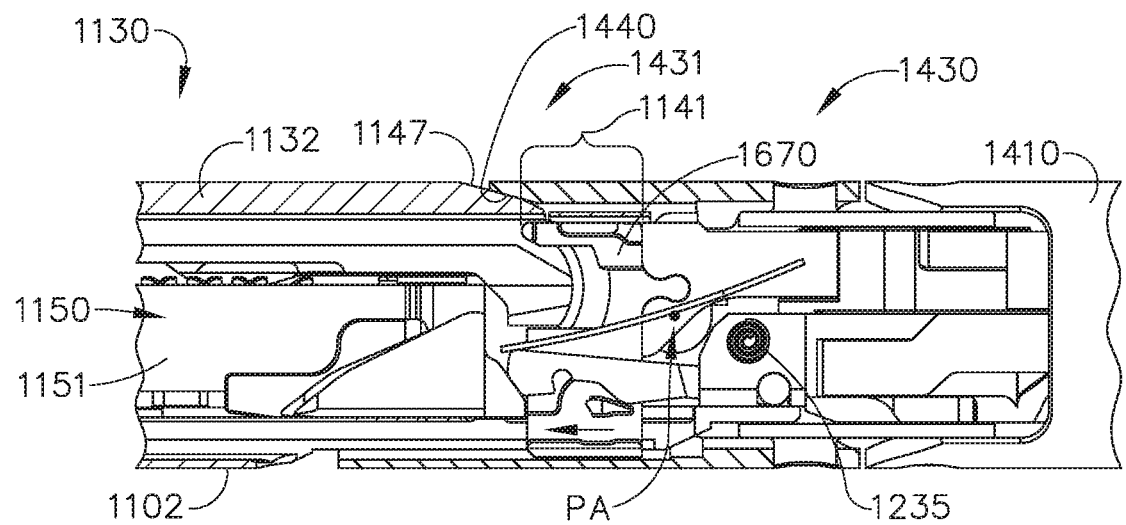
FIG. 20 is another cross-sectional side view of the surgical end effector of FIGS. 18 and 19 with the anvil thereof in a fully closed position.

Referring again to FIG. 17, the anvil mounting portion 1134 defines a firing member "parking area" 1141 which accommodates the firing member 1670 therein when the firing member 1670 is in a starting (unfired) position. In the illustrated arrangement, at least a portion of the parking area 1141 is proximal to the pivot axis. See, for example, FIG. 19. Such arrangement may reduce the negative moment arm that is created from the tissue that is clamped between the anvil 1130 and the surgical staple cartridge 1150 that is supported in the elongate channel 1102. In one example, an anvil cap or cover 1142 is attached to the anvil mounting portion 1134 to provide a pre-closure surface 1143 for contact by a distal camming ramp or surface 1440 formed on a distal end 1431 of the distal closure member 1430. See FIG. 20. In one arrangement, the anvil cap 1142 includes a pair of downwardly extending legs 1144 that are configured to snappingly engage attachment lugs 1145 that are formed on the anvil mounting walls 1136. As can be seen in FIG. 16, for example, the anvil cap 1142 includes a distally extending transition portion 1146 that extends between the anvil mounting walls 1136 and covers the firing member 1670 when it is in the firing member parking area 1141. The transition portion 1146 extends between the anvil mounting walls 1136 and forms a transition from the pre-closure surface 1143 and an anvil cam surface 1147 formed on the anvil mounting portion 1134. In addition, the anvil cap 1142 may minimize pinch points that may otherwise be present between the anvil mounting portion 1134 and the distal end 1431 of the distal closure member 1430 when the anvil 1130 is in its fully opened position.

Figure 18A:
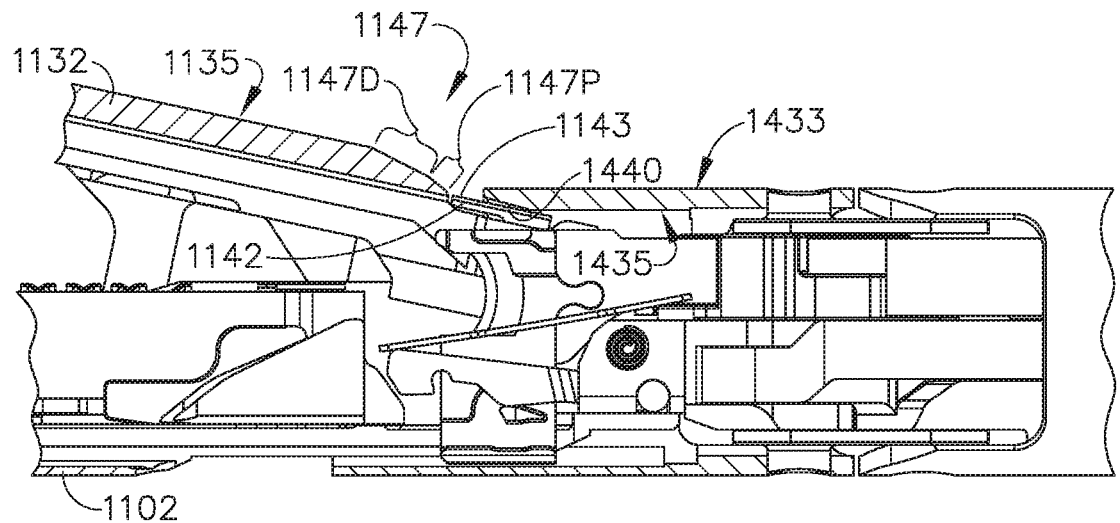
FIG. 18A is a cross-sectional side view of the surgical end effector of FIG. 18.
Figure 20A:
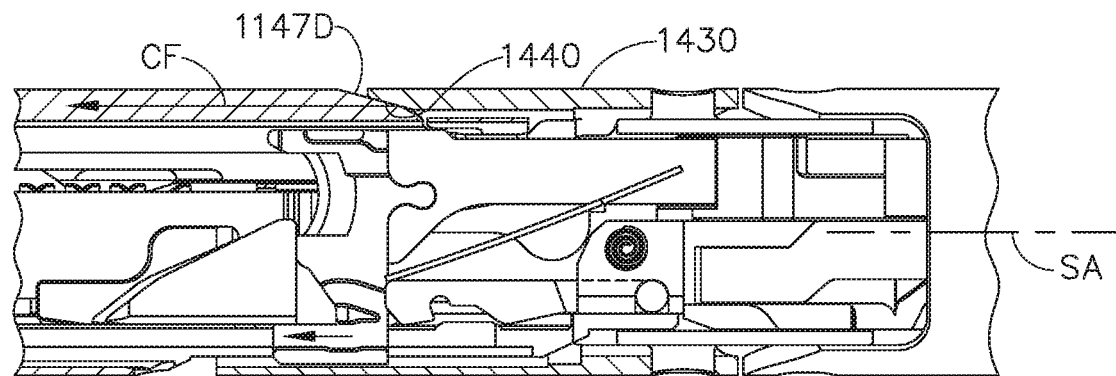
FIG. 20A is another cross-sectional side view of the surgical end effector of FIG. 20 after a firing member thereof has been advanced distally out of a firing member parking area.
Figure 21:
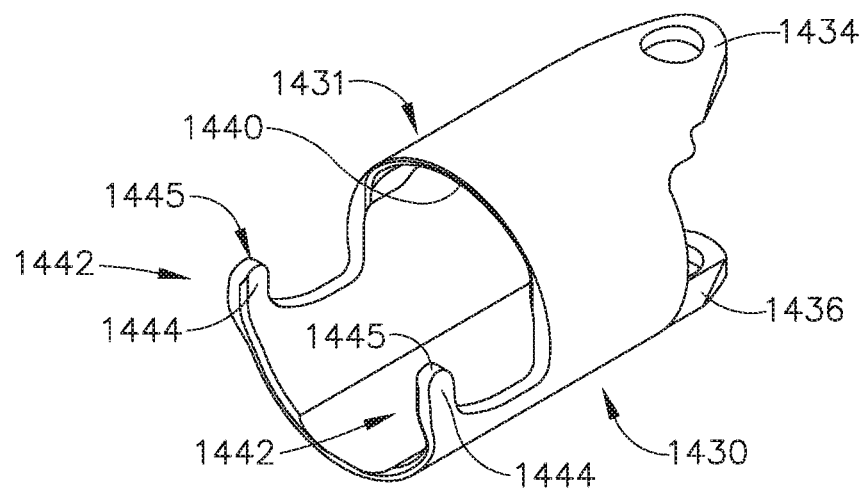
FIG. 21 is a perspective view of a distal closure member embodiment.

Operation of the closure process employed in this example will now be described with reference to FIGS. 18A, 19 and 20A. In the illustrated arrangement, the anvil body portion 1132 defines an upper anvil surface 1135. As can be seen in FIG. 18A, the cam area or cam surface 1147 that is formed on the anvil mounting portion 1134 gradually transitions to the upper anvil surface 1135. More specifically, in the illustrated arrangement, the cam surface 1147 comprises two surface portions: a proximal cam surface portion 1147P and a distal cam surface portion 1147D. In at least one example, the proximal cam surface portion 1147P extends from a proximal end of the anvil body portion 1132 to the distal cam surface portion 1147D. The distal cam surface portion 1147D extends from the proximal cam surface portion 1147P to the upper anvil surface 1135. In one arrangement, the proximal cam surface portion 1147P may have a slightly steeper angle than the distal cam surface portion 1147D. In other arrangements, the cam surface on the anvil mounting portion may comprise one continuous cam surface oriented relative to the outer surface at a single cam angle.

As can be seen in FIG. 19, the distal closure member 1430 has a distal end surface 1431 formed on a distal end thereof. A distal camming surface 1440 extends at an obtuse cam angle CA relative to the distal end surface 1431. In the illustrated arrangement, the distal closure member 1430 comprises a distal closure tube that has an outer surface 1433 and an inner surface 1435 that defines a cross-sectional thickness CT therebetween. The distal end surface 1431 comprises a portion of the cross-sectional thickness CT. The distal camming surface 1440 extends from the distal end surface 1431 to the inner surface 1435 of the distal closure member 1430. An initial cam area 1437 comprises the line or point of intersection between the distal end surface 1431 and the distal camming surface 1440.

FIG. 18A illustrates the distal closure member 1430 in a starting position with the anvil 1130 in an open position. As can be seen in FIG. 18A, the distal camming surface 1440 is in contact with the pre-closure surface 1143 on the anvil cap 1142. To begin the closure process, the distal closure member 1430 is axially advanced in the distal direction DD. When the initial cam area 1437 and/or the distal end surface 1431 initially contacts the cam surface 1147 (proximal cam surface portion 1147P) an initial closure motion or initial closure force ICF is applied thereto. See FIG. 19. This initial closure force ICF is normal or perpendicular to the proximal cam surface portion 1147P. Continued axial advancement of the distal closure member 1430 brings the distal camming surface 1440 into camming engagement with the cam surface 1147 (distal cam surface 1147D) and essentially applies a closure force CF that is essentially parallel to the shaft axis SA. See FIG. 20A.

In the above-described example, the anvil mounting walls 1136 may have a length that is somewhat longer than the anvil mounting configurations employed by other anvil arrangements. Such elongated anvil mounting walls 1136 serve to enable the pivot axis to be located relatively close to the articulation axis that is defined by the articulation joint 1200. This arrangement facilitates establishment of a longer initial moment arm MAI (FIG. 19) between the pivot axis PA and the initial closure force ICF. Such arrangement also facilitates the location of the pivot axis PA in a position that is slightly closer to the bottom of the elongate channel 1102 when compared to other anvil/channel mounting arrangements. Thus, in the illustrated arrangement, the distance between the pivot axis PA and the axis along which the closure force CF is applied is somewhat greater than other arrangements (larger moment arm). This arrangement may also lead to the establishment of a greater closure force CF when compared to other anvil mounting arrangements. Thus, the anvil mounting arrangement of the illustrated example may offer a larger mechanical closure advantage than is commonly attainable with other anvil mounting arrangements. Another advantage that may be gained by the foregoing example, is that locating at least a portion of the firing member parking area 1141 proximal to the pivot axis PA may help to reduce the "negative" moment arm that is applied to the anvil by the tissue that is clamped between the anvil and the cartridge.

Figure 22:
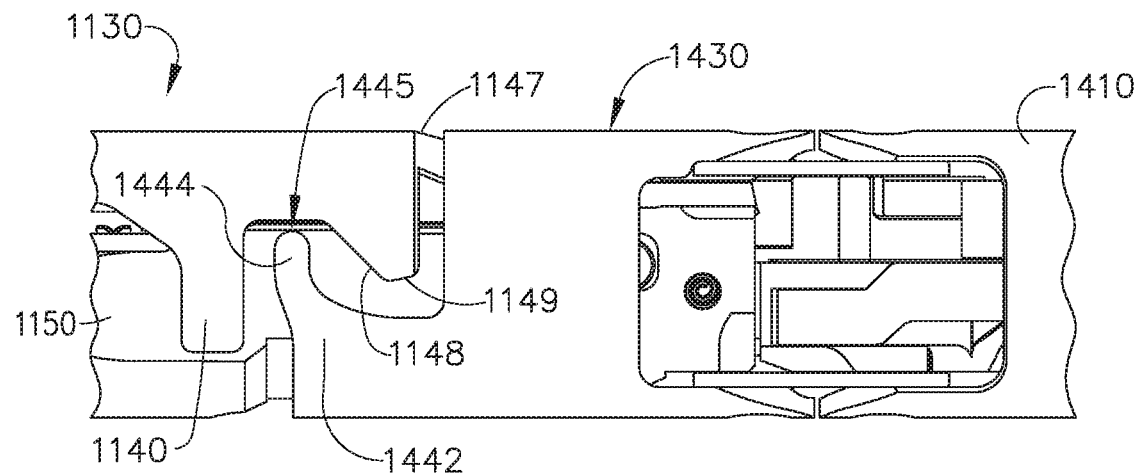
FIG. 22 is a side elevational view of a portion of an interchangeable surgical tool assembly employing the distal closure member of FIG. 21 with an anvil of a surgical end effector portion thereof in a fully closed position.
Figure 23:
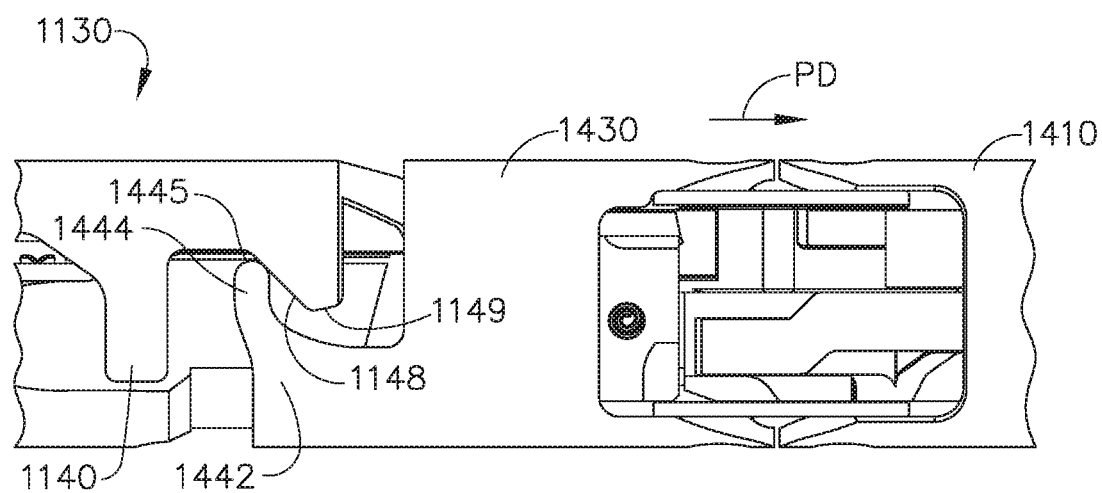
FIG. 23 is another side elevational view of the portion of the interchangeable surgical tool assembly of FIG. 22, with the distal closure member in an initial opening position.
Figure 24:
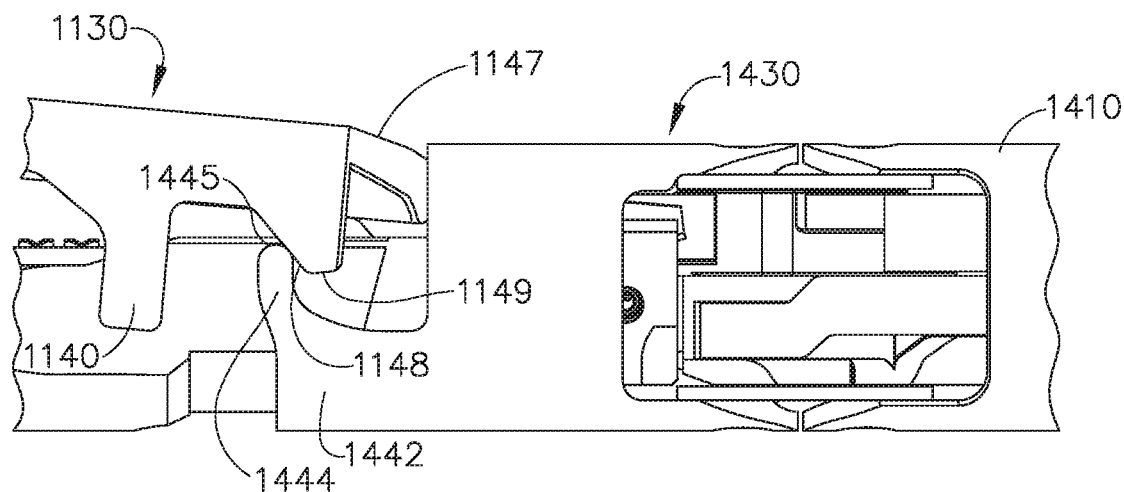
FIG. 24 is another side elevational view of the portion of the interchangeable surgical tool assembly of FIG. 22, with the distal closure member in another opening position.
Figure 25:
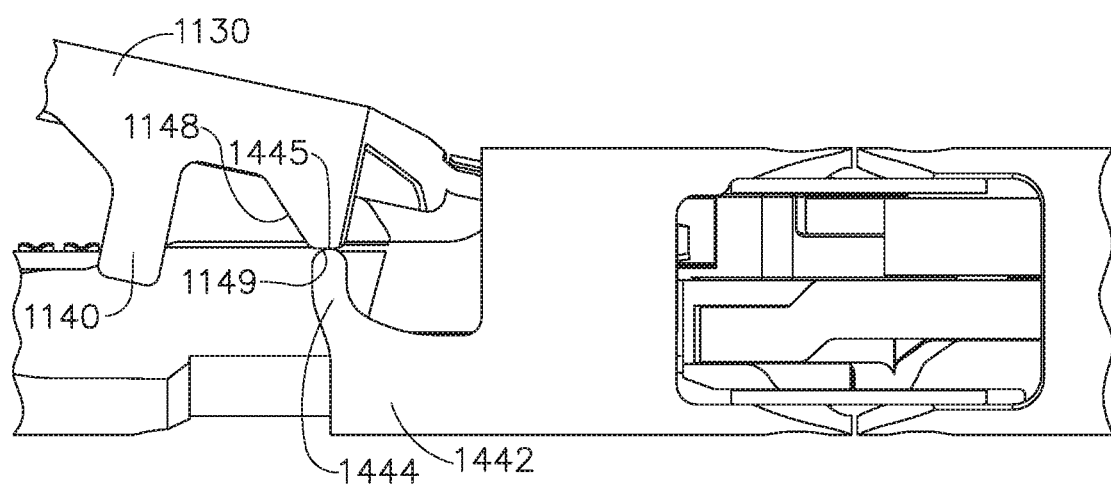
FIG. 25 is another side elevational view of the portion of the interchangeable surgical tool assembly of FIG. 22, with the anvil thereof in a fully opened position.

Turning now to FIGS. 21-25, the distal closure member 1430 is formed with at least one and preferably two, positive jaw opening hooks or tabs 1442. Tabs 1442 may also be referred to herein as "primary positive jaw opening tabs". In one example, the positive jaw opening tabs are integrally formed into the distal closure member 1430. For example, the positive jaw opening tabs 1442 are cut out of the walls of the tubular structure comprising the distal closure member 1430. Each of the positive jaw opening tabs 1442 include an upwardly protruding hook portion 1444 that has a rounded camming end 1445 formed thereon that is configured for camming engagement with a corresponding anvil opening ramp 1148 extending downwardly from the anvil body portion 1132. FIG. 22 illustrates the position of the anvil 1130 and distal closure member 1430 when the anvil 1130 is in a closed orientation. FIG. 23 illustrates the beginning of the opening process wherein the distal closure member 1430 has started to be retracted in the proximal direction PD. As can be seen in FIG. 23, the camming end 1445 has initially contacted the anvil opening ramp 1148. FIG. 24 illustrates the anvil 1130 in a partially opened position and FIG. 25 illustrates the anvil 1130 in a fully opened position. As can be seen in FIG. 25, the camming end 1445 is on the bottom end 1149 of the anvil opening ramp to retain the anvil 1130 in the fully opened position. Such use of features on the distal closure member to effectuate the opening of the anvil from a fully closed position to a fully open position may be referred to herein as "positive jaw opening" features. Other suitable positive jaw opening arrangements are disclosed in U.S. patent application Ser. No. 14/742,925, entitled SURGICAL END EFFECTORS WITH POSITIVE JAW OPENING ARRANGEMENTS, which has been incorporated by reference in its entirety herein.

Figure 26:
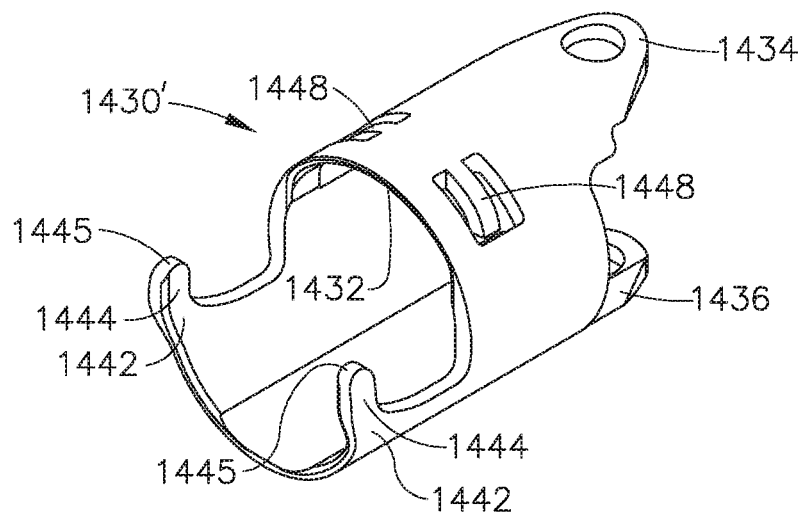
FIG. 26 is a perspective view of another distal closure member embodiment.
Figure 27:
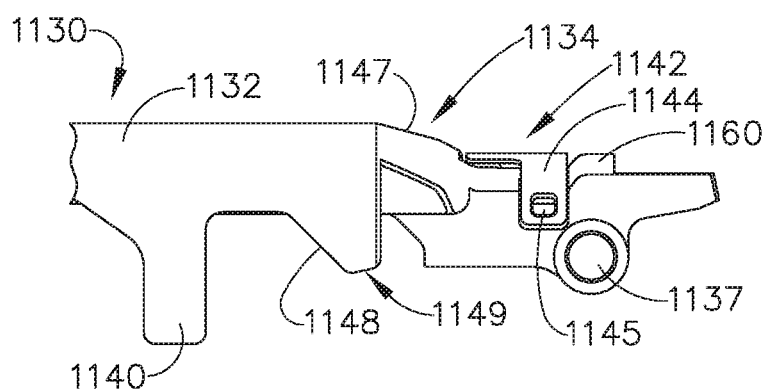
FIG. 27 is a side view of another anvil embodiment.
Figure 28:
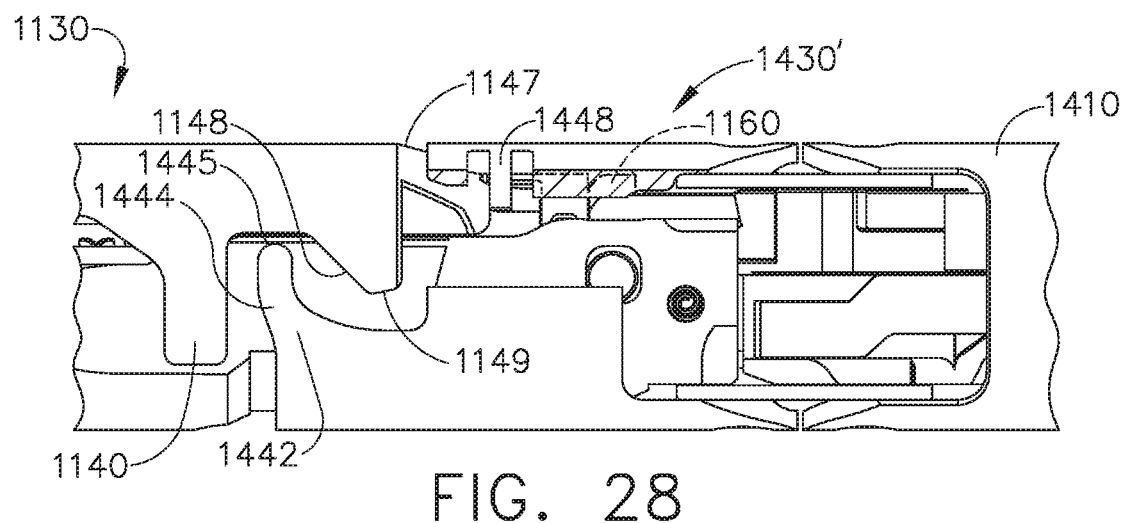
FIG. 28 is a partial cross-sectional side view of another interchangeable surgical tool assembly employing the distal closure member of FIG. 26 and the anvil embodiment of FIG. 27 with the anvil in a fully closed position.
Figure 29:
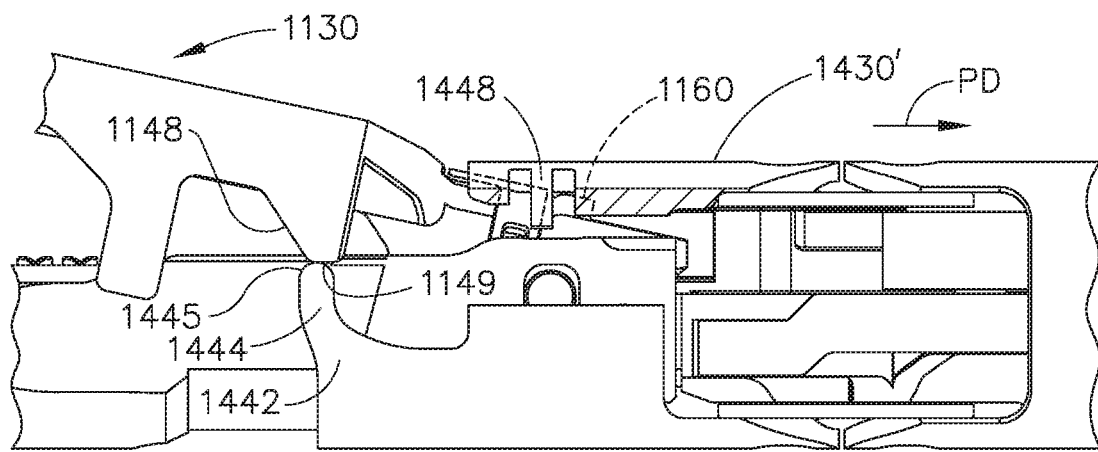
FIG. 29 is another partial cross-sectional side view of the interchangeable surgical tool assembly of FIG. 28 with the anvil thereof in a fully open position.

FIGS. 26-29 illustrate an alternative distal closure member 1430' that employs secondary positive jaw opening tabs 1448 that are configured to cooperate with secondary jaw opening features 1160 that are formed on the anvil mounting walls 1136. See FIGS. 16, 17 and 27. As can be seen in FIG. 26, the secondary positive jaw opening tabs 1448 may be cut into the walls of the distal closure tube or member 1430' and bent inward so as to be able to contact the secondary jaw opening features 1160 on the anvil 1130 as the distal closure tube or member 1430' is moved in the proximal direction PD. FIG. 29 illustrates the anvil 1130 in a fully opened position. As the distal closure member 1430' is moved proximally, the primary positive jaw opening tabs 1442 cam up the corresponding anvil opening ramp 1148 on the anvil 1130 and begin to pivot the anvil open. Thereafter, during the closing process, the secondary positive jaw opening tabs 1448 in the distal closure member 1430' contact the secondary jaw opening features 1160 that are formed on the anvil mounting walls 1136 to further assist with moving the anvil 1130 to the fully opened position. As can be seen in FIG. 26 the secondary positive jaw opening tabs 1448 generally follow the contour of the distal closure tube 1430'.

Figure 30:
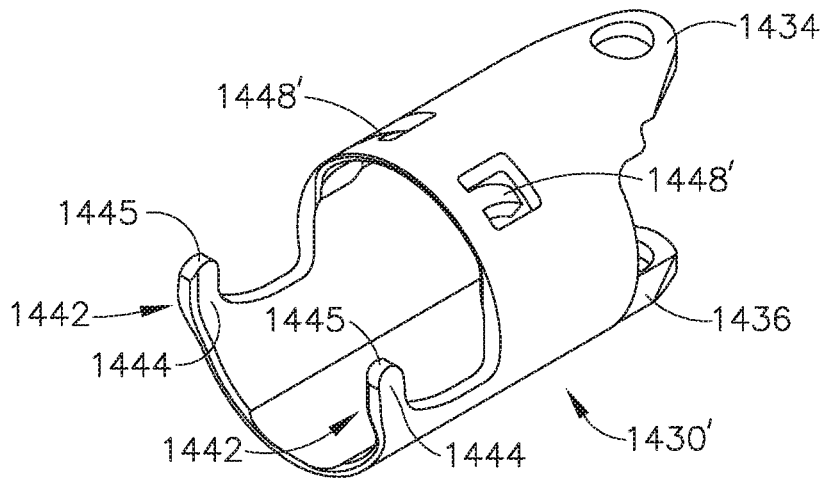
FIG. 30 is a perspective view of another distal closure member embodiment.
Figure 31:
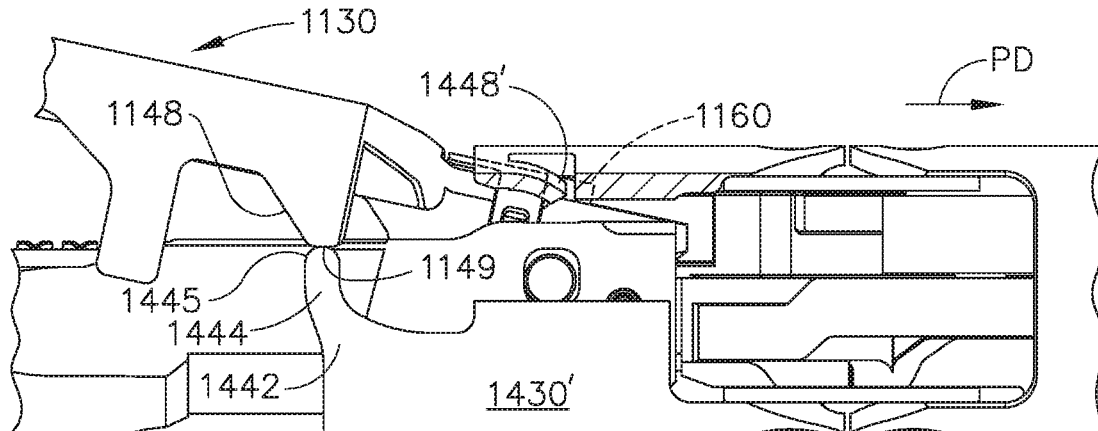
FIG. 31 is a partial cross-sectional side view of another interchangeable surgical tool assembly employing the distal closure member embodiment of FIG. 30 and with an anvil thereof in a fully open position.

FIG. 30 illustrates an alternative distal closure member 1430' wherein the secondary positive jaw opening tabs 1448' are integrally formed into the wall of the distal closure tube 1430', but they extend proximally inward to contact the secondary jaw opening features 1160 on the anvil 1130 as the distal closure tube or member 1430' is moved in the proximal direction PD. FIG. 31 illustrates the anvil 1130 in a fully opened position. Such primary and secondary anvil opening or jaw opening features may therefore serve to sequentially apply opening motions to the anvil as the distal closure member moves from a fully actuated position which corresponds to the fully closed position of the anvil to an unactuated position which corresponds to the fully open position of the anvil. In such arrangement, as the distal closure tube 1430' is moved in the proximal direction, the primary positive jaw opening tabs 1442 cam the anvil into a "mostly open" position. The secondary positive jaw opening tabs 1448 serve to assure that the anvil is moved into its fully open position when the distal closure member is moved back to the unactuated position.

Figure 32:
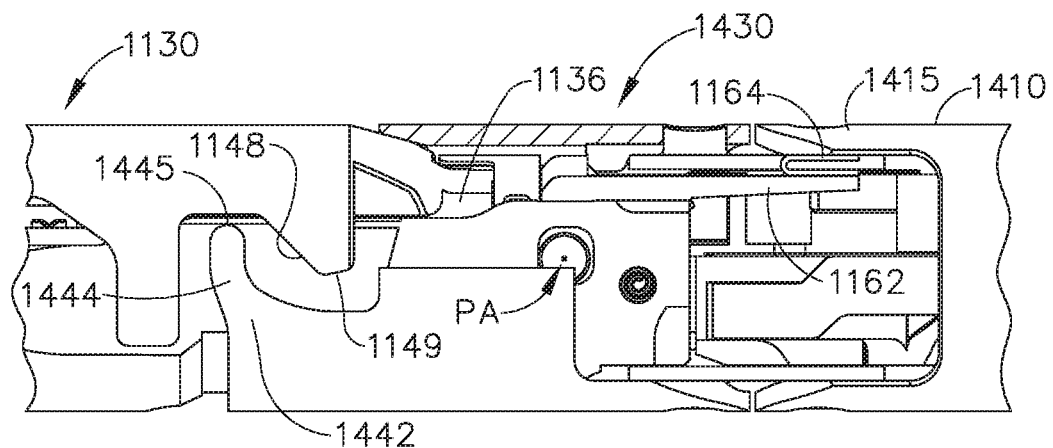
FIG. 32 is a partial cross-sectional side view of another interchangeable surgical tool assembly with an anvil thereof in a fully closed position.
Figure 33:
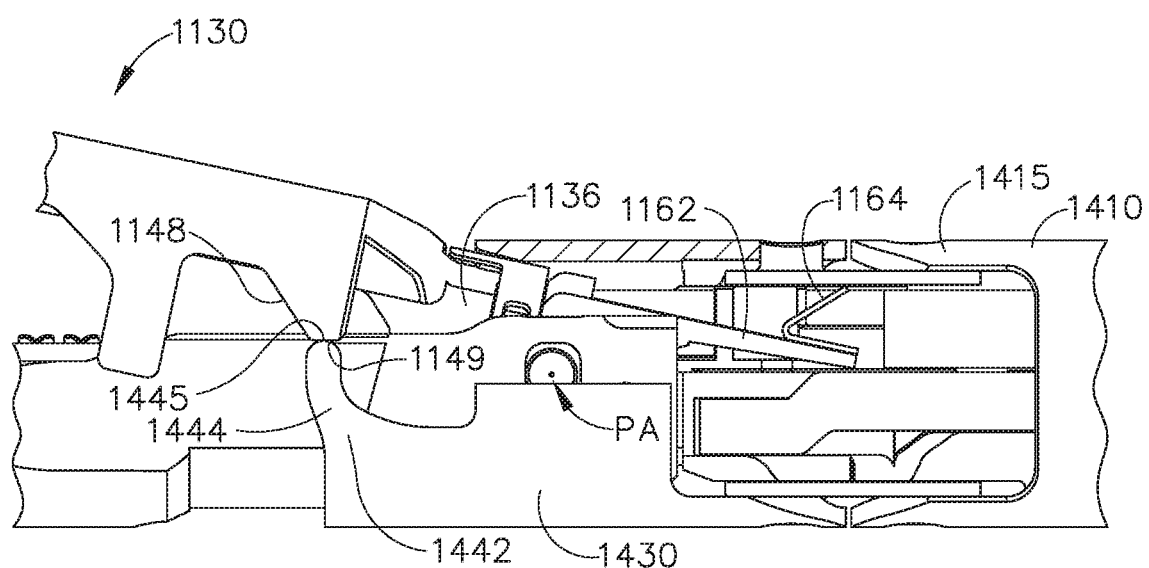
FIG. 33 is another partial cross-sectional side view of the interchangeable surgical tool assembly of FIG. 32 with the anvil thereof in a fully open position.

FIGS. 32 and 33 illustrate an alternative secondary positive jaw opening arrangement wherein the anvil mounting walls 1136 include a proximal anvil extension 1162 that cooperates with a corresponding secondary anvil biasing spring 1164 to bias the anvil into an open position. As the distal closure member 1430 is moved proximally, the primary positive jaw opening tabs 1442 cam up the corresponding anvil opening ramp 1148 on the anvil 1130 and begin to pivot the anvil open. In addition, the secondary anvil biasing spring 1164 applies a biasing force to the proximal anvil extension 1162 to further assist with moving the anvil 1130 to the fully opened position. In prior jaw opening arrangements, there is commonly a "lag time" between actuation of the jaw opening system (e.g., firing trigger) and the active opening of the jaws. In the above-described example, the secondary anvil biasing spring 1164 is located proximal to the pivot axis PA about which the anvil pivots relative to the elongate channel. Such arrangement may serve to increase the biasing (opening) motion to the anvil as well as to minimize the occurrence of any "dead zone" that might otherwise occur between initial retraction of the closure member and a point wherein the closure member actually starts to apply a sufficient amount of opening motion to the anvil to cause the anvil to move to the open position.

Figure 34:
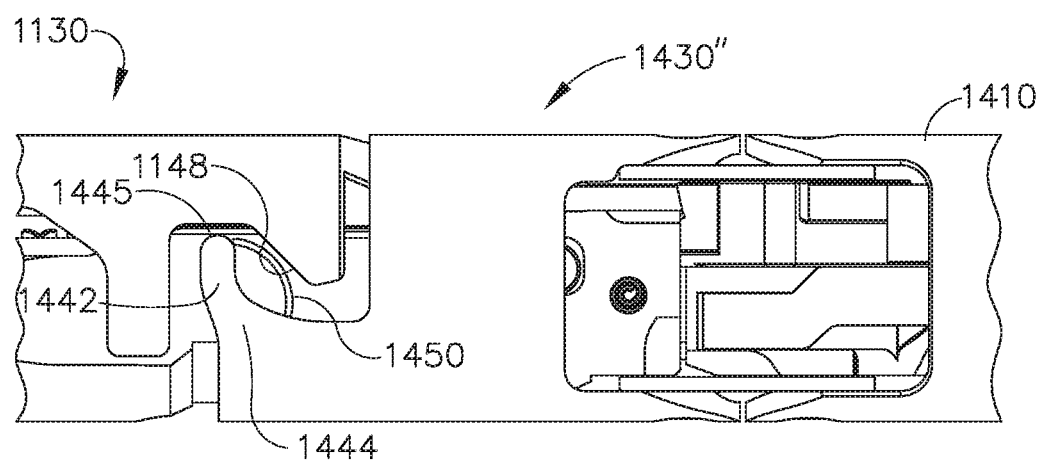
FIG. 34 is a side elevational view of a portion of another interchangeable surgical tool assembly with an anvil thereof in a fully closed position.
Figure 35:
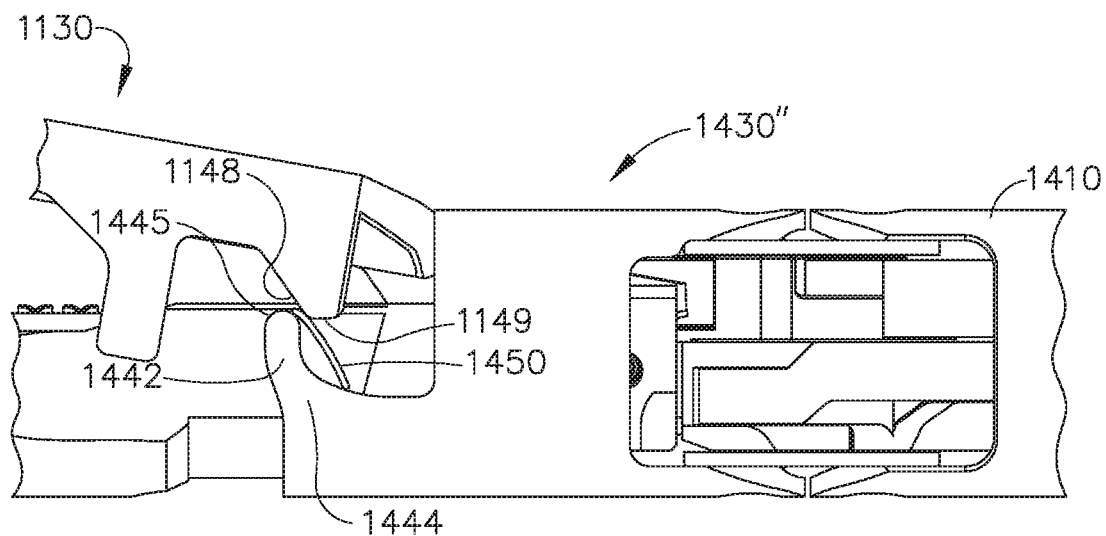
FIG. 35 is another side elevational view of the portion of the interchangeable surgical tool assembly of FIG. 34 with the anvil thereof in a fully open position.
Figure 36:
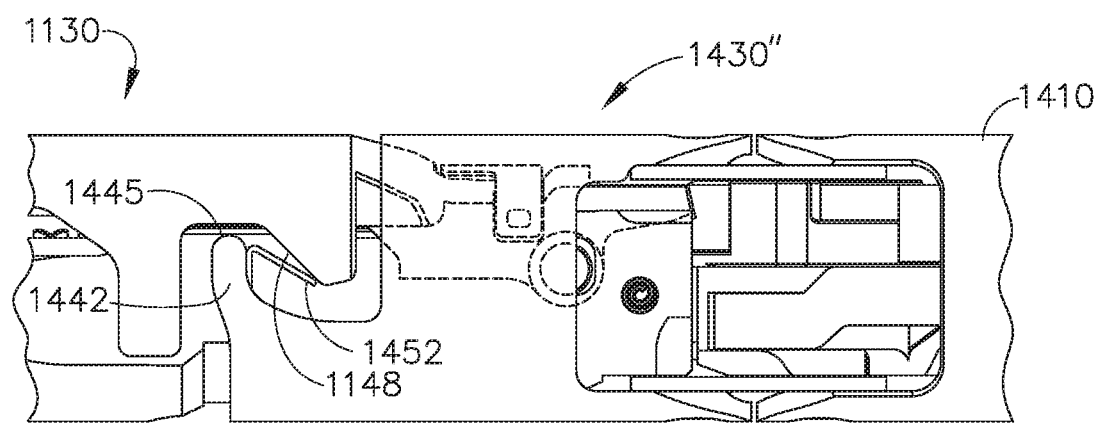
FIG. 36 is a side elevational view of a portion of another interchangeable surgical tool assembly with an anvil thereof in a fully closed position.
Figure 37:
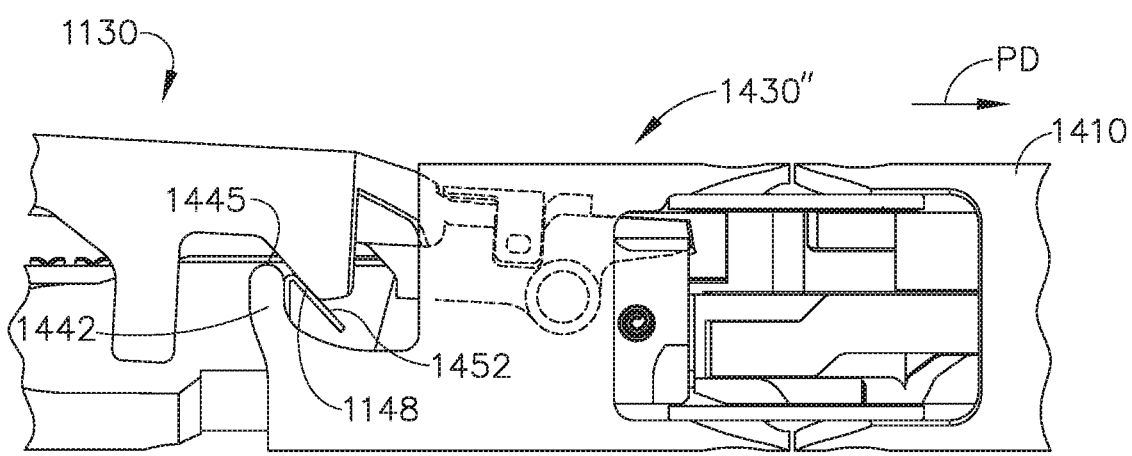
FIG. 37 is another side elevational view of the portion of the interchangeable surgical tool assembly of FIG. 36 with the anvil thereof in a partially open position.

FIGS. 34 and 35 illustrate an alternative distal closure member 1430" that employs a positive jaw biasing member 1450 on each of the positive jaw opening tabs 1442. The positive jaw biasing members 1450 may form leaf-type spring arrangements formed from metal or the like and serve to apply additional opening forces to the anvil opening ramps 1148 on the anvil 1130 as the distal closure member 1430" is moved in the proximal direction PD. FIG. 34 illustrates the anvil 1130 in a fully closed position and FIG. 35 illustrates the anvil 1130 in a fully opened position. FIGS. 36 and 37 illustrate an alternative distal closure member 1430" that employs another form of positive jaw biasing member 1452 on each of the positive jaw opening tabs 1442. The positive jaw biasing members 1452 may have a somewhat V-shape configuration and be formed from spring steel or the like. FIG. 36 illustrates the anvil 1130 in a fully closed position and FIG. 37 illustrates the anvil 1130 in a partially opened position as the distal closure member 1430" initially moves in the proximal direction. The positive jaw biasing members 1452 serve to ensure that the anvil 1130 is raised against the distal closure member 1430" from the beginning of the opening process.

Figure 38:
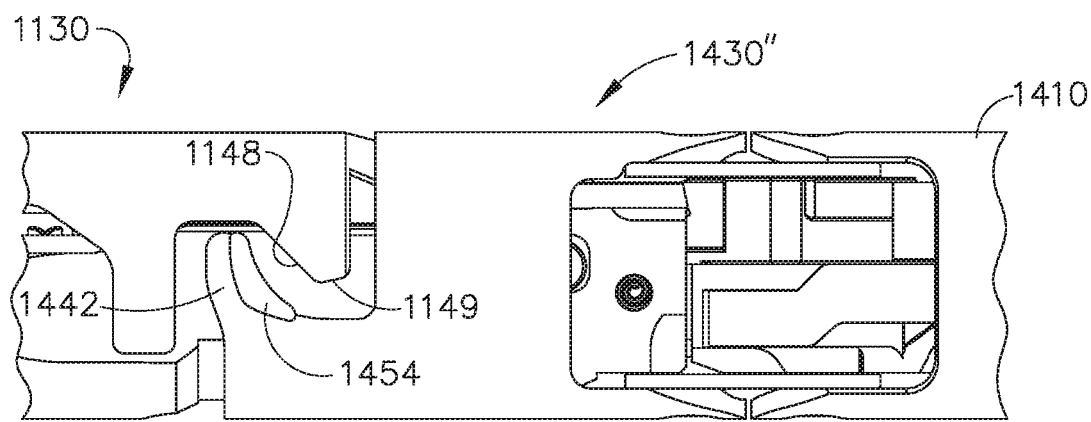
FIG. 38 is a side elevational view of a portion of another interchangeable surgical tool assembly with an anvil thereof in a fully closed position.
Figure 39:
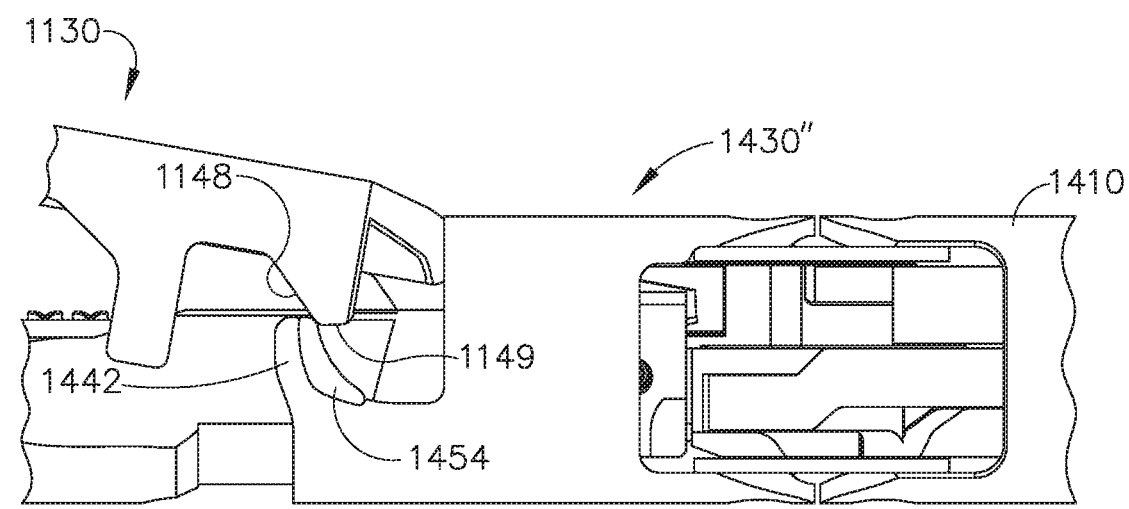
FIG. 39 is another side elevational view of the portion of the interchangeable surgical tool assembly of FIG. 38 with the anvil thereof in a partially open position.

FIGS. 38 and 39 illustrate an alternative distal closure member 1430" wherein each of the positive jaw opening tabs 1442 have a compliant portion 1454 thereon that serves to ensure that the anvil 1130 is raised against the distal closure member 1430" from the beginning of the opening process. The compliant portion 1454 may comprise rubber or similar material formed onto the hook portions 1444 of the positive jaw opening tabs 1442. In other arrangements, the portions 1454 may not be formed from compliant material, but instead may be formed from a hardened material to prevent wear on the positive jaw opening tabs 1442. FIG. 38 illustrates the anvil 1130 in a fully closed position and FIG. 39 illustrates the anvil 1130 in a partially opened position. Such compliant arrangements and biasing member arrangements may serve to urge the anvil open while the closure member cam features remain in camming engagement with the cam ramps on the anvil to minimize any dead zone lag occurring between actuation of the closure system (to open the anvil) and the actual opening of the anvil. Such configurations may also serve to establish solid camming surfaces that would enable the user to overpower an anvil jam by operating the closure trigger.

Figure 40:
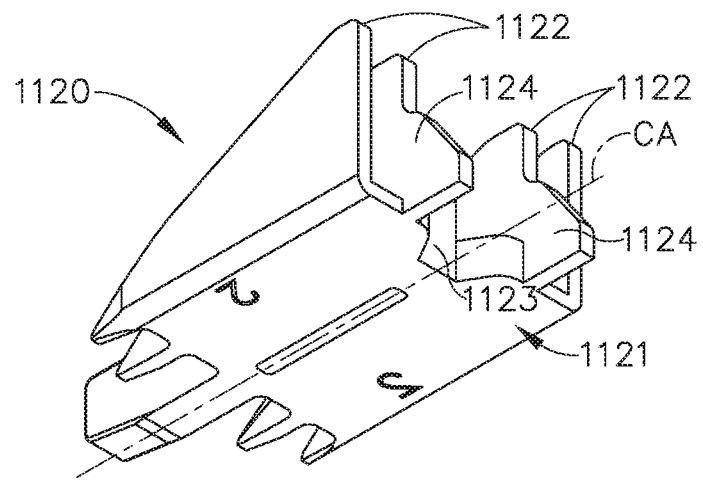
FIG. 40 is a bottom perspective view of a camming or sled assembly embodiment.
Figure 41:
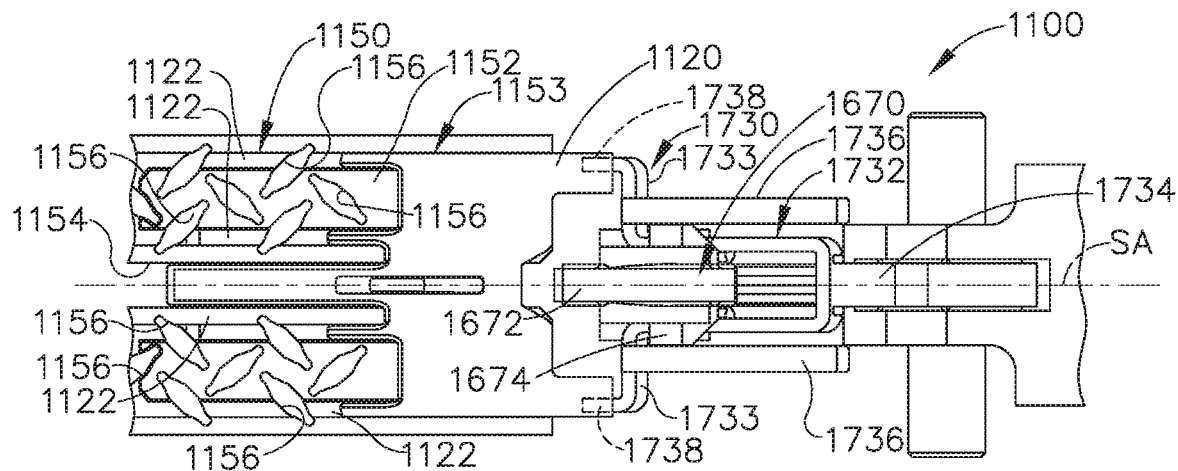
FIG. 41 a top view of a portion of a surgical end effector embodiment with an unfired surgical staple cartridge installed therein and with a camming assembly thereof in a starting position and in unlocking engagement with a firing member lock member.
Figure 42:
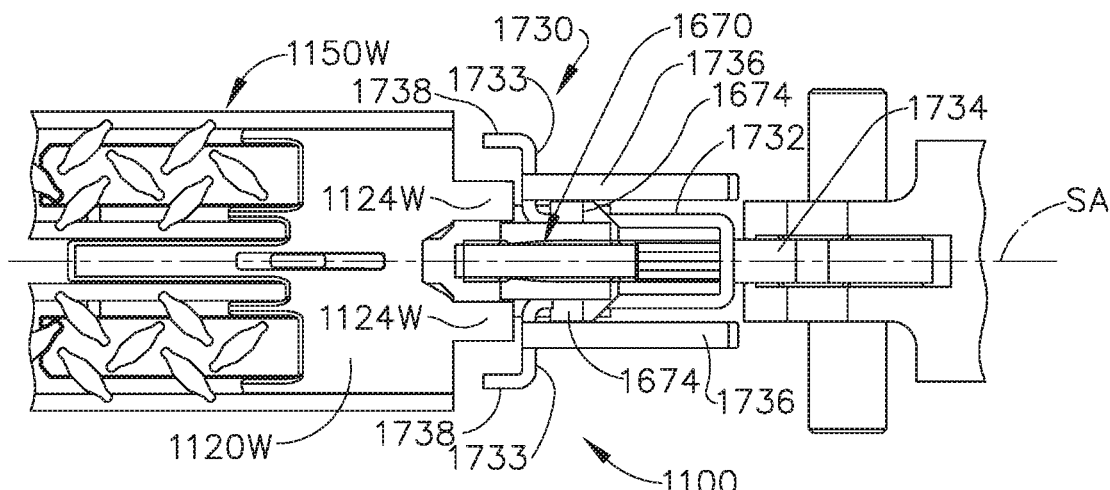
FIG. 42 is a top view of a portion of the surgical end effector embodiment of FIG. 41 that has an improper unfired surgical staple cartridge installed therein with a camming assembly thereof in a starting position and with a firing member lock in locking engagement with the firing member.

Turning next to FIGS. 40-42, the firing member 1670 is configured to operably interface with a sled or cam assembly 1120 that is operably supported within the body 1151 of the surgical staple cartridge 1150. The cam assembly 1120 is slidably displaceable within the surgical staple cartridge body 1151 from a proximal starting position adjacent the proximal end 1153 of the cartridge body 1151 to an ending position adjacent a distal end 1155 of the cartridge body 1151. The cartridge body 1151 operably supports therein a plurality of staple drivers (not shown) that are aligned in rows on each side of a centrally disposed slot 1154. The centrally disposed slot 1154 enables the firing member 1670 to pass therethrough and cut the tissue that is clamped between the anvil 1130 and the surgical staple cartridge 1150. The drivers are associated with corresponding pockets 1156 that open through the upper deck surface 1152 of the cartridge body 1151. Each of the staple drivers supports one or more surgical staple or fastener (not shown) thereon. Thus, a plurality of surgical staples are arranged in lines or rows situated on both sides of the slot 1154. The cam assembly 1120 includes a plurality of sloped or wedge-shaped cams 1122 wherein each cam 1122 corresponds to a particular line of fasteners or drivers located on a side of the slot 1154. When the firing member 1670 is fired or driven distally, the firing member 1670 drives the cam assembly 1120 distally as well. As the firing member 1670 moves distally through the surgical staple cartridge 1150, the tissue cutting feature 1676 cuts the tissue that is clamped between the anvil 1130 and the surgical staple cartridge 1150 and the cam assembly 1120 drives the drivers upwardly in the cartridge which drive the corresponding staples or fasteners into forming contact with the anvil 1130.

In those embodiments wherein the firing member includes a tissue cutting surface or tissue cutting feature, it may be desirable for the elongate shaft assembly to be configured in such a way so as to prevent the inadvertent advancement of the firing member unless an unfired or new staple cartridge is properly supported in the elongate channel 1102 of the surgical end effector 1100. If, for example, no staple cartridge is present at all and the firing member is distally advanced through the end effector, the tissue would be severed, but not stapled. Similarly, if a spent staple cartridge (i.e., a staple cartridge wherein at least some of the staples have already been fired therefrom) is present in the end effector and the firing member is advanced, the tissue may be severed, but may not be completely stapled, if at all. It will be appreciated that such occurrences could lead to undesirable catastrophic results during the surgical procedure. U.S. Pat. No. 6,988,649 entitled SURGICAL STAPLING INSTRUMENT HAVING A SPENT CARTRIDGE LOCKOUT, U.S. Pat. No. 7,044,352 entitled SURGICAL STAPLING INSTRUMENT HAVING A SINGLE LOCKOUT MECHANISM FOR PREVENTION OF FIRING, and U.S. Pat. No. 7,380,695 entitled SURGICAL STAPLING INSTRUMENT HAVING A SINGLE LOCKOUT MECHANISM FOR PREVENTION OF FIRING, and U.S. patent application Ser. No. 14/742,933, entitled SURGICAL STAPLING INSTRUMENTS WITH LOCKOUT ARRANGEMENTS FOR PREVENTING FIRING SYSTEM ACTUATION WHEN A CARTRIDGE IS SPENT OR MISSING each disclose various firing member lockout arrangements that may be employed. Each of those references is hereby incorporated by reference in their entireties herein.

An "unfired", "unspent", "fresh" or "new" surgical staple cartridge 1150 means herein that the surgical staple cartridge 1150 has all of its fasteners in their "ready-to-be-fired" positions when properly loaded within the end effector. When in that position, the cam assembly 1120 is located in its starting position. The new surgical staple cartridge 1150 is seated within the elongate channel 1102 and may be retained therein by snap features on the cartridge body that are configured to retainingly engage corresponding portions of the elongate channel 1102. FIG. 41 illustrates portions of the surgical end effector 1100 with a new or unfired surgical staple cartridge 1150 seated therein. As can be seen in FIG. 41, the cam assembly 1120 is in the starting position. To prevent the firing system from being activated and, more precisely, to prevent the firing member 1670 from being distally driven through the end effector 1100 unless an unfired or new surgical staple cartridge has been properly seated within the elongate channel 1102, the illustrated interchangeable surgical tool assembly 1000 employs a firing member lockout system generally designated as 1730 that, in certain aspects, may be similar to the lockout systems disclosed in U.S. patent application Ser. No. 15/385,958, filed on Dec. 21, 2016, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT, the entire disclosure of which is hereby incorporated by reference herein in its entirety.

In the illustrated example, the firing member lockout system 1730 includes a movable lock member 1732 that is configured to retainingly engage the firing member 1670 when an unspent or unfired surgical staple cartridge 1150 is not properly seated within the elongate channel 1102. The lock member 1732 comprises a pair of lateral spring arms 1733 that are interconnected by a central mount tab feature 1734. As can be seen in FIG. 41, each of the lateral spring arms 1733 are laterally offset from the shaft axis SA. When the lock member 1732 is installed, the mount tab feature 1734 is configured to bias the lock member 1732 upward. In addition, the lock member 1732 includes two lateral anvil spring arms 1736 that angle upward to engage the bottom surface of a corresponding anvil mounting wall 1136 on the anvil mounting portion 1134 to bias the lock member 1732 downward when the anvil 1130 is closed. The distal portion of each lateral spring arm 1733 terminates in a sled tab 1738 that are each further laterally offset from the shaft axis SA. Each of the sled tabs 1738 are oriented to contact a corresponding unlocking feature or sled boss 1124 that is formed on the proximal end portion 1121 of the cam assembly 1120. As can be seen in FIG. 40, for example, in the illustrated arrangement, the cam assembly 1120 has a central axis CA. When the sled assembly 1120 is in its starting position within an unfired staple cartridge that is properly supported in the elongate channel, the central axis CA is laterally aligned with the shaft axis SA. As can be seen in FIG. 40, the sled bosses are laterally offset from the central axis CA (and ultimately the shaft axis SA) so as to define a central area 1123 therebetween. When the firing member is distally advanced through the end effector, the firing member contacts the cam assembly 1120 in the central area to drive the cam assembly 1120 distally through the cartridge body. In alternative arrangements, only one lateral spring arm 1733 may be employed and therefore only one lateral sled tab 1738 is provided. In such arrangement, only one corresponding sled boss 1124 is formed on the cam assembly 1120. In still other arrangements, the lock member 1732 may have two lateral spring arms 1733, but only one of the lateral spring arms may be provided with a sled tab 1738. In the illustrated arrangement, each of the proximally facing sled bosses 1124 includes a ramp 1127 to facilitate easier interfacing between the sled bosses 1124 and the lateral sled tabs 1738 during installation of the cartridge in the elongate channel.

Each of the lateral spring arms 1733 includes a lock notch therein that is configured to lockingly engage a corresponding central lock lug 1674 that extends laterally from a firing member body portion 1672. FIG. 41 illustrates the cam assembly 1120 in a starting position wherein the sled bosses 1124 have lifted the lock member 1732 out of locking engagement with the lock lugs 1674. FIG. 42 illustrates an improper surgical staple cartridge 1150W installed in relation to the lock member 1732. As can be seen in FIG. 42, although the cartridge 1150W has a cam assembly 1120W with proximally extending features 1124W that are laterally offset from a central axis of the cam assembly, the features 1124W are in not in unlocking engagement with the sled tabs 1738 of the lock member 1732. Thus, the cam assembly 1120W, even though in its starting position, will not move the lock member 1732 out of locking engagement with the firing member 1670.

In alternative arrangements, the lock member may be configured to complete an electrical circuit when it is moved down into contact with a corresponding portion of a sled of a properly loaded unfired cartridge (when the sled is in its proper firing position). In such arrangement, for example, when the circuit is open, the motor is inoperable. In one arrangement, the lock member may also be able to mechanically engage the firing member in the above-described manner to thereby facilitate both mechanical and electrical lockout features/capabilities.

Figure 43:
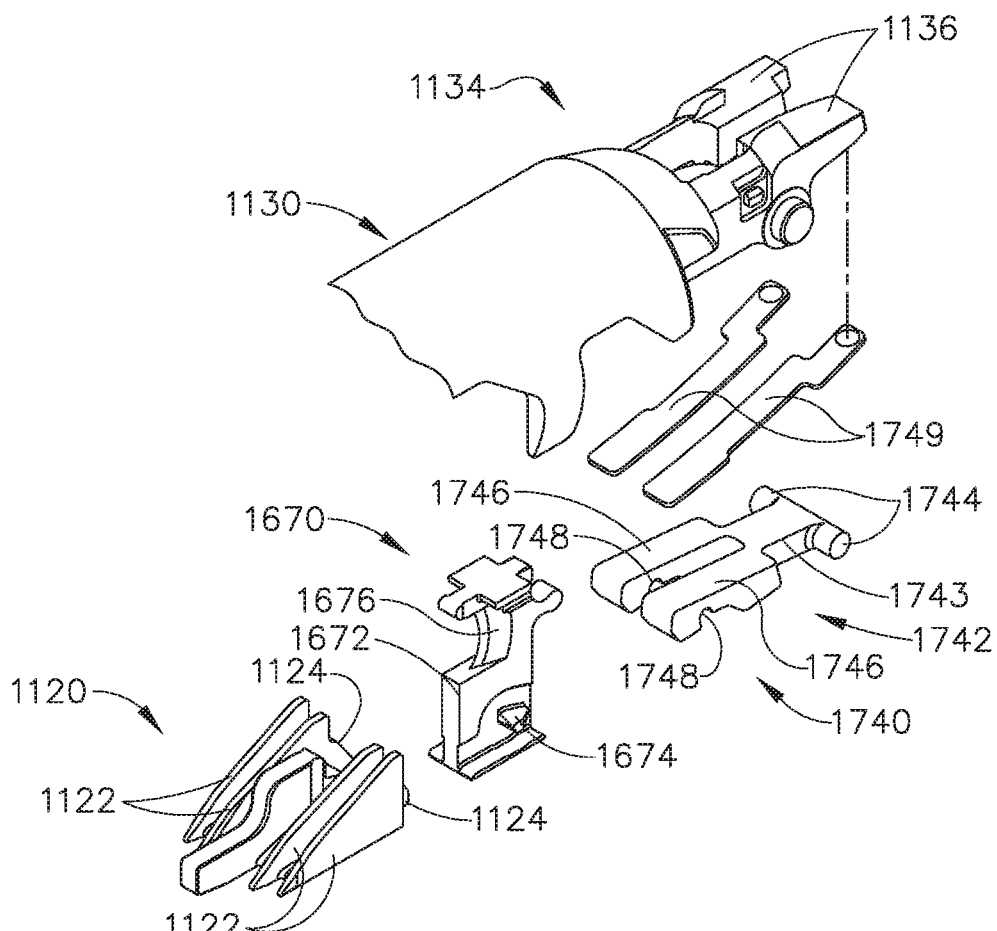
FIG. 43 is an exploded perspective view of portions of an anvil, a firing member, a sled assembly and firing member lock embodiment of another interchangeable surgical tool assembly embodiment.
Figure 44:
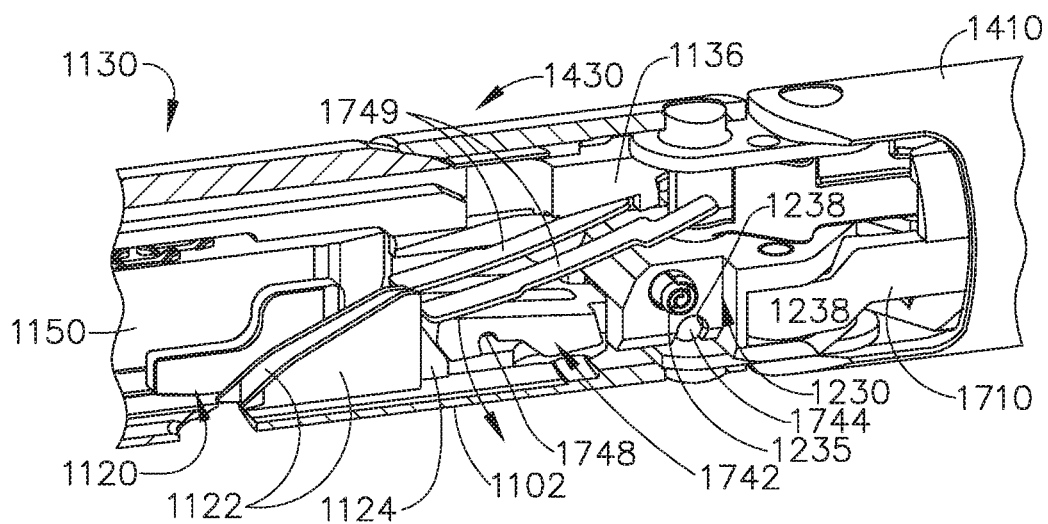
FIG. 44 is a partial cross-sectional view of a distal portion of the interchangeable surgical tool assembly of FIG. 43 with the firing member thereof omitted for clarity.

FIGS. 43-50 illustrate another firing member lockout system 1740 that may be employed in connection with the various end effector embodiments disclosed herein. In this embodiment, the firing member lockout system 1740 includes a firing member lock 1742 that is supported for pivotal travel between a locked position wherein the firing member lock 1742 is in locking engagement with the firing member 1670 and an unlocked position wherein the firing member 1670 is free to be distally advanced through the surgical staple cartridge 1150. As can be seen in FIG. 43, the firing member lock 1742 includes a mounting portion 1743 that has a pivot member 1744 protruding laterally from each side thereof. The pivot members 1744 are pivotally captured within pivot notches 1238 provided in the underside of the end effector mounting assembly 1230. See FIG. 44. As can be seen in FIG. 44, the pivot members 1744 are rotatably captured in the pivot notches 1238 by the lower double pivot link 1222. As can also be seen in FIG. 43, a pair of hook arms 1746 extends distally from the mounting portion 1743.

Each hook arm 1746 includes a lock notch 1748 that is formed in the underside thereof that is configured to engage a corresponding one of the central lock lugs 1674 on the firing member 1670. The firing member lockout system 1740 further includes a pair of biasing members 1749 in the form of leaf springs or the like that engage the corresponding anvil mounting walls 1136 on the anvil 1130 and the firing member lock 1742 to bias the firing member lock 1742 downwardly.

Figure 45:
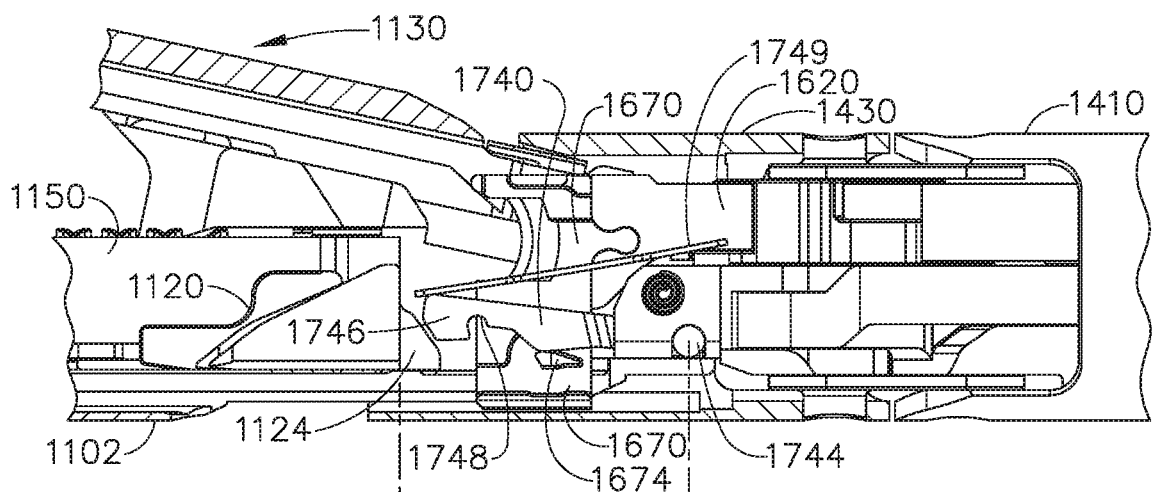
FIG. 45 is another partial cross-sectional view of the distal portion of the interchangeable surgical tool assembly of FIG. 44 with an unfired surgical staple cartridge properly seated within a surgical end effector thereof and with an anvil thereof in an open position and the firing member in a starting position.

FIG. 45 illustrates the surgical end effector 1100 with the anvil 1130 and the elongate channel 1102 in their fully opened position which occurs during the loading of an unspent or unfired surgical staple cartridge 1150 therein. When in the open position, the firing member 1670 cannot be distally advanced at least due to the misalignment of portions of the firing member with corresponding passages within the anvil 1130. In addition, the instrument may employ various sensor arrangements that are configured to detect the position of the anvil and/or configurations of other portions of the anvil closure system to prevent actuation of firing system components unless the anvil is in a fully closed position. As can be seen in FIG. 45, when in the open position, the hook arms 1746 are oriented in an unactuated position wherein a portion of each of the hook arms 1746 is received on the corresponding central lock lug 1674 of the firing member 1670 such that the lock notch 1748 is not in position to engage the corresponding central lock lug 1674.

Figure 46:
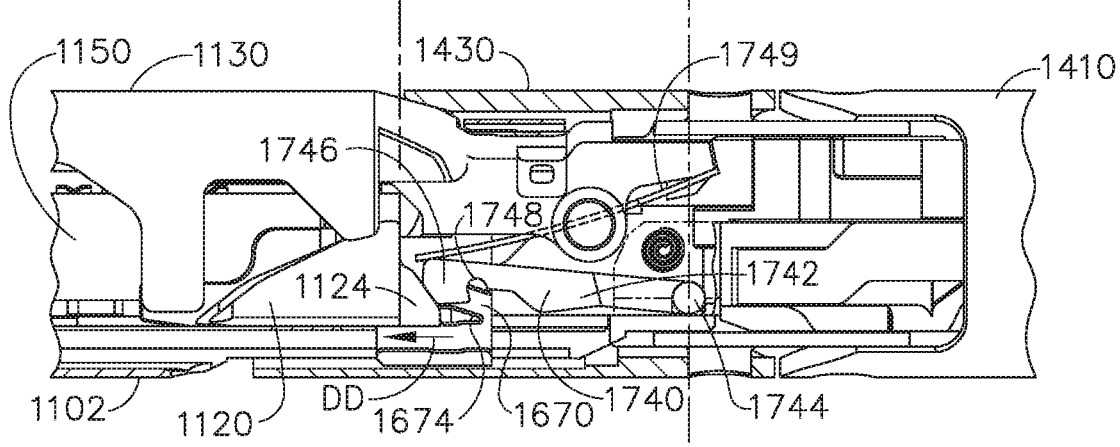
FIG. 46 is another partial cross-sectional view of the distal portion of the interchangeable surgical tool assembly of FIG. 45 with the anvil in a fully closed position and the firing member in an initial firing position.
Figure 47:
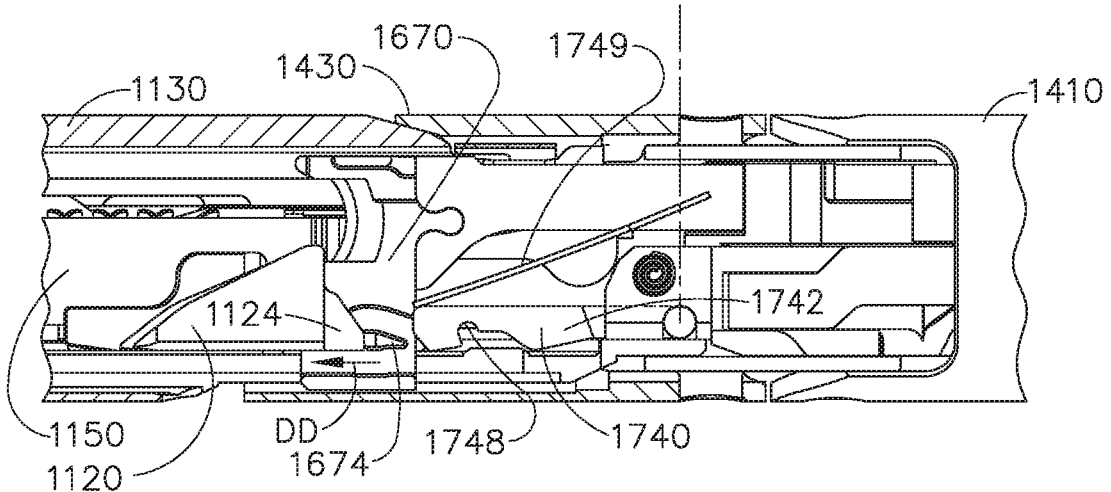
FIG. 47 is another partial cross-sectional view of the distal portion of the interchangeable surgical tool assembly of FIG. 45 with the anvil in a fully closed position and the firing member further distally advanced within the surgical end effector.

FIG. 46 illustrates the end effector after an unfired surgical staple cartridge 1150 with a sled assembly or cam assembly 1120 has been properly installed in the elongate channel 1102 and the anvil 1130 has been is closed. When in such configuration, the biasing member 1749 applies a downward biasing motion onto the firing member lock 1742, which is now in contact with the sled bosses 1124 as well as the central lock lug 1674 on the firing member 1670. As can be further seen in FIG. 46, the sled bosses 1124 on the sled assembly 1120 serve to lift the firing member lock 1742 upward so that the lock notches 148 therein are out of locking engagement with the central lock lugs 1674 on the firing member 1670. Thus, the firing member 1670 is free to be distally advanced as illustrated in FIG. 47. As can be seen in FIG. 47, the firing member lock 1742 is out of engagement with the firing member 1670 as well as the sled assembly 1120 and the biasing members 1749 have pivoted the firing member lock 1742 downward.

Figure 48:
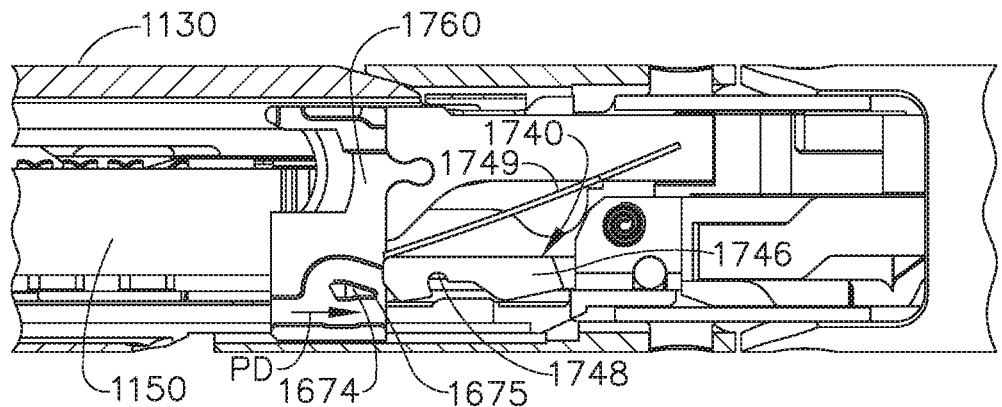
FIG. 48 is another partial cross-sectional view of the distal portion of the interchangeable surgical tool assembly of FIG. 47 with the anvil in a fully closed position and the firing member being retracted back to a starting position just prior to contacting the firing member lock.
Figure 49:
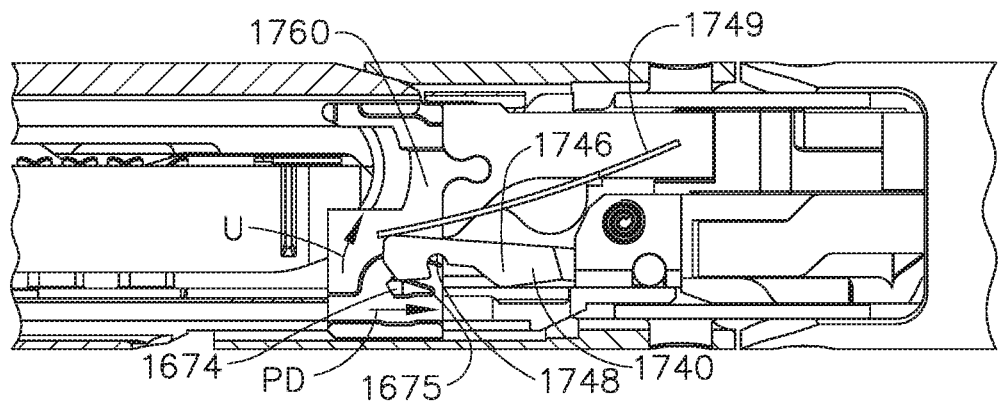
FIG. 49 is another partial cross-sectional view of the distal portion of the interchangeable surgical tool assembly of FIG. 48 with the anvil in a fully closed position and the firing member being retracted back to a starting position after initially contacting the firing member lock.
Figure 50:
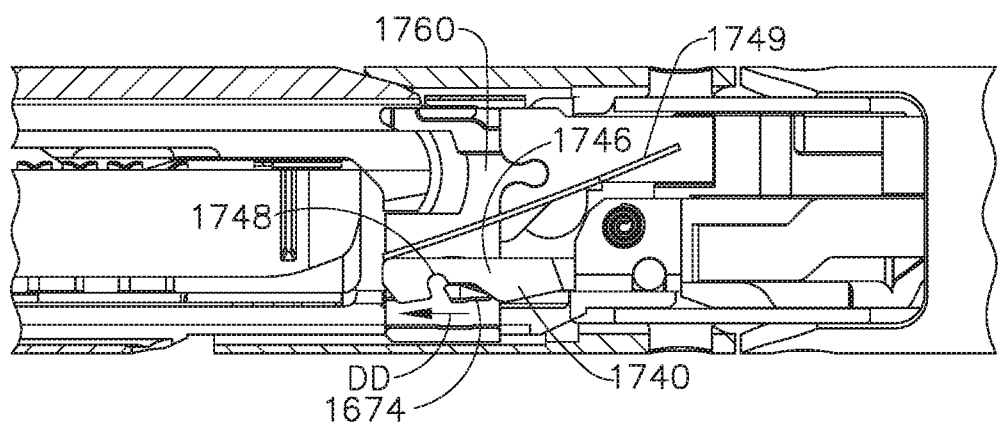
FIG. 50 is another partial cross-sectional view of the distal portion of the interchangeable surgical tool assembly of FIG. 49 with the anvil in a fully closed position and the firing member being retracted back to the starting position.

FIGS. 48-50 illustrate the retraction of the firing member 1670. FIG. 48 shows the position of the firing member 1670 and the firing member lock 1742 at the beginning of the retraction process. FIG. 49 illustrates the position of the firing member 1670 after the tapered proximal ends 1675 of the central lock lugs 1674 have contacted the angled surfaces on the distal ends of the hook arms 1746 and pivoted the hook arms 1746 upward (arrow U). FIG. 50 illustrates the firing member 1670 in its fully retracted or starting position. As can be seen in FIG. 50, the hook arms 1746 have pivoted downward into a "pre-locked" position. When the lock member is in the pre-locked position, the firing member 1670 can be moved distally until the central lock lugs 1674 thereon lockingly engage the hook harms 1746 which serve to prevent further distal advancement of the firing member 1670. Thus, in the illustrated example, the firing member lock 1742 will not be moved from an unlocked or unactivated position to an actuated position unless the anvil is first moved to a closed position. In this context, the term "closed position" means that the anvil is moved to a position relative to the cartridge and firing member that would otherwise enable the firing member to be distally advanced therein but for the firing member lockout system, for example.

Figure 51:
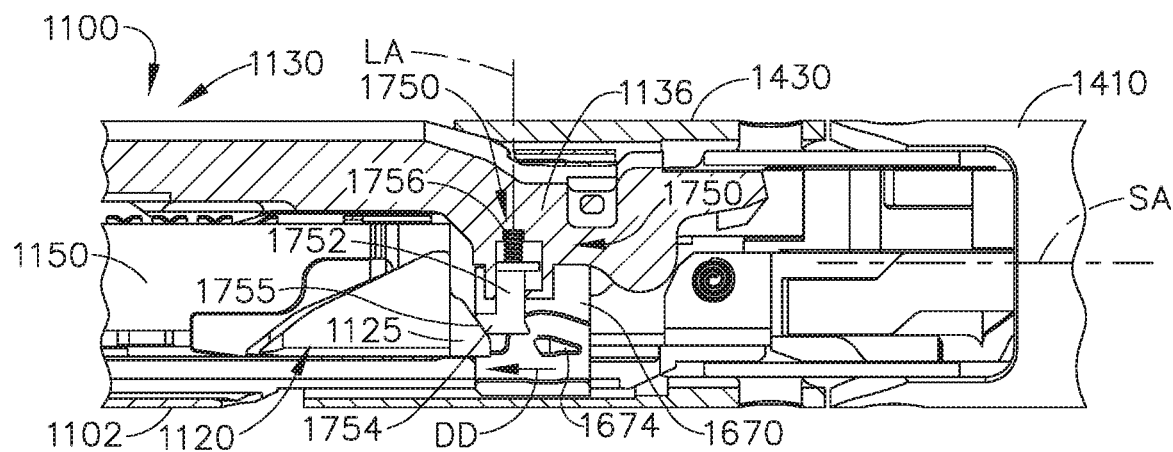
FIG. 51 is a side cross-sectional view of a portion of another interchangeable surgical tool assembly embodiment with an unfired surgical staple cartridge loaded in a surgical end effector thereof and a firing member in a starting position or configuration.
Figure 52:
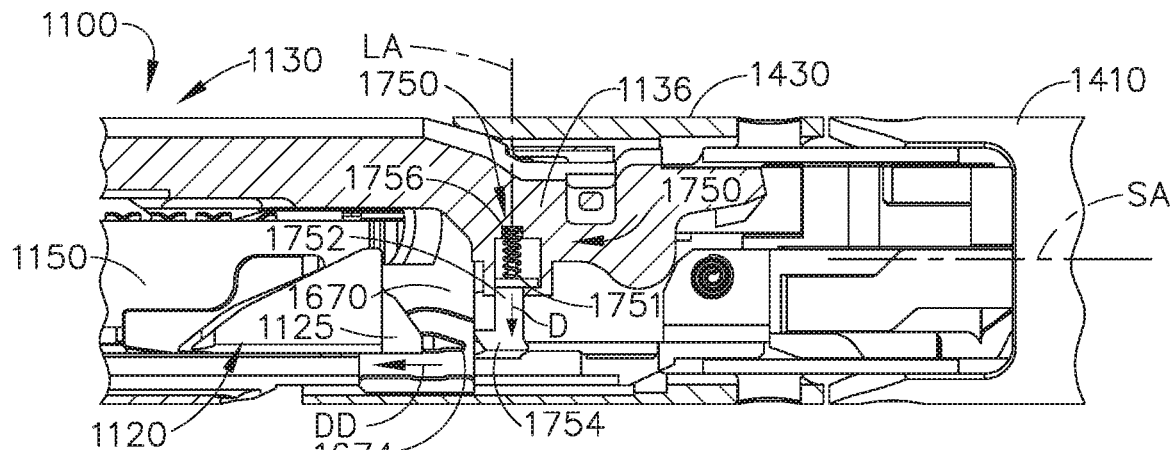
FIG. 52 is another side cross-sectional view of the interchangeable surgical tool assembly embodiment of FIG. 51 after the firing member has started to be distally advanced through the surgical end effector.

FIGS. 51-55 illustrate another firing member lockout system 1750 that may be employed in connection with the various end effector embodiments disclosed herein. In this embodiment, the firing member lockout system 1750 includes at least one firing member lock 1752 that is supported for vertical travel along a lock axis LA that is transverse to the shaft axis SA. In one example, a firing member lock 1752 corresponds to each of the anvil mounting walls 1136. In other examples, only one firing member lock 1752 may be employed. Only one firing member lock 1752 is shown in the Figures for clarity purposes. In the illustrated example, each firing member lock 1752 has an L-shape and a latch portion 1754. The firing member lock 1752 is movably journaled on a corresponding mounting rod 1751 that is attached to the corresponding anvil mounting wall 1136 or other portion of the anvil. A corresponding lock spring or biasing member 1756 biases the firing member lock 1752 downward (arrow D in FIGS. 52 and 53). FIG. 51 illustrates the surgical end effector 1100 with the anvil 1130 and the elongate channel 1102 in their fully closed position with an unspent or unfired surgical staple cartridge 1150 properly supported therein. As can be seen in FIG. 51, a tapered end 1755 of each of the latch portions 1754 has been engaged by corresponding unlocking features 1125 on the sled assembly 1120. The unlocking features 1125 serve to vertically displace the latch portions 1754 so that the central lock lugs 1674 on the firing member 1670 may pass thereunder. Thus, the firing member 1670 is free to be distally advanced. FIG. 52 illustrates the position of the firing member 1670 at the beginning of the firing process wherein it has been advanced distally from its starting position. As can be seen in FIG. 52, the unlocking features 1125 are no longer in contact with the latch portions 1754.

Figure 53:
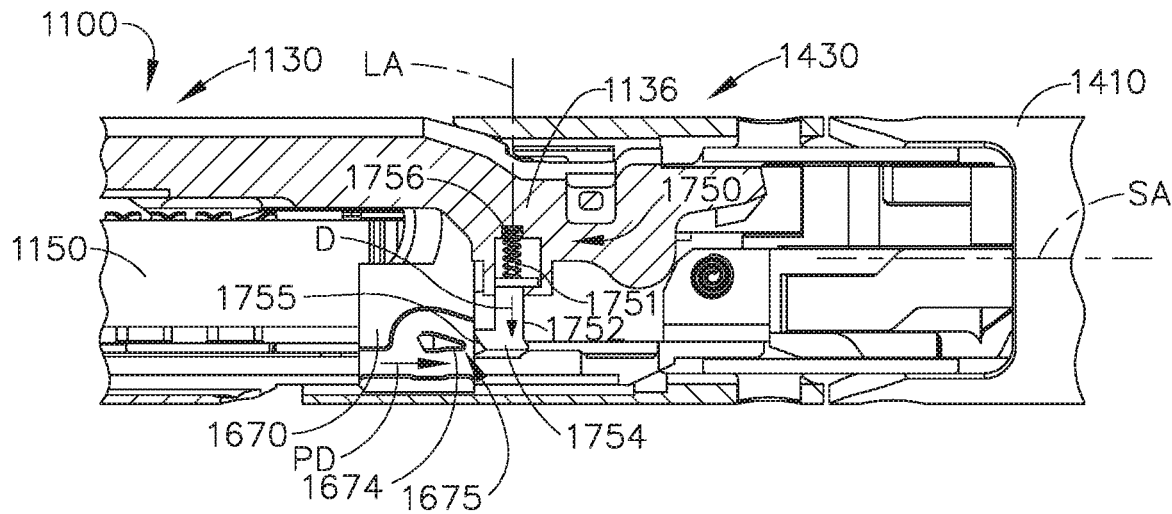
FIG. 53 is another side cross-sectional view of the interchangeable surgical tool assembly embodiment of FIGS. 51 and 52 during the retraction of the firing member back to the starting position.
Figure 54:
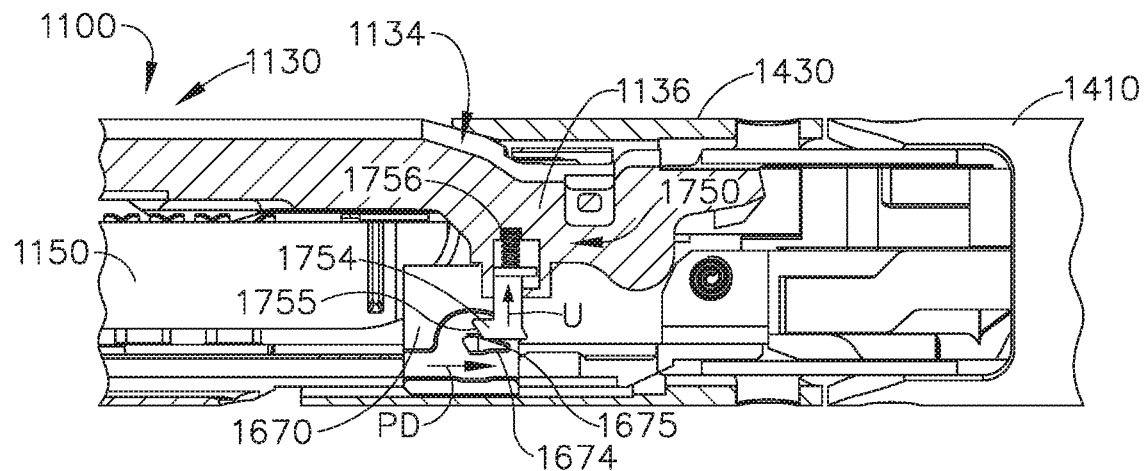
FIG. 54 is another side cross-sectional view of the interchangeable surgical tool assembly embodiment of FIGS. 51-53 after the firing member has been further retracted toward the starting position.
Figure 55:
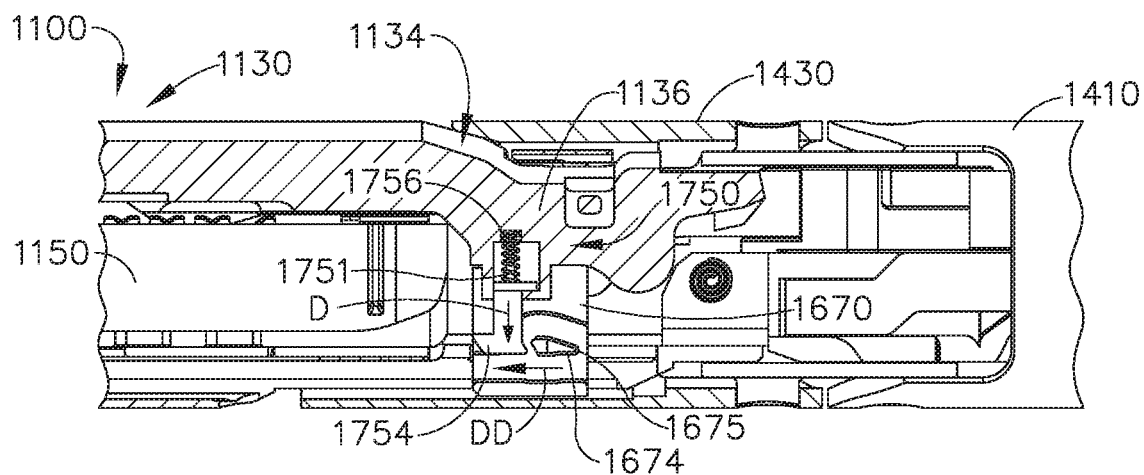
FIG. 55 is another side cross-sectional view of the interchangeable surgical tool assembly embodiment of FIGS. 51-54 after the firing member has been fully retracted back to the starting position.

FIGS. 53-55 illustrate the retraction of the firing member 1670. FIG. 53 shows the position of the firing member 1670 and the firing member lock 1752 at the beginning of the retraction process. FIG. 54 illustrates the position of the firing member 1670 after the tapered proximal ends 1675 of the central lock lugs 1674 have contacted the angled surfaces or tapered ends 1755 of the latch portions 1754 to vertically displace the firing member lock 1752 in the up direction (arrow U—FIGS. 54 and 55). FIG. 55 illustrates the firing member 1670 in its fully retracted or starting position. As can be seen in FIG. 55, the firing member lock 1752 is in a locked or bottom position wherein, if the firing member 1670 were to be moved distally, the central lock lug 1674 on the firing member 1670 would contact the latch portions 1754 of the corresponding firing member lock 1752. When in that position, the firing member 1670 cannot be distally advanced. Because the firing member locks 1752 are attached to the anvil, when the anvil is in an open position, the firing member locks 1752 are not in a locked position wherein they can prevent the axial advancement of the firing member 1670. Thus, to actuate the firing member lockout system 1750, the anvil 1130 must first be moved to a closed position. In this context, the term "closed position" means that the anvil is moved to a position relative to the cartridge and firing member that would otherwise enable the firing member to be distally advanced therein, but for the firing member lockout system, for example.

FIGS. 56-63 illustrate another firing member lockout system 1760 that includes a movable lock member 1762 that is configured to retainingly engage the firing member 1670 when a surgical staple cartridge 1150 is not properly seated within the elongate channel 1102. The lock member 1762 comprises at least one laterally moving locking portion 1764 that is configured to retainingly engage a corresponding portion of the firing member when the sled assembly 1120 is not present within the surgical staple cartridge 1150 in its starting position. In the illustrated arrangement, the lock member 1762 employs two laterally moving locking portions 1764 wherein each locking portion 1764 engages a laterally extending portion of the firing member 1670.

Figure 56:
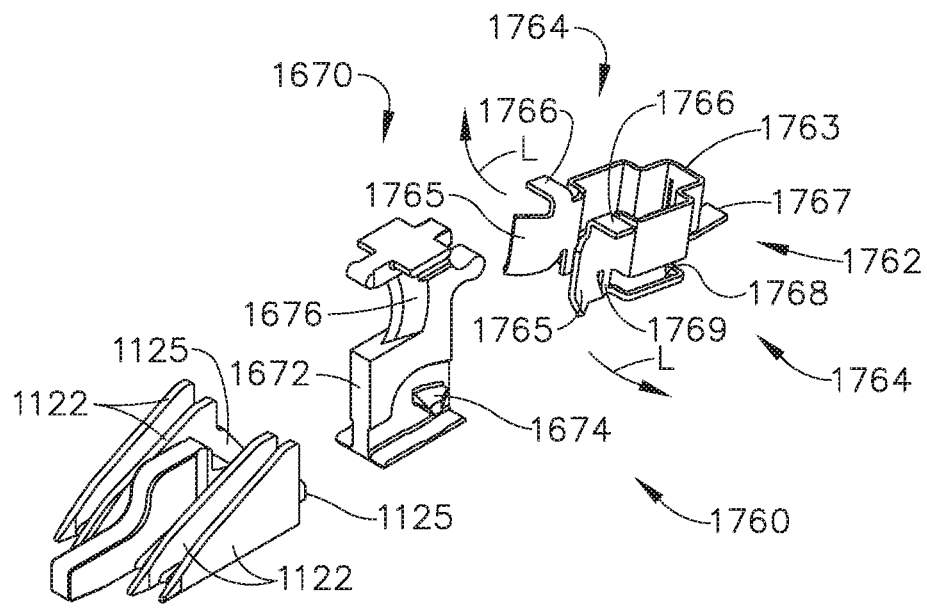
FIG. 56 is an exploded perspective view of portions of a firing member, a sled assembly, a firing member and firing member lock member of another interchangeable surgical tool assembly embodiment.
Figure 57:
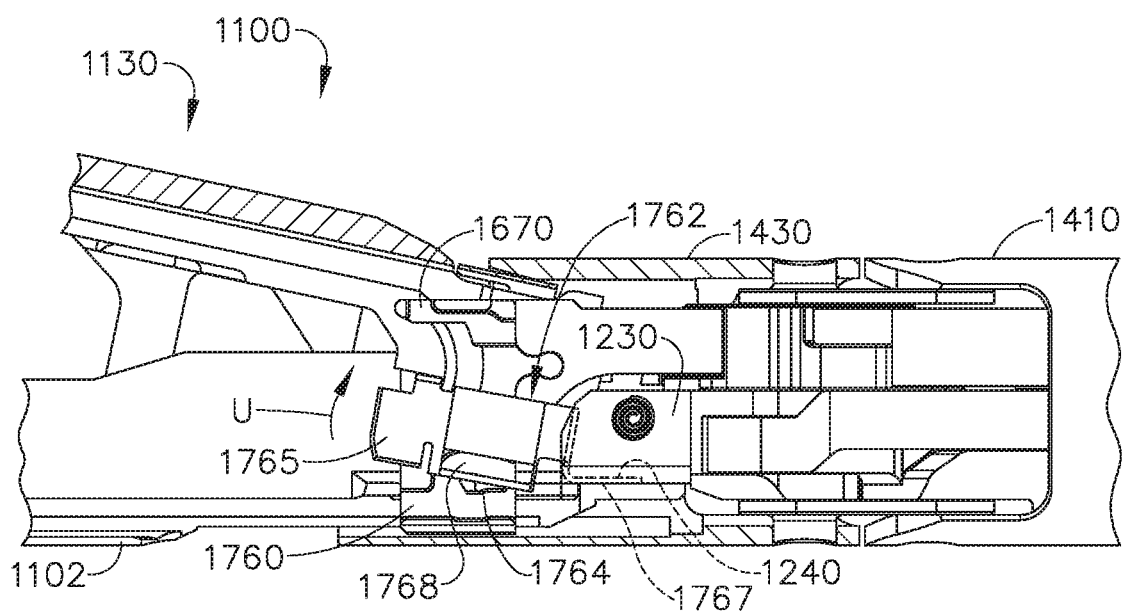
FIG. 57 is a side cross-sectional view of a portion of the interchangeable surgical tool assembly embodiment of FIG. 56 with an anvil of a surgical end effector thereof in an open position prior to installation of an unfired surgical staple cartridge within the surgical end effector and with the firing member in a starting position.
Figure 59:
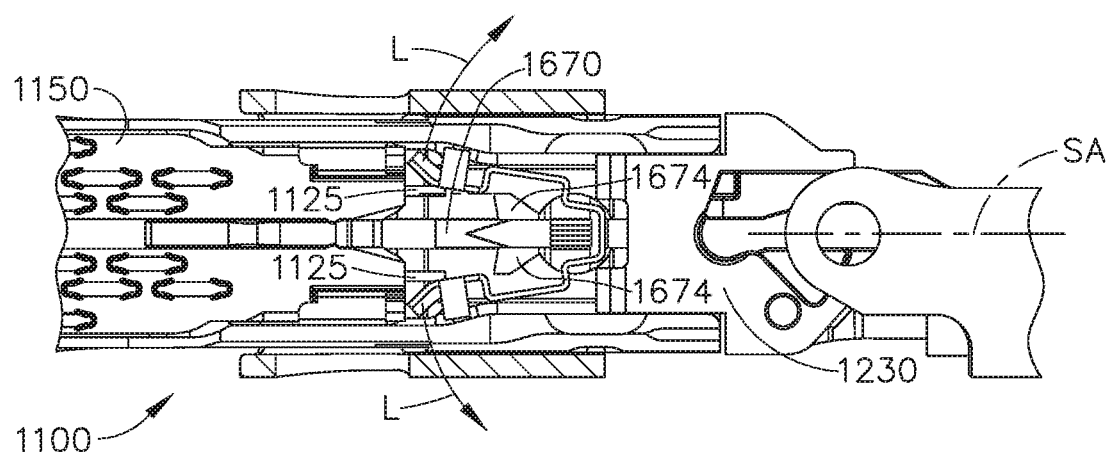
FIG. 59 is a top cross-sectional view of the portion of the interchangeable surgical tool assembly embodiment of FIG. 58 with the firing member lock in a disengaged configuration relative to the firing member.
Figure 60:
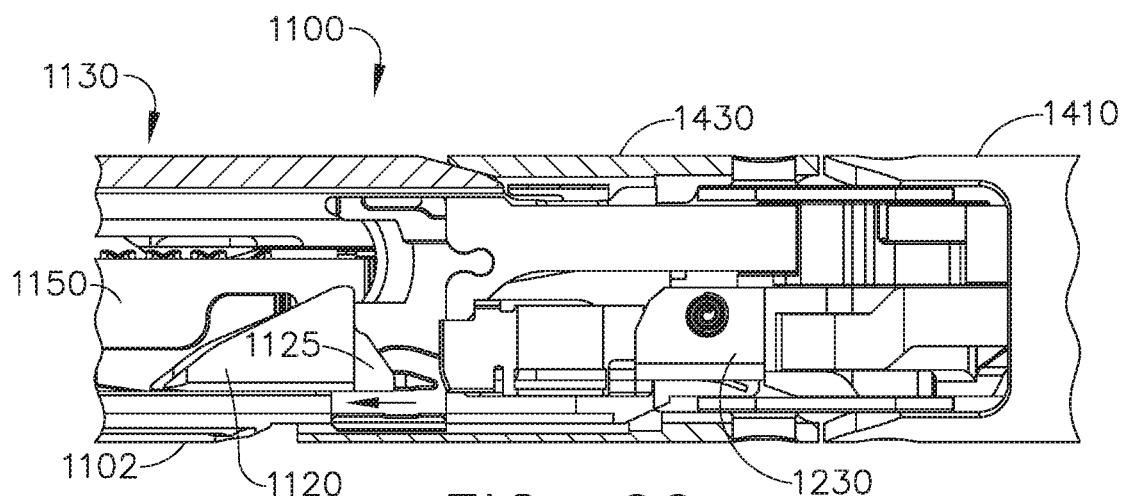
FIG. 60 is another side cross-sectional view of a portion of the interchangeable surgical tool assembly embodiment of FIGS. 58 and 59 after the firing member has been initially distally advanced.
Figure 62:
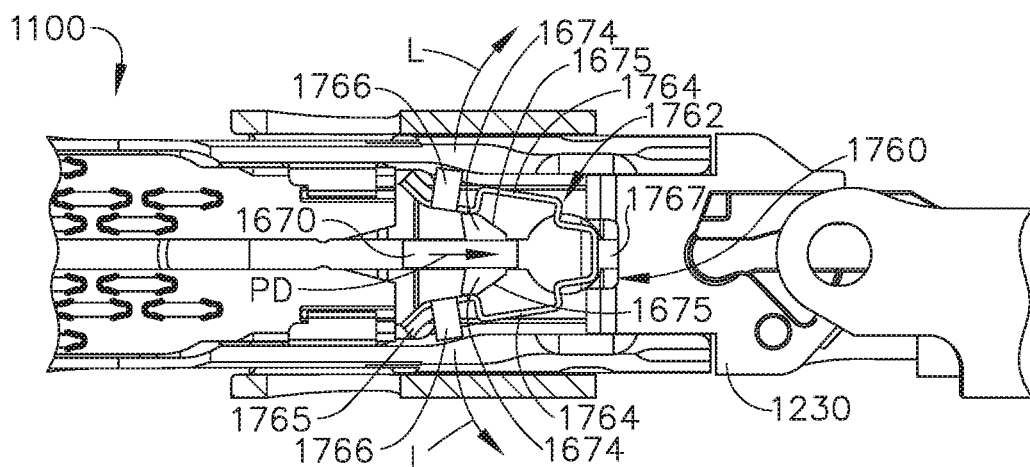
FIG. 62 is a top view of the portion of the interchangeable surgical tool assembly embodiment of FIG. 61.

In the illustrated embodiment, the lock member 1762 comprises a generally U-shaped spring member wherein each laterally movable leg or locking portion 1764 extends from a central spring portion 1763 and is configured to move in lateral directions represented by arrows "L" in FIGS. 56, 59 and 62. It will be appreciated that the term "lateral directions" refers to directions that are transverse to the shaft axis SA. The spring or lock member 1762 may be fabricated from high strength spring steel or similar material. The central spring portion 1763 may include a proximally extending spring tab 1767 that is retained within a notch 1240 in the end effector mounting assembly 1230. See FIG. 57. In the illustrated example, the spring tab 1767 serves to bias the lock member 1762 into an unlocked configuration when the anvil 1130 is in an open position. FIG. 57 illustrates the anvil 1130 in an open position ready for an unfired or new cartridge to be installed in the elongate channel 1102. As can be seen in FIG. 57, the mounting tab 1767 biases the lock member 1762 in an upward direction (arrow U). When in that unlocked position, the lock member 1762 is not in a position to prevent the distal advancement of the firing member 1762. The instrument may, however, employ other sensors and lockout arrangements to detect the position of the anvil and otherwise prevent actuation of the firing system unless the anvil has been moved to a closed position.

Figure 58:
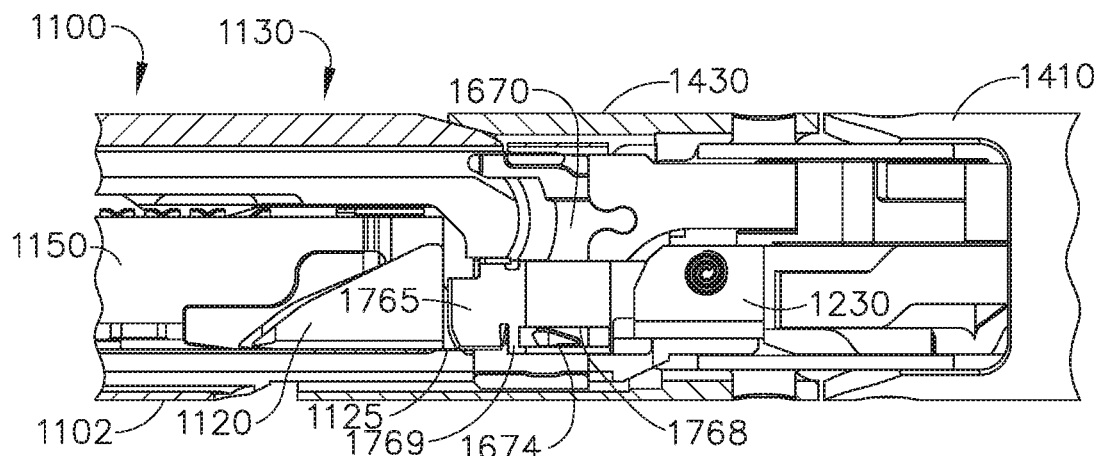
FIG. 58 is another side cross-sectional view of a portion of the interchangeable surgical tool assembly embodiment of FIG. 57 with an unfired surgical staple cartridge installed within the surgical end effector and the anvil in a closed position.

FIG. 58 illustrates a portion of the surgical end effector 1100 with an unfired staple cartridge 1150 loaded or properly supported within the elongate channel 1102 and after the anvil 1130 has been moved to a closed position. As the anvil 1130 is moved to the closed position, the anvil mounting walls 1136 contact corresponding laterally extending anvil tabs 1766 that are formed on the lock member 1762. See FIG. 56. The anvil mounting walls 1136 thereby serve to move the lock member 1762 from a disengaged position to a locked position wherein the lock member 1762 is in locking engagement with the firing member 1670. In one example, each of the laterally movable legs or locking portions 1764 of the lock member 1762 includes a locking window 1768 therein. When the lock member 1762 is in a locked position, the central lock lug 1674 on each lateral side of the firing member 1670 extends into the corresponding locking window 1768 to retainingly prevent the firing member 1670 from being distally axially advanced.

As can be seen in FIG. 56, the sled or cam assembly 1120 includes an unlocking feature 1125 that corresponds to each of the laterally movable locking portions 1764. In the illustrated arrangement, an unlocking feature 1125 is provided on, or extends proximally from, each of the central wedge-shaped cams 1122. In alternative arrangements, the unlocking feature 1125 may comprise a proximally protruding portion of the corresponding wedge-shaped cam 1122. As can be seen in FIG. 59, when the sled assembly 1120 is in its starting position, the unlocking features 1125 engage and bias the corresponding locking portions 1764 laterally in a direction that is transverse to the shaft axis SA (arrows L). When the locking portions 1764 are in those unlocked orientations, the central lock lugs 1674 are not in retaining engagement with their corresponding locking window 1768.

When in those orientations, the firing member 1670 may be distally axially advanced (fired). However, when an unfired surgical staple cartridge 1150 is not present in the elongate channel 1102 or the sled assembly 1120 has been moved out of its starting position (which may mean that the cartridge is at least partially or completely fired), the locking portions 1764 spring laterally into retaining engagement with the firing member 1670. When in that position as illustrated in FIG. 58, the central lock lugs 1674 are received within their respective locking windows 1768 and are prevented from moving distally by a lockout stop 1769. When in such position, the firing member 1670 cannot be moved distally.

Figure 61:
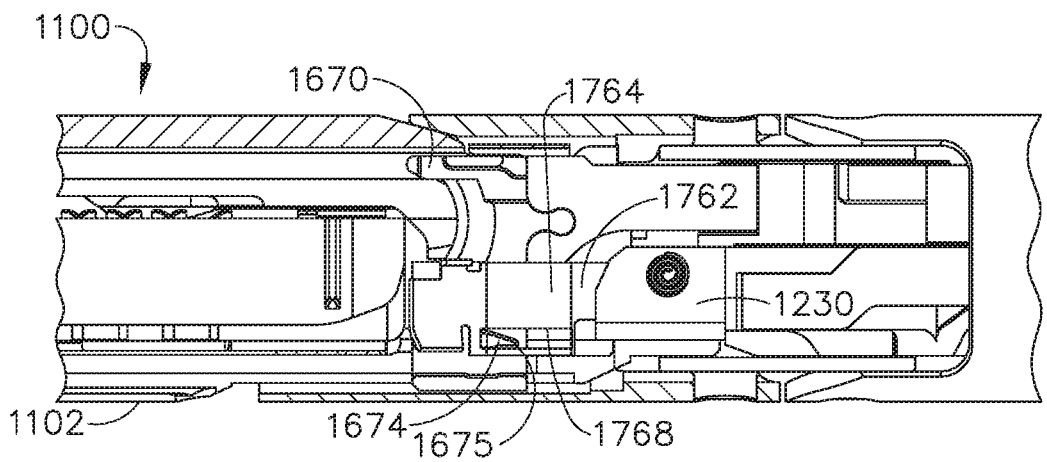
FIG. 61 is another side cross-sectional view of a portion of the interchangeable surgical tool assembly embodiment of FIGS. 58-60 during retraction back to a starting position.
Figure 63:
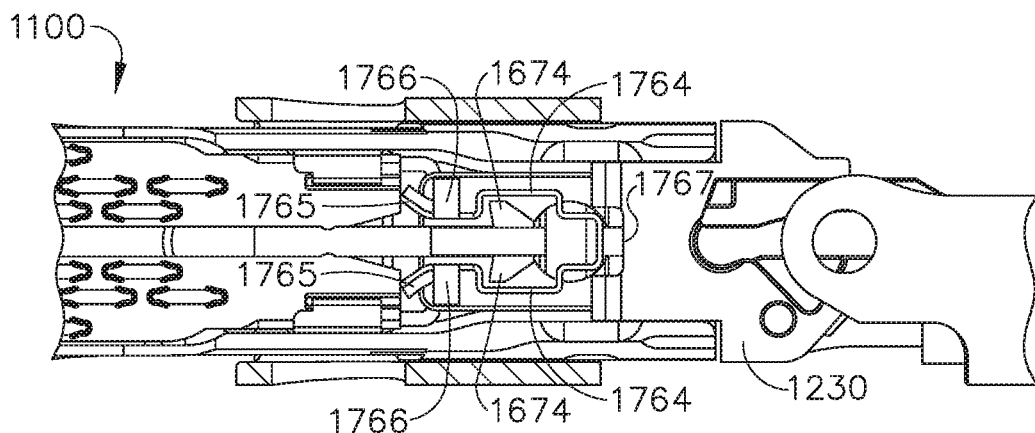
FIG. 63 is another side cross-sectional view of a portion of the interchangeable surgical tool assembly embodiment of FIGS. 58-62 after the firing member has been fully retracted back to a starting position and is in locking engagement with the firing member lock.

FIG. 61 illustrates the firing member 1670 as it is being retracted to its starting or unfired position. As the tapered or tapered proximal ends 1675 of the central lock lugs 1674 contact the radiused distal ends 1765 of the movable locking portions 1764, the movable locking portions 1764 are biased laterally outward as shown in FIG. 62 until each of the central lock lugs 1674 once again are completely received within the lock window portions 1768 in the locking portions 1764 (FIG. 63). When the firing member 1670 has been fully retracted to the starting position shown in FIG. 63, the firing member 1670 is once again locked in place by the lock member 1762 and prevented from being distally advanced until another fresh cartridge has been properly loaded into the elongate channel 1102 as described above. When the anvil 1130 is opened, the spring tab 1767 once again biases the lock member 1762 back to the unlocked or pre-actuated position. Thus, to actuate the firing member lockout system 1760, the user must first move the anvil to a closed position. In this context, the term "closed position" means that the anvil is moved to a position relative to the cartridge and firing member that would otherwise enable the firing member to be distally advanced therein, but for the firing member lockout system, for example.

FIGS. 64-70 illustrate an alternative articulation lock arrangement 1910 for locking a surgical end effector 1100' in an articulated position about an articulation axis B-B relative to a shaft axis SA. In the illustrated example, the surgical end effector 1100' is pivotally coupled to a spine assembly 1500'. The spine assembly 1500' may be attached to the chassis 1800 (FIG. 4) in the above described manner. A distal end portion 1540 of the spine assembly 1500' is formed with a downwardly protruding articulation pin 1542 that defines the articulation axis B-B. The articulation pin 1542 is configured to be rotatably or pivotally received within a spine attachment hole 1254 that is provided in a mounting base 1252 of an end effector mounting assembly 1250. The end effector mounting assembly 1250 is attached to a proximal end 1103 of the elongate channel 1102 by a spring pin connector 1235 (FIG. 6) that extends through a transverse mounting hole 1251 in the mounting assembly 1250 to be received within the channel mounting holes 1106 (FIG. 6) that are provided in the proximal end 1103 of the elongate channel 1102.

Figure 64:
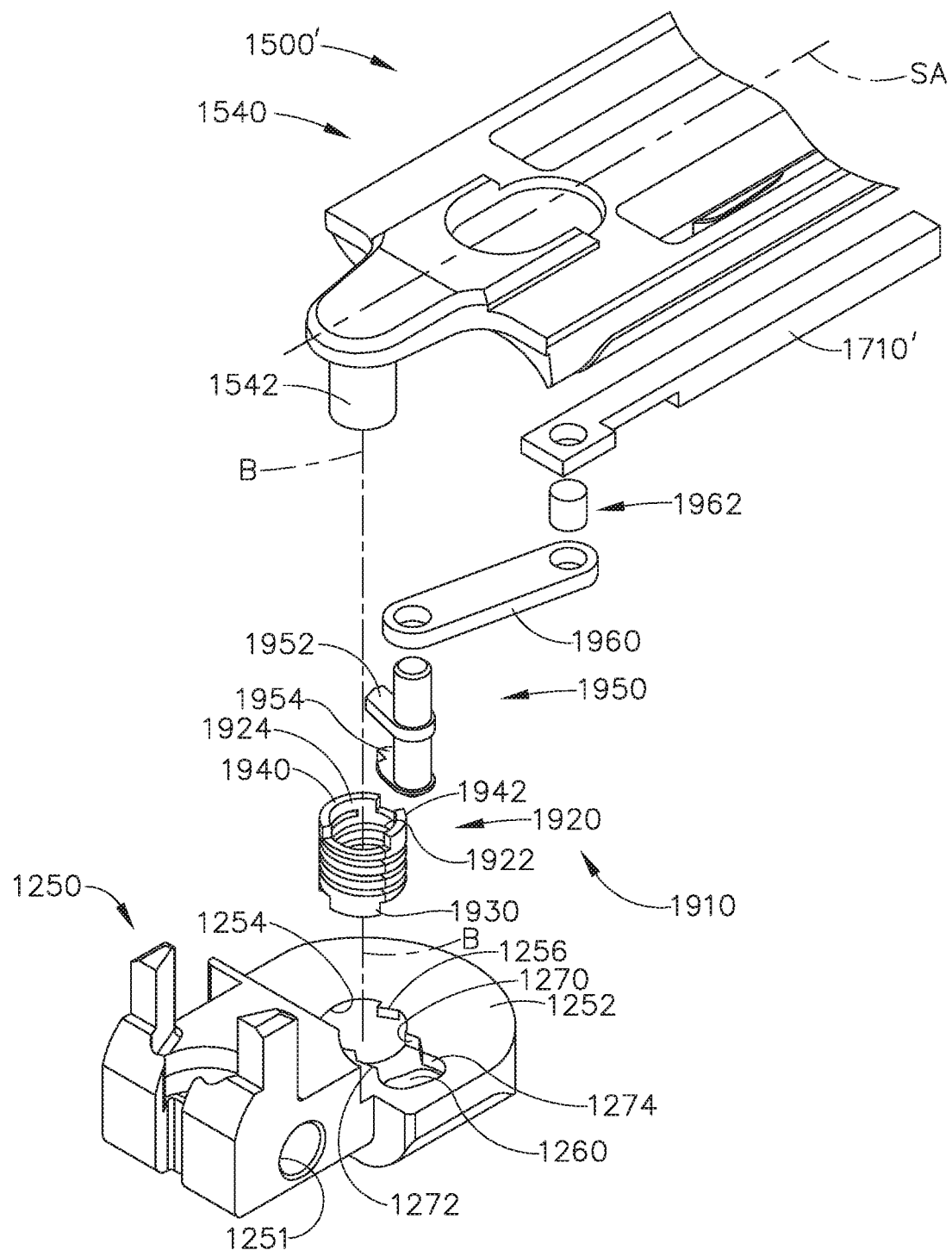
FIG. 64 is an exploded perspective view of portions of an articulation joint and articulation lock embodiment of another interchangeable surgical tool assembly embodiment.
Figure 65:
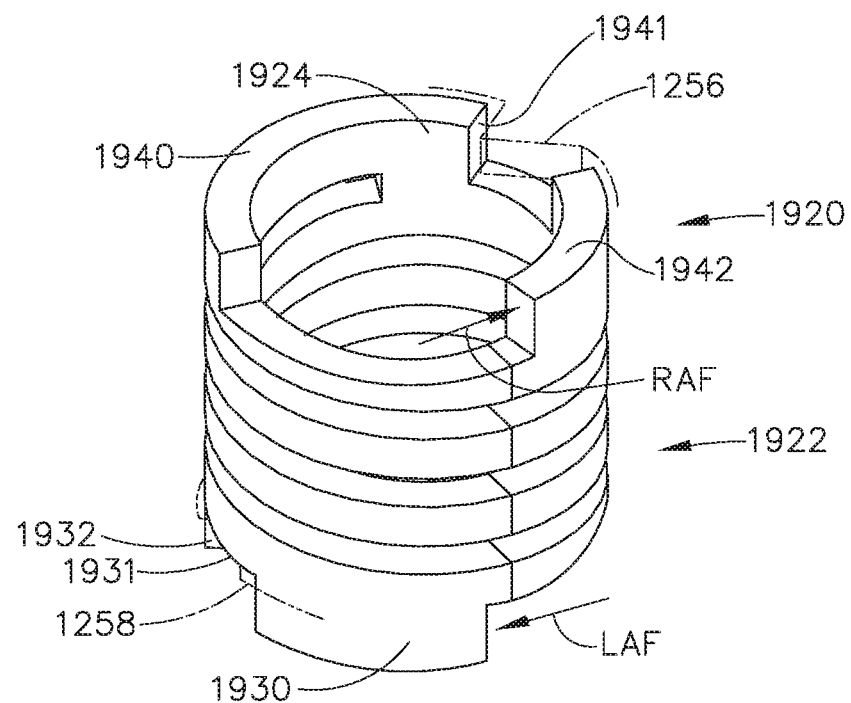
FIG. 65 is a perspective view of a lock spring assembly embodiment of the articulation lock embodiment of FIG. 64.
Figure 66:
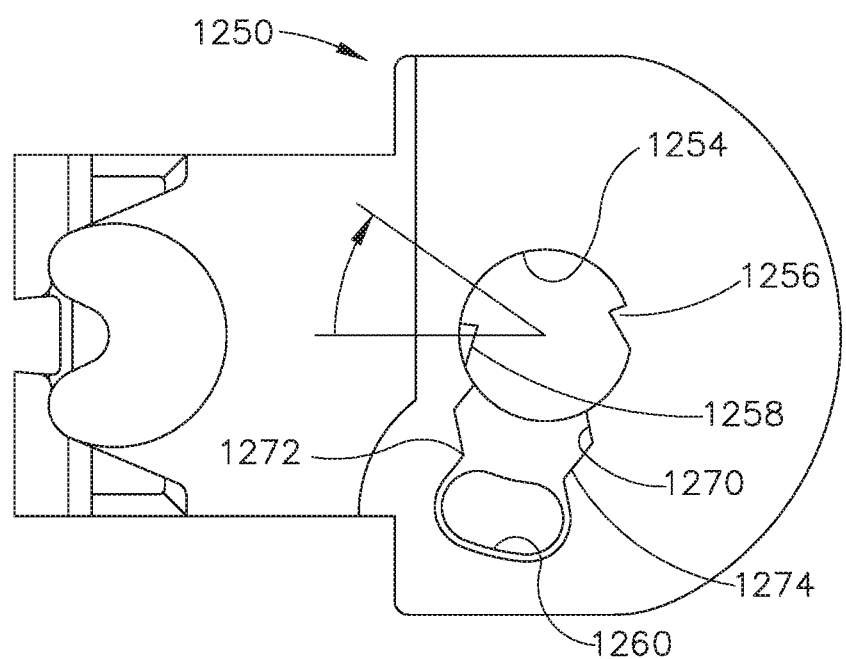
FIG. 66 is a top view of an end effector mounting assembly embodiment of the interchangeable surgical tool assembly embodiment of FIG. 64.
Figure 67:
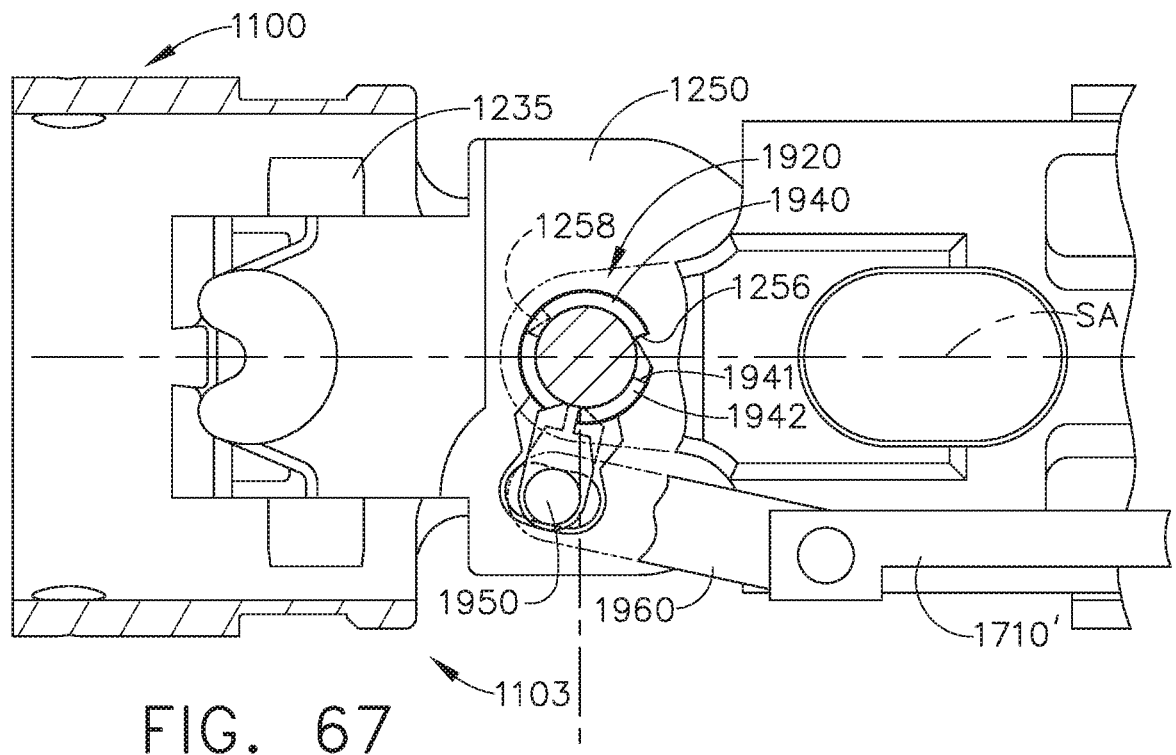
FIG. 67 is a top view of portions of the interchangeable surgical tool assembly embodiment of FIG. 64 with a surgical end effector thereof in an unarticulated configuration.

Referring to FIGS. 64 and 65, in one example, the articulation lock arrangement 1910 comprises a lock spring assembly 1920 that includes a central spring body portion 1922 that defines a central pin hole 1924 and which includes bottom release ring segments 1930 and 1932 and top release ring segments 1940 and 1942. The lock spring assembly 1920 is sized to be rotatably received within the spine attachment hole 1254 in the mounting base 1252. In one example, an upper release stop 1256 and a lower release stop 1258 each protrude inwardly within the spine attachment hole 1254. The articulation lock arrangement 1910 further includes a release pin assembly 1950 that includes an upper release arm 1952 and a lower release arm 1954. The release pin assembly 1950 is attached to a distal articulation link 1960 that is pinned to a distal end of the distal articulation link 1710' by a link pin 1962. The distal articulation link 1710' may interface with the articulation systems described herein for axially moving the distal articulation link 1710' in the distal and proximal directions depending upon the direction of articulation desired. A bottom portion (not shown) of the release pin assembly 1950 is configured to be pivotally and slidably supported within a lower arcuate release pin slot 1260 that is formed in the end effector mounting assembly 1250. A second upper release arm slot 1270 is also formed in the end effector mounting assembly and is configured to movably accommodate the upper and lower release arms 1952 and 1954. As can be seen in FIG. 67, an upper balance formation 1272 protrudes into the second upper release arm slot 1270 and is configured to operably interface with the upper release arm 1952. Likewise, a lower balance formation 1274 protrudes into the second upper release arm slot 1270 and is configured to operably interface with the lower release arm 1954.

In the illustrated example, the articulation pin 1542 is rotatably received within the central pin hole 1924 in the lock spring assembly 1920. The lock spring assembly 1920 is received within the spine attachment hole 1254 in the end effector mounting assembly 1250 such that the upper release stop 1256 is received within an upper lock space 1941 that is formed between the top release ring segments 1940 and 1942 and the lower release stop 1258 is located within a lower lock space 1931 formed between the bottom release ring segments 1930 and 1932. FIG. 67 illustrates the surgical end effector 1100 in an unarticulated position. As can be seen in FIG. 67, the upper release stop 1256 is in abutting engagement with the top release ring segment 1940. The lower release stop 1258 may also be in abutting engagement with the bottom release ring segment 1932. Such configuration retains the lock spring assembly 1920 in frictional engagement with the articulation pin 1542 to retain the surgical end effector 1100 in the unarticulated position.

Figure 68:
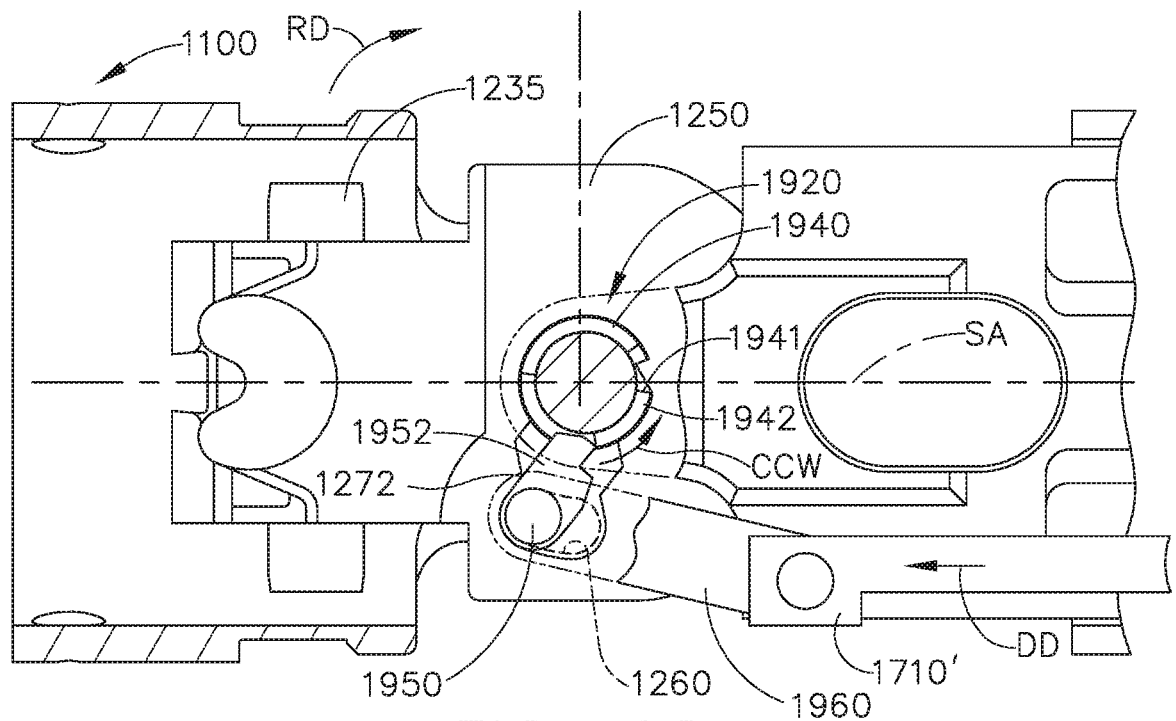
FIG. 68 is another top view of the portions of the interchangeable surgical tool assembly embodiment of FIG. 67 during an initial application of an articulation motion to the articulation joint.
Figure 69:
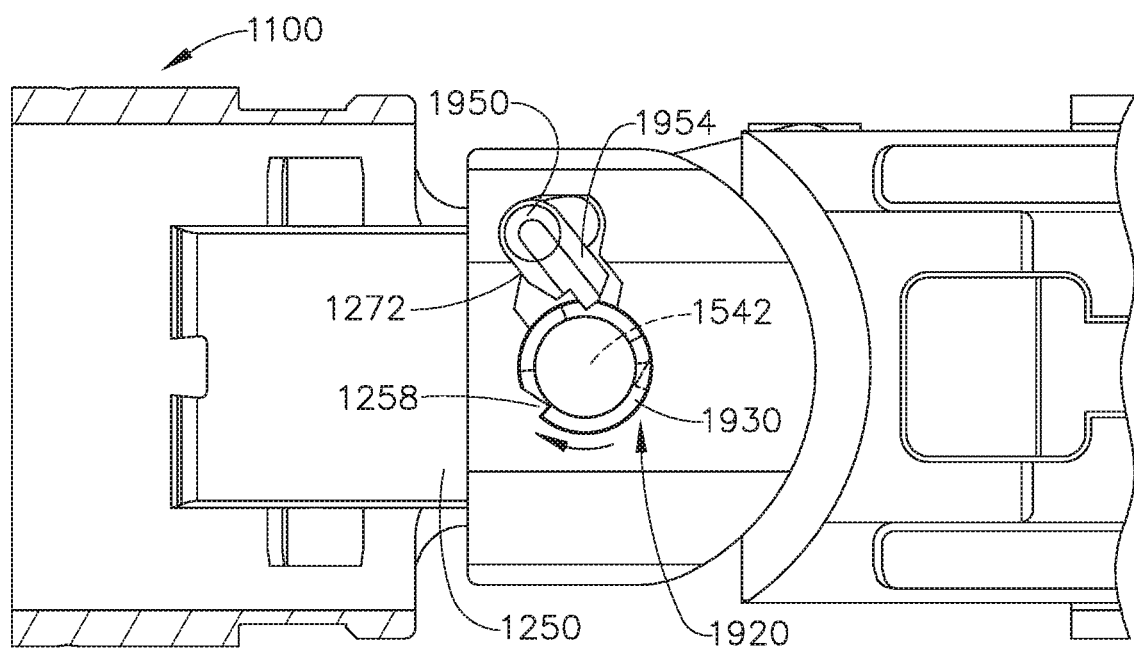
FIG. 69 is a bottom view of the portions of the interchangeable surgical tool assembly embodiment of FIG. 68.
Figure 70:
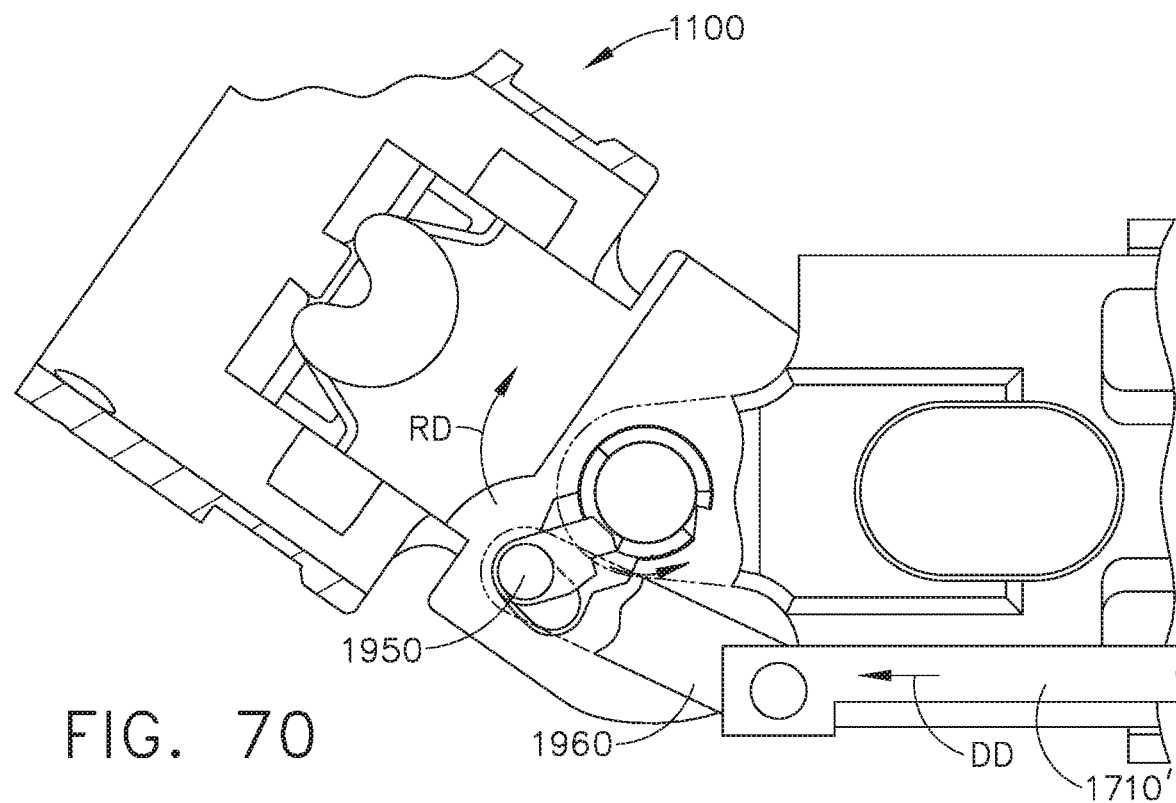
FIG. 70 is another bottom view of the portions of the interchangeable surgical tool assembly embodiment of FIG. 69 with the surgical end effector in an articulated configuration.

FIG. 68 is a top view of the articulation lock arrangement 1910 upon initiation of articulation of the surgical end effector to the right (arrow RD) about the articulation axis. As can be seen in FIG. 68, the right articulation process is initiated by axially advancing the distal articulation link 1710' in the distal direction DD. Distal advancement of the distal articulation link 1710' causes the distal articulation link 1960 to move the release pin assembly 1950 distally such that the upper release arm 1952 is brought into abutting engagement with the upper balance formation 1272 on the end effector mounting assembly 1250. Such contact between the upper balance formation 1272 and the upper release arm 1952 causes the upper release arm 1952 to contact the top release ring segment 1942 and apply the right articulation force RAF thereto. Such movement causes the top release ring segment 1942 to move counterclockwise CCW to thereby cause the lock spring assembly 1920 to open or expand to disengage from frictional engagement with the articulation pin 1542. FIG. 69 is a bottom view of the articulation lock arrangement 1910 as illustrated in FIG. 68. As can be seen in FIG. 69, the lower release stop 1258 is in abutting engagement with the bottom release ring segment 1930 which prevents the bottom release ring segment 1930 from moving. As a result, the lock spring assembly 1920 expands to release the articulation pin 1542. Further distal advancement of the distal articulation link 1710' causes the release pin assembly 1950 to apply the articulation motion to the surgical end effector mounting assembly 1250 in the right direction RD while also moving the lock spring assembly 1920 out of locking engagement with the articulation pin 1542. See FIG. 70. To articulate the surgical end effector 1100 in the left direction, the distal articulation link 1710' is moved in the proximal direction which causes the release pin assembly to expand the lock spring assembly 1920 and move the surgical end effector mounting assembly 1250 in the left direction in an opposite, but similar manner. Thus, as may be appreciated from the forgoing description, the locking spring assembly essentially comprises a spring assembly that is expandable from a first locked or retention configuration wherein the lock spring assembly 1920 is in frictional retaining engagement with the articulation pin 1542 and a second unlocked position wherein the lock spring assembly 1920 is free to pivot about the articulation pin 1542 with the surgical end effector mounting assembly 1250 as articulation motions are applied thereto.

FIGS. 71-77 illustrate an alternative articulation lock arrangement 2010 for locking a surgical end effector 1100 in an articulated position about an articulation axis B-B relative to a shaft axis SA. In the illustrated example, the surgical end effector 1100 is pivotally coupled to a spine assembly 1500'. The spine assembly 1500' may be attached to the chassis 1800 (FIG. 4) in the above described manner. A distal end portion 1540 of the spine assembly 1500' is formed with a downwardly protruding articulation pin 1542 that defines the articulation axis B-B. The articulation pin 1542 is configured to be rotatably or pivotally received within a spine attachment hole 1254 that is provided in a mounting base 1252' of an end effector mounting assembly 1250'. The end effector mounting assembly 1250' is attached to a proximal end 1103 of the elongate channel 1102 by a spring pin connector 1235 (FIG. 6) that extends through a transverse mounting hole 1251 in the mounting assembly 1250' to be received within the channel mounting holes 1106 (FIG. 6) that are provided in the proximal end 1103 of the elongate channel 1102.

Figure 71:
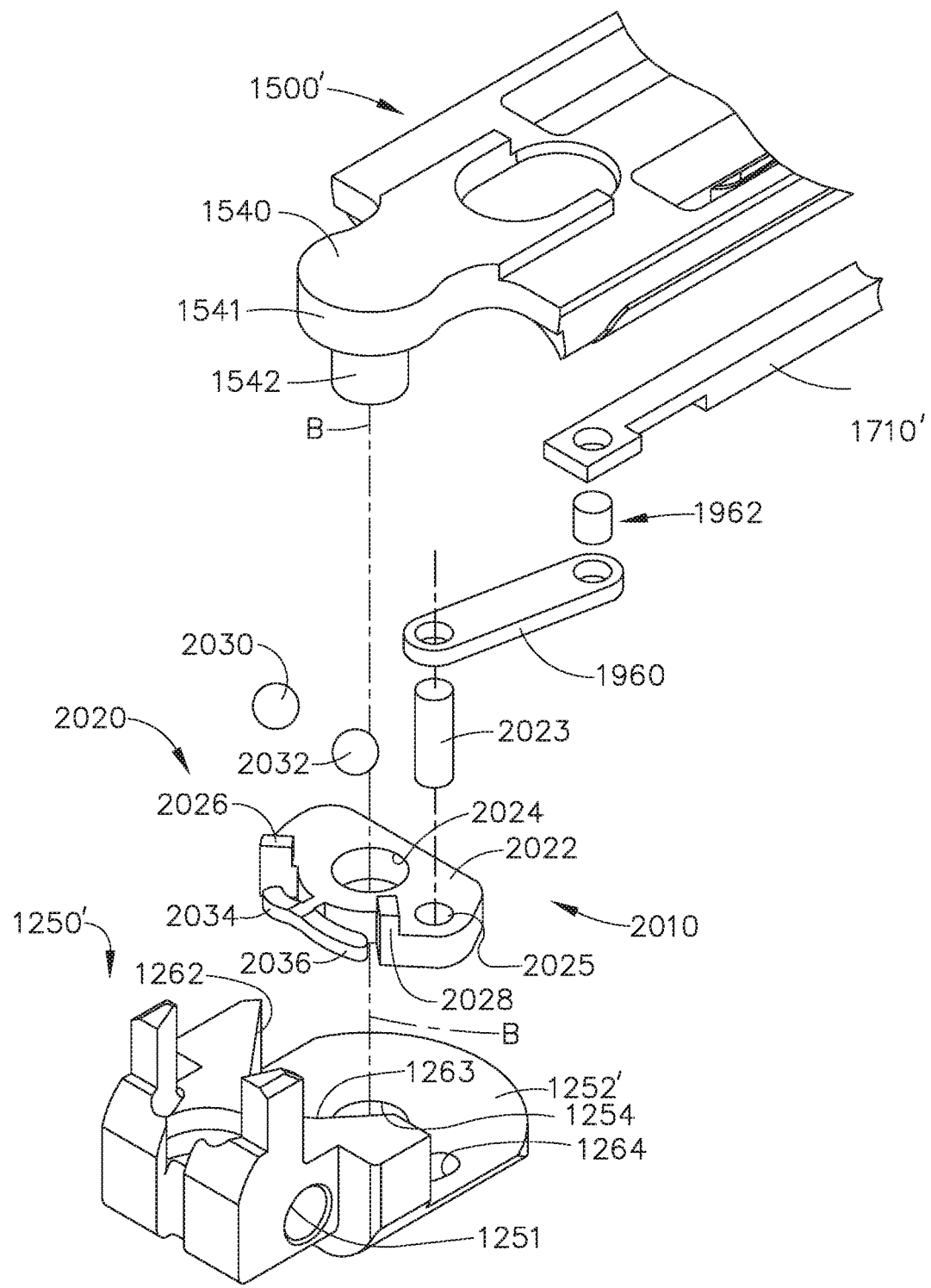
FIG. 71 is an exploded perspective view of portions of an articulation joint and articulation lock embodiment of another interchangeable surgical tool assembly embodiment.
Figure 72:
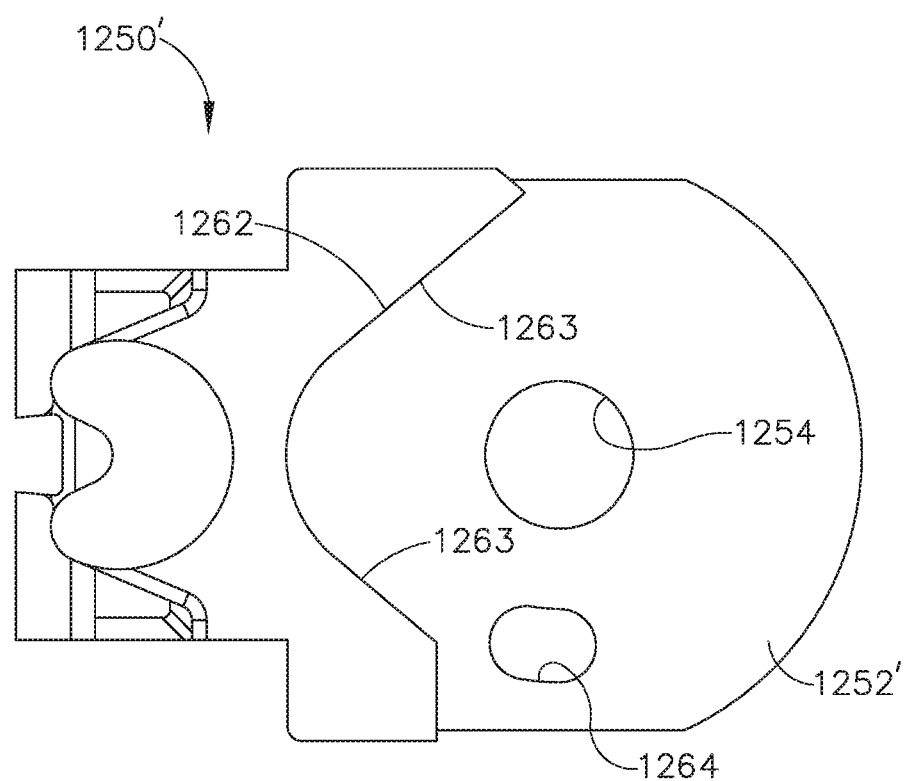
FIG. 72 is a top view of an end effector mounting assembly embodiment of the interchangeable surgical tool assembly embodiment of FIG. 71.
Figure 73:
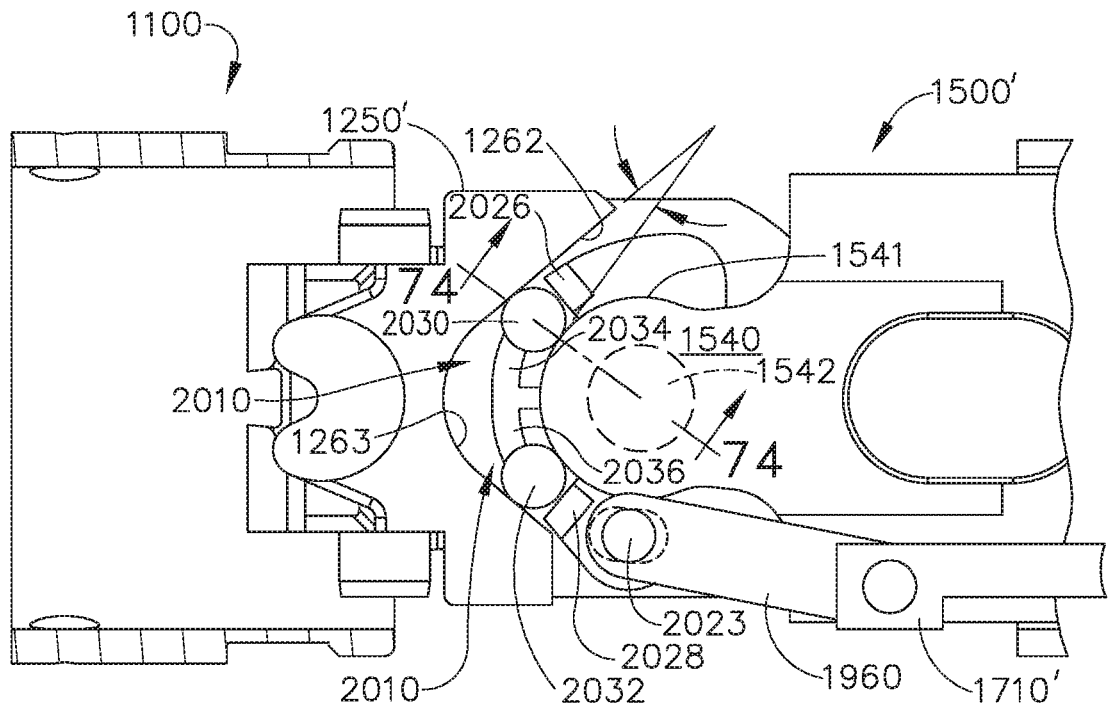
FIG. 73 is a top view of portions of the interchangeable surgical tool assembly embodiment of FIG. 71 with a surgical end effector thereof in an unarticulated configuration.

Referring to FIGS. 71 and 73, in one example, the articulation lock arrangement 2010 comprises a ball lock assembly 2020 that includes a ball retainer base 2022 that has a central pivot hole 2024 therein that is configured to receive the articulation pin 1542 therethrough. The ball retainer base 2022 is attached to an articulation lock link 1960 by an articulation pin 2023 that extends through a pin hole 2025 in the ball retainer base 2022 into an articulation slot 1264 in the mounting base 1252' of the surgical end effector mounting assembly 1250'. The articulation lock link 1960 is pinned to a distal end of the distal articulation link 1710' by a link pin 1962. The distal articulation link 1710' may interface with the articulation systems described herein for axially moving the distal articulation link 1710' in the distal and proximal directions depending upon the direction of articulation desired. The ball retainer base 2022 further includes two upstanding ball stop members 2026 and 2028 that serve to retain two locking balls 2030 and 2032 between a distal locking surface 1263 formed on a locking cradle 1262 on the surgical end effector mounting assembly 1250' and a proximal locking surface 1541 formed on the distal end portion 1540 of the spine assembly 1500'. The ball retainer base 2022 further includes two centering springs 2034 and 2036 that serve to also support the locking balls 2030, 2032, respectively.

Figure 74:
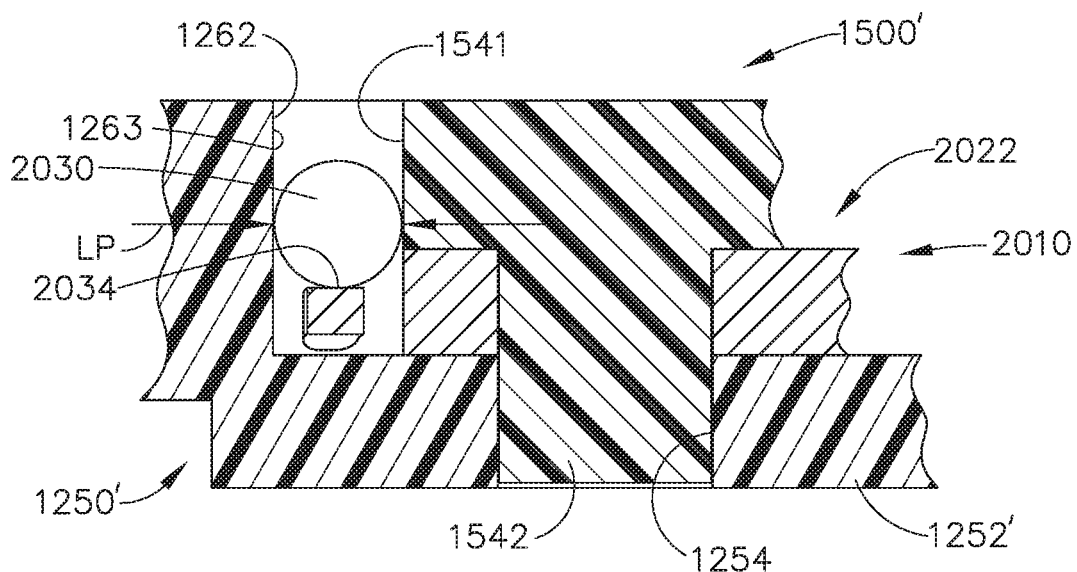
FIG. 74 is a partial cross-sectional view of portions of the articulation lock embodiment of FIG. 73 taken along line 74-74 in FIG. 73.
Figure 75:
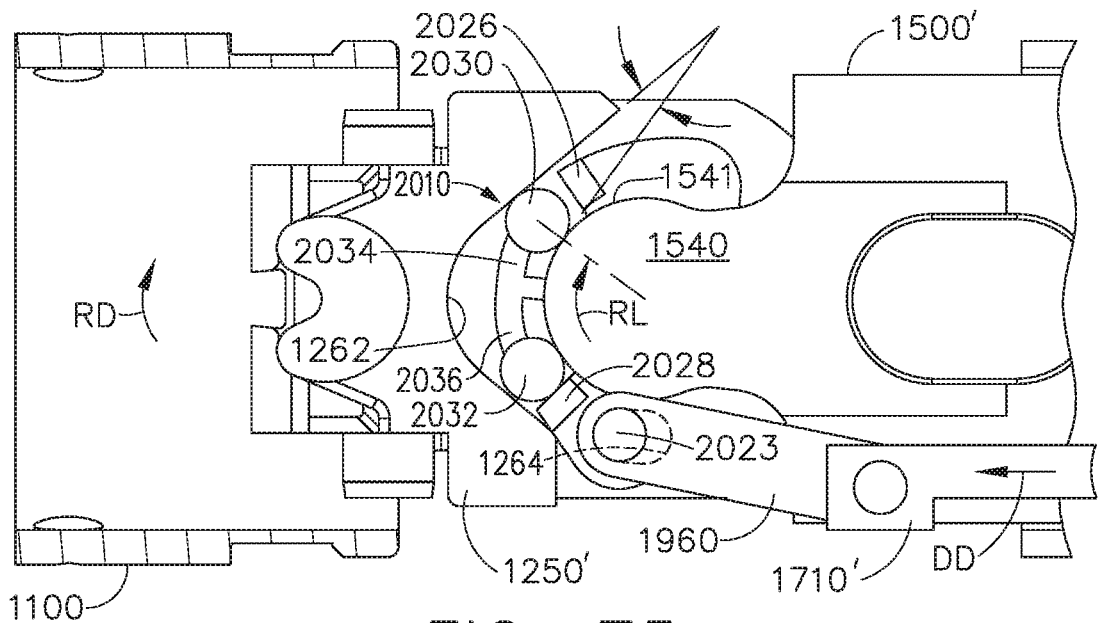
FIG. 75 is another top view of the portions of the interchangeable surgical tool assembly embodiment of FIG. 73 during an initial application of an articulation motion to the articulation joint.
Figure 76:
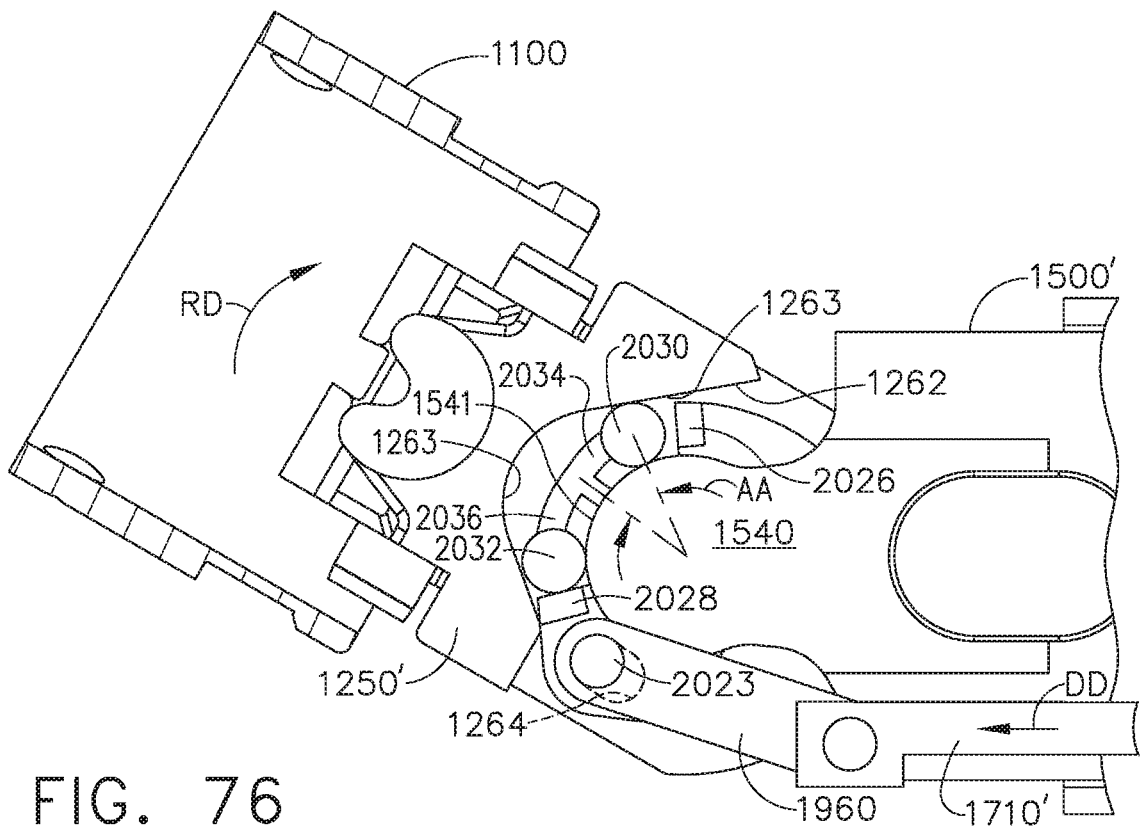
FIG. 76 is another top view of the portions of the interchangeable surgical tool assembly embodiment of FIG. 75 with the surgical end effector thereof in an articulated configuration and the articulation lock in an unlocked configuration.
Figure 77:
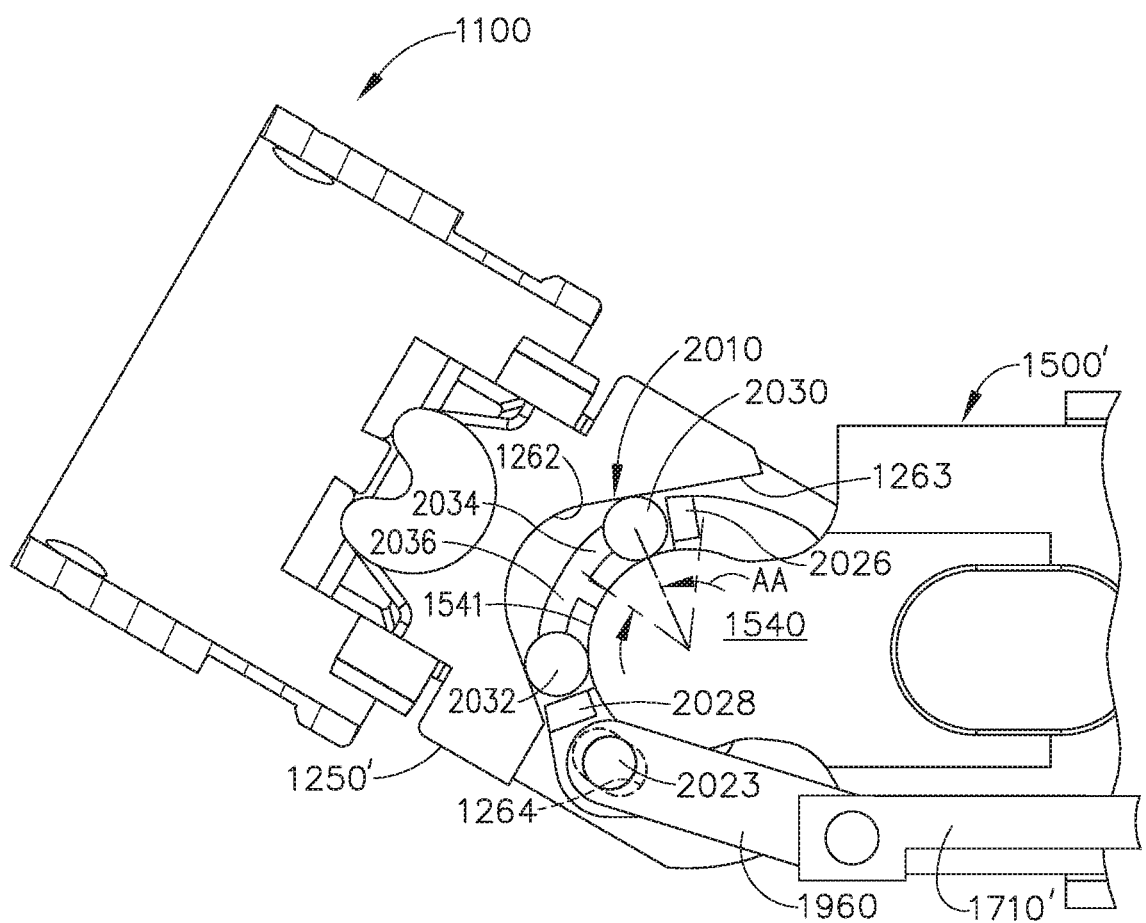
FIG. 77 is another top view of the portions of the interchangeable surgical tool assembly embodiment of FIG. 75 with the surgical end effector thereof in an articulated configuration and the articulation lock in a locked configuration.
Figure 78:
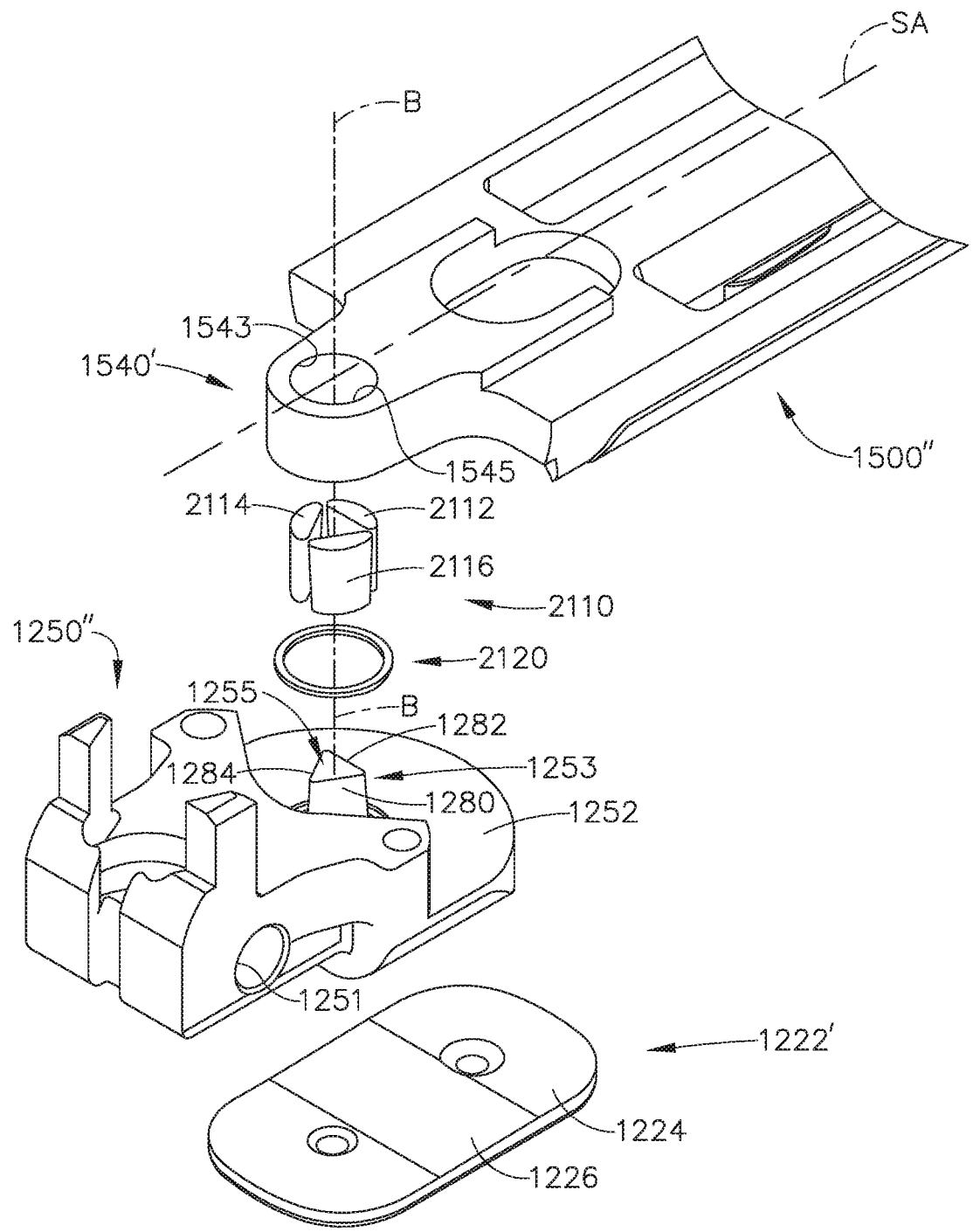
FIG. 78 is an exploded perspective view of portions of an articulation joint and articulation lock embodiment of another interchangeable surgical tool assembly embodiment.
Figure 79:
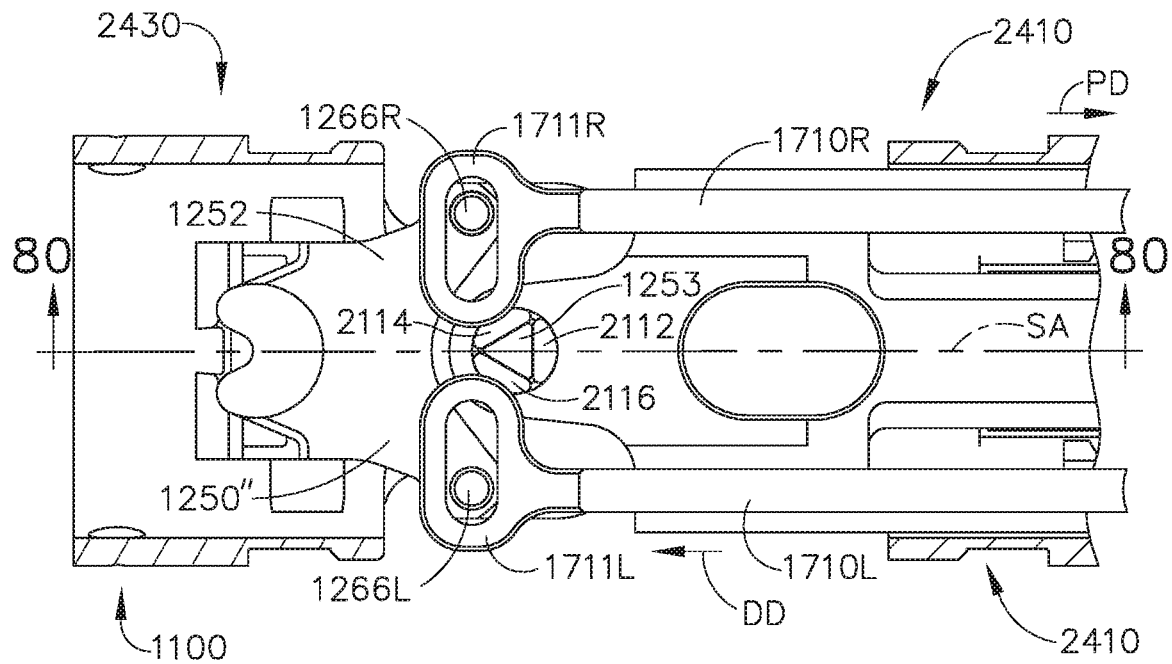
FIG. 79 is a top view of portions of the interchangeable surgical tool assembly embodiment of FIG. 78 with a surgical end effector thereof in an unarticulated configuration.

FIG. 73 illustrates the surgical end effector 1100 in an unarticulated position. As can be seen in FIG. 73, the locking balls 2030, 2032 are captured in locking engagement between the distal locking surface 1263 on the locking cradle 1262 and the proximal locking surface 1541 on the distal end portion 1540 of the spine assembly 1500' to retain the surgical end effector 1100 in the unarticulated position. FIG. 74 illustrates a locking plane LP that extends through the points of contact between the locking ball 2030 and the distal locking surface 1263 on the locking cradle 1262 and the proximal locking surface 1541. FIG. 75 is a top view of the articulation lock arrangement 2010 upon initiation of articulation of the surgical end effector to the right (arrow RD) about the articulation axis. As can be seen in FIG. 75, the right articulation process is initiated by axially advancing the distal articulation link 1710' in the distal direction DD. Distal advancement of the distal articulation link 1710' causes the articulation lock link 1960 to move the articulation pin 2023 distally within the articulation slot 1264 in the mounting base 1252' of the end effector mounting assembly 1250' while also applying a release load RL to the ball retainer base 2022. Movement of the ball retainer base 2022 in the right direction RD causes the ball stop 2026 to move the locking ball 2032 out of locking engagement with the distal locking surface 1263 on the locking cradle 1262. Although the ball stop 2026 has moved out of engagement with locking ball 2030, initially, the locking ball 2030 remains in temporary engagement with the distal locking surface 1263 on the locking cradle 1262 and the proximal locking surface 1541. Further distal advancement of the distal articulation link 1710' causes the articulation pin 2023 to apply the articulation motion to the surgical end effector mounting assembly 1250' in the right direction RD while also moving the ball retainer base 2022 in the right direction RD. The articulation angle AA represents the amount of articulation experienced by the surgical end effector 1100. As the ball retainer base 2022 moves in the right direction RD, the locking ball 2030 also moves out of locking engagement with the distal locking surface 1263 and the proximal locking surface 1541. Ball stop 2028 also holds the locking ball 2032 out of locking engagement with the distal locking surface 1263 and the proximal locking surface 1541 during articulation. Once the surgical end effector 1100 has been articulated to a desired position, the distal advancement of the distal articulation link 1710' is discontinued. Thereafter, the centering springs 2034 and 2036 urge the locking balls 2030 and 2032 into locking engagement with the distal locking surface 1263 and the proximal locking surface 1541 to retain the surgical end effector 1100 in the articulated position. As can be seen in FIG. 76, when in the locked articulated position, the act of the centering springs biasing the locking balls 2030, 2032 into retaining engagement with the distal locking surface 1263 and the proximal locking surface 1541, also results in the movement of the articulation pin 2023 to a neutral position within the articulation slot 1264. To articulate the surgical end effector 1100 in the left direction, the distal articulation link 1710' is moved in the proximal direction which causes the ball lock assembly 2020 and the surgical end effector 1100 to pivot in the left direction and operates in a similar manner.

FIGS. 78-82 illustrate an alternative articulation lock arrangement 2110 for locking a surgical end effector 1100 in an articulated position about an articulation axis B-B relative to a shaft axis SA. In the illustrated example, the surgical end effector 1100 is pivotally coupled to a spine assembly 1500". The spine assembly 1500" may be attached to the chassis 1800 (FIG. 4) in the above described manner. A distal end portion 1540' of the spine assembly 1500" includes a pivot hole 1543 that defines the articulation axis B-B. An end effector mounting assembly 1250" is attached to a proximal end 1103 of the elongate channel 1102 by a spring pin connector 1235 (FIGS. 80-82) that extends through a transverse mounting hole 1251 in the mounting assembly 1250"

to be received within the channel mounting holes 1106 (FIG. 6) that are provided in the proximal end 1103 of the elongate channel 1102. In the illustrated example, the surgical end effector mounting assembly 1250" includes a tapered mounting column 1253 that extends upward from the mounting base 1252 to be received within the pivot hole 1543 in the spine assembly 1500". In one arrangement, the tapered mounting column 1253 tapers away from the mounting base 1252. Stated another way, the cross-sectional area of the end 1255 of the tapered mounting column 1253 is smaller than the cross-sectional area of the portion of the tapered mounting column 1253 adjacent the mounting base 1252.

Figure 80:
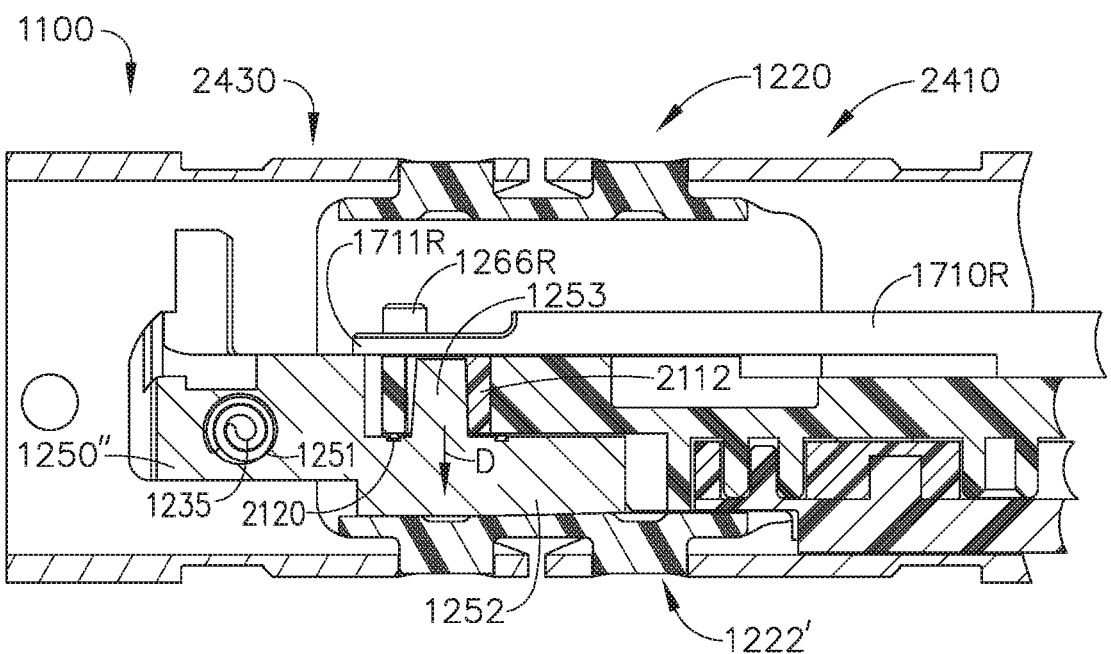
FIG. 80 is a side cross-sectional view of the portions of the interchangeable surgical tool assembly of FIG. 79 taken along line 80-80 in FIG. 79.
Figure 81:
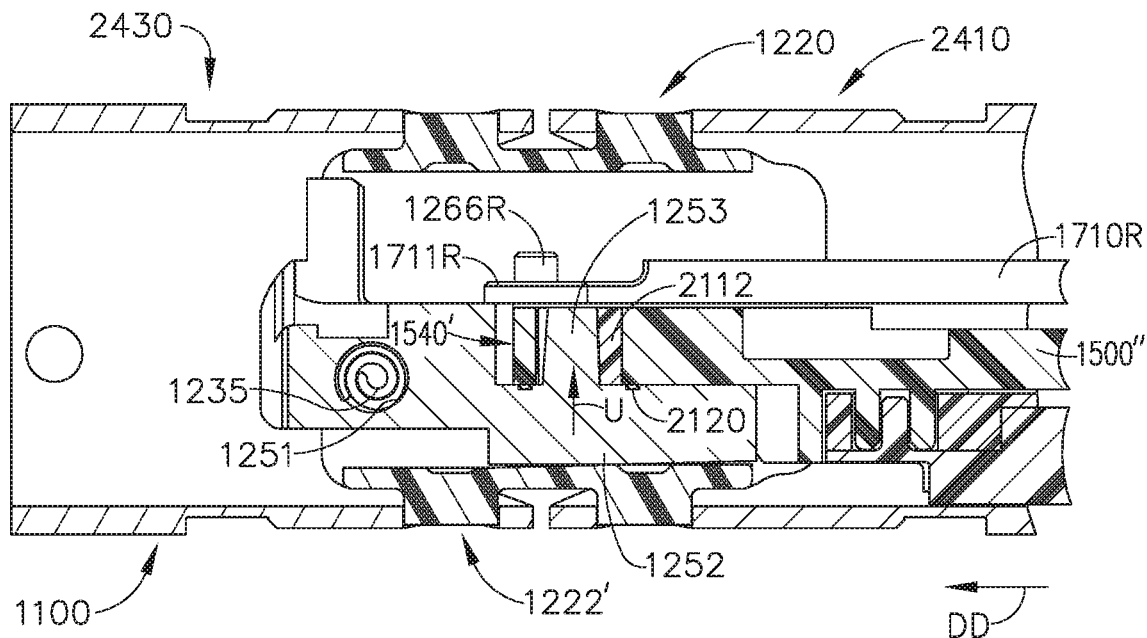
FIG. 81 is another side cross-sectional view of the portions of the interchangeable surgical tool assembly of FIG. 80 during an initial application of articulation motion to the articulation lock thereof.
Figure 82:
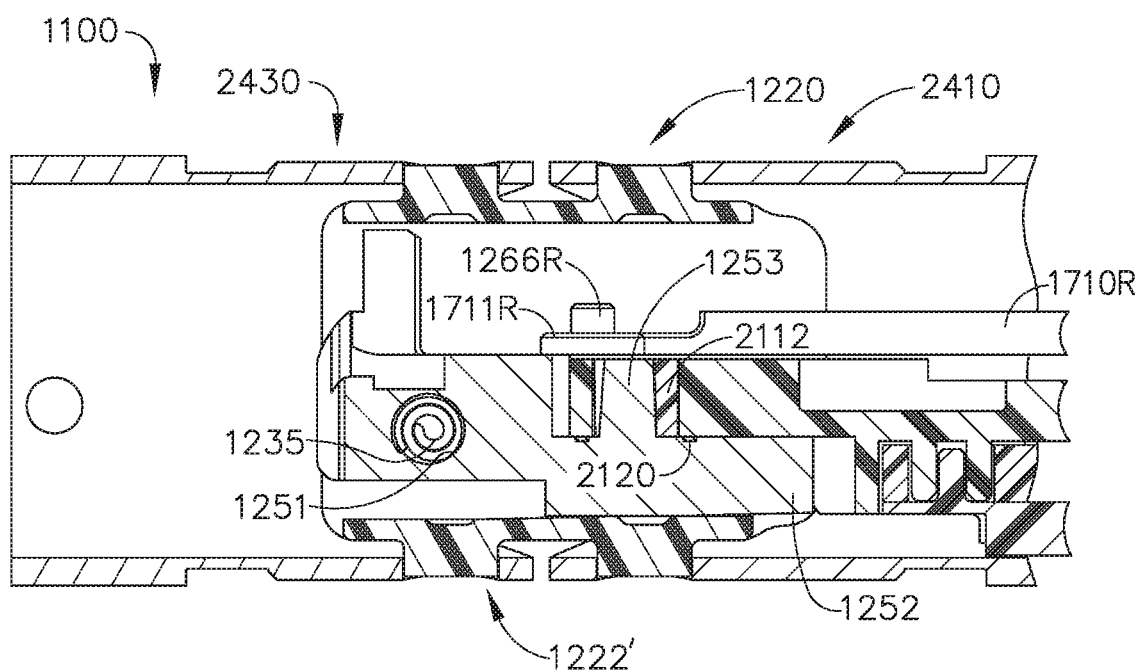
FIG. 82 is another side cross-sectional view of the portions of the interchangeable surgical tool assembly of FIG. 81 with the articulation joint locked in position by the articulation lock.

The articulation lock arrangement 2110 comprises at least one locking member or locking shoe that is movably supported between the mounting column 1253 and an inner wall 1545 of the pivot hole 1543. In the illustrated arrangement, the mounting column 1253 has a triangular cross sectional shape that defines three column sides 1280, 1282, 1284. Thus, (in the illustrated example), three locking members or locking shoes 2112, 2114, 2116 are employed wherein locking shoe 2112 is arranged adjacent the column wall 1282 and locking shoe 2114 is arranged adjacent column wall 1284 and locking shoe 2116 is adjacent column wall 1280. Mounting columns having other shapes and other numbers of locking shoes may also be employed. Each of the locking shoes 2112, 2114, 2116 are received on a wave washer 2120 that is mounted on the mounting base 1252 of the end effector mounting assembly 1250". The illustrated arrangement includes a proximal closure member 2410 that may be axially advanced and retracted in the various manners described herein with respect to proximal closure member 1410, for example. The proximal closure member 2410 is pivotally coupled to a distal closure member 2430 that is similar in construction and operation to distal closure member 1430. As can be seen in FIGS. 80-82, the distal closure member 2430 is coupled to the proximal closure member 2410 by an upper double pivot link 1220 and a lower double pivot link 1222'. In one embodiment, the lower double pivot link 1222' is formed with a tapered ramp 1226 on the upper surface 1224 thereof. See FIG. 78. The illustrated arrangement employs two articulation links 1710R and 1710L to apply left and right articulation motions to the surgical end effector 1100. See FIG. 79. To articulate the surgical end effector 1100 to the right, the articulation link 1710R is axially retracted in the proximal direction PD and the articulation link 1710L is axially advanced in the distal direction DD. Conversely, to articulate the surgical end effector 1100 in the left direction, the articulation link 1710L is axially retracted in the proximal direction PD and the articulation link 1710R is axially advanced in the distal direction DD. The articulation control motions may be generated and applied to the articulation links 1710R, 1710L by various known articulation system arrangements and other articulation system arrangements disclosed herein. The articulation link 1710R has a slotted end portion 1711R that is received on a right articulation pin 1266R that is attached to the end effector mounting assembly 1250". Likewise, the articulation link 1710L has a slotted end portion 1711L that is received on a left articulation pin 1266L that is attached to the end effector mounting assembly 1250".

Turning now to FIG. 80, in the illustrated arrangement, the wave washer 2120 biases the mounting base 1252 of the end effector mounting assembly 1250" downward (arrow D) when the closure system is in an unactuated state. In FIG. 80, the proximal closure member 2410 is in a proximal position. Likewise, the lower double pivot link 1222' is also in a proximal position which permits the mounting base 1252 to be driven downward. Because the mounting base 1252 is in its down-most or unlocked position, the tapered mounting column 1253 has released the locking shoes 2112, 2114, 2116 from retaining engagement with the distal end portion 1540' of the spine assembly 1500" (first unlocked position). Thus, when in that position, the surgical end effector 1100 may be articulated about the articulation axis B-B by the articulation links 1710R, 1710L. Once the surgical end effector 1100 has been articulated to a desired position, the articulation lock arrangement 2110 may be reactivated by distally advancing the proximal closure member 2410.

FIG. 81 illustrates the initiation of the locking process. As can be seen in that Figure, the proximal closure member 2410, as well as the lower double pivot link 1222', has been initially moved in the distal direction DD. As the lower double pivot link 1222' moves distally, the ramp 1226 thereon drives the mounting base 1252 of the end effector mounting assembly 1250" upward to collapse the wave washer 2120. As the mounting base 1252 moves upward (arrow U), the tapered mounting column 1253 urges the locking shoes 2112, 2114, 2116 from a first unlocked position into retaining locking engagement with the distal end portion 1540' of the spine assembly 1500" (second locked position) to lock the surgical end effector 1100 in the articulated position. This locking of the surgical end effector 1100 takes place before the jaws of the surgical end effector are fully closed. FIG. 82 illustrates the positions of the proximal closure member 2410, the lower double pivot link 1222', and the articulation lock arrangement 2110 when the closure system components have been moved to the fully closed position wherein the end effector has been fully closed. Thus, the articulation lock arrangement 2110 may be actuated or moved between a locked state and an unlocked state by actuating the closure system a small amount. Alternative arrangements are contemplated wherein the mounting column is attached to the distal end of the spine assembly and the pivot hole is provide in a proximal portion of the surgical end effector.

Figure 83:
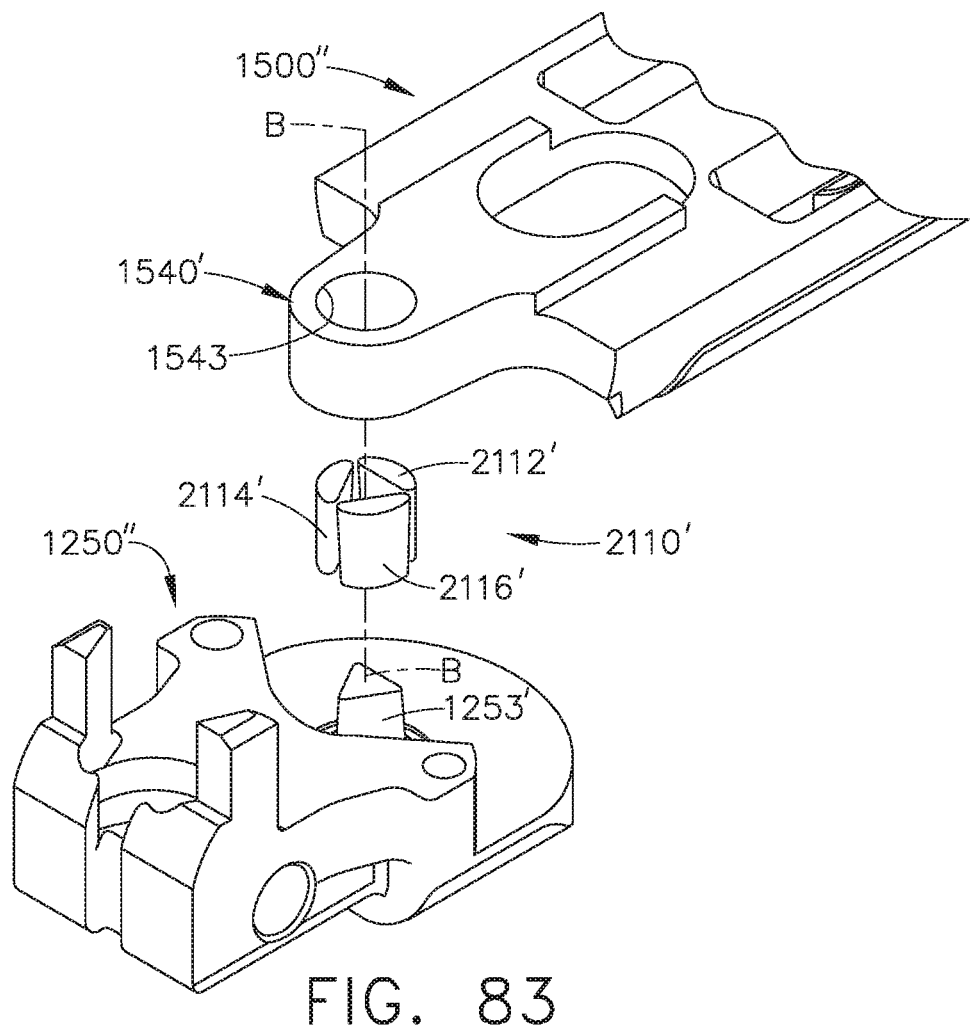
FIG. 83 is an exploded perspective view of portions of a spine assembly, an articulation joint and articulation lock embodiment of another interchangeable surgical tool assembly embodiment.
Figure 84:
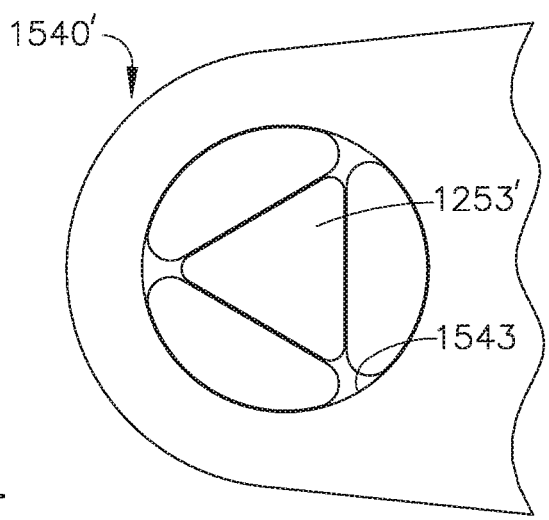
FIG. 84 is a top view of a portion of a distal end of the spine assembly and the articulation lock arrangement of the interchangeable surgical tool assembly embodiment of FIG. 83.

FIGS. 83 and 84 illustrate an alternative articulation lock arrangement 2110' for locking a surgical end effector 1100 in an articulated position about an articulation axis B-B relative to a shaft axis SA. In the illustrated example, the surgical end effector 1100 is pivotally coupled to a spine assembly 1500". The spine assembly 1500" may be attached to the chassis 1800 (FIG. 4) in the above described manner. A distal end portion 1540' of the spine assembly 1500" includes a pivot hole 1543 that defines the articulation axis B-B. An end effector mounting assembly 1250" is attached to a proximal end 1103 of the elongate channel 1102 by a spring pin connector 1235 (FIG. 6) that extends through a transverse mounting hole 1251 in the mounting assembly 1250" to be received within the channel mounting holes 1106 (FIG. 6) that are provided in the proximal end 1103 of the elongate channel 1102. The surgical end effector mounting assembly 1250" includes a mounting column 1253' that extends upward from the mounting base 1252 to be received within the pivot hole 1543 in the spine assembly 1500". In this embodiment, the mounting column 1253' may not be tapered.

This embodiment also includes a plurality of locking shoes 2112', 2114', 2116' that are each fabricated from electrically activated polymer material (EAP). Such material, for example, may expand when it has been electrically excited. For example, electrical current may be applied to one or more of the locking shoes 2112', 2114', 2116' by a conductor (not shown) that extends from the housing or handle arrangement or robotic control system, etc. Thus, once the surgical end effector 1100 has been articulated to a desired position, one or more of the locking shoes 2112', 2114', 2116' are expanded by applying an electrical current thereto. In other arrangements, one or more of the locking shoes 2112', 2114', 2116' may be configured to be pneumatically or hydraulically inflated. In other arrangements, the locking shoes 2112', 2114', 2116' may not be expandable. In such arrangements, the mounting column 1253 may be fabricated from EAP and be selectively expandable by applying an electrical current thereto. In other arrangements, the mounting column 1253 may be selectively pneumatically or hydraulically expandable.

FIGS. 85-89 illustrate an alternative articulation lock arrangement 2210 for locking a surgical end effector 1100 in an articulated position about an articulation axis B-B relative to a shaft axis SA. In the illustrated example, the surgical end effector 1100 is pivotally coupled to a spine assembly 1500'. The spine assembly 1500' may be attached to the chassis 1800 (FIG. 4) in the above described manner. A distal end portion 1540 of an upper portion 1539 of the spine assembly 1500' is formed with a downwardly protruding articulation pin 1542 that defines the articulation axis B-B. The articulation pin 1542 is configured to be rotatably or pivotally received within a spine attachment hole 1254 that is provided in a mounting base 1252 of an end effector mounting assembly 1250". The end effector mounting assembly 1250" is attached to a proximal end 1103 of the elongate channel 1102 by a spring pin connector 1235 (FIG. 6) that extends through a transverse mounting hole 1251 in the mounting assembly 1250" to be received within the channel mounting holes 1106 (FIG. 6) that are provided in the proximal end 1103 of the elongate channel 1102.

Figure 85:
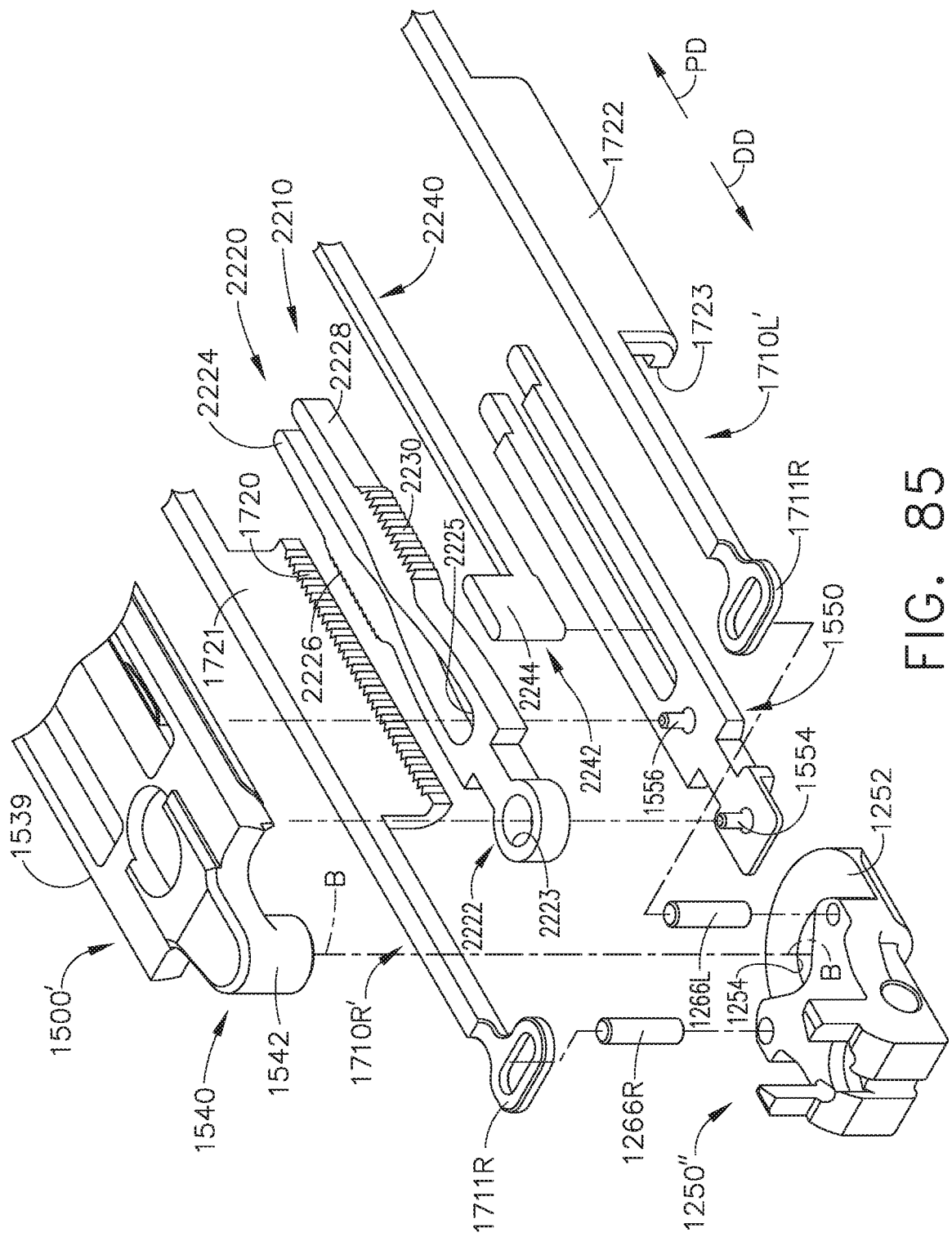
FIG. 85 is an exploded perspective view of portions of a spine assembly, an articulation joint and articulation lock embodiment of another interchangeable surgical tool assembly embodiment.

Referring to FIG. 85, the illustrated arrangement employs two articulation links 1710R' and 1710L' to apply left and right articulation motions to the surgical end effector 1100. In other examples, however, only one articulation link may be employed. In the illustrated arrangement, to articulate the surgical end effector 1100 to the right, the articulation link 1710R' is axially retracted in the proximal direction PD and the articulation link 1710L' is axially advanced in the distal direction DD. Conversely, to articulate the surgical end effector 1100 in the left direction, the articulation link 1710L' is axially retracted in the proximal direction PD and the articulation link 1710R' is axially advanced in the distal direction DD. The articulation link 1710R' has a slotted end portion 1711R that is received on a right articulation pin 1266R that is attached to the end effector mounting assembly 1250". Likewise, the articulation link 1710L' has a slotted end portion 1711L that is received on a left articulation pin 1266L that is attached to the end effector mounting assembly 1250".

Still referring to FIG. 85, the articulation lock arrangement 2210 in the illustrated embodiment includes a locking assembly 2220 that includes a distal end 2222 that has a right locking member or fork 2224 and a left locking member or fork 2228 protruding therefrom. The right locking member 2224 includes a right locking gear rack 2226 that is laterally adjacent to and in confronting relationship therewith a corresponding right articulation gear rack 1720 that is formed on a downwardly extending portion of the right articulation link 1710R'. Similarly, the left locking member 2228 includes a left locking gear rack 2230 that is laterally adjacent to and in confronting relationship with a corresponding left articulation gear rack 1723 that is formed on a downwardly extending portion 1722 of the left articulation link 1710L'. In an unactuated state, the right locking member 2224 and the left locking member 2228 are centrally located between the right articulation link 1710R' and the left articulation link 1710L' and are not in engagement therewith. As can also be seen in FIG. 85, the locking assembly 2220 is supported between a lower distal spine portion 1550 and the upper spine portion 1539. The lower distal spine portion 1550 includes an upwardly extending distal support pin 1554 that extends through a mounting hole 2223 in the distal end 2222 of the locking assembly 2220 to be received in a distal boss 1544 formed on the underside of the upper spine portion 1539. See FIG. 86. The lower distal spine portion 1550 further includes an upwardly extending proximal support pin 1556 that extends through a locking opening 2225 between the right and left locking members 2224, 2228 to be received in a proximal boss 1546 formed on the underside of the upper spine portion 1539.

In the illustrated arrangement, the articulation lock arrangement 2210 also includes an axially movable locking bar assembly 2240 that operably interfaces with an articulation transmission 2250 that is operably supported within the shaft assembly 1400'. The locking bar assembly 2240 includes a locking wedge 2244 that is formed on a distal end 2242 thereof. The articulation transmission 2250 is configured to operably interface with the distal firing bar 1620 that is operably supported in the shaft assembly 1400'. In this context, the distal firing bar 1620 may comprise a firing actuator.

Figure 86:
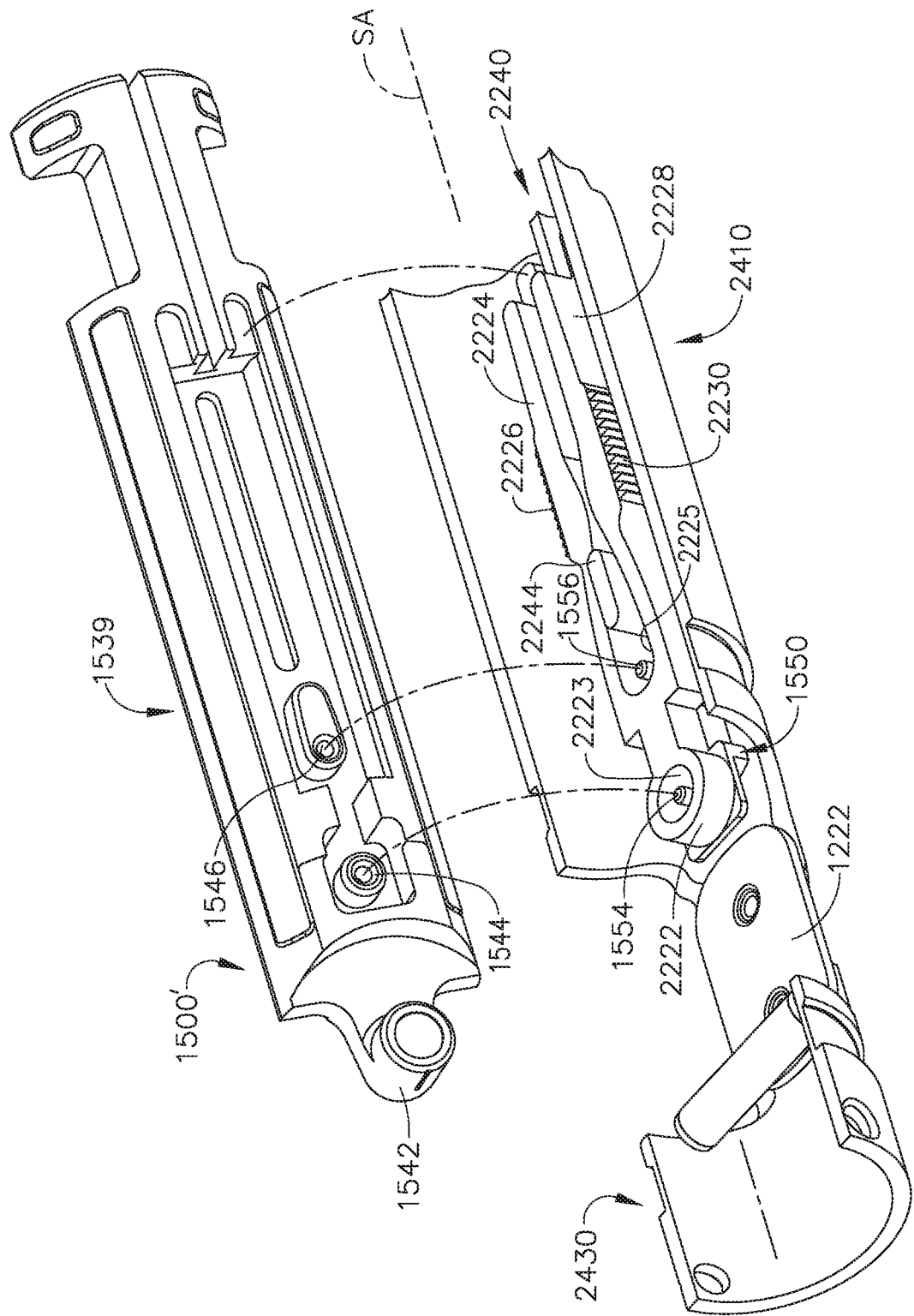
FIG. 86 is another exploded perspective view of portions of the spine assembly and articulation joint and articulation lock of the interchangeable surgical tool assembly of FIG. 85.
Figure 87:
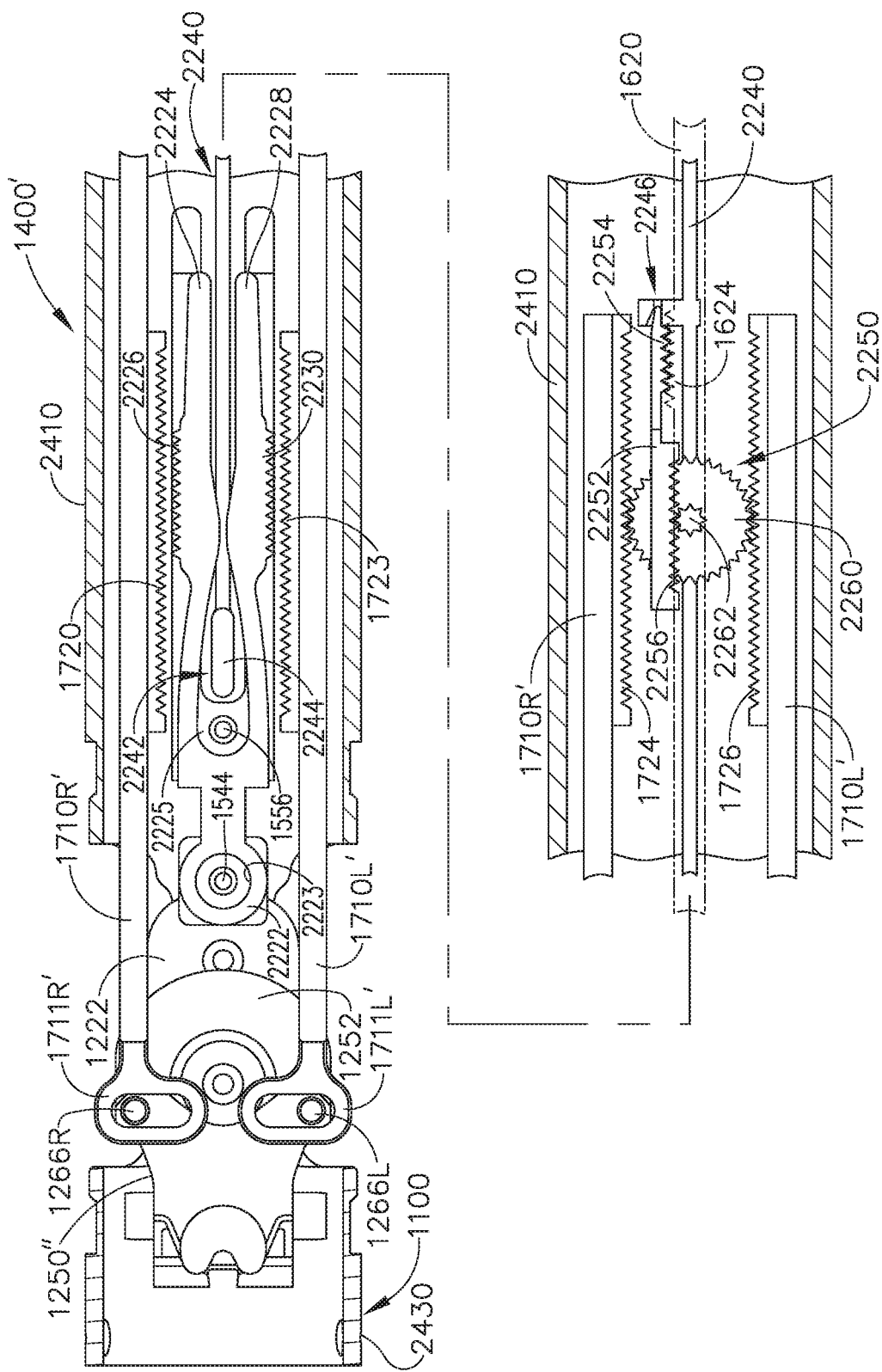
FIG. 87 is a top cross-sectional view of the interchangeable surgical tool assembly of FIG. 85 with a surgical end effector thereof in an unarticulated configuration.

Turning now to FIGS. 85-87, in the illustrated arrangement, one form of the articulation transmission 2250 includes a firing rack 1624 that is formed on a portion of the distal firing bar 1620 and which is configured to operably engage a shifter drive rack 2254 that is formed on a shifter 2252. A proximal end 2253 of the shifter 2252 is configured to operably interface with a lock bar coupler 2246 that is formed on the locking bar assembly 2240. As can also be seen in FIGS. 85-87, the shifter 2252 further includes a shifter driven rack 2256 that is in meshing engagement with an articulation pinion gear 2262 that is attached to an articulation sprocket gear 2260. The articulation sprocket gear 2260 is rotatably supported within the shaft assembly 1400' and is in meshing engagement with a right articulation drive rack 1724 that is formed on or attached to the right distal articulation link 1710R' as well as in meshing engagement with a left articulation drive rack 1726 that is formed on or otherwise attached to the left distal articulation link 1710L'.

Operation of the articulation transmission 2250 as well as the articulation lock arrangement 2210 will be explained with reference to FIGS. 87-89. FIG. 87 illustrates the surgical end effector 1100 in an unarticulated position. The locking bar assembly 2240 is in its distal-most "unlocked position" wherein the locking wedge 2244 is received within the locking opening 2225 located between the right and left locking members 2224, 2228. The right and left locking members 2224, 2228 are in their unactuated state and not in engagement with the right and left articulation links 1710R', 1710L'. Thus, the right locking gear rack 2226 on the right locking member 2224 is out of engagement with the right articulation gear rack 1720 on the right distal articulation link 1710R' and the left locking gear rack 2230 is out of meshing engagement with the left articulation gear rack 1723 on the left distal articulation link 1710L'. As such, the articulation lock arrangement 2210 is in an "unlocked" configuration. However, friction between the various components may keep the surgical end effector 1100 from flopping or rotating about the articulation axis B-B.

Figure 88:
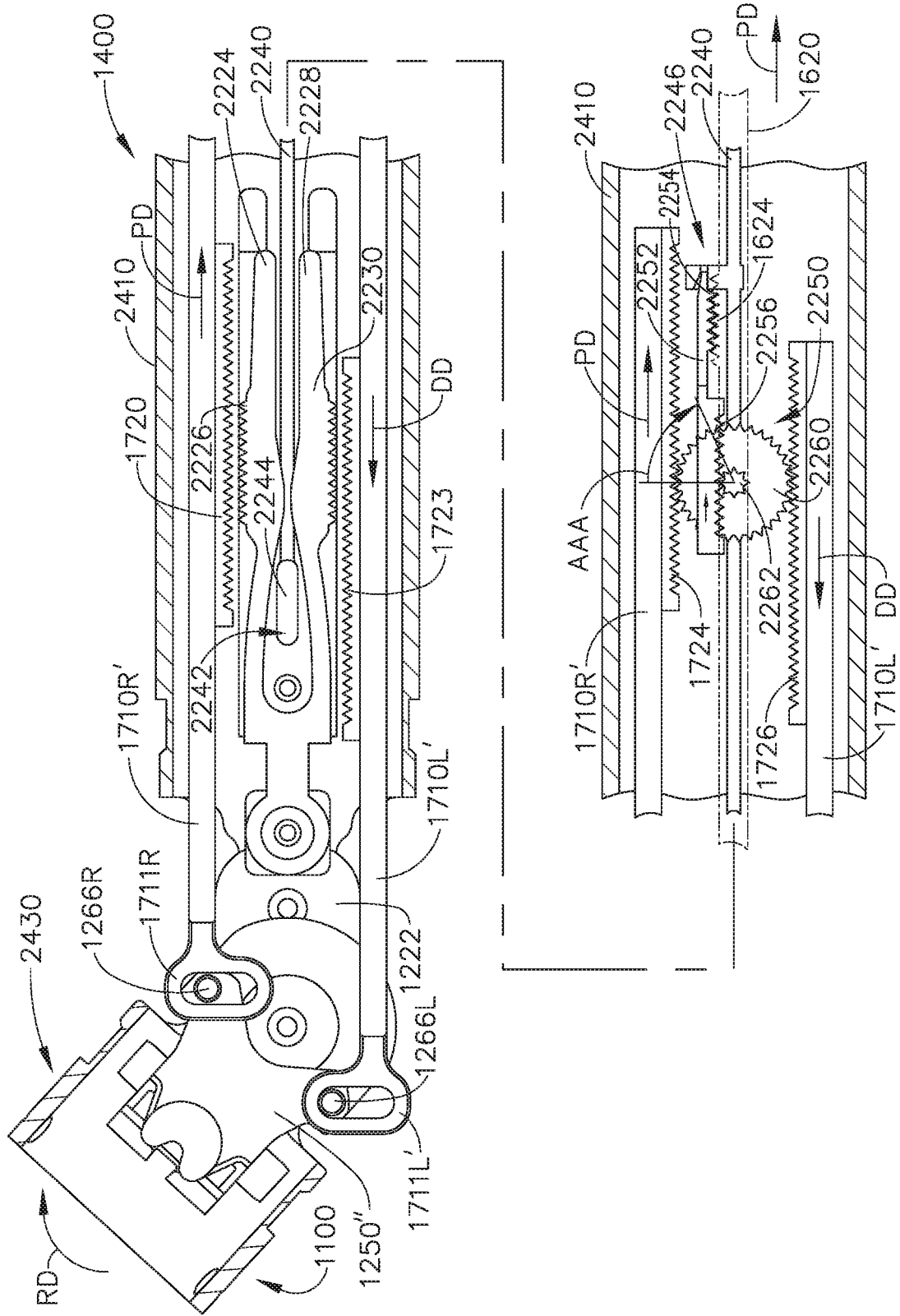
FIG. 88 is another top cross-sectional view of the interchangeable surgical tool assembly of FIG. 87 with the surgical end effector thereof in an articulated configuration and the articulation lock in an unlocked configuration.

FIG. 88 illustrates initiation of the articulation process. As can be seen in FIG. 88, the proximal end 2253 of the shifter 2252 is operably engaged with the lock bar coupler 2246 and the locking bar assembly 2240 is in the unlocked orientation. When the shifter 2252 is engaged with the locking bar assembly 2240 in this manner, the shifter drive rack 2254 is in meshing engagement with the firing rack 1624 on the distal firing bar 1620. The articulation process is then initiated by axially moving the distal firing bar 1620. In the example shown in FIG. 88, the end effector 1100 is articulated about the articulation axis in the right direction RD by axially moving the distal firing bar 1620 in the proximal direction PD. Axial actuation of the distal firing bar 1620 in the proximal and distal directions has been discussed in detail herein. Because the lock bar coupler 2246 is retaining the shifter drive rack 2254 in meshing engagement with the firing rack 1624 on the distal firing bar 1620, the shifter 2252 moves proximally with the distal firing bar 1620. Movement of the shifter 2252 in the proximal direction PD, by virtue of the meshing engagement of the shifter driven rack 2256 with the articulation pinion gear 2262, causes the articulation pinion gear 2262 and the articulation sprocket gear 2260 to rotate in the clockwise direction through an articulation actuation angle AAA. As the articulation sprocket gear 2260 rotates, the right distal articulation link 1710R' is driven in the proximal direction PD and the left distal articulation link 1710L' is driven in the distal direction DD which ultimately causes the surgical end effector to pivot about the articulation axis in the right direction RD. Once the surgical end effector 1100 has been articulated to the desired position, the user can lock the end effector 1100 in that articulated position by axially advancing the locking bar assembly 2240 in the proximal direction PD to cause the locking wedge 2244 to move proximally into driving contact with two actuation detents 2227, 2229 formed on the right locking member 2224 and left locking member 2228, respectively to laterally bias the right locking member 2224 and left locking member 2228 laterally outward into locking engagement with the right and left articulation gear racks 1720, 1723, respectively. Such proximal movement of the locking bar assembly 2240 also serves to decouple the lock bar coupler 2246 from the shifter 2252 as shown in FIG. 89.

Figure 89:
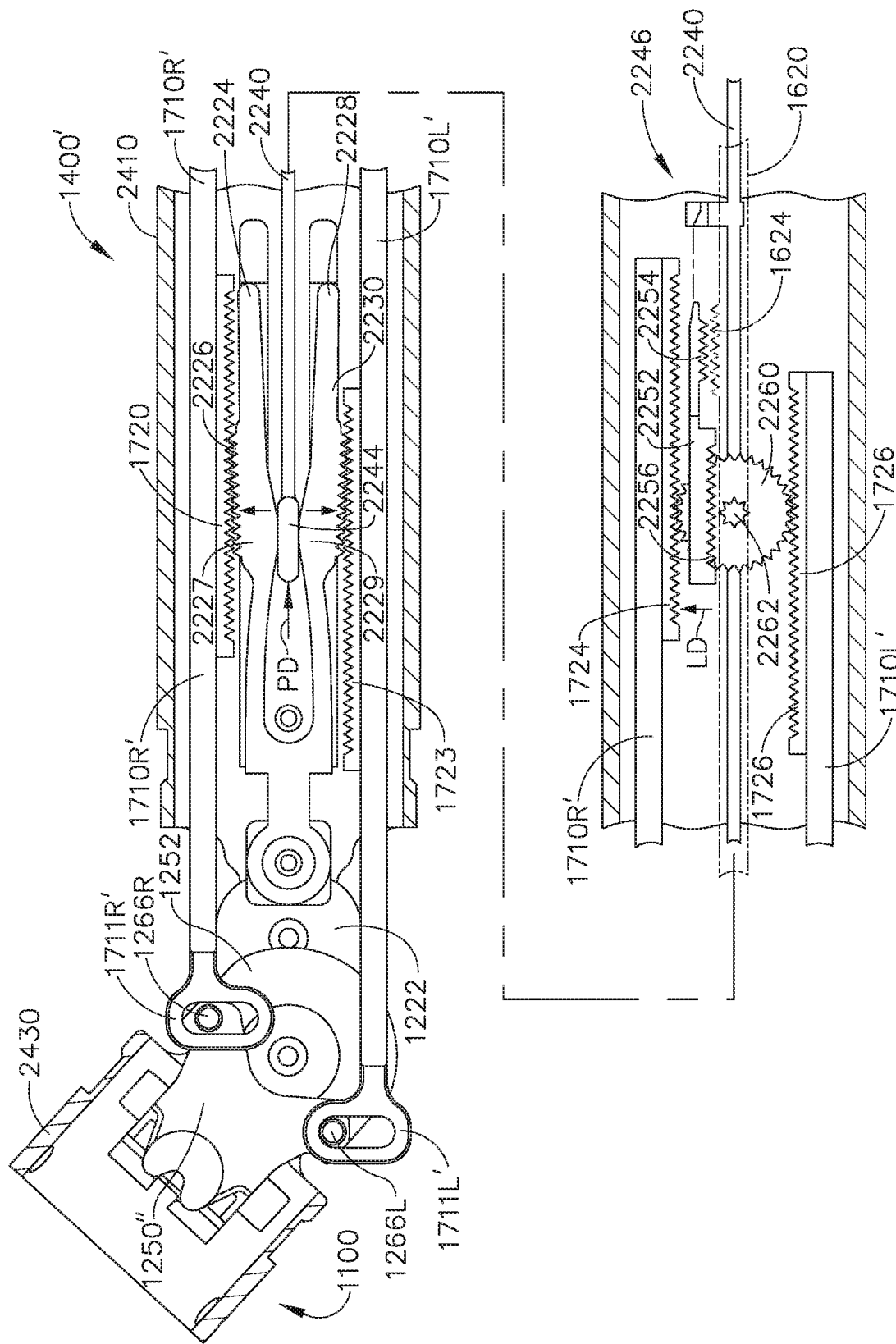
FIG. 89 is another top cross-sectional view of the interchangeable surgical tool assembly of FIG. 88 with the surgical end effector thereof in an articulated configuration and the articulation lock in a locked configuration.

As can be seen in FIG. 89, when the shifter 2252 has been decoupled from the locking bar assembly 2240, the shifter drive rack 2254 is no longer in meshing engagement with the firing rack 1624 on the distal firing bar 1620 and the shifter driven rack 2256 is no longer in meshing engagement with the articulation pinion gear 2262. Thus, the distal firing bar 1620 can now be distally advanced to apply firing motions to the surgical end effector and then retracted in the proximal direction back to the starting position shown in FIG. 87. Once the distal firing bar 1620 has returned to the starting position, the user may then distally advance the locking bar assembly 2240 so as to bring the lock bar coupler 2246 into operable engagement with the proximal end 2253 of the shifter 2252 and move the locking wedge 2244 back into its starting or unlocked position wherein the right locking member 2224 and the left locking member 2228 can spring back or otherwise return to their unlocked positions. The user may then apply axial motion to the distal firing bar 1620 in the appropriate axial direction to return the surgical end effector 1100 to its unarticulated position.

FIGS. 90-95 illustrate an alternative articulation lock arrangement 2310 for locking a surgical end effector 1100 in an articulated position about an articulation axis B-B relative to a shaft axis SA. In the illustrated example, the surgical end effector 1100 is pivotally coupled to a spine assembly 1500'. The spine assembly 1500' may be attached to the chassis 1800 (FIG. 4) in the above-described manner. A distal end portion 1540 of an upper spine portion 1539 of the spine assembly 1500' is formed with a downwardly protruding articulation pin 1542 that defines the articulation axis B-B. The articulation pin 1542 is configured to be rotatably or pivotally received within a spine attachment hole 1254 that is provided in a mounting base 1252 of an end effector mounting assembly 1250". The end effector mounting assembly 1250" is attached to a proximal end 1103 of the elongate channel 1102 by a spring pin connector 1235 (FIG. 6) that extends through a transverse mounting hole 1251 in the mounting assembly 1250" to be received within the channel mounting holes 1106 (FIG. 6) that are provided in the proximal end 1103 of the elongate channel 1102.

Figure 90:
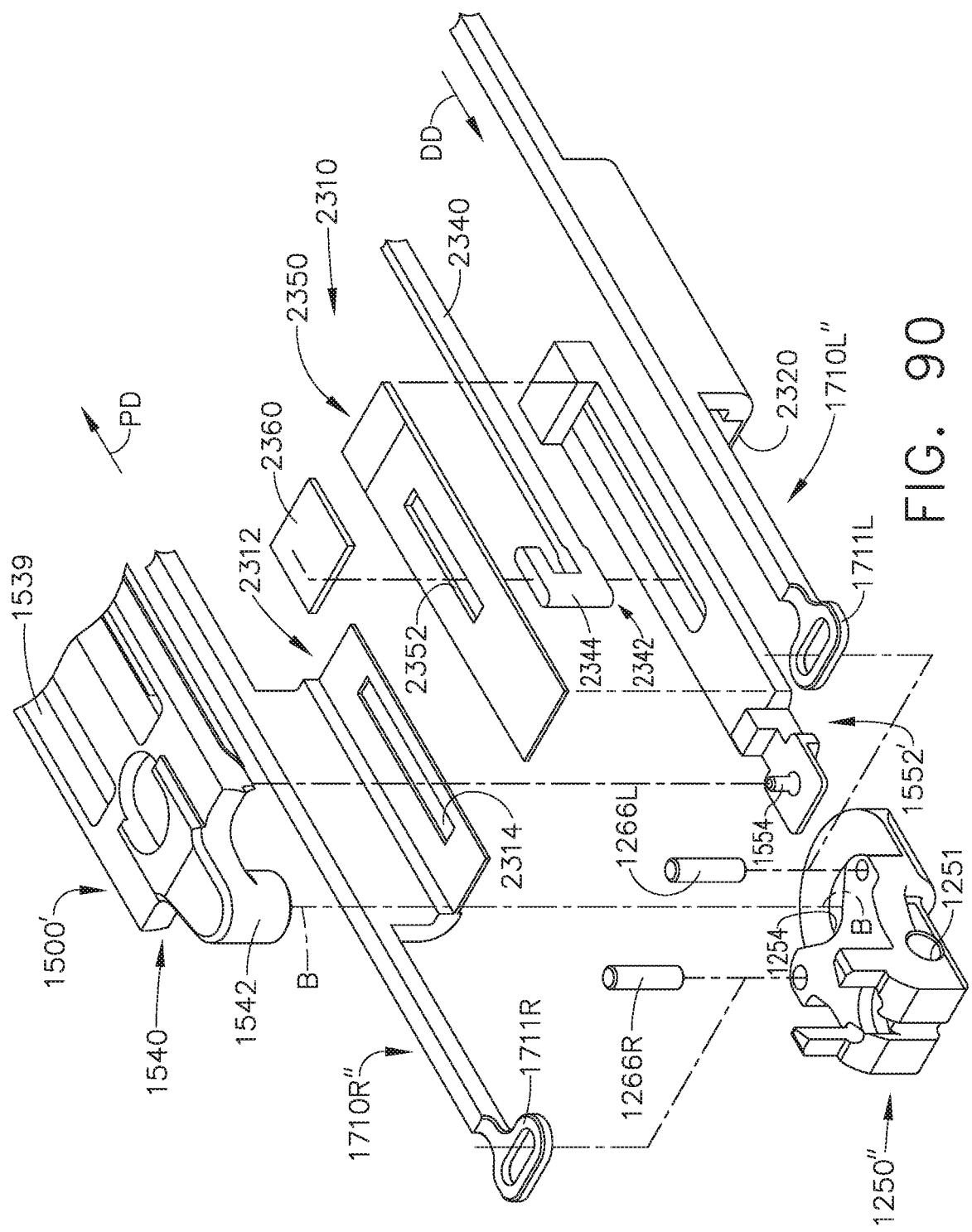
FIG. 90 is an exploded perspective view of portions of a spine assembly, an articulation joint and articulation lock embodiment of another interchangeable surgical tool assembly embodiment.

Referring to FIG. 90, the illustrated arrangement employs two articulation links 1710R" and 1710L" to apply right and left articulation motions to the surgical end effector 1100. To articulate the surgical end effector 1100 to the right, the articulation link 1710R" is axially retracted in the proximal direction PD and the articulation link 1710L" is axially advanced in the distal direction DD. Conversely, to articulate the surgical end effector 1100 in the left direction, the articulation link 1710L" is axially retracted in the proximal direction PD and the articulation link 1710R" is axially advanced in the distal direction DD. The right distal articulation link 1710R" has a slotted end portion 1711R that is received on a right articulation pin 1266R that is attached to the end effector mounting assembly 1250". Likewise, the left distal articulation link 1710L" has a slotted end portion 1711L that is received on a left articulation pin 1266L that is attached to the end effector mounting assembly 1250".

Still referring to FIG. 90, a right brake plate 2312 is formed on the right distal articulation link 1710R" and a left brake plate 2320 is formed on the left distal articulation link 1710L". As can also be seen in FIG. 90, the right and left brake plates 2312, 2320 are supported between a lower distal spine portion 1552' and the upper spine portion 1539. The lower distal spine portion 1552' includes an upwardly extending distal support pin 1554 that is configured to be received in a distal boss (not shown) that is formed on the underside of the upper spine portion 1539. In the illustrated arrangement, the articulation lock arrangement 2310 also includes an axially movable and lockable locking bar assembly 2340 that may operably interface with an articulation transmission of the type described herein or otherwise interface with a lock bar control arrangement (not shown) that is configured to apply axial control motions thereto in the distal direction DD and proximal direction PD. The locking bar assembly 2340 includes a locking clamp 2344 that is formed on a distal end 2342 thereof. The locking clamp 2344 extends through a right brake slot 2314 in the right brake plate 2312 and a left brake slot 2322 in the left brake plate 2320 as well as through an axial slot 2352 provided through a wedge plate 2350 to engage a clamp plate 2360.

Figure 91:
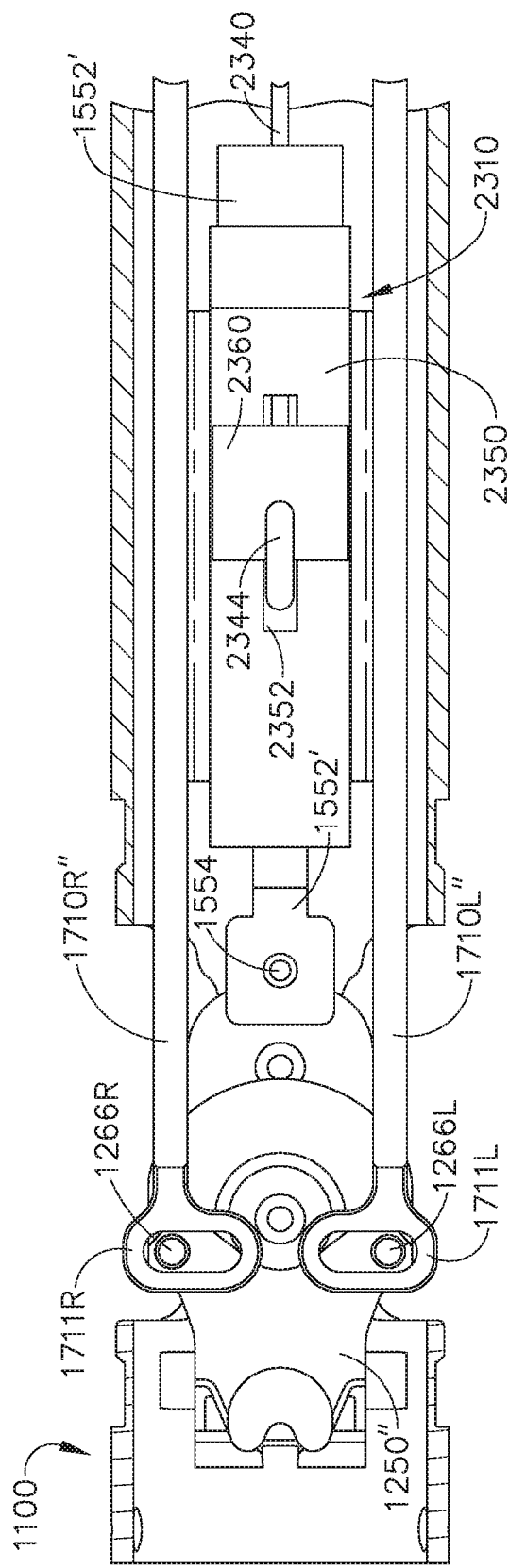
FIG. 91 is a top cross-sectional view of the interchangeable surgical tool assembly of FIG. 90 with a surgical end effector thereof in an unarticulated configuration.
Figure 94:
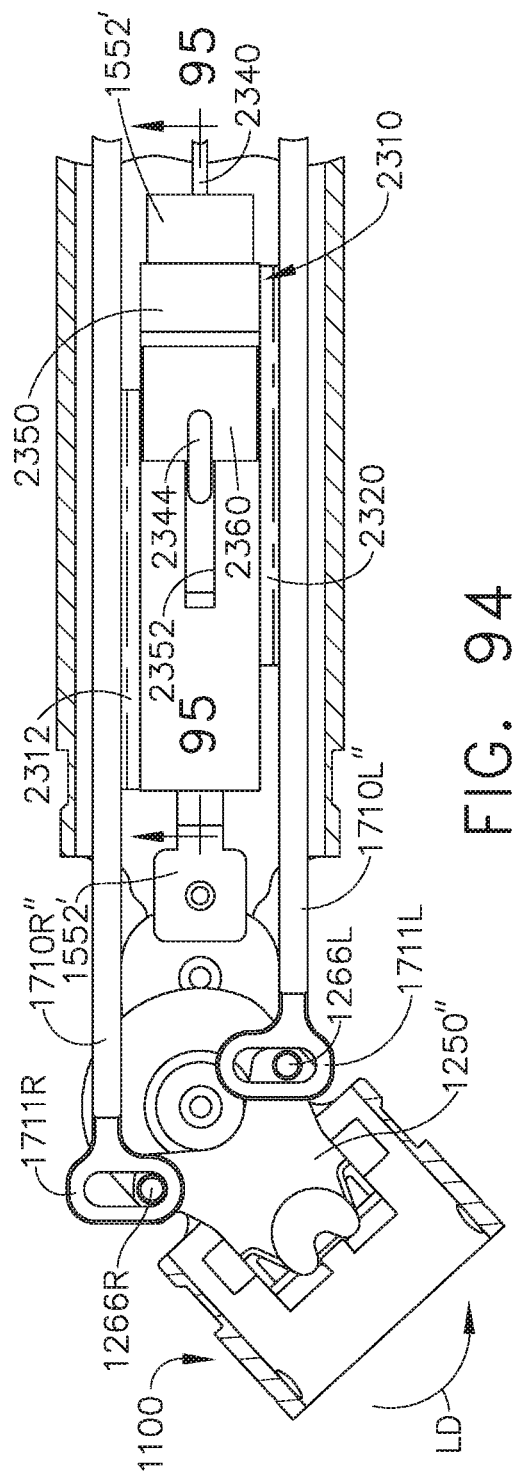
FIG. 94 is another top cross-sectional view of the interchangeable surgical tool assembly of FIG. 91 with the surgical end effector thereof in an articulated configuration and the articulation lock in a locked configuration.
Figure 95:
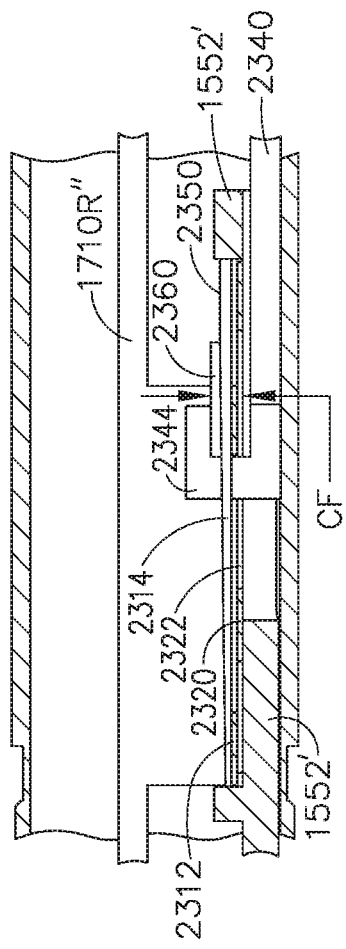
FIG. 95 is a partial cross-sectional view of the articulation lock of FIG. 94 taken along line 95-95 in FIG. 94.

Operation of the articulation lock arrangement 2310 will be explained with reference to FIGS. 91-95. FIG. 91 illustrates the surgical end effector 1100 in an unarticulated position. The locking bar assembly 2340 is in an unlocked position wherein the clamp portion 2344 is not applying any clamping force to the right and left brake plates 2312, 2320. Thus, the right distal articulation link 1710R" and the left distal articulation link 1710L" are free to move axially when articulation motions are applied thereto. Friction between the various components may keep the surgical end effector 1100 from flopping or rotating about the articulation axis B-B. FIG. 92 illustrates articulation of the surgical end effector 1100 in the left direction LD by axially moving the right distal articulation link 1710R" in the distal direction DD and moving the left distal articulation link 1710L" in the proximal direction PD. FIG. 93 illustrates the articulation lock arrangement 2310 in the unlocked configuration. FIGS. 94 and 95 illustrate the articulation lock arrangement 2310 in the locked configuration. The articulation lock arrangement 2310 is locked by applying an actuation motion to the locking bar assembly 2340 in the proximal direction. Such action causes the clamping portion thereof to clamp the right and left brake plates 2312, 2320 to be retainingly clamped between the wedge plate 2350 and the lower distal spine portion 1552'. Such arrangement serves to apply a clamping force CF between the clamping plate 2360 and the lower distal spine portion 1552' to thereby prevent any further axial movement of the right distal articulation link 1710R" and the left distal articulation link 1710L".

Figure 96:
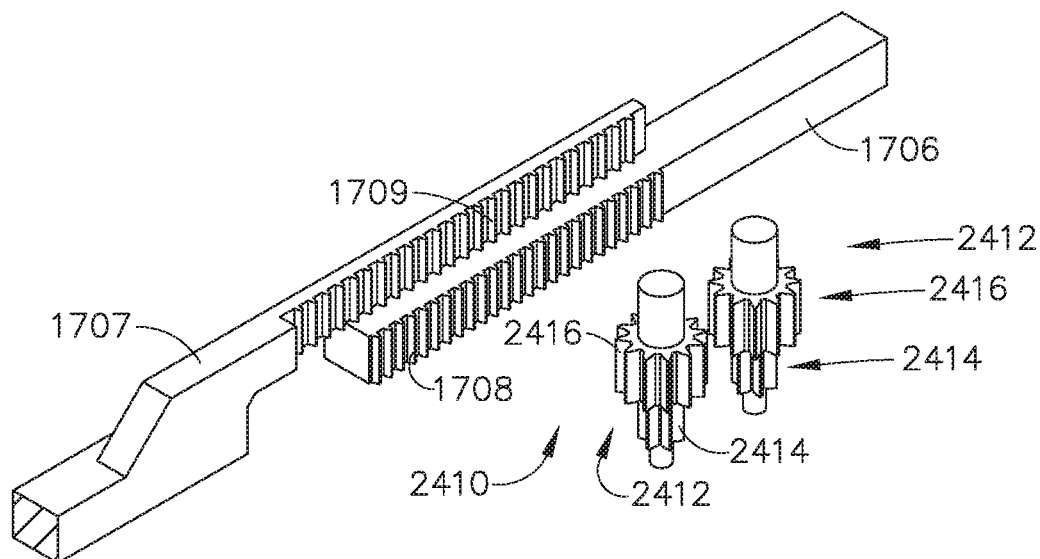
FIG. 96 is a perspective view of portions of an articulation stroke multiplier embodiment.
Figure 97:
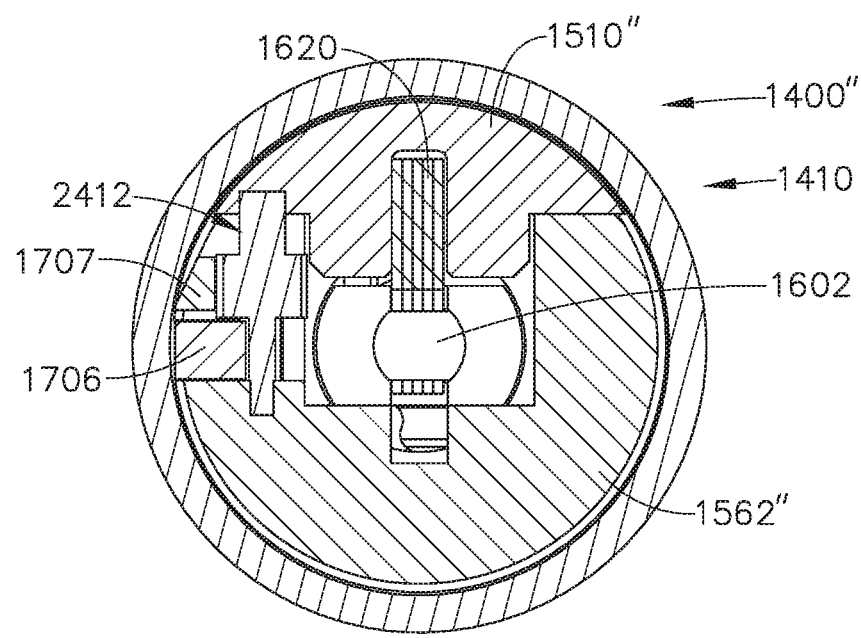
FIG. 97 is a cross-sectional end view of a shaft assembly of an interchangeable surgical tool assembly embodiment with the articulation stroke multiplier embodiment of FIG. 96 therein.

FIGS. 96 and 97 illustrate an example of an articulation stroke multiplier transmission arrangement 2410 that may be employed with various articulation link arrangements disclosed herein. Turning first to FIG. 97, a cross-sectional view is illustrated of a portion of a shaft assembly 1400" that includes a proximal closure member 1410 as well as an upper intermediate spine segment 1510" and a distal spine extension 1562". The intermediate spine segment 1510" and a distal spine extension 1562" serve to operably support a distal firing bar 1620 as well as the proximal firing shaft segment 1602 in the various manners disclosed herein. This embodiment includes an intermediate articulation link segment 1706 and a distal articulation link segment 1707 that may interface with an end effector mounting assembly in any of the various ways disclosed herein. The intermediate articulation link 1706 may operably interface with an articulation lock 1210 in the various manners disclosed herein. As can be seen in FIG. 96, the intermediate articulation link segment 1706 includes an intermediate or first gear rack 1708 formed thereon and the distal articulation link segment 1707 includes a second or distal gear rack 1709. The gear racks 1708 and 1709 are in meshing engagement with at least one and preferably at least two multiplier pinion gear sets 2412 that are rotatably supported between an upper intermediate spine segment 1510" and the distal spine extension 1562". See FIG. 97. In the illustrated arrangement for example, each multiplier gear set 2412 comprises a smaller drive gear 2414 that is supported in meshing engagement with the first gear rack 1708 and a larger multiplier gear 2416 that is supported in meshing engagement with the distal gear rack 1709.

FIGS. 98A-98C illustrate operation of the articulation stroke multiplier transmission arrangement 2410. FIG. 98A illustrates the positions of the intermediate articulation link segment 1706 and a distal articulation link segment 1707 when in a neutral or unarticulated position. FIG. 98B illustrates the positions of the intermediate articulation link segment 1706 and a distal articulation link segment 1707 after the intermediate articulation link segment 1706 has been axially advanced in the distal direction from the neutral position in FIG. 98A a distance $D_{1R}$. As can also be seen in FIG. 98B, the distal articulation link 1707 moved an axial distance $D_{2R}$. In the illustrated example, $D_{2R} > D_{1R}$. FIG. 98C illustrates the positions of the intermediate articulation link segment 1706 and a distal articulation link segment 1707 after the intermediate articulation link segment 1706 has been axially advanced in the proximal direction PD from the neutral position illustrated in FIG. 98A a distance $D_{1L}$. As can also be seen in FIG. 98C, the distal articulation link 1707 moved an axial distance $D_{2L}$. In the illustrated example, $D_{2L} > D_{1L}$. Thus, such an arrangement enables additional axial articulation stroke to be gained and employed to articulate the end effector through greater ranges of articulation about the articulation axis.

FIGS. 99A-99B illustrate an example of an articulation stroke multiplier transmission 2510 that may be employed with various articulation link arrangements disclosed herein. The articulation stroke multiplier 2510 operably interfaces with a proximal articulation driver 1700" which may be identical to the proximal articulation driver 1700 except for the noted differences. In particular, the proximal articulation driver 1700" includes a drive rack 1701 that is formed on the distal end thereof. The drive rack is configured to meshingly engage a gear segment 2522 that is formed on a swing gear 2520 that is pivotally pinned to a corresponding portion of the spine assembly. In the illustrated arrangement, the swing gear 2520 is pivotable about a swing gear axis that is transverse to the axial directions in which the proximal articulation driver 1700" is configured to travel. The swing gear 2520 further includes a transfer slot 2524 that is configured to receive a transfer pin 1713 that is attached to a proximal end 1716 of an intermediate articulation link segment 1706". As can be seen in FIGS. 99A-99B, the distal end of the intermediate articulation link segment 1706" is configured to operably interface with an articulation lock 1210 in the various manners disclosed herein.

Figures 99C, 99D:
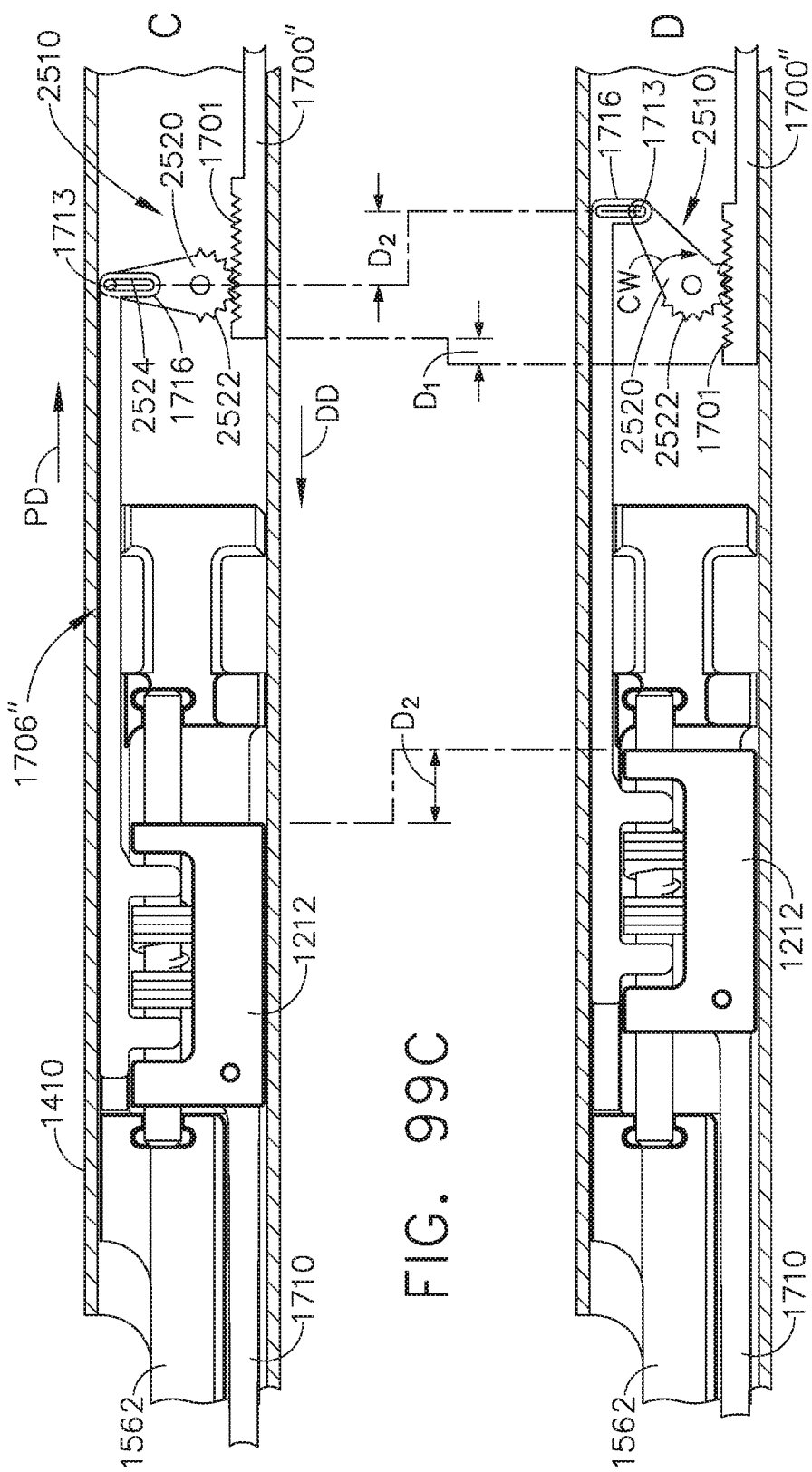
FIG. 99C is a top cross-sectional view of portions of a shaft assembly of another interchangeable surgical tool assembly embodiment with another articulation stroke multiplier embodiment in an unactuated configuration.
FIG. 99D is another top cross-sectional view of the shaft assembly and articulation stroke multiplier of FIG. 99C after an axial articulation motion has been applied thereto in a first axial direction.

FIG. 99A, illustrates the articulation stroke multiplier transmission 2510 in a neutral position wherein no articulation motion has been applied to the proximal articulation driver 1700". FIG. 99B illustrates the position of the articulation stroke multiplier transmission 2510 after the proximal articulation driver 1700" has been axially advanced in the distal direction DD a first axial distance $D_1$. Such movement of the proximal articulation driver 1700" in the distal direction causes the swing gear 2520 to pivot in a clockwise direction CW about the swing gear axis. Such movement of the swing gear 2520 drives the intermediate articulation link segment 1706" in the proximal direction a second axial distance $D_2$. In such example, $D_2 > D_1$. FIGS. 99C-99D illustrate a similar arrangement, except that the transfer slot 2524 is provided in the proximal end 1716 of the intermediate articulation link segment 1706" and the transfer pin 1713 is provided in the swing gear 2520.

Replaceable staple cartridges can be designed for different uses and applications. For example, certain replaceable staple cartridges can be designed for use with different types of tissue and/or for different surgical procedures. Consequently, replaceable staple cartridges can have different dimensions, different quantities of staples, different staple sizes, and/or different staple arrangements, for example. Moreover, different replaceable staple cartridges can be designed for use with different surgical instruments or different end effectors. For example, a particular replaceable staple cartridge can be compatible with one or more particular end effectors and incompatible with one or more other end effectors. The compatibility of a replaceable staple cartridge and an end effector can depend on the dimensions and/or features of the staple cartridge and the end effector.

In certain instances, it is desirable to ensure that a staple cartridge is installed in an appropriate (i.e. compatible) end effector. For example, if an end effector is designed to receive a particular type of staple cartridge, such as a 45 mm staple cartridge having three rows of longitudinally-oriented staple cavities, it can be desirable to ensure that the particular staple cartridge is fully insertable in such an end effector. It can be correspondingly desirable to prevent other staple cartridges, such as 30 mm staple cartridges and/or 45 mm staple cartridges have a different arrangement of staple cavities, for example, from being installed in such an end effector. While certain incompatible staple cartridges may be too large to install (e.g. a 60 mm staple cartridge in an end effector designed to receive a 45 mm staple cartridge), other incompatible staple cartridges may appear to fit within the end effector. Moreover, certain staple cartridges can appear to be similar but can have different internal components or properties, such as different sized staples, different staple drivers, and/or different sleds, for example.

Certain incompatible staples cartridges that appear to fit within an end effector can have the same width and/or the same length as a compatible staple cartridge. In the present disclosure, staple cartridges of the "same width" refers to staple cartridges having substantially the same or the same width, staple cartridges of the "same length" refers to staple cartridges having substantially the same or the same length, and staple cartridges having the "same length" of staple rows refers to staple cartridges having substantially the same or the same length of staple rows. For the purposes of this disclosure, a dimensional difference that is indiscernible or unnoticeable to an ordinary observer is considered to be the same or substantially the same. Additionally, for the purposes of this disclosure, a dimensional difference of less than or equal to fifteen percent is considered to be substantially the same. For example, in certain instances, an incompatible staple cartridge can have a length of 60 mm and a compatible staple cartridge can have a length of 55 mm. To an ordinary observer, the incompatible and compatible staple cartridges appear to have the same length. In fact, the length of the compatible staple cartridge is eight percent smaller than the length of the incompatible staple cartridge, however, the incompatible and compatible staple cartridges are considered to have substantially the same length and, thus, the "same length" in the present disclosure. As another example, an incompatible staple cartridge can have a width that is 1 mm narrower than a compatible staple cartridge, however, the cartridges can be considered to have the "same width" because the 1 mm difference is unnoticeable to ordinary observer. As described herein, an incompatible staple cartridge can have the same length, the same width, the same quantity of staples, and/or the same length staple row as a compatible staple cartridge.

In such instances, it can be desirable to incorporate cooperating and/or mating alignment features between the end effector and the compatible staple cartridges. Such alignment features can be designed to interlock when a staple cartridge is inserted in the appropriate end effector. Similarly, such alignment features can result in interference and, thus, incomplete insertion when an operator attempts to install an incompatible staple cartridge into the end effector. Moreover, because the interference can prevent an incompatible staple cartridge from sliding or snapping into the elongate channel, the incomplete insertion can trigger a missing cartridge lockout and/or an incomplete clamp lockout.

Figure 100:
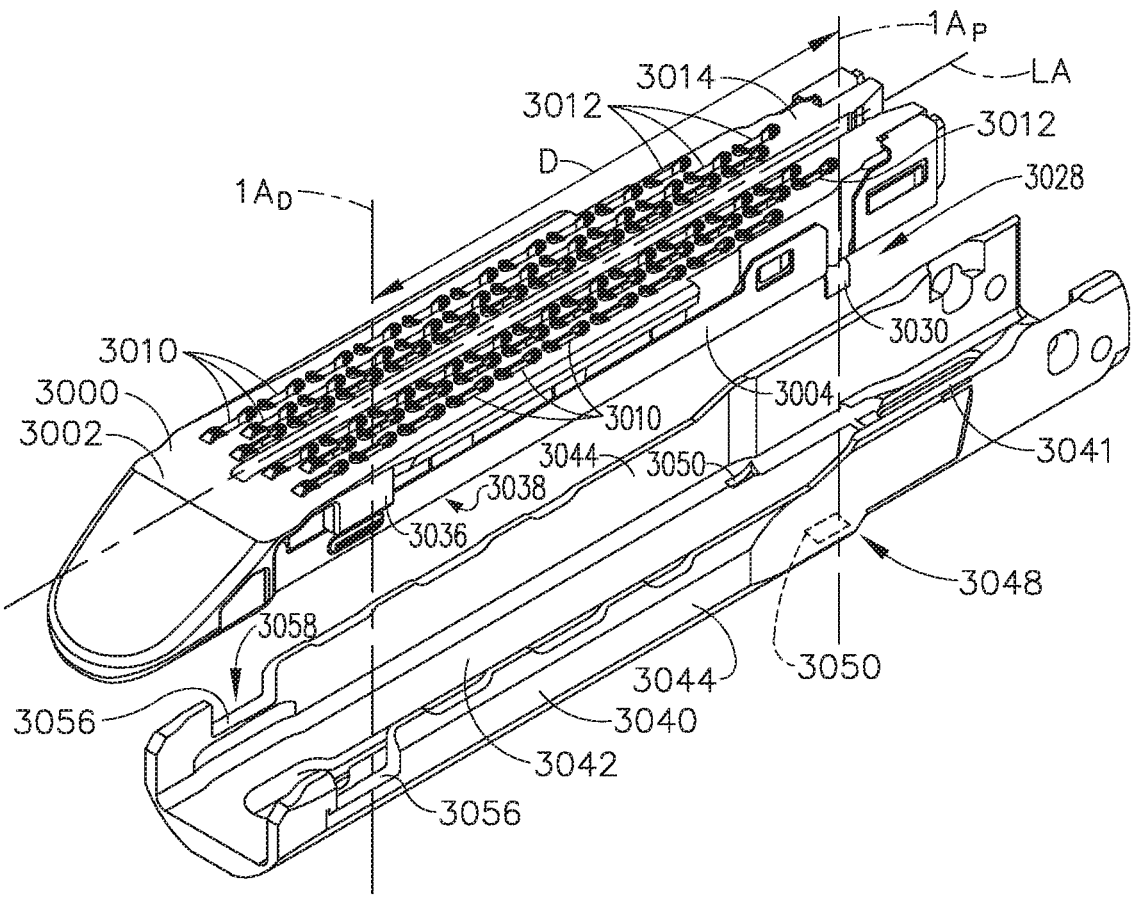
FIG. 100 is an exploded perspective view of a channel and a staple cartridge.
Figure 101:
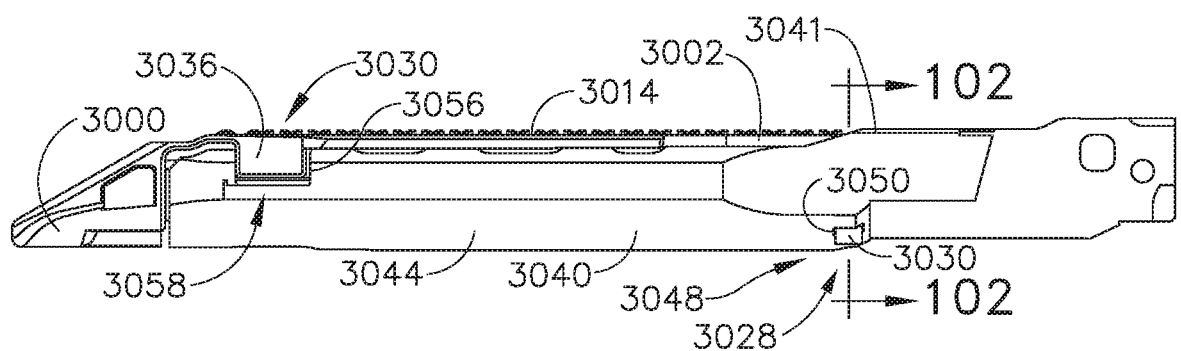
FIG. 101 is an elevation view of the channel and the staple cartridge of FIG. 100.
Figure 102:
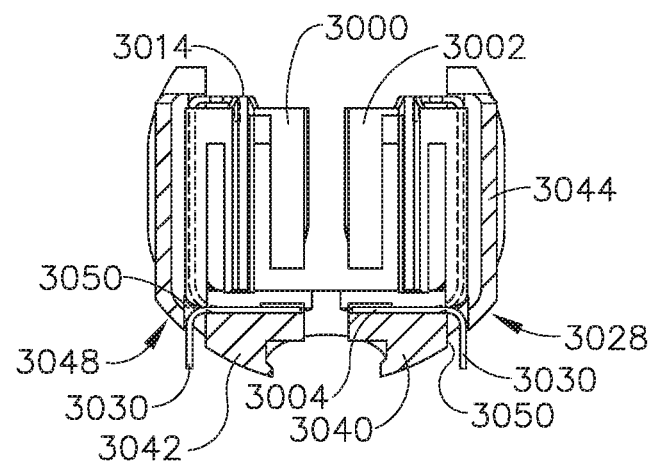
FIG. 102 is a cross-sectional elevation view of the channel and the staple cartridge of FIG. 100 taken across the plane indicated in FIG. 101.

A staple cartridge 3000 is depicted in FIGS. 100-102. The staple cartridge 3000 is compatible with an elongate channel 3040, which is part of a surgical end effector. Various surgical end effectors having elongate channels, which are similar in many aspects to the channel 3040, for example, are further described herein. The elongate channel 3040 is configured to receive the staple cartridge 3000. For example, the dimensions and structure of the elongate channel 3040 are compatible with the dimensions and structure of the staple cartridge 3000.

The staple cartridge 3000 includes a cartridge body 3002 and a pan 3004 positioned partially around the cartridge body 3002. The cartridge body 3002 is a molded body into which staple cavities 3010 (FIG. 100) are defined. A staple can be removably positioned in each staple cavity 3010. In certain instances, each staple can be supported by a staple driver movably positioned in each staple cavity 3010. Each staple cavity 3010 defines an opening 3012 in a deck 3014 of the cartridge body 3002. The pan 3004 wraps around a portion of the cartridge body 3002. The cartridge body 3002 can be comprised of a plastic material, for example, and the pan 3004 can be comprised of a metal material, for example.

The staple cartridge 3000 also includes proximal alignment features 3028 and distal alignment features 3038, which interlock or mate with corresponding proximal alignment features 3048 and distal alignment features 3058, respectively, on the channel 3040. In the staple cartridge 3000, the proximal alignment features 3028 include downwardly-protruding tabs 3030. The tabs 3030 extend from a proximal portion of the bottom or base of the pan 3004. More specifically, the tabs 3030 protrude from the base or bottom surface of the staple cartridge 3000 in the vicinity of the proximal-most staple cavities 3010. In other instances, the tabs 3030 can be proximal to the proximal-most staple cavities or distal to the proximal-most staple cavities.

In certain instances, the tabs 3030 are tags or flaps of metal from the pan 3004 that are bent or folded downward away from the cartridge body 3002 and toward the channel 3040. The staple cartridge 3000 includes a pair of symmetrical tabs 3030. The tabs 3030 are symmetrical with respect to a longitudinal axis LA (FIG. 100) of the staple cartridge 3000. In other instances, the tabs 3030 may be asymmetrical with respect to the longitudinal axis LA and/or the proximal alignment features 3028 can consist of a single downwardly-protruding tab. In certain instances, the downwardly-protruding tabs 3030 can be nubs, pins, bosses, or protrusions on the bottom of the pan 3004.

The channel 3040 includes proximal alignment features 3048 that corresponds to the proximal alignment features 3028 of the staple cartridge 3000. The proximal alignment features 3048 include apertures 3050, which are defined in a bottom 3042 of the channel 3040 and configured to receive the tabs 3030. The perimeter of the apertures 3050 corresponds to the dimensions of the tabs 3030. In other words, the tabs 3030 are configured to fit snuggly within the apertures 3050. In certain instances, the tabs 3030 can slidingly engage the apertures 3050 as the tabs 3030 move into engagement with the apertures 3050. In such instances, the clearance between the tabs 3030 and the apertures 3050 can be sufficient to prevent interference while minimizing non-axial movement of the tabs 3030 relative to the apertures 3050. More specifically, the tabs 3030 can move along proximal installation axes (see proximal installation axis $IA_P$ in FIG. 100) as the staple cartridge 3000 is positioned in the channel 3040. Lateral and/or longitudinal movement of the tabs 3030 relative to the proximal installation axes $IA_P$ can be restrained by the dimensions of the apertures 3050.

The reader will appreciate that the tabs 3030 and the corresponding apertures 3050 can define different geometries than those shown in FIGS. 100-102. For example, the tabs 3030 can be shorter, longer, wider, and/or narrower. In other instances, the spacing between the tabs 3030 can be different. In instances where the tabs 3030 define a different geometry than those shown in FIGS. 100-102, the apertures 3050 can define a correspondingly different geometry such that the apertures 3050 guide or lead the tabs 3030 along the proximal installation axes $IA_P$. As further described herein, the proximal position of the tabs 3030 ensures that the proximal end of the staple cartridge 3000 is properly seated in the channel 3040. If the proximally-positioned tabs 3030 are not aligned with the apertures 3050, the tabs 3030 can be configured to abut an inner surface of the channel 3040 and lift a proximal portion of the staple cartridge 3000 away from the channel 3040, which can prevent the closing of an anvil jaw relative to the channel 3040.

In other instances, the proximal alignment features 3028 can comprise apertures in the staple cartridge 3000, and the corresponding proximal alignment features 3048 in the channel 3040 can include pins protruding from the channel 3040 and configured to slidingly engage the apertures in the staple cartridge 3000. For example, the channel 3040 can include machined posts protruding upward, and the staple cartridge 3000 can include cutouts or pinholes dimensioned to receive the posts. In at least one instance, one or more posts can extend from a proximal portion of the channel 3040 and corresponding cutout(s) can be molded into the cartridge body. The geometry and/or arrangement of posts and cutouts can vary between cartridge types. For example, the posts and cutouts can be shifted, staggered, and/or repeated along the longitudinal axis.

In the staple cartridge 3000, the distal alignment features 3038 include laterally-extending lugs 3036. The lugs 3036 protrude from the sides of the staple cartridge 3000. The lugs 3036 are formed with the cartridge body 3002. For example, the lugs 3036 can be molded features on the cartridge body 3002. The lugs 3036 define rectangular protrusions from the cartridge body 3002. Although only a single lug 3036 is depicted in FIGS. 100 and 101, the reader will appreciate that symmetrical lugs are positioned on each side of the staple cartridge 3000. In other instances, the distal alignment features 3038 can consist of a single lug on one side of the staple cartridge 3000.

The channel 3040 includes corresponding distal alignment features 3058. For example, the channel 3040 includes sidewalls 3044 having cutouts 3056 defined therein. The cutouts 3056 are positioned and dimensioned to receive the lugs 3036. The perimeter of the cutouts 3056 corresponds to the dimensions of the lugs 3036. In other words, the lugs 3036 are configured to fit snuggly within the cutouts 3056. In certain instances, the lugs 3036 can slidingly engage the cutouts 3056 as the lugs 3036 move into engagement with the cutouts 3056. In such instances, the clearance between the lugs 3036 and the cutouts 3056 can be sufficient to prevent interference while minimizing non-axial movement of the lugs 3036 relative to the cutouts 3056. More specifically, the lugs 3036 can move along a distal installation axis $IA_D$ (FIG. 100) as the staple cartridge 3000 is positioned in the channel 3040. The distal installation axis $IA_D$ is parallel to the proximal installation axis $IA_P$ and spaced apart from the proximal installation axis $IA_P$ by a longitudinal distance D (FIG. 100). Lateral and/or longitudinal movement of the lugs 3036 relative to the distal installation axis $IA_D$ can be restrained by the dimensions of the cutouts 3056. As the staple cartridge 3000 approaches the elongate channel 3040 along the installation axes, the staple cartridge 3000 can slide or snap in place in the elongate channel 3040. For example, the proximal alignment features 3028 can interlock with the corresponding proximal alignment features 3048, and the distal alignment features 3038 can interlock with the corresponding distal alignment features 3058.

Mating engagement of the proximal alignment features 3028, 3048 and mating engagement of the distal alignment features 3038, 3058 is configured to ensure that the staple cartridge 3000 can be completely inserted or installed in the channel 3040. For example, when the tabs 3030 are positioned in the apertures 3050 and the lugs 3036 are positioned in the cutouts 3056, the staple cartridge 3000 fits within the channel 3040 like an interlocking puzzle piece. In such instances, an outer bottom surface of the staple cartridge 3000 can be positioned flush against an inner bottom surface of the channel 3040 (see FIG. 102). Moreover, the staple cartridge 3000 and the channel 3040 can be aligned with the longitudinal axis LA. In other words, the staple cartridge 3000 is not tilted or skewed within the channel 3040. Referring primarily to FIGS. 101 and 102, when the staple cartridge 3000 is fully inserted in the channel 3040, a proximal portion of the deck 3014 is positioned below an upper edge 3041 of the channel 3040.

The alignment features 3028, 3038, 3048, and 3058 are also configured to ensure that an incompatible staple cartridge is not positioned in the channel 3040. An incompatible staple cartridge can be a staple cartridge having a different length, different quantity of staples, different arrangement of staples, and/or other differing features. Additionally, an incompatible staple cartridge can include incompatible alignment features (i.e. interference features). For example, an incompatible staple cartridge may include proximal tabs having incompatible dimensions (e.g. too large) with respect to the apertures 3050. In other instances, the spacing and/or the positioning of the proximal tabs of an incompatible staple cartridge can be different than the spacing and/or positioning of the apertures 3050. Additionally or alternatively, the longitudinal distance between the proximal tabs and the distal lugs 3036 can be different than the distance D (FIG. 100). In instances in which the proximal tabs are incompatible with the apertures 3050, the proximal tabs of the incompatible staple cartridge can interfere with the channel 3040. More specifically, the proximal tabs can be positioned against an inner surface of the bottom 3042 of the channel. As a result, the proximal tabs can lift a proximal portion of the incompatible staple cartridge away from the channel 3040. Consequently, the proximal end of the deck 3014 of the incompatible staple cartridge can be raised above the channel 3040, which can prevent the closing of an anvil jaw relative to the channel 3040. In various instances, the incomplete closing of the anvil jaw can trigger an incomplete clamping lockout, which can prevent a firing stroke.

Figure 103:
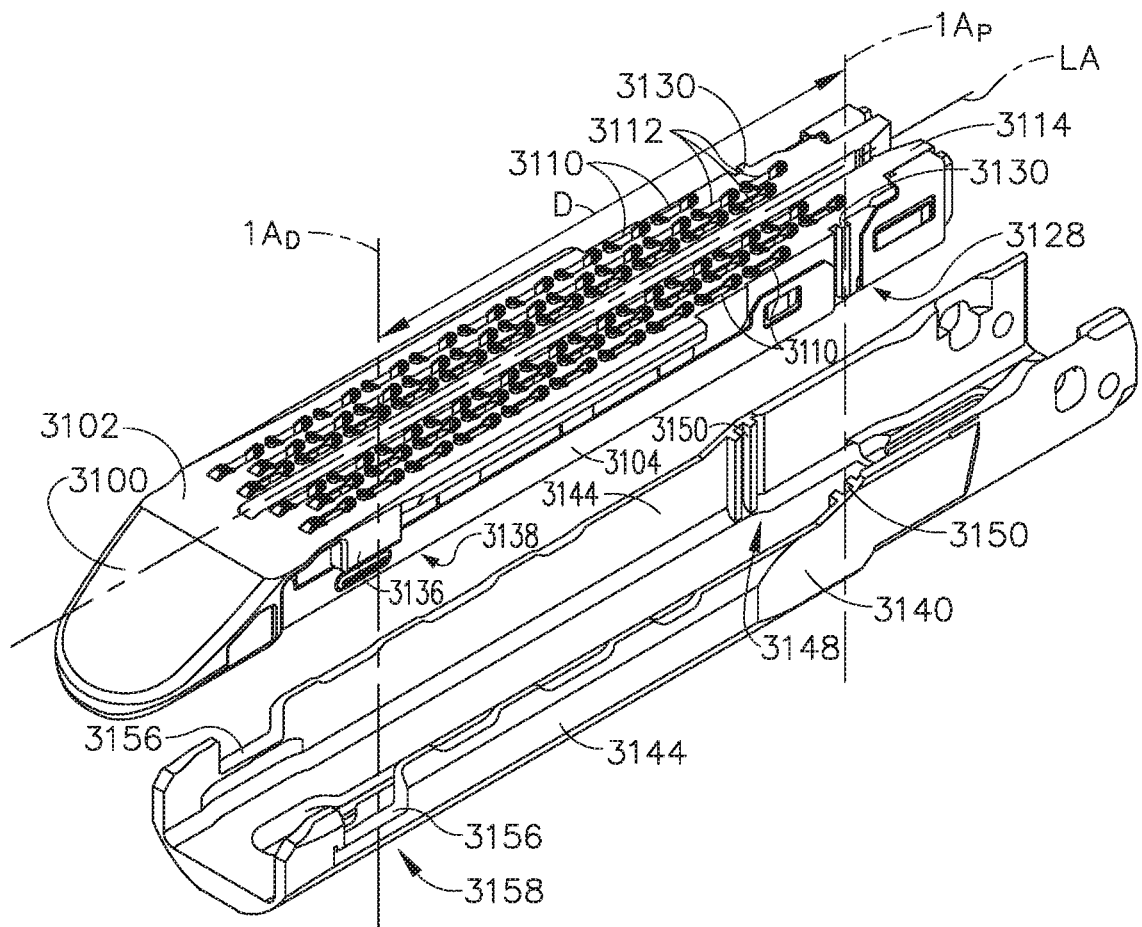
FIG. 103 is an exploded perspective view of a channel and a staple cartridge.
Figure 104:
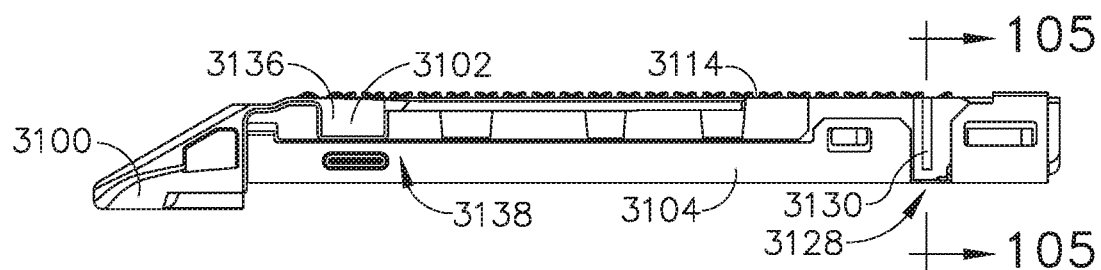
FIG. 104 is an elevation view of the staple cartridge of FIG. 103.
Figure 105:
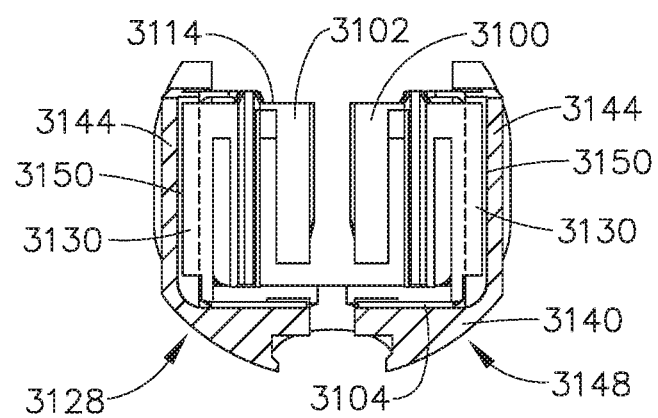
FIG. 105 is a cross-sectional elevation view of the channel and the staple cartridge of FIG. 103 taken across the plane indicated in FIG. 104.

A staple cartridge 3100 is depicted in FIGS. 103-105. The staple cartridge 3100 is compatible with an elongate channel 3140, which is part of a surgical end effector. Various surgical end effectors having elongate channels, which are similar in many aspects to the elongate channel 3140, for example, are further described herein. The elongate channel 3140 is configured to receive the staple cartridge 3100. For example, the dimensions and structure of the elongate channel 3140 are compatible with the dimensions and structure of the staple cartridge 3100.

The staple cartridge 3100 includes a cartridge body 3102 and a pan 3104 positioned partially around the cartridge body 3102. The cartridge body 3102 is a molded body into which staple cavities 3110 (FIG. 103) are defined. A staple can be ejectably positioned in each staple cavity 3110. In certain instances, each staple can be supported by a staple driver movably positioned in each staple cavity 3110. Each staple cavity 3110 defines an opening 3112 in a deck 3114 of the cartridge body 3102. The pan 3104 wraps around a portion of the cartridge body 3102. The cartridge body 3102 can be comprised of a plastic material, for example, and the pan 3104 can be comprised of a metal material, for example.

The staple cartridge 3100 also includes proximal alignment features 3128 and distal alignment features 3138, which interlock or mate with corresponding proximal alignment features 3148 and distal alignment features 3158, respectively, on the channel 3140. In the staple cartridge 3100, the proximal alignment features 3128 include lateral ribs or tongues 3130, which protrude from a proximal portion of the staple cartridge 3100. More specifically, the ribs 3130 are positioned in the vicinity of the proximal-most staple cavities 3110. In other instances, the ribs 3130 can be proximal to the proximal-most staple cavities or distal to the proximal-most staple cavities.

The ribs 3130 are formed with the cartridge body 3102. For example, the ribs 3130 are molded features on the sidewalls of the cartridge body 3102. In the cartridge body 3102, a single rib is defined in each lateral side of the cartridge body 3102. In other instances, two or more ribs can be defined on two or more lateral sides of the cartridge body 3102. The staple cartridge 3100 includes a pair of symmetrical ribs 3130. The ribs 3130 are symmetrical with respect to a longitudinal axis LA (FIG. 103) of the staple cartridge 3100. In other instances, the ribs 3130 may be asymmetrical with respect to the longitudinal axis LA and/or the proximal alignment features 3128 can consist of a single rib. In other instances, the profile of one or more of the ribs 3130 can be rounded and/or otherwise contoured. Additionally or alternatively, one of more of the ribs 3130 can define angled and/or jagged sides and/or edges.

The channel 3140 includes proximal alignment features 3148 that corresponds to the proximal alignment features 3128 of the staple cartridge 3100. The proximal alignment features 3148 include grooves 3150, which are defined in the sidewalls 3144 of the channel 3140 and are configured to receive the ribs 3130. The width of the grooves 3150 corresponds to the width of the ribs 3130. In other words, the ribs 3130 are configured to fit snuggly within the grooves 3150. In certain instances, the ribs 3130 can slidingly engage the grooves 3150 as the ribs 3130 move into engagement with the grooves 3150. In such instances, the clearance between the ribs 3130 and the grooves 3150 can be sufficient to prevent interference while minimizing non-axial movement of the ribs 3130 relative to the grooves 3150. More specifically, the ribs 3130 can move along proximal installation axes (see proximal installation axis $IA_P$ in FIG. 103) as the staple cartridge 3100 is positioned in the channel 3140. Longitudinal movement of the ribs 3130 relative to the proximal installation axes $IA_P$ can be restrained by the dimensions of the grooves 3150.

The reader will appreciate that the ribs 3130 and the corresponding grooves 3150 can define different geometries than those shown in FIGS. 103-105. For example, the ribs 3130 can be shorter, longer, wider, and/or narrower. In instances where the ribs 3130 define a different geometry than those shown in FIGS. 103-105, the grooves 3150 can define a correspondingly different geometry such that the grooves 3150 guide or lead the ribs 3130 along the proximal installation axes $IA_P$. In other instances, the proximal alignment features 3128 can comprise grooves in the staple cartridge 3100, and the corresponding proximal alignment features 3148 in the channel 3140 can include ribs protruding from the channel 3140 and configured to slidingly engage the grooves in the staple cartridge 3100. As further described herein, the proximal position of the ribs 3130 ensures that the proximal end of the staple cartridge 3100 is properly seated in the channel 3140. If the proximally-positioned ribs 3130 are not aligned with the grooves 3150, the ribs 3130 can be configured to lift a proximal portion of the staple cartridge 3100 away from the channel 3140, which can prevent the closing of an anvil jaw relative to the channel 3140.

In the staple cartridge 3100, the distal alignment features 3138 include laterally-extending lugs 3136. The lugs 3136 are identical to the lugs 3036 (FIGS. 100 and 101) on the staple cartridge 3000. The channel 3140 includes corresponding distal alignment features 3158. For example, the channel 3140 includes sidewalls 3144 having cutouts 3156 defined therein. The cutouts 3156 are identical to the cutouts 3056 (FIGS. 100 and 101) in the channel 3040. The lugs 3136 can move along a distal installation axis $IA_D$ as the staple cartridge 3100 is positioned in the channel 3140. The distal installation axis $IA_D$ is parallel to the proximal installation axis $IA_P$ and spaced apart from the proximal installation axis $IA_P$ by a longitudinal distance D (FIG. 103). Lateral and/or longitudinal movement of the lugs 3136 relative to the distal installation axis $IA_D$ can be restrained by the dimensions of the cutouts 3156. As the staple cartridge 3100 approaches the elongate channel 3140 along the installation axes, the staple cartridge 3100 can slide or snap in place in the elongate channel 3140.

Mating engagement of the proximal alignment features 3128, 3148 and mating engagement of the distal alignment features 3138, 3158 is configured to ensure that the staple cartridge 3100 can by completely inserted or installed in the channel 3140. For example, when the ribs 3130 are positioned in the grooves 3150 and the lugs 3136 are positioned in the cutouts 3156, the staple cartridge 3100 fits within the channel 3140 like an interlocking puzzle piece. In such instances, an outer bottom surface of the staple cartridge 3100 can be positioned flush against an inner bottom surface of the channel 3140 (see FIG. 105). Moreover, the staple cartridge 3100 and the channel 3140 can be aligned with the longitudinal axis LA. In other words, the staple cartridge 3100 is not tilted or skewed within the channel 3140.

The alignment features 3128, 3138, 3148, and 3158 are also configured to ensure that an incompatible staple cartridge is not positioned in the channel 3140. An incompatible staple cartridge can be a staple cartridge having a different length, different quantity of staples, different arrangement of staples, and/or other differing features. Additionally, an incompatible staple cartridge can include incompatible alignment features (i.e. interference features). For example, an incompatible staple cartridge can include proximal ribs having incompatible dimensions (e.g. too large) with respect to the grooves 3150. In other instances, the spacing and/or the positioning of the proximal ribs of an incompatible staple cartridge can be different than the spacing and/or positioning of the grooves 3150. Additionally or alternatively, the longitudinal distance between the proximal ribs and the distal lugs 3136 can be different than the distance D (FIG. 103). In instances in which the proximal ribs are incompatible with the grooves 3150, the proximal ribs of the incompatible staple cartridge can interfere with the channel 3140. As a result, the proximal ribs can lift a proximal portion of the incompatible staple cartridge away from the channel 3140. Consequently, the proximal end of the deck 3114 of the incompatible staple cartridge can be raised above the channel 3140, which can prevent the closing of an anvil jaw relative to the channel 3140. In various instances, the incomplete closing of the anvil jaw can trigger an incomplete clamping lockout, which can prevent a firing stroke.

The elongate channels 3040 and 3140 are keyed to receive the staple cartridges 3000 and 3100, respectively. Consequently, the staple cartridge 3100 could not be fully or completely inserted in the elongate channel 3040 because an interference would result between the proximal alignment features 3128 and the elongate channel 3040. More specifically, the ribs 3130 would not fit within the elongate channel 3040 because the elongate channel 3040 does not include grooves for receiving the ribs 3130. Additionally, the staple cartridge 3000 could not be fully or completely inserted in the elongate channel 3140 because an interference would result between the proximal alignment features 3028 and the elongate channel 3140. More specifically, because the elongate channel 3040 does not include apertures for receiving the tabs 3030, the tabs 3030 would block or obstruct seating of the staple cartridge 3000 flush against the elongate channel 3140.

The reader will appreciate that the alignment features described herein physically prevent a staple cartridge from being fully seated in an incompatible elongate channel. Stated differently, the alignment features physically prevent an elongate channel from fully receiving an incompatible staple cartridge. Furthermore, the alignment features can provide a visible height difference which can communicate the incomplete installation of a staple cartridge. For example, the proximal end of an incompatible staple cartridge can be raised or tilted relative to the elongate channel. Such a visible difference can provide a signal to the operator of the end effector than an incompatible staple cartridge has been inserted into the elongate channel.

As described above, a staple cartridge and an elongate channel can include complementary alignment features that ensure the staple cartridge is installed in a compatible elongate channel. For example, when an alignment feature of an elongate channel comprises an obstruction, the corresponding alignment feature of a compatible staple cartridge can comprise a complementary anti-obstruction. The alignment features can define unique matching contours between the sidewalls and/or bottom of the staple cartridge with the sidewalls and/or bottom of the elongate channel. Alignment features can include one or more tabs, ribs, nubs, projections, recesses, pins, bosses, holes, apertures, grooves and/or combinations thereof. The alignment features provide a keyed fit between the staple cartridge and the elongate channel. Moreover, each type of staple cartridge can be a unique cartridge key requiring a unique elongate channel key for an accurate fit.

Figure 106:
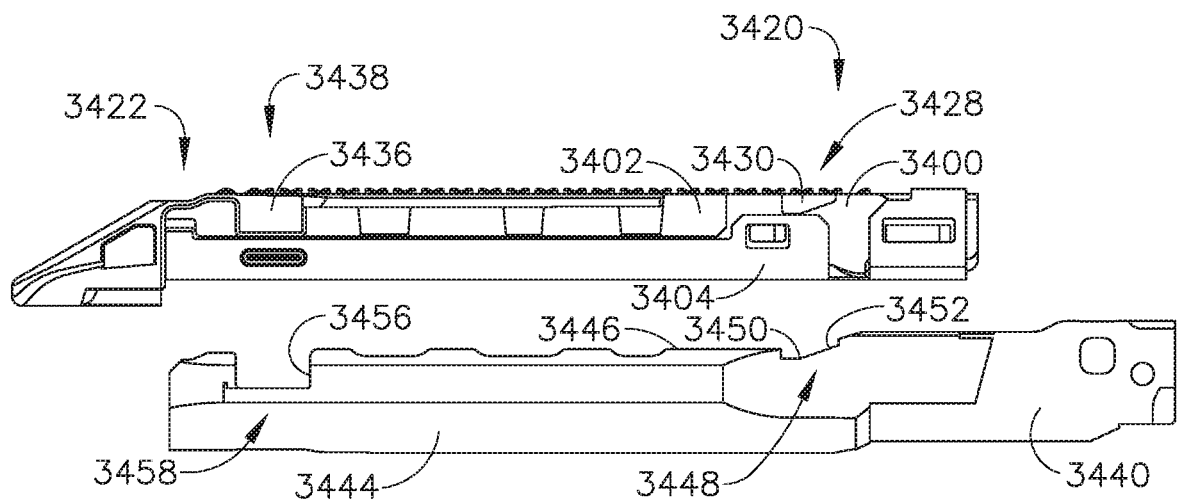
FIG. 106 is an exploded elevation view of a channel and a staple cartridge.
Figure 107:
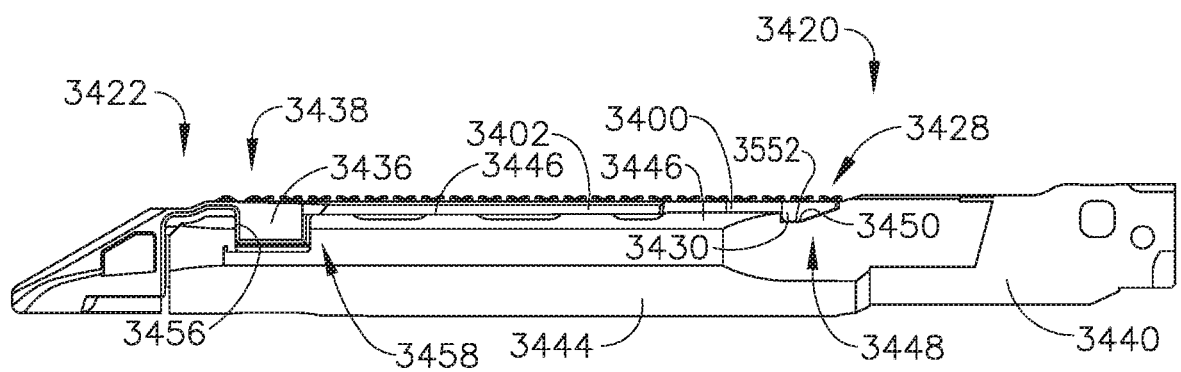
FIG. 107 is an elevation view of the channel and the staple cartridge of FIG. 106 depicting the staple cartridge completely installed in the channel.

A staple cartridge 3400 is depicted in FIGS. 106 and 107. The staple cartridge 3400 is compatible with an elongate channel 3440, which is part of a surgical end effector. Various surgical end effectors having elongate channels, which are similar in many aspects to the channel 3440, for example, are further described herein. The elongate channel 3440 is configured to receive the staple cartridge 3400. For example, the dimensions and structure of the elongate channel 3440 are compatible with the dimensions and structure of the staple cartridge 3400.

The staple cartridge 3400 includes a cartridge body 3402 and a pan 3404 positioned partially around the cartridge body 3402. The cartridge body 3402 is a molded body into which staple cavities are defined. A staple can be ejectably positioned in each staple cavity. In certain instances, each staple can be supported by a staple driver movably positioned in each staple cavity. Each staple cavity defines an opening in a deck of the cartridge body 3402. The pan 3404 wraps around a portion of the cartridge body 3402. The cartridge body 3402 can be comprised of a plastic material, for example, and the pan 3404 can be comprised of a metal material, for example.

The staple cartridge 3400 also includes a proximal end portion 3420 having proximal alignment features 3428, and a distal end portion 3422 having distal alignment features 3438. The proximal alignment features 3428 and the distal alignment features 3438 interlock or mate with corresponding proximal alignment features 3448 and distal alignment features 3458, respectively, on the channel 3440. In the staple cartridge 3400, the proximal alignment features 3428 include keys 3430, which extend from the proximal portion 3420 of the cartridge body 3402. More specifically, the keys 3430 protrude from the lateral sides of the cartridge body 3402 in the vicinity of the proximal-most staple cavities. In other instances, the keys 3430 can be proximal to the proximal-most staple cavities or distal to the proximal-most staple cavities.

Although only a single key 3430 is depicted in FIGS. 106 and 107, the reader will appreciate that symmetrical keys are positioned on each side of the staple cartridge 3400. The keys 3430 are symmetrical with respect to a longitudinal axis of the staple cartridge 3400. In other instances, the keys 3430 may be asymmetrical with respect to the longitudinal axis and/or the proximal alignment features 3428 can consist of a single key. In certain instances, the proximal alignment features 3428 can include two or more proximal keys on two or more lateral sides of the cartridge body 3402.

The keys 3430 are formed with the cartridge body 3402. For example, the keys 3430 are molded features on the sidewalls of the cartridge body 3402. In the staple cartridge 3400, the keys 3430 are wedge-shaped protrusions extending from a lateral side of the cartridge body 3402. The wedge-shaped protrusion comprises a polygon having two pairs of parallel sides and one oblique or ramped side forming the wedge.

The channel 3440 includes proximal alignment features 3448 that correspond to the proximal alignment features 3428 of the staple cartridge 3400. The proximal alignment features 3448 include a keyed profile 3450 along a top edge 3446 of each channel sidewall 3444. The keyed profiles 3450 correspond to the dimensions of the keys 3430. In other words, each key 3430 is configured to fit snuggly within one of the keyed profiles 3450. The keyed profiles 3450 define a wedge-shaped cutout 3452 that corresponds to the shape and size of the wedge-shaped key 3430. Referring primarily to FIG. 107, when the staple cartridge 3400 is fully seated in the channel 3440, the key 3430 is configured to nest entirely within the keyed profile 3450. The keyed profile 3450 and cutout 3452 also create an obstruction or impediment to the keys of incompatible staple cartridges, as further described herein.

The reader will appreciate that the keys 3430 and the corresponding keyed profiles 3450 can define different geometries than those shown in FIGS. 106-107. For example, the key(s) 3430 can be round, angled, and/or define a varied depth. In such instances, the keyed profiles 3450 can define correspondingly different geometries such that the different keys fit or nest entirely within the keyed profiles 3450. In certain instances, the staple cartridge 3400 can comprise one or more cutouts and the elongate channel 3440 can include one or more corresponding keys. As further described herein, the proximal position of the keys 3430 ensures that the proximal end 3420 of the staple cartridge 3400 is properly seated in the channel 3440. If the keys 3430 are not aligned with the cutouts 3452 of the keyed profile 3450, the tabs 3430 are configured to lift the proximal portion 3420 of the staple cartridge 3400 away from or partially out of the channel 3440, which can prevent the closing of an anvil jaw relative to the channel 3440. In various instances, the incomplete closing of the anvil jaw can trigger an incomplete clamping lockout, which can prevent a firing stroke.

In the staple cartridge 3400, the distal alignment features 3438 include laterally-extending lugs 3436. The lugs 3436 protrude from the sides of the staple cartridge 3400. The lugs 3436 are formed with the cartridge body 3402. For example, the lugs 3436 can be molded features on the cartridge body 3402. The lugs 3436 define rectangular protrusions from the cartridge body 3402. Although only a single lug 3436 is depicted in FIGS. 106 and 107, the reader will appreciate that symmetrical lugs are positioned on each side of the staple cartridge 3400. In other instances, the distal alignment features 3438 can consist of a single lug on one side of the staple cartridge 3400. In still other instances, the distal alignment features 3438 can include two or more distal lugs on two or more lateral sides of the cartridge body 3402.

The channel 3440 includes distal alignment features 3458 that correspond to the distal alignment features 3438 of the staple cartridge 3400. For example, the channel 3440 includes sidewalls 3444 having cutouts 3456 defined therein. The cutouts 3456 are positioned and dimensioned to receive the lugs 3436. The perimeter of the cutouts 3456 corresponds to the dimensions of the lugs 3436. In other words, the lugs 3436 are configured to fit snuggly within the cutouts 3456. In certain instances, the lugs 3436 can slidingly engage the cutouts 3456 as the lugs 3436 move into engagement with the cutouts 3456. In such instances, the clearance between the lugs 3436 and the cutouts 3456 can be sufficient to prevent interference while minimizing non-axial movement of the lugs 3436 relative to the cutouts 3456.

Mating engagement of the proximal alignment features 3428, 3448 and mating engagement of the distal alignment features 3438, 3458 is configured to ensure that the staple cartridge 3400 can be completely inserted or installed in the channel 3440. For example, when the keys 3430 are positioned in the cutouts 3452 and the lugs 3436 are positioned in the cutouts 3456, the staple cartridge 3400 fits within the channel 3440 like an interlocking puzzle piece. In such instances, an outer bottom surface of the staple cartridge 3400 can be positioned flush against an inner bottom surface of the channel 3440. Moreover, the staple cartridge 3400 and the channel 3440 can be aligned with the longitudinal axis. In other words, the staple cartridge 3400 is not tilted or skewed within the channel 3440. Referring to FIG. 107, when the staple cartridge 3400 is fully inserted in the channel 3440, the proximal portion 3420 is positioned below an upper edge of the channel 3440.

Figure 108:
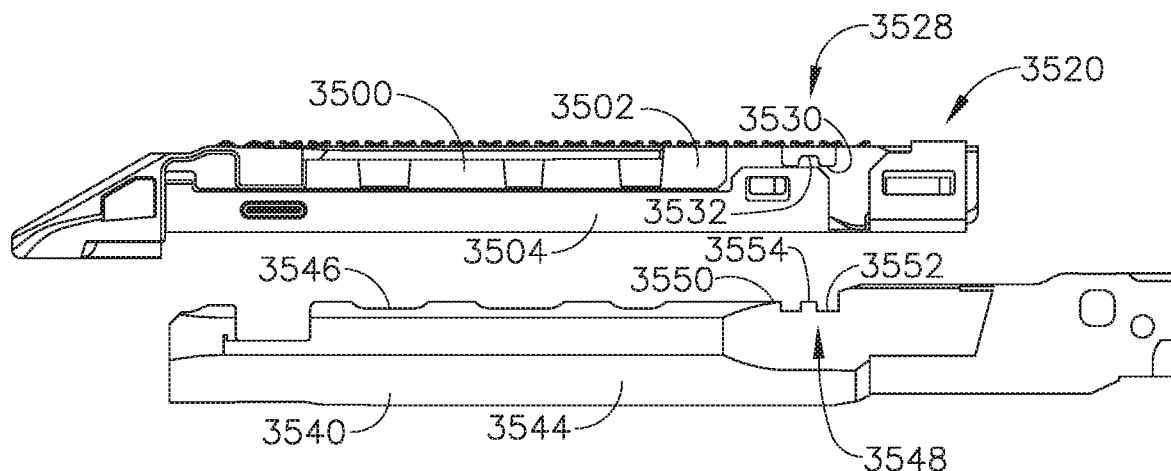
FIG. 108 is an exploded elevation view of a channel and a staple cartridge.
Figure 109:
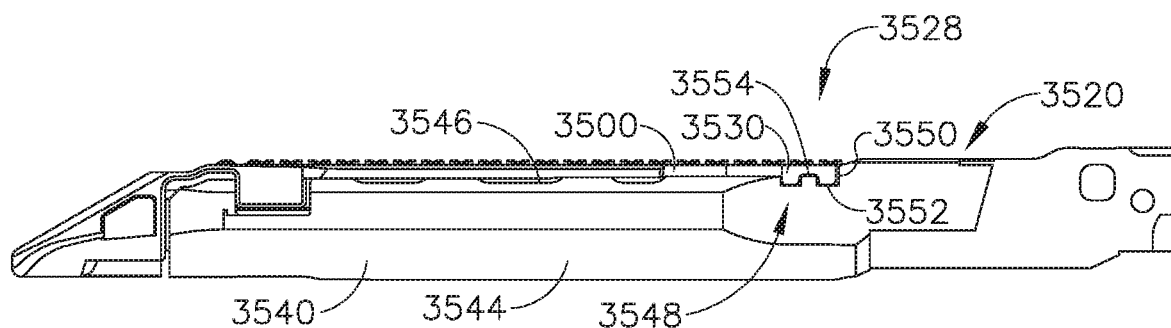
FIG. 109 is an elevation view of the channel and the staple cartridge of FIG. 108 depicting the staple cartridge completely installed in the channel.

A staple cartridge 3500 is depicted in FIGS. 108 and 109. The staple cartridge 3500 is identical to the staple cartridge 3400 with the exception of proximal alignment features 3528 which differ from the proximal alignment features 3428. More specifically, the proximal alignment features 3528 include keys 3530, which comprise a different geometry than the keys 3430. The keys 3530 extend from a proximal portion 3520 of the cartridge body 3502. More specifically, the keys 3530 protrude from the lateral sides of the cartridge body 3502 in the vicinity of the proximal-most staple cavities. In other instances, the keys 3530 can be proximal to the proximal-most staple cavities or distal to the proximal-most staple cavities.

Although only a single key 3530 is depicted in FIGS. 108 and 109, the reader will appreciate that symmetrical keys are positioned on each side of the staple cartridge 3500. The keys 3530 are symmetrical with respect to a longitudinal axis of the staple cartridge 3500. In other instances, the keys 3530 may be asymmetrical with respect to the longitudinal axis and/or the proximal alignment features 3528 can consist of a single key. In certain instances, the proximal alignment features 3528 can include two or more proximal keys on two or more lateral sides of the cartridge body 3502.

The keys 3530 are formed with the cartridge body 3502. For example, the keys 3530 are molded features on the sidewalls of the cartridge body 3502. In the staple cartridge 3500, the keys 3530 are rectangular lugs having a notched edge 3532. The notched edge 3532 consists of a single notch; however, in other instances, the notched edge 3532 can include two or more notches or other indents. In still other instances, the keys 3530 can include ribbed or grooved edges, which can extend into complementary notches in a keyed profile of an elongate channel 3540.

The staple cartridge 3500 is compatible with the elongate channel 3540 (FIGS. 108 and 109), which is identical to the staple cartridge 3400 (FIGS. 106 and 107) with the exception of the proximal alignment features 3548 which differ from the proximal alignment features 3448. The channel 3540 includes proximal alignment features 3548, which correspond to the proximal alignment features 3528 on the staple cartridge 3500. The proximal alignment features 3548 include a keyed profile 3550 along a top edge 3546 of each channel sidewall 3544. The keyed profiles 3550 correspond to the dimensions of the keys 3530. In other words, each key 3530 is configured to fit snuggly within one of the keyed profiles 3550. The keyed profiles 3550 define a rectangular cutout 3552 having a tabbed edge 3554. The geometry and placement of the cutout 3552 corresponds to the geometry and placement of the key 3530. Referring primarily to FIG. 109, when the staple cartridge 3500 is fully seated in the channel 3540, the key 3530 is configured to nest entirely within the keyed profile 3550. The keyed profile 3550 and tabbed edge 3552 also create an obstruction or impediment to the keys of incompatible staple cartridges, as further described herein.

The reader will appreciate that the keys 3530 and the corresponding keyed profiles 3550 can define different geometries than those shown in FIGS. 108 and 109. In such instances, the keyed profiles 3550 can define correspondingly different geometries such that the different keys fit or nest entirely within the keyed profiles 3550. In certain instances, the staple cartridge 3500 can comprise one or more cutouts and the elongate channel 3540 can include one or more corresponding keys. As further described herein, the proximal position of the keys 3530 ensures that the proximal end 3520 of the staple cartridge 3500 is properly seated in the channel 3540. If the keys 3530 are not aligned with the cutouts 3552 of the keyed profile 3550, the tabs 3530 are configured to lift the proximal portion 3520 of the staple cartridge 3500 away from or partially out of the channel 3540, which can prevent the closing of an anvil jaw relative to the channel 3540. In various instances, the incomplete closing of the anvil jaw can trigger an incomplete clamping lockout, which can prevent a firing stroke.

The alignment features 3528 and 3548 are also configured to ensure that an incompatible staple cartridge is not positioned in the channel 3540. An incompatible staple cartridge can be a staple cartridge having a different length, different quantity of staples, different arrangement of staples, and/or other differing features. Moreover, an incompatible staple cartridge may include a different key which prevents the incompatible staple cartridge from being fully seated in the elongate channel 3540.

Figure 110:
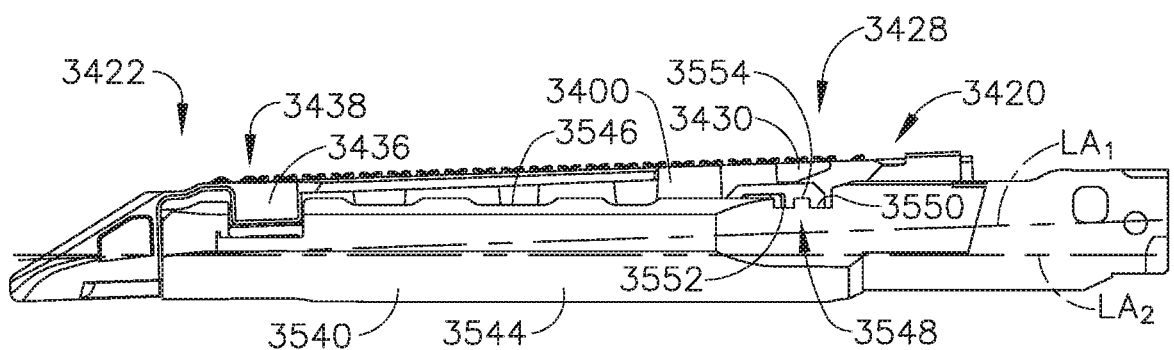
FIG. 110 is an elevation view of the staple cartridge of FIG. 106 and the channel of FIG. 108 depicting the staple cartridge incompletely installed in the channel.

Referring now to FIG. 110, the staple cartridge 3400 is depicted in the elongate channel 3540. As described herein, the staple cartridge 3400 is compatible with the elongate channel 3440 (FIGS. 106 and 107) and the elongate channel 3540 is compatible with the staple cartridge 3500 (FIGS. 108 and 109). However, the staple cartridge 3400 is incompatible with the elongate channel 3540. More specifically, the keyed profile 3550 creates an obstruction or impediment to the complete insertion of the staple cartridge 3400. The key 3430 on the staple cartridge 3400 does not complement the keyed profile 3550. In other words, the key 3430 is a non-complementary anti-obstruction to the keyed profile 3550. As a result, the complete insertion of the staple cartridge 3400 into the elongate channel 3540 is prevented. The proximal portion 3420 of the staple cartridge 3400 is lifted away from the elongate channel 3540. As a result, the staple cartridge 3400 is tilted or skewed relative to the elongate channel 3540. For example, the longitudinal axis $LA_1$ of the staple cartridge 3400 is obliquely-oriented relative to the longitudinal axis $LA_2$ of the elongate channel 3540. For compatible staple cartridges, the axes can be collinear. Moreover, the raised cartridge deck at the proximal end 3420 of the staple cartridge 3400 can prevent the closure of an anvil relative to the elongate channel 3540.

The geometry of the key 3430 does not complement the geometry of the keyed profile 3550. The reader will appreciate that other staple cartridges having different arrangements of keys also define non-complementary geometries which are incompatible with the elongate channel 3540. In certain instances, the size or shape of a key can create an interference and/or the placement and/or spacing between keys and/or between other cartridge features, such as the distal alignment features, for example, can create an interference.

In various instances, the elongate channel 3540 and/or the staple cartridge 3400 can include a sensor for detecting if the staple cartridge 3400 is completely inserted in the elongate channel 3540. The sensor can be an electronic sensor, mechanical sensor, or an electromechanical sensor, for example. In various instances, the sensor can comprise a switch circuit positioned on an inside bottom surface of a proximal portion of the elongate channel and/or on an outer bottom surface of proximal portion 3420 of the staple cartridge 3400. If the staple cartridge 3400 were completely inserted in the elongate channel 3540, the switch circuit can be closed, or switched, to indicate the complete installation. However, when the staple cartridge 3400 is not completely inserted in the elongate channel 3540, as depicted in FIG. 110, the switch circuit may remain open, or unswitched, for example. In certain instances, placement of a staple cartridge flush against the elongate channel 3540 can activate the sensor. Accordingly, when the staple cartridge 3500 is fully inserted in the elongate channel 3540, as shown in FIG. 109, a sensor can indicate that a staple cartridge is completely inserted in the elongate channel 3540.

Additionally or alternatively, when an anvil is not fully clamped against the staple cartridge, such as when an incompatible staple cartridge prevents complete clamping, the path of the firing member through the anvil, such as the upper flange of an I-beam, for example, can be obstructed. Furthermore, when a staple cartridge is incompletely installed in an elongate channel, the staple cartridge can physically block and/or obstruct the firing path of a firing member to inhibit the firing stroke. The reader will further appreciate that the various elongate channels and/or staple cartridges described herein can include sensors for detecting if a staple cartridge is completed inserted in the elongate channel and/or lockouts for preventing a firing stroke if an incompatible staple cartridge is installed and/or the anvil is incompletely clamped.

The reader will appreciate that the keys described herein physically prevent a staple cartridge from being fully seated in an incompatible elongate channel. Stated differently, the keys physically prevent an elongate channel from fully receiving an incompatible staple cartridge. Furthermore, the keys can provide a visible height difference which can communicate the incomplete installation of a staple cartridge. For example, the proximal end of an incompatible staple cartridge can be raised or tilted relative to the elongate channel. Such a visible difference can provide a signal to the operator of the end effector than an incompatible staple cartridge has been inserted into the elongate channel.

The proximal placement of the keys 3430, 3530 and the distal placement of the lugs 3436, 3536 provides proximal and distal alignment features for the staple cartridges 3400, 3500, respectively. Because the staple cartridges include proximal and distal alignment features, the staple cartridges can define a unique key which is compatible with specific elongate channels. In various instances, the proximal and distal alignment features can be shifted, staggered, and/or repeated to create unique profiles for different staple cartridge types. Consequently, each type of staple cartridge can be a unique cartridge key requiring a unique elongate channel key for an accurate fit.

As described herein, in various instances, an end effector and a replaceable staple cartridge can include cooperating features that physically or bodily prevent and/or obstruct the complete insertion of an incompatible replaceable staple cartridge into the end effector. Such cooperating features can prevent an improper type of staple cartridge from being inserted into an end effector. Consequently, the cooperating features can prevent an end effector from firing an incompatible staple cartridge, which could result in an incomplete, imperfect, and/or otherwise defective firing of the incompatible staple cartridge. Moreover, as described herein, the proximal portion of an incompatible staple cartridge can be raised or lifted relative to the channel. In certain instances, an anvil can be configured to bow along the longitudinal axis and the deflection of the anvil can increase toward the distal end. However, the deflection can be minimal or negligible at a proximal location along the anvil. Consequently, deflection at the proximal location can be insufficient to conceal or accommodate the raised proximal end of an improperly-inserted staple cartridge and, as a result, the raised proximal end can create an apparent interference.

Figures 111, 112:
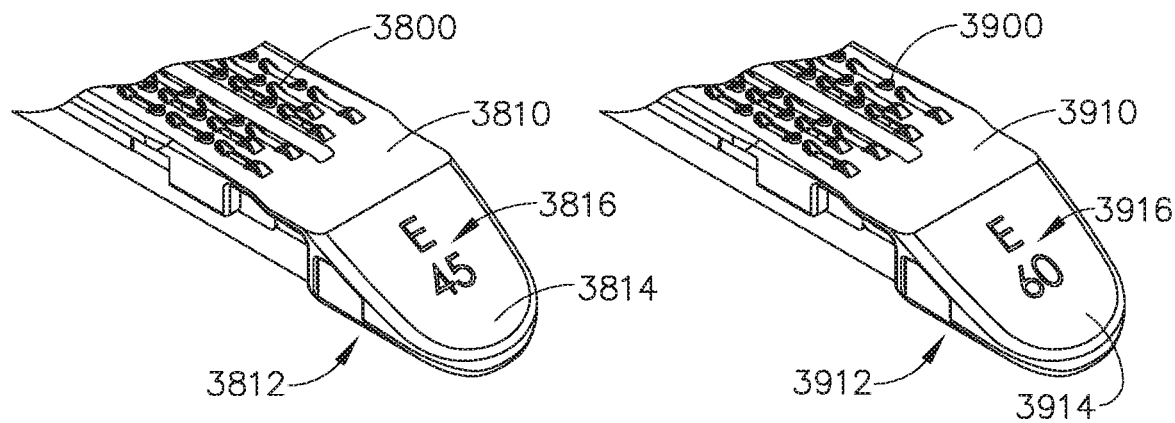
Figure 113:
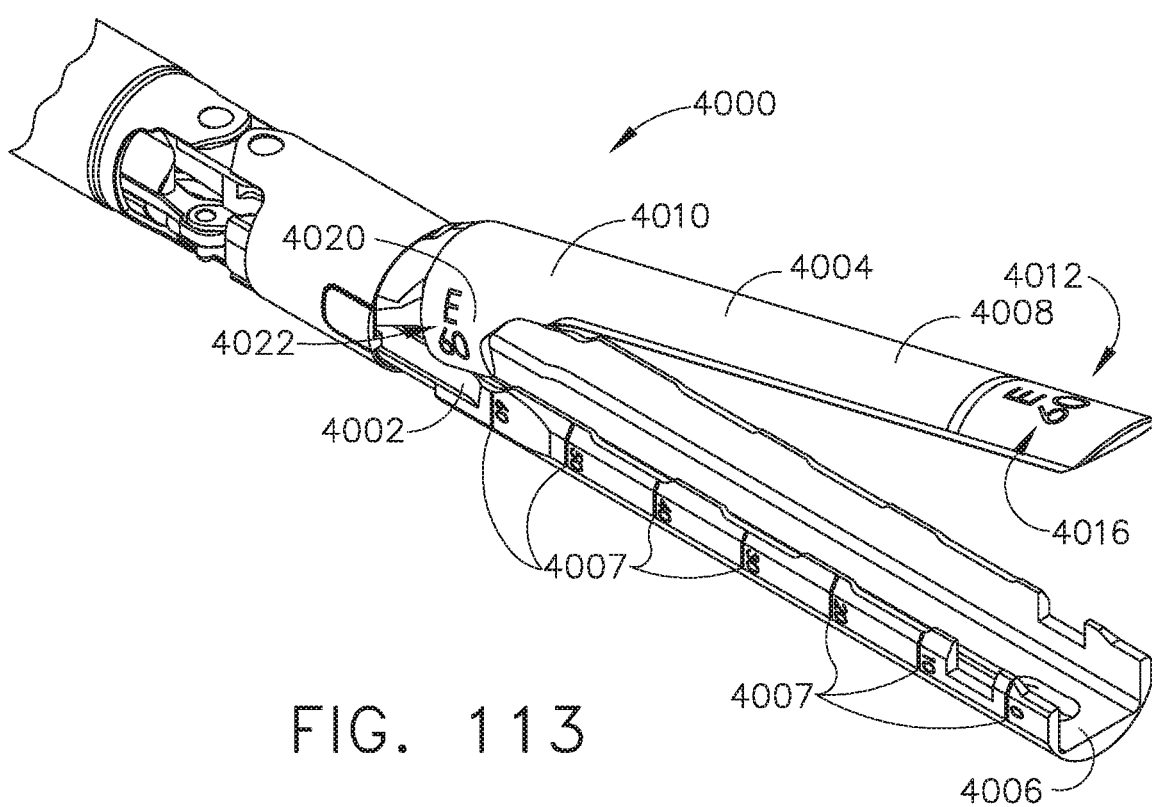

Additionally or alternatively, in certain instances, end effectors and replaceable staple cartridges can include identifications (IDs) or markings, which can indicate to an operator which staple cartridges are compatible with which end effectors. The identifications can be a code, symbol, or other classifying indicia, for example. Referring now to FIGS. 111-113, stapling system components having identifications are shown. For example, FIG. 111 depicts a staple cartridge 3800 having an outer surface 3810 and a distal end portion 3812. The distal end portion 3812 defines a nose portion 3814 of the staple cartridge 3800. An identification 3816 is inscribed on the outer surface 3810 of the staple cartridge 3800. More specifically, the identification 3816 is inscribed on the outer surface 3810 of the distal nose portion 3814. The identification 3816 is an end effector compatibility indicator, which indicates which type(s) of end effector is compatible with the staple cartridge 3800.

FIG. 112 depicts a staple cartridge 3900 having an outer surface 3910 and a distal end portion 3912. Although it may not be apparent, the staple cartridge 3900 can be different from the staple cartridge 3800 (FIG. 111). For example, the staple cartridges 3800 and 3900 can comprise different lengths and/or different arrangements of staple cavities. In certain instances, the internal components and/or features of the staple cartridges 3800 and 3900 can be different. For example, the staple cartridges 3800 and 3900 can include different size staples, different types of staples, different staple drivers, and/or different firing elements.

The distal end portion 3912 defines a nose portion 3914 of the staple cartridge 3900. An identification 3916 is inscribed on the outer surface 3910 of the staple cartridge 3900. More specifically, the identification 3916 is inscribed on the outer surface 3910 of the distal nose portion 3914. The identification 3916 is an end effector compatibility indicator, which indicates which type(s) of end effector is compatible with the staple cartridge 3900.

Referring primarily now to FIG. 113, an end effector 4000 is depicted. The end effector 4000 includes a first jaw 4002 and a second jaw 4004. The jaws 4002 and 4004 are pivotably connected. The first jaw 4002 comprises an elongate channel 4006, which is configured to receive a compatible staple cartridge therein. The elongate channel 4006 includes markings 4007, which correspond to the length of a firing stroke. For example, the markings 4007 indicate the 60 mm active length of the end effector 4000. When a compatible staple cartridge is positioned in the end effector 4000, the resultant staple line from a full firing stroke of the end effector 4000 can be 60 mm. The markings 4007 can provide a guide to the length of the firing stroke remaining during firing. The second jaw 4004 comprises an anvil 4008 having a forming surface for staples fired from a staple cartridge. Additionally or alternatively, the anvil 4008 can include markings for tracking the firing stroke.

The end effector 4000 has an outer surface 4010 and a distal end portion 4012. A distal identification 4016 is inscribed on the outer surface 4010 of the anvil 4008. More specifically, the distal identification 4016 is inscribed on the outer surface 4010 of the distal end portion 4012 of the anvil 4008.

The anvil 4008 also includes a tissue stop 4020, which is positioned to prevent tissue from extending proximally past the tissue stop 4020. A proximal identification 4022 is inscribed in the tissue stop 4020. Although only a single proximal identification 4022 is depicted in FIG. 113, the reader will appreciate that tissue stops 4020 can be positioned on each lateral side of the anvil 4008, and proximal identifications 4022 are positioned on each tissue stop 4020. In other instances, the proximal identification 4022 can consist of a single proximal identification 4022 on one side of the anvil 4008. In the end effector 4000, the proximal identification 4022 matches the distal identification 4016. In other instances, the proximal identification 4022 and the distal identification 4016 can be similar, complementary, or otherwise related. In certain instances, the anvil 4008 can include the proximal identification 4022 or the distal identification 4016. The identification 4016 and 4022 are cartridge compatibility indicators, which indicates which type(s) of staple cartridge is compatible with the end effector 4000.

The identifications 3816, 3916, 4016 and 4022 are alphanumeric codes, which indicate a type of replaceable staple cartridge. For example, the identification 3816 indicates a first type of replaceable staple cartridge and the identification 3916 indicates a different type of replaceable staple cartridge. More specifically, the alphanumeric codes can include one or more numbers corresponding to the active length of the staple cartridge and one or more letters corresponding to a name or feature of the staple cartridge. Additionally or alternatively, the identifications 3816, 3916, 4016 and 4022 can include symbols and/or colors for indicating compatibility.

Referring again to the stapling system components depicted in FIGS. 111-113, the staple cartridge 3900 (FIG. 112) can be compatible with the end effector 4000 (FIG. 113). Accordingly, the identification 3916 can match the identification 4016 and 4022. In other instances, the compatibility can be indicated with coordinated or complementary identifications, such as markings of the same color and/or same shape. The staple cartridge 3800 (FIG. 11) is incompatible with the end effector 4000. For example, the staple cartridge 3800 can be too short (only 45 mm rather than 60 mm) for the end effector 4000.

Because the identifications 3816 (FIG. 111) and 3916 (FIG. 112) are positioned on the nose portions 3814 and 3914, respectively, the identifications 3816 and 3916 are quickly apparent or noticeable to the operator of the surgical instrument. For example, the identifications 3816 and 3916 can be quickly and easily viewed by the operator when the operator is selecting a staple cartridge for insertion into an end effector. Moreover, the identifications 3816 and 3916 can be viewed by the operator when the staple cartridge has been inserted into an end effector and the jaws of the end effector are open. Consequently, the operator is able to continually or sporadically reconfirm that the appropriate staple cartridge is positioned in the end effector throughout a surgical procedure. In other instances, the identifications 3816 and 3916 can be inscribed or otherwise positioned on another portion of the staple cartridge that is also readily viewable by the operator.

Similarly, because the identifications 4016 and 4022 (FIG. 113) are positioned on the outer surface 4010, the identifications 4016 and 4022 are quickly apparent or noticeable to the operator of the surgical instrument. For example, the identifications 4016 and 4022 can be quickly and easily viewed by the operator when the operator is positioning a staple cartridge in the end effector. Consequently, the operator is able to continually or sporadically reconfirm that the appropriate staple cartridge is positioned in the end effector throughout a surgical procedure. In other instances, the identifications 4016 and 4022 can be inscribed or otherwise positioned on another portion of the end effector 4000 that is also readily viewable by the operator.

In various instances, one or more end effector compatibility indicators (e.g. identifications 3816 and 3916) and one or more cartridge compatibility indicators (e.g. identifications 4016 and 4022) can be within the peripheral vision of the operator during a surgical procedure. For example, if the operator of the end effector 4000 is viewing the end effector 4000 from an elevation view during a laparoscopic procedure, the proximal indicator 4022 can be within the operator's peripheral vision. Moreover, the indicator on the nose portion of the staple cartridge (e.g. 3800 or 3900) positioned in the end effector 4000 can also be within the operator's peripheral vision. For example, the indicators can longitudinally overlap relative to a longitudinal axis of the end effector. Similarly, if the operator of the end effector 4000 is viewing the end effector 4000 from a top view during a laparoscopic procedure, the distal indicator 4016 can be within the operator's peripheral vision. Moreover, the indicator on the nose portion of the staple cartridge (e.g. 3800 or 3900) positioned in the end effector 4000 can also be within the operator's peripheral vision. In fact, the distal indicator 4016 and a nose portion indicator (e.g. 3816 or 3916) can be within the operator's line or sight. Because the indicators can be viewed simultaneously, the indicators can be seen at the same time and can provide a visual cue or confirmation to the operator.

The reader will appreciate that the identifications 3816, 3916, 4016, and 4022 can be marked on the stapling components in various suitable ways. For example, the identifications can be inscribed, printed, embossed, engraved, and/or applied to the components as a sticker and/or stamp, for example.

Referring now to FIGS. 114 and 115, exemplary identifications or labels are shown. For example, in FIG. 114, the identification for a first end effector 4120 can be either 4102 or 4104 depending on the length of the end effector, the identification for a second end effector 4122 can be either 4106 or 4108 depending on the length of the end effector, and the identification for a third end effector 4124 can be either 4110 or 4112 depending on the length of the end effector. The labels 4102, 4104, 4106, 4108, 4110 and 4112 are alphanumeric codes including a number that corresponds to the length of the end effector (e.g., 45 mm, 60 mm, 40 mm, or 55 mm). The labels 4102, 4104, 4106, 4108, 4110 and 4112 also include a letter, which corresponds to the type of end effector. The types of end effectors can indicate the brand name and/or manufacturer, for example.

Alternatively, referring now to FIG. 115, the identification for the first end effector 4120 can be either 4132 or 4134 depending on the length of the end effector, the identification for the second end effector 4122 can be either 4136 or 4138 depending on the length of the end effector, and the identification for the third end effector 4124 can be either 4140 or 4142 depending on the length of the end effector. The labels 4132, 4134, 4136, 4138, 4140 and 4142 are symbols or codes including a number that corresponds to the length of the end effector (e.g., 45 mm, 60 mm, 40 mm, or 55 mm). The labels 4132, 4134, 4136, 4138, 4140 and 4142 also include a shape (e.g., square, triangle and circle), which corresponds to a type of end effector. The types of end effectors can indicate the brand name and/or manufacturer, for example.

EXAMPLES

Example 1

A surgical tool assembly comprising a surgical end effector movably coupled to a shaft assembly by an articulation joint. The articulation joint is configured to selectively facilitate selective articulation of the surgical end effector relative to the shaft assembly about an articulation axis. The articulation axis is transverse to a shaft axis that is defined by the shaft assembly. The shaft assembly comprises a proximal end, a distal end operably coupled to the articulation joint, and an elongate notch in the shaft assembly. The elongate notch is on one lateral side of the shaft axis and is located adjacent to the distal end.

Example 2

The surgical tool assembly of Example 1, wherein the articulation joint is configured to restrict articulation of the surgical end effector about the articulation axis to the one lateral side of the shaft axis.

Example 3

The surgical tool assembly of Examples 1 or 2, wherein the shaft assembly comprises a spine assembly and a proximal closure member. The spine assembly comprises a distal spine end operably coupled to the articulation joint. The proximal closure member is supported on the spine assembly for selective axial travel relative thereto. The elongate notch further comprises an elongate spine notch in the distal spine end on the one lateral side of the shaft axis and an elongate closure member notch in the proximal closure member on the one lateral side of the shaft axis and corresponding with the elongate spine notch.

Example 4

The surgical tool assembly of Example 3, wherein the surgical end effector comprises a first jaw operably coupled to the articulation joint and a second jaw supported for selective movable travel relative to the first jaw in response to closure motions applied thereto.

Example 5

The surgical tool assembly of Example 4, wherein the shaft assembly further comprises a distal closure member movably coupled to the proximal closure member for selective axial travel therewith, the distal closure member operably interfacing with the second jaw to apply the closure motions thereto.

Example 6

The surgical tool assembly of Examples 1 or 2, wherein the surgical tool assembly further comprises means for preventing buckling of the distal end of the shaft assembly when an axial actuation motion is applied to the proximal end of the shaft assembly.

Example 7

The surgical tool assembly of Examples 3, 4, or 5, wherein the surgical tool assembly further comprises means for preventing buckling of the distal end of the shaft assembly when an axial actuation motion is applied to the proximal end of the shaft assembly.

Example 8

The surgical tool assembly of Example 7, wherein the means for preventing buckling comprises at least one alignment member protruding from the proximal closure member and extending into a corresponding axial slot in the spine assembly.

Example 9

The surgical tool assembly of Example 8, wherein the at least one alignment member comprises at least one first alignment member protruding from the proximal closure member at a first location and extending into a corresponding first axial slot in the spine assembly for axial travel therein and at least one second alignment member protruding from the proximal closure member at a second location that is diametrically opposed to the first location. The second alignment member extends into a corresponding second axial slot in the spine assembly.

Example 10

The surgical tool assembly of Examples 8 or 9, wherein at least one of the at least one alignment member has an L-shaped cross-sectional shape.

Example 11

A surgical tool assembly comprising a surgical end effector movably coupled to a shaft assembly by an articulation joint. The articulation joint is configured to facilitate selective articulation of the surgical end effector relative to the shaft assembly about an articulation axis. The articulation axis is transverse to a shaft axis that is defined by the shaft assembly. The shaft assembly comprises a proximal portion including an uninterrupted outer proximal perimeter and a distal portion extending from the proximal portion and operably coupled to the articulation joint. The distal portion includes a distal outer perimeter, which includes a discontinuous distal portion that is located on one lateral side of the shaft axis.

Example 12

The surgical tool assembly of Example 11, wherein the articulation joint is configured to restrict articulation of the surgical end effector about the articulation axis to the one lateral side of the shaft axis.

Example 13

The surgical tool assembly of Examples 11 or 12, wherein the shaft assembly comprises a spine assembly comprising a distal spine end operably coupled to the articulation joint and a proximal closure member supported on the spine assembly for selective axial travel relative thereto. The discontinuous distal portion comprises an elongate closure member notch in the proximal closure member on the one lateral side of the shaft axis.

Example 14

The surgical tool assembly of Example 13, wherein the surgical tool assembly further comprises an elongate closure member notch.

Example 15

The surgical tool assembly of Examples 13 or 14, wherein the surgical tool assembly further comprises means for preventing buckling of the distal end of the shaft assembly when an axial actuation motion is applied to the proximal portion of the shaft assembly.

Example 16

The surgical tool assembly of Example 15, wherein the means for preventing buckling comprises at least one alignment member protruding from the proximal closure member and extending into a corresponding axial slot in the spine assembly.

Example 17

The surgical tool assembly of Example 16, wherein the at least one alignment member comprises at least one first alignment member protruding from the proximal closure member at a first location and extending into a corresponding first axial slot in the spine assembly for axial travel therein and at least one second alignment member protruding from the proximal closure member at a second location that is diametrically opposed to the first location. The second alignment member extends into a corresponding second axial slot in the spine assembly.

Example 18

The surgical tool assembly of Examples 16 or 17, wherein at least one of the at least one alignment member has an L-shaped cross-sectional shape.

Example 19

The surgical tool assembly of Examples 11, 12, 13, 14, 15, 16, 17, or 18, wherein the distal portion includes a distal axial length. The proximal portion includes a proximal axial length, and the proximal axial length is greater than the distal axial length.

Example 20

A surgical tool assembly comprising a surgical end effector movably coupled to a shaft assembly by an articulation joint. The articulation joint is configured to facilitate selective articulation of the surgical end effector relative to the shaft assembly about an articulation axis. The articulation axis is transverse to a shaft axis that is defined by the shaft assembly. The shaft assembly comprises a proximal end, a distal end operably coupled to the articulation joint, an elongate notch, and an axially displaceable firing member axially aligned with the shaft axis. The elongate notch is in the shaft assembly on one lateral side of the shaft axis and located adjacent to the distal end.

Example 21

A surgical tool assembly comprising a shaft assembly, a surgical end effector, and a protective cap member. The shaft assembly comprises an axially movable closure member and an axially movable firing member selectively axially movable between an unfired position and a fired position. The surgical end effector comprises a first jaw and a second jaw comprising a mounting portion including a pair of mounting walls. The mounting walls are configured to movably engage a portion of the first jaw to movably support the second jaw on the first jaw. The mounting portion defines a cam area configured for engagement by the axially movable closure member to move the second jaw from an open position to a closed position relative to the first jaw. The mounting walls define an open topped parking area therebetween for accommodating the firing member therein when the firing member is in the unfired position. The protective cap member is attached to the mounting walls and covers at least a portion of the open topped parking area.

Example 22

The surgical tool assembly of Example 21, wherein each of the mounting walls are configured to pivotally engage corresponding portions of the first jaw to facilitate pivotal travel of the second jaw relative to the first jaw about a pivot axis.

Example 23

The surgical tool assembly of Example 22, wherein each of the mounting walls protrude proximally from the cam area. The protective cap comprises a transition portion configured to cover at least a portion of the open topped parking area proximal to the cam area and forming a pre-closure cam surface that is proximal to the cam area and at least one attachment portion extending from the transition portion to couple the protective cap to at least one of the mounting walls.

Example 24

The surgical tool assembly of Example 23, wherein the at least one attachment member comprises a first leg extending downward from the transition portion and being configured to retainingly engage a corresponding one of the mounting walls and a second leg extending downward from the transition portion and being configured to retainingly engage a corresponding another one of the mounting walls.

Example 25

The surgical tool assembly of Example 24, wherein the first and second legs are removably attachable to the mounting walls.

Example 26

The surgical tool assembly of Example 25, wherein the first leg comprises a first attachment opening configured to retainingly receive therein a first attachment lug formed on the corresponding one of the mounting walls. The second leg comprises a second attachment opening configured to retainingly receive therein a second attachment lug formed on the corresponding other one of the mounting walls.

Example 27

The surgical tool assembly of Examples 23, 24, 25, or 26, wherein the closure member comprises a distal camming surface configured to cammingly engage the pre-closure cam surface on the protective cap as well as the cam area on the mounting portion to move the second jaw from the open position to the closed position.

Example 28

The surgical tool assembly of Examples 22, 23, 24, 25, 26, or 27, wherein the surgical tool assembly further comprises means for biasing the second jaw to the open position.

Example 29

The surgical tool assembly of Example 28, wherein the surgical tool assembly further comprises means for preventing the second jaw from being opened beyond a maximum open position.

Example 30

The surgical tool assembly of Examples 22, 23, 24, 25, 26, 27, 28, or 29, wherein the second jaw is configured to be selectively pivotal about a pivot axis relative to the first jaw, and wherein at least a portion of the open topped parking area is proximal to the pivot axis.

Example 31

The surgical tool assembly of Examples 22, 23, 24, 25, 26, 27, 28, 29, or 30, wherein the second jaw comprises a pair of trunnions pivotally supported in the mounting walls.

Example 32

The surgical tool assembly of Example 31, wherein the pair of trunnions comprises a first trunnion configured to be pivotally supported in a first transverse pivot hole in a first one of the mounting walls and a second trunnion configured to be pivotally supported in a second transverse pivot hole in a second one of the mounting walls. The first and second trunnions define a pivot axis about which the second jaw is pivotable.

Example 33

The surgical tool assembly of Example 32, wherein the surgical tool assembly further comprises a first installation slot in the first one of the mounting walls and a second installation slot in the second one of the mounting walls. The first installation slot extends transversely to the first transverse pivot hole from a first top edge of the first one of the mounting walls to the first transverse pivot hole. The second installation slot extends transversely to second transverse pivot hole from a second top edge of said second one of said mounting walls to said second transverse pivot hole.

Example 34

A surgical tool assembly comprising a shaft assembly, a surgical end effector, and a protective cap member. The shaft assembly comprises an axially movable closure member and an axially movable firing member selectively axially movable between an unfired position and a fired position. The surgical end effector comprises an elongate channel configured to operably support a surgical staple cartridge therein and an anvil comprising an anvil mounting portion. The anvil mounting portion includes a pair of anvil mounting walls pivotally supported on the elongate channel for selective pivotal travel relative thereto about a pivot axis. The anvil mounting portion defines a cam area configured for engagement by the axially movable closure member to move the anvil from an open position to a closed position relative to the elongate channel. The anvil mounting walls define an open topped parking area therebetween for accommodating the firing member therein when the firing member is in the unfired position. The protective cap member is attached to the anvil mounting walls and covers at least a portion of the open topped parking area.

Example 35

The surgical tool assembly of Example 34, wherein at least a portion of the open topped parking area is proximal to the pivot axis.

Example 36

The surgical tool assembly of Examples 34 or 35, wherein the firing member comprises a vertically extending firing body comprising a tissue cutting edge, top anvil engaging tabs, and bottom channel engaging tabs. The top anvil engaging tabs extend laterally from a top end of the firing body and are configured to engage the anvil as the firing member is axially advanced from the unfired position to the fired position. The bottom channel engaging tabs extend laterally from a bottom portion of the firing body and configured to engage the channel as the firing member is axially advanced from the unfired position to the fired position to retain an underside of the anvil a desired distance from a cartridge deck of a surgical staple cartridge supported in the elongate channel.

Example 37

The surgical tool assembly of Examples 34, 35, or 36, wherein each of the mounting walls protrude proximally from the cam area. The protective cap comprises a transition portion configured to cover at least a portion of the open topped parking area proximal to the cam area and form a pre-closure cam surface that is proximal to the cam area and at least one attachment portion extending from the transition portion to couple the protective cap to at least one of the anvil mounting walls.

Example 38

The surgical tool assembly of Example 37, wherein the at least one attachment portion comprises a first leg extending downward from the transition portion and is configured to retainingly engage a corresponding one of the anvil mounting walls and a second leg extending downward from the transition portion and is configured to retainingly engage a corresponding another one of the anvil mounting walls.

Example 39

The surgical tool assembly of Examples 34, 35, 36, 37, or 38, wherein the surgical tool assembly further comprises means for biasing the anvil to the open position when the closure member is in a starting position.

Example 40

A surgical tool assembly comprising a shaft assembly and a surgical end effector. The shaft assembly comprises an axially movable closure member and an axially movable firing member selectively axially movable between an unfired position and a fired position. The surgical end effector comprises a first jaw and a second jaw comprising a mounting portion. The mounting portion includes a pair of mounting walls configured to movably engage a portion of the first jaw to movably support the second jaw on the first jaw. The mounting portion defines a cam area configured for engagement by the axially movable closure member to move the second jaw from an open position to a closed position relative to the first jaw. The mounting walls define an open topped parking area therebetween for accommodating the firing member therein when the firing member is in the unfired position. The surgical tool assembly further comprises means for at least partially covering at least a portion of the open topped parking area and defining a pre-closure cam surface that is proximal to the cam area.

Example 41

A surgical tool assembly comprising a first jaw, a second jaw, and a shaft assembly. The second jaw is movably supported on the first jaw for selective movement relative to the first jaw between an open position and a closed position about a fixed pivot axis. The shaft assembly is configured to apply an initial closure motion to a cam surface on the second jaw in a first closure direction that is normal to the cam surface and an additional closure motion to the cam surface in a second closure direction that is parallel to the shaft axis as the closure member is axially advanced on the cam surface.

Example 42

The surgical tool assembly of Example 41, wherein the cam surface is formed on a second jaw mounting portion, and wherein the second jaw further comprises first and second mounting walls that are each pivotally attached to the first jaw for selective pivotal travel about the pivot axis.

Example 43

The surgical tool assembly of Examples 41 or 42, wherein the axially movable closure member comprises a distal closure tube comprising a distal end surface and a distal camming surface configured to cammingly engage the cam surface on the second jaw.

Example 44

The surgical tool assembly of Example 43, wherein the distal end surface is configured to apply the initial closure motion to the cam surface and the distal camming surface is configured to apply the additional closure motion to the cam surface.

Example 45

The surgical tool assembly of Example 44, wherein the distal end surface comprises a portion of a cross-sectional thickness of the closure tube and wherein the camming surface extends from the distal end surface and comprises another portion of the cross-sectional thickness of the closure tube.

Example 46

The surgical tool assembly of Example 45, wherein the closure tube comprises an outer surface, an inner surface, and a distal end defining the distal end surface. The distal camming surface extends from the distal end surface to the inner surface at an obtuse angle relative to the distal end surface.

Example 47

The surgical tool assembly of Example 42, wherein the shaft assembly further comprises an axially movable firing member selectively axially movable between the first and second mounting walls between a starting position and an ending position.

Example 48

The surgical tool assembly of Example 47, wherein at least a portion of the firing member is proximal to the cam surface when the firing member is in the starting position.

Example 49

A surgical tool assembly comprising an end effector and a shaft assembly. The end effector comprises an elongate channel configured to operably support a surgical staple cartridge therein and an anvil. The anvil comprises an anvil mounting portion movably supported on the elongate channel for selective movement relative to the elongate channel about a fixed pivot axis between an open position and closed positions. The shaft assembly defines a shaft axis and comprises an axially movable closure member that is configured to apply an initial closure motion to a cam surface on the anvil mounting portion in a first closure direction that is normal to the cam surface and an additional closure motion to the cam surface in a second closure direction that is parallel to the shaft axis as the closure member is axially advanced on the cam surface.

Example 50

The surgical tool assembly of Example 49, wherein the anvil further comprises first and second anvil mounting walls that are each pivotally attached to the elongate channel for selective pivotal travel about the pivot axis.

Example 51

The surgical tool assembly of Examples 49 or 50, wherein the axially movable closure member comprises a distal closure tube comprising a distal end surface and a distal camming surface configured to cammingly engage the cam surface on the anvil mounting portion.

Example 52

The surgical tool assembly of Example 51, wherein the distal end surface is configured to apply the initial closure motion to the cam surface, and the distal camming surface is configured to apply the additional closure motion to the cam surface.

Example 53

The surgical tool assembly of Example 52, wherein the distal end surface comprises a portion of a cross-sectional thickness of the closure tube, and wherein the camming surface extends from the distal end surface and comprises another portion of the cross-sectional thickness of the closure tube.

Example 54

The surgical tool assembly of Example 50, wherein the shaft assembly further comprises an axially movable firing member that is selectively axially movable between the first and second anvil mounting walls between a starting position and an ending position.

Example 55

The surgical tool assembly of Example 54, wherein at least a portion of the firing member is proximal to the cam surface when the firing member is in the starting position.

Example 56

A surgical tool assembly comprising an end effector and a shaft assembly defining a shaft axis and comprising an axially movable closure member. The end effector comprises an elongate channel configured to operably support a surgical cartridge therein and an anvil movably comprising an anvil mounting portion supported on the elongate channel for selective movement relative to the elongate channel between an open position and a closed position. The surgical tool assembly further comprises first closure means on the closure member for applying an initial closure motion to a cam surface on the anvil mounting portion in a first closure direction that is normal to the cam surface and second closure means on the closure member for applying additional closure motion to the cam surface in a second closure direction that is parallel to the shaft axis as the closure member is axially advanced on the cam surface.

Example 57

The surgical tool assembly of Example 56, wherein the first closure means comprises a distal cam surface on a portion of a distal end of the closure member, and wherein the second closure means comprises a distal camming surface on another portion of the distal end and extending from the distal cam surface at an obtuse angle relative thereto.

Example 58

The surgical tool assembly of Examples 56 or 57, wherein the cam surface is formed on an anvil mounting portion, and wherein the anvil further comprises first and second mounting walls that are each pivotally attached to the elongate channel for selective pivotal travel about the pivot axis.

Example 59

The surgical tool assembly of Example 58, wherein the shaft assembly further comprises an axially movable firing member selectively axially movable between the first and second mounting walls between a starting position and an ending position.

Example 60

The surgical tool assembly of Example 59, wherein at least a portion of the firing member is proximal to the cam surface when the firing member is in the starting position.

Example 61

A surgical tool assembly comprising a surgical end effector and a closure member axially movable in response to closing and opening motions applied thereto. The surgical end effector comprises a first jaw and a second jaw comprising a second jaw body portion and a second jaw mounting portion. The second jaw mounting portion is movably coupled to the first jaw for selective movement relative thereto between an open position and closed positions. The closure member comprises at least one opening cam formed thereon, and the at least one opening cam is configured to movably engage a corresponding cam surface formed on the second jaw body portion such that upon application of the opening motion to the closure member, the at least one opening cam movably engages the corresponding cam surface to move the second jaw to the open position. Upon application of the closure motion to the closure member, the closure member engages the second jaw to move the second jaw to one of the closed positions.

Example 62

The surgical tool assembly of Example 61, wherein the at least one opening cam comprises a first hook portion extending distally from a distal end of the closure member and being configured to cammingly engage a first one of the cam surfaces formed on the second jaw body portion and a second hook portion extending distally from the distal end of the closure member and being configured to cammingly engage a second one of the cam surfaces formed on the second jaw body portion.

Example 63

The surgical tool assembly of Examples 61 or 62, wherein the cam surface comprises a downwardly extending ramp surface formed on the second jaw body portion.

Example 64

The surgical tool assembly of Example 63, wherein each of the at least one opening cam comprises a camming end formed thereon configured to cammingly engage the corresponding ramp surface upon application of the opening motion to the closure member.

Example 65

The surgical tool assembly of Example 64, wherein each ramp surface comprises a ramp surface end, and wherein each camming end is configured to engage the ramp surface end of the corresponding ramp surface to retain the second jaw in a fully open position relative to the first jaw.

Example 66

The surgical tool assembly of Examples 61, 62, 63, 64, or 65, wherein the surgical tool assembly further comprises secondary jaw opening means for applying additional opening motion to the second jaw.

Example 67

The surgical tool assembly of Example 66, wherein the secondary jaw opening means comprises at least one secondary jaw opening member on the closure member configured to engage a corresponding jaw opening feature on the second jaw to apply the additional opening motion to the second jaw as the opening motion is applied to the closure member.

Example 68

The surgical tool assembly of Example 67, wherein the secondary jaw opening feature comprises at least one first jaw opening tab integrally formed in the closure member and configured to contact a corresponding one of the corresponding jaw opening feature and at least one second jaw opening tab integrally formed in the closure member and configured to contact another corresponding one of the corresponding jaw opening feature.

Example 69

The surgical tool assembly of Examples 66, 67, or 68, wherein the secondary jaw opening means comprises at least one biasing member configured to apply additional opening motion to the second jaw.

Example 70

The surgical tool assembly of Examples 62, 63, 64, 65, 66, 67, 68, or 69, wherein the first and second hook portions each comprise a compliant portion thereon.

Example 71

The surgical tool assembly of Example 70, wherein the compliant portion comprises a compliant material attached to each of the first and second hook portions.

Example 72

The surgical tool assembly of Examples 70 or 71, wherein the at least one biasing member comprises a spring corresponding to each of the first and second hook portions and being attached thereto.

Example 73

A surgical tool assembly comprising a surgical end effector and a closure member axially movable in response to closing and opening motions applied thereto. The surgical end effector comprises an elongate channel configured to operably support a surgical staple cartridge therein and an anvil comprising an anvil body and an anvil mounting portion, the anvil mounting portion pivotally supported on the elongate channel for selective movement relative thereto between an open position and closed positions. The closure member comprises at least one opening cam formed thereon, wherein the at least one opening cam is configured to movably engage a corresponding cam surface formed on the anvil body portion such that upon application of the opening motion to the closure member. The at least one opening cam movably engages the corresponding cam surface to move the anvil to the open position and upon application of the closure motion to the closure member, the closure member engages the anvil to move the anvil to one of the closed positions.

Example 74

The surgical tool assembly of Example 73, wherein the surgical tool assembly further comprises at least one tissue stop formed on the anvil body and wherein the at least one cam surface is located proximal to the at least one tissue stop.

Example 75

The surgical tool assembly of Examples 73 or 74, wherein the at least one opening cam comprises a first hook portion extending distally from a distal end of the closure member and being configured to cammingly engage a first one of the cam surfaces formed on the anvil body and a second hook portion extending distally from the distal end of the closure member and being configured to cammingly engage a second one of the cam surfaces formed on the anvil body.

Example 76

The surgical tool assembly of Example 75, wherein the first and second hook portions each comprise a compliant portion thereon.

Example 77

The surgical tool assembly of Examples 73 or 74, wherein the first and second hook portions each comprise a compliant portion thereon.

Example 78

The surgical tool assembly of Examples 73, 74, 75, 76, or 77, wherein the surgical tool assembly further comprises secondary anvil opening means for applying additional opening motion to the second jaw.

Example 79

The surgical tool assembly of Example 78, wherein the anvil is pivotally coupled to the elongate channel for selective pivotal travel between the open and closed positions about a pivot axis. The secondary anvil opening means is located proximal to the pivot axis.

Example 80

A surgical tool assembly comprising a surgical end effector and a closure member. The surgical end effector comprises an elongate channel configured to operably support a surgical staple cartridge therein and an anvil comprising an anvil body and an anvil mounting portion. The anvil mounting portion is pivotally supported on the elongate channel for selective movement relative thereto between an open position and closed positions. The closure member is axially movable between a fully actuated position corresponding to a fully closed one of the closed positions and an unactuated position corresponding to the open position. The closure member comprises a closure system configured to sequentially apply initial opening motions to the anvil and additional secondary motions to the anvil as the closure member is moved from the fully actuated position to the unactuated position.

Example 81

A surgical end effector comprising a first jaw configured to operably support a surgical staple cartridge therein, a second jaw movably supported relative to the first jaw for selective movement between open and closed positions, a firing member, and a firing member lockout system. The firing member is supported for axial movement within the first jaw along a shaft axis between a starting position and an ending position upon applications of firing and retraction motions thereto. The firing member lockout system is movable by second jaw between an unactuated position and a locking position wherein when the firing member is initially distally advanced from the starting position, the firing member lockingly engages the firing member lockout system to prevent further distal advancement of the firing member unless an unfired surgical staple cartridge comprising a cam assembly that is located in an unfired position is supported within the first jaw.

Example 82

The surgical end effector of Example 81, wherein the firing member lockout system comprises a lock member mounted to the first jaw.

Example 83

The surgical end effector of Example 82, wherein the lock member further comprises a spring tab configured to support the lock member on the first jaw and bias the lock member into the unlocked position.

Example 84

The surgical end effector of Examples 82 or 83, wherein the lock member comprises at least one laterally movable locking portion configured to lockingly engage a portion of the firing member upon the initial distal advancement of the firing member when the second jaw is in the closed position unless the unfired surgical staple cartridge is supported within the first jaw.

Example 85

The surgical end effector of Example 84, wherein the firing member comprises a firing member body comprising a lock protrusion that corresponds to each of the laterally movable locking portions, each lock protrusion oriented for locking engagement with the corresponding laterally movable locking portion upon the initial distal advancement of the firing member when the second jaw is in the closed position unless the unfired surgical staple cartridge is supported within the first jaw.

Example 86

The surgical end effector of Example 85, wherein the cam assembly comprises an unlocking feature corresponding to each laterally movable locking portion to laterally bias each of the corresponding laterally movable locking portions out of locking engagement with the corresponding lock protrusion when the unfired surgical staple cartridge is supported in the first jaw and the cam assembly thereof is in the unfired position.

Example 87

The surgical end effector of Examples 85 or 86, wherein each of the laterally movable locking portions comprises a locking window configured to lockingly receive a portion of the corresponding lock protrusion when the laterally movable locking portion is in the locking engagement with the corresponding lock protrusion.

Example 88

The surgical end effector of Examples 81, 82, 83, 84, 85, 86, or 87, wherein the firing member lockout system comprises at least one lock member movably coupled to said second jaw for travel along a corresponding lock axis that is transverse to said shaft axis when said anvil is in said closed position.

Example 89

The surgical end effector of Examples 81, 82, 83, 84, 85, 86, 87, or 88, wherein the firing member lockout system comprises a locking member movably supported for travel between the unlocked position and the locking position wherein upon the initial distal advancement of the firing member, at least a portion of the locking member is configured to hookingly engage a corresponding portion of the firing member to prevent the firing member from being advanced from the starting position to the ending position.

Example 90

A surgical end effector comprising an elongate channel configured to operably support a surgical staple cartridge therein, an anvil supported relative to the elongate channel such that the anvil is selectively movable relative to the elongate channel between open and closed positions, a firing member, and a firing member lockout system. The firing member is supported for axial movement within the elongate channel along a shaft axis between a starting position and an ending position upon applications of firing and retraction motions thereto. The firing member lockout system is movably by the anvil between an unactuated position and a locking position, wherein when the firing member is initially distally advanced from the starting position, the firing member lockingly engages the firing member lockout system to prevent further distal advancement of the firing member unless an unfired surgical staple cartridge comprising a cam assembly that is located in an unfired position is supported within the elongate channel. The firing member lockout system is configured to be moved from the unactuated position to the locking position when the anvil is moved to the closed position.

Example 91

The surgical end effector of Example 90, wherein the firing member lockout system comprises a lock member. The lock member comprises a pair of laterally movable locking portions, a mounting portion configured to support the lock member on the surgical end effector and bias the lock member into the unactuated position, and at least one anvil tab on the lock member for contact by a corresponding portion of the anvil as the anvil is moved to the closed position.

Example 92

The surgical end effector of Example 91, wherein each laterally movable locking portion comprises a locking window configured to retainingly engage a corresponding portion of the firing member when the lock member is in the locking position unless an unfired surgical staple cartridge is supported within the elongate channel.

Example 93

The surgical end effector of Example 92, wherein each corresponding portion of the firing member comprises a laterally protruding lock lug corresponding to each of the lock windows of the corresponding laterally movable locking portions and sized to be retainingly received therein in locking engagement therewith when the lock member is in the locking position unless an unfired surgical staple cartridge comprising a cam assembly that is located in an unfired position is supported within the elongate channel.

Example 94

The surgical end effector of Example 93, wherein the cam assembly comprises an unlocking feature corresponding to each laterally movable locking portion to laterally bias each of the corresponding laterally movable locking portions out of locking engagement with the corresponding lock lug when the unfired surgical staple cartridge is supported in the elongate channel and the cam assembly thereof is in the unfired position.

Example 95

The surgical end effector of Examples 90, 91, 92, 93, or 94, wherein the firing member lockout system comprises at least one lock member and wherein the anvil comprises an anvil body and an anvil mounting portion comprising a pair of spaced anvil mounting walls, each anvil mounting wall being pivotally supported on the elongate channel, and wherein each anvil mounting wall movably supports a corresponding one of the lock members therein.

Example 96

The surgical end effector of Examples 90, 91, 92, 93, 94, or 95, wherein the firing member lockout system comprises at least one lock member movably coupled to the anvil for travel along a corresponding lock axis that is transverse to the shaft axis when the anvil is in the closed position.

Example 97

The surgical end effector of Examples 90, 91, 92, 93, 94, 95, or 96, wherein the surgical end effector further comprises a tissue cutting surface on the firing member.

Example 98

A surgical instrument comprising an elongate shaft defining a shaft axis, an elongate channel operably coupled to the elongate shaft and being configured to operably support a surgical staple cartridge therein, and an anvil supported relative to the elongate channel such that the anvil is selectively movable relative to the elongate channel between open and closed positions. The surgical instrument further comprises a firing member supported for axial travel within the elongate channel between a starting position and an ending position upon applications of firing and retraction motions thereto and means for preventing the firing member from moving from the starting to the ending position unless the anvil is in the closed position and an unfired surgical staple cartridge comprising a cam assembly that is located in an unfired position is supported within the elongate channel.

Example 99

The surgical instrument of Example 98, wherein the anvil comprises an anvil body and a pair of anvil mounting walls extending from the anvil body portion. Each anvil mounting wall is pivotally coupled to the elongate channel such that the anvil is selectively movable relative to the elongate channel between the open and closed positions upon application of closing and opening motions to the anvil by a closure portion of the elongate shaft assembly.

Example 100

The surgical instrument of Examples 98 or 99, wherein the means for preventing comprises a locking member movably supported for travel between the unlocked position and the locked position, wherein at least a portion is configured to hookingly engage a corresponding portion of the firing member to prevent the firing member from being advanced from the starting position to the ending position and means for biasing the firing member to the unlocked position.

Example 101

A surgical instrument comprising a surgical end effector, an elongate shaft defining a shaft axis, a closure member, and an articulation joint. The surgical end effector comprises a first jaw and a second just movably supported on the first jaw for selective travel between open and closed positions relative to the first jaw. The closure member is movably supported on the elongate shaft and is configured to selectively move in a closing direction from an open position to closed positions and in an opening direction from the closed positions to the open position. The articulation joint couples the surgical end effector to the elongate shaft such that the surgical end effector is selectively articulatable relative thereto about an articulation axis that is transverse to the shaft axis. The articulation joint comprises an articulation lock arrangement configured to move from a locked configuration, wherein the surgical end effector is prevented from articulating about the articulation axis and an unlocked configuration wherein the surgical end effector is articulatable about the articulation axis. The articulation lock arrangement moves from the locked configuration to the unlocked configuration when the closure member is moved from the open position in the closing direction. The surgical instrument further comprises means for applying an articulation motion to the surgical end effector when the articulation lock arrangement is in the unlocked configuration.

Example 102

The surgical instrument of Example 101, wherein the articulation lock arrangement comprises at least one locking member movable between a first position corresponding to the unlocked configuration and a second position wherein the at least one locking member is in frictional engagement with a mounting portion of the surgical end effector and a distal end portion of the elongate shaft. The at least one locking member operably interfaces with the closure member such that the initial movement of the closure member in the closing direction causes the at least one locking member to move from the first position to the second position.

Example 103

The surgical instrument of Example 102, wherein the mounting portion of the surgical end effector comprises an upstanding mounting column including a plurality of column sides, and wherein the at least one locking member comprises a locking member corresponding to each of the column sides.

Example 104

The surgical instrument of Example 103, wherein the distal end portion of the elongate shaft comprises a pivot hole that defines the articulation axis, and wherein the upstanding mounting column extends into the pivot hole such that each of the locking members is movably supported within the pivot hole between the corresponding column side and an internal wall of the pivot hole.

Example 105

The surgical instrument of Example 104, wherein the upstanding mounting column is configured to move the plurality of locking members into frictional engagement with the internal wall of the pivot hole and the corresponding column side when the closure member is moved in the closing direction.

Example 106

The surgical instrument of Example 105, wherein the closure member comprises a proximal closure member interfacing with a source of closing and opening motions to move the proximal closure member in the closing and opening directions and a distal closure member pivotally coupled to the proximal closure member by a linkage arrangement, wherein a portion of the linkage arrangement is configured to interface with the upstanding mounting column so as to cause the upstanding mounting column to move the plurality of locking members into frictional engagement with the internal wall of the pivot hole and the corresponding column sidewalls when the closure member is initially moved in the closing direction.

Example 107

The surgical instrument of Example 106, wherein the linkage arrangement comprises an upper double pivot link pivotally coupled to the proximal closure member and the distal closure member and extending therebetween and a lower double pivot link pivotally coupled to the proximal closure member and the distal closure member and extending therebetween. The lower double pivot link is configured to operably interface with the upstanding mounting column to apply a locking motion thereto when the lower double pivot link is initially moved in the closing direction.

Example 108

The surgical instrument of Example 107, wherein the upstanding mounting column comprises a first end portion attached to a mounting based adjacent the lower double pivot link, the upstanding column tapering to a free end, wherein a cross-sectional area of the free end is smaller than another cross-sectional area of the first end portion of the column.

Example 109

The surgical instrument of Examples 101, 102, 103, 104, 105, 106, 107, or 108, wherein the first jaw comprises an elongate channel configured to operably support a surgical staple cartridge therein and wherein the second jaw comprises an anvil.

Example 110

The surgical instrument of Examples 101, 102, 103, 104, 105, 106, 107, 108, or 109, wherein the means for applying an articulation motion to the surgical end effector comprises means for applying a first articulation motion to the surgical end effector to cause the surgical end effector to articulate about the articulation axis in a first articulation direction and means for applying a second articulation motion to the surgical end effector to cause the surgical end effector to articulate about the articulation axis in a second articulation direction.

Example 111

A surgical instrument comprising an elongate shaft comprising a distal end portion and defining a shaft axis, a surgical end effector, an articulation lock arrangement, and an articulation member. The surgical end effector comprises an end effector mounting portion, wherein one of the distal end portion of the elongate shaft and the end effector mounting portion comprises a pivot hole and the other of the distal end portion of the elongate shaft and the end effector mounting portion defines an articulation pin pivotally received within the pivot hole and defining an articulation axis that is transverse to the shaft axis about which the surgical end effector is articulatable relative to the elongate shaft upon application of articulation motions to the surgical end effector. The articulation lock arrangement is supported within the pivot hole between the articulation pin and an inner wall of the pivot hole. The articulation lock arrangement is movable from a first locked configuration wherein the articulation lock arrangement frictionally engages the articulation pin and the inner wall of the pivot hole to prevent relative pivotal travel of the articulation pin and the distal end portion of the elongate shaft and an unlocked configuration wherein the articulation pin and the distal end portion are pivotable relative to each other. The articulation member interfaces with the surgical end effector such that actuation of the articulation member causes the articulation member to apply the articulation motions to the surgical end effector. The articulation member interfaces with the articulation lock arrangement such that an initial actuation of the articulation member causes the articulation lock arrangement to move from the locked configuration to the unlocked configuration and upon deactivation of the articulation member, the articulation lock arrangement moves from the unlocked configuration to the locked configuration.

Example 112

The surgical instrument of Example 111, wherein the articulation lock arrangement comprises a torsion spring supported between the articulation pin and the inner wall of the pivot hole.

Example 113

The surgical instrument of Example 112, wherein the torsion spring is rotatable from a first position wherein the torsion spring frictionally engages the articulation pin and the inner wall of the pivot hole to prevent relative pivotal travel of the distal end portion of the elongate shaft and the surgical end effector and positions wherein the torsion spring does not prevent the relative pivotal travel.

Example 114

The surgical instrument of Examples 111, 112, or 113, wherein the articulation lock arrangement comprises at least one locking ball movably supported between the articulation pin and the inner wall of the pivot hole between a first position, wherein each locking ball frictionally engages the articulation pin and the inner wall of the pivot hole to prevent relative pivotal travel of the distal end portion of the elongate shaft and the surgical end effector and positions wherein each said locking ball does not prevent said relative pivotal travel.

Example 115

The surgical instrument of Examples 111, 112, 113, or 114, wherein the surgical end effector comprises a first jaw and a second jaw supported for movable travel relative to the first jaw.

Example 116

The surgical instrument of Example 115, wherein the first jaw comprises an elongate channel configured to operably support a surgical staple cartridge therein and wherein the second jaw comprises an anvil.

Example 117

The surgical instrument of Examples 111, 112, 113, 114, 115, or 116, wherein the articulation member comprises an axially movable articulation member that is pivotally linked to the surgical end effector such that axial movement thereof in a first axial direction causes the surgical end effector to articulate in a first articulation direction about the articulation axis and movement of the axially movable articulation member in a second axial direction causes the surgical end effector to articulate in a second articulation direction about the articulation axis.

Example 118

A surgical instrument comprising a surgical end effector, an elongate shaft defining a shaft axis, closure means, and an articulation joint. The surgical end effector comprises a first jaw movably coupled to the elongate shaft for selective articulation relative thereto about an articulation axis that is transverse to the shaft axis and a second jaw movably supported on the first jaw for selective travel between open and closed positions relative to the first jaw. The closure means selectively moves the second jaw from the open position to the closed positions, the closure means being further configured to selectively move the second jaw from the closed positions to the open position. The articulation joint couples the surgical end effector to the elongate shaft such that the surgical end effector is selectively articulatable relative thereto about an articulation axis that is transverse to the shaft axis. The articulation joint comprises an articulation lock arrangement configured to move from a locked configuration, wherein the surgical end effector is prevented from articulating about the articulation axis and an unlocked configuration wherein the surgical end effector is articulatable about the articulation axis. The articulation lock arrangement moves from the locked configuration to the unlocked configuration when the closure means moves the second jaw from the open position towards the closed positions. The surgical instrument further comprises means for applying an articulation motion to the surgical end effector when the articulation lock arrangement is in the unlocked configuration.

Example 119

The surgical instrument of Example 118, wherein the first jaw comprises an elongate channel configured to operably support a surgical staple cartridge therein and wherein the second jaw comprises an anvil.

Example 120

The surgical instrument of Examples 119 or 120, wherein the articulation lock arrangement comprises at least one locking member movable between a first position corresponding to the unlocked configuration and a second position wherein the at least one locking member is in frictional engagement with a mounting portion of the first jaw and a distal end portion of the elongate shaft. The at least one locking member operably interfaces with the closure member such that the initial movement of the closure member in the closing direction causes the at least one locking member to move from the first position to the second position.

Example 121

A surgical instrument comprising an elongate shaft defining a shaft axis, a surgical end effector, at least one articulation link, and an articulation lock arrangement. The surgical end effector is coupled to the elongate shaft for selective articulation relative to the elongate shaft about an articulation axis that is transverse to the shaft axis. The at least one articulation link operably interfaces with a source of articulation motions and is coupled to the surgical end effector for applying the articulation motions thereto. The articulation lock arrangement comprises an articulation lock member corresponding to each articulation link, each articulation lock member is configured to laterally move into locking engagement with the corresponding articulation link from an unlocked position that is laterally adjacent to the corresponding articulation link. The surgical instrument further comprises actuation means operably interfacing with each of the articulation lock members to selectively laterally move each articulation lock member from the unlocked position into locking engagement with the corresponding articulation link.

Example 122

The surgical instrument of Example 121, wherein each at least one articulation link comprises an articulation gear rack, and wherein the articulation lock member corresponding thereto comprises a locking gear rack corresponding to each articulation gear rack and is oriented relative thereto in a lateral confronting relationship for the meshing engagement therewith when the corresponding articulation lock member is laterally advanced toward the articulation link.

Example 123

The surgical instrument of Examples 121 or 122, wherein the at least one articulation link comprises an axially movable right articulation link including a right articulation gear rack thereon and an axially movable left articulation link including a left articulation gear rack thereon. The articulation lock member comprises a right articulation lock member including a right locking gear rack that is in lateral confronting relationship with the right articulation gear rack for meshing engagement therewith when the right articulation lock member is laterally advanced toward the right articulation link and a left articulation lock member including a left locking gear rack that is in lateral confronting relationship with the left articulation gear rack for meshing engagement therewith when the left articulation lock member is laterally advanced toward the left articulation link.

Example 124

The surgical instrument of Example 123, wherein the actuation means comprises a locking actuator movably positioned relative to the right articulation lock member and the left articulation lock member such that axial movement of the locking actuator in a first axial direction causes the right articulation lock member to move laterally toward the right articulation link so as to bring the right locking gear rack into locking engagement with the right articulation gear rack and the left articulation lock member to move laterally toward the left articulation link so as to bring the left locking gear rack into locking engagement with the left articulation gear rack.

Example 125

The surgical instrument of Examples 121, 122, 123, or 124, wherein the source of articulations motions comprises an axially movable firing actuator configured to selectively apply firing motions to a corresponding portion of the surgical end effector and an articulation transmission operably interfacing with the axially movable firing actuator and the at least one articulation link such that actuation of the axially movable firing actuator in a first axial firing direction moves the at least one articulation link in a first axial articulation direction and movement of the axially movable firing actuator in a second axial retraction direction moves the at least one articulation link in a second axial articulation direction.

Example 126

The surgical instrument of Examples 123 or 124, wherein the source of articulation motions comprises an axially movable firing actuator configured to selectively apply firing motions to a corresponding portion of the surgical end effector and an articulation transmission operably interfacing with the right and left articulation links and the axially movable firing member such that actuation of the axially movable firing actuator in a first axial firing direction moves the right articulation link in the first axial direction and the left articulation link in a second axial direction and movement of the axially movable firing actuator in the second axial direction moves the right articulation link in the second axial direction and the left articulation link in the first axial direction.

Example 127

The surgical instrument of Example 126, wherein the articulation lock arrangement further comprises a locking actuator movably positioned relative to the right articulation lock member and the left articulation lock member such that axial movement of the locking actuator in the first axial direction causes the right articulation lock member to move laterally toward the right articulation link so as to bring the right locking gear rack into locking engagement with the right articulation gear rack and the left articulation lock member to move laterally toward the left articulation link so as to bring the left locking gear into locking engagement with the left articulation gear rack.

Example 128

The surgical instrument of Example 127, wherein the articulation transmission comprises a gear assembly in meshing engagement with the right and left articulation links and a shifter configured for selective meshing engagement with the gear assembly and the axially movable firing actuator. The shifter is configured for selective operable engagement with the locking actuator such that when the shifter is in operable engagement with the locking actuator, the shifter is moved into meshing engagement with the axially movable firing actuator and the gear assembly and movement of the shifter out of operable engagement with the locking actuator also moves the shifter out of meshing engagement with the gear assembly and the axially movable firing actuator.

Example 129

The surgical instrument of Example 125, wherein the corresponding portion of the surgical end effector comprises a firing member attached to the axially movable firing actuator. The firing member is supported for axial travel through the surgical end effector between a starting and ending position therein.

Example 130

A surgical instrument comprising an elongate shaft defining a shaft axis, a surgical end effector, a firing actuator, at least one articulation link configured for selective operable engagement with the firing actuator, and an articulation lock arrangement. The surgical end effector is coupled to the elongate shaft for selective articulation relative to the elongate shaft about an articulation axis that is transverse to the shaft axis. The firing actuator is selectively axially movable in first and second axial directions to apply firing motions to a firing member operably supported in the surgical end effector. Axial movement of the firing actuator is transmitted to each of the at least one articulation links. The articulation lock arrangement is configured to laterally move between a locked configuration, wherein each of the at least one articulation links are non-movably locked in position and an unlocked configuration, and wherein each of the at least one articulation links are movable in response to movement of the firing actuator. The articulation lock arrangement interfaces with the firing actuator such that when the articulation lock arrangement is in the unlocked configuration, the firing actuator is in operable engagement with each of the at least one articulation links and when the articulation lock arrangement is in the locked configuration, each of the at least one articulation links is prevented from operable engagement with the firing actuator.

Example 131

The surgical instrument of Example 130, wherein the articulation lock arrangement comprises an articulation lock member corresponding to each articulation link. Each articulation lock member is configured to laterally move into locking engagement with the corresponding articulation link from an unlocked position that is laterally adjacent to the corresponding articulation link.

Example 132

The surgical instrument of Example 131, wherein each of the at least one articulation link comprises an articulation gear rack and wherein each corresponding articulation lock member comprises a locking gear rack oriented relative to the articulation gear rack of the corresponding articulation link in lateral confronting relationship relative thereto for meshing engagement therewith when the articulation lock member is laterally advanced toward the corresponding articulation link.

Example 133

The surgical instrument of Example 132, wherein the at least one articulation link comprises an axially movable right articulation link including a right articulation gear rack thereon and an axially movable left articulation link including a left articulation gear rack thereon. The articulation lock member comprises a right articulation lock member including a right locking gear rack that is in lateral confronting relationship with the right articulation gear rack for meshing engagement therewith when the right articulation lock member is laterally advanced toward the right articulation link and a left articulation lock member including a left locking gear rack that is in lateral confronting relationship with the left articulation gear rack for meshing engagement therewith when the left articulation lock member is laterally advanced toward the left articulation link.

Example 134

The surgical instrument of Examples 130, 131, 132, or 133, wherein the surgical end effector comprises a firing member coupled to the firing actuator and supported for axial travel through the surgical end effector.

Example 135

The surgical instrument of Example 134, wherein the surgical end effector comprises an elongate channel configured to operably support a surgical staple cartridge therein and an anvil movably supported on the elongate channel for selective movement between open and closed positions. The elongate channel is coupled to the elongate shaft for selective articulation relative thereto about the articulation axis. The firing member comprises a tissue cutting feature.

Example 136

The surgical instrument of Example 133, wherein the surgical instrument further comprises an articulation transmission operably interfacing with the right and left articulation links and the axially movable firing actuator such that actuation of the axially movable firing actuator in a first axial firing direction moves the right articulation link in the first axial direction and the left articulation link in a second axial direction and movement of the axially movable firing actuator in the second axial direction moves the right articulation link in the second axial direction and the left articulation link in the first axial direction.

Example 137

The surgical instrument of Examples 133 or 136, wherein the articulation lock arrangement further comprises a locking actuator movably positioned relative to the right articulation lock member and the left articulation lock member such that axial movement of the locking actuator in a first axial direction causes the right articulation lock member to move laterally toward the right articulation link so as to bring the right locking gear rack into locking engagement with the right articulation gear rack and the left articulation lock member to move laterally toward the left articulation link so as to bring the left locking gear into locking engagement with the left articulation gear rack.

Example 138

The surgical instrument of Example 136, wherein the articulation transmission comprises a gear assembly in meshing engagement with the right and left articulation links and a shifter configured for selective meshing engagement with the gear assembly and the axially movable firing actuator. The shifter is configured for selective operable engagement with the locking actuator such that when the shifter is in operable engagement with the locking actuator, the shifter is moved into meshing engagement with the axially movable firing actuator and the gear assembly. When the shifter is out of operable engagement with the locking actuator, the shifter is moved out of meshing engagement with the gear assembly and the axially movable firing actuator.

Example 139

A surgical instrument comprising an elongate shaft defining a shaft axis, a surgical end effector coupled to the elongate shaft for selective articulation relative to the elongate shaft about an articulation axis that is transverse to the shaft axis, means for generating axial firing motions, and articulation means. The articulation means interface with the means for generating and the articulation means are configured to apply articulation motions to the surgical end effector in response to the axial firing motions generated by the means for generating. The surgical instrument further comprises means for selectively locking the articulation means in a non-movable configuration and unlocking the articulation means and operably coupling the articulation means with the means for generating such that the means for generating may apply the axial firing motions to the articulation means.

Example 140

The surgical instrument of Example 139, wherein the surgical end effector comprises an elongate channel configured to operably support a surgical staple cartridge therein and an anvil movably supported on the elongate channel for selective movement between open and closed positions. The elongate channel is coupled to the elongate shaft for selective articulation relative thereto about the articulation axis. The firing member comprises a tissue cutting feature.

Example 141

A surgical tool assembly comprising an elongate shaft defining a shaft axis, a surgical end effector coupled to the elongate shaft for selective articulation relative to the elongate shaft about an articulation axis that is transverse to the shaft axis, a first articulation link, a second articulation link, and an articulation stroke multiplier. The first articulation link operably interfaces with a source of articulation motions to selectively axially move the first articulation link a first axial distance in a first articulation direction. The second articulation link operably interfaces with the surgical end effector to apply articulation motions thereto. The articulation stroke multiplier operably interfaces with the first articulation link and the second articulation link such that when the first articulation link is axially moved the first axial distance in the first axial direction, the articulation stroke multiplier moves the second articulation link another first axial distance in the first axial direction that is greater than the first axial distance.

Example 142

The surgical tool assembly of Example 141, wherein the source of articulation motions is configured to additionally axially move the first articulation link a second axial distance in a second axial direction and wherein when the first articulation link is moved the second axial distance in the second axial direction, the articulation stroke multiplier moves the second articulation link another second axial distance in the second axial direction that is greater than the second axial distance.

Example 143

The surgical tool assembly of Examples 141 or 142, wherein the first articulation link comprises a first articulation gear rack, wherein the second articulation link comprises a second articulation gear rack, and wherein the articulation stroke multiplier comprises at least one gear set in meshing engagement with the first and second articulation gear racks.

Example 144

The surgical tool assembly of Example 143, wherein each of the at least one gear set comprises a first gear rotatably supported in meshing engagement with the first articulation gear rack and a first gear rotatably supported in meshing engagement with the first articulation gear rack.

Example 145

The surgical tool assembly of Examples 141, 142, 143, or 144, wherein the second articulation link operably interfaces with an articulation lock assembly that is operably coupled to the surgical end effector.

Example 146

The surgical tool assembly of Examples 141, 142, 143, 144, or 145, wherein the first articulation link comprises a first articulation gear rack and wherein the articulation stroke multiplier comprises a swing gear in meshing engagement with the first articulation gear rack and slidably coupled to the second articulation link.

Example 147

The surgical tool assembly of Examples 141, 142, 143, 144, 145, or 146, wherein the swing gear is supported for rotational travel about a swing gear mounting axis that is transverse to the first and second articulation links.

Example 148

The surgical tool assembly of Examples 146 or 147, wherein the second articulation link comprises a slotted distal end slidably engaging a portion of the swing gear therein.

Example 149

The surgical tool assembly of Examples 146, 147, or 148, wherein the swing gear has a slot therein configured to slidably engage a distal end portion of the second articulation link.

Example 150

A surgical tool assembly comprising an elongate shaft defining a shaft axis, a surgical end effector, a first articulation link, a second articulation link, and an articulation stroke multiplier. The surgical end effector comprises an elongate channel configured to operably support a surgical staple cartridge therein and coupled to the elongate shaft for selective articulation relative to the elongate shaft about an articulation axis that is transverse to the shaft axis and an anvil movably supported on the elongate channel. The first articulation link operably interfaces with a source of articulation motions to selectively axially move the first articulation link a first axial distance in a first articulation direction. The second articulation link operably interfaces with the surgical end effector to apply articulation motions thereto. The articulation stroke multiplier operably interfaces with the first articulation link and the second articulation link such that when the first articulation link is axially moved the first axial distance in the first axial direction. The articulation stroke multiplier moves the second articulation link another first axial distance in the first axial direction that is greater than the first axial distance.

Example 151

The surgical tool assembly of Example 150, wherein the source of articulation motions comprises a firing member assembly operably interfacing with a firing member that is supported for axial travel within the elongate channel and a clutch assembly operably interfacing with the first articulation link and the firing member assembly and being selectively configurable between a firing mode, wherein axial movement of the firing member assembly is applied to the firing member and an articulation mode, and wherein the axial movement of the firing member assembly is applied to the first articulation link.

Example 152

The surgical tool assembly of Example 151, wherein when the clutch assembly is in the articulation mode, the firing member assembly is configured to additionally axially move the first articulation link a second axial distance in a second axial direction and wherein when the first articulation link is moved the second axial distance in the second axial direction, the articulation stroke multiplier moves the second articulation link another second axial distance in the second axial direction that is greater than the secondary axial distance.

Example 153

The surgical tool assembly of Examples 151 or 152, wherein the first articulation link comprises a first articulation gear rack, wherein the second articulation link comprises a second articulation gear rack, and wherein the articulation stroke multiplier comprises at least one gear set in meshing engagement with the first and second articulation gear racks.

Example 154

The surgical tool assembly of Example 153, wherein each of the at least one gear set comprises a first gear rotatably supported in meshing engagement with the first articulation gear rack and a second gear attached to the first gear for rotation therewith. The second gear has a larger diameter than a diameter of the first gear, and the second gear is in meshing engagement with the second articulation gear rack.

Example 155

The surgical tool assembly of Examples 151, 152, 153, or 154, wherein the second articulation link operably interfaces with an articulation lock assembly that is operably coupled to the surgical end effector.

Example 156

The surgical tool assembly of Examples 151, 152, 153, 154, or 155, wherein the first articulation link comprises a first articulation gear rack and wherein the articulation stroke multiplier comprises a swing gear in meshing engagement with the first articulation gear rack and slidably coupled to the second articulation link.

Example 157

The surgical tool assembly of Example 156, wherein the swing gear is supported for rotational travel about a swing gear mounting axis that is transverse to the first and second articulation links.

Example 158

The surgical tool assembly of Examples 156 or 157, wherein the second articulation link comprises a slotted distal end slidably engaging a portion of the swing gear therein.

Example 159

The surgical tool assembly of Examples 156, 157, or 158, wherein the swing gear has a slot therein configured to slidably engage a distal end portion of the second articulation link.

Example 160

A surgical tool assembly comprising an elongate shaft defining a shaft axis, a surgical end effector, a first articulation link, a second articulation link, and an articulation stroke multiplying means. The surgical end effector is coupled to the elongate shaft for selective articulation relative to the elongate shaft about an articulation axis that is transverse to the shaft axis. A first articulation link operably interfaces with a source of articulation motions to selectively axially move the first articulation link a first axial distance in a first articulation direction. A second articulation link operably interfaces with the surgical end effector to apply articulation motions thereto. The articulation stroke multiplying means operably interfaces with the first articulation link and the second articulation link to move the second articulation a second axial distance in response to movement of the first articulation link a first axial distance that is less than the second axial distance.

Example 161

A surgical tool assembly comprising an elongate shaft assembly defining a shaft axis, a surgical end effector, and a distal articulation member. The surgical end effector is movably coupled to the elongate shaft assembly by a distal support link that is pivotally coupled to the surgical end effector to define an articulation axis that is transverse to the shaft axis. The distal support link is pivotally and axially movably coupled to the elongate shaft assembly to facilitate selective articulation of the surgical end effector relative to the elongate shaft assembly about the articulation axis between a first unarticulated position, wherein the surgical end effector is aligned with the elongate shaft assembly along the shaft axis and articulation positions located on one side of the shaft axis. The distal articulation member operably interfaces with a source of articulation motions and is pivotally coupled to the surgical end effector to apply the articulation motions thereto.

Example 162

The surgical tool assembly of Example 161, wherein the distal articulation member is configured to axially move on the one side of the shaft axis in response to the articulation motions applied thereto and wherein the distal support link is configured to axially move relative to the elongate shaft assembly along the shaft axis.

Example 163

The surgical tool assembly of Examples 161 or 162, wherein the distal support link comprises a distal end pivotally coupled to the surgical end effector for pivotal travel about the articulation axis and a proximal end comprising a proximal axial slot configured to receive a corresponding articulation pin therein that is attached to a distal end of elongate shaft assembly.

Example 164

The surgical tool assembly of Examples 161, 162, or 163, wherein the surgical tool assembly further comprises a proximal articulation member operably interfacing with the source of articulation motions and an articulation lock assembly operably coupled to the proximal articulation member and a proximal end of the distal articulation member to selectively lock the distal articulation member in an axial position.

Example 165

The surgical tool assembly of Example 164, wherein the proximal end of the distal articulation member is pivotally coupled to the articulation lock assembly.

Example 166

The surgical tool assembly of Examples 161, 162, 163, 164, or 165, wherein the distal support link is pivotally and axially movably coupled to a distal spine member of the elongate shaft assembly.

Example 167

The surgical tool assembly of Examples 161, 162, 163, 164, 165, or 166, wherein the surgical end effector comprises an elongate channel configured to operably support a surgical staple cartridge therein and an anvil movably supported on the elongate channel for selective movement relative thereto between an open position and closed positions.

Example 168

The surgical tool assembly of Example 167 wherein the elongate channel is pivotally coupled to the distal support link by an end effector mounting assembly coupled to the elongate channel.

Example 169

The surgical tool assembly of Examples 161, 162, 163, 164, 165, 166, 167, or 168, wherein the distal articulation member is configured to axially move in first and second axial directions such that when the distal articulation member is moved in the first axial direction, the surgical end effector is articulated in a first articulation direction from the first unarticulated position to any one of the articulation positions, and when the distal articulation member is axially moved in the second axial direction, the surgical end effector is moved in a second articulation direction from any one of the articulation positions to the first unarticulated position.

Example 170

The surgical tool assembly of Example 169, wherein the surgical tool assembly further comprises means for preventing movement of the surgical end effector in the second articulation direction beyond the first unarticulated position when the distal articulation member is moved in the second axial direction.

Example 171

A surgical tool assembly comprising an elongate shaft assembly defining a shaft axis, a surgical end effector, a distal support link, and a distal articulation member. The surgical end effector comprises an elongate channel configured to operably support a surgical staple cartridge therein and an anvil supported for movable travel relative to the surgical staple cartridge. The distal support link is pivotally coupled to the elongate channel to define an articulation axis that is transverse to the shaft axis and about which the elongate channel may articulate relative to the elongate shaft assembly. The distal support link is attached to a distal end of the elongate shaft assembly for axial and pivotal travel relative thereto along the shaft axis. The distal articulation member is supported for axial travel on one side of the shaft axis, the distal articulation member being pivotally coupled to the elongate channel and operably interfacing with a source of articulation motions.

Example 172

The surgical tool assembly of Example 171, wherein a proximal end of the distal support link comprises a proximal axial slot that is configured to receive a corresponding articulation pin therein that is attached to the distal end of said elongate shaft assembly.

Example 173

The surgical tool assembly of Examples 171 or 172, wherein the surgical tool assembly further comprises a proximal articulation member operably interfacing with the source of articulation motions and an articulation lock assembly operably coupled to the proximal articulation member and a proximal end of the distal articulation member to selectively lock the distal articulation member in an axial position.

Example 174

The surgical tool assembly of Example 173, wherein the proximal end of the distal articulation member is pivotally coupled to the articulation lock assembly.

Example 175

The surgical tool assembly of Examples 171, 172, 173, or 174, wherein the distal support link is pivotally and axially movably coupled to a distal spine member of the elongate shaft assembly.

Example 176

The surgical tool assembly of Examples 171, 172, 173, 174, or 175, wherein the distal articulation member is configured to move in first and second axial directions such that when the distal articulation member is moved in the first axial direction, the surgical end effector is articulated in a first articulation direction from the first unarticulated position to any one of the articulation positions and when the distal articulation member is moved in the second axial direction, the surgical end effector is moved in a second articulation direction from any one of the articulation positions to the first unarticulated position.

Example 177

The surgical tool assembly of Example 176, wherein the surgical tool assembly further comprises means for preventing movement of the surgical end effector in the second articulation direction beyond the first unarticulated position when the distal articulation member is moved in the second axial direction.

Example 178

A surgical tool assembly comprising an elongate shaft assembly defining a shaft axis, means for coupling a surgical end effector to a distal end of the elongate shaft assembly such that the surgical end effector may be selectively articulated about an articulation axis that is transverse to the shaft axis between an unarticulated position wherein the surgical end effector is aligned with the elongate shaft along the shaft axis and articulation positions located on one side of the shaft axis, and means for applying articulation motions to the surgical end effector. The means for coupling are coupled to the elongate shaft assembly for axial and pivotal travel relative thereto.

Example 179

The surgical tool assembly of Example 178, wherein the means for applying is pivotally coupled to the surgical end effector at a location that is laterally offset from the shaft axis.

Example 180

The surgical tool assembly of Examples 178 or 179, wherein the means for applying further comprises means for selectively locking the surgical end effector in any one of the articulation positions.

Example 181

A surgical staple cartridge is configured to be supported within a jaw of a surgical end effector wherein at least one jaw of the surgical end effector is movable relative to a second jaw of the surgical end effector between open and closed positions. The surgical end effector includes a lock member that is moved from an unlocked configuration to a locked configuration when the at least one jaw is moved to the closed position to prevent axial travel of a firing member through the surgical end effector. The surgical end effector comprises a cartridge body sized to be seated within the surgical end effector, the cartridge body operably supporting a plurality of surgical staples arranged in staple lines therein and a cam assembly. The cam assembly is movable between a starting position and an ending position within the cartridge body, the cam assembly defining a central axis and a plurality of cam features thereon wherein each cam feature corresponds to at least one of the staple lines. The cam assembly further comprises at least one unlocking feature thereon that is laterally offset from the central axis and is configured to unlockingly engage a corresponding portion of the lock member when the cartridge body is seated within the surgical end effector and the cam assembly is in the starting position to thereby prevent the locking member from attaining the locked configuration when the at least one jaw is moved to the closed position.

Example 182

The surgical staple cartridge of Example 181, wherein the at least one unlocking feature comprises a first unlocking ramp formed on a proximal end of the cam assembly in a position that is laterally offset to one side of the central axis and a second unlocking ramp formed on the proximal end of the cam assembly in another position that is laterally offset on an opposite side of the central axis.

Example 183

The surgical staple cartridge of Examples 181 or 182, wherein each unlocking feature is configured to bias the lock member into the unlocked configuration.

Example 184

The surgical staple cartridge of Example 182, wherein the proximal end of the cam assembly defines a central contact area located between the first and second unlocking ramps that is configured for engagement by the firing member as the firing member is axially advanced through the surgical end effector.

Example 185

A surgical end effector comprising a first jaw, an anvil, a firing member, a lock member, and a surgical staple cartridge. The anvil is supported relative to the first jaw for selective movement relative to the first jaw between an open position and a closed position relative to each other. The firing member is supported for axial movement within the end effector between a beginning position and an ending position upon applications of firing and retraction motions thereto. The lock member is movable between a locked configuration wherein the firing member is prevented from axial travel through the surgical end effector and an unlocked configuration wherein the firing member is axially advanceable through the surgical end effector. The surgical staple cartridge comprises a cartridge body and a cam assembly. The cartridge body is sized to be seated within the first jaw, the cartridge body operably supporting a plurality of surgical staples arranged in staple lines therein. The cam assembly is movable between a starting position and an end position within the cartridge body, the cam assembly defining a central axis and comprising a plurality of cam features thereon wherein each cam feature corresponds to at least one of the staple lines. The cam assembly further comprises at least one unlocking feature thereon laterally offset from the central axis and being configured to unlockingly engage a corresponding portion of the lock member when the cartridge body is seated within the first jaw and the cam assembly is in the starting position to thereby prevent the lock member from attaining the locked configuration when the anvil is moved to the closed position.

Example 186

The surgical end effector of Example 185, wherein the at least one unlocking feature comprises a first unlocking ramp formed on a proximal end of the cam assembly in a position that is laterally offset to one side of the central axis and a second unlocking ramp formed on the proximal end of the cam assembly in another position that is laterally offset on an opposite side of the central axis.

Example 187

The surgical end effector of Examples 185 or 186, wherein the anvil is configured to move the lock member in a first direction into locking engagement with the firing member when the anvil is moved to the closed position and wherein each unlocking feature is configured to bias the corresponding portion of the lock member in a second direction that is opposite to the first direction.

Example 188

The surgical end effector of Example 186, wherein the proximal end of the cam assembly defines a central contact area located between the first and second unlocking ramps that is configured for engagement by the firing member as the firing member is axially advanced through the surgical end effector.

Example 189

The surgical end effector of Examples 181, 182, 183, or 184, wherein the surgical staple cartridge comprises an elongate slot configured to slidably receive the firing member therein as the firing member is moved between the beginning and ending positions and wherein the lock member is configured to axially align the firing member with the elongate slot.

Example 190

The surgical end effector of Examples 185, 186, 187, or 188, wherein the firing member comprises two lateral sides and wherein the lock member is configured to retainingly engage each lateral side of the firing member when the lock member is in the locked configuration.

Example 191

The surgical end effector of Example 190, wherein the lock member comprises a spring arm corresponding to each lateral side of the firing member and a lock notch in each spring arm configured to releasably engage a corresponding lock lug on each lateral side of the firing member.

Example 192

The surgical end effector of Examples 185, 186, 187, 188, 190, or 191, wherein the surgical end effector further comprises a tissue cutting surface on the firing member.

Example 193

The surgical end effector of Examples 185, 186, 187, 188, 190, 191, or 192, wherein the anvil comprises an anvil body, an axial slot in the anvil body to permit a portion of the firing member to axially pass therethrough, and an axial passage within the anvil body on each side of the axial slot.

Example 194

The surgical end effector of Example 193, wherein the firing member comprises a foot configured to slidably pass within a corresponding passage within the first jaw and laterally extending anvil engagement features extending laterally from a top portion of the firing member body and configured to pass through a corresponding one of the axial passages within the anvil body and wherein the first and second engagement features are located between the foot and the anvil engagement features.

Example 195

A surgical staple cartridge is configured to be supported within a jaw of a surgical end effector that defines a shaft axis and wherein at least one jaw of the surgical end effector is movable relative to a second jaw of the surgical end effector between open and closed positions. The surgical end effector includes a lock member that is movable between a locked configuration wherein a firing member is prevented from axial travel through the surgical end effector and an unlocked configuration wherein the firing member is axially advanceable through the surgical end effector. The surgical staple cartridge comprises a cartridge body sized to be seated within the one jaw of the surgical end effector, the cartridge body operably supporting a plurality of surgical staples arranged in staple rows therein and staple camming means for camming the staples out of the cartridge body as the camming means is axially moved within the cartridge body from a starting position to an ending position. The staple camming means is configured to unlockingly engage at least one corresponding portion of the lock member that is laterally offset from the shaft axis when the cartridge body is seated within the jaw of the surgical end effector and the staple camming means is in the starting position to thereby prevent the locking member from attaining the locked configuration when the at least one jaw is moved to the closed position.

Example 196

A method comprises obtaining a first staple cartridge having a first row of staples and obtaining a second staple cartridge having a second row of staples, wherein the first row of staples and the second row of staples comprise the same length. The method further comprises inserting the first staple cartridge into a channel comprising a keyed profile, wherein complete insertion of the first staple cartridge into the channel is prevented by an interference between the keyed profile and the channel and inserting the second staple cartridge into the channel, wherein complete insertion of the second staple cartridge into the channel is permitted by the keyed profile.

Example 197

The method of Example 196, wherein inserting the second staple cartridge into the channel further comprises aligning key features on the second staple cartridge with the keyed profile on the channel.

Example 198

The method of Examples 196 or 197, wherein the method further comprises a bottom surface of the first staple cartridge being spaced apart from the channel when the first staple cartridge is inserted into the channel.

Example 199

The method of Example 198, wherein the method further comprises a bottom surface of the second staple cartridge being positioned against the channel when the second staple cartridge is inserted into the channel.

Example 200

The method of Examples 196, 197, 198, or 199, wherein the method further comprises a proximal portion of the first staple cartridge obstructing clamping of an anvil against a distal portion of the first staple cartridge when the first staple cartridge is inserted into the channel.

Example 201

The method of Examples 196, 197, 198, 199, or 200, wherein the method further comprises a firing lockout of the first staple cartridge preventing a firing stroke when the first staple cartridge is inserted into the channel.

Example 202

A method comprising obtaining a first staple cartridge comprising a first quantity of staples and obtaining a second staple cartridge comprising the first quantity of staples. The method further comprises inserting the first staple cartridge into a channel comprising a keyed profile, wherein the complete insertion of the first staple cartridge into the channel is prevented by the keyed profile and inserting the first staple cartridge into a channel comprising a keyed profile, wherein the complete insertion of the first staple cartridge into the channel is prevented by the keyed profile.

Example 203

The method of Example 202, wherein inserting the second staple cartridge into the channel further comprises aligning key features on the second staple cartridge with the keyed profile on the channel.

Example 204

The method of Examples 202 or 203, wherein the method further comprises a bottom surface of the first staple cartridge being spaced apart from the channel when the first staple cartridge is inserted into the channel.

Example 205

The method of Example 204, wherein the method further comprises a bottom surface of the first staple cartridge being spaced apart from the channel when the first staple cartridge is inserted into the channel.

Example 206

The method of Examples 202, 203, 204, or 205, wherein the method further comprises the first staple cartridge obstructing clamping of an anvil against the first staple cartridge when the first staple cartridge is inserted into the channel.

Example 207

The method of Examples 202, 203, 204, 205, or 206, wherein the method further comprises a firing lockout of the first staple cartridge preventing a firing stroke when the first staple cartridge is inserted into the channel.

Example 208

A method comprises obtaining a channel, obtaining a compatible staple cartridge comprising a proximal alignment protrusion and a distal alignment protrusion, and aligning the proximal alignment protrusion with a corresponding proximal alignment feature in a channel. The method further comprises aligning the distal alignment protrusion with a corresponding distal alignment feature in the channel and inserting the compatible staple cartridge into the channel such that the proximal alignment protrusion interlocks with the corresponding proximal alignment feature and the distal alignment protrusion interlocks with the corresponding distal alignment feature.

Example 209

The method of Example 208, wherein the method further comprises a bottom surface of the compatible staple cartridge being positioned against the channel when the compatible staple cartridge is inserted into the channel.

Example 210

The method of Examples 208 or 209, wherein the method further comprises a firing lockout of the compatible staple cartridge preventing a firing stroke until the compatible staple cartridge is inserted into the channel.

Example 211

The method of Examples 208, 209, or 210, wherein the method further comprises attempting to insert an incompatible staple cartridge into the channel, wherein the incompatible staple cartridge further comprises an interference feature relative to the corresponding proximal alignment feature on the channel.

Example 212

The method of Example 211, wherein the method further comprises a bottom surface of the incompatible staple cartridge being spaced apart from the channel when the incompatible staple cartridge is inserted into the channel.

Example 213

The method of Example 212, wherein the method further comprises a proximal portion of the incompatible staple cartridge obstructing clamping of an anvil against a distal portion of the incompatible staple cartridge when the incompatible staple cartridge is inserted into the channel.

Example 214

The method of Examples 211, 212, or 213, wherein the method further comprises a lockout preventing at least one surgical function when the incompatible staple cartridge is positioned in the channel.

Example 215

The method of Examples 208, 209, 210, 211, 212, 213, or 214, wherein the channel comprises a jaw of an end effector, and the method further comprises matching a classifying indication on the end effector with a classifying indication on the compatible staple cartridge.

Example 216

A system comprising a replaceable staple cartridge and a channel configured to receive the replaceable staple cartridge. The replaceable staple cartridge comprises a plurality of staples, a first downwardly-protruding tab, and a second downwardly-protruding tab. The channel comprises a first receptacle positioned and dimensioned to receive the first downwardly-protruding tab and a second receptacle positioned and dimensioned to receive the second downwardly-protruding tab.

Example 217

The system of Example 216, wherein the replaceable staple cartridge further comprises a cartridge body and a pan positioned around a portion of the cartridge body, wherein the pan further comprises a base, and wherein the first downwardly-protruding tab and the second downwardly-protruding tab protrude from the base.

Example 218

The system of Example 217, wherein the first downwardly-protruding tab and the second downwardly-protruding tab are comprised of metal.

Example 219

The system of Examples 216, 217, or 218, wherein the replaceable staple cartridge further comprises a first laterally-extending lug and a second laterally-extending lug.

Example 220

The system of Example 219, wherein the replaceable staple cartridge further comprises a first sidewall comprising a first cutout, wherein the first cutout is positioned and dimensioned to receive the first laterally-extending lug and a second sidewall comprising a second cutout, wherein the second cutout is positioned and dimensioned to receive the second laterally-extending lug.

Example 221

The system of Example 220, wherein the replaceable staple cartridge further comprises a molded cartridge body, and wherein the first laterally-extending lug and the second laterally-extending lug are molded features of the molded cartridge body.

Example 222

The system of Example 221, wherein the cartridge body is comprised of a plastic material.

Example 223

The system of Examples 219, 220, 221, or 222, wherein the first laterally-extending lug and the second laterally-extending lug are located distal to the first downwardly-protruding tab and second downwardly-protruding tab.

Example 224

A system comprising a replaceable staple cartridge and a channel configured to receive the replaceable staple cartridge. The replaceable staple cartridge comprises a plurality of staples and an outer surface comprising a plurality of ribs. The channel comprises a plurality of slots, wherein each of the slots is configured to receive one of the ribs.

Example 225

The system of Example 224, wherein the plurality of ribs comprises a first rib and a second rib.

Example 226

The system of Example 225, wherein the plurality of slots comprises a first slot and a second slot, and wherein the channel further comprises a first sidewall comprising the first slot and a second sidewall comprising the second slot.

Example 227

The system of Examples 224, 225, or 226, wherein the replaceable staple cartridge further comprises a molded cartridge body, and wherein the ribs are molded features of the molded cartridge body.

Example 228

The system of Examples 224, 225, 226, or 227, wherein the replaceable staple cartridge further comprises a first laterally-extending lug and a second laterally-extending lug.

Example 229

The system of Examples 224, 225, 226, 227, or 228, wherein the channel further comprises a first sidewall comprising a first cutout, wherein the first cutout is positioned and dimensioned to receive the first laterally-extending lug and a second sidewall comprising a second cutout, wherein the second cutout is positioned and dimensioned to receive the second laterally-extending lug.

Example 230

The system of Example 229, wherein the replaceable staple cartridge further comprises a molded cartridge body, and wherein the first laterally-extending lug and the second laterally-extending lug are molded in the molded cartridge body.

Example 231

The system of Example 230, wherein the molded cartridge body is comprised of a plastic material.

Example 232

The system of Example 231, wherein the first laterally-extending lug and the second laterally-extending lug are located distal to the rubs.

Example 233

A system comprising a compatible staple cartridge comprising a plurality of staples and a channel. The system further comprises means for permitting complete insertion of the compatible staple cartridge and for preventing an incompatible staple cartridge from being completely inserted in the channel, wherein the incompatible staple cartridge and the compatible staple cartridge comprise the same length and the same width.

Example 234

The system of Example 233, wherein the means comprises proximal and distal alignment keys.

Example 235

The system of Examples 233 or 234, wherein the system further comprises a second channel, and wherein the incompatible staple cartridge is compatible with the second channel.

Example 236

A system comprising a replaceable staple cartridge and a channel configured to receive the replaceable staple cartridge. The replaceable staple cartridge comprises a plurality of staples, a proximal laterally-protruding lug, and a distal laterally-protruding lug. The channel comprises a sidewall comprising a proximal receptacle positioned and dimensioned to receive the proximal laterally-protruding lug and a distal receptacle positioned and dimensioned to receive the distal laterally-protruding lug.

Example 237

The system of Example 236, wherein the channel further comprises an obstruction, and wherein the replaceable staple cartridge further comprises a complementary anti-obstruction positioned and dimensioned to overcome the obstruction.

Example 238

The system of Example 237, wherein the system further comprises a second replaceable staple cartridge comprising a non-complementary anti-obstruction positioned and dimensioned to interfere with the obstruction.

Example 239

The system of Examples 236, 237, or 238, wherein the proximal receptacle defines a cutout in the sidewall, and wherein the cutout comprises a depression and a projection.

Example 240

The system of Example 239, wherein the projection is positioned within the depression.

Example 241

The system of Examples 236, 237, 238, 239, or 240, wherein the system further comprises a second replaceable staple cartridge comprising a second plurality of staples, a second proximal laterally-protruding lug, and a second distal laterally-protruding lug.

Example 242

The system of Example 241, wherein the second distal laterally-protruding lug is spaced apart from the second proximal laterally-protruding lug by a distance, and wherein the distance is different than a first distance between the proximal laterally-protruding lug and the distal laterally-protruding lug of the replaceable staple cartridge.

Example 243

The system of Examples 241 or 242, wherein the second distal laterally-protruding lug matches the distal laterally-protruding lug, and wherein the second proximal laterally-protruding lug is different than the proximal laterally protruding-lug.

Example 244

The system of Examples 241, 242, or 243, wherein the second replaceable staple cartridge further comprises a deck, wherein the channel further comprises a bottom surface, and wherein the deck is obliquely oriented relative to the bottom surface when the second replaceable staple cartridge is positioned in the channel.

Example 245

The system of Examples 241, 242, 243, or 244, wherein the replaceable staple cartridge and the second replaceable staple cartridge comprise the same width and the same length.

Example 246

The system of Examples 241, 242, 243, 244, or 245, wherein the plurality of staples and the second plurality of staples comprise the same quantity of staples.

Example 247

The system of Examples 236, 237, 238, 239, 240, 241, 242, 243, 244, 245, or 246, wherein the distal laterally-protruding lug comprises a different geometry than the proximal laterally-protruding lug.

Example 248

The system of Example 247, wherein the proximal laterally-protruding lug comprises a wedge.

Example 249

The system of Examples 247 or 248, wherein the proximal laterally-protruding lug comprises a cutout that matches a projection in the proximal receptacle.

Example 250

The system of Examples 236, 237, 238, 239, 240, 241, 242, 243, 244, 245, 246, 247, 248, or 249, wherein the proximal laterally-protruding lug protrudes from a first side of the replaceable staple cartridge, and wherein the distal laterally-protruding lug protrudes from a second side of the replaceable staple cartridge.

Example 251

The system of Examples 236, 237, 238, 239, 240, 241, 242, 243, 244, 245, 246, 247, 248, 249, or 250, wherein the replaceable staple cartridge further comprises a deck, wherein the channel further comprises a bottom surface, and wherein the deck is parallel to the bottom surface when the replaceable staple cartridge is positioned in the channel.

Example 252

A system comprising a channel comprising an obstruction, a compatible staple cartridge comprising a complementary anti-obstruction positioned and dimensioned to complement the obstruction when the compatible staple cartridge is received in said channel, and an incompatible staple cartridge comprising a non-complementary anti-obstruction positioned and dimensioned to interfere with the obstruction when the incompatible staple cartridge is received in the channel.

Example 253

The system of Example 252, wherein the compatible staple cartridge and the incompatible staple cartridge comprise rows of staples of the same length.

Example 254

The system of Examples 252 or 253, wherein the compatible staple cartridge and the incompatible staple cartridge comprise the same quantity of staples.

Example 255

The system of Examples 252, 253, or 254, wherein the obstruction further comprises a cutout comprising a depression and a projection.

Example 256

A system comprising a compatible staple cartridge comprising a first quantity of staples, an incompatible staple cartridge comprising the first quantity of staples, and a channel comprising means for permitting complete insertion of the compatible staple cartridge and for preventing the incompatible staple cartridge from being completely inserted into the channel.

Example 257

A system comprising an end effector configured to receive a compatible replaceable staple cartridge, wherein the end effector comprises a first outer surface, and wherein a classifying identification of the end effector is inscribed on the first outer surface, and the compatible replaceable staple cartridge comprising a second outer surface, wherein a classifying identification of the compatible replaceable staple cartridge is inscribed on the second outer surface, and wherein the classifying identification of the compatible replaceable staple cartridge corresponds to the classifying identification of the end effector.

Example 258

The system of Example 257, wherein the system further comprises an incompatible replaceable staple cartridge, wherein the incompatible replaceable staple cartridge comprises a third outer surface, wherein a classifying identification of the incompatible replaceable staple cartridge is positioned on the third outer surface, and wherein the classifying identification of the compatible replaceable staple cartridge is different than the classifying identification of the end effector.

Example 259

The system of Examples 257 or 258, wherein the end effector further comprises a distal portion, and wherein the classifying identification of the end effector is positioned on the distal portion.

Example 260

The system of Example 259, wherein the end effector further comprises an anvil, and wherein the classifying identification of the end effector is positioned at a distal end of the anvil.

Example 261

The system of Examples 257, 258, 259, or 260, wherein the end effector further comprises an anvil comprising a pair of tissue stops, and wherein a secondary classifying identification of the end effector is positioned on each of the tissue stops.

Example 262

The system of Examples 257, 258, 259, 260, or 261, wherein the compatible replaceable staple cartridge further comprises a wedge-shaped distal nose, and wherein the classifying identification of the compatible replaceable staple cartridge is positioned on the wedge-shaped distal nose.

Example 263

The system of Examples 257, 258, 259, 260, 261, or 262, wherein the classifying identification of the end effector and the classifying identification of the compatible replaceable staple cartridge comprise the same alphanumeric characters.

Example 264

The system of Example 263, wherein the same alphanumeric characters indicates a length of a resultant staple line fired from the compatible replaceable staple cartridge.

Example 265

The system of Example 264, wherein the same alphanumeric character indicates a type of end effector.

Example 266

The system of Examples 257, 258, 259, 260, 261, 262, 263, 264, or 265, wherein the classifying identification of the end effector and the classifying identification of the compatible replaceable staple cartridge comprise the same shape.

Example 267

The system of Examples 257, 258, 259, 260, 261, 262, 263, 264, 265, or 266, wherein the classifying identification of the end effector and the classifying identification of the compatible replaceable staple cartridge comprise the same color.

Example 268

The system of Examples 257, 258, 259, 260, 261, 262, 263, 264, 265, 266, or 267, wherein the system further comprises a lockout configured to prevent at least one surgical function unless the compatible replaceable staple cartridge is positioned in the end effector.

Example 269

A system comprising an end effector configured to receive a compatible replaceable staple cartridge, wherein the end effector comprises a first distal end comprising a cartridge compatibility indicator and the compatible replaceable staple cartridge comprising a plurality of staples, wherein the compatible replaceable staple cartridge comprises a second distal end comprising an end effector compatibility indicator.

Example 270

The system of Example 269, wherein the cartridge compatibility indicator is embossed on an outer surface of the end effector.

Example 271

The system of Example 270, wherein the end effector compatibility indicator is embossed on an outer surface of the compatible replaceable staple cartridge.

Example 272

The system of Examples 269, 270, or 271, wherein the cartridge compatibility indicator longitudinally overlaps the end effector compatibility indicator when the compatible replaceable staple cartridge is positioned in the end effector.

Example 273

A system comprising an end effector configured to receive a compatible replaceable staple cartridge, wherein the end effector comprises a first outer surface comprising a first code and the compatible replaceable staple cartridge comprising a plurality of staples and a second outer surface, wherein the second outer surface comprises a second code, and wherein the second code matches the first code.

Example 274

The system of Example 273, wherein the first code is embossed on the first outer surface, and wherein the second code is embossed on the second outer surface.

Example 275

The system of Examples 273 or 274, wherein the first code and the second code indicate a length of the compatible replaceable staple cartridge.

Example 276

The system of Examples 273, 274, or 275, wherein the first code and the second code include at least one number and at least one letter.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES; now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009; now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012; now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Patent Application Publication No. 2014/0263551;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method, comprising:
    obtaining a first staple cartridge having a first row of staples;
    obtaining a second staple cartridge having a second row of staples, wherein the first row of staples and the second row of staples comprise the same length;

inserting the first staple cartridge into a channel comprising a keyed profile, wherein complete insertion of the first staple cartridge into the channel is prevented by an interference between the keyed profile and the first staple cartridge; and inserting the second staple cartridge into the channel when the first staple cartridge is not inserted into the channel, wherein complete insertion of the second staple cartridge into the channel is permitted by the keyed profile.

2. The method of claim 1, wherein inserting the second staple cartridge into the channel further comprises aligning key features on the second staple cartridge with the keyed profile on the channel.

3. The method of claim 1, further comprising a bottom surface of the first staple cartridge being spaced apart from the channel when the first staple cartridge is inserted into the channel, wherein a gap is defined between at least a portion of the bottom surface of the first staple cartridge and the channel when the first staple cartridge is inserted into the channel.

4. The method of claim 3, further comprising a bottom surface of the second staple cartridge being positioned against the channel when the second staple cartridge is inserted into the channel.

5. The method of claim 1, further comprising a proximal portion of the first staple cartridge obstructing clamping of an anvil against a distal portion of the first staple cartridge when the first staple cartridge is inserted into the channel.

6. The method of claim 1, further comprising a firing lockout of the first staple cartridge preventing a firing stroke when the first staple cartridge is inserted into the channel.

7. A method, comprising:
obtaining a first staple cartridge comprising a first quantity of staples;
obtaining a second staple cartridge comprising the first quantity of staples;
inserting the first staple cartridge into a channel comprising a keyed profile, wherein the complete insertion of the first staple cartridge into the channel is prevented by the keyed profile; and
inserting the second staple cartridge into the channel in lieu of the first staple cartridge, wherein the complete insertion of the second staple cartridge into the channel is permitted by the keyed profile.

8. The method of claim 7, wherein inserting the second staple cartridge into the channel further comprises aligning key features on the second staple cartridge with the keyed profile on the channel.

9. The method of claim 7, further comprising a bottom surface of the first staple cartridge being spaced apart from the channel when the first staple cartridge is inserted into the channel, wherein a gap is defined between at least a portion of the bottom surface of the first staple cartridge and the channel when the first staple cartridge is inserted into the channel.

10. The method of claim 9, further comprising a bottom surface of the second staple cartridge being positioned against the channel when the second staple cartridge is inserted into the channel.

11. The method of claim 7, further comprising the first staple cartridge obstructing clamping of an anvil against the first staple cartridge when the first staple cartridge is inserted into the channel.

12. The method of claim 7, further comprising a firing lockout of the first staple cartridge preventing a firing stroke when the first staple cartridge is inserted into the channel.

13. A method, comprising:
obtaining a channel;
obtaining a compatible staple cartridge comprising a proximal alignment protrusion and a distal alignment protrusion, wherein the compatible staple cartridge has a first length, and wherein the compatible staple cartridge comprises a row of staples having a first row length;
aligning the proximal alignment protrusion with a corresponding proximal alignment feature in the channel;
aligning the distal alignment protrusion with a corresponding distal alignment feature in the channel;
inserting the compatible staple cartridge into the channel such that the proximal alignment protrusion interlocks with the corresponding proximal alignment feature and the distal alignment protrusion interlocks with the corresponding distal alignment feature;
obtaining an incompatible staple cartridge having a second length, wherein the second length is the same as the first length, wherein the incompatible staple cartridge comprises a row of staples having a second row length, and wherein the first row length of the compatible staple cartridge is the same as the second row length of the incompatible staple cartridge;
attempting to insert the incompatible staple cartridge into the channel when the compatible staple cartridge is not inserted into the channel, wherein the complete insertion of the incompatible staple cartridge is prevented.

14. The method of claim 13, further comprising a bottom surface of the compatible staple cartridge being positioned against the channel when the compatible staple cartridge is inserted into the channel.

15. The method of claim 13, further comprising a firing lockout of the compatible staple cartridge preventing a firing stroke until the compatible staple cartridge is inserted into the channel.

16. The method of claim 13, wherein the incompatible staple cartridge further comprises an interference feature relative to the corresponding proximal alignment feature on the channel.

17. The method of claim 16, further comprising a lockout preventing at least one surgical function when the incompatible staple cartridge is positioned in the channel.

18. The method of claim 13, further comprising a bottom surface of the incompatible staple cartridge being spaced apart from the channel when the incompatible staple cartridge is inserted into the channel, wherein a gap is defined between at least a portion of the bottom surface of the incompatible staple cartridge and the channel when the incompatible staple cartridge is inserted into the channel.

19. The method of claim 18, further comprising a proximal portion of the incompatible staple cartridge obstructing clamping of an anvil against a distal portion of the incompatible staple cartridge when the incompatible staple cartridge is inserted into the channel.

20. The method of claim 13, wherein the channel comprises a jaw of an end effector, and further comprising matching a classifying indication on the end effector with a classifying indication on the compatible staple cartridge.

* * * * *